US012577597B2

(12) United States Patent
Van Dyke-Blodgett et al.

(10) Patent No.: US 12,577,597 B2
(45) Date of Patent: Mar. 17, 2026

(54) TRANSGENIC MICROORGANISMS AND SYNTHESIS OF PIPERAZIC ACID, PIPERAZIC ACID CONTAINING PRODUCTS, AND DERIVATIVES THEREOF

(71) Applicants: Joshua Van Dyke-Blodgett, St. Louis, MO (US); Yifei Hu, St. Louis, MO (US)

(72) Inventors: Joshua Van Dyke-Blodgett, St. Louis, MO (US); Yifei Hu, St. Louis, MO (US)

(73) Assignee: Washington University, St. Louis, MO (US)

( * ) Notice: Subject to any disclaimer, the term of this patent is extended or adjusted under 35 U.S.C. 154(b) by 488 days.

(21) Appl. No.: 17/203,035

(22) Filed: Mar. 16, 2021

(65) Prior Publication Data

US 2022/0372533 A1 Nov. 24, 2022

Related U.S. Application Data

(63) Continuation of application No. 16/024,077, filed on Jun. 29, 2018, now abandoned.

(60) Provisional application No. 62/527,586, filed on Jun. 30, 2017.

(51) Int. Cl.

| | |
|---|---|
| ***C12P 7/40*** | (2006.01) |
| ***C12N 9/02*** | (2006.01) |
| ***C12N 9/88*** | (2006.01) |
| ***C12P 17/12*** | (2006.01) |

(52) U.S. Cl.

CPC ............ *C12P 17/12* (2013.01); *C12N 9/0073* (2013.01); *C12N 9/88* (2013.01); *C12Y 114/1381* (2013.01); *C12Y 403/01012* (2013.01)

(58) Field of Classification Search

None

See application file for complete search history.

(56) References Cited

U.S. PATENT DOCUMENTS 6,632,942 B2 10/2003 Robidoux et al.
8,962,329 B2 2/2015 Liu et al.

FOREIGN PATENT DOCUMENTS

WO WO-2016183294 A1 * 11/2016 ......... C12N 15/1096

OTHER PUBLICATIONS

Singh et al., Curr. Protein Pept. Sci. 18:1-11, 2017 (Year: 2017).*
Zhang et al., Structure 26:1474-1485, 2018 (Year: 2018).*
Trower et al., Mol. Microbiol. 6:2125-2134, 1992 (Year: 1992).*
Qian et al., Biotechnol. Bioengineer. 104:651-662, 2009 (Year: 2009).*
Bren, K., "Engineered Biomolecular Catalysts", J. Am. Chem. Soc. 139:14331-14334, 2017 (Year: 2017).*
Supplementary Information for Nat. Chem. Biol. 13:836-838, 2017, 27 pages, Jun. 19, 2017 (Year: 2017).*
UniProt Database Accession No. A0A1C4NEF4, Jan. 2017, 1 page (Year: 2017).*
Du et al. (2014) Identification and characterization of the biosynthetic gene cluster of polyoxypeptin A, a potent apoptosis inducer, BMC Microbiology, vol. 14, No. 30, 12 pages.
Du et al. (Jun. 19, 2017) A heme-dependent enzyme forms the nitrogen-nitrogen bond in piperazate, Nature Chemical Biology, vol. 13, No. 8, pp. 836-838, Online Methods, and Supplemental Information (32 pages).
Guo et al., Mini-review: In vitro Metabolic Engineering for Biomanufacturing of High-value Products, Comp. Struct. Biotechnol. J. 15:161-167, Jan. 19, 2017.
Hatanaka et al., pTONA5: A hyperexpression vector in streptomycetes, Prat. Exp. Purif. 62:244-248, 2008.
Henmi et al. (2004) Highly efficient synthesis of (R)- and (S)-piperazic acids using proline-catalyzed asymmetric α-hydrazination, Tetrahedron: Asymmetry, vol. 15, pp. 3477-3481.
Hu et al., Bioinformatic and Functional Evaluation of Actinobacterial Piperazate Metabolism, ACS Chem. Biol. 2019, 14, 696-703.
Morgan et al., Piperazic acid-containing natural products: structures and biosynthesis, Nat. Prod. Rep. 36: 1628-1653, 2019.
Neumann et al. (2012) Biosynthesis of Piperazic Acid via N5-Hydroxy-ornithine in *Kutzneria* spp. 744, ChemBioChem, vol. 13, No. 7, pp. 972-976.
Oelke et al. (2011) Piperazic acid-containing natural products: Isolation, biological relevance and total synthesis, Natural Product Reports, vol. 28, pp. 1445-1471.

* cited by examiner

*Primary Examiner* — David Steadman

(57) ABSTRACT

Among the various aspects of the present disclosure is the provision of a biological and biochemical production of piperazic acid derived from the newly discovered production pathway for L-piperazic acid. One aspect of the present disclosure includes a transgenic microorganism (e.g., bacteria) engineered to accumulate piperazic acid and derivatives thereof, including a piperazic acid (Piz)-containing product. Another aspect of the present disclosure includes biochemical and biological methods for producing piperazic acid and derivatives thereof, including a piperazic acid (Piz)-containing product. Another aspect of the present disclosure includes compositions and methods of using isotopically labeled piperazic acid and derivatives thereof, including a piperazic acid (Piz)-containing product.

26 Claims, 9 Drawing Sheets

Specification includes a Sequence Listing.

sanglifehrin A padanamide A luzopeptin A

Sch392583 azinothricin kutzneride 2

SEQUENCE LISTING

<160> NUMBER OF SEQ ID NOS: 181

<210> SEQ ID NO 1
<211> LENGTH: 494
<212> TYPE: PRT
<213> ORGANISM: Mycobacterium marinum

<400> SEQUENCE: 1

```
Met Gln Gln Arg Leu Thr Met Trp Ser Ala Thr Gly Leu Ile Phe Gly
1               5                   10                  15

His Ala Leu Cys Met Asn Thr Cys Arg Thr Met Val Val Pro Arg Gly
            20                  25                  30

Lys Pro Leu Cys Ile Glu Arg Val Pro Pro Leu Pro Cys Gln Pro Lys
        35                  40                  45

Met Gly Glu Ser Thr Met Pro Ser Gly Gly Ile Ala Asp Pro Glu Leu
    50                  55                  60

Ala Leu Val Asp Arg Thr Leu Ser Val Val Gly Val Gly Phe Gly Val
65                  70                  75                  80

Thr Gly Leu Ala Leu Ala Ala Ala Leu His Glu Ala Glu Met Thr Glu
                85                  90                  95

Asp Ala Leu Phe Leu Glu Ser Arg Pro Lys Phe Gly Trp His Asp Asp
            100                 105                 110

Met Leu Ile Glu Gly Ser Ser Met Gln Val Ser Phe Leu Lys Asp Ile
        115                 120                 125

Val Thr Met Arg Asn Pro Thr Ser Arg Phe Ser Phe Ile Ser Tyr Leu
    130                 135                 140

His Ala Met Gly Arg Leu Thr Asn Phe Ile Asn His Gly Val Leu Thr
145                 150                 155                 160

Pro Ser Arg Arg Glu Phe Ala Asp Tyr Leu Arg Trp Val Ala Arg Gln
                165                 170                 175

Leu Asp His Leu Val Arg Tyr Asp Val His Val Thr Asp Val Arg Pro
            180                 185                 190

Val Tyr Glu Gly Ala Thr Val Ser Ala Leu Asp Ile Val Ala Gly Glu
        195                 200                 205

Asn Ala Val Val Arg Thr Arg Asn Leu Val Leu Gly Thr Gly Leu Arg
    210                 215                 220

Pro Arg Met Pro Gln Gly Val Ile Pro Asn Arg Arg Val Trp His Ser
225                 230                 235                 240

Ser Glu Leu Leu Ser Arg Leu Ala Glu Cys Gly Asp Tyr Leu Ala Arg
                245                 250                 255

Gln Ile Val Val Val Gly Ala Gly Gln Ser Ala Ala Glu Ile Ala Leu
            260                 265                 270

Tyr Leu Leu Asp Arg Tyr Pro Asp Ser Gln Val Cys Pro Val Phe Ala
        275                 280                 285

Arg Tyr Gly Tyr Ser Ala Val Asp Ala Ser Pro Phe Ala Asn Arg Ile
    290                 295                 300

Phe Asp Pro Ser Gly Val Asp Asp Phe Tyr Ala Ala Ser Pro Ser Val
305                 310                 315                 320

Lys Ala Ser Leu Leu Arg Tyr His Gly Asn Thr Asn Tyr Ser Val Val
                325                 330                 335

Ser Ser Asp Val Leu Gly Ala Leu Tyr Arg Arg Gln Tyr Glu Gln Ser
            340                 345                 350

Val Ile Gly Asp Pro Arg Leu Arg Ile Phe His Ala Ser Arg Leu His
        355                 360                 365
```

```
Leu Val Ser Phe Asn Asp Asp Ser Val Val Ala Asp Ile Glu Phe Leu
    370                 375                 380

Pro Thr Gly Glu Val Thr Arg Leu Asp Thr Asp Leu Val Val Ile Tyr
385                 390                 395                 400

Ala Thr Gly Tyr Glu Ser Arg Asp Pro Lys His Leu Leu Thr Ser Leu
                405                 410                 415

Ala Gly Tyr Leu Arg Thr Asp Glu Leu Gly Ala Leu Arg Leu Asp Arg
            420                 425                 430

Arg Tyr Arg Val Lys Thr Val Glu Gly Phe Arg Cys Gly Ile Phe Val
        435                 440                 445

Gln Gly Ala Thr Glu Ser Thr His Gly Ile Ala Ser Thr Leu Leu Ser
    450                 455                 460

Val Ala Ala Val Arg Ala Gly Glu Ile Ser Gln Ser Leu Met Glu Thr
465                 470                 475                 480

Ser Gln Ala Arg Pro Pro Ala Gly Ser Val Thr His Arg His
                485                 490


<210> SEQ ID NO 2
<211> LENGTH: 423
<212> TYPE: PRT
<213> ORGANISM: Lentzea flaviverrucosa

<400> SEQUENCE: 2

Val Thr Ser Glu Pro Tyr Asp Val Val Gly Ile Gly Phe Gly Pro Ser
1               5                   10                  15

Asn Leu Ser Leu Ala Ile Ala Leu Glu Glu Thr Gly Gly Leu Ser Ala
            20                  25                  30

Ala Phe Phe Glu Lys Gln Asp Ser Leu Arg Trp His Ser Gly Met Leu
        35                  40                  45

Val Pro Gly Ala Lys Met Gln Val Ser Phe Leu Lys Asp Leu Ala Thr
    50                  55                  60

Pro Arg Asn Pro Val Ser Ser Tyr Ser Phe Val Ser Tyr Leu His Asp
65                  70                  75                  80

Arg Gly Arg Phe Ala Arg Phe Val Asn Asn Ser Asp Phe Phe Pro Thr
                85                  90                  95

Arg Arg Glu Phe Gln Asp Tyr Leu Arg Trp Ala Glu Ala Arg Leu Ser
            100                 105                 110

Pro Pro Val His Tyr Arg Ala Glu Val Val Ser Val Arg Arg Ala Glu
        115                 120                 125

Gly Val Leu Arg Val His Val Arg Asp Thr Glu Ser Gly Ala Thr Arg
    130                 135                 140

Thr Val Asp Thr Arg Asn Ile Val Ile Ser Thr Gly Leu Val Pro Arg
145                 150                 155                 160

Met Pro Val Gly Leu Glu Ala Gly Glu Ser Val Trp His Ser Ser Gln
                165                 170                 175

Phe Leu His Arg Phe His Ala Leu Gly Asp Arg Asp Val Arg Arg Val
            180                 185                 190

Ala Val Val Gly Ala Gly Gln Ser Ala Ala Glu Leu Val Arg Tyr Leu
        195                 200                 205

His Glu Asn Leu Pro Ser Ala Gln Val Phe Ala Val Leu Pro Ser Tyr
    210                 215                 220

Gly Tyr Ala Ile Ala Asp Ser Thr Pro Phe Ala Asn Glu Val Phe Asp
225                 230                 235                 240

Ala Asp Ala Val Asp Val Phe Tyr Asp Ala Ser Asp Lys Ala Lys Ala
                245                 250                 255
```

Ala Ile Trp Arg Tyr His Arg Asn Thr Asn Tyr Ser Val Val Asp Asp
260 265 270

Glu Val Ile Arg Asp Leu Tyr Gln Arg Ala Tyr Asp Asp Glu Val Arg
275 280 285

Gly Glu Pro Arg Leu Arg Phe Leu Pro Leu Thr Arg Val Val Gly Ala
290 295 300

Lys Gln Asp Arg Asp Gly Ile Thr Leu Leu Thr His Ser Thr Val Asp
305 310 315 320

Asp Gln Ala Arg Asp Leu Pro Leu Asp Leu Val Val Cys Ala Thr Gly
325 330 335

Tyr Asp Pro Met Asp Pro Gly Glu Leu Leu Ala Gly Leu Gly Cys Ser
340 345 350

Val Ala Tyr Asp Glu Leu Gly Arg His Leu Val Gly Arg Asp His Arg
355 360 365

Leu Val Thr Glu Pro Asp Gln Asp Cys Gly Ile Tyr Leu Gln Gly Gly
370 375 380

Thr Glu His Thr His Gly Leu Thr Ser Ser Leu Leu Ser Asn Ile Ala
385 390 395 400

Val Arg Gly Gly Glu Ile Thr Gln Ser Ile Leu Arg Arg Arg Ala Glu
405 410 415

Gln Arg Asn Gly Ala Pro Ala
420

<210> SEQ ID NO 3
<211> LENGTH: 433
<212> TYPE: PRT
<213> ORGANISM: Streptomyces aureofaciens

<400> SEQUENCE: 3

Val Gly Glu Arg Gln Arg Ser Gly Val Val Ala Gly Thr Gly Ile Val
1 5 10 15

Asp Val Ala Gly Ile Gly Phe Gly Pro Ser Asn Leu Ala Leu Ala Ala
20 25 30

Ala Ile Ala Glu Ile Ala Gly Glu Ala Pro Val Ser Ala Arg Phe Phe
35 40 45

Glu Ala Gln Pro Arg Phe Gly Trp His Arg Gly Met Leu Ile Glu Gly
50 55 60

Ala Thr Met Gln Val Ser Tyr Leu Lys Asp Leu Val Thr Met Arg Asn
65 70 75 80

Pro Thr Ser Pro Tyr Ser Phe Leu Cys Tyr Leu Gln Ala Arg Gly Arg
85 90 95

Leu Ala Asp Phe Ile Asn Thr Lys Ser Pro Tyr Pro Leu Arg Val Glu
100 105 110

Phe His Asp Tyr Leu Glu Trp Val Ala Glu Ser Phe Ala Asp Leu Val
115 120 125

Ser Tyr Gly Ala Arg Val Val Ser Val Glu Pro Val Ser Ala Glu Gln
130 135 140

Gly Val Glu Phe Leu Asp Val His Phe Val Ala Pro Asp Gly Thr Arg
145 150 155 160

Gln Val Gln Arg Ala Arg Asn Leu Val Ile Ala Ala Gly Ile Glu Pro
165 170 175

Arg Leu Pro Ala Gly Leu Pro Ala Ser Pro Arg Ile Trp His Thr Ala
180 185 190

Lys Phe Leu Pro Glu Val Asp Arg Ile Ala Arg Gln Asp Pro Arg Ser

```
        195                 200                 205

Phe Val Val Leu Gly Ser Gly Gln Ser Ala Ala Glu Ala Ile Glu His
    210                 215                 220

Leu His Ala Arg Phe Pro Arg Ala Gln Val His Ser Val His Ala Arg
225                 230                 235                 240

Tyr Gly Phe Ser Val Ala Asp Asp Ser Pro Phe Ala Asn Gln Val Phe
                245                 250                 255

Asn Pro Glu Ala Val Asp Arg Phe His Thr Ala Pro Asp Asp Val Arg
            260                 265                 270

Gln Arg Leu Ile Asp Tyr His Ala Ser Thr Asn Tyr Ser Val Val Asp
        275                 280                 285

Ala Asp Leu Leu His Ser Leu Phe Gln Gln Ala Tyr Leu Glu Lys Val
    290                 295                 300

Ala Gly Asn Pro Arg Leu Asn Phe His Asn Val Ser Arg Val Ser Glu
305                 310                 315                 320

Val Thr Glu Thr Pro Asp Gly Leu Arg Ile Asp Val Glu Ser Leu Ser
                325                 330                 335

Ser Gly Thr Ser Thr Val Ile Glu Ala Gln Ala Leu Val Cys Ala Thr
            340                 345                 350

Gly Tyr Thr Arg Thr Asp Pro Ala Val Phe Leu Asp Gly Leu Leu Pro
        355                 360                 365

His Cys Pro Leu Asp Asp Gln Gly Arg Leu Arg Leu Asp Arg Glu His
    370                 375                 380

Arg Val Val Thr Asp Glu Ser Val Arg Cys Gly Ile Tyr Val Gln Gly
385                 390                 395                 400

Phe Gly Glu His Ser His Gly Leu Ser Glu Thr Leu Leu Ser Leu Ser
                405                 410                 415

Ala Val Arg Ala Gly Glu Ile Gly Asp Met Leu Val Lys Ala Leu Ser
            420                 425                 430

Gly


<210> SEQ ID NO 4
<211> LENGTH: 439
<212> TYPE: PRT
<213> ORGANISM: Streptomyces diastatochromogenes

<400> SEQUENCE: 4

Val Asn Val Ser Glu Pro Gly Ser Asp Gln Val Val Asp Val Val Gly
1               5                   10                  15

Ile Gly Phe Gly Pro Ser Asn Leu Ala Leu Ala Val Ala Leu Gly Glu
            20                  25                  30

Gly Gly Arg Lys Ala Ser Glu Lys Pro Val Thr Ser Val Phe Phe Glu
        35                  40                  45

Arg Lys Glu Arg Phe Thr Trp His Gly Gly Met Leu Ile Asp Gly Ala
    50                  55                  60

Thr Met Gln Ile Ser Phe Leu Lys Asp Leu Val Thr Leu Arg Asp Pro
65                  70                  75                  80

Arg Ser Pro Tyr Thr Phe Leu His Tyr Leu His Gln Val Gly Arg Leu
                85                  90                  95

Pro Asp Phe Ile Asn His Lys Leu Leu Phe Pro Ser Arg Ile Glu Phe
            100                 105                 110

His Asp Tyr Leu Cys Trp Val Ala Glu Ser Phe Asp His Gln Val Arg
        115                 120                 125

Tyr Gly Ala Asp Val Val Asp Val Arg Pro Val His Ser Asp Gly Ala
```

```
    130                 135                 140

Val Asn His Leu Asp Val Val Val Arg His Glu Gly Pro Glu Gly Glu
145                 150                 155                 160

Arg Ile Ser Val Gln Arg Thr Arg Asn Val Val Val Gly Thr Gly Leu
                165                 170                 175

Glu Ala His Met Pro Ala Gly Ala Ala Pro Gly Asp Arg Val Trp His
            180                 185                 190

Thr Ser Glu Leu Leu His Lys Val Ala Ala Leu Lys Glu Glu Pro Arg
        195                 200                 205

Arg Ile Val Val Val Gly Ala Gly Gln Ser Ala Ala Glu Ala Thr Glu
    210                 215                 220

Tyr Leu His Arg Arg Phe Glu Ala Ala Glu Ile Cys Pro Val Phe Thr
225                 230                 235                 240

Arg Tyr Gly Tyr Ser Pro Ala Asp Asp Ser Pro Phe Ala Asn Arg Ile
                245                 250                 255

Phe Asp Pro Leu Ala Val Asp Asp Tyr Tyr Ala Ala Thr Pro Glu Val
            260                 265                 270

Lys Arg Met Leu Leu Gly Tyr His Arg Asn Thr Asn Tyr Ser Val Val
        275                 280                 285

Asp Ala Glu Leu Ile Asp Glu Leu Tyr Arg Arg Val Tyr Gln Glu Lys
    290                 295                 300

Val Gln Gly Arg His Arg Leu Lys Val Phe Asn Ala Ser Arg Leu Ala
305                 310                 315                 320

Glu Val Lys Ala Gly Ala Glu Gly Val Gln Val Thr Val Glu Ser Val
                325                 330                 335

Ile Ser Arg Cys Arg Thr Val Leu Asp Ala Asp Cys Val Val Tyr Ala
            340                 345                 350

Thr Gly Tyr Arg Pro Thr Asp Val Arg Arg Leu Ile Gly Gly Met Ala
        355                 360                 365

Gly Leu Cys Lys Ala Asp Glu Met Gly Arg Leu His Ala Asp Arg Asp
    370                 375                 380

Tyr Arg Val Val Thr Glu Gly Asp Val His Cys Gly Ile Tyr Leu Gln
385                 390                 395                 400

Gly Ala Thr Glu His Ser His Gly Ile Ser Ser Ser Leu Leu Ser Asn
                405                 410                 415

Thr Ala Val Arg Ala Gly Glu Ile Ala Asp Ser Ile Val Ala Gly Val
            420                 425                 430

Val Gly Ala Thr Ala Ser Glu
        435


<210> SEQ ID NO 5
<211> LENGTH: 447
<212> TYPE: PRT
<213> ORGANISM: Streptomyces sp. DvalAA-43

<400> SEQUENCE: 5

Met Asp Ala Ser Ala Arg Glu Thr Tyr Asp Val Val Gly Ile Gly Phe
1               5                   10                  15

Gly Pro Ser Asn Leu Ser Leu Ala Ile Ala Leu Glu Glu His Glu Ala
            20                  25                  30

Asn Val Pro Ala Arg Pro Ile Ser Ala Ala Phe Phe Glu Arg Gln Pro
        35                  40                  45

Ser Phe Gly Trp His Arg Asn Met Leu Leu Pro Ala Ala Thr Met Gln
    50                  55                  60
```

-continued

```
Ile Ser Phe Leu Lys Asp Leu Ala Thr Phe Arg Asn Pro Val Ser Arg
65                  70                  75                  80

Tyr Ser Phe Ile Ala Tyr Leu His Ala Ala Asp Arg Leu Val Gln Phe
                85                  90                  95

Val Asn Asn Gln Thr Phe Phe Pro Thr Arg Gln Glu Phe His Gln Tyr
            100                 105                 110

Leu Glu Trp Ala Glu Ser Ser Phe Ser Asp Arg Val Ser Tyr Asn Ser
        115                 120                 125

Glu Val Thr Ala Ile Arg Arg Ala Thr Gly Thr Gly Pro Gly Glu Pro
    130                 135                 140

Asp Cys Leu Gln Ile Glu Val Arg Asp Gly Ile Gly Gly Gly Cys Arg
145                 150                 155                 160

Leu Val His Ala Arg Asn Val Ala Ile Ser Thr Gly Leu Val Pro Arg
                165                 170                 175

Met Pro Ala Gly Val Glu Arg Asp Asp Arg Val Trp His Ser Ser Glu
            180                 185                 190

Phe Leu Glu Lys Tyr Gly Gln Val Asp Pro Asn Ala Leu Lys Ser Val
        195                 200                 205

Ala Val Val Gly Ala Gly Gln Ser Ala Ala Glu Ile Thr Arg Phe Leu
    210                 215                 220

His Asp Ala Leu Pro His Ala Arg Val Phe Ala Val Val Pro Ser Tyr
225                 230                 235                 240

Gly Tyr Ser Val Ala Asp Asp Thr Pro Phe Ala Asn Arg Val Phe Asp
                245                 250                 255

Pro Ser Ala Val Asp Asp Tyr Tyr Phe Gly Thr Glu Gln Thr Arg Glu
            260                 265                 270

Ala Phe Trp Arg Tyr His Arg Asn Thr Asn Tyr Ser Val Val Asp Asp
        275                 280                 285

Glu Ile Ile Arg Asp Leu His Gln Arg Ser Tyr Asp Glu Asp Val Arg
    290                 295                 300

Asn Asp Arg Arg Leu His Phe Leu Asn Leu Thr Arg Val Asp Asp Val
305                 310                 315                 320

Gln Arg Ile Gly Thr Glu Ile Arg Val Gly Leu Arg Ser Leu Ile Asp
                325                 330                 335

Val Glu Ala Gln Thr Leu Asp Val Asp Ala Leu Val Phe Ala Thr Gly
            340                 345                 350

Tyr Gly Ala Met Gln Pro Thr Gly Leu Leu Gly Asp Leu Asp Arg His
        355                 360                 365

Cys Leu Arg Asp Ala Ala Gly Arg His Arg Ala Glu Arg Asp Tyr Arg
    370                 375                 380

Leu Val Thr Thr Pro Glu Leu Ser Cys Gly Ile Tyr Leu Gln Gly Gly
385                 390                 395                 400

Thr Glu His Thr His Gly Leu Thr Ser Ser Leu Leu Ser Asn Val Ala
                405                 410                 415

Val Arg Ser Gly Glu Ile Ala Asp Ser Ile Val Arg Arg Arg Ala Glu
            420                 425                 430

Glu His Glu Pro Val Ala Ser Leu Gly Thr Ser Gly Arg Thr Ser
        435                 440                 445
```

<210> SEQ ID NO 6
<211> LENGTH: 375
<212> TYPE: PRT
<213> ORGANISM: Collimonas fungivorans

<400> SEQUENCE: 6

```
Met Gln Val Cys Phe Leu Lys Asp Leu Ala Met Leu Arg Asn Pro Thr
1               5                   10                  15

Ser Pro Phe Thr Phe Leu Ser Tyr Leu His Asp Lys Asn Arg Leu Val
            20                  25                  30

Asp Phe Val Asn His Lys Ile Leu Phe Ser Ser Arg Val Glu Phe His
        35                  40                  45

Asp Tyr Leu Glu Trp Ala Ala Ala Lys Leu Lys Arg Leu Val Gln Tyr
    50                  55                  60

Asp Ala Glu Val Val Glu Val Ser Pro Val Ile Cys Asp Gly Val Val
65                  70                  75                  80

Lys Trp Leu Asp Val Val Val Gln Arg Asp Gly Asn Pro Ser His His
                85                  90                  95

Glu Ile Tyr Arg Thr His Asn Leu Val Ile Ala Pro Gly Leu Glu Pro
            100                 105                 110

Thr Met Pro Pro Gly Ile Ser Arg Ser Glu Arg Val Trp His Ser Ser
        115                 120                 125

Glu Val Leu Asp Arg Ile Ala His Leu Thr Glu Glu Pro Gln Gln Phe
    130                 135                 140

Thr Val Val Gly Ala Gly Gln Ser Ala Ala Glu Ile Thr Ala Tyr Leu
145                 150                 155                 160

His Asp His Phe Lys Tyr Ala Lys Val Arg Ser Ile Phe Ser Arg Tyr
                165                 170                 175

Gly Tyr Ser Ala Ala Asp Asp Ser Pro Phe Thr Asn Arg Ile Phe Asp
            180                 185                 190

Pro Leu Ala Val Asp Glu Tyr Tyr Gln Ala Arg Asp Asp Val Lys Lys
        195                 200                 205

Met Leu Leu Asn Phe His Arg Asn Thr Asn Tyr Ser Val Val Asp Ala
    210                 215                 220

Asp Leu Leu Glu Asp Leu Tyr Arg Arg His Tyr Gln Glu Met Val Arg
225                 230                 235                 240

Gly Glu Ser Arg Leu Glu Phe Met Asn Val Ser Lys Val Phe Gly Ala
                245                 250                 255

Val Ala Asp Arg Asp Ser Val Asp Leu Ser Val Glu Phe Leu Pro Thr
            260                 265                 270

Gly Asp Met Arg Lys Leu Arg Ser Asp Ile Val Val Phe Gly Ser Gly
        275                 280                 285

Tyr Lys Ile Ala Asp Pro Ile Arg Tyr Phe Ser Asp Phe Ala Gly Lys
    290                 295                 300

Cys Ile Arg Asp Ser Phe Gly Gln Leu Arg Val Ala Arg Asn Tyr Arg
305                 310                 315                 320

Ile Cys Thr Ser Glu Asp Val Glu Cys Gly Ile Tyr Leu Gln Gly Thr
                325                 330                 335

Thr Glu His Thr His Gly Leu Ser Ser Thr Leu Leu Ser Asn Thr Ala
            340                 345                 350

Val Arg Ala Gly Glu Ile Leu Glu Ala Met Thr Trp Glu Arg Asp Asn
        355                 360                 365

Lys Lys Ile Ser Ser His Ala
    370                 375
```

<210> SEQ ID NO 7
<211> LENGTH: 446
<212> TYPE: PRT
<213> ORGANISM: Streptomyces reticuli -continued

<400> SEQUENCE: 7

Met Thr Arg Leu Ala Gly Gln Ala Pro Thr Ala Gln His Ser Pro Glu
1 5 10 15

Ser Glu Val Arg Asp Val Thr Gly Ile Gly Phe Gly Ala Ala Asn Leu
20 25 30

Ala Leu Ala Val Ala Leu His Glu Ser Gly Ala Gly Asp Arg Ala Leu
35 40 45

Phe Leu Glu Lys Gln Lys Glu Phe Gly Trp His Arg Gly Met Leu Ile
50 55 60

Glu Gly Ser Ser Leu Gln Val Ser Phe Leu Lys Asp Ile Ala Thr Met
65 70 75 80

Arg Asn Pro Thr Ser Asp Phe Gly Phe Leu Ser Tyr Leu Gln Glu Lys
85 90 95

Gly Arg Leu Val Asp Phe Ile Asn Gln His Thr Leu Leu Pro Ser Arg
100 105 110

Ile Glu Tyr His Asp Tyr Leu Gln Trp Ala Ala Asp Arg Leu Gly His
115 120 125

Met Val Glu Tyr Gly Val Glu Ala Thr Gly Val Arg Pro Val Thr Asp
130 135 140

Ala Gly Glu Val Val Ala Leu Asp Val Leu Ala Gly Asp Arg Val Val
145 150 155 160

Thr Arg Thr Arg Asn Leu Val Ile Ala Ser Gly Leu Arg Pro Arg Leu
165 170 175

Pro Glu Gly Ala Glu Thr Gly Glu Arg Val Trp His Ser Ser Gln Leu
180 185 190

Leu His Arg Leu Pro Ala Phe Asp Glu Arg Pro Pro Arg Arg Ala Val
195 200 205

Val Val Gly Ala Gly Gln Ser Ala Ala Glu Val Ala Ala His Leu Met
210 215 220

Glu Arg Tyr Pro Gln Ala Glu Val Cys Ala Val Phe Ser Arg Tyr Gly
225 230 235 240

Tyr Ser Val Ala Asp Ser Ser Pro Phe Ala Asn Arg Val Phe Asp Pro
245 250 255

Ala Ala Val Asp Asp Phe Tyr Phe Ala Pro Pro Glu Val Lys Gln Ala
260 265 270

Ile Met Arg Tyr His Gly Gly Thr Asn Tyr Ala Val Val Asp Glu Asp
275 280 285

Val Leu Gln Gly Leu Tyr Arg Arg Gln Tyr Glu Gln Lys Val Thr Gly
290 295 300

Thr Pro Arg Leu Arg Val Met Asn Ala Ser Arg Leu Val Ser Val Glu
305 310 315 320

Pro Arg Gly Glu Thr Ala Ala Val Arg Val Glu Phe Leu Pro Thr Gly
325 330 335

Glu His Ala Asp Leu Asp Ala Asp Leu Val Val Tyr Ala Thr Gly Tyr
340 345 350

Arg Ser Ala Asp Pro Ala Glu Leu Leu Gly Gly Val Ala Gly Ser Leu
355 360 365

Arg Arg Asp Ala Ala Gly Gln Val Leu Ile Gly Arg Asp Tyr Arg Leu
370 375 380

Ser Thr Thr Gly Asp Phe Arg Cys Gly Ile Tyr Val Gln Gly Ala Thr
385 390 395 400

Glu Ala Thr His Gly Ile Ala Ser Thr Leu Leu Ser Met Val Ala Val
405 410 415

```
Arg Ala Gly Glu Ile Ala Gln Ser Ile Ile Gly Gly Arg Arg Asp Pro
            420                 425                 430

Asp Arg Thr Ala Gly Thr Lys Ala Val Ala Gly Asn Arg Gly
        435                 440                 445


<210> SEQ ID NO 8
<211> LENGTH: 442
<212> TYPE: PRT
<213> ORGANISM: Streptomyces scabies

<400> SEQUENCE: 8

Met Glu Ala His Thr Asp Ala Tyr Glu Val Val Gly Ile Gly Phe Gly
1               5                   10                  15

Pro Ser Asn Leu Ser Leu Ala Ile Ala Leu Glu Glu Gln Arg Gly Lys
            20                  25                  30

Asp Glu Lys Pro Leu Thr Ala Ala Phe Phe Glu Lys Gln Ala Ser Leu
        35                  40                  45

Gly Trp His Arg Asn Met Leu Leu Pro Asp Thr Lys Met Gln Ile Ser
    50                  55                  60

Phe Leu Lys Asp Leu Ala Thr Phe Arg Asn Pro Ala Ser Gln Trp Ser
65                  70                  75                  80

Phe Ile Ala Tyr Leu His Ala Ala Gly Arg Leu Ala Gln Phe Val Asn
                85                  90                  95

Asn Gln Asn Phe Phe Pro Thr Arg Asn Glu Phe His Asp Tyr Leu Asp
            100                 105                 110

Trp Ala Glu Ser Ser Phe Ser Asp Arg Val Thr Tyr Asn Cys Glu Val
        115                 120                 125

Asn Ala Val His Leu Pro Asp Gly Tyr Thr Gly Gly Pro Val Asp Thr
    130                 135                 140

Val Arg Val Glu Val Lys Asp Asn Thr Pro Arg Gly Gly Thr Arg Leu
145                 150                 155                 160

Val Glu Ala Arg Asn Leu Val Ile Ser Thr Gly Leu Val Pro Thr Met
                165                 170                 175

Pro Thr Gly Ile Glu Arg Gly Glu Arg Val Trp His Ser Ser Glu Phe
            180                 185                 190

Leu Gly Arg Phe Gly Thr Leu Asp Arg Asp Arg Val Arg Arg Phe Ala
        195                 200                 205

Val Val Gly Ala Gly Gln Ser Ala Ala Glu Ile Thr Arg Tyr Val Tyr
    210                 215                 220

Asp Thr Val Pro Asn Ala Glu Val Tyr Ala Ile Met Pro Ser Tyr Gly
225                 230                 235                 240

Tyr Ser Ile Ala Asp Asp Thr Pro Tyr Ala Asn Arg Ile Phe Asp Ala
                245                 250                 255

Asp Ala Val Asp Asp Tyr Tyr Gly Gly Thr Asp His Thr Arg Glu Ser
            260                 265                 270

Phe Trp Arg Tyr His Arg Asn Thr Asn Tyr Gly Val Ala Asp Asp Glu
        275                 280                 285

Val Ile Arg Asp Leu Tyr Gln Arg Ala Tyr Asp Asp Glu Val Ala Arg
    290                 295                 300

Ile Lys Arg Leu His Leu Leu Asn Leu Ser Arg Val Arg Thr Val Glu
305                 310                 315                 320

Gln Thr Val Asp Gly Ala Arg Leu Thr Met His Ser Val Arg Asp Asp
                325                 330                 335

Ser Thr Tyr Gly Leu Asp Val Asp Ala Ile Val Phe Ala Thr Gly Tyr
```

```
            340                 345                 350

Asp Ser Met Asp Pro Thr Ala Leu Leu Gly Asp Leu Ala Pro His Cys
        355                 360                 365

Leu Arg Asp Glu Glu Gly Arg Leu Arg Val Glu Arg Asp Tyr Arg Leu
    370                 375                 380

Val Thr Ser Pro Asp Leu Asn Val Gly Ile Tyr Leu Gln Gly Gly Thr
385                 390                 395                 400

Glu His Thr His Gly Leu Ala Ser Ala Leu Leu Ser Asn Ile Ala Ile
                405                 410                 415

Arg Ser Gly Glu Ile Ala Asp Ala Ile Ala Ile Asp Leu Ala Ala Arg
            420                 425                 430

Gln His Thr Thr Ala Arg Ser Thr Ile Gly
        435                 440


<210> SEQ ID NO 9
<211> LENGTH: 65
<212> TYPE: PRT
<213> ORGANISM: Kutzneria albida

<400> SEQUENCE: 9

Met Gln Arg Asp Tyr Arg Val Val Thr Val Pro Glu Met Arg Cys Gly
1               5                   10                  15

Ile Tyr Leu Gln Gly Gly Thr Glu His Thr His Gly Leu Thr Ser Ser
            20                  25                  30

Leu Leu Ser Asn Ile Val Ile Arg Thr Gly Glu Ile Thr Asp Ser Ile
        35                  40                  45

Ile Thr Arg Arg Ala Glu Leu Asn Val Gly Glu Arg Arg Thr Val Asn
    50                  55                  60

Gly
65


<210> SEQ ID NO 10
<211> LENGTH: 439
<212> TYPE: PRT
<213> ORGANISM: Streptomyces albus

<400> SEQUENCE: 10

Met Thr Gly Pro Glu Val Tyr Asp Ile Val Gly Val Gly Phe Gly Pro
1               5                   10                  15

Ala Asn Leu Ala Leu Ala Val Ala Leu Thr Glu Arg Gly Ser Ser Thr
            20                  25                  30

Pro Leu Arg Ala Leu Phe Leu Asp Arg Asn Glu Ser Phe Ser Trp His
        35                  40                  45

Pro Gly Met Leu Ile His Asp Ala Thr Met Gln Val Asn Phe Leu Lys
    50                  55                  60

Asp Leu Ile Thr Leu Arg Asn Pro Ala Ser Asp Phe Ser Phe Leu Ser
65                  70                  75                  80

Tyr Leu Lys Ala Arg Gly Arg Leu Val Asp Phe Ile Asn His Lys Thr
                85                  90                  95

Phe Phe Pro Thr Arg Val Glu Phe His Asp Tyr Leu Glu Trp Ala Ala
            100                 105                 110

Gly Arg Val Gly Asp Val Val Glu Tyr Gly Thr Glu Val Val Asp Val
        115                 120                 125

Arg Pro Val Glu Arg Asp Gly Glu Val Val Tyr Phe Asp Val Val Gly
    130                 135                 140

His Gln Gln Val Gly Gly Val Ser Gln Ala Val Val Cys Arg Ala Arg
```

```
145                 150                 155                 160

Asn Val Val Val Ala Pro Gly Leu Val Pro Arg Leu Pro Gly Glu Ala
                165                 170                 175

Ser Gln Ser Glu Arg Val Trp His Ser Ser Glu Leu Leu His Arg Val
            180                 185                 190

Gly Asp Leu Pro Thr Asp Lys Arg Met Gln Phe Val Val Val Gly Ala
        195                 200                 205

Gly Gln Ser Ala Ala Glu Val Val Gly Tyr Leu His Ala Arg Tyr Glu
    210                 215                 220

Cys Ala Asp Val His Ala Val His Ser Arg Tyr Gly Tyr Ser Pro Ala
225                 230                 235                 240

Asp Asp Thr Pro Phe Ala Asn Arg Val Phe Asp Pro Ala Ala Val Glu
                245                 250                 255

His Phe Phe His Ala Pro Pro Ser Val Lys Asp Lys Phe Phe Glu Tyr
            260                 265                 270

His Ala Asn Thr Asn Tyr Ser Val Val Asp Val Glu Leu Ile Glu Asp
        275                 280                 285

Leu Tyr Ala Arg Val Tyr Arg Glu Ser Val Thr Glu Arg Arg Arg Leu
    290                 295                 300

His Ile His Gly Met Ser Glu Leu Thr Glu Val Ala Asp Gly Pro Glu
305                 310                 315                 320

Gly Leu Arg Val Ser Val Arg Phe Leu Pro Asp Gly Thr Thr Thr Val
                325                 330                 335

Leu Glu Pro Asp His Val Val Tyr Ala Thr Gly Tyr Lys Pro Ala Asp
            340                 345                 350

Val Asn Arg Val Ile Gly Val Val Ala Glu Leu Cys Lys Arg Asp Ser
        355                 360                 365

Ser Gly Asn Leu Arg Leu Leu His Asp Tyr Arg Val Asp Met Ala Ser
    370                 375                 380

His Val Arg Cys Gly Ile Tyr Leu Gln Gly Gly Thr Glu His Ser His
385                 390                 395                 400

Gly Ile Thr Ser Ser Leu Leu Ser Asn Leu Ala Asp Arg Ala Ala Glu
                405                 410                 415

Ile Leu Asp Ser Val Leu Ala His Gly Gly Gln Leu Ser Ala Asp Ala
            420                 425                 430

Ala Ala Trp Glu Val Ala Ser
        435


<210> SEQ ID NO 11
<211> LENGTH: 424
<212> TYPE: PRT
<213> ORGANISM: Rhodococcus fascians

<400> SEQUENCE: 11

Met Gly Ala Gln Ser Gly Ser Ser Val Ala Asp Val Val Gly Val Gly
1               5                   10                  15

Phe Gly Pro Ser Asn Leu Ala Leu Ala Ile Ala Leu Gln Glu Ser Ile
            20                  25                  30

Gln Pro Gly Pro Val Pro Ala Lys Phe Ser Met Lys Phe Tyr Glu Leu
        35                  40                  45

Gln Pro Arg Phe Gly Trp His Arg Gly Met Leu Met Glu Asp Ala Thr
    50                  55                  60

Met Gln Val Ser Phe Leu Lys Asp Leu Ala Thr Met Arg Asn Pro Met
65                  70                  75                  80
```

-continued

```
Ser Arg Tyr Thr Phe Val Ser Tyr Leu Arg Glu Lys Glu Arg Ile Ala
                85                  90                  95

Glu Phe Ile Asn Ser Lys Thr Leu Tyr Pro Leu Arg Val Glu Phe His
            100                 105                 110

Asp Tyr Leu Glu Trp Ala Ala Ser Gln Phe Gln Ser Asn Val Ser Tyr
        115                 120                 125

Gly Ser Glu Ile Lys Asp Ile Arg Pro Val Val Glu Asn Gly Val Val
    130                 135                 140

Glu Tyr Val Asp Val Val Gly Pro Asp Asp Val Val Gln Arg Ala Arg
145                 150                 155                 160

Asn Ile Val Ile Gly Met Gly Leu Thr Pro Arg Leu Pro Asp Gly Val
                165                 170                 175

Asn Arg Ser Glu Arg Ile Trp His Ser Ser Gln Leu Leu Gly Arg Ala
            180                 185                 190

Ala Ala Val Thr Tyr Val Pro Gln Asn Phe Val Val Val Gly Ser Gly
        195                 200                 205

Gln Ser Ala Ala Glu Val Ala Asp Tyr Leu His Arg Thr Phe Pro Arg
    210                 215                 220

Ala Asn Val His Thr Val Leu Ser Arg Tyr Gly Tyr Ser Val Ala Asp
225                 230                 235                 240

Asp Ser Pro Tyr Ala Asn Gly Ile Phe Asp Pro Glu Gly Val Asp Arg
                245                 250                 255

Phe Phe Ser Ala Pro Thr Asp Glu Lys Gln Arg Leu Leu Glu Tyr His
            260                 265                 270

Ala Asn Thr Asn Tyr Ser Val Val Asp Leu Asp Ile Ser Gln Ser Leu
        275                 280                 285

Tyr Leu Lys Ser Tyr Gln Glu Lys Val Leu Gly Lys Gln Arg Leu Arg
    290                 295                 300

Met Ile Asn Thr Ser Arg Val Thr Ser Val Asp Glu Asp Thr Asp Gly
305                 310                 315                 320

Val Arg Val Glu Val Thr Ser Ser Ala Thr Gly Leu Thr His Thr Ile
                325                 330                 335

Glu Ala Asp Val Ile Val Tyr Ala Thr Gly Tyr Arg Pro Ser Asp Pro
            340                 345                 350

Ala Pro Leu Leu Gln Gly Leu Met Arg Glu Cys Lys His Asp Glu Gln
        355                 360                 365

Gly Arg Leu Ser Val Gly Arg Asp Tyr Arg Val Thr Thr Ser Asp Ala
    370                 375                 380

Val Arg Ala Gly Ile Tyr Val His Gly Ala Ser Thr Glu His Ser His
385                 390                 395                 400

Gly Leu Ser Ala Gly Leu Leu Ser Asn Thr Ala Val Arg Ser Gly Glu
                405                 410                 415

Ile Ala Gln Ser Ile Leu Arg Arg
            420


<210> SEQ ID NO 12
<211> LENGTH: 439
<212> TYPE: PRT
<213> ORGANISM: Streptomyces neyagawaensis

<400> SEQUENCE: 12

Met Glu Ala Asn Thr Glu Ala Tyr Glu Val Val Gly Ile Gly Phe Gly
1               5                   10                  15

Pro Ala Asn Leu Ser Leu Ala Ile Ala Leu Glu Glu Gln Arg Gly Lys
            20                  25                  30
```

```
Asp Glu Lys Gln Leu Thr Ala Ala Phe Phe Glu Lys Gln Pro Ser Leu
        35                  40                  45

Gly Trp His Arg Asn Met Leu Leu Pro Asp Thr Lys Met Gln Ile Ser
    50                  55                  60

Phe Leu Lys Asp Leu Ala Thr Phe Arg Asn Pro Ala Ser Gln Trp Ser
65                  70                  75                  80

Phe Ile Ala Tyr Leu His Ala Ala Gly Arg Leu Ala Gln Phe Val Asn
                85                  90                  95

Asn Gln Asn Phe Phe Pro Thr Arg Asn Glu Phe His Asp Tyr Leu Glu
            100                 105                 110

Trp Ala Glu Ser Ser Phe Ser Asp Arg Val Thr Tyr Asn Ser Glu Val
        115                 120                 125

Asn Ala Val His Leu Pro Asp Gly His Asp Gly Gly Pro Val Asp Thr
    130                 135                 140

Val Arg Val Glu Val Lys Asp Asn Gly Pro Arg Gly Gly Thr Arg Leu
145                 150                 155                 160

Val Glu Ala Arg Asn Leu Val Ile Ser Thr Gly Leu Val Pro Lys Met
                165                 170                 175

Pro Asp Gly Val Asp Arg Gly Glu Arg Val Trp His Ser Ser Glu Phe
            180                 185                 190

Leu Gly Arg Phe His Thr Leu Asp Pro Ser Arg Val Arg Arg Phe Ala
        195                 200                 205

Val Val Gly Ala Gly Gln Ser Ala Ala Glu Ile Thr Arg Tyr Val Tyr
    210                 215                 220

Asp Thr Ile Pro Asp Ala Glu Val Tyr Ala Ile Met Pro Ser Tyr Gly
225                 230                 235                 240

Tyr Ser Ile Ala Asp Asp Thr Pro Tyr Ala Asn Arg Ile Phe Asp Ala
                245                 250                 255

Asp Ala Val Asp Asp Tyr Tyr Gly Gly Thr Asp Arg Thr Arg Glu Ser
            260                 265                 270

Phe Trp Arg Tyr His Arg Asn Thr Asn Tyr Gly Val Ala Asp Asp Glu
        275                 280                 285

Val Ile Arg Asp Leu Tyr Gln Arg Ala Tyr Asp Asp Glu Val Ala Arg
    290                 295                 300

Ile Lys Arg Leu His Leu Leu Asn Leu Ser Arg Val Gln Arg Val Asp
305                 310                 315                 320

Gln Arg Ala Asp Gly Ala Arg Leu Thr Met His Ser Val Arg Asp Asp
                325                 330                 335

Ser Val Tyr Asp Leu Asp Val Asp Ala Ile Val Phe Ala Thr Gly Tyr
            340                 345                 350

Asp Ser Met Asp Pro Thr Ala Leu Leu Gly Asp Leu Ala Pro Tyr Cys
        355                 360                 365

Leu Arg Asp Asp Glu Gly Arg Leu Arg Val Glu Arg Asp Tyr Arg Leu
    370                 375                 380

Val Thr Lys Pro Glu Leu Asn Val Gly Ile Tyr Leu Gln Gly Gly Thr
385                 390                 395                 400

Glu His Thr His Gly Leu Ala Ser Ser Leu Leu Ser Asn Ile Ala Ile
                405                 410                 415

Arg Ser Gly Glu Ile Ala Asp Ala Ile Ala Ile Ala Ile Asp Leu Ala
            420                 425                 430

Ser Arg Arg His Thr Thr Val
        435
```

<210> SEQ ID NO 13
<211> LENGTH: 435
<212> TYPE: PRT
<213> ORGANISM: Kutzneria buriramensis

<400> SEQUENCE: 13

```
Met Asp Thr Arg Gly Ser Glu Thr Tyr Asp Val Val Gly Ile Gly Phe
1               5                   10                  15

Gly Pro Ala Asn Leu Ser Leu Ala Ile Ala Leu Glu Glu Ser Pro Gln
            20                  25                  30

Arg Leu Thr Ser Ala Phe Phe Glu Arg Gln Pro Ser Leu Gly Trp His
        35                  40                  45

Arg Gly Met Leu Val Pro Ala Ala Lys Met Gln Val Ala Phe Leu Lys
    50                  55                  60

Asp Leu Val Thr Phe Arg Asn Pro Thr Ser Thr Phe Ser Phe Val Ser
65                  70                  75                  80

Tyr Leu His Asp Arg Gly Arg Leu Ala Arg Phe Val Asn Asn Gln Asp
                85                  90                  95

Phe Phe Pro Thr Arg Arg Glu Phe His Asp Tyr Leu Glu Trp Ala Glu
            100                 105                 110

Ser Arg Val Ser His Arg Val Ser Tyr Gln Ser Glu Val Thr Ala Met
        115                 120                 125

Arg Leu Pro Cys Ala Gln Arg Pro Gly Glu Asp Asp His Val Glu Val
    130                 135                 140

Glu Val Arg Asp Arg Thr Ala Pro Ser Gly Ser Arg Thr Val Ala Ala
145                 150                 155                 160

Arg Asn Val Val Ile Ser Thr Gly Leu Val Pro Arg Met Pro Ala Gly
                165                 170                 175

Leu Gln Thr Asp Glu Phe Val Trp His Ser Ser Glu Phe Leu His Lys
            180                 185                 190

Phe Ser Arg Ala Asp His Ser Gly Leu Lys Arg Val Ala Val Val Gly
        195                 200                 205

Ala Gly Gln Ser Ala Ala Glu Ile Val Arg Phe Leu Tyr Asp Met Leu
    210                 215                 220

Pro Asp Ala Asn Val Phe Ala Ile Ile Pro Ser Tyr Gly Tyr Ser Ile
225                 230                 235                 240

Ala Asp Asn Thr Pro Phe Ala Asn Gln Ile Phe Asp Pro Ala Ala Val
                245                 250                 255

Asp Asp Phe Tyr Ala Gly Ser Asp Gln Ala Lys Asp Ala Ile Trp Arg
            260                 265                 270

Tyr His Arg Asn Thr Asn Tyr Ser Val Val Asp Asp Glu Val Ile Lys
        275                 280                 285

Asp Leu Tyr Arg Arg Gln Tyr Asp Asp Asp Leu Gly Arg Pro Gly Arg
    290                 295                 300

Leu Ala Phe Leu Asn Leu Ser Arg Val Leu Asp Val Lys Arg Val Gly
305                 310                 315                 320

Glu Asp Thr Arg Val Thr Val His Ser Thr Ala Thr Glu Gln Ala Ala
                325                 330                 335

Asp Leu Asp Val Asp Val Leu Val Cys Ala Thr Gly Tyr Ser Pro Met
            340                 345                 350

Glu Pro Ala Asp Leu Leu Gly Asp Leu Ala Arg Tyr Cys Val Tyr Asp
        355                 360                 365

Gly Asp Gly Arg Tyr Gln Val Asp Arg Asp Tyr Arg Leu Val Thr Pro
    370                 375                 380
```

Asp Leu Asp Cys Gly Ile Tyr Leu Gln Gly Gly Thr Glu His Thr His
385 390 395 400

Gly Leu Ser Ser Ser Leu Leu Ser Asn Ile Ala Val Arg Ser Gly Glu
405 410 415

Ile Ala Ala Ser Ile Ala Arg Arg Arg Leu Ser Thr Asn Gly Asn Gly
420 425 430

Val His Ala
435

<210> SEQ ID NO 14
<211> LENGTH: 448
<212> TYPE: PRT
<213> ORGANISM: Streptomyces yanglinensis

<400> SEQUENCE: 14

Met Ser Asn Arg Glu Gln Thr Tyr Asp Val Val Gly Ile Gly Phe Gly
1 5 10 15

Pro Ser Asn Leu Ser Leu Ala Ile Ala Leu Glu Glu Phe Gly Ala His
20 25 30

Gly Met Glu Asn Glu Ile Ser Ser Leu Phe Leu Glu Arg Gln Pro Ser
35 40 45

Phe Gly Trp His Arg Asn Met Leu Leu Pro Ser Ala Thr Met Gln Ile
50 55 60

Ser Phe Leu Lys Asp Leu Val Thr Phe Arg Asn Pro Thr Ser Gly Phe
65 70 75 80

Ser Phe Ile Ala Tyr Leu His Ala Ser Gly Arg Leu Pro Gln Phe Val
85 90 95

Asn Asn Gln Asp Phe Phe Pro Thr Arg Gln Glu Phe His Gln Tyr Leu
100 105 110

Glu Trp Ala Gln Ala Gln Val Ala Gly Arg Ile Glu Tyr Gly Ala Glu
115 120 125

Val Thr Ser Ile Arg Leu Pro Ser Gly Thr Ala Pro Gln Glu Gly Ala
130 135 140

Asp Arg Leu Val Leu Glu Val Ala Glu Gly Ala Gly Arg Thr Gly Arg
145 150 155 160

Ala Val Glu Ala Arg Asn Val Val Ile Ser Thr Gly Leu Val Pro Ser
165 170 175

Met Pro Ala Gly Ala Glu Arg Asp Glu Arg Val Trp His Ser Ser Glu
180 185 190

Phe Leu Asp Lys Tyr Arg Arg Thr Asp His Arg Glu Leu Arg Arg Val
195 200 205

Ala Val Val Gly Ala Gly Gln Ser Ala Ala Glu Ile Ala Arg Phe Leu
210 215 220

Tyr Asp Glu Leu Pro His Ala Gln Val Ser Ala Ile Ile Pro Ser Tyr
225 230 235 240

Gly Tyr Ala Val Ala Asp Asp Thr Pro Phe Ala Asn Arg Ile Phe Asp
245 250 255

Pro Ser Ala Val Asp Asp Tyr Tyr Phe Gly Thr Glu Gln Thr Arg Glu
260 265 270

Ser Phe Trp Arg Tyr His Arg Asn Thr Asn Tyr Ser Val Val Asp Asp
275 280 285

Glu Val Ile Arg Asp Leu Tyr Arg Arg Ser Tyr Asp Asp Glu Val Arg
290 295 300

Gly Val Thr Arg Leu Gln Leu Leu Asn Leu Thr Arg Val Thr Gly Val 305 310 315 320

Lys Arg Ala Gly Ala Glu Thr Arg Val Ser Leu Gln Val Gly Pro Asp
325 330 335

Ala Glu Leu Arg Glu Leu Asp Phe Asp Leu Leu Val Cys Ala Thr Gly
340 345 350

Tyr Asp Gly Met Glu Pro Thr Gly Leu Leu Gly Glu Leu Asp Arg Tyr
355 360 365

Cys Leu Arg Asp Glu Ala Gly Arg Tyr Arg Val Glu Arg Asp Tyr Arg
370 375 380

Ile Val Thr Thr Pro Glu Leu Arg Cys Gly Ile Tyr Leu Gln Gly Gly
385 390 395 400

Thr Glu His Thr His Gly Leu Thr Ser Ser Leu Leu Ser Asn Leu Ala
405 410 415

Val Arg Ser Gly Glu Ile Ala Asp Ser Ile Ile Ala Arg Arg Ala Gly
420 425 430

Tyr Gly Ala Glu Arg Glu Val Leu Ala Lys Ile Gly Gly Asp Ile Ala
435 440 445

<210> SEQ ID NO 15
<211> LENGTH: 448
<212> TYPE: PRT
<213> ORGANISM: Streptomyces griseochromogenes

<400> SEQUENCE: 15

Met Ser Asp Arg Glu His Glu Thr Tyr Asp Val Val Gly Ile Gly Phe
1 5 10 15

Gly Pro Ser Asn Leu Ser Leu Ala Ile Ala Leu Glu Glu Tyr Arg Ala
20 25 30

Asn Gly Pro Glu Asn Glu Ile Ser Ala Leu Phe Leu Glu Arg Gln Ser
35 40 45

Ala Phe Gly Trp His Arg Asn Met Leu Leu Pro Ser Thr Thr Met Gln
50 55 60

Ile Ser Phe Leu Lys Asp Leu Val Thr Phe Arg Asn Pro Thr Ser Ser
65 70 75 80

Phe Ser Phe Ile Ala Tyr Leu His Ala Ser Gly Arg Leu Pro Gln Phe
85 90 95

Val Asn Asn Gln Asp Phe Phe Pro Thr Arg Gln Glu Phe His Gln Tyr
100 105 110

Leu Glu Trp Ala Gln Ala Arg Val Ala Asp Arg Val Ala Tyr Gly Ser
115 120 125

Glu Val Thr Ser Ile Arg Leu Pro Pro Gly Ala Asp Pro Glu Arg Ser
130 135 140

Asp Arg Leu Arg Leu Glu Val Ala Asp Ala Thr Gly Arg Asn Gly Arg
145 150 155 160

Val Val Glu Ala Arg Asn Val Val Ile Ser Thr Gly Leu Val Pro Ser
165 170 175

Met Pro Val Gly Thr Glu Arg Asp Glu Arg Val Trp His Ser Ser Glu
180 185 190

Phe Leu Glu Lys Tyr Arg Arg Met Asn Pro Ala Glu Leu Arg Arg Val
195 200 205

Ala Val Val Gly Ala Gly Gln Ser Ala Ala Glu Ile Thr Arg Phe Leu
210 215 220

Tyr Asp Glu Leu Pro His Ala Glu Val Cys Ala Val Ile Pro Ser Tyr
225 230 235 240

-continued

```
Gly Tyr Ser Val Ala Asp Asp Thr Pro Phe Ala Asn Gln Ile Phe Asp
                245                 250                 255

Pro Gly Ala Val Asp Asp Tyr Tyr Phe Gly Thr Glu Gln Thr Arg Glu
            260                 265                 270

Ala Phe Trp Arg Tyr His Arg Asn Thr Asn Tyr Ser Val Val Asp Asp
        275                 280                 285

Glu Val Ile Arg Asp Leu Tyr Arg Arg Ser Tyr Asp Asp Glu Val Arg
    290                 295                 300

Gly Val Arg Arg Leu Gln Phe Leu Asn Leu Thr Arg Val Thr Ser Val
305                 310                 315                 320

Lys Arg Val Gly Ala Glu Thr Arg Val Ser Leu Gln Val Gly Pro Asp
                325                 330                 335

Asp Glu Val Arg Glu Leu Asp Phe Asp Ala Leu Val Cys Ala Thr Gly
            340                 345                 350

Tyr Ser Thr Met Glu Pro Thr Asp Leu Leu Gly Asp Leu Asp Arg His
        355                 360                 365

Cys Leu Arg Asp Glu Ala Gly Arg Tyr Arg Val Glu Arg Asp Tyr Arg
    370                 375                 380

Ile Val Thr Ala Pro Glu Met Arg Cys Gly Ile Tyr Leu Gln Gly Gly
385                 390                 395                 400

Thr Glu His Thr His Gly Leu Thr Ser Ser Leu Leu Ser Asn Ile Ala
                405                 410                 415

Val Arg Ser Gly Glu Ile Ala Asp Ser Ile Val Ala Gly Arg Ala Gly
            420                 425                 430

Arg Asn Ala Glu Arg Ala Leu Leu Ala Glu Val Gly Gly Asp Thr Arg
        435                 440                 445
```

<210> SEQ ID NO 16
<211> LENGTH: 450
<212> TYPE: PRT
<213> ORGANISM: Streptomyces incarnatus

<400> SEQUENCE: 16

```
Met Asp Ile Ala Gly Arg Pro Ser Gln Glu Ile Tyr Asp Val Val Gly
1               5                   10                  15

Ile Gly Phe Gly Pro Ser Asn Met Ser Leu Ala Ile Ala Leu Glu Glu
            20                  25                  30

His Glu Ala Ser Ser Pro Gln His Pro Leu Lys Cys His Phe Phe Glu
        35                  40                  45

Arg Gln Pro Thr Phe Gly Trp His Arg Asn Met Leu Leu Pro Ser Thr
    50                  55                  60

Thr Met Gln Ile Ser Phe Leu Lys Asp Leu Ala Thr Phe Arg Asn Pro
65                  70                  75                  80

Thr Ser Arg Phe Ser Phe Ile Ser Tyr Leu His Ala Ala Asp Arg Leu
                85                  90                  95

Val Gln Phe Val Asn Asn Gln Asp Phe Phe Pro Thr Arg Gln Glu Phe
            100                 105                 110

His Gln Tyr Leu Glu Trp Ala Ala Ala Gly Leu Arg Asp Arg Val Thr
        115                 120                 125

Tyr Gly Ala Glu Val Thr Ser Ile Arg Pro Ala Gly Glu Ala Gly Ser
    130                 135                 140

Gly Thr Ser Asp Ile Leu Glu Ile Glu Val Arg Gly Gly Asp Gly Thr
145                 150                 155                 160

Thr Ser Val Val Ser Ala Arg Asn Val Val Ile Ser Thr Gly Leu Val
                165                 170                 175
```

Pro Arg Leu Pro Glu Gly Val Thr Ser Asp Glu Arg Val Trp His Ser
180 185 190

Ser Glu Phe Leu Ser Arg Phe His Ala Gln Ala Pro Gly Asp Leu Lys
195 200 205

Ser Val Ala Val Val Gly Ala Gly Gln Ser Ala Ala Glu Ile Thr Arg
210 215 220

Phe Leu Tyr Asp Ser Leu Pro His Ala Gln Val Thr Ala Val Ile Pro
225 230 235 240

Ser Tyr Gly Tyr Ser Val Ala Asp Asp Thr Pro Phe Ala Asn Gln Val
245 250 255

Phe Asp Pro Ser Ala Val Asp Glu Tyr Tyr Phe Gly Thr Glu Arg Ala
260 265 270

Arg Asp Ser Phe Trp Arg Tyr His Arg Asn Thr Asn Tyr Ser Val Val
275 280 285

Asp Ala Asp Val Ile Arg Ala Leu Tyr Gln Arg Ser Tyr Asp Glu Gln
290 295 300

Val Arg Gly Ser Gln Arg Leu His Phe Arg Asn Leu Thr Arg Val Asp
305 310 315 320

Glu Val Glu Arg Val Gly Ser Gly Ala Arg Val Val Val Arg Ser Val
325 330 335

Leu Asp Asp Arg Thr Glu Glu Leu Ala Leu Asp Ala Leu Val Phe Ala
340 345 350

Thr Gly Tyr Asp Gly Leu Asp Pro Ala Arg Leu Leu Gly Asp Phe Asp
355 360 365

Arg His Phe Leu Arg Asp Ala Ala Gly Arg His Arg Val Glu Arg Asp
370 375 380

Tyr Arg Leu Val Pro Ala Ser Gly Leu Thr Ala Gly Val Tyr Leu Gln
385 390 395 400

Gly Gly Thr Glu His Thr His Gly Leu Ser Ser Ala Leu Leu Ser Asn
405 410 415

Ile Ala Val Arg Ser Gly Glu Ile Ala Asp Ser Ile Val Leu Arg Arg
420 425 430

Thr Glu Arg Glu Leu Gly Ser Gly Arg Pro Val Gln Ala Ala Arg Ser
435 440 445

Ala Ala
450

<210> SEQ ID NO 17
<211> LENGTH: 444
<212> TYPE: PRT
<213> ORGANISM: Streptomyces albulus

<400> SEQUENCE: 17

Met Glu Ser His Arg Met Thr Gly Pro Glu Val Tyr Asp Ile Val Gly
1 5 10 15

Val Gly Phe Gly Pro Ala Asn Leu Ala Leu Ala Val Ala Leu Thr Glu
20 25 30

Arg Gly Ser Ser Thr Pro Leu Arg Ala Leu Phe Leu Asp Arg Asn Glu
35 40 45

Ser Phe Ser Trp His Pro Gly Met Leu Ile His Asp Ala Thr Met Gln
50 55 60

Val Asn Phe Leu Lys Asp Leu Ile Thr Leu Arg Asn Pro Ala Ser Asp
65 70 75 80

Phe Ser Phe Leu Ser Tyr Leu Lys Ala Arg Gly Arg Leu Val Asp Phe

-continued

```
                85                  90                  95

Ile Asn His Lys Thr Phe Phe Pro Thr Arg Val Glu Phe His Asp Tyr
            100                 105                 110

Leu Glu Trp Ala Ala Gly Arg Val Gly Asp Val Val Glu Tyr Gly Thr
        115                 120                 125

Glu Val Val Asp Val Arg Pro Val Glu Arg Asp Gly Glu Val Val Tyr
    130                 135                 140

Phe Asp Val Val Gly His Gln Gln Val Gly Gly Val Ser Gln Ala Val
145                 150                 155                 160

Val Cys Arg Ala Arg Asn Val Val Val Ala Pro Gly Leu Val Pro Arg
                165                 170                 175

Leu Pro Gly Glu Ala Ser Gln Ser Glu Arg Val Trp His Ser Ser Glu
            180                 185                 190

Leu Leu His Arg Val Gly Asp Leu Pro Thr Asp Lys Arg Met Gln Phe
        195                 200                 205

Val Val Val Gly Ala Gly Gln Ser Ala Ala Glu Val Val Gly Tyr Leu
    210                 215                 220

His Ala Arg Tyr Glu Cys Ala Asp Val His Ala Val His Ser Arg Tyr
225                 230                 235                 240

Gly Tyr Ser Pro Ala Asp Asp Thr Pro Phe Ala Asn Arg Val Phe Asp
                245                 250                 255

Pro Ala Ala Val Glu His Phe Phe His Ala Pro Pro Ser Val Lys Asp
            260                 265                 270

Lys Phe Phe Glu Tyr His Ala Asn Thr Asn Tyr Ser Val Val Asp Val
        275                 280                 285

Glu Leu Ile Glu Asp Leu Tyr Ala Arg Val Tyr Arg Glu Ser Val Thr
    290                 295                 300

Glu Arg Arg Arg Leu His Ile His Gly Met Ser Glu Leu Thr Glu Val
305                 310                 315                 320

Ala Asp Gly Pro Glu Gly Leu Arg Val Ser Val Arg Phe Leu Pro Asp
                325                 330                 335

Gly Thr Thr Thr Val Leu Glu Pro Asp His Val Val Tyr Ala Thr Gly
            340                 345                 350

Tyr Lys Pro Ala Asp Val Asn Arg Val Ile Gly Val Val Ala Glu Leu
        355                 360                 365

Cys Lys Arg Asp Ser Ser Gly Asn Leu Arg Leu Leu His Asp Tyr Arg
    370                 375                 380

Val Asp Met Ala Ser His Val Arg Cys Gly Ile Tyr Leu Gln Gly Gly
385                 390                 395                 400

Thr Glu His Ser His Gly Ile Thr Ser Ser Leu Leu Ser Asn Leu Ala
                405                 410                 415

Asp Arg Ala Ala Glu Ile Leu Asp Ser Val Leu Ala His Gly Gly Gln
            420                 425                 430

Leu Ser Ala Asp Ala Ala Ala Trp Glu Val Ala Ser
        435                 440


<210> SEQ ID NO 18
<211> LENGTH: 450
<212> TYPE: PRT
<213> ORGANISM: Streptomyces tsukubaensis

<400> SEQUENCE: 18

Met Gly Ile Thr Gly Arg Gly Lys His Glu Val Leu Asp Leu Val Gly
1               5                   10                  15
```

-continued

```
Ile Gly Phe Gly Pro Ser Asn Leu Ala Leu Ala Ile Ala Leu Asp Glu
            20                  25                  30

His Gly Ala Ser Ala Pro Gln His Pro Val Thr Ser His Phe Phe Glu
        35                  40                  45

Arg Gln Pro Ala Phe Gly Trp His Arg Asn Met Leu Leu Pro Ser Thr
    50                  55                  60

Thr Met Gln Ile Ser Phe Leu Lys Asp Leu Ala Thr Phe Arg Asn Pro
65                  70                  75                  80

Met Ser Arg Phe Ser Phe Val Ser Tyr Leu His Ala Ser Asn Arg Leu
                85                  90                  95

Val Gln Phe Val Asn Asn Gln Asp Phe Tyr Pro Thr Arg Gln Glu Phe
            100                 105                 110

His Gln Tyr Leu Glu Trp Ala Ala Ala Ala Leu Gly Asp Arg Val Thr
        115                 120                 125

Tyr Gly Ala Glu Val Ala Ser Ile Arg Pro Arg Thr Gly Pro Gly Ser
    130                 135                 140

Arg Thr Ala Asp Leu Leu Glu Ile Glu Val Arg Arg Gly Asp Gly Thr
145                 150                 155                 160

Thr Gly Thr Val Thr Ala Arg Asn Val Ala Ile Ser Thr Gly Leu Val
                165                 170                 175

Pro Arg Leu Pro Lys Gly Val Thr Ser Gly Pro Arg Val Trp His Ser
            180                 185                 190

Ser Glu Phe Leu Gly Arg Phe Gly Ala Gln Thr Pro Ala Asp Leu Arg
        195                 200                 205

His Val Ala Val Val Gly Ala Gly Gln Ser Ala Ala Glu Ile Thr Arg
    210                 215                 220

Phe Leu His Asp Ser Leu Pro His Ala Gln Val Ser Ala Val Ile Pro
225                 230                 235                 240

Ser Tyr Gly Tyr Ser Ile Ala Asp Asp Thr Pro Phe Ala Asn Gln Val
                245                 250                 255

Phe Asp Pro Gly Ala Val Asp Glu Tyr Tyr Tyr Gly Thr Gln Arg Ala
            260                 265                 270

Arg Asp Ala Phe Trp Arg Tyr His Gly Asn Thr Asn Tyr Ser Val Val
        275                 280                 285

Asp Ala Asp Val Ile Arg Asp Leu Tyr Arg Arg Ser Tyr Asp Glu Glu
    290                 295                 300

Val Arg Gly Gly Arg Arg Leu His Phe Arg Asn Leu Thr Arg Val Val
305                 310                 315                 320

Glu Val Glu Gly Ser Ala Ser Gly Ala Trp Val Met Leu Arg Ser Leu
                325                 330                 335

Leu Asp Asp Arg Arg Glu Glu Leu Ala Val Asp Ala Leu Val Phe Ala
            340                 345                 350

Thr Gly Tyr Asp Gly Met Asp Pro Ala Arg Leu Leu Gly Asp Phe Asp
        355                 360                 365

Arg His Phe Gln Arg Asp Ala Ala Gly Arg His Arg Leu Glu Arg Asp
    370                 375                 380

Tyr Arg Leu Val Ser Ala Ser Gly Leu Thr Cys Gly Val Tyr Leu Gln
385                 390                 395                 400

Gly Gly Thr Glu His Ser His Gly Leu Ser Ser Ser Leu Leu Ser Asn
                405                 410                 415

Thr Ala Val Arg Ser Gly Glu Ile Ala Asp Ser Ile Val Met Arg Arg
            420                 425                 430

Thr Arg Gln Glu Leu Gly Arg Ser Arg Ser Val Ala Glu Ser Pro Ser
```

```
        435                 440                 445

Ala Ala
    450


<210> SEQ ID NO 19
<211> LENGTH: 432
<212> TYPE: PRT
<213> ORGANISM: Streptomyces himastatinicus

<400> SEQUENCE: 19

Met Ala His Glu Thr Glu Ile Tyr Asp Val Val Gly Ile Gly Phe Gly
1               5                   10                  15

Pro Ser Asn Leu Ser Leu Ala Ile Ala Leu Glu Glu Ser Pro Asp Pro
            20                  25                  30

Val Thr Ser Leu Phe Phe Glu Arg Gln Pro Thr Leu Gly Trp His Arg
        35                  40                  45

Gly Met Leu Leu Pro Ser Ala Lys Met Gln Val Ser Phe Leu Lys Asp
    50                  55                  60

Leu Ala Thr Phe Arg Asn Pro Ala Ser Gly Phe Gly Phe Ile Ser Tyr
65                  70                  75                  80

Leu His Asp Met Gly Arg Leu Thr Arg Phe Val Asn Asn Gln Asp Phe
                85                  90                  95

Phe Pro Thr Arg Arg Glu Phe His Asp Tyr Leu Glu Trp Ala Ala Ser
            100                 105                 110

Lys Leu Thr Gly Arg Val Ser Tyr Asp Ser Glu Val Thr Ala Val Ser
        115                 120                 125

Ala Val Ala Ala Ala Gly Glu Gly Pro Ala Asp Arg Val Arg Val Thr
    130                 135                 140

Val Arg Gly Ala Asp Gly Ala Pro Arg Gln Val Glu Ala Arg Asn Val
145                 150                 155                 160

Val Ile Ser Thr Gly Leu Val Pro Arg Met Pro Val Asn Leu Glu Ala
                165                 170                 175

Gly Glu Arg Val Trp His Ser Ser Glu Phe Leu His Arg Phe Arg Gln
            180                 185                 190

Arg Glu Gly Glu Leu Thr Arg Val Ala Val Val Gly Ala Gly Gln Ser
        195                 200                 205

Ala Ala Glu Ile Val Arg Phe Leu Tyr Asp Thr Leu Pro Glu Val Arg
    210                 215                 220

Val Ser Ala Val Ile Pro Ser Phe Gly Tyr Ala Ile Ala Asp Asp Thr
225                 230                 235                 240

Pro Phe Ala Asn Gln Val Phe Asp Pro Asp Ala Val Asp Ser Tyr Tyr
                245                 250                 255

His Gly Thr Gln Ala Ser Lys Asp Ala Val Trp Gln Tyr His Lys Asn
            260                 265                 270

Thr Asn Tyr Ser Val Val Asp Asp Glu Val Ile Arg Gly Leu Tyr Glu
        275                 280                 285

Arg Ala Tyr Glu Asp Glu Leu Ser Gly His Gly Arg Leu Asp Phe Arg
    290                 295                 300

Asn Leu Ala Arg Val Leu Asp Ala Glu Pro Thr Gly Asp Gly Thr Arg
305                 310                 315                 320

Ile Thr Val Tyr Ser Leu Val Asp Asp Ala Ser Tyr Asp Leu Asp Val
                325                 330                 335

Asp Val Leu Ile Cys Ala Thr Gly Tyr Asp Pro Met Asn Pro Ala Arg
            340                 345                 350
```

-continued

```
Val Leu Gly Glu Leu Asp Lys Tyr Cys Val His Asp Thr Glu Gly Arg
        355                 360                 365

His Arg Val Asp Arg Asp Tyr Arg Leu Val Thr Thr Ser Asp Leu Thr
    370                 375                 380

Cys Gly Ile Tyr Leu Gln Gly Gly Thr Glu His Thr His Gly Leu Gly
385                 390                 395                 400

Ser Ser Leu Leu Ser Asn Ile Ala Val Arg Ser Gly Asp Ile Ala Gln
                405                 410                 415

Ser Ile Thr Ala Arg Cys Ala Gly Ala Pro Lys Lys Gly Leu Thr Ala
            420                 425                 430


<210> SEQ ID NO 20
<211> LENGTH: 446
<212> TYPE: PRT
<213> ORGANISM: Streptomyces flaveolus

<400> SEQUENCE: 20

Met Thr Arg Leu Ala Glu Gln Ser Ser Thr Ala Gln Gln Ser Pro Glu
1               5                   10                  15

Ser Glu Val Leu Asp Val Thr Gly Ile Gly Phe Gly Ala Ala Asn Leu
            20                  25                  30

Ala Leu Ala Val Ala Leu His Glu Ser Glu Ala Ala Gly Lys Ala Leu
        35                  40                  45

Phe Leu Glu Lys Gln Lys Glu Phe Gly Trp His Arg Gly Met Leu Leu
    50                  55                  60

Gly Gly Ser Ser Leu Gln Val Ser Phe Leu Lys Asp Ile Ala Thr Met
65                  70                  75                  80

Arg Asn Pro Thr Ser Asp Phe Gly Phe Leu Ser Tyr Leu Gln Glu Lys
                85                  90                  95

Asp Arg Leu Val Asp Phe Ile Asn Gln His Thr Leu Leu Pro Ser Arg
            100                 105                 110

Ile Glu Tyr His Asp Tyr Leu Gln Trp Ala Ala Asp Arg Leu Asn His
        115                 120                 125

Leu Val Glu Tyr Gly Val Glu Ala Thr Gly Val Arg Pro Val Thr Glu
    130                 135                 140

Ala Gly Glu Val Val Ala Leu Asp Val Leu Ala Gly Asp Arg Val Val
145                 150                 155                 160

Ala Arg Thr Arg Asn Leu Val Leu Ala Ser Gly Leu Arg Pro Arg Leu
                165                 170                 175

Pro Glu Gly Ala Glu Thr Gly Glu Arg Val Trp His Ser Ser Gln Leu
            180                 185                 190

Leu His Arg Leu Pro Ala Phe Asp Glu Arg Pro Pro Arg Arg Ala Val
        195                 200                 205

Val Val Gly Ala Gly Gln Ser Ala Ala Glu Val Ala Ala His Leu Met
    210                 215                 220

Asp Arg Tyr Pro Gln Ala Glu Val Cys Ala Val Phe Ala Arg Tyr Gly
225                 230                 235                 240

Tyr Ser Val Ala Asp Ser Ser Pro Phe Ala Asn Arg Val Phe Asp Pro
                245                 250                 255

Ala Ala Val Asp Asp Phe Tyr Phe Ala Pro Pro Glu Val Lys Gln Ala
            260                 265                 270

Ile Met Arg Tyr His Gly Gly Thr Asn Tyr Ala Val Val Asp Glu Asp
        275                 280                 285

Val Leu Gln Gly Leu Tyr Arg Arg Gln Tyr Glu Gln Lys Val Ser Gly
    290                 295                 300
```

-continued

Ala Pro Arg Leu Arg Val Met Asn Ala Ser Arg Leu Val Ser Val Glu
305 310 315 320

Pro Arg Gln Glu Ser Ala Ala Val Arg Val Glu Phe Leu Pro Thr Gly
325 330 335

Glu His Thr Asp Leu Asp Ala Asp Leu Val Val Tyr Ala Thr Gly Tyr
340 345 350

Asp Ser Thr Asp Pro Ala Glu Leu Leu Gly Gly Val Ser Gly Ala Leu
355 360 365

Arg Arg Asp Glu Ala Gly Glu Leu Leu Ile Gly Arg Asp Tyr Arg Leu
370 375 380

Gly Thr Thr Gly Asp Phe Arg Cys Gly Ile Tyr Val Gln Gly Ala Thr
385 390 395 400

Glu Ala Thr His Gly Ile Ala Ser Thr Leu Leu Ser Met Val Ala Val
405 410 415

Arg Ala Gly Glu Ile Ala Arg Ser Ile Thr Gly Gly Arg Cys Asp Pro
420 425 430

Asp Arg Ser Thr Gly Ser Lys Ala Ala Ala Gly Asn Arg Gly
435 440 445

<210> SEQ ID NO 21
<211> LENGTH: 436
<212> TYPE: PRT
<213> ORGANISM: Streptomyces aurantiacus

<400> SEQUENCE: 21

Met Gly Thr Arg Glu His Glu Ile Tyr Asp Ile Val Gly Ile Gly Phe
1 5 10 15

Gly Pro Ser Asn Leu Ser Leu Ala Ile Ala Leu Glu Glu His Gln Ala
20 25 30

Asn Ser Ser Gln Gln Pro Val Arg Ala Ala Phe Phe Glu Arg Gln Pro
35 40 45

Ser Phe Gly Trp His Arg Asn Met Leu Leu Pro Gln Ala Thr Met Gln
50 55 60

Ile Ser Phe Leu Lys Asp Leu Ala Thr Phe Arg Asn Pro Leu Ser Arg
65 70 75 80

Tyr Ser Phe Val Ser Tyr Leu His Ala Ser Asp Arg Leu Val Gln Phe
85 90 95

Val Asn Asn Gln Asp Phe Phe Pro Thr Arg Gln Glu Phe His Gln Tyr
100 105 110

Leu Glu Trp Ala Glu Ser Gly Phe Arg Asp Arg Val Thr Tyr Asn Ser
115 120 125

Glu Val Thr Glu Ile Arg Val Ser Asp Glu Gly Ser Gly Gly Glu Gln
130 135 140

Leu Leu Glu Ile Val Val Arg Asp Thr Val Gly Gly Gly Thr Arg Val
145 150 155 160

Val Gln Ala Arg Asn Val Thr Val Ser Thr Gly Leu Val Pro Arg Met
165 170 175

Pro Asp Gly Met Leu Arg Asp Glu Arg Val Trp His Ser Ser Glu Phe
180 185 190

Leu Ala Lys Tyr Gly Arg Met Arg Pro Glu Asp Leu Lys Asn Val Ala
195 200 205

Val Val Gly Ala Gly Gln Ser Ala Ala Glu Ile Thr Lys Tyr Leu His
210 215 220

Asp Lys Leu Pro His Ala Gln Val Ser Ala Ile Leu Pro Ser Tyr Gly

```
225                 230                 235                 240

Tyr Ser Val Ala Asp Asp Thr Pro Phe Ala Asn Gln Val Phe Asp Pro
                245                 250                 255

Thr Ala Val Asp His Tyr Tyr Phe Gly Thr Glu Asn Thr Arg Asp Ala
            260                 265                 270

Phe Trp Arg Tyr His Lys Asn Thr Asn Tyr Ser Val Val Asp Asp Asp
        275                 280                 285

Val Ile Arg Glu Leu Phe Arg Arg Ser Tyr Glu Glu Glu Val Ala Gly
    290                 295                 300

Glu Lys Arg Leu His Phe Leu Asn Leu Thr Arg Val Lys Glu Val Lys
305                 310                 315                 320

Arg Ser Gly Asn Asp Thr Arg Val Val Leu His Ser Leu Leu Asp Gly
                325                 330                 335

Glu Ser Glu Gln Glu Met Asp Val Asp Ala Leu Val Phe Ala Thr Gly
            340                 345                 350

Tyr Ser Thr Met Asp Ala Thr Arg Leu Leu Gly Asp Leu Asp Arg Phe
        355                 360                 365

Cys Glu Arg Asp Glu Glu Gly Arg His Arg Val Glu Arg Asp Tyr Arg
    370                 375                 380

Val Val Thr Ser Gly Glu Leu Ser Cys Gly Ile Tyr Leu Gln Gly Gly
385                 390                 395                 400

Thr Glu His Thr His Gly Leu Thr Ser Ser Leu Leu Ser Asn Ile Ala
                405                 410                 415

Val Arg Ser Gly Glu Ile Ala Asp Ser Ile Val Glu Arg Arg Gly Ala
            420                 425                 430

Gly Gln Arg Val
        435


<210> SEQ ID NO 22
<211> LENGTH: 448
<212> TYPE: PRT
<213> ORGANISM: Streptomyces sp. RJA2928

<400> SEQUENCE: 22

Met Thr Asp Ser Ala Pro Glu Asp Arg Thr Val Asp Val Thr Gly Ile
1               5                   10                  15

Gly Phe Gly Pro Ser Asn Leu Ala Leu Ala Thr Ala Leu Ala Glu Pro
            20                  25                  30

Ser Ala Thr Gly Pro Gly Arg Pro Leu Glu Ala Val Tyr Phe Glu Arg
        35                  40                  45

Lys Asn Arg Phe Ser Trp His Gly Gly Met Leu Leu Asp Gly Ala Thr
    50                  55                  60

Met Gln Ile Ser Phe Leu Lys Asp Leu Val Thr Leu Arg Asp Pro Arg
65                  70                  75                  80

Ser Pro Tyr Ser Phe Leu Ser Tyr Leu His His Ala Gly Arg Leu Ser
                85                  90                  95

Asp Phe Ile Asn His Lys Leu Leu Phe Pro Ser Arg Ile Glu Phe His
            100                 105                 110

Asp Tyr Leu Glu Trp Val Ala Gly Phe Phe Glu Glu Gln Val Val Tyr
        115                 120                 125

Gly Ser Glu Val Val Asp Val Arg Pro Val Ala Arg Glu Asp Ala Val
    130                 135                 140

Glu His Met Asp Val Val Val Arg Gln Arg Thr Ala Ala Gly Glu Arg
145                 150                 155                 160
```

-continued

Thr Val Val Gln Arg Thr Arg Asp Leu Val Val Ala Thr Gly Leu Glu
165 170 175

Pro Ser Leu Pro Pro Gly Thr Val Cys Ser Asp Arg Val Trp His Ser
180 185 190

Ser Glu Leu Leu Tyr Arg Val Glu Arg Leu Pro Pro Thr Pro Arg Arg
195 200 205

Ile Val Val Val Gly Ala Gly Gln Ser Ala Ala Glu Ala Ala Glu Phe
210 215 220

Leu His Ser Arg Phe Pro Ser Thr Asp Ile Cys Ala Val Phe Ser Arg
225 230 235 240

Tyr Gly Tyr Ser Pro Ser Asp Asp Ser Pro Phe Ala Asn Arg Ile Phe
245 250 255

Asp Pro Ala Ala Val Asp Asp Tyr Cys Ala Ala Ala Pro Glu Thr Arg
260 265 270

Arg Met Leu Leu Asp Tyr His Arg Asn Thr Asn Tyr Ser Val Val Asp
275 280 285

Pro Glu Leu Ile Asp Glu Leu Tyr Arg Arg Val Tyr Gln Glu Lys Val
290 295 300

Arg Gly Arg Pro Arg Leu Asn Ile Leu Gly Ala Ser Arg Leu Met Ala
305 310 315 320

Ala Glu Pro Ala Gly Asp Gly Val Asp Val Val Val Glu Ser Leu Val
325 330 335

Thr Gly Glu Arg Thr Pro Met Arg Ala Asp Cys Val Val Tyr Ala Thr
340 345 350

Gly Tyr Arg Pro Thr Asp Ala Arg Gly Leu Leu Gly Ser Met Ala Gly
355 360 365

Leu Cys Lys Ala Asp Glu Leu Gly Arg Leu Glu Ala Asp Arg Arg Tyr
370 375 380

Arg Val Ile Thr Glu Gly Asp Val Arg Cys Ala Ile Tyr Leu Gln Gly
385 390 395 400

Ala Thr Glu His Ser His Gly Ile Ser Ser Ser Leu Leu Ser Asn Thr
405 410 415

Ala Val Arg Ala Gly Glu Ile Ala Asp Ala Ile Arg Ala Asp Ala Val
420 425 430

Arg Ala Gly Ala Arg Ala Thr Thr Arg Ser Gln Pro Gln Pro Gln Thr
435 440 445

<210> SEQ ID NO 23
<211> LENGTH: 443
<212> TYPE: PRT
<213> ORGANISM: Frankia alni

<400> SEQUENCE: 23

Met Ser Ala Arg Glu Phe Asp Ile Tyr Asp Val Val Gly Ile Gly Phe
1 5 10 15

Gly Pro Ser Asn Leu Ser Leu Ala Val Ala Leu Asp Glu Phe Arg Val
20 25 30

Asn Gly Met Gly Asn Val Phe Ser Asn Ile Phe Phe Glu Arg Arg Ser
35 40 45

Ser Phe Ala Trp His Pro Ser Met Leu Leu Pro Ser Ala Thr Met Gln
50 55 60

Ile Ser Phe Leu Lys Asp Leu Val Thr Phe Arg Asn Pro Thr Ser Ser
65 70 75 80

Phe Ser Phe Val Ala Tyr Leu His Glu Ser Gly Arg Leu Pro Arg Phe
85 90 95

```
Val Asn Asn Gln Asp Phe Phe Pro Thr Arg Glu Glu Phe His Gln Tyr
            100                 105                 110

Leu Glu Trp Ala Gln Ala Arg Val Ala His Arg Val Ala Tyr Gly Ser
        115                 120                 125

Glu Ala Arg Ser Leu Arg Leu Pro Ala Gly Val Gly Pro Glu Arg Ala
    130                 135                 140

Asp Arg Leu Cys Leu Gln Val Ala Asp Ala Ala Ser Gly Thr Ser Arg
145                 150                 155                 160

Met Val Glu Ala Arg Asn Val Val Ile Ser Thr Gly Leu Val Pro Thr
                165                 170                 175

Met Pro Thr Gly Val Glu Arg Gly Glu Arg Val Trp His Ser Ser Glu
            180                 185                 190

Phe Leu Glu Arg Phe Arg Arg Thr Ser Pro Ala Arg Ile Arg Arg Val
        195                 200                 205

Ala Val Val Gly Ala Gly Gln Ser Ala Ala Glu Ile Thr Arg Phe Leu
    210                 215                 220

Tyr Asp Glu Leu Pro His Ala Glu Val Ser Ala Ile Ile Pro Ser Tyr
225                 230                 235                 240

Gly Tyr Cys Val Ala Asp Asp Thr Pro Phe Ala Asn Glu Val Phe Asp
                245                 250                 255

Pro Glu Ala Ile Asp Asp Tyr Tyr Tyr Ala Thr Glu Arg Thr Arg Glu
            260                 265                 270

Ala Leu Trp Arg Tyr His Ser Asn Thr Asn Tyr Ser Val Val Asp Asp
        275                 280                 285

Ser Val Ile Arg Asp Leu Tyr Arg Arg Ser Tyr Glu Asp Asp Leu Arg
    290                 295                 300

Asp Val Gly Arg Leu Arg Phe Leu Arg Leu Thr Arg Val Ala Gly Val
305                 310                 315                 320

Arg Ser Val Gly Ala Gln Thr Arg Val Ser Leu Arg Ala Gly Ile Asp
                325                 330                 335

Gly Asp Leu Arg Asp Leu Asp Val Asp Val Leu Val Cys Ala Thr Gly
            340                 345                 350

Tyr Ala Ala Met Glu Pro Thr Gly Leu Leu Gly Asp Leu Asp Gln Tyr
        355                 360                 365

Cys Leu Arg Asp Glu Ala Gly Arg Tyr Arg Ile Glu Arg Asp Tyr Arg
    370                 375                 380

Ile Val Thr Ala Pro Glu Met Gln Cys Gly Ile Tyr Leu Gln Gly Gly
385                 390                 395                 400

Thr Glu His Thr His Gly Leu Ser Ser Ser Leu Leu Ser Asn Ile Ala
                405                 410                 415

Val Arg Ser Gly Glu Ile Ile Asp Ser Ile Val Ala Arg Ser Ala Glu
            420                 425                 430

Arg Thr Ala Pro Cys Ala Val Leu Ala Glu Ala
        435                 440
```

<210> SEQ ID NO 24
<211> LENGTH: 422
<212> TYPE: PRT
<213> ORGANISM: Actinosynnema mirum

<400> SEQUENCE: 24

```
Met Thr Ala Val Val Gln Gly Ala Asp Ala Pro Arg Asp Val Val Gly
1               5                   10                  15

Val Gly Phe Gly Pro Ser Asn Leu Ala Leu Ala Val Ala Leu Ala Glu
```

```
            20                  25                  30

Arg Asp Gly Pro Ser Ser Ala Phe Phe Glu Arg Gln Pro Arg Phe Gly
        35                  40                  45

Trp His Arg Gly Met Leu Leu Asp Gly Ala Thr Met Gln Val Ser Phe
    50                  55                  60

Leu Lys Asp Leu Val Ser Met Arg Asn Pro Thr Ser Pro Tyr Ser Phe
65                  70                  75                  80

Val Ser Tyr Leu His Ala Arg Gly Arg Met Pro Glu Phe Val Asn Ala
                85                  90                  95

Lys Thr Leu Tyr Pro Leu Arg Val Glu Phe His Asp Tyr Leu Glu Trp
            100                 105                 110

Val Ala Gly His Phe Ala Gly Ser Val Ser Tyr Gly Ser Glu Ile Thr
        115                 120                 125

Ala Leu Glu Pro Val Ala Glu Asp Gly Val Val Gly His Leu Asp Val
    130                 135                 140

Val Ala Arg Arg Asp Gly Arg Thr Thr Thr Thr Arg Ala Arg Asn Val
145                 150                 155                 160

Val Val Ala Thr Gly Leu Glu Pro Arg Leu Pro Asp Gly Val Thr Gly
                165                 170                 175

Gly Glu Arg Val Trp His Ser Gly Glu Leu Leu His Arg Val Pro Trp
            180                 185                 190

Leu Arg Glu Arg Arg Val Arg Lys Val Ala Val Val Gly Ala Gly Gln
        195                 200                 205

Ser Ala Ala Glu Val Thr Glu Tyr Leu His Arg Thr Leu Pro Gly Ala
    210                 215                 220

Glu Val Ile Ala Val Phe Ser Arg Phe Gly Tyr Ser Val Ala Asp Asp
225                 230                 235                 240

Thr Pro Phe Val Asn Glu Val Phe Asp Pro Asp Ser Val Asp Leu Phe
                245                 250                 255

Tyr Gly Ser Pro Pro Ser Val Arg Gln Ala Leu Leu Ala His His Gly
            260                 265                 270

Asn Thr Asn Tyr Ser Val Val Asp Ala Asp Leu Ser Leu Glu Leu Tyr
        275                 280                 285

Arg Arg Arg Tyr Gln Glu Arg Val Thr Gly Ser Ser Arg Leu Arg Val
    290                 295                 300

Val Asn Val Ser Arg Val Arg Ser Val Arg Glu Arg Pro Asp Gly Val
305                 310                 315                 320

Ala Leu Gln Val Glu Tyr Leu Pro Thr Gly Val Val Gly Thr Leu Ala
                325                 330                 335

Ala Asp Ala Val Val Cys Ala Thr Gly Tyr Arg Pro Ala Asp Pro Thr
            340                 345                 350

Pro Leu Leu Arg Gly Leu Ala Lys Leu Asp Gly Ala Gly Arg Pro Val
        355                 360                 365

Leu Asp Arg Asp His Arg Val Val Thr Ser Gly Ser Val Arg Ala Gly
    370                 375                 380

Ile Tyr Leu Gln Gly Ala Val Thr Glu Pro Thr His Gly Leu Ser Ala
385                 390                 395                 400

Gly Leu Leu Ser Thr Thr Ala Val Arg Ala Gly Glu Ile Val Arg Ala
                405                 410                 415

Ile Leu Asp Glu Gly Arg
            420
```

<210> SEQ ID NO 25

<211> LENGTH: 424
<212> TYPE: PRT
<213> ORGANISM: Kutzneria sp. 744

<400> SEQUENCE: 25

```
Met Thr Val Ala His Ala Gly Glu Ser Pro Thr His Asp Val Val Gly
1               5                   10                  15

Val Gly Phe Gly Pro Ala Asn Leu Ser Leu Ala Val Ala Leu Glu Glu
            20                  25                  30

Ser Pro Ala Ala Leu Thr Ser Ala Phe Phe Glu Arg Arg Ala Ser Ile
        35                  40                  45

Ser Trp His Gln Gly Met Leu Leu Pro Ala Ala Lys Met Gln Val Ser
    50                  55                  60

Phe Leu Lys Asp Leu Ala Thr Phe Arg Asn Pro Ala Ser Arg Phe Ser
65                  70                  75                  80

Phe Val Ser Phe Leu His Glu Arg Gly Arg Leu Val Arg Phe Ala Asn
                85                  90                  95

Asn His Asp Phe Phe Pro Thr Arg Arg Glu Phe His Asp Tyr Leu Glu
            100                 105                 110

Trp Ala Glu Ser Lys Leu Ala His Glu Val Ser Tyr Asp Ser Glu Val
        115                 120                 125

Thr Ala Ile Arg Pro Gly Pro Gly Arg Pro Val Asp Ser Val Leu Val
    130                 135                 140

Asp Val Ser Thr Pro Glu Ala Thr Arg Thr Val Glu Ala Arg Asn Ile
145                 150                 155                 160

Val Ile Ser Thr Gly Leu Val Pro Arg Met Pro Ala Gly Val Gln Ser
                165                 170                 175

Asp Glu Phe Val Trp His Ser Ser Arg Phe Leu Asp His Phe Arg Asp
            180                 185                 190

Arg Asp Pro Arg Ser Leu Arg Arg Val Ala Val Ala Gly Gly Gly Gln
        195                 200                 205

Ser Ala Ala Glu Ile Val Arg Phe Leu His Asp Asn Arg Pro Asp Thr
    210                 215                 220

Val Val His Ala Ile Met Pro Ser Tyr Gly Tyr Val Val Ala Asp Asn
225                 230                 235                 240

Thr Pro Phe Ala Asn Gln Ile Phe Asp Pro Ala Ala Val Asp Asp Tyr
                245                 250                 255

Phe Asp Gly Ser Lys Gln Ala Lys Asp Ala Phe Trp Arg Tyr His Arg
            260                 265                 270

Asn Thr Asn Tyr Ser Val Val Asp Asp Glu Val Ile Arg Asp Leu Tyr
        275                 280                 285

Arg Arg Gly Tyr Asp Asp Glu Val Ala Gly Ala Pro Arg Leu Asn Phe
    290                 295                 300

Val Asn Leu Ala His Val Val Gly Ala Lys Arg Ile Ala Asp Asp Thr
305                 310                 315                 320

Arg Val Thr Val Tyr Ser Met Ala Arg Glu Glu Ser Tyr Asp Leu Asp
                325                 330                 335

Val Asp Val Leu Val Cys Ala Thr Gly Tyr Asp Pro Met Asp Pro Gly
            340                 345                 350

Asp Leu Leu Gly Glu Leu Ala Glu His Cys Val Gln Asp Ala Glu Gly
        355                 360                 365

Arg Trp Gln Val Asp Arg Asp Tyr Arg Met Val Thr Thr Pro Asp Leu
    370                 375                 380

Arg Cys Gly Ile Tyr Leu Gln Gly Gly Thr Glu His Thr His Gly Leu
```

385 390 395 400

Ser Ser Ser Leu Leu Ser Asn Leu Ala Thr Arg Ser Gly Glu Ile Val
405 410 415

Ser Ser Ile Glu Arg Arg Lys Ser
420

<210> SEQ ID NO 26
<211> LENGTH: 446
<212> TYPE: PRT
<213> ORGANISM: Kibdelosporangium sp. MJ126-NF4

<400> SEQUENCE: 26

Val Thr Asp Ile His Asp Leu Val Gly Val Gly Phe Gly Pro Ser Asn
1 5 10 15

Leu Ala Leu Ser Ile Ala Ala Ala Glu Ala Asp Val Pro Leu Arg Ala
20 25 30

Val Phe Leu Glu Arg Ser Glu Arg Phe Gly Trp His Arg Asp Met Leu
35 40 45

Ile Asp Asp Ala Thr Met Gln Val Ala Phe Leu Lys Asp Leu Ala Thr
50 55 60

Pro Arg Asn Pro Val Ser Arg Phe Gly Phe Val Pro Tyr Leu Trp Ala
65 70 75 80

Arg Asp Arg Leu Ser Ala Phe Ile Asn Gln Lys Thr Leu Phe Pro Thr
85 90 95

Arg Val Glu Phe His Asp Tyr Leu Glu Trp Ala Ala Ala Gln Val Asp
100 105 110

Asp Val Val Glu Tyr Ala Ala Glu Val Val Asp Ile Arg Pro Val His
115 120 125

Asp Asn Gly Glu Val Ala Phe Leu Asp Val Val Ser Val Arg Pro Asp
130 135 140

Gly Gln Ala Arg Val Arg Arg Thr Arg Asn Val Val Leu Ala Leu Gly
145 150 155 160

Leu Gln Pro Val Val Pro Pro Gly Val His Pro Ser Pro Arg Val Trp
165 170 175

His Ser Ala Asp Leu Leu Gly Arg Ala Ala Thr Leu Asp Arg Ala Lys
180 185 190

Pro Leu Arg Phe Ala Val Val Gly Ala Gly Gln Ser Ala Ala Glu Cys
195 200 205

Val Ser Tyr Leu His Arg Ala Phe Glu Gln Ala Glu Val His Ala Val
210 215 220

Phe Gly Arg Tyr Gly Tyr Ser Pro Ala Asp Asp Ser Pro Phe Ala Asn
225 230 235 240

Arg Ile Phe Asp Pro Ala Ala Val Asp Asp Tyr Phe Val Ser Pro Asp
245 250 255

Gln Val Lys Gln Arg Phe Phe Asp Tyr His Ala Asn Thr Asn Tyr Ser
260 265 270

Ala Val Asp Thr Glu Leu Leu Glu Glu Leu Ser His Arg Val Tyr Arg
275 280 285

Glu Ser Leu Ser Gly Arg Gln Arg Leu Phe Thr His His Leu Ser Ala
290 295 300

Ile Thr Asp Leu Ala Asp Thr Asp Asp Gly Val Ser Val Ser Val Glu
305 310 315 320

Phe Leu Pro Thr Gly Glu Arg Thr Met Leu Arg Val Asp His Val Ile
325 330 335

-continued

His Ala Thr Gly Tyr Arg Pro Thr Asp Pro Ile Pro Leu Leu Gly Thr
            340                 345                 350

Thr Ala Glu Leu Cys His Lys Asp Thr Leu Gly Arg Leu Arg Val Glu
        355                 360                 365

Arg Asp Tyr Arg Val Val Thr Lys Pro Asp Val Arg Thr Gly Ile Tyr
    370                 375                 380

Leu Gln Gly Gly Thr Glu His Ser His Gly Ile Ser Ser Ser Leu Leu
385                 390                 395                 400

Ser Asn Val Ala Val Arg Ala Gly Glu Ile Leu Ala Ser Ile Gln Glu
                405                 410                 415

Arg Pro Gln Arg Arg Asp Gly Asp Gln Asp Glu Arg Thr Ala Arg Ala
            420                 425                 430

Gly Asp Asp Pro Ala Arg Arg Ala Ala Ala Leu Pro Arg Arg
        435                 440                 445

<210> SEQ ID NO 27
<211> LENGTH: 398
<212> TYPE: PRT
<213> ORGANISM: Mycobacterium xenopi

<400> SEQUENCE: 27

Met Leu Pro Gly Glu Asp Asp Ser Asp Leu Asp Phe Ile Gly Ile Gly
1               5                   10                  15

Phe Gly Pro Ser Asn Leu Ala Leu Ala Val Ala Ala Glu Glu Leu Ile
            20                  25                  30

Pro Asn Trp Arg Gly Leu Phe Leu Glu Arg Ser Gln Ser Phe Gln Trp
        35                  40                  45

His Pro Gly Met Met Leu Glu Gly Ala Arg Met Gln Ile Ser Phe Leu
    50                  55                  60

Lys Asp Leu Ala Thr Leu Arg Asn Pro Ala Ser Arg Tyr Thr Phe Leu
65                  70                  75                  80

Gln Tyr Ala Lys Ala Arg Gly Arg Leu Glu Gln Phe Val Asn Ile Asn
                85                  90                  95

Glu Phe Arg Pro Thr Arg Leu Glu Tyr Asn Asp Tyr Leu Lys Trp Val
            100                 105                 110

Ala Glu Ser Phe Ala Asp Arg Val Arg Tyr Gly Ala Val Val Thr Ala
        115                 120                 125

Val Val Pro Leu Arg Asp Ser Pro Ser Pro Ala Gly Arg Phe Gly Arg
    130                 135                 140

Leu Arg Val Tyr Val Arg Asp Glu Ser Thr Gly Val Glu Thr Cys Phe
145                 150                 155                 160

Ser Ser Pro Asn Val Val Tyr Gly Gly Gly Gly Val Pro Arg Leu Leu
                165                 170                 175

Gly Ala Arg Asn Thr Ser Ala Val Val His Ser Ser Ala Phe Leu Pro
            180                 185                 190

Asn Phe Pro Asn Arg Phe Asn Glu Pro Asp Lys Ala Tyr Arg Phe Ala
        195                 200                 205

Val Val Gly Asn Gly Gln Ser Ala Ala Glu Ile Ala Glu Tyr Leu Leu
    210                 215                 220

Ser His Tyr Arg Arg Ala Thr Thr His Leu Phe Ile Ser Asp His Thr
225                 230                 235                 240

Leu Arg Ala Thr Asp His Ser Pro Phe Ile Asn Glu His Phe Phe Ser
                245                 250                 255

Val Asn Ala Ala Glu Phe Tyr Asp Tyr Pro Pro Ala Lys Arg Ala Ala
            260                 265                 270

```
Leu Arg Asn Glu Leu Arg Leu Thr Asn Tyr Gly Val Val Asp Ala Asp
        275                 280                 285

Val Leu Gln Lys Leu Tyr Gln Ile Ala Tyr Leu Asp Glu Val Arg Gly
    290                 295                 300

Cys Arg Arg Leu Phe Leu His Gly Glu Ser Arg Leu Ser Arg Val Glu
305                 310                 315                 320

Glu Ile Asp Gly Arg Val Val Ala Arg Phe Glu Asp Arg Phe Ser Gly
                325                 330                 335

Glu Ser His Glu Phe Asp Phe Asp Gly Ala Val Leu Ala Thr Gly Tyr
            340                 345                 350

Asp Arg Val Leu Asp Ala Glu Ile Phe Arg Glu Val Leu Pro His Val
        355                 360                 365

Leu Arg Asp Glu Ser Gly Glu Ile Ser Leu Ser Arg Ser Cys Arg Val
    370                 375                 380

Asn Thr Gly Pro Ala Leu Thr Ala Gly Leu Phe Leu Gln Gly
385                 390                 395


<210> SEQ ID NO 28
<211> LENGTH: 450
<212> TYPE: PRT
<213> ORGANISM: Streptomyces mirabilis

<400> SEQUENCE: 28

Met Gly Ile Thr Gly Arg Arg Ser Gln Glu Ile Tyr Asp Val Val Gly
1               5                   10                  15

Ile Gly Phe Gly Pro Ser Asn Leu Ser Leu Ala Ile Ala Leu Glu Glu
            20                  25                  30

His Gly Ala Ser Ala Pro Gln His Pro Val Lys Ser Leu Phe Phe Glu
        35                  40                  45

Arg Gln Ser Arg Phe Gly Trp His Arg Asn Met Leu Leu Pro Ser Thr
    50                  55                  60

Thr Met Gln Ile Ser Phe Leu Lys Asp Leu Ala Thr Tyr Arg Asn Pro
65                  70                  75                  80

Thr Ser Arg Phe Ser Phe Ile Ser Tyr Leu His Ala Ser Asn Arg Leu
                85                  90                  95

Val Gln Phe Val Asn Asn Gln Asp Phe Tyr Pro Thr Arg Gln Glu Phe
            100                 105                 110

His Gln Tyr Leu Glu Trp Ala Ala Ala Gly Leu Arg Asp Arg Val Thr
        115                 120                 125

Tyr Gly Ala Glu Val Thr Ser Ile Arg Pro Gly Thr Glu Ala Gly Ser
    130                 135                 140

Arg Thr Pro Asp Leu Leu Glu Val Glu Val Arg Thr Gly Asp Gly Thr
145                 150                 155                 160

Thr Ser Val Val Thr Ala Arg Asn Val Val Ile Ser Thr Gly Leu Val
                165                 170                 175

Pro Arg Leu Pro Gln Gly Val Thr Ser Asp Glu Arg Val Trp His Ser
            180                 185                 190

Ser Glu Phe Leu Ser Arg Phe Asn Ala Gln Ala Pro Gly Asp Leu Lys
        195                 200                 205

Ser Val Ala Val Val Gly Ala Gly Gln Ser Ala Ala Glu Ile Thr Arg
    210                 215                 220

Phe Leu His Asp Ser Leu Pro His Ala Gln Val Cys Ala Val Ile Pro
225                 230                 235                 240

Ser Tyr Gly Tyr Ser Val Ala Asp Asp Thr Pro Phe Ala Asn Gln Val
```

-continued

```
                245                 250                 255

Phe Asp Pro Gly Ala Val Asp Glu Tyr Tyr Phe Gly Thr Glu Gln Ala
            260                 265                 270

Gln Asp Ala Phe Trp Arg Tyr His Arg Asn Thr Asn Tyr Ala Val Val
        275                 280                 285

Asp Ala Asp Val Ile Arg Ala Leu Tyr Gln Arg Ser Tyr Asp Glu Gln
    290                 295                 300

Val His Gly Ser Arg Arg Leu His Phe Arg Asn Leu Thr Arg Val Ala
305                 310                 315                 320

Glu Val Lys Arg Thr Gly Ser Gly Thr Arg Val Val Leu Arg Ser Leu
                325                 330                 335

Leu Glu Asp Arg Thr Glu Glu Leu Ala Val Asp Ala Leu Val Phe Ala
            340                 345                 350

Thr Gly Tyr Asp Gly Leu Asp Pro Ala His Leu Leu Gly Asp Phe Asp
        355                 360                 365

Gln His Phe Leu Arg Asp Ala Ala Gly Arg His Arg Val Glu Arg Asp
    370                 375                 380

Tyr Ser Leu Val Thr Ala Ser Gly Leu Thr Cys Gly Val Tyr Leu Gln
385                 390                 395                 400

Gly Gly Thr Glu His Ser His Gly Leu Ser Ser Ser Leu Leu Ser Asn
                405                 410                 415

Ile Ala Val Arg Ser Gly Glu Ile Ala Asp Ser Ile Val Leu Arg Arg
            420                 425                 430

Thr Glu Arg Glu Leu Gly Ser Thr Cys Pro Val Lys Val Ala Ser Ser
        435                 440                 445

Ala Ala
    450


<210> SEQ ID NO 29
<211> LENGTH: 450
<212> TYPE: PRT
<213> ORGANISM: Streptomyces scabrisporus

<400> SEQUENCE: 29

Met Gly Met Phe Gly His Glu Ile His Asp Val Val Gly Ile Gly Phe
1               5                   10                  15

Gly Pro Ser Asn Leu Ser Leu Ala Ile Ala Leu Glu Glu His Gln Ala
            20                  25                  30

Asn Glu Ser Ala Arg Pro Val Thr Ala Ala Phe Phe Glu Arg Gln Pro
        35                  40                  45

Ala Phe Gly Trp His Arg Asn Met Leu Leu Pro Ser Thr Thr Met Gln
    50                  55                  60

Ile Ser Phe Leu Lys Asp Leu Ala Thr Phe Arg Asn Pro Val Ser Arg
65                  70                  75                  80

Phe Gly Phe Ile Ser Tyr Leu His Ala Ser Gly Arg Leu Pro Gln Phe
                85                  90                  95

Val Asn Ala Gln Asp Phe Phe Pro Thr Arg Gln Glu Phe His Gln Tyr
            100                 105                 110

Leu Glu Trp Ala Glu Ser Ser Val Thr Asp Arg Val Ser Tyr Gly Ser
        115                 120                 125

Asp Val Thr Ser Ile Arg Pro Pro Gln Gly Ile Ala Ala Arg Asp Ala
    130                 135                 140

Lys His Leu Glu Ile Glu Val Glu Asp Leu Val Ser Gly Ala Thr Arg
145                 150                 155                 160
```

-continued

Leu Val Lys Ala Arg Asn Val Thr Val Ser Thr Gly Leu Val Pro Arg
165 170 175

Leu Pro Gln Gly Ile Glu Arg Asp Glu Arg Val Trp His Ser Ser Glu
180 185 190

Phe Leu Glu Lys Phe Gly Arg Met Asp Ala Ala Gly Leu Gly Ser Val
195 200 205

Ala Val Val Gly Ala Gly Gln Ser Ala Ala Glu Ile Thr Arg Phe Leu
210 215 220

Tyr Asp Thr Leu Pro His Ala Arg Val Ser Ala Ile Leu Pro Ala Tyr
225 230 235 240

Gly Tyr Ser Val Ala Asp Asp Thr Pro Phe Ala Asn Gln Val Phe Asp
245 250 255

Pro Gly Ala Val Asp Glu Tyr Tyr Phe Gly Ser Asp Arg Thr Arg Glu
260 265 270

Ala Phe Trp Arg Tyr His Lys Asn Thr Asn Tyr Ser Val Val Asp Asp
275 280 285

Glu Val Ile Arg Asp Leu Tyr Arg Arg Ser Tyr Glu Glu Glu Val Arg
290 295 300

Gly Val Arg Arg Leu Asn Phe Leu Asn Leu Thr Arg Val Asp Gln Val
305 310 315 320

Lys Arg Ser Gly Asp Glu Thr Arg Val Ser Leu Arg Ser Leu Leu Asp
325 330 335

Asp Arg Val Arg Glu Leu Asp Val Asp Ala Leu Val Phe Ala Thr Gly
340 345 350

Tyr Asp Ser Pro Glu Pro Ser Gly Leu Leu Gly Asp Leu Asp Arg Tyr
355 360 365

Cys Leu Arg Asp Glu Ala Gly Arg His Arg Val Gly Arg Asp Tyr Arg
370 375 380

Leu Val Thr Ser Pro Glu Leu Ser Cys Gly Ile Tyr Leu Gln Gly Gly
385 390 395 400

Thr Glu His Thr His Gly Leu Thr Ser Ser Leu Leu Ser Asn Ile Ala
405 410 415

Ile Arg Ser Gly Glu Ile Ala Asp Ser Val Ile Arg Arg Arg Val Glu
420 425 430

His Glu Leu Glu Leu Glu Arg Asn Ala Ala Leu Glu Val Ala Arg Glu
435 440 445

Thr Arg
450

<210> SEQ ID NO 30
<211> LENGTH: 424
<212> TYPE: PRT
<213> ORGANISM: Streptomyces sp. TAA040

<400> SEQUENCE: 30

Met His Asp Leu Val Val Val Gly Ala Gly Pro Tyr Gly Leu Ser Ile
1 5 10 15

Ala Ala His Ala Ala Ala Ala Gly Leu Gln Pro Arg Val Leu Gly Thr
20 25 30

Pro Met Ala Ser Trp Arg Asp His Met Pro Gln Gly Met Tyr Leu Lys
35 40 45

Ser Glu Pro Trp Ser Ser Asp Leu Ser Asp Pro Ala Gly Ala His Thr
50 55 60

Leu Ala Ala Tyr Cys Ala Thr Arg Gly Leu Val Ala Glu His Gly Asn
65 70 75 80

```
Pro Leu Pro Ile Glu Val Phe Thr Asp Tyr Gly Cys Trp Phe Ala Gly
                85                  90                  95

Arg Ala Ala Pro Pro Val Glu Glu Arg Thr Val Val Ala Val Arg Pro
            100                 105                 110

His Gly Asp Gly Tyr Arg Val Glu Thr Ala Glu Gly Glu Arg Ile Thr
        115                 120                 125

Thr Arg Thr Val Ala Leu Ala Val Gly Val Met Pro Phe Val His His
    130                 135                 140

Pro Ser Ala Leu Ala Ala Leu Pro Ala Glu Leu Ala Thr His Ser Ser
145                 150                 155                 160

Asp His Arg Asp Leu Ala Arg Phe Arg Gly Arg Asp Val Thr Val Val
                165                 170                 175

Gly Ala Gly Gln Ala Ala Leu Glu Thr Ala Thr Leu Leu Thr Glu His
            180                 185                 190

Gly Ala Arg Ala Arg Val Leu Ala Arg Ala Asp Arg Ile Asn Trp Asn
        195                 200                 205

Thr Pro Pro Gln Pro Leu Glu Arg Gly Leu Trp Lys Ser Leu Arg Asp
    210                 215                 220

Pro His Cys Gly Leu Gly Thr Gly Trp Ser Ser Trp Leu Trp Ser Glu
225                 230                 235                 240

Arg Pro Ser Ala Val Arg Arg Leu Pro Ala Gly Leu Arg Ala Ala Ile
                245                 250                 255

Ala Gly Ser Ala Leu Gly Pro Ala Gly Ala Trp Trp Leu Arg Glu Arg
            260                 265                 270

Phe Glu Gln Ala Val Pro Val Leu Leu Gly His Arg Leu Leu Ala Ala
        275                 280                 285

Glu Gln Val Gly Gly Arg Val Arg Leu Asp Val Arg Leu Ala Asp Gly
    290                 295                 300

Thr Ala Arg Asn Leu His Thr Asp His Val Val Ala Ala Thr Gly Phe
305                 310                 315                 320

Thr Pro Glu Leu Asp Arg Leu Gly Leu Leu Ala Leu Ser Leu Thr Gly
                325                 330                 335

Thr Leu Arg Arg Val Pro Gly Thr Gly Ala Pro Glu Leu Gly Arg Cys
            340                 345                 350

Phe Glu Ser Ser Arg Pro Gly Leu Phe Phe Gly Gly Leu Leu Thr Ala
        355                 360                 365

Pro Ser Phe Gly Pro Ala Met Arg Phe Val His Gly Ala Gly Phe Thr
    370                 375                 380

Ala Gly Arg Leu Val Glu Gly Val Arg Arg Arg Leu Gly Ser Gly Ala
385                 390                 395                 400

Ala Ser Arg Thr Arg Ala Val Pro Gln Ala Ala Gly Ser Val Gly Arg
                405                 410                 415

Ala Ala Ala Glu Arg Pro Pro Gly
            420
```

<210> SEQ ID NO 31
<211> LENGTH: 434
<212> TYPE: PRT
<213> ORGANISM: Actinoalloteichus cyanogriseus

<400> SEQUENCE: 31

```
Met Tyr Gly Ser Val Pro Val Asp Gly Asn Gln Val Ser Asp Val Val
1               5                   10                  15

Gly Val Gly Phe Gly Pro Ser Asn Leu Ala Leu Ala Val Ala Ile Ala
```

-continued

```
            20                  25                  30

Glu His Asn Glu Thr Ala Pro Pro Lys Thr Arg Leu Arg Ala Gln Phe
        35                  40                  45

Leu Glu Arg Gln Pro Val Phe Gly Trp His Arg Gly Met Leu Leu Pro
    50                  55                  60

Asp Thr Thr Leu Gln Val Ser Phe Leu Lys Asp Leu Val Thr Leu Arg
65                  70                  75                  80

Asn Pro Arg Ser Ser Phe Gly Phe Val Ser Tyr Leu His Asp Arg Asn
                85                  90                  95

Arg Leu Val Asp Phe Val Asn His Gln Ser Phe Phe Pro Ser Arg Arg
            100                 105                 110

Glu Tyr His Asp Tyr Leu Glu Trp Val Ala Gly Arg Phe Thr Gly Ser
        115                 120                 125

Val His Tyr Gly His Glu Val Val Asp Val Leu Pro Val Asn Glu Gly
    130                 135                 140

Pro Asp Val Val Ala Phe Asp Val Val Ala Ala His Gly Gly Val Gly
145                 150                 155                 160

Ala Thr Arg Arg Val Arg Thr Arg Asn Val Val Leu Ala Pro Gly Leu
                165                 170                 175

Glu Pro Val Leu Pro Gln Gly Ile Thr Pro Ser Asp Arg Val Trp His
            180                 185                 190

Ser Ser Glu Leu Leu His Arg Leu Asp Gly Val Arg Glu Leu Leu Pro
        195                 200                 205

Ser Arg Pro Arg Phe Val Val Val Gly Ala Gly Gln Ser Ala Ala Glu
    210                 215                 220

Val Met Ala His Leu His Asp Ala Phe Pro Thr Ala Thr Val Arg Ser
225                 230                 235                 240

Val Cys Ser Arg Tyr Gly Phe Ala Pro Ala Asp Asp Ser Pro Phe Val
                245                 250                 255

Asn Gln Leu Phe Asp Pro Ala Gly Val Asp Glu Phe Phe Glu Ala Ala
            260                 265                 270

Leu Pro Ala Arg Glu Asn Leu Leu Arg Thr His Ala Gly Thr Asn Tyr
        275                 280                 285

Ser Ala Val Asp Gly Gly Leu Ile Asn Glu Leu Tyr Arg Arg Ser Tyr
    290                 295                 300

Gln Glu Arg Val Ala Gly Glu Pro Arg Leu Leu Phe Glu Arg Leu Ser
305                 310                 315                 320

Arg Val Val Ala Thr Glu Glu Gly Asp Asp Glu Val Ser Val Ala Val
                325                 330                 335

Arg Ser Leu Ala Asp Gly Arg Val Thr Asn Arg Arg Cys Asp Val Val
            340                 345                 350

Val Leu Ala Thr Gly Tyr Arg Pro Arg Asp Ala Leu Arg Pro Leu Gly
        355                 360                 365

Glu Leu Ala Ala Leu Cys Lys Leu Asp Ala Asn Gly Trp Pro Arg Val
    370                 375                 380

Glu Arg Asp Tyr Arg Ile Thr Thr Thr Glu Thr Val Arg Ala Gly Ile
385                 390                 395                 400

Tyr Leu Gln Gly Gly Thr Glu His Ser His Gly Leu Ser Ser Thr Leu
                405                 410                 415

Leu Ser Asn Leu Ala Val Arg Ser Gly Glu Ile Thr Arg Ala Leu Val
            420                 425                 430

Ser Arg
```

<210> SEQ ID NO 32
<211> LENGTH: 451
<212> TYPE: PRT
<213> ORGANISM: Streptomyces sp. HNS054

<400> SEQUENCE: 32

```
Met Gly Ile Thr Gly Arg Arg His Gln Glu Ile Tyr Asp Val Ile Gly
1               5                   10                  15

Ile Gly Phe Gly Pro Ser Asn Met Ser Leu Ala Ile Ala Leu Glu Glu
            20                  25                  30

His Glu Ala Ser Ala Pro Gln Gln Pro Leu Arg Tyr His Phe Phe Glu
        35                  40                  45

Arg Gln Pro Thr Phe Gly Trp His Arg Asn Met Leu Leu Pro Ser Thr
    50                  55                  60

Thr Met Gln Ile Ser Phe Leu Lys Asp Leu Ala Thr Phe Arg Asn Pro
65                  70                  75                  80

Leu Ser Arg Phe Ser Phe Ile Ser Phe Leu His Ser Ser Asn Arg Leu
                85                  90                  95

Val Gln Phe Val Asn Asn Gln Asp Phe Phe Pro Thr Arg Gln Glu Phe
            100                 105                 110

His Gln Tyr Leu Glu Trp Ala Ala Ala Gly Leu Ser Asp Arg Val Thr
        115                 120                 125

Tyr Gly Thr Glu Val Val Ser Ile Arg Pro Gly Thr Glu Gly Gly Thr
    130                 135                 140

Leu Thr Pro Asp Leu Leu Glu Ile Glu Val Arg Asp Gly Asp Gly Thr
145                 150                 155                 160

Thr Ser Val Val Val Thr Arg Asn Val Val Ile Ser Thr Gly Leu Val
                165                 170                 175

Pro Arg Leu Pro Glu Gly Val Thr Ala Asp Glu Arg Val Trp His Ser
            180                 185                 190

Ser Gln Phe Leu Ser Lys Phe His Ala Arg Asp Pro Arg Glu Leu Lys
        195                 200                 205

Arg Val Ala Val Val Gly Ala Gly Gln Ser Ala Ala Glu Ile Thr Arg
    210                 215                 220

Phe Phe Tyr Asp Ser Leu Pro His Ala Glu Val Leu Ala Val Ile Pro
225                 230                 235                 240

Ser Tyr Gly Tyr Ser Val Ala Asp Asp Thr Pro Phe Ala Asn Gln Val
                245                 250                 255

Phe Asp Pro Gly Ala Val Asp Glu Tyr Tyr Tyr Gly Thr Asp Arg Ala
            260                 265                 270

Arg Asp Ala Phe Trp Arg Tyr His Arg Asn Thr Asn Tyr Ser Val Val
        275                 280                 285

Asp Thr Asp Val Ile Arg Ala Leu Tyr Gln Arg Ser Tyr Asp Glu Gln
    290                 295                 300

Val Arg Gly Thr Gln Arg Leu His Phe Arg Asn Leu Thr Arg Val Val
305                 310                 315                 320

Glu Val Gly Ser Thr Gly Glu Gly Thr Arg Val Val Leu Arg Ser Leu
                325                 330                 335

Leu Asp Asp Arg Arg Glu Asp Leu Ala Val Asp Ala Leu Val Phe Ala
            340                 345                 350

Thr Gly Tyr Asp Gly Val Asp Pro Ala Arg Leu Leu Gly Asp Gly Phe
        355                 360                 365

Asp Ala His Phe Glu Arg Asp Ala Ala Gly Arg His Arg Val Glu Arg
    370                 375                 380
```

Asp Tyr Arg Leu Val Ser Ser Ser Gly Leu Thr Cys Gly Val Tyr Leu
385 390 395 400

Gln Gly Gly Thr Glu His Ser His Gly Leu Thr Ser Ser Leu Leu Ser
405 410 415

Asn Met Ala Val Arg Ser Gly Glu Ile Ala Asp Ser Ile Val Leu Gly
420 425 430

Arg Thr Gly Arg Glu Leu Asp Arg Thr His Ser Val Glu Glu Ala Ser
435 440 445

Ser Ala Ala
450

<210> SEQ ID NO 33
<211> LENGTH: 453
<212> TYPE: PRT
<213> ORGANISM: Streptomyces sp. AW19M42

<400> SEQUENCE: 33

Val Cys Arg Gly Ala Ala Thr Phe Leu Glu Thr Thr Leu Thr Thr Pro
1 5 10 15

Leu Glu Thr Ala Arg Ser Ala Ala Pro His Asp Pro Ala Asp Gly Ala
20 25 30

Pro Leu Asp Val Leu Gly Val Gly Phe Gly Pro Ser Asn Leu Ala Leu
35 40 45

Ala Ile Ala Leu Ser Glu Val Glu Arg Pro Arg Pro Arg Val His Phe
50 55 60

Tyr Asp Arg Ser Ser Arg Phe Ser Trp His Gly Gly Met Leu Leu Lys
65 70 75 80

Gly Ala Thr Met Gln Val His Phe Leu Lys Asp Leu Val Thr Leu Arg
85 90 95

Asn Pro Gly Ser Pro Tyr Ser Phe Leu Ser Tyr Leu His Asp Arg Glu
100 105 110

Arg Leu Val Asp Phe Ile Asn His Lys Ala Leu Phe Pro Ser Arg Val
115 120 125

Glu Phe His Asp Tyr Leu Glu Trp Ala Ala Gln Ala Cys Ser Asp Arg
130 135 140

Val Thr Tyr Gly Ser Glu Val Ser Arg Ile Glu Pro Glu Trp Val Asp
145 150 155 160

Gly Glu Val His Arg Phe Arg Val His Leu Thr His Ser Glu Pro Gly
165 170 175

Glu Arg Gly Val Arg His Glu Val Arg Ser Ala Arg Asn Val Val Leu
180 185 190

Ala Pro Gly Leu Arg Pro His Leu Pro Glu Gly Thr Ala Glu Ser Glu
195 200 205

His Val Trp His Ser Ser Arg Leu Leu Ser Arg Leu Glu Asp Ile Pro
210 215 220

Lys Asp Ala Pro Val Arg Phe Thr Val Val Gly Ala Gly Gln Ser Gly
225 230 235 240

Ala Glu Val Thr Ala Tyr Leu His Gly Arg Phe Pro Gln Ala Gln Val
245 250 255

Arg Ala Val Phe Ser Pro Tyr Gly Tyr Asn Pro Ala Asp Asp Ser Pro
260 265 270

Phe Ala Asn Arg Ile Phe Asp Pro Ala Ala Val Asp Glu Phe Phe Gly
275 280 285

Ala Pro Gln Ala Val Arg Glu Met Leu Val Asp Arg His Gly Asn Thr 290 295 300

Asn Tyr Ser Val Val Asp Gln Asp Leu Ile Ala Glu Leu Tyr Arg Ile
305 310 315 320

Trp Tyr Gln Glu Lys Val Thr Asp Glu Arg Arg Leu Ile Ile Asp Asn
325 330 335

Val Ser Arg Leu Val Gly Val Arg Glu Ala Ser Gly Leu Arg Leu Thr
340 345 350

Ile Glu Ser Leu Ala Thr Arg Glu Arg His Glu Val Asp Ser Asp Tyr
355 360 365

Leu Val Tyr Ala Thr Gly Tyr Arg Pro Val Ala Pro Asp Asp Leu Val
370 375 380

Asp Pro Glu Ile Met Lys Leu Cys Arg Arg Asp Ala Ala Gly Gly Leu
385 390 395 400

Arg Val Asn Arg Asp Tyr Arg Val Gln Thr Glu Asp Met Val Arg Cys
405 410 415

Gly Leu Tyr Val Gln Gly Ala Thr Glu His Thr His Gly Leu Ser Ser
420 425 430

Thr Leu Leu Ser Asn Thr Ala Val Arg Ala Gly Glu Ile Ala Ser Ser
435 440 445

Leu Leu Gly Arg Met
450

<210> SEQ ID NO 34
<211> LENGTH: 449
<212> TYPE: PRT
<213> ORGANISM: Salinispora pacifica

<400> SEQUENCE: 34

Val Phe Asp Glu Pro Ser Val Tyr Asp Val Leu Gly Ile Gly Phe Gly
1 5 10 15

Pro Ser Asn Leu Ser Leu Ala Ile Ala Leu His Glu Met Gly Asp Val
20 25 30

Glu Gly Arg Pro Leu Ala Ala Arg Phe Phe Glu Gln Gln Pro Ser Phe
35 40 45

Gly Trp His Arg Asn Met Leu Leu Pro Ser Ala Lys Met Gln Val Ser
50 55 60

Phe Leu Lys Asp Leu Val Thr Phe Arg Asn Pro His Ser Arg Phe Thr
65 70 75 80

Phe Val Ser Tyr Leu His Glu Met Asn Arg Leu Ala Arg Phe Ile Asn
85 90 95

Asn Cys Asp Phe Phe Pro Thr Arg Glu Glu Phe His Gly Tyr Leu Glu
100 105 110

Trp Ala Ala Ala Asn Phe Ala Asp Gln Val Thr Tyr Gly Ala Thr Ile
115 120 125

Thr Ser Ile Ser Val Pro Pro Asp Ser Gly Pro Gly Asp Pro Ile Asp
130 135 140

Arg Val Arg Val Asn Leu Ala Ser Gly Pro Thr Gly Ala Glu Ser Ser
145 150 155 160

Ser Val Glu Ala Arg Asn Val Val Leu Gly Thr Gly Leu Val Pro Arg
165 170 175

Phe Pro Ala Gly Leu Thr Ser Asp Asp Arg Val Trp His Ser Ser Glu
180 185 190

Phe Leu Gly Lys Phe Gln Arg Cys Asp Thr Thr Lys Leu Lys Arg Val
195 200 205

-continued

```
Leu Val Val Gly Gly Gly Gln Ser Ala Ala Glu Ile Ala His Phe Val
    210                 215                 220

Tyr Asp Asn Val Pro Gly Val Thr Val Thr Ala Val Ile Pro Ser Tyr
225                 230                 235                 240

Gly Tyr Ser Ile Ala Asp Ala Thr Pro Phe Ala Asn Arg Val Phe Asp
                245                 250                 255

Pro Ser Ala Ile Asp Asp Tyr Tyr Tyr Gly Asp Glu Asn Ser Lys Asp
            260                 265                 270

Ala Phe Trp Arg Tyr His Arg Asn Thr Asn Tyr Ala Val Val Asp Ser
        275                 280                 285

Asn Leu Ile Ser Asp Leu Asn Arg Lys Ala Tyr Asp Glu Ala Val Thr
    290                 295                 300

Gly Glu Thr Arg Leu Arg Phe Ala Glu Leu Ser Arg Leu Ser Gly Val
305                 310                 315                 320

Arg Arg Arg Asp Asp Gly Val Val Val Ser Ile His Ser Met Leu Ser
                325                 330                 335

Asn Arg Thr Ser Glu Val Asp Ala Asp Ile Val Ile Cys Ala Thr Gly
            340                 345                 350

Tyr Glu Pro Met Glu Ile Gly Asp Met Leu Gly Pro Leu Asp Arg Phe
        355                 360                 365

Cys Ile Arg Asp Glu Gln Gly Arg Tyr Arg Val Glu Arg Asp Tyr Arg
    370                 375                 380

Leu Ala Thr Thr Glu His Leu Arg Cys Gly Ile Tyr Leu Gln Gly Gly
385                 390                 395                 400

Met Glu His Thr His Gly Leu Ser Ser Ser Leu Leu Ser Asn Leu Ala
                405                 410                 415

Val Arg Asn Gly Asp Ile Ser Thr Ser Val Ala Arg Arg Ala Gln Ser
            420                 425                 430

Gln Ser His Asp Asp Gly Arg Val Leu Gln Gly Leu Val Pro Thr Gly
        435                 440                 445

Ser


<210> SEQ ID NO 35
<211> LENGTH: 449
<212> TYPE: PRT
<213> ORGANISM: Salinispora pacifica

<400> SEQUENCE: 35

Val Phe Asp Glu Pro Ser Val Tyr Asp Val Leu Gly Ile Gly Phe Gly
1               5                   10                  15

Pro Ser Asn Leu Ser Leu Ala Ile Ala Leu His Glu Met Gly Asp Val
            20                  25                  30

Glu Gly Arg Pro Leu Ala Ala Arg Phe Phe Glu Gln Gln Pro Ser Phe
        35                  40                  45

Gly Trp His Arg Asn Met Leu Leu Pro Ser Ala Lys Met Gln Val Ser
    50                  55                  60

Phe Leu Lys Asp Leu Val Thr Phe Arg Asn Pro His Ser Arg Phe Thr
65                  70                  75                  80

Phe Val Ser Tyr Leu His Glu Met Asn Arg Leu Ala Arg Phe Ile Asn
                85                  90                  95

Asn Cys Asp Phe Phe Pro Thr Arg Glu Glu Phe His Gly Tyr Leu Glu
            100                 105                 110

Trp Ala Ala Ala Asn Phe Ala Asp Gln Val Thr Tyr Gly Ala Thr Ile
        115                 120                 125
```

-continued

```
Thr Ser Ile Ser Val Pro Pro Asp Ser Gly Pro Gly Asp Pro Ile Asp
    130                 135                 140

Arg Val Arg Val Asn Leu Ala Ser Gly Pro Thr Gly Ala Glu Ser Ser
145                 150                 155                 160

Ser Val Glu Ala Arg Asn Val Val Leu Gly Thr Gly Leu Val Pro Arg
                165                 170                 175

Phe Pro Ala Gly Leu Thr Ser Asp Asp Arg Val Trp His Ser Ser Glu
            180                 185                 190

Phe Leu Gly Lys Phe Gln Arg Cys Asp Thr Thr Lys Leu Lys Arg Val
        195                 200                 205

Leu Val Val Gly Gly Gly Gln Ser Ala Ala Glu Ile Ala His Phe Val
    210                 215                 220

Tyr Asp Asn Val Pro Gly Val Thr Val Thr Ala Val Ile Pro Ser Tyr
225                 230                 235                 240

Gly Tyr Ser Ile Ala Asp Ala Thr Pro Phe Ala Asn Arg Val Phe Asp
                245                 250                 255

Pro Ser Ala Ile Asp Asp Tyr Tyr Tyr Gly Asp Glu Asn Ser Lys Asp
            260                 265                 270

Ala Phe Trp Arg Tyr His Arg Asn Thr Asn Tyr Ala Val Val Asp Ser
        275                 280                 285

Asn Leu Ile Ser Asp Leu Asn Arg Lys Ala Tyr Asp Glu Ala Val Thr
    290                 295                 300

Gly Glu Thr Arg Leu Arg Phe Ala Glu Leu Ser Arg Leu Ser Gly Val
305                 310                 315                 320

Arg Arg Arg Asp Asp Gly Val Val Val Ser Ile His Ser Met Leu Ser
                325                 330                 335

Asn Arg Thr Ser Glu Val Asp Ala Asp Ile Val Ile Cys Ala Thr Gly
            340                 345                 350

Tyr Glu Pro Met Glu Ile Gly Asp Met Leu Gly Pro Leu Asp Arg Phe
        355                 360                 365

Cys Ile Arg Asp Glu Gln Gly Arg Tyr Arg Val Glu Arg Asp Tyr Arg
    370                 375                 380

Leu Ala Thr Thr Glu His Leu Arg Cys Gly Ile Tyr Leu Gln Gly Gly
385                 390                 395                 400

Met Glu His Thr His Gly Leu Ser Ser Ser Leu Leu Ser Asn Leu Ala
                405                 410                 415

Val Arg Asn Gly Asp Ile Ser Thr Ser Val Ala Arg Arg Ala Gln Ser
            420                 425                 430

Gln Ser His Asp Asp Gly Arg Val Leu Gln Gly Leu Val Pro Thr Gly
        435                 440                 445

Ser


<210> SEQ ID NO 36
<211> LENGTH: 456
<212> TYPE: PRT
<213> ORGANISM: Salinispora tropica

<400> SEQUENCE: 36

Val Thr Gly Lys Val His Ile Val Phe Asp Glu Pro Ser Val Tyr Asp
1               5                   10                  15

Val Leu Gly Ile Gly Phe Gly Pro Ser Asn Leu Ser Leu Ala Ile Ala
            20                  25                  30

Leu His Glu Met Gly Asp Val Glu Gly Arg Pro Leu Ala Ala Arg Phe
        35                  40                  45
```

-continued

```
Phe Glu Gln Gln Pro Ser Phe Gly Trp His Arg Asn Met Leu Leu Pro
    50                  55                  60

Ser Ala Lys Met Gln Val Ser Phe Leu Lys Asp Leu Val Thr Phe Arg
65                  70                  75                  80

Asn Pro His Ser Arg Phe Thr Phe Val Ser Tyr Leu His Glu Met Asn
                85                  90                  95

Arg Leu Ala Arg Phe Val Asn Asn Cys Asp Phe Phe Pro Thr Arg Glu
            100                 105                 110

Glu Phe His Gly Tyr Leu Glu Trp Ala Ala Thr Asn Phe Ala Asp Gln
        115                 120                 125

Val Thr Tyr Gly Ala Thr Ile Thr Ser Ile Ser Val Pro Pro Asp Ser
    130                 135                 140

Gly Pro Gly Asp Pro Ile Asp Arg Val Arg Val His Leu Ala Ser Gly
145                 150                 155                 160

Pro Thr Gly Thr Glu Ser Ser Ser Val Glu Ala Arg Asn Val Val Leu
                165                 170                 175

Gly Thr Gly Leu Val Pro Arg Phe Pro Ala Gly Leu Thr Ser Asp Asp
            180                 185                 190

Arg Val Trp His Ser Ser Glu Phe Leu Gly Lys Phe Gln Arg Cys Asp
        195                 200                 205

Thr Thr Lys Leu Lys Arg Val Leu Val Val Gly Gly Gly Gln Ser Ala
    210                 215                 220

Ala Glu Ile Ala His Phe Val Tyr Glu Asn Val Pro Gly Ala Thr Val
225                 230                 235                 240

Thr Ala Val Ile Pro Ser Tyr Gly Tyr Ser Ile Ala Asp Ala Thr Pro
                245                 250                 255

Phe Ala Asn Arg Val Phe Asp Pro Ser Ala Ile Asp Asp Tyr Tyr Tyr
            260                 265                 270

Gly Asp Glu Asn Ser Arg Asp Ala Phe Trp Arg Tyr His Arg Asn Thr
        275                 280                 285

Asn Tyr Ala Val Val Asp Ser Asp Leu Ile Ser Asp Leu Asn Arg Lys
    290                 295                 300

Ala Tyr Asp Glu Ala Val Thr Gly Glu Ile Arg Leu Arg Phe Ala Glu
305                 310                 315                 320

Leu Ser Arg Leu Ser Gly Val Arg Arg Arg Asp Asp Gly Val Val Val
                325                 330                 335

Ser Ile His Ser Met Leu Ser Asn Arg Thr Ser Glu Val Asp Ala Asp
            340                 345                 350

Ile Val Ile Cys Ala Thr Gly Tyr Glu Pro Met Glu Ile Gly Asp Met
        355                 360                 365

Leu Gly Pro Leu Asp Arg Phe Cys Ile Arg Asp Glu His Gly Arg Tyr
    370                 375                 380

Arg Val Glu Arg Asp Tyr Arg Leu Ala Thr Thr Glu His Leu Arg Cys
385                 390                 395                 400

Gly Ile Tyr Leu Gln Gly Gly Met Glu His Thr His Gly Leu Ser Ser
                405                 410                 415

Ser Leu Leu Ser Asn Leu Ala Val Arg Asn Gly Asp Ile Ser Thr Ser
            420                 425                 430

Val Ala Arg Arg Ala Gln Ser Gln Pro His Gly Asp Gly Arg Val Leu
        435                 440                 445

Gln Gly Leu Val Pro Thr Gly Ser
    450                 455
```

-continued

<210> SEQ ID NO 37
<211> LENGTH: 449
<212> TYPE: PRT
<213> ORGANISM: Salinispora arenicola

<400> SEQUENCE: 37

```
Val Phe Asp Glu Pro Ser Val Tyr Asp Val Leu Gly Ile Gly Phe Gly
1               5                   10                  15

Pro Ser Asn Leu Ser Leu Ala Ile Ala Leu His Glu Met Gly Asp Val
            20                  25                  30

Glu Gly Arg Pro Leu Ala Ala Arg Phe Phe Glu Gln Gln Pro Ser Phe
        35                  40                  45

Gly Trp His Arg Asn Met Leu Leu Pro Ser Ala Lys Met Gln Val Ser
    50                  55                  60

Phe Leu Lys Asp Leu Val Thr Phe Arg Asn Pro His Ser Arg Phe Thr
65                  70                  75                  80

Phe Val Ser Tyr Leu His Glu Met Asn Arg Leu Ala Arg Phe Ile Asn
                85                  90                  95

Asn Cys Asp Phe Phe Pro Thr Arg Glu Glu Phe His Gly Tyr Leu Glu
            100                 105                 110

Trp Ala Ala Ala Thr Phe Ala Asp Gln Val Thr Tyr Gly Ala Thr Ile
        115                 120                 125

Thr Ser Ile Ser Val Pro Pro Asp Ser Gly Pro Gly Asp Pro Ile Asp
    130                 135                 140

Arg Val Arg Val His Leu Ala Ser Gly Pro Thr Gly Thr Glu Ser Ser
145                 150                 155                 160

Ser Val Glu Ala Arg Asn Val Val Leu Gly Thr Gly Leu Val Pro Arg
                165                 170                 175

Phe Pro Ala Gly Leu Thr Ser Asp Asp Arg Val Trp His Ser Ser Glu
            180                 185                 190

Phe Leu Gly Lys Phe Gln Arg Cys Asp Thr Thr Lys Leu Lys Arg Val
        195                 200                 205

Leu Val Val Gly Gly Gly Gln Ser Ala Ala Glu Ile Ala His Phe Val
    210                 215                 220

Tyr Glu Asn Val Pro Gly Ala Thr Val Thr Ala Val Ile Pro Ser Tyr
225                 230                 235                 240

Gly Tyr Ser Ile Ala Asp Ala Thr Pro Phe Ala Asn Arg Val Phe Asp
                245                 250                 255

Pro Ser Ala Ile Asp Asp Tyr Tyr Tyr Gly Asp Glu Asn Ser Lys Asp
            260                 265                 270

Ala Phe Trp Arg Tyr His Arg Asn Thr Asn Tyr Ala Val Val Asp Ser
        275                 280                 285

Asp Leu Ile Ser Asp Leu Asn Arg Lys Ala Tyr Asp Glu Ala Val Thr
    290                 295                 300

Gly Glu Thr Arg Leu Arg Phe Ala Glu Leu Ser Arg Leu Ser Gly Val
305                 310                 315                 320

Arg Arg Arg Asp Asp Gly Val Val Val Ser Ile His Ser Met Leu Ser
                325                 330                 335

Asn Arg Thr Ser Glu Val Asp Ala Asp Ile Val Ile Cys Ala Thr Gly
            340                 345                 350

Tyr Glu Pro Met Glu Ile Gly Asp Met Leu Gly Pro Leu Asp Arg Phe
        355                 360                 365

Cys Ile Arg Asp Glu Gln Gly Arg Tyr Arg Val Glu Arg Asp Tyr Arg
    370                 375                 380
```

Leu Ala Thr Thr Glu His Leu Arg Cys Gly Ile Tyr Leu Gln Gly Gly
385 390 395 400

Met Glu His Thr His Gly Leu Ser Ser Ser Leu Leu Ser Asn Leu Ala
405 410 415

Val Arg Asn Gly Asp Ile Ser Thr Ser Val Ala Arg Arg Ala Gln Ser
420 425 430

Gln Pro His Asp Asp Gly Arg Val Leu Gln Gly Leu Val Pro Thr Gly
435 440 445

Ser

<210> SEQ ID NO 38
<211> LENGTH: 449
<212> TYPE: PRT
<213> ORGANISM: Salinispora arenicola

<400> SEQUENCE: 38

Val Phe Asp Glu Pro Ser Val Tyr Asp Val Leu Gly Ile Gly Phe Gly
1 5 10 15

Pro Ser Asn Leu Ser Leu Ala Ile Ala Leu His Glu Met Gly Asp Val
20 25 30

Glu Gly Arg Pro Leu Ala Ala Arg Phe Phe Glu Gln Gln Pro Ser Phe
35 40 45

Gly Trp His Arg Asn Met Leu Leu Pro Ser Ala Lys Met Gln Val Ser
50 55 60

Phe Leu Lys Asp Leu Val Thr Phe Arg Asn Pro His Ser Arg Phe Thr
65 70 75 80

Phe Val Ser Tyr Leu His Glu Met Asn Arg Leu Ala Arg Phe Ile Asn
85 90 95

Asn Cys Asp Phe Phe Pro Thr Arg Glu Glu Phe His Gly Tyr Leu Glu
100 105 110

Trp Ala Ala Ala Thr Phe Ala Asp Gln Val Thr Tyr Gly Ala Thr Ile
115 120 125

Thr Ser Ile Ser Val Pro Pro Asp Ser Gly Pro Gly Asp Pro Ile Asp
130 135 140

Arg Val Arg Val His Leu Ala Ser Gly Pro Thr Gly Thr Glu Ser Ser
145 150 155 160

Ser Val Glu Ala Arg Asn Val Val Leu Gly Thr Gly Leu Val Pro Arg
165 170 175

Phe Pro Ala Gly Leu Thr Ser Asp Asp Arg Val Trp His Ser Ser Glu
180 185 190

Phe Leu Gly Lys Phe Gln Arg Cys Asp Thr Thr Lys Leu Lys Arg Val
195 200 205

Leu Val Val Gly Gly Gly Gln Ser Ala Ala Glu Ile Ala His Phe Val
210 215 220

Tyr Glu Asn Val Pro Gly Ala Thr Val Thr Ala Val Ile Pro Ser Tyr
225 230 235 240

Gly Tyr Ser Ile Ala Asp Ala Thr Pro Phe Ala Asn Arg Val Phe Asp
245 250 255

Pro Ser Ala Ile Asp Asp Tyr Tyr Tyr Gly Asp Glu Asn Ser Lys Asp
260 265 270

Ala Phe Trp Arg Tyr His Arg Asn Thr Asn Tyr Ala Val Val Asp Ser
275 280 285

Asp Leu Ile Ser Asp Leu Asn Arg Lys Ala Tyr Asp Glu Ala Val Thr
290 295 300

-continued

```
Gly Glu Thr Arg Leu Arg Phe Ala Glu Leu Ser Arg Leu Ser Gly Val
305                 310                 315                 320

Arg Arg Arg Asp Asp Gly Val Val Val Ser Ile His Ser Met Leu Ser
                325                 330                 335

Asn Arg Thr Ser Glu Val Asp Ala Asp Ile Val Ile Cys Ala Thr Gly
            340                 345                 350

Tyr Glu Pro Met Glu Ile Gly Asp Met Leu Gly Pro Leu Asp Arg Phe
        355                 360                 365

Cys Ile Arg Asp Glu Gln Gly Arg Tyr Arg Val Glu Arg Asp Tyr Arg
    370                 375                 380

Leu Ala Thr Thr Glu His Leu Arg Cys Gly Ile Tyr Leu Gln Gly Gly
385                 390                 395                 400

Met Glu His Thr His Gly Leu Ser Ser Ser Leu Leu Ser Asn Leu Ala
                405                 410                 415

Val Arg Asn Gly Asp Ile Ser Thr Ser Val Ala Arg Arg Ala Gln Ser
            420                 425                 430

Gln Pro His Asp Asp Gly Arg Val Leu Gln Gly Leu Val Pro Thr Gly
        435                 440                 445

Ser


<210> SEQ ID NO 39
<211> LENGTH: 456
<212> TYPE: PRT
<213> ORGANISM: Salinispora tropica

<400> SEQUENCE: 39

Val Thr Gly Lys Val His Ile Val Phe Asp Glu Pro Ser Val Tyr Asp
1               5                   10                  15

Val Leu Gly Ile Gly Phe Gly Pro Ser Asn Leu Ser Leu Ala Ile Ala
            20                  25                  30

Leu His Glu Met Gly Asp Val Glu Gly Arg Pro Leu Ala Ala Arg Phe
        35                  40                  45

Phe Glu Gln Gln Pro Ser Phe Gly Trp His Arg Asn Met Leu Leu Pro
    50                  55                  60

Ser Ala Lys Met Gln Val Ser Phe Leu Lys Asp Leu Val Thr Phe Arg
65                  70                  75                  80

Asn Pro His Ser Arg Phe Thr Phe Val Ser Tyr Leu His Glu Met Asn
                85                  90                  95

Arg Leu Ala Arg Phe Val Asn Asn Cys Asp Phe Phe Pro Thr Arg Glu
            100                 105                 110

Glu Phe His Gly Tyr Leu Glu Trp Ala Ala Thr Asn Phe Ala Asp Gln
        115                 120                 125

Val Thr Tyr Gly Ala Thr Ile Thr Ser Ile Ser Val Pro Pro Asp Ser
    130                 135                 140

Gly Pro Gly Asp Pro Ile Asp Arg Val Arg Val His Leu Ala Ser Gly
145                 150                 155                 160

Pro Thr Gly Thr Glu Ser Ser Ser Val Glu Ala Arg Asn Val Val Leu
                165                 170                 175

Gly Thr Gly Leu Val Pro Arg Phe Pro Ala Gly Leu Thr Ser Asp Asp
            180                 185                 190

Arg Val Trp His Ser Ser Glu Phe Leu Gly Lys Phe Gln Arg Cys Asp
        195                 200                 205

Thr Thr Lys Leu Lys Arg Val Leu Val Val Gly Gly Gly Gln Ser Ala
    210                 215                 220
```

```
Ala Glu Ile Ala His Phe Val Tyr Glu Asn Val Pro Gly Ala Thr Val
225                 230                 235                 240

Thr Ala Val Ile Pro Ser Tyr Gly Tyr Ser Ile Ala Asp Ala Thr Pro
                245                 250                 255

Phe Ala Asn Arg Val Phe Asp Pro Ser Ala Ile Asp Asp Tyr Tyr Tyr
            260                 265                 270

Gly Asp Glu Asn Ser Arg Asp Ala Phe Trp Arg Tyr His Arg Asn Thr
        275                 280                 285

Asn Tyr Ala Val Val Asp Ser Asp Leu Ile Ser Asp Leu Asn Arg Lys
    290                 295                 300

Ala Tyr Asp Glu Ala Val Thr Gly Glu Ile Arg Leu Arg Phe Ala Glu
305                 310                 315                 320

Leu Ser Arg Leu Ser Gly Val Arg Arg Arg Asp Asp Gly Val Val Val
                325                 330                 335

Ser Ile His Ser Met Leu Ser Asn Arg Thr Ser Glu Val Asp Ala Asp
            340                 345                 350

Ile Val Ile Cys Ala Thr Gly Tyr Glu Pro Met Glu Ile Gly Asp Met
        355                 360                 365

Leu Gly Pro Leu Asp Arg Phe Cys Ile Arg Asp Glu His Gly Arg Tyr
    370                 375                 380

Arg Val Glu Arg Asp Tyr Arg Leu Ala Thr Thr Glu His Leu Arg Cys
385                 390                 395                 400

Gly Ile Tyr Leu Gln Gly Gly Met Glu His Thr His Gly Leu Ser Ser
                405                 410                 415

Ser Leu Leu Ser Asn Leu Ala Val Arg Asn Gly Asp Ile Ser Thr Ser
            420                 425                 430

Val Ala Arg Arg Ala Gln Ser Gln Pro His Gly Asp Gly Arg Val Leu
        435                 440                 445

Gln Gly Leu Val Pro Thr Gly Ser
    450                 455
```

<210> SEQ ID NO 40
<211> LENGTH: 456
<212> TYPE: PRT
<213> ORGANISM: Salinispora tropica

<400> SEQUENCE: 40

```
Val Thr Gly Lys Val His Ile Val Phe Asp Glu Pro Ser Val Tyr Asp
1               5                   10                  15

Val Leu Gly Ile Gly Phe Gly Pro Ser Asn Leu Ser Leu Ala Ile Ala
            20                  25                  30

Leu His Glu Met Gly Asp Val Glu Gly Arg Pro Leu Ala Ala Arg Phe
        35                  40                  45

Phe Glu Gln Gln Pro Ser Phe Gly Trp His Arg Asn Met Leu Leu Pro
    50                  55                  60

Ser Ala Lys Met Gln Val Ser Phe Leu Lys Asp Leu Val Thr Phe Arg
65                  70                  75                  80

Asn Pro His Ser Arg Phe Thr Phe Val Ser Tyr Leu His Glu Met Asn
                85                  90                  95

Arg Leu Ala Arg Phe Val Asn Asn Cys Asp Phe Phe Pro Thr Arg Glu
            100                 105                 110

Glu Phe His Gly Tyr Leu Glu Trp Ala Ala Thr Asn Phe Ala Asp Gln
        115                 120                 125

Val Thr Tyr Gly Ala Thr Ile Thr Ser Ile Ser Val Pro Pro Asp Ser
    130                 135                 140
```

Gly Pro Gly Asp Pro Ile Asp Arg Val Arg Val His Leu Ala Ser Gly
145 150 155 160

Pro Thr Gly Thr Glu Ser Ser Ser Val Glu Ala Arg Asn Val Val Leu
165 170 175

Gly Thr Gly Leu Val Pro Arg Phe Pro Ala Gly Leu Thr Ser Asp Asp
180 185 190

Arg Val Trp His Ser Ser Glu Phe Leu Gly Lys Phe Gln Arg Cys Asp
195 200 205

Thr Thr Lys Leu Lys Arg Val Leu Val Val Gly Gly Gly Gln Ser Ala
210 215 220

Ala Glu Ile Ala His Phe Val Tyr Glu Asn Val Pro Gly Ala Thr Val
225 230 235 240

Thr Ala Val Ile Pro Ser Tyr Gly Tyr Ser Ile Ala Asp Ala Thr Pro
245 250 255

Phe Ala Asn Arg Val Phe Asp Pro Ser Ala Ile Asp Asp Tyr Tyr Tyr
260 265 270

Gly Asp Glu Asn Ser Arg Asp Ala Phe Trp Arg Tyr His Arg Asn Thr
275 280 285

Asn Tyr Ala Val Val Asp Ser Asp Leu Ile Ser Asp Leu Asn Arg Lys
290 295 300

Ala Tyr Asp Glu Ala Val Thr Gly Glu Ile Arg Leu Arg Phe Ala Glu
305 310 315 320

Leu Ser Arg Leu Ser Gly Val Arg Arg Arg Asp Asp Gly Val Val Val
325 330 335

Ser Ile His Ser Met Leu Ser Asn Arg Thr Ser Glu Val Asp Ala Asp
340 345 350

Ile Val Ile Cys Ala Thr Gly Tyr Glu Pro Met Glu Ile Gly Asp Met
355 360 365

Leu Gly Pro Leu Asp Arg Phe Cys Ile Arg Asp Glu His Gly Arg Tyr
370 375 380

Arg Val Glu Arg Asp Tyr Arg Leu Ala Thr Thr Glu His Leu Arg Cys
385 390 395 400

Gly Ile Tyr Leu Gln Gly Gly Met Glu His Thr His Gly Leu Ser Ser
405 410 415

Ser Leu Leu Ser Asn Leu Ala Val Arg Asn Gly Asp Ile Ser Thr Ser
420 425 430

Val Ala Arg Arg Ala Gln Ser Gln Pro His Gly Asp Gly Arg Val Leu
435 440 445

Gln Gly Leu Val Pro Thr Gly Ser
450 455

<210> SEQ ID NO 41
<211> LENGTH: 456
<212> TYPE: PRT
<213> ORGANISM: Salinispora tropica

<400> SEQUENCE: 41

Val Thr Gly Lys Val His Ile Val Phe Asp Glu Pro Ser Val Tyr Asp
1 5 10 15

Val Leu Gly Ile Gly Phe Gly Pro Ser Asn Leu Ser Leu Ala Ile Ala
20 25 30

Leu His Glu Met Gly Asp Val Glu Gly Arg Pro Leu Ala Ala Arg Phe
35 40 45

Phe Glu Gln Gln Pro Ser Phe Gly Trp His Arg Asn Met Leu Leu Pro

```
    50                  55                  60

Ser Ala Lys Met Gln Val Ser Phe Leu Lys Asp Leu Val Thr Phe Arg
65                  70                  75                  80

Asn Pro His Ser Arg Phe Thr Phe Val Ser Tyr Leu His Glu Met Asn
                85                  90                  95

Arg Leu Ala Arg Phe Val Asn Asn Cys Asp Phe Phe Pro Thr Arg Glu
            100                 105                 110

Glu Phe His Gly Tyr Leu Glu Trp Ala Ala Thr Asn Phe Ala Asp Gln
        115                 120                 125

Val Thr Tyr Gly Ala Thr Ile Thr Ser Ile Ser Val Pro Pro Asp Ser
    130                 135                 140

Gly Pro Gly Asp Pro Ile Asp Arg Val Arg Val His Leu Ala Ser Gly
145                 150                 155                 160

Pro Thr Gly Thr Glu Ser Ser Ser Val Glu Ala Arg Asn Val Val Leu
                165                 170                 175

Gly Thr Gly Leu Val Pro Arg Phe Pro Ala Gly Leu Thr Ser Asp Asp
            180                 185                 190

Arg Val Trp His Ser Ser Glu Phe Leu Gly Lys Phe Gln Arg Cys Asp
        195                 200                 205

Thr Thr Lys Leu Lys Arg Val Leu Val Val Gly Gly Gly Gln Ser Ala
    210                 215                 220

Ala Glu Ile Ala His Phe Val Tyr Glu Asn Val Pro Gly Ala Thr Val
225                 230                 235                 240

Thr Ala Val Ile Pro Ser Tyr Gly Tyr Ser Ile Ala Asp Ala Thr Pro
                245                 250                 255

Phe Ala Asn Arg Val Phe Asp Pro Ser Ala Ile Asp Asp Tyr Tyr Tyr
            260                 265                 270

Gly Asp Glu Asn Ser Arg Asp Ala Phe Trp Arg Tyr His Arg Asn Thr
        275                 280                 285

Asn Tyr Ala Val Val Asp Ser Asp Leu Ile Ser Asp Leu Asn Arg Lys
    290                 295                 300

Ala Tyr Asp Glu Ala Val Thr Gly Glu Thr Arg Leu Arg Phe Ala Glu
305                 310                 315                 320

Leu Ser Arg Leu Ser Gly Val Arg Arg Arg Asp Asp Gly Val Val Val
                325                 330                 335

Ser Ile His Ser Met Leu Ser Asn Arg Thr Ser Glu Val Asp Ala Asp
            340                 345                 350

Ile Val Ile Cys Ala Thr Gly Tyr Glu Pro Met Glu Ile Gly Asp Met
        355                 360                 365

Leu Gly Pro Leu Asp Arg Phe Cys Ile Arg Asp Glu His Gly Arg Tyr
    370                 375                 380

Arg Val Glu Arg Asp Tyr Arg Leu Ala Thr Thr Glu His Leu Arg Cys
385                 390                 395                 400

Gly Ile Tyr Leu Gln Gly Gly Met Glu His Thr His Gly Leu Ser Ser
                405                 410                 415

Ser Leu Leu Ser Asn Leu Ala Val Arg Asn Gly Asp Ile Ser Thr Ser
            420                 425                 430

Val Ala Arg Arg Ala Gln Ser Gln Pro His Gly Asp Gly Arg Val Leu
        435                 440                 445

Gln Gly Leu Val Pro Thr Gly Ser
    450                 455
```

<210> SEQ ID NO 42

-continued

<211> LENGTH: 42
<212> TYPE: PRT
<213> ORGANISM: Streptomyces sp. PsTaAH-137

<400> SEQUENCE: 42

```
Met Asp Thr Pro Gly Ser Leu Ser Gln Glu Ile Tyr Asp Val Val Gly
1               5                   10                  15

Ile Gly Phe Gly Pro Ser Asn Leu Ser Leu Ala Val Ala Leu Glu Glu
            20                  25                  30

Gln Gly Ala Ser Ser Ala Gln His Pro Val
        35                  40
```

<210> SEQ ID NO 43
<211> LENGTH: 447
<212> TYPE: PRT
<213> ORGANISM: Salinispora arenicola

<400> SEQUENCE: 43

```
Met Ser Asn Gln His Glu Thr Tyr Asp Leu Val Gly Ile Gly Phe Gly
1               5                   10                  15

Pro Ser Asn Leu Ser Leu Ala Ile Ala Leu Lys Glu Tyr Glu Ala Asn
            20                  25                  30

Gly Gln Glu Asn Gly Ile Ser Thr Leu Phe Phe Glu Arg Gln Ser Ser
        35                  40                  45

Phe Gly Trp His Arg Asn Met Leu Leu Pro Ser Thr Thr Met Gln Ile
    50                  55                  60

Ser Phe Leu Lys Asp Leu Val Thr Phe Arg Asn Pro Thr Ser Gly Phe
65                  70                  75                  80

Ser Phe Ile Ser Tyr Leu His Ala Ser Gly Arg Leu Pro Gln Phe Val
                85                  90                  95

Asn Asn Gln Asp Phe Phe Pro Thr Arg Gln Glu Phe His Gln Tyr Leu
            100                 105                 110

Glu Trp Ala Glu Glu Arg Met Ala Gly Arg Val Ala Tyr Gly Ser Glu
        115                 120                 125

Val Thr Ser Ile Arg Leu Pro Ser Gly Thr Val Pro Glu Leu Ser Asp
    130                 135                 140

Arg Leu Arg Leu Glu Val Thr Asp Ala Ala Gly Arg Val Gly Arg Val
145                 150                 155                 160

Val Glu Ala Arg Asn Val Val Ile Ser Thr Gly Leu Val Pro Arg Met
                165                 170                 175

Pro Glu Gly Ile Glu Arg Asp Glu Arg Val Trp His Ser Ser Glu Phe
            180                 185                 190

Leu Gln Lys Tyr Arg Arg Met Asn Pro Gly Asp Leu Arg Arg Val Ala
        195                 200                 205

Val Val Gly Ala Gly Gln Ser Ala Ala Glu Ile Thr Arg Phe Leu His
    210                 215                 220

Asp Glu Leu Pro His Ala Glu Val Trp Val Val Ile Pro Ser Tyr Gly
225                 230                 235                 240

Tyr Ser Val Ala Asp Asp Thr Pro Phe Ala Asn Gln Ile Phe Asp Pro
                245                 250                 255

Glu Ala Val Asp Asp Tyr Tyr Phe Gly Thr Glu Gln Thr Arg Asp Ala
            260                 265                 270

Phe Trp Arg Tyr His Arg Asn Thr Asn Tyr Ser Val Val Asp Asp Glu
        275                 280                 285

Val Ile Arg Asp Leu Tyr Arg Arg Val Tyr Asp Ala Glu Val Arg Gly
    290                 295                 300
```

```
Ile Lys Arg Leu Gln Ile Leu Asn Leu Thr Arg Ile Thr Gly Val Lys
305                 310                 315                 320

Arg Ala Ala Ala Glu Thr Arg Val Glu Leu Gln Val Gly Pro Asp Ser
                325                 330                 335

Glu Val Arg Glu Leu Asp Val Asp Ala Leu Val Cys Ala Thr Gly Tyr
            340                 345                 350

Asp Gly Met Glu Pro Thr His Leu Leu Gly Asp Leu Asp Arg Leu Cys
        355                 360                 365

Leu Arg Asp Lys Ala Gly Arg His Gln Ile Glu Arg Asp Tyr Arg Ile
    370                 375                 380

Ala Thr Ala Pro Glu Met Arg Cys Gly Ile Tyr Leu Gln Gly Gly Thr
385                 390                 395                 400

Glu His Thr His Gly Leu Ser Ser Ser Leu Leu Ser Asn Ile Ala Val
                405                 410                 415

Arg Ser Gly Glu Ile Ala Asp Ser Ile Val Ser Arg Arg Ala Arg His
            420                 425                 430

Asn Ser Glu Tyr Ala Leu Ala Ala Gly Ala Glu Gly Asp Thr Cys
        435                 440                 445


<210> SEQ ID NO 44
<211> LENGTH: 447
<212> TYPE: PRT
<213> ORGANISM: Salinispora arenicola

<400> SEQUENCE: 44

Met Ser Asn Gln His Glu Thr Tyr Asp Leu Val Gly Ile Gly Phe Gly
1               5                   10                  15

Pro Ser Asn Leu Ser Leu Ala Ile Ala Leu Lys Glu Tyr Glu Ala Asn
            20                  25                  30

Gly Gln Glu Asn Gly Ile Ser Thr Leu Phe Phe Glu Arg Gln Ser Ser
        35                  40                  45

Phe Gly Trp His Arg Asn Met Leu Leu Pro Ser Thr Thr Met Gln Ile
    50                  55                  60

Ser Phe Leu Lys Asp Leu Val Thr Phe Arg Asn Pro Thr Ser Gly Phe
65                  70                  75                  80

Ser Phe Ile Ser Tyr Leu His Ala Ser Gly Arg Leu Pro Gln Phe Val
                85                  90                  95

Asn Asn Gln Asp Phe Phe Pro Thr Arg Gln Glu Phe His Gln Tyr Leu
            100                 105                 110

Glu Trp Ala Glu Glu Arg Met Ala Gly Arg Val Ala Tyr Gly Ser Glu
        115                 120                 125

Val Thr Ser Ile Arg Leu Pro Ser Gly Thr Val Pro Glu Leu Ser Asp
    130                 135                 140

Arg Leu Arg Leu Glu Val Thr Asp Ala Ala Gly Arg Val Gly Arg Val
145                 150                 155                 160

Val Glu Ala Arg Asn Val Val Ile Ser Thr Gly Leu Val Pro Arg Met
                165                 170                 175

Pro Glu Gly Ile Glu Arg Asp Glu Arg Val Trp His Ser Ser Glu Phe
            180                 185                 190

Leu Gln Lys Tyr Arg Arg Met Asn Pro Gly Asp Leu Arg Arg Val Ala
        195                 200                 205

Val Val Gly Ala Gly Gln Ser Ala Ala Glu Ile Thr Arg Phe Leu His
    210                 215                 220

Asp Glu Leu Pro His Ala Glu Val Trp Val Val Ile Pro Ser Tyr Gly
```

```
225                 230                 235                 240

Tyr Ser Val Ala Asp Asp Thr Pro Phe Ala Asn Gln Ile Phe Asp Pro
                245                 250                 255

Glu Ala Val Asp Asp Tyr Tyr Phe Gly Thr Glu Gln Thr Arg Asp Ala
            260                 265                 270

Phe Trp Arg Tyr His Arg Asn Thr Asn Tyr Ser Val Val Asp Asp Glu
        275                 280                 285

Val Ile Arg Asp Leu Tyr Arg Arg Val Tyr Asp Ala Glu Val Arg Gly
    290                 295                 300

Ile Lys Arg Leu Gln Ile Leu Asn Leu Thr Arg Ile Thr Gly Val Lys
305                 310                 315                 320

Arg Ala Ala Ala Glu Thr Arg Val Glu Leu Gln Val Gly Pro Asp Ser
                325                 330                 335

Glu Val Arg Glu Leu Asp Val Asp Ala Leu Val Cys Ala Thr Gly Tyr
            340                 345                 350

Asp Gly Met Glu Pro Thr His Leu Leu Gly Asp Leu Asp Arg Leu Cys
        355                 360                 365

Leu Arg Asp Lys Ala Gly Arg His Gln Ile Glu Arg Asp Tyr Arg Ile
    370                 375                 380

Ala Thr Ala Pro Glu Met Arg Cys Gly Ile Tyr Leu Gln Gly Gly Thr
385                 390                 395                 400

Glu His Thr His Gly Leu Ser Ser Ser Leu Leu Ser Asn Ile Ala Val
                405                 410                 415

Arg Ser Gly Glu Ile Ala Asp Ser Ile Val Ser Arg Arg Ala Arg His
            420                 425                 430

Asn Ser Glu Tyr Ala Leu Ala Ala Gly Ala Glu Gly Asp Thr Cys
        435                 440                 445


<210> SEQ ID NO 45
<211> LENGTH: 447
<212> TYPE: PRT
<213> ORGANISM: Salinispora pacifica

<400> SEQUENCE: 45

Met Ser Asn Gln His Glu Thr Tyr Asp Leu Val Gly Ile Gly Phe Gly
1               5                   10                  15

Pro Ser Asn Leu Ser Leu Ala Ile Ala Leu Lys Glu Tyr Glu Ala Asn
            20                  25                  30

Gly Gln Glu Asn Gly Ile Ser Thr Leu Phe Phe Glu Arg Gln Ser Ser
        35                  40                  45

Phe Gly Trp His Arg Asn Met Leu Leu Pro Ser Thr Thr Met Gln Ile
    50                  55                  60

Ser Phe Leu Lys Asp Leu Val Thr Phe Arg Asn Pro Thr Ser Gly Phe
65                  70                  75                  80

Ser Phe Ile Ser Tyr Leu His Ala Ser Gly Arg Leu Pro Gln Phe Val
                85                  90                  95

Asn Asn Gln Asp Phe Phe Pro Thr Arg Gln Glu Phe His Gln Tyr Leu
            100                 105                 110

Glu Trp Ala Glu Glu Arg Met Ala Gly Arg Val Ala Tyr Cys Ser Glu
        115                 120                 125

Val Thr Ser Ile Arg Leu Pro Ser Gly Thr Val Pro Glu Leu Ser Asp
    130                 135                 140

Arg Leu Arg Leu Glu Val Thr Asp Ala Ala Gly Arg Val Gly Arg Val
145                 150                 155                 160
```

-continued

Val Glu Ala Arg Asn Val Val Ile Ser Thr Gly Leu Val Pro Arg Met
165 170 175

Pro Glu Gly Ile Glu Arg Asp Glu Arg Val Trp His Ser Ser Glu Phe
180 185 190

Leu Gln Lys Tyr Arg Arg Met Asn Pro Gly Asp Leu Arg Arg Val Ala
195 200 205

Val Val Gly Ala Gly Gln Ser Ala Ala Glu Ile Thr Arg Phe Leu His
210 215 220

Asp Glu Leu Pro His Ala Glu Val Trp Val Val Ile Pro Ser Tyr Gly
225 230 235 240

Tyr Ser Val Ala Asp Asp Thr Pro Phe Ala Asn Gln Ile Phe Asp Pro
245 250 255

Glu Ala Val Asp Asp Tyr Tyr Phe Gly Thr Glu Gln Thr Arg Asp Ala
260 265 270

Phe Trp Arg Tyr His Arg Asn Thr Asn Tyr Ser Val Val Asp Asp Glu
275 280 285

Val Ile Arg Asp Leu Tyr Arg Arg Val Tyr Asp Ala Glu Val Arg Gly
290 295 300

Ile Lys Arg Leu Gln Ile Leu Asn Leu Thr Arg Ile Thr Gly Val Lys
305 310 315 320

Arg Ala Ala Ala Glu Thr Arg Val Glu Leu Gln Val Gly Pro Asp Ser
325 330 335

Glu Val Arg Glu Leu Asp Val Asp Ala Leu Val Cys Ala Thr Gly Tyr
340 345 350

Asp Gly Met Glu Pro Thr His Leu Leu Gly Asp Leu Asp Arg Leu Cys
355 360 365

Leu Arg Asp Lys Ala Gly Arg His Gln Ile Glu Arg Asp Tyr Arg Ile
370 375 380

Ala Thr Ala Pro Glu Met Arg Cys Gly Ile Tyr Leu Gln Gly Gly Thr
385 390 395 400

Glu His Thr His Gly Leu Ser Ser Ser Leu Leu Ser Asn Ile Ala Val
405 410 415

Arg Ser Gly Glu Ile Ala Asp Ser Ile Val Ser Arg Arg Ala Arg His
420 425 430

Asn Ser Glu Tyr Ala Leu Ala Ala Gly Ala Glu Gly Asp Thr Cys
435 440 445

<210> SEQ ID NO 46
<211> LENGTH: 432
<212> TYPE: PRT
<213> ORGANISM: Actinomadura atramentaria

<400> SEQUENCE: 46

Val Thr Gly Pro Ala Thr Asp Ala Asp Asp Ile Leu Asp Ile Val Gly
1 5 10 15

Val Gly Phe Gly Pro Ser Asn Leu Ala Leu Ala Val Ala Val Arg Glu
20 25 30

His Asn Ala Asp Arg Pro Ala Ala Glu His Leu Thr Gln Val Tyr Phe
35 40 45

Glu Lys Gln Pro Ala Phe Gly Trp His Arg Gly Met Leu Ile Asp Gly
50 55 60

Ala Thr Met Gln Val Ser Phe Ile Lys Asp Leu Val Thr Met Arg Asn
65 70 75 80

Pro Ala Ser Glu Tyr Gly Phe Leu Ser Tyr Leu His Asp Asn Asp Arg
85 90 95

```
Leu Ala Asp Phe Ile Asn His Lys Ser Leu Phe Pro Ser Arg Val Glu
            100                 105                 110

Phe His Asp Tyr Leu Glu Trp Val Ala Arg Arg Phe Gln Asp Val Ala
        115                 120                 125

Arg Tyr Gly Ser Glu Val Val Ala Met Arg Pro Gly Pro Gly Gly Asp
    130                 135                 140

His Ile Glu Val Ile Val Arg Arg Gly Gly Glu His Arg Val Gln Arg
145                 150                 155                 160

Ala Arg Asn Val Val Val Ala Val Gly Gln Glu Pro Ala Leu Pro Asp
                165                 170                 175

Asp Ile Glu Leu Gly Asp Arg Ile Trp His Cys Ala Gln Leu Leu Glu
            180                 185                 190

Arg Val Glu Arg Leu Thr Glu Glu Pro Arg Arg Ala Val Val Val Gly
        195                 200                 205

Ala Gly Gln Ser Ala Ala Glu Thr Thr Glu Phe Leu His Arg Arg Phe
    210                 215                 220

Glu Asn Ala Glu Val Ser Ala Ile Phe Leu Arg Tyr Gly Tyr Ser Val
225                 230                 235                 240

Ala Asp Asp Thr Pro Phe Ala Asn Arg Ile Phe Asp Pro Glu Ser Val
                245                 250                 255

Asp Val Phe Tyr Gly Ala Pro Glu Asn Val Lys Arg Met Leu Phe Asp
            260                 265                 270

Tyr His Arg Asn Thr Asn Tyr Ser Val Val Asp Gln Glu Leu Ala Asp
        275                 280                 285

Glu Leu Tyr Arg Arg Val Tyr Gln Glu Arg Val Arg Gly Val Glu Arg
    290                 295                 300

Leu Arg Ile Leu Asn Ala Ser Arg Leu His Ala Val Arg Arg Asp Val
305                 310                 315                 320

Thr Gly Asp Gly Leu Arg Val Asp Val Glu His Leu Pro Thr Gly Glu
                325                 330                 335

Lys Arg Ser Phe Gly Val Asp Leu Val Val Tyr Ala Thr Gly Tyr Arg
            340                 345                 350

Pro Ile Asp Pro Ala Asn Val Leu Gly Glu Val Ala Glu Tyr Cys Arg
        355                 360                 365

Arg Asp Ala Gly Lys Arg Pro Ala Ile Thr Arg Asp Tyr Arg Leu Glu
    370                 375                 380

Thr Asp Asp Arg Leu Arg Ala Gly Ile Tyr Leu Gln Gly Gly Thr Glu
385                 390                 395                 400

Gln Thr His Gly Ile Ser Ala Gln Leu Leu Ser Asn Thr Ala Val Arg
                405                 410                 415

Ala Gly Glu Ile Val Arg Ser Ile Ala Gly Ala Arg Val Gly Ala Val
            420                 425                 430
```

<210> SEQ ID NO 47
<211> LENGTH: 431
<212> TYPE: PRT
<213> ORGANISM: Streptomyces drozdowiczii

<400> SEQUENCE: 47

```
Met Thr Val Asn Leu Gly Ser Thr Ser Val Leu Glu Val Ala Gly Ile
1               5                   10                  15

Gly Phe Gly Pro Ser Asn Met Ala Leu Ala Ile Ala Leu Glu Glu Met
            20                  25                  30

His Gly Ala Arg Ala Asn Ser Pro Gly Pro Ala Met Glu Phe Phe Glu
```

```
        35                  40                  45

Lys Gln Pro Ala Phe Gly Trp His Arg Gly Met Leu Met Glu Asp Ala
    50                  55                  60

Thr Met Gln Val Ser Phe Leu Lys Asp Leu Ala Thr Met Arg Asp Pro
65                  70                  75                  80

Gln Ser Arg Tyr Thr Phe Met Ala Tyr Leu Lys Ala Lys Gly Arg Ile
                85                  90                  95

Ala Arg Phe Ile Asn Ser Lys Thr Leu Phe Pro Leu Arg Val Glu Phe
            100                 105                 110

His Asp Tyr Leu Glu Trp Val Ala Asp Leu Leu Ala Pro Val Val Ser
        115                 120                 125

Tyr Gly Ser Asp Val Leu Ala Ile Arg Pro Val Val Glu Asp Gly Val
    130                 135                 140

Met Glu Cys Leu Asp Val Val Val Arg Thr Ser Ala Gly Asp Gly Glu
145                 150                 155                 160

Pro Ile Val Arg Arg Ala Arg Asn Val Val Ile Gly Thr Gly Leu Thr
                165                 170                 175

Pro Arg Leu Pro Asp Gly Thr Glu Glu Ser Ala Arg Val Trp His Ser
            180                 185                 190

Ser Arg Leu Met Asp Arg Ala Ala Ser Ile Ala Ala Ala Pro Arg Gly
        195                 200                 205

Phe Val Val Val Gly Ala Gly Gln Ser Ala Ala Glu Ala Thr Glu Tyr
    210                 215                 220

Leu His Arg Ser Phe Pro Gly Thr Pro Val Ser Ala Val Phe Ala Arg
225                 230                 235                 240

Tyr Gly Tyr Ser Val Ala Asp Asp Ser Pro Phe Thr Asn Gly Ile Phe
                245                 250                 255

Asp Pro Glu Ala Val Asp Glu Phe Tyr Ala Ala Ser Arg Asp Val Lys
            260                 265                 270

Gln Asp Leu Leu Asp Tyr His Gly Asn Thr Asn Tyr Ala Val Val Asp
        275                 280                 285

Leu Ser Leu Thr Glu Glu Leu Tyr Arg Arg Ala Tyr Gln Glu Glu Val
    290                 295                 300

Leu Gly Arg Glu Arg Leu Arg Phe His Asn Ala Ser Arg Val Leu Lys
305                 310                 315                 320

Val Glu Glu His Pro Asp Arg Val Arg Val Thr Val Glu His Leu Pro
                325                 330                 335

Asp Arg Thr Val Glu Thr Leu Asp Ala Asp Ala Val Val Tyr Ala Thr
            340                 345                 350

Gly Tyr Arg Pro Ser Asp Pro Thr Pro Leu Leu Gln Asn Leu Leu Pro
        355                 360                 365

Glu Cys Lys Leu Asp Asp Ala Gly Arg Ile Thr Leu Asp Arg Asp Tyr
    370                 375                 380

Arg Ile Val Thr Ser Gly Asp Val Arg Cys Gly Ile Tyr Leu His Gly
385                 390                 395                 400

Ala Ser Ala Glu Cys Thr His Gly Leu Ser Ala Gly Leu Leu Ser Asn
                405                 410                 415

Thr Ala Val Arg Ser Gly Glu Ile Ala Asp Ser Ile Ile Lys Arg
            420                 425                 430
```

<210> SEQ ID NO 48
<211> LENGTH: 448
<212> TYPE: PRT
<213> ORGANISM: Streptomyces sp. RSD-27

<400> SEQUENCE: 48

Met Gly Ile Thr Gly Arg Arg Asp Glu Glu Ile Tyr Asp Val Ile Gly
1               5                   10                  15

Ile Gly Phe Gly Pro Ser Asn Met Ser Leu Ala Ile Ala Leu Gln Glu
            20                  25                  30

His Gly Ala Gly Val Pro Leu His Pro Val Arg Ser His Phe Phe Glu
        35                  40                  45

Arg Gln Pro Thr Phe Gly Trp His Arg Asn Met Leu Leu Pro Ser Thr
    50                  55                  60

Thr Met Gln Ile Ser Phe Leu Lys Asp Leu Ala Thr Phe Arg Asn Pro
65                  70                  75                  80

Met Ser Arg Phe Ser Phe Val Ser Tyr Leu His Ala Ser Asn Arg Leu
                85                  90                  95

Val Gln Phe Val Asn Asn Gln Ser Phe Ile Pro Thr Arg Gln Glu Phe
            100                 105                 110

His Gln Tyr Leu Glu Trp Ala Ala Ala Gly Leu Arg Asp Gln Val Thr
        115                 120                 125

Tyr Gly Ala Glu Val Thr Ser Val Arg Pro Val Thr Ala Ala Gly Ser
    130                 135                 140

Arg Thr Pro Asp Leu Leu Glu Val Glu Val Arg Thr Gly Asp Glu Val
145                 150                 155                 160

Ser Val Val Thr Ala Arg Asn Val Val Val Ser Thr Gly Leu Val Pro
                165                 170                 175

Arg Met Pro Glu Gly Val Pro Ala Gly Glu Arg Val Trp His Ser Ser
            180                 185                 190

Glu Phe Leu Ala Arg Phe Asn Ala Gln Asp Pro Ala Glu Leu Lys Ser
        195                 200                 205

Val Ala Val Val Gly Ala Gly Gln Ser Ala Ala Glu Val Thr Arg Phe
    210                 215                 220

Leu Tyr Asp Ser Leu Pro His Ala Glu Val Ser Ala Val Ile Pro Ser
225                 230                 235                 240

Tyr Gly Tyr Ser Val Ala Asp Asp Thr Pro Phe Ala Asn Gln Val Phe
                245                 250                 255

Asp Pro Asp Thr Val Asp Glu Tyr Tyr Phe Gly Thr Glu Gly Ala Arg
            260                 265                 270

Asp Ala Phe Trp Arg Tyr His Arg Asn Thr Asn Tyr Ser Val Val Asp
        275                 280                 285

Ala Asp Val Ile Arg Ser Leu Tyr Gln Arg Trp Tyr Asp Glu Gln Val
    290                 295                 300

Arg Gly Val Gln Arg Leu Arg Phe Arg Asn Leu Thr Arg Val Asp Gly
305                 310                 315                 320

Val Glu Gly Ser Gly Ser Gly Ala Arg Met Val Leu Arg Ser Leu Leu
                325                 330                 335

Asp Asp Ser Arg Glu Glu Leu Ala Val Asp Ala Val Val Phe Ala Ser
            340                 345                 350

Gly Tyr Asp Gly Leu Asp Pro Ala Arg Leu Leu Gly Glu Asp Phe Asp
        355                 360                 365

Arg His Phe Gln Arg Asp Ala Ala Gly Arg His Arg Val Glu Arg Asp
    370                 375                 380

Tyr Arg Leu Val Ser Thr Ser Gly Leu Thr Cys Gly Val Tyr Leu Gln
385                 390                 395                 400

Gly Gly Thr Glu His Ser His Gly Leu Thr Ser Ala Leu Leu Ser Asn

-continued

```
                405                 410                 415

Ile Ala Ile Arg Ser Gly Glu Ile Ala Asp Ser Ile Val Leu Arg Arg
            420                 425                 430

Thr Glu Arg Glu Leu Gly Arg His Ala Glu Glu Ala Pro Ser Ala Ala
        435                 440                 445


<210> SEQ ID NO 49
<211> LENGTH: 434
<212> TYPE: PRT
<213> ORGANISM: Actinoalloteichus spitiensis

<400> SEQUENCE: 49

Met Asp Gly Ser Phe Pro Val Asp Gly Asn Gln Val Ser Asp Val Val
1               5                   10                  15

Gly Val Gly Phe Gly Pro Ser Asn Leu Ala Leu Ala Val Ala Val Ala
            20                  25                  30

Glu His Asn Glu Ala Val Gly Pro Glu Glu Arg Leu Arg Ala Arg Phe
        35                  40                  45

Leu Glu Arg Gln Pro Asp Phe Gly Trp His Arg Gly Met Leu Leu Pro
    50                  55                  60

Asp Thr Thr Leu Gln Val Ser Phe Leu Lys Asp Leu Val Ser Leu Arg
65                  70                  75                  80

Asn Pro Arg Ser Ser Phe Ser Phe Ile Ser Tyr Leu His Asp Arg Asn
                85                  90                  95

Arg Leu Val Asp Phe Val Asn His Gln Cys Phe Phe Pro Ser Arg Arg
            100                 105                 110

Glu Tyr His Asp Tyr Leu Glu Trp Val Ala Gly Arg Phe Val Asp Ser
        115                 120                 125

Val His Tyr Asp His Asp Val Val Asp Val Leu Pro Val His Glu Gly
    130                 135                 140

Pro Asp Val Val Ala Phe Asp Val Val Ala Val Gln Gly Gly Ala Gly
145                 150                 155                 160

Ala Thr Arg Arg Leu Arg Thr Arg Asn Val Val Leu Ala Pro Gly Leu
                165                 170                 175

Glu Pro Val Leu Pro Gln Gly Ile Thr Pro Ser Asp Arg Val Trp His
            180                 185                 190

Ser Ser Glu Leu Leu His Arg Leu Asp Gly Phe Arg Asp Arg Leu Pro
        195                 200                 205

Asp Arg Pro Arg Phe Val Val Val Gly Ala Gly Gln Ser Ala Ala Glu
    210                 215                 220

Val Met Ala His Leu His Gly Val Phe Pro Lys Ala Thr Val Arg Ser
225                 230                 235                 240

Val Cys Ser Arg Tyr Gly Phe Ala Pro Ala Asp Asp Ser Pro Phe Val
                245                 250                 255

Asn Gln Leu Phe Asp Pro Ala Ala Val Asp Glu Phe Phe Glu Ala Ala
            260                 265                 270

Leu Pro Ala Arg Glu Asn Ile Leu Arg Val His Ala Gly Thr Asn Tyr
        275                 280                 285

Ser Ala Val Asp Gly Asp Leu Ile Ser Glu Leu Tyr Arg Arg Ser Tyr
    290                 295                 300

Gln Glu Arg Val Ser Gly Glu Pro Arg Leu His Phe Glu Arg Leu Ala
305                 310                 315                 320

Arg Val Val Ala Thr Glu Glu Arg Asp Glu Glu Val Ser Val Ser Val
                325                 330                 335
```

```
Leu Ser Leu Thr Asp Gly Arg Val Thr Asp Arg Gly Cys Asp Val Val
            340                 345                 350

Val Leu Ala Thr Gly Tyr Arg Pro Arg Asp Ala Leu Arg Pro Leu Gly
        355                 360                 365

Gln Leu Ala Ala Leu Cys Lys Leu Asp Ala Asn Gly Trp Pro Arg Val
    370                 375                 380

Glu Arg Asn Tyr Arg Ile Thr Thr Thr Glu Thr Val Arg Ala Gly Ile
385                 390                 395                 400

Tyr Leu Gln Gly Gly Thr Glu His Ser His Gly Leu Ser Ser Thr Leu
                405                 410                 415

Leu Ser Asn Leu Ala Val Arg Ser Gly Glu Ile Thr Arg Ala Leu Ala
            420                 425                 430

Ala Pro


<210> SEQ ID NO 50
<211> LENGTH: 446
<212> TYPE: PRT
<213> ORGANISM: Streptomyces sp. PBH53

<400> SEQUENCE: 50

Met Thr Arg Leu Ala Gly Gln Ala Pro Thr Ala Gln His Ser Pro Glu
1               5                   10                  15

Ser Glu Val Arg Asp Val Thr Gly Ile Gly Phe Gly Ala Ala Asn Leu
            20                  25                  30

Ala Leu Ala Val Ala Leu His Glu Ser Gly Ala Gly Gly Arg Ala Leu
        35                  40                  45

Phe Leu Glu Lys Gln Lys Glu Phe Gly Trp His Arg Gly Met Leu Ile
    50                  55                  60

Glu Gly Ser Ser Leu Gln Val Ser Phe Leu Lys Asp Ile Ala Thr Met
65                  70                  75                  80

Arg Asn Pro Thr Ser Asp Phe Gly Phe Leu Ser Tyr Leu Gln Glu Lys
                85                  90                  95

Gly Arg Leu Val Asp Phe Ile Asn Gln His Thr Leu Leu Pro Ser Arg
            100                 105                 110

Ile Glu Tyr His Asp Tyr Leu Gln Trp Ala Ala Asp Arg Leu Gly His
        115                 120                 125

Met Val Glu Tyr Gly Val Glu Ala Thr Gly Val Arg Pro Val Thr Asp
    130                 135                 140

Ala Gly Glu Val Val Ala Leu Asp Val Leu Ala Gly Asp Arg Val Val
145                 150                 155                 160

Thr Arg Thr Arg Asn Leu Val Ile Ala Ser Gly Leu Arg Pro Arg Leu
                165                 170                 175

Pro Glu Gly Ala Glu Thr Gly Glu Arg Val Trp His Ser Ser Gln Leu
            180                 185                 190

Leu His Arg Leu Pro Ala Phe Asp Glu Arg Pro Pro Arg Arg Ala Val
        195                 200                 205

Val Val Gly Ala Gly Gln Ser Ala Ala Glu Val Ala Ala His Leu Met
    210                 215                 220

Glu Arg Tyr Pro Gln Ala Glu Val Cys Ala Val Phe Ser Arg Tyr Gly
225                 230                 235                 240

Tyr Ser Val Ala Asp Ser Ser Pro Phe Ala Asn Arg Val Phe Asp Pro
                245                 250                 255

Ala Ala Val Asp Asp Phe Tyr Phe Ala Pro Pro Glu Val Lys Gln Ala
            260                 265                 270
```

```
Ile Met Arg Tyr His Gly Gly Thr Asn Tyr Ala Val Val Asp Glu Asp
        275                 280                 285

Val Leu Gln Gly Leu Tyr Arg Arg Gln Tyr Glu Gln Lys Val Thr Gly
    290                 295                 300

Thr Pro Arg Leu Arg Val Met Asn Ala Ser Arg Leu Val Ser Val Glu
305                 310                 315                 320

Pro Arg Gly Glu Thr Ala Ala Val Arg Val Glu Phe Leu Pro Thr Gly
                325                 330                 335

Glu His Ala Asp Leu Asp Ala Asp Leu Val Val Tyr Ala Thr Gly Tyr
            340                 345                 350

Arg Ser Ala Asp Pro Ala Glu Leu Leu Gly Gly Val Ala Gly Ser Leu
        355                 360                 365

Arg Arg Asp Ala Ala Gly Gln Val Leu Ile Gly Arg Asp Tyr Arg Leu
    370                 375                 380

Ser Thr Thr Gly Asp Phe Arg Cys Gly Ile Tyr Val Gln Gly Ala Thr
385                 390                 395                 400

Glu Ala Thr His Gly Ile Ala Ser Thr Leu Leu Ser Met Val Ala Val
                405                 410                 415

Arg Ala Gly Glu Ile Ala Gln Ser Ile Ile Gly Gly Arg Arg Asp Pro
            420                 425                 430

Asp Arg Thr Ala Gly Thr Lys Ala Val Ala Gly Asn Arg Gly
        435                 440                 445
```

<210> SEQ ID NO 51
<211> LENGTH: 447
<212> TYPE: PRT
<213> ORGANISM: Salinispora arenicola

<400> SEQUENCE: 51

```
Met Ser Asn Gln His Glu Thr Tyr Asp Leu Val Gly Ile Gly Phe Gly
1               5                   10                  15

Pro Ser Asn Leu Ser Leu Ala Ile Ala Leu Lys Glu Tyr Glu Ala Asn
            20                  25                  30

Gly Gln Glu Asn Gly Ile Ser Thr Leu Phe Phe Glu Arg Gln Ser Ser
        35                  40                  45

Phe Gly Trp His Arg Asn Met Leu Leu Pro Ser Thr Thr Met Gln Ile
    50                  55                  60

Ser Phe Leu Lys Asp Leu Val Thr Phe Arg Asn Pro Thr Ser Gly Phe
65                  70                  75                  80

Ser Phe Ile Ser Tyr Leu His Ala Ser Gly Arg Leu Pro Gln Phe Val
                85                  90                  95

Asn Asn Gln Asp Phe Phe Pro Thr Arg Gln Glu Phe His Gln Tyr Leu
            100                 105                 110

Glu Trp Ala Glu Glu Arg Met Ala Gly Arg Val Ala Tyr Gly Ser Glu
        115                 120                 125

Val Thr Ser Ile Arg Leu Pro Ser Gly Thr Val Pro Glu Leu Ser Asp
    130                 135                 140

Arg Leu Arg Leu Glu Val Thr Asp Ala Ala Gly Arg Val Gly Arg Val
145                 150                 155                 160

Val Glu Ala Arg Asn Val Val Ile Ser Thr Gly Leu Val Pro Arg Met
                165                 170                 175

Pro Glu Gly Ile Glu Arg Asp Glu Arg Val Trp His Ser Ser Glu Phe
            180                 185                 190

Leu Gln Lys Tyr Arg Arg Met Asn Pro Gly Asp Leu Arg Arg Val Ala
        195                 200                 205
```

Val Val Gly Ala Gly Gln Ser Ala Ala Glu Ile Thr Arg Phe Leu His
210 215 220

Asp Glu Leu Pro His Ala Glu Val Trp Val Val Ile Pro Ser Tyr Gly
225 230 235 240

Tyr Ser Val Ala Asp Asp Thr Pro Phe Ala Asn Gln Ile Phe Asp Pro
245 250 255

Glu Ala Val Asp Asp Tyr Tyr Phe Gly Thr Glu Gln Thr Arg Asp Ala
260 265 270

Phe Trp Arg Tyr His Arg Asn Thr Asn Tyr Ser Val Val Asp Asp Glu
275 280 285

Val Ile Arg Asp Leu Tyr Arg Arg Val Tyr Asp Ala Glu Val Arg Gly
290 295 300

Ile Lys Arg Leu Gln Ile Leu Asn Leu Thr Arg Ile Thr Gly Val Lys
305 310 315 320

Arg Ala Ala Ala Glu Thr Arg Val Glu Leu Gln Val Gly Pro Asp Ser
325 330 335

Glu Val Arg Glu Leu Asp Val Asp Ala Leu Val Cys Ala Thr Gly Tyr
340 345 350

Asp Gly Met Glu Pro Thr His Leu Leu Gly Asp Leu Asp Arg Leu Cys
355 360 365

Leu Arg Asp Lys Ala Gly Arg His Gln Ile Glu Arg Asp Tyr Arg Ile
370 375 380

Ala Thr Ala Pro Glu Met Arg Cys Gly Ile Tyr Leu Gln Gly Gly Thr
385 390 395 400

Glu His Thr His Gly Leu Ser Ser Ser Leu Leu Ser Asn Ile Ala Val
405 410 415

Arg Ser Gly Glu Ile Ala Asp Ser Ile Val Ser Arg Arg Ala Arg His
420 425 430

Asn Ser Glu Tyr Ala Leu Ala Ala Gly Ala Glu Gly Asp Thr Cys
435 440 445

<210> SEQ ID NO 52
<211> LENGTH: 431
<212> TYPE: PRT
<213> ORGANISM: Streptomyces sp. MNU77

<400> SEQUENCE: 52

Val Glu Ala Ser Ala Ser Val Thr Asp Val Val Gly Val Gly Phe Gly
1 5 10 15

Pro Ala Asn Leu Ala Leu Ala Ile Ala Leu Arg Glu Leu Gly Ala Gly
20 25 30

Pro Pro Gly Gly Asp Gly Leu Thr Ala Ala Phe Leu Glu Ala Gln Pro
35 40 45

Gln Phe Gly Trp His Ser Gly Met Leu Ile Glu Asp Ser Thr Met Gln
50 55 60

Val Ser Phe Leu Lys Asp Leu Val Thr Pro Arg Asn Pro Val Ser Pro
65 70 75 80

Phe Ser Phe Val Ala Tyr Leu His Ala Val Gly Arg Leu Gly Arg Phe
85 90 95

Met Asp Ser Lys Met Met Tyr Pro Leu Arg Ile Glu Phe His Asn Tyr
100 105 110

Leu Glu Trp Val Ala Gly His Phe Ala Asn Gln Val Ala Tyr Ser Arg
115 120 125

Arg Val Thr Ala Leu Arg Pro Val His Gly Gln Asp Gly Val Glu Ala 130 135 140

Leu Asp Val Val Ala Arg Asp Ala Asp Gly Thr Glu Arg Val Leu Arg
145 150 155 160

Ala Arg Ser Val Val Leu Ala Cys Gly Leu Arg Pro Arg Leu Pro Glu
165 170 175

Gly Leu Thr Gly Ser Asp Arg Val Trp His Thr Ala Asp Leu Leu Pro
180 185 190

Arg Ala Arg Arg Leu Leu Glu Ser Gly Ala Ala Pro Thr Ser Phe Val
195 200 205

Val Leu Gly Ala Gly Gln Ser Ser Ala Glu Ala Ala His Tyr Leu His
210 215 220

Arg Thr Phe Thr Arg Ser Ser Val Ser Val Val His Ser Arg Tyr Gly
225 230 235 240

Phe Ser Val Ser Asp Asp Ser Pro Phe Ala Asn Ala Val Phe Gly Ala
245 250 255

Lys Ala Val Asp Glu Phe Tyr Gly Ala Pro Asp Glu Val Lys Arg Met
260 265 270

Val Leu Asp Tyr His Ala Asn Thr Asn Tyr Ala Val Val Asp Glu Asp
275 280 285

Leu Ile His Arg Leu Tyr Gly Asp Val Tyr Arg Glu Ser Leu Thr Gly
290 295 300

Asp Asp Arg Leu Arg Phe His His Leu Ser Arg Leu Ser Thr Val Thr
305 310 315 320

Pro Gly Glu Asp Ala Val Arg Val Glu Val Glu Ala Leu His Asp Gly
325 330 335

Arg Arg Thr Val Ile Asp Ala Asp Ala Leu Val Cys Ala Thr Gly Tyr
340 345 350

Arg Pro Ser Asp Pro Ala Asp Leu Met Gly Asp Leu Leu Pro Leu Cys
355 360 365

Ala Arg Asp Glu Gln Asp Arg Leu Val Leu Asp Arg Asp Arg Arg Leu
370 375 380

Val Thr Arg Glu Pro Leu Ala Gly Gly Val Tyr Val Thr Gly Tyr Gly
385 390 395 400

Glu His Thr His Gly Ile Ala Glu Ser Leu Leu Ser Leu Thr Ala Gln
405 410 415

Arg Ala Gly Glu Leu Thr Glu Ala Leu Ala Lys Thr Phe Val Thr
420 425 430

<210> SEQ ID NO 53
<211> LENGTH: 425
<212> TYPE: PRT
<213> ORGANISM: Micromonospora pattaloongensis

<400> SEQUENCE: 53

Met Ser Glu Thr Asp Ser Ala Thr Val Arg Gln Val Val Gly Val Gly
1 5 10 15

Phe Gly Pro Ala Asn Leu Ala Leu Ala Ile Ala Ala Gly Glu Val Ala
20 25 30

Gly Pro Asp Gly Arg Thr Leu Leu Asp Glu Cys Val Phe Leu Glu Arg
35 40 45

Gln Pro Ser Phe Gly Trp His Arg Gly Met Leu Leu Asp Gly Ala Thr
50 55 60

Met Gln Val Ser Phe Leu Lys Asp Leu Ala Thr Leu Arg Ser Pro Ser
65 70 75 80

```
Ser Arg Tyr Thr Phe Thr Ser Tyr Leu His Asp Val Gly Arg Leu Thr
                85                  90                  95

Asp Phe Ile Asn Ser Lys Thr Leu Tyr Pro Tyr Arg Thr Asp Phe His
            100                 105                 110

Thr Tyr Leu Glu Trp Ala Ala Asp Arg Leu Pro Ala Asp Val Arg Tyr
        115                 120                 125

Gly Thr Glu Val Val Ser Val Thr Pro Glu Arg Thr Asp Asp Val Val
    130                 135                 140

Arg Glu Leu Leu Val Arg Thr Gly Asp Gly Arg Thr Phe Arg Thr Arg
145                 150                 155                 160

Asn Leu Val Ile Gly Thr Gly Met Thr Pro Cys Phe Pro Asp Gly Val
                165                 170                 175

Gln Arg Gly Pro Arg Val Trp His Ser Ala Glu Leu Leu Thr Arg Leu
            180                 185                 190

Ala Ala Pro Ala Pro Thr Arg Pro Arg Thr Phe Ala Val Val Gly Ala
        195                 200                 205

Gly Gln Ser Ala Ala Glu Val Val Glu His Leu His Ala Thr His Pro
    210                 215                 220

Glu Ala Asp Val His Ala Ile Phe Gly Arg Phe Gly Tyr Ser Met Ser
225                 230                 235                 240

Asp Asp Ser Pro Phe Ala Asn Gln Ile Phe Asp Pro Asp Ser Val Asp
                245                 250                 255

Glu Phe Tyr His Ala Pro Gly Glu Val Arg Asp Ala Leu Met Gly Tyr
            260                 265                 270

His Ala Asn Thr Asn Tyr Ser Val Val Asp Leu Asp Leu Ile Arg Ser
        275                 280                 285

Leu His Gly Thr Ala Tyr Arg Glu His Ile Ala Gly Arg Arg Arg Leu
    290                 295                 300

His Phe His His Ala Ser Arg Ile Thr Arg Gln Thr Val Thr Gly Glu
305                 310                 315                 320

Gly Val His Leu Asp Val Glu Phe Leu Pro Thr Gly Thr Ile Arg Gln
                325                 330                 335

Ile Asp Ala Asp Ala Ile Val Tyr Ala Thr Gly Tyr Arg Pro Ser Asp
            340                 345                 350

Pro Arg Gln Leu Leu Gly Asp Leu Ala Asp Glu Cys Lys Thr Asp Asp
        355                 360                 365

Arg Gly Arg Leu Ala Leu Ala Arg Asp Tyr Arg Val Ile Thr Ser Asp
    370                 375                 380

Gly Val Arg Cys Gly Ile Tyr Val His Gly Ala Ala Ala Glu Arg Thr
385                 390                 395                 400

His Gly Leu Ser Ala Gly Leu Leu Ser Asn Val Ala Val Arg Ala Gly
                405                 410                 415

Glu Ile Leu Ala Ala Ile Arg Ser Leu
            420                 425
```

<210> SEQ ID NO 54
<211> LENGTH: 450
<212> TYPE: PRT
<213> ORGANISM: Streptacidiphilus carbonis

<400> SEQUENCE: 54

```
Met Gly Ala Arg Glu Asn Ala Thr Tyr Asp Val Val Gly Ile Gly Phe
1               5                   10                  15

Gly Pro Ser Asn Leu Ser Leu Ala Ile Ala Leu Glu Glu Arg Cys Ala
            20                  25                  30
```

-continued

```
Asn Val Leu Thr Asn Ser Ile Thr Ser Ala Phe Phe Glu Arg Gln Ser
        35                  40                  45

Ser Phe Gly Trp His Arg Asn Met Leu Leu Pro Ser Ala Thr Met Gln
    50                  55                  60

Ile Ser Phe Leu Lys Asp Leu Val Thr Phe Arg Asn Pro Val Ser Arg
65                  70                  75                  80

Phe Ser Phe Val Ala Phe Leu His Ala Lys Gly Arg Leu Gly Gln Phe
                85                  90                  95

Val Asn Arg Lys Asp Phe Phe Pro Thr Arg Gln Glu Phe His Gln Tyr
            100                 105                 110

Leu Glu Trp Ala Ala Ala Lys Met Ala Asp Ala Val Thr Tyr Asp Ser
        115                 120                 125

Thr Val Thr Ser Val Gln Leu Pro Pro Asp His Gly Ser Gly Gly Asp
    130                 135                 140

Gly Tyr Val Gln Leu Glu Val Arg Asp Thr Ala Ala Gly Ser Thr Arg
145                 150                 155                 160

Arg Val Asn Thr Arg Asn Val Val Val Ser Thr Gly Leu Val Pro Arg
                165                 170                 175

Met Pro Asp Gly Ile Ala Arg Asp Asp Arg Val Trp His Ser Ser Glu
            180                 185                 190

Phe Leu Thr Arg Tyr Gly Arg Thr Asp Pro Glu Val Leu Arg Ser Val
        195                 200                 205

Ala Val Val Gly Ala Gly Gln Ser Ala Ala Glu Ile Thr Gln Phe Phe
    210                 215                 220

His Gly Arg Leu Pro His Ala Gln Val His Ala Ile Met Pro Ser Tyr
225                 230                 235                 240

Gly Tyr Ser Val Ala Asp Asp Thr Pro Phe Ala Asn Gln Val Phe Asp
                245                 250                 255

Ala Asp Ala Val Glu Asp Tyr Tyr Asp Gly Asp Glu Pro Ala Arg Asp
            260                 265                 270

Ala Phe Trp Arg Tyr His Arg Asn Thr Asn Tyr Gly Val Val Asp Ser
        275                 280                 285

Ala Asp Ile Gln Ala Leu Tyr Gln Thr Gln Tyr Asp Glu Gly Val Ala
    290                 295                 300

Gly Ala Lys Arg Leu His Phe His Asn Leu Thr Lys Val Arg Ala Val
305                 310                 315                 320

Glu Arg Asn Gly Ser Ala Arg Arg Val Thr Leu Gln Ser Leu Arg His
                325                 330                 335

His Glu Val Arg Gln Leu Asp Val Asp Ala Ile Val Phe Ala Thr Gly
            340                 345                 350

Tyr Ala Ser Met Asp Pro Thr Gln Leu Leu Gly Asp Leu Asp Arg Tyr
        355                 360                 365

Cys Leu Arg Asp Glu Ser Gly His His Arg Val Thr Arg Asp Tyr Arg
    370                 375                 380

Leu Val Thr Thr Pro Glu Leu Ser Cys Gly Ile Tyr Leu Gln Gly Gly
385                 390                 395                 400

Thr Glu His Thr His Gly Leu Thr Ser Ser Leu Leu Ser Asn Ile Ala
                405                 410                 415

Val Arg Ser Gly Glu Ile Ala Asp Ser Ile Ile Cys Arg Arg Ala Glu
            420                 425                 430

Ser Glu Leu Ala Thr Ile Ala Ala Glu Val Arg Glu Ala Val Ala Glu
        435                 440                 445
```

```
Arg Leu
    450


<210> SEQ ID NO 55
<211> LENGTH: 448
<212> TYPE: PRT
<213> ORGANISM: Streptomyces sp. MnatMP-M27

<400> SEQUENCE: 55

Met Thr Asp Ser Ala Pro Gly Asp Arg Thr Val Asp Val Thr Gly Ile
1               5                   10                  15

Gly Phe Gly Pro Ser Asn Leu Ala Leu Ala Thr Ala Leu Ala Glu Pro
            20                  25                  30

Ser Ala Thr Gly Pro Gly Arg Pro Leu Glu Ala Val Tyr Phe Glu Arg
        35                  40                  45

Lys Asn Arg Phe Ser Trp His Gly Gly Met Leu Leu Asp Gly Ala Thr
    50                  55                  60

Met Gln Ile Ser Phe Leu Lys Asp Leu Val Thr Leu Arg Asp Pro Arg
65                  70                  75                  80

Ser Pro Tyr Ser Phe Leu Ser Tyr Leu His His Ala Gly Arg Leu Ser
                85                  90                  95

Asp Phe Ile Asn His Lys Leu Leu Phe Pro Ser Arg Ile Glu Phe His
            100                 105                 110

Asp Tyr Leu Glu Trp Val Ala Gly Phe Phe Glu Glu Gln Val Val Tyr
        115                 120                 125

Gly Ser Glu Val Val Asp Val Arg Pro Val Ala Arg Glu Asp Ala Val
    130                 135                 140

Glu His Met Asp Val Val Val Arg Gln Arg Thr Ala Ala Gly Glu Arg
145                 150                 155                 160

Thr Val Val Gln Arg Thr Arg Asp Leu Val Val Ala Thr Gly Leu Glu
                165                 170                 175

Pro Ser Leu Pro Pro Gly Thr Val Cys Ser Asp Arg Val Trp His Ser
            180                 185                 190

Ser Glu Leu Leu Tyr Arg Val Glu Arg Leu Pro Pro Thr Pro Arg Arg
        195                 200                 205

Ile Val Val Val Gly Ala Gly Gln Ser Ala Ala Glu Ala Ala Glu Phe
    210                 215                 220

Leu His Ser Arg Phe Pro Ser Thr Asp Ile Cys Ala Val Phe Ser Arg
225                 230                 235                 240

Tyr Gly Tyr Ser Pro Ser Asp Asp Ser Pro Phe Ala Asn Arg Ile Phe
                245                 250                 255

Asp Pro Ala Ala Val Asp Asp Tyr Cys Ala Ala Ala Pro Glu Thr Arg
            260                 265                 270

Arg Met Leu Leu Asp Tyr His Arg Asn Thr Asn Tyr Ser Val Val Asp
        275                 280                 285

Pro Glu Leu Ile Asp Glu Leu Tyr Arg Arg Val Tyr Gln Glu Lys Val
    290                 295                 300

Arg Gly Arg Pro Arg Leu Asn Ile Leu Gly Ala Ser Arg Leu Thr Ala
305                 310                 315                 320

Ala Glu Pro Ala Gly Asp Gly Val Asp Val Val Val Glu Ser Leu Val
                325                 330                 335

Thr Gly Glu Arg Thr Pro Met Arg Ala Asp Cys Val Val Tyr Ala Thr
            340                 345                 350

Gly Tyr Arg Pro Thr Asp Ala Arg Gly Leu Leu Gly Ser Met Ala Gly
        355                 360                 365
```

```
Leu Cys Lys Ala Asp Glu Leu Gly Arg Leu Glu Ala Asp Arg Arg Tyr
    370                 375                 380

Arg Val Ile Thr Glu Gly Asp Val Arg Cys Ala Ile Tyr Leu Gln Gly
385                 390                 395                 400

Ala Thr Glu His Ser His Gly Ile Ser Ser Ser Leu Leu Ser Asn Thr
                405                 410                 415

Ala Val Arg Ala Gly Glu Ile Ala Asp Ala Ile Arg Ala Asp Ala Val
            420                 425                 430

Arg Ala Gly Ala Arg Ala Thr Thr Arg Ser Gln Pro Gln Pro Gln Thr
        435                 440                 445


<210> SEQ ID NO 56
<211> LENGTH: 452
<212> TYPE: PRT
<213> ORGANISM: Pseudonocardia sp. EC080625-04

<400> SEQUENCE: 56

Met Cys Thr Cys Lys Ser Asp Val Tyr Asp Val Val Gly Ile Gly Phe
1               5                   10                  15

Gly Pro Ser Asn Leu Ser Leu Ala Ile Ala Leu Gly Glu His Gln Gly
            20                  25                  30

Asn Arg Ala Gly His Pro Val Lys Ala Ala Phe Phe Glu Arg Gln Gln
        35                  40                  45

Ser Phe Gly Trp His Arg Asn Met Leu Leu Pro Glu Thr Thr Met Gln
    50                  55                  60

Ile Ser Phe Met Lys Asp Leu Val Thr Phe Arg Asn Pro Arg Ser Arg
65                  70                  75                  80

Phe Ser Phe Val Asn Tyr Leu His Glu Ser Gly Arg Leu Thr Gln Phe
                85                  90                  95

Cys Asn Asn Gln Asp Phe Phe Pro Thr Arg Gln Glu Phe His Arg Tyr
            100                 105                 110

Leu Glu Trp Val Gly Ser Ser Phe Asp Asp Gln Val Ser Tyr Asp Ser
        115                 120                 125

Glu Val Leu Gly Val Thr Leu Ala Pro Glu Pro Cys Glu Cys Ala Gln
    130                 135                 140

Arg Tyr Leu Lys Leu Glu Ile Ser Asn Gly Ala Ile Gly Ala Thr Glu
145                 150                 155                 160

Ile Val Asn Ala Arg Asn Ile Ser Ile Ser Thr Gly Leu Val Pro Lys
                165                 170                 175

Val Pro Asp Asn Val Ala Thr Gly Asp Arg Ile Trp His Ser Ser Gln
            180                 185                 190

Phe Leu Glu Lys Leu Arg Asp Val Asp Pro Ala Asp Leu Arg Asn Val
        195                 200                 205

Ala Val Val Gly Gly Gly Gln Ser Ala Ala Glu Ile Ala Arg Tyr Leu
    210                 215                 220

His Ala Thr Leu Pro Glu Ala Gln Ile Tyr Ala Ile Val Pro Ser Tyr
225                 230                 235                 240

Gly Tyr Ser Val Ala Asp Asp Thr Pro Phe Ala Asn Gln Val Phe Asp
                245                 250                 255

Pro Glu Ala Val Asp Asp Tyr Tyr Phe Gly Ser Asp Glu Thr Arg Asp
            260                 265                 270

Ala Phe Trp Arg Tyr His Arg Asn Thr Asn Tyr Ser Val Val Asp Asp
        275                 280                 285

Asp Ile Ile Arg Asp Leu His Arg Ala Ser Tyr Ala Glu Gln Val Thr
```

-continued

```
    290                 295                 300

Gly Glu Arg Arg Leu His Phe Leu Asn Leu Thr Arg Val Arg Ala Val
305                 310                 315                 320

Thr Arg Asn Gly Ala Thr Asn Arg Val Ser Leu His Ser Leu Ile Asp
                325                 330                 335

Arg Glu Thr Arg Glu Leu Asp Ile Asp Ala Leu Val Leu Ala Thr Gly
            340                 345                 350

Tyr Thr Glu Met Thr Pro Thr Gly Leu Ile Gly Asp Val Asp His Phe
        355                 360                 365

Cys His Arg Asp Pro Glu Gly Arg Tyr Arg Ile Glu Arg Asp Tyr Arg
    370                 375                 380

Leu Met Thr Asp Pro Glu Phe Pro Cys Gly Ile Tyr Leu Gln Gly Gly
385                 390                 395                 400

Thr Glu His Thr His Gly Leu Thr Ser Ser Leu Leu Ser Asn Val Ala
                405                 410                 415

Val Arg Gly Gly Glu Ile Ala Asp Ser Val Ile Thr Arg Thr Arg Ala
            420                 425                 430

Asp Ala Pro Thr Met Gln Arg Ser Thr Arg Arg Ile Glu Gln Ala Trp
        435                 440                 445

Glu Arg Ala Gly
    450


<210> SEQ ID NO 57
<211> LENGTH: 452
<212> TYPE: PRT
<213> ORGANISM: Pseudonocardia sp. HH130629-09

<400> SEQUENCE: 57

Met Cys Thr Cys Lys Ser Asp Val Tyr Asp Val Val Gly Ile Gly Phe
1               5                   10                  15

Gly Pro Ser Asn Leu Ser Leu Ala Ile Ala Leu Gly Glu His Gln Gly
            20                  25                  30

Asn Arg Ala Gly His Pro Val Lys Ala Ala Phe Phe Glu Arg Gln Gln
        35                  40                  45

Ser Phe Gly Trp His Arg Asn Met Leu Leu Pro Glu Thr Thr Met Gln
    50                  55                  60

Ile Ser Phe Met Lys Asp Leu Val Thr Phe Arg Asn Pro Arg Ser Arg
65                  70                  75                  80

Phe Ser Phe Val Asn Tyr Leu His Glu Ser Gly Arg Leu Thr Gln Phe
                85                  90                  95

Cys Asn Asn Gln Asp Phe Phe Pro Thr Arg Gln Glu Phe His Arg Tyr
            100                 105                 110

Leu Glu Trp Val Gly Ser Ser Phe Asp Asp Gln Val Ser Tyr Asp Ser
        115                 120                 125

Glu Val Leu Gly Val Thr Leu Ala Pro Glu Pro Cys Glu Cys Ala Gln
    130                 135                 140

Leu Tyr Leu Lys Leu Glu Ile Ser Asn Gly Ala Ile Gly Ala Thr Glu
145                 150                 155                 160

Ile Val Asn Ala Arg Asn Ile Ser Ile Ser Thr Gly Leu Val Pro Lys
                165                 170                 175

Val Pro Asp Asn Val Pro Thr Gly Asp Arg Ile Trp His Ser Ser Gln
            180                 185                 190

Phe Leu Glu Lys Leu Arg Asp Val Asp Pro Ala Asp Leu Arg Asn Val
        195                 200                 205
```

```
Ala Val Val Gly Gly Gly Gln Ser Ala Ala Glu Ile Ala Arg Tyr Leu
    210                 215                 220

His Ala Thr Leu Pro Glu Ala Gln Ile Tyr Ala Ile Val Pro Ser Tyr
225                 230                 235                 240

Gly Tyr Ser Val Ala Asp Asp Thr Pro Phe Ala Asn Gln Val Phe Asp
                245                 250                 255

Pro Glu Ala Val Asp Asp Tyr Tyr Phe Gly Ser Asp Glu Thr Arg Asp
            260                 265                 270

Ala Phe Trp Arg Tyr His Arg Asn Thr Asn Tyr Ser Val Val Asp Asp
        275                 280                 285

Asp Ile Ile Arg Asp Leu His Arg Ala Ser Tyr Ala Glu Gln Val Thr
    290                 295                 300

Gly Glu Arg Arg Leu His Phe Leu Asn Leu Thr Arg Val Arg Ala Val
305                 310                 315                 320

Thr Arg Asn Gly Ala Thr Asn Arg Val Ser Leu His Ser Leu Ile Asp
                325                 330                 335

Arg Glu Thr Arg Glu Leu Asp Ile Asp Ala Leu Val Leu Ala Thr Gly
            340                 345                 350

Tyr Thr Glu Met Thr Pro Thr Gly Leu Ile Gly Asp Val Asp His Phe
        355                 360                 365

Cys His Arg Asp Pro Glu Gly Arg Tyr Arg Ile Glu Arg Asp Tyr Arg
    370                 375                 380

Leu Met Thr Asp Pro Glu Phe Pro Cys Gly Ile Tyr Leu Gln Gly Gly
385                 390                 395                 400

Thr Glu His Thr His Gly Leu Thr Ser Ser Leu Leu Ser Asn Val Ala
                405                 410                 415

Val Arg Gly Gly Glu Ile Ala Asp Ser Val Ile Thr Arg Thr Arg Ala
            420                 425                 430

Asp Ala Pro Thr Met Gln Arg Ser Thr Arg Arg Ile Glu Gln Ala Trp
        435                 440                 445

Glu Arg Ala Gly
    450


<210> SEQ ID NO 58
<211> LENGTH: 450
<212> TYPE: PRT
<213> ORGANISM: Streptomyces parvulus

<400> SEQUENCE: 58

Met Gly Ile Thr Gly Arg Arg Asn Glu Glu Ile Leu Asp Val Val Gly
1               5                   10                  15

Ile Gly Phe Gly Pro Ser Asn Leu Ser Leu Ala Ile Ala Leu Glu Glu
            20                  25                  30

His Gly Ala Ser Ala Pro Arg His Pro Val Thr Ser His Phe Phe Glu
        35                  40                  45

Arg Gln Pro Thr Phe Gly Trp His Arg Asn Met Leu Leu Pro Ser Thr
    50                  55                  60

Thr Met Gln Ile Ser Phe Leu Lys Asp Leu Ala Thr Phe Arg Asn Pro
65                  70                  75                  80

Met Ser Arg Phe Ser Phe Ile Ser Tyr Leu His Ala Ser Asp Arg Leu
                85                  90                  95

Val Gln Phe Val Asn Asn Gln Asp Phe Phe Pro Thr Arg Gln Glu Phe
            100                 105                 110

His Gln Tyr Leu Glu Trp Ala Ala Ser Gly Leu Ser Asp Arg Val Thr
        115                 120                 125
```

Tyr Gly Ala Glu Val Thr Ala Ile Arg Pro Gly Ser Asp Gly Asn Gly
    130                 135                 140

Leu Ser Pro Asp Leu Leu Glu Val Glu Ala Arg Thr Ala Asp Gly Thr
145                 150                 155                 160

Thr Arg Val Val Thr Ala Arg Asn Val Ala Ile Ser Thr Gly Leu Val
                165                 170                 175

Pro Arg Leu Pro Glu Gly Val Thr Ala Asp Glu Arg Val Trp His Ser
            180                 185                 190

Ser Gln Phe Leu Ser Arg Phe Asn Ala Gln Ser Pro Asp Asp Leu Lys
        195                 200                 205

Ser Val Ala Val Val Gly Ala Gly Gln Ser Ala Ala Glu Ile Thr Arg
    210                 215                 220

Phe Leu His Asp Ala Leu Pro His Ala Gln Val Cys Ala Val Val Pro
225                 230                 235                 240

Ser Tyr Gly Tyr Ser Val Ala Asp Asp Thr Pro Phe Ala Asn Gln Val
                245                 250                 255

Phe Asp Pro Ala Ala Val Asp Asp Tyr Tyr Phe Gly Thr Asp Arg Gly
            260                 265                 270

Arg Asp Ala Phe Trp Arg Tyr His Arg Asn Thr Asn Tyr Ser Val Val
        275                 280                 285

Asp Ala Asp Val Ile Arg Asp Leu His Gln Arg Thr Tyr Asp Glu Glu
    290                 295                 300

Val Arg Gly Thr Arg Arg Leu His Phe Arg Asn Leu Thr Arg Val Ala
305                 310                 315                 320

Glu Val Glu Arg Ser Gly Ser Thr Thr Arg Val Val Leu Arg Ser Leu
                325                 330                 335

Leu Asp Asp Arg Thr Glu Asp Leu Ser Val Asp Ala Leu Val Phe Ala
            340                 345                 350

Thr Gly Tyr Asp Gly Leu Asp Pro Val Arg Leu Leu Gly Asp Phe Asp
        355                 360                 365

Arg His Phe Arg Arg Asp Ala Ala Gly Arg His Arg Leu Glu Arg Asp
    370                 375                 380

Tyr Arg Leu Val Pro Ala Thr Asp Leu Thr Cys Gly Val Tyr Leu Gln
385                 390                 395                 400

Gly Gly Thr Glu His Ser His Gly Leu Ser Ser Ser Leu Leu Ser Asn
                405                 410                 415

Ile Ala Val Arg Ser Gly Glu Ile Ala Asp Ser Ile Val Leu Arg Arg
            420                 425                 430

Thr Glu Arg Glu Leu Glu Arg Asp Arg Pro Val Glu Val Ala Pro Pro
        435                 440                 445

Val Ala
    450

<210> SEQ ID NO 59
<211> LENGTH: 430
<212> TYPE: PRT
<213> ORGANISM: Streptomyces sp. CFMR 7

<400> SEQUENCE: 59

Met Ala Ile Arg Ala Gly Ser His Ile Leu Asp Val Val Gly Ile Gly
1               5                   10                  15

Phe Gly Pro Ser Asn Leu Ala Leu Ala Ile Ala Leu Gln Glu Met Ile
            20                  25                  30

Lys Ala Asp Thr Gly Arg Thr Glu Tyr Ala Met Ala Phe His Glu Arg

```
        35                  40                  45

Gln Pro Arg Phe Gly Trp His Arg Gly Met Leu Met Glu Asp Ala Thr
    50                  55                  60

Met Gln Val Ser Phe Leu Lys Asp Leu Ala Thr Met Arg Asn Ala Thr
65                  70                  75                  80

Ser Arg Tyr Thr Phe Val Ala Tyr Leu Gln Glu Gln Gly Arg Val Ala
                85                  90                  95

Glu Phe Ile Asn Ser Lys Thr Leu Tyr Pro Leu Arg Val Glu Phe His
            100                 105                 110

Asp Tyr Leu Glu Trp Ala Ala Gln Gln Phe Asp Ala Ser Val Ser Tyr
        115                 120                 125

Gly Ser Glu Ile Val Ala Val Arg Pro Val Ile Glu Ser Gly Ser Val
    130                 135                 140

Glu Tyr Val Asp Val Val Ala Arg Ser Ala Ser Gly Gly Ser Ser Thr
145                 150                 155                 160

Val Val Gln Arg Ala Arg Asn Val Val Ile Gly Met Gly Leu Thr Pro
                165                 170                 175

Arg Leu Pro Asp Gly Ile Glu Glu Ser Glu Arg Ile Trp His Ser Ser
            180                 185                 190

Gln Leu Leu His Arg Ala Asp Ser Leu Pro Tyr Arg Pro Arg Asn Phe
        195                 200                 205

Val Val Val Gly Ser Gly Gln Ser Ala Ala Glu Val Ala Asp Tyr Leu
    210                 215                 220

His Arg Thr Phe Ser Asp Ala Asn Val His Thr Val Leu Ser Arg Tyr
225                 230                 235                 240

Gly Tyr Ser Val Ala Asp Asp Ser Pro Phe Ala Asn Gly Val Phe Asp
                245                 250                 255

Pro Glu Ala Val Asp Arg Phe Tyr Thr Ser Ser Ala Asp Ala Lys Gln
            260                 265                 270

Arg Leu Leu Asp Tyr His Gly Asn Thr Asn Tyr Ser Val Val Asp Leu
        275                 280                 285

Glu Val Ser Gln Asp Leu Tyr Arg Arg Ser Tyr Gln Glu Lys Val Leu
    290                 295                 300

Gly Lys Gln Arg Leu Arg Met Leu Asn Ser Ser Arg Val Thr Ser Ala
305                 310                 315                 320

Glu Glu His Ala Asp Gly Val Arg Val Thr Val Glu Ala Met Asp Ser
                325                 330                 335

Gly Ser Val Arg Thr Met Asp Ala Asp Val Ile Val Tyr Ala Thr Gly
            340                 345                 350

Tyr Arg Pro Ser Asp Ala Ala Pro Leu Leu Ser Glu Leu Ala Gly Glu
        355                 360                 365

Cys Lys Arg Asp Glu Glu Gly Arg Leu Ala Val Glu Arg Asp Tyr Arg
    370                 375                 380

Val Ile Thr Ser Glu Ala Val Arg Cys Gly Ile Tyr Val His Gly Ala
385                 390                 395                 400

Val Thr Glu His Ser His Gly Leu Ser Ala Gly Leu Leu Ser Asn Thr
                405                 410                 415

Ala Val Arg Ser Gly Glu Ile Ala Arg Ser Ile Leu Arg Arg
            420                 425                 430
```

<210> SEQ ID NO 60
<211> LENGTH: 430
<212> TYPE: PRT
<213> ORGANISM: Streptomyces sp. DvalAA-19

<400> SEQUENCE: 60

Met Ala Ile Arg Ala Gly Ser His Ile Ser Asp Val Val Gly Ile Gly
1               5                   10                  15

Phe Gly Pro Ser Asn Leu Ala Leu Ala Ile Ala Leu Gln Glu Met Ile
            20                  25                  30

Lys Ala Asp Thr Gly Arg Thr Glu Tyr Ala Met Ala Phe His Glu Arg
        35                  40                  45

Gln Pro Arg Phe Gly Trp His Arg Gly Met Leu Met Glu Asp Ala Thr
    50                  55                  60

Met Gln Val Ser Phe Leu Lys Asp Leu Ala Thr Met Arg Asn Ala Thr
65                  70                  75                  80

Ser Arg Tyr Thr Phe Val Ala Tyr Leu Gln Glu Lys Gly Arg Val Ala
                85                  90                  95

Glu Phe Ile Asn Ser Lys Thr Leu Tyr Pro Leu Arg Val Glu Phe His
            100                 105                 110

Asp Tyr Leu Glu Trp Ala Ala Gln Gln Phe Asp Ala Ser Val Ser Tyr
        115                 120                 125

Gly Ser Glu Ile Val Ala Val Arg Pro Val Ile Glu Ser Gly Ser Val
    130                 135                 140

Glu Tyr Val Asp Val Val Ala Arg Ser Ala Ser Gly Gly Ser Ser Thr
145                 150                 155                 160

Val Val Gln Arg Ala Arg Asn Val Val Ile Gly Met Gly Leu Thr Pro
                165                 170                 175

Arg Leu Pro Asp Gly Ile Glu Glu Ser Glu Arg Ile Trp His Ser Ser
            180                 185                 190

Gln Leu Leu His Arg Ala Asp Ser Leu Pro Tyr Arg Pro Arg Asn Phe
        195                 200                 205

Val Val Val Gly Ser Gly Gln Ser Ala Ala Glu Val Ala Asp Tyr Leu
    210                 215                 220

His Arg Thr Phe Ser Asp Ala Asn Val His Thr Val Leu Ser Arg Tyr
225                 230                 235                 240

Gly Tyr Ser Val Ala Asp Asp Ser Pro Phe Ala Asn Gly Val Phe Asp
                245                 250                 255

Pro Glu Ala Val Asp Arg Phe Tyr Thr Ser Ser Ala Asp Ala Lys Gln
            260                 265                 270

Arg Leu Leu Asp Tyr His Gly Asn Thr Asn Tyr Ser Val Val Asp Leu
        275                 280                 285

Glu Val Ser Gln Asp Leu Tyr Arg Arg Ser Tyr Gln Glu Lys Val Leu
    290                 295                 300

Gly Lys Gln Arg Leu Arg Met Leu Asn Ser Ser Arg Val Thr Ser Ala
305                 310                 315                 320

Glu Glu His Ala Asp Gly Val Arg Val Thr Val Glu Ala Met Asp Ser
                325                 330                 335

Gly Ser Val Arg Thr Met Asp Ala Asp Val Ile Val Tyr Ala Thr Gly
            340                 345                 350

Tyr Arg Pro Ser Asp Ala Ala Pro Leu Leu Ser Glu Leu Ala Gly Glu
        355                 360                 365

Cys Lys Arg Asp Glu Glu Gly Arg Leu Ala Val Glu Arg Asp Tyr Arg
    370                 375                 380

Val Ile Thr Ser Glu Ala Val Arg Cys Gly Ile Tyr Val His Gly Ala
385                 390                 395                 400

Val Thr Glu His Ser His Gly Leu Ser Ala Gly Leu Leu Ser Asn Thr

```
            405                 410                 415

Ala Val Arg Ser Gly Glu Ile Ala Arg Ser Ile Leu Arg Arg
            420                 425                 430


<210> SEQ ID NO 61
<211> LENGTH: 424
<212> TYPE: PRT
<213> ORGANISM: Rhodococcus fascians

<400> SEQUENCE: 61

Met Gly Ala Gln Ser Gly Ser Ser Val Ala Asp Val Val Gly Val Gly
1               5                   10                  15

Phe Gly Pro Ser Asn Leu Ala Leu Ala Ile Ala Leu Gln Glu Ser Ile
            20                  25                  30

Gln Pro Gly Pro Val Pro Ala Lys Phe Ser Met Lys Phe Tyr Glu Leu
        35                  40                  45

Gln Pro Arg Phe Gly Trp His Arg Gly Met Leu Met Glu Asp Ala Thr
    50                  55                  60

Met Gln Val Ser Phe Leu Lys Asp Leu Ala Thr Met Arg Asn Pro Met
65                  70                  75                  80

Ser Arg Tyr Thr Phe Val Ser Tyr Leu Arg Glu Lys Glu Arg Ile Ala
                85                  90                  95

Glu Phe Ile Asn Ser Lys Thr Leu Tyr Pro Leu Arg Val Glu Phe His
            100                 105                 110

Asp Tyr Leu Glu Trp Ala Ala Ser Gln Phe Gln Ser Asn Val Ser Tyr
        115                 120                 125

Gly Ser Glu Ile Lys Asp Ile Arg Pro Val Val Glu Asn Gly Val Val
    130                 135                 140

Glu Tyr Val Asp Val Val Gly Pro Asp Asp Val Val Gln Arg Ala Arg
145                 150                 155                 160

Asn Ile Val Ile Gly Met Gly Leu Thr Pro Arg Leu Pro Asp Gly Val
                165                 170                 175

Asn Arg Ser Glu Arg Ile Trp His Ser Ser Gln Leu Leu Gly Arg Ala
            180                 185                 190

Ala Ala Val Thr Tyr Val Pro Gln Asn Phe Val Val Val Gly Ser Gly
        195                 200                 205

Gln Ser Ala Ala Glu Val Ala Asp Tyr Leu His Arg Thr Phe Pro Arg
    210                 215                 220

Ala Asn Val His Thr Val Leu Ser Arg Tyr Gly Tyr Ser Val Ala Asp
225                 230                 235                 240

Asp Ser Pro Tyr Ala Asn Gly Ile Phe Asp Pro Glu Gly Val Asp Arg
                245                 250                 255

Phe Phe Ser Ala Pro Thr Asp Glu Lys Gln Arg Leu Leu Glu Tyr His
            260                 265                 270

Ala Asn Thr Asn Tyr Ser Val Val Asp Leu Asp Ile Ser Gln Ser Leu
        275                 280                 285

Tyr Leu Lys Ser Tyr Gln Glu Lys Val Leu Gly Lys Gln Arg Leu Arg
    290                 295                 300

Met Ile Asn Thr Ser Arg Val Thr Ser Val Asp Glu Asp Thr Asp Gly
305                 310                 315                 320

Val Arg Val Glu Val Thr Ser Ser Ala Thr Gly Leu Thr His Thr Ile
                325                 330                 335

Glu Ala Asp Val Ile Val Tyr Ala Thr Gly Tyr Arg Pro Ser Asp Pro
            340                 345                 350
```

-continued

```
Ala Pro Leu Leu Gln Gly Leu Met Arg Glu Cys Lys His Asp Glu Gln
        355                 360                 365

Gly Arg Leu Ser Val Gly Arg Asp Tyr Arg Val Thr Thr Ser Asp Ala
    370                 375                 380

Val Arg Ala Gly Ile Tyr Val His Gly Ala Ser Thr Glu His Ser His
385                 390                 395                 400

Gly Leu Ser Ala Gly Leu Leu Ser Asn Thr Ala Val Arg Ser Gly Glu
                405                 410                 415

Ile Ala Gln Ser Ile Leu Arg Arg
            420


<210> SEQ ID NO 62
<211> LENGTH: 424
<212> TYPE: PRT
<213> ORGANISM: Rhodococcus fascians

<400> SEQUENCE: 62

Met Gly Ala Gln Ser Gly Ser Ser Val Ala Asp Val Val Gly Val Gly
1               5                   10                  15

Phe Gly Pro Ser Asn Leu Ala Leu Ala Ile Ala Leu Gln Glu Ser Ile
            20                  25                  30

Gln Pro Gly Pro Val Pro Ala Lys Phe Ser Met Lys Phe Tyr Glu Leu
        35                  40                  45

Gln Pro Arg Phe Gly Trp His Arg Gly Met Leu Met Glu Asp Ala Thr
    50                  55                  60

Met Gln Val Ser Phe Leu Lys Asp Leu Ala Thr Met Arg Asn Pro Met
65                  70                  75                  80

Ser Arg Tyr Thr Phe Val Ser Tyr Leu Arg Glu Lys Glu Arg Ile Ala
                85                  90                  95

Glu Phe Ile Asn Ser Lys Thr Leu Tyr Pro Leu Arg Val Glu Phe His
            100                 105                 110

Asp Tyr Leu Glu Trp Ala Ala Ser Gln Phe Gln Ser Asn Val Ser Tyr
        115                 120                 125

Gly Ser Glu Ile Lys Asp Ile Arg Pro Val Val Glu Asn Gly Val Val
    130                 135                 140

Glu Tyr Val Asp Val Val Gly Pro Asp Asp Val Val Gln Arg Ala Arg
145                 150                 155                 160

Asn Ile Val Ile Gly Met Gly Leu Thr Pro Arg Leu Pro Asp Gly Val
                165                 170                 175

Asn Arg Ser Glu Arg Ile Trp His Ser Ser Gln Leu Leu Gly Arg Ala
            180                 185                 190

Ala Ala Val Thr Tyr Val Pro Gln Asn Phe Val Val Val Gly Ser Gly
        195                 200                 205

Gln Ser Ala Ala Glu Val Ala Asp Tyr Leu His Arg Thr Phe Pro Arg
    210                 215                 220

Ala Asn Val His Thr Val Leu Ser Arg Tyr Gly Tyr Ser Val Ala Asp
225                 230                 235                 240

Asp Ser Pro Tyr Ala Asn Gly Ile Phe Asp Pro Glu Gly Val Asp Arg
                245                 250                 255

Phe Phe Ser Ala Pro Thr Asp Glu Lys Gln Arg Leu Leu Glu Tyr His
            260                 265                 270

Ala Asn Thr Asn Tyr Ser Val Val Asp Leu Asp Ile Ser Gln Ser Leu
        275                 280                 285

Tyr Leu Lys Ser Tyr Gln Glu Lys Val Leu Gly Lys Gln Arg Leu Arg
    290                 295                 300
```

Met Ile Asn Thr Ser Arg Val Thr Ser Val Asp Glu Asp Thr Asp Gly
305 310 315 320

Val Arg Val Glu Val Thr Ser Ser Ala Thr Gly Leu Thr His Thr Ile
325 330 335

Glu Ala Asp Val Ile Val Tyr Ala Thr Gly Tyr Arg Pro Ser Asp Pro
340 345 350

Ala Pro Leu Leu Gln Gly Leu Met Arg Glu Cys Lys His Asp Glu Gln
355 360 365

Gly Arg Leu Ser Val Gly Arg Asp Tyr Arg Val Thr Thr Ser Asp Ala
370 375 380

Val Arg Ala Gly Ile Tyr Val His Gly Ala Ser Thr Glu His Ser His
385 390 395 400

Gly Leu Ser Ala Gly Leu Leu Ser Asn Thr Ala Val Arg Ser Gly Glu
405 410 415

Ile Ala Gln Ser Ile Leu Arg Arg
420

<210> SEQ ID NO 63
<211> LENGTH: 424
<212> TYPE: PRT
<213> ORGANISM: Rhodococcus fascians

<400> SEQUENCE: 63

Met Gly Ala Gln Ser Gly Ser Ser Val Ala Asp Val Val Gly Val Gly
1 5 10 15

Phe Gly Pro Ser Asn Leu Ala Leu Ala Ile Ala Leu Gln Glu Ser Ile
20 25 30

Gln Pro Gly Pro Val Pro Ala Lys Phe Ser Met Lys Phe Tyr Glu Leu
35 40 45

Gln Pro Arg Phe Gly Trp His Arg Gly Met Leu Met Glu Asp Ala Thr
50 55 60

Met Gln Val Ser Phe Leu Lys Asp Leu Ala Thr Met Arg Asn Pro Met
65 70 75 80

Ser Arg Tyr Thr Phe Val Ser Tyr Leu Arg Glu Lys Glu Arg Ile Ala
85 90 95

Glu Phe Ile Asn Ser Lys Thr Leu Tyr Pro Leu Arg Val Glu Phe His
100 105 110

Asp Tyr Leu Glu Trp Ala Ala Ser Gln Phe Gln Ser Asn Val Ser Tyr
115 120 125

Gly Ser Glu Ile Lys Asp Ile Arg Pro Val Val Glu Asn Gly Val Val
130 135 140

Glu Tyr Val Asp Val Val Gly Pro Asp Asp Val Val Gln Arg Ala Arg
145 150 155 160

Asn Ile Val Ile Gly Met Gly Leu Thr Pro Arg Leu Pro Asp Gly Val
165 170 175

Asn Arg Ser Glu Arg Ile Trp His Ser Ser Gln Leu Leu Gly Arg Ala
180 185 190

Ala Ala Val Thr Tyr Val Pro Gln Asn Phe Val Val Val Gly Ser Gly
195 200 205

Gln Ser Ala Ala Glu Val Ala Asp Tyr Leu His Arg Thr Phe Pro Arg
210 215 220

Ala Asn Val His Thr Val Leu Ser Arg Tyr Gly Tyr Ser Val Ala Asp
225 230 235 240

Asp Ser Pro Tyr Ala Asn Gly Ile Phe Asp Pro Glu Gly Val Asp Arg

-continued

```
                245                 250                 255

Phe Phe Ser Ala Pro Thr Asp Glu Lys Gln Arg Leu Leu Glu Tyr His
            260                 265                 270

Ala Asn Thr Asn Tyr Ser Val Val Asp Leu Asp Ile Ser Gln Ser Leu
        275                 280                 285

Tyr Leu Lys Ser Tyr Gln Glu Lys Val Leu Gly Lys Gln Arg Leu Arg
    290                 295                 300

Met Ile Asn Thr Ser Arg Val Thr Ser Val Asp Glu Asp Thr Asp Gly
305                 310                 315                 320

Val Arg Val Glu Val Thr Ser Ser Ala Thr Gly Leu Thr His Thr Ile
                325                 330                 335

Glu Ala Asp Val Ile Val Tyr Ala Thr Gly Tyr Arg Pro Ser Asp Pro
            340                 345                 350

Ala Pro Leu Leu Gln Gly Leu Met Arg Glu Cys Lys His Asp Glu Gln
        355                 360                 365

Gly Arg Leu Ser Val Gly Arg Asp Tyr Arg Val Thr Thr Ser Asp Ala
    370                 375                 380

Val Arg Ala Gly Ile Tyr Val His Gly Ala Ser Thr Glu His Ser His
385                 390                 395                 400

Gly Leu Ser Ala Gly Leu Leu Ser Asn Thr Ala Val Arg Ser Gly Glu
                405                 410                 415

Ile Ala Gln Ser Ile Leu Arg Arg
            420


<210> SEQ ID NO 64
<211> LENGTH: 424
<212> TYPE: PRT
<213> ORGANISM: Rhodococcus fascians

<400> SEQUENCE: 64

Met Gly Ala Gln Ser Gly Ser Ser Val Ala Asp Val Val Gly Val Gly
1               5                   10                  15

Phe Gly Pro Ser Asn Leu Ala Leu Ala Ile Ala Leu Gln Glu Ser Ile
            20                  25                  30

Gln Pro Gly Pro Val Pro Ala Lys Phe Ser Met Lys Phe Tyr Glu Leu
        35                  40                  45

Gln Pro Arg Phe Gly Trp His Arg Gly Met Leu Met Glu Asp Ala Thr
    50                  55                  60

Met Gln Val Ser Phe Leu Lys Asp Leu Ala Thr Met Arg Asn Pro Met
65                  70                  75                  80

Ser Arg Tyr Thr Phe Val Ser Tyr Leu Arg Glu Lys Glu Arg Ile Ala
                85                  90                  95

Glu Phe Ile Asn Ser Lys Thr Leu Tyr Pro Leu Arg Val Glu Phe His
            100                 105                 110

Asp Tyr Leu Glu Trp Ala Ala Ser Gln Phe Gln Ser Asn Val Ser Tyr
        115                 120                 125

Gly Ser Glu Ile Lys Asp Ile Arg Pro Val Val Glu Asn Gly Val Val
    130                 135                 140

Glu Tyr Val Asp Val Val Gly Pro Asp Asp Val Val Gln Arg Ala Arg
145                 150                 155                 160

Asn Ile Val Ile Gly Met Gly Leu Thr Pro Arg Leu Pro Asp Gly Val
                165                 170                 175

Asn Arg Ser Glu Arg Ile Trp His Ser Ser Gln Leu Leu Gly Arg Ala
            180                 185                 190
```

```
Ala Ala Val Thr Tyr Val Pro Gln Asn Phe Val Val Val Gly Ser Gly
        195                 200                 205

Gln Ser Ala Ala Glu Val Ala Asp Tyr Leu His Arg Thr Phe Pro Arg
    210                 215                 220

Ala Asn Val His Thr Val Leu Ser Arg Tyr Gly Tyr Ser Val Ala Asp
225                 230                 235                 240

Asp Ser Pro Tyr Ala Asn Gly Ile Phe Asp Pro Glu Gly Val Asp Arg
                245                 250                 255

Phe Phe Ser Ala Pro Thr Asp Glu Lys Gln Arg Leu Leu Glu Tyr His
            260                 265                 270

Ala Asn Thr Asn Tyr Ser Val Val Asp Leu Asp Ile Ser Gln Ser Leu
        275                 280                 285

Tyr Leu Lys Ser Tyr Gln Glu Lys Val Leu Gly Lys Gln Arg Leu Arg
    290                 295                 300

Met Ile Asn Thr Ser Arg Val Thr Ser Val Asp Glu Asp Thr Asp Gly
305                 310                 315                 320

Val Arg Val Glu Val Thr Ser Ser Ala Thr Gly Leu Thr His Thr Ile
                325                 330                 335

Glu Ala Asp Val Ile Val Tyr Ala Thr Gly Tyr Arg Pro Ser Asp Pro
            340                 345                 350

Ala Pro Leu Leu Gln Gly Leu Met Arg Glu Cys Lys His Asp Glu Gln
        355                 360                 365

Gly Arg Leu Ser Val Gly Arg Asp Tyr Arg Val Thr Thr Ser Asp Ala
    370                 375                 380

Val Arg Ala Gly Ile Tyr Val His Gly Ala Ser Thr Glu His Ser His
385                 390                 395                 400

Gly Leu Ser Ala Gly Leu Leu Ser Asn Thr Ala Val Arg Ser Gly Glu
                405                 410                 415

Ile Ala Gln Ser Ile Leu Arg Arg
            420


<210> SEQ ID NO 65
<211> LENGTH: 424
<212> TYPE: PRT
<213> ORGANISM: Rhodococcus fascians

<400> SEQUENCE: 65

Met Gly Ala Gln Ser Gly Ser Ser Val Ala Asp Val Val Gly Val Gly
1               5                   10                  15

Phe Gly Pro Ser Asn Leu Ala Leu Ala Ile Ala Leu Gln Glu Ser Ile
            20                  25                  30

Gln Pro Gly Pro Val Pro Ala Lys Phe Ser Met Lys Phe Tyr Glu Leu
        35                  40                  45

Gln Pro Arg Phe Gly Trp His Arg Gly Met Leu Met Glu Asp Ala Thr
    50                  55                  60

Met Gln Val Ser Phe Leu Lys Asp Leu Ala Thr Met Arg Asn Pro Met
65                  70                  75                  80

Ser Arg Tyr Thr Phe Val Ser Tyr Leu Arg Glu Lys Glu Arg Ile Ala
                85                  90                  95

Glu Phe Ile Asn Ser Lys Thr Leu Tyr Pro Leu Arg Val Glu Phe His
            100                 105                 110

Asp Tyr Leu Glu Trp Ala Ala Ser Gln Phe Gln Ser Asn Val Ser Tyr
        115                 120                 125

Gly Ser Glu Ile Lys Asp Ile Arg Pro Val Val Glu Asn Gly Val Val
    130                 135                 140
```

```
Glu Tyr Val Asp Val Val Gly Pro Asp Asp Val Val Gln Arg Ala Arg
145                 150                 155                 160

Asn Ile Val Ile Gly Met Gly Leu Thr Pro Arg Leu Pro Asp Gly Val
                165                 170                 175

Asn Arg Ser Glu Arg Ile Trp His Ser Ser Gln Leu Leu Gly Arg Ala
            180                 185                 190

Ala Ala Val Thr Tyr Val Pro Gln Asn Phe Val Val Val Gly Ser Gly
        195                 200                 205

Gln Ser Ala Ala Glu Val Ala Asp Tyr Leu His Arg Thr Phe Pro Arg
    210                 215                 220

Ala Asn Val His Thr Val Leu Ser Arg Tyr Gly Tyr Ser Val Ala Asp
225                 230                 235                 240

Asp Ser Pro Tyr Ala Asn Gly Ile Phe Asp Pro Glu Gly Val Asp Arg
                245                 250                 255

Phe Phe Ser Ala Pro Thr Asp Glu Lys Gln Arg Leu Leu Glu Tyr His
            260                 265                 270

Ala Asn Thr Asn Tyr Ser Val Val Asp Leu Asp Ile Ser Gln Ser Leu
        275                 280                 285

Tyr Leu Lys Ser Tyr Gln Glu Lys Val Leu Gly Lys Gln Arg Leu Arg
    290                 295                 300

Met Ile Asn Thr Ser Arg Val Thr Ser Val Asp Glu Asp Thr Asp Gly
305                 310                 315                 320

Val Arg Val Glu Val Thr Ser Ser Ala Thr Gly Leu Thr His Thr Ile
                325                 330                 335

Glu Ala Asp Val Ile Val Tyr Ala Thr Gly Tyr Arg Pro Ser Asp Pro
            340                 345                 350

Ala Pro Leu Leu Gln Gly Leu Met Arg Glu Cys Lys His Asp Glu Gln
        355                 360                 365

Gly Arg Leu Ser Val Gly Arg Asp Tyr Arg Val Thr Thr Ser Asp Ala
    370                 375                 380

Val Arg Ala Gly Ile Tyr Val His Gly Ala Ser Thr Glu His Ser His
385                 390                 395                 400

Gly Leu Ser Ala Gly Leu Leu Ser Asn Thr Ala Val Arg Ser Gly Glu
                405                 410                 415

Ile Ala Gln Ser Ile Leu Arg Arg
            420


<210> SEQ ID NO 66
<211> LENGTH: 424
<212> TYPE: PRT
<213> ORGANISM: Rhodococcus fascians

<400> SEQUENCE: 66

Met Gly Ala Gln Ser Gly Ser Ser Val Ala Asp Val Val Gly Val Gly
1               5                   10                  15

Phe Gly Pro Ser Asn Leu Ala Leu Ala Ile Ala Leu Gln Glu Ser Ile
            20                  25                  30

Gln Pro Gly Pro Val Pro Ala Lys Phe Ser Met Lys Phe Tyr Glu Leu
        35                  40                  45

Gln Pro Arg Phe Gly Trp His Arg Gly Met Leu Met Glu Asp Ala Thr
    50                  55                  60

Met Gln Val Ser Phe Leu Lys Asp Leu Ala Thr Met Arg Asn Pro Met
65                  70                  75                  80

Ser Arg Tyr Thr Phe Val Ser Tyr Leu Arg Glu Lys Glu Arg Ile Ala
```

-continued

```
                85                  90                  95

Glu Phe Ile Asn Ser Lys Thr Leu Tyr Pro Leu Arg Val Glu Phe His
            100                 105                 110

Asp Tyr Leu Glu Trp Ala Ala Ser Gln Phe Gln Ser Asn Val Ser Tyr
        115                 120                 125

Gly Ser Glu Ile Lys Asp Ile Arg Pro Val Val Glu Asn Gly Val Val
    130                 135                 140

Glu Tyr Val Asp Val Val Gly Pro Asp Asp Val Val Gln Arg Ala Arg
145                 150                 155                 160

Asn Ile Val Ile Gly Met Gly Leu Thr Pro Arg Leu Pro Asp Gly Val
                165                 170                 175

Asn Arg Ser Glu Arg Ile Trp His Ser Ser Gln Leu Leu Gly Arg Ala
            180                 185                 190

Ala Ala Val Thr Tyr Val Pro Gln Asn Phe Val Val Val Gly Ser Gly
        195                 200                 205

Gln Ser Ala Ala Glu Val Ala Asp Tyr Leu His Arg Thr Phe Pro Arg
    210                 215                 220

Ala Asn Val His Thr Val Leu Ser Arg Tyr Gly Tyr Ser Val Ala Asp
225                 230                 235                 240

Asp Ser Pro Tyr Ala Asn Gly Ile Phe Asp Pro Glu Gly Val Asp Arg
                245                 250                 255

Phe Phe Ser Ala Pro Thr Asp Glu Lys Gln Arg Leu Leu Glu Tyr His
            260                 265                 270

Ala Asn Thr Asn Tyr Ser Val Val Asp Leu Asp Ile Ser Gln Ser Leu
        275                 280                 285

Tyr Leu Lys Ser Tyr Gln Glu Lys Val Leu Gly Lys Gln Arg Leu Arg
    290                 295                 300

Met Ile Asn Thr Ser Arg Val Thr Ser Val Asp Glu Asp Thr Asp Gly
305                 310                 315                 320

Val Arg Val Glu Val Thr Ser Ser Ala Thr Gly Leu Thr His Thr Ile
                325                 330                 335

Glu Ala Asp Val Ile Val Tyr Ala Thr Gly Tyr Arg Pro Ser Asp Pro
            340                 345                 350

Ala Pro Leu Leu Gln Gly Leu Met Arg Glu Cys Lys His Asp Glu Gln
        355                 360                 365

Gly Arg Leu Ser Val Gly Arg Asp Tyr Arg Val Thr Thr Ser Asp Ala
    370                 375                 380

Val Arg Ala Gly Ile Tyr Val His Gly Ala Ser Thr Glu His Ser His
385                 390                 395                 400

Gly Leu Ser Ala Gly Leu Leu Ser Asn Thr Ala Val Arg Ser Gly Glu
                405                 410                 415

Ile Ala Gln Ser Ile Leu Arg Arg
            420


<210> SEQ ID NO 67
<211> LENGTH: 424
<212> TYPE: PRT
<213> ORGANISM: Rhodococcus fascians

<400> SEQUENCE: 67

Met Gly Ala Gln Ser Gly Ser Ser Val Ala Asp Val Val Gly Val Gly
1               5                   10                  15

Phe Gly Pro Ser Asn Leu Ala Leu Ala Ile Ala Leu Gln Glu Ser Ile
            20                  25                  30
```

```
Gln Pro Gly Pro Val Pro Ala Lys Phe Ser Met Lys Phe Tyr Glu Leu
        35                  40                  45

Gln Pro Arg Phe Gly Trp His Arg Gly Met Leu Met Glu Asp Ala Thr
    50                  55                  60

Met Gln Val Ser Phe Leu Lys Asp Leu Ala Thr Met Arg Asn Pro Met
65                  70                  75                  80

Ser Arg Tyr Thr Phe Val Ser Tyr Leu Arg Glu Lys Glu Arg Ile Ala
                85                  90                  95

Glu Phe Ile Asn Ser Lys Thr Leu Tyr Pro Leu Arg Val Glu Phe His
            100                 105                 110

Asp Tyr Leu Glu Trp Ala Ala Ser Gln Phe Gln Ser Asn Val Ser Tyr
        115                 120                 125

Gly Ser Glu Ile Lys Asp Ile Arg Pro Val Val Glu Asn Gly Val Val
    130                 135                 140

Glu Tyr Val Asp Val Val Gly Pro Asp Asp Val Val Gln Arg Ala Arg
145                 150                 155                 160

Asn Ile Val Ile Gly Met Gly Leu Thr Pro Arg Leu Pro Asp Gly Val
                165                 170                 175

Asn Arg Ser Glu Arg Ile Trp His Ser Ser Gln Leu Leu Gly Arg Ala
            180                 185                 190

Ala Ala Val Thr Tyr Val Pro Gln Asn Phe Val Val Val Gly Ser Gly
        195                 200                 205

Gln Ser Ala Ala Glu Val Ala Asp Tyr Leu His Arg Thr Phe Pro Arg
    210                 215                 220

Ala Asn Val His Thr Val Leu Ser Arg Tyr Gly Tyr Ser Val Ala Asp
225                 230                 235                 240

Asp Ser Pro Tyr Ala Asn Gly Ile Phe Asp Pro Glu Gly Val Asp Arg
                245                 250                 255

Phe Phe Ser Ala Pro Thr Asp Glu Lys Gln Arg Leu Leu Glu Tyr His
            260                 265                 270

Ala Asn Thr Asn Tyr Ser Val Val Asp Leu Asp Ile Ser Gln Ser Leu
        275                 280                 285

Tyr Leu Lys Ser Tyr Gln Glu Lys Val Leu Gly Lys Gln Arg Leu Arg
    290                 295                 300

Met Ile Asn Thr Ser Arg Val Thr Ser Val Asp Glu Asp Thr Asp Gly
305                 310                 315                 320

Val Arg Val Glu Val Thr Ser Ser Ala Thr Gly Leu Thr His Thr Ile
                325                 330                 335

Glu Ala Asp Val Ile Val Tyr Ala Thr Gly Tyr Arg Pro Ser Asp Pro
            340                 345                 350

Ala Pro Leu Leu Gln Gly Leu Met Arg Glu Cys Lys His Asp Glu Gln
        355                 360                 365

Gly Arg Leu Ser Val Gly Arg Asp Tyr Arg Val Thr Thr Ser Asp Ala
    370                 375                 380

Val Arg Ala Gly Ile Tyr Val His Gly Ala Ser Thr Glu His Ser His
385                 390                 395                 400

Gly Leu Ser Ala Gly Leu Leu Ser Asn Thr Ala Val Arg Ser Gly Glu
                405                 410                 415

Ile Ala Gln Ser Ile Leu Arg Arg
            420
```

<210> SEQ ID NO 68
<211> LENGTH: 424
<212> TYPE: PRT

<213> ORGANISM: Rhodococcus fascians

<400> SEQUENCE: 68

Met Gly Ala Gln Ser Gly Ser Ser Val Ala Asp Val Val Gly Val Gly
1 5 10 15

Phe Gly Pro Ser Asn Leu Ala Leu Ala Ile Ala Leu Gln Glu Ser Ile
20 25 30

Gln Pro Gly Pro Val Pro Ala Lys Phe Ser Met Lys Phe Tyr Glu Leu
35 40 45

Gln Pro Arg Phe Gly Trp His Arg Gly Met Leu Met Glu Asp Ala Thr
50 55 60

Met Gln Val Ser Phe Leu Lys Asp Leu Ala Thr Met Arg Asn Pro Met
65 70 75 80

Ser Arg Tyr Thr Phe Val Ser Tyr Leu Arg Glu Lys Glu Arg Ile Ala
85 90 95

Glu Phe Ile Asn Ser Lys Thr Leu Tyr Pro Leu Arg Val Glu Phe His
100 105 110

Asp Tyr Leu Glu Trp Ala Ala Ser Gln Phe Gln Ser Asn Val Ser Tyr
115 120 125

Gly Ser Glu Ile Lys Asp Ile Arg Pro Val Val Glu Asn Gly Val Val
130 135 140

Glu Tyr Val Asp Val Val Gly Pro Asp Asp Val Val Gln Arg Ala Arg
145 150 155 160

Asn Ile Val Ile Gly Met Gly Leu Thr Pro Arg Leu Pro Asp Gly Val
165 170 175

Asn Arg Ser Glu Arg Ile Trp His Ser Ser Gln Leu Leu Gly Arg Ala
180 185 190

Ala Ala Val Thr Tyr Val Pro Gln Asn Phe Val Val Val Gly Ser Gly
195 200 205

Gln Ser Ala Ala Glu Val Ala Asp Tyr Leu His Arg Thr Phe Pro Arg
210 215 220

Ala Asn Val His Thr Val Leu Ser Arg Tyr Gly Tyr Ser Val Ala Asp
225 230 235 240

Asp Ser Pro Tyr Ala Asn Gly Ile Phe Asp Pro Glu Gly Val Asp Arg
245 250 255

Phe Phe Ser Ala Pro Thr Asp Glu Lys Gln Arg Leu Leu Glu Tyr His
260 265 270

Ala Asn Thr Asn Tyr Ser Val Val Asp Leu Asp Ile Ser Gln Ser Leu
275 280 285

Tyr Leu Lys Ser Tyr Gln Glu Lys Val Leu Gly Lys Gln Arg Leu Arg
290 295 300

Met Ile Asn Thr Ser Arg Val Thr Ser Val Asp Glu Asp Thr Asp Gly
305 310 315 320

Val Arg Val Glu Val Thr Ser Ser Ala Thr Gly Leu Thr His Thr Ile
325 330 335

Glu Ala Asp Val Ile Val Tyr Ala Thr Gly Tyr Arg Pro Ser Asp Pro
340 345 350

Ala Pro Leu Leu Gln Gly Leu Met Arg Glu Cys Lys His Asp Glu Gln
355 360 365

Gly Arg Leu Ser Val Gly Arg Asp Tyr Arg Val Thr Thr Ser Asp Ala
370 375 380

Val Arg Ala Gly Ile Tyr Val His Gly Ala Ser Thr Glu His Ser His
385 390 395 400

```
Gly Leu Ser Ala Gly Leu Leu Ser Asn Thr Ala Val Arg Ser Gly Glu
            405                 410                 415

Ile Ala Gln Ser Ile Leu Arg Arg
            420


<210> SEQ ID NO 69
<211> LENGTH: 424
<212> TYPE: PRT
<213> ORGANISM: Rhodococcus fascians

<400> SEQUENCE: 69

Met Gly Ala Gln Ser Gly Ser Ser Val Ala Asp Val Val Gly Val Gly
1               5                   10                  15

Phe Gly Pro Ser Asn Leu Ala Leu Ala Ile Ala Leu Gln Glu Ser Ile
            20                  25                  30

Gln Pro Gly Pro Val Pro Ala Lys Phe Ser Met Lys Phe Tyr Glu Leu
        35                  40                  45

Gln Pro Arg Phe Gly Trp His Arg Gly Met Leu Met Glu Asp Ala Thr
    50                  55                  60

Met Gln Val Ser Phe Leu Lys Asp Leu Ala Thr Met Arg Asn Pro Met
65                  70                  75                  80

Ser Arg Tyr Thr Phe Val Ser Tyr Leu Arg Glu Lys Glu Arg Ile Ala
                85                  90                  95

Glu Phe Ile Asn Ser Lys Thr Leu Tyr Pro Leu Arg Val Glu Phe His
            100                 105                 110

Asp Tyr Leu Glu Trp Ala Ala Ser Gln Phe Gln Ser Asn Val Ser Tyr
        115                 120                 125

Gly Ser Glu Ile Lys Asp Ile Arg Pro Val Val Glu Asn Gly Val Val
    130                 135                 140

Glu Tyr Val Asp Val Val Gly Pro Asp Asp Val Val Gln Arg Ala Arg
145                 150                 155                 160

Asn Ile Val Ile Gly Met Gly Leu Thr Pro Arg Leu Pro Asp Gly Val
                165                 170                 175

Asn Arg Ser Glu Arg Ile Trp His Ser Ser Gln Leu Leu Gly Arg Ala
            180                 185                 190

Ala Ala Val Thr Tyr Val Pro Gln Asn Phe Val Val Val Gly Ser Gly
        195                 200                 205

Gln Ser Ala Ala Glu Val Ala Asp Tyr Leu His Arg Thr Phe Pro Arg
    210                 215                 220

Ala Asn Val His Thr Val Leu Ser Arg Tyr Gly Tyr Ser Val Ala Asp
225                 230                 235                 240

Asp Ser Pro Tyr Ala Asn Gly Ile Phe Asp Pro Glu Gly Val Asp Arg
                245                 250                 255

Phe Phe Ser Ala Pro Thr Asp Glu Lys Gln Arg Leu Leu Glu Tyr His
            260                 265                 270

Ala Asn Thr Asn Tyr Ser Val Val Asp Leu Asp Ile Ser Gln Ser Leu
        275                 280                 285

Tyr Leu Lys Ser Tyr Gln Glu Lys Val Leu Gly Lys Gln Arg Leu Arg
    290                 295                 300

Met Ile Asn Thr Ser Arg Val Thr Ser Val Asp Glu Asp Thr Asp Gly
305                 310                 315                 320

Val Arg Val Glu Val Thr Ser Ser Ala Thr Gly Leu Thr His Thr Ile
                325                 330                 335

Glu Ala Asp Val Ile Val Tyr Ala Thr Gly Tyr Arg Pro Ser Asp Pro
            340                 345                 350
```

```
Ala Pro Leu Leu Gln Gly Leu Met Arg Glu Cys Lys His Asp Glu Gln
        355                 360                 365

Gly Arg Leu Ser Val Gly Arg Asp Tyr Arg Val Thr Thr Ser Asp Ala
    370                 375                 380

Val Arg Ala Gly Ile Tyr Val His Gly Ala Ser Thr Glu His Ser His
385                 390                 395                 400

Gly Leu Ser Ala Gly Leu Leu Ser Asn Thr Ala Val Arg Ser Gly Glu
                405                 410                 415

Ile Ala Gln Ser Ile Leu Arg Arg
            420


<210> SEQ ID NO 70
<211> LENGTH: 424
<212> TYPE: PRT
<213> ORGANISM: Rhodococcus fascians

<400> SEQUENCE: 70

Met Gly Ala Gln Ser Gly Ser Ser Val Ala Asp Val Val Gly Val Gly
1               5                   10                  15

Phe Gly Pro Ser Asn Leu Ala Leu Ala Ile Ala Leu Gln Glu Ser Ile
            20                  25                  30

Gln Pro Gly Pro Val Pro Ala Lys Phe Ser Met Lys Phe Tyr Glu Leu
        35                  40                  45

Gln Pro Arg Phe Gly Trp His Arg Gly Met Leu Met Glu Asp Ala Thr
    50                  55                  60

Met Gln Val Ser Phe Leu Lys Asp Leu Ala Thr Met Arg Asn Pro Met
65                  70                  75                  80

Ser Arg Tyr Thr Phe Val Ser Tyr Leu Arg Glu Lys Glu Arg Ile Ala
                85                  90                  95

Glu Phe Ile Asn Ser Lys Thr Leu Tyr Pro Leu Arg Val Glu Phe His
            100                 105                 110

Asp Tyr Leu Glu Trp Ala Ala Ser Gln Phe Gln Ser Asn Val Ser Tyr
        115                 120                 125

Gly Ser Glu Ile Lys Asp Ile Arg Pro Val Val Glu Asn Gly Val Val
    130                 135                 140

Glu Tyr Val Asp Val Val Gly Pro Asp Asp Val Val Gln Arg Ala Arg
145                 150                 155                 160

Asn Ile Val Ile Gly Met Gly Leu Thr Pro Arg Leu Pro Asp Gly Val
                165                 170                 175

Asn Arg Ser Glu Arg Ile Trp His Ser Ser Gln Leu Leu Gly Arg Ala
            180                 185                 190

Ala Ala Val Thr Tyr Val Pro Gln Asn Phe Val Val Val Gly Ser Gly
        195                 200                 205

Gln Ser Ala Ala Glu Val Ala Asp Tyr Leu His Arg Thr Phe Pro Arg
    210                 215                 220

Ala Asn Val His Thr Val Leu Ser Arg Tyr Gly Tyr Ser Val Ala Asp
225                 230                 235                 240

Asp Ser Pro Tyr Ala Asn Gly Ile Phe Asp Pro Glu Gly Val Asp Arg
                245                 250                 255

Phe Phe Ser Ala Pro Thr Asp Glu Lys Gln Arg Leu Leu Glu Tyr His
            260                 265                 270

Ala Asn Thr Asn Tyr Ser Val Val Asp Leu Asp Ile Ser Gln Ser Leu
        275                 280                 285

Tyr Leu Lys Ser Tyr Gln Glu Lys Val Leu Gly Lys Gln Arg Leu Arg
```

```
    290                 295                 300

Met Ile Asn Thr Ser Arg Val Thr Ser Val Asp Glu Asp Thr Asp Gly
305                 310                 315                 320

Val Arg Val Glu Val Thr Ser Ser Ala Thr Gly Leu Thr His Thr Ile
                325                 330                 335

Glu Ala Asp Val Ile Val Tyr Ala Thr Gly Tyr Arg Pro Ser Asp Pro
            340                 345                 350

Ala Pro Leu Leu Gln Gly Leu Met Arg Glu Cys Lys His Asp Glu Gln
        355                 360                 365

Gly Arg Leu Ser Val Gly Arg Asp Tyr Arg Val Thr Thr Ser Asp Ala
    370                 375                 380

Val Arg Ala Gly Ile Tyr Val His Gly Ala Ser Thr Glu His Ser His
385                 390                 395                 400

Gly Leu Ser Ala Gly Leu Leu Ser Asn Thr Ala Val Arg Ser Gly Glu
                405                 410                 415

Ile Ala Gln Ser Ile Leu Arg Arg
            420


<210> SEQ ID NO 71
<211> LENGTH: 424
<212> TYPE: PRT
<213> ORGANISM: Rhodococcus fascians

<400> SEQUENCE: 71

Met Gly Ala Gln Ser Gly Ser Ser Val Ala Asp Val Val Gly Val Gly
1               5                   10                  15

Phe Gly Pro Ser Asn Leu Ala Leu Ala Ile Ala Leu Gln Glu Ser Ile
            20                  25                  30

Gln Pro Gly Pro Val Pro Ala Lys Phe Ser Met Lys Phe Tyr Glu Leu
        35                  40                  45

Gln Pro Arg Phe Gly Trp His Arg Gly Met Leu Met Glu Asp Ala Thr
    50                  55                  60

Met Gln Val Ser Phe Leu Lys Asp Leu Ala Thr Met Arg Asn Pro Met
65                  70                  75                  80

Ser Arg Tyr Thr Phe Val Ser Tyr Leu Arg Glu Lys Glu Arg Ile Ala
                85                  90                  95

Glu Phe Ile Asn Ser Lys Thr Leu Tyr Pro Leu Arg Val Glu Phe His
            100                 105                 110

Asp Tyr Leu Glu Trp Ala Ala Ser Gln Phe Gln Ser Asn Val Ser Tyr
        115                 120                 125

Gly Ser Glu Ile Lys Asp Ile Arg Pro Val Val Glu Asn Gly Val Val
    130                 135                 140

Glu Tyr Val Asp Val Val Gly Pro Asp Asp Val Val Gln Arg Ala Arg
145                 150                 155                 160

Asn Ile Val Ile Gly Met Gly Leu Thr Pro Arg Leu Pro Asp Gly Val
                165                 170                 175

Asn Arg Ser Glu Arg Ile Trp His Ser Ser Gln Leu Leu Gly Arg Ala
            180                 185                 190

Ala Ala Val Thr Tyr Val Pro Gln Asn Phe Val Val Val Gly Ser Gly
        195                 200                 205

Gln Ser Ala Ala Glu Val Ala Asp Tyr Leu His Arg Thr Phe Pro Arg
    210                 215                 220

Ala Asn Val His Thr Val Leu Ser Arg Tyr Gly Tyr Ser Val Ala Asp
225                 230                 235                 240
```

```
Asp Ser Pro Tyr Ala Asn Gly Ile Phe Asp Pro Glu Gly Val Asp Arg
                245                 250                 255

Phe Phe Ser Ala Pro Thr Asp Glu Lys Gln Arg Leu Leu Glu Tyr His
            260                 265                 270

Ala Asn Thr Asn Tyr Ser Val Val Asp Leu Asp Ile Ser Gln Ser Leu
        275                 280                 285

Tyr Leu Lys Ser Tyr Gln Glu Lys Val Leu Gly Lys Gln Arg Leu Arg
    290                 295                 300

Met Ile Asn Thr Ser Arg Val Thr Ser Val Asp Glu Asp Thr Asp Gly
305                 310                 315                 320

Val Arg Val Glu Val Thr Ser Ser Ala Thr Gly Leu Thr His Thr Ile
                325                 330                 335

Glu Ala Asp Val Ile Val Tyr Ala Thr Gly Tyr Arg Pro Ser Asp Pro
            340                 345                 350

Ala Pro Leu Leu Gln Gly Leu Met Arg Glu Cys Lys His Asp Glu Gln
        355                 360                 365

Gly Arg Leu Ser Val Gly Arg Asp Tyr Arg Val Thr Thr Ser Asp Ala
    370                 375                 380

Val Arg Ala Gly Ile Tyr Val His Gly Ala Ser Thr Glu His Ser His
385                 390                 395                 400

Gly Leu Ser Ala Gly Leu Leu Ser Asn Thr Ala Val Arg Ser Gly Glu
                405                 410                 415

Ile Ala Gln Ser Ile Leu Arg Arg
            420
```

<210> SEQ ID NO 72
<211> LENGTH: 447
<212> TYPE: PRT
<213> ORGANISM: Salinispora arenicola

<400> SEQUENCE: 72

```
Met Ser Asn Gln His Glu Thr Tyr Asp Leu Val Gly Ile Gly Phe Gly
1               5                   10                  15

Pro Ser Asn Leu Ser Leu Ala Ile Ala Leu Lys Glu Tyr Glu Ala Asn
            20                  25                  30

Gly Gln Glu Asn Gly Ile Ser Thr Leu Phe Phe Glu Arg Gln Ser Ser
        35                  40                  45

Phe Gly Trp His Arg Asn Met Leu Leu Pro Ser Thr Thr Met Gln Ile
    50                  55                  60

Ser Phe Leu Lys Asp Leu Val Thr Phe Arg Asn Pro Thr Ser Gly Phe
65                  70                  75                  80

Ser Phe Ile Ser Tyr Leu His Ala Ser Gly Arg Leu Pro Gln Phe Val
                85                  90                  95

Asn Asn Gln Asp Phe Phe Pro Thr Arg Gln Glu Phe His Gln Tyr Leu
            100                 105                 110

Glu Trp Ala Glu Glu Arg Met Ala Gly Arg Val Ala Tyr Gly Ser Glu
        115                 120                 125

Val Thr Ser Ile Arg Leu Pro Ser Gly Thr Val Pro Glu Leu Ser Asp
    130                 135                 140

Arg Leu Arg Leu Glu Val Thr Asp Ala Ala Gly Arg Val Gly Arg Val
145                 150                 155                 160

Val Glu Ala Arg Asn Val Val Ile Ser Thr Gly Leu Val Pro Arg Met
                165                 170                 175

Pro Glu Gly Ile Glu Arg Asp Glu Arg Val Trp His Ser Ser Glu Phe
            180                 185                 190
```

-continued

Leu Gln Lys Tyr Arg Arg Met Asn Pro Gly Asp Leu Arg Arg Val Ala
        195                 200                 205

Val Val Gly Ala Gly Gln Ser Ala Ala Glu Ile Thr Arg Phe Leu His
    210                 215                 220

Asp Glu Leu Pro His Ala Glu Val Trp Val Val Ile Pro Ser Tyr Gly
225                 230                 235                 240

Tyr Ser Val Ala Asp Asp Thr Pro Phe Ala Asn Gln Ile Phe Asp Pro
                245                 250                 255

Glu Ala Val Asp Asp Tyr Tyr Phe Gly Thr Glu Gln Thr Arg Asp Ala
            260                 265                 270

Phe Trp Arg Tyr His Arg Asn Thr Asn Tyr Ser Val Val Asp Asp Glu
        275                 280                 285

Val Ile Arg Asp Leu Tyr Arg Arg Val Tyr Asp Ala Glu Val Arg Gly
    290                 295                 300

Ile Lys Arg Leu Gln Ile Leu Asn Leu Thr Arg Ile Thr Gly Val Lys
305                 310                 315                 320

Arg Ala Ala Ala Glu Thr Arg Val Glu Leu Gln Val Gly Pro Asp Ser
                325                 330                 335

Glu Val Arg Glu Leu Asp Val Asp Ala Leu Val Cys Ala Thr Gly Tyr
            340                 345                 350

Asp Gly Met Glu Pro Thr His Leu Leu Gly Asp Leu Asp Arg Leu Cys
        355                 360                 365

Leu Arg Asp Lys Ala Gly Arg His Gln Ile Glu Arg Asp Tyr Arg Ile
    370                 375                 380

Ala Thr Ala Pro Glu Met Arg Cys Gly Ile Tyr Leu Gln Gly Gly Thr
385                 390                 395                 400

Glu His Thr His Gly Leu Ser Ser Ser Leu Leu Ser Asn Ile Ala Val
                405                 410                 415

Arg Ser Gly Glu Ile Ala Asp Ser Ile Val Ser Arg Arg Ala Arg His
            420                 425                 430

Asn Ser Glu Tyr Ala Leu Ala Ala Gly Ala Glu Gly Asp Thr Cys
        435                 440                 445

<210> SEQ ID NO 73
<211> LENGTH: 447
<212> TYPE: PRT
<213> ORGANISM: Salinispora arenicola

<400> SEQUENCE: 73

Met Ser Asn Gln His Glu Thr Tyr Asp Leu Val Gly Ile Gly Phe Gly
1               5                   10                  15

Pro Ser Asn Leu Ser Leu Ala Ile Ala Leu Lys Glu Tyr Glu Ala Asn
            20                  25                  30

Gly Gln Glu Asn Gly Ile Ser Thr Leu Phe Phe Glu Arg Gln Ser Ser
        35                  40                  45

Phe Gly Trp His Arg Asn Met Leu Leu Pro Ser Thr Thr Met Gln Ile
    50                  55                  60

Ser Phe Leu Lys Asp Leu Val Thr Phe Arg Asn Pro Thr Ser Gly Phe
65                  70                  75                  80

Ser Phe Ile Ser Tyr Leu His Ala Ser Gly Arg Leu Pro Gln Phe Val
                85                  90                  95

Asn Asn Gln Asp Phe Phe Pro Thr Arg Gln Glu Phe His Gln Tyr Leu
            100                 105                 110

Glu Trp Ala Glu Glu Arg Met Ala Gly Arg Val Ala Tyr Gly Ser Glu 115 120 125

Val Thr Ser Ile Arg Leu Pro Ser Gly Thr Val Pro Glu Leu Ser Asp
130 135 140

Arg Leu Arg Leu Glu Val Thr Asp Ala Ala Gly Arg Val Gly Arg Val
145 150 155 160

Val Glu Ala Arg Asn Val Val Ile Ser Thr Gly Leu Val Pro Arg Met
165 170 175

Pro Glu Gly Ile Glu Arg Asp Glu Arg Val Trp His Ser Ser Glu Phe
180 185 190

Leu Gln Lys Tyr Arg Arg Met Asn Pro Gly Asp Leu Arg Arg Val Ala
195 200 205

Val Val Gly Ala Gly Gln Ser Ala Ala Glu Ile Thr Arg Phe Leu His
210 215 220

Asp Glu Leu Pro His Ala Glu Val Trp Val Val Ile Pro Ser Tyr Gly
225 230 235 240

Tyr Ser Val Ala Asp Asp Thr Pro Phe Ala Asn Gln Ile Phe Asp Pro
245 250 255

Glu Ala Val Asp Asp Tyr Tyr Phe Gly Thr Glu Gln Thr Arg Asp Ala
260 265 270

Phe Trp Arg Tyr His Arg Asn Thr Asn Tyr Ser Val Val Asp Asp Glu
275 280 285

Val Ile Arg Asp Leu Tyr Arg Arg Val Tyr Asp Ala Glu Val Arg Gly
290 295 300

Ile Lys Arg Leu Gln Ile Leu Asn Leu Thr Arg Ile Thr Gly Val Lys
305 310 315 320

Arg Ala Ala Ala Glu Thr Arg Val Glu Leu Gln Val Gly Pro Asp Ser
325 330 335

Glu Val Arg Glu Leu Asp Val Asp Ala Leu Val Cys Ala Thr Gly Tyr
340 345 350

Asp Gly Met Glu Pro Thr His Leu Leu Gly Asp Leu Asp Arg Leu Cys
355 360 365

Leu Arg Asp Lys Ala Gly Arg His Gln Ile Glu Arg Asp Tyr Arg Ile
370 375 380

Ala Thr Ala Pro Glu Met Arg Cys Gly Ile Tyr Leu Gln Gly Gly Thr
385 390 395 400

Glu His Thr His Gly Leu Ser Ser Ser Leu Leu Ser Asn Ile Ala Val
405 410 415

Arg Ser Gly Glu Ile Ala Asp Ser Ile Val Ser Arg Arg Ala Arg His
420 425 430

Asn Ser Glu Tyr Ala Leu Ala Ala Gly Ala Glu Gly Asp Thr Cys
435 440 445

<210> SEQ ID NO 74
<211> LENGTH: 447
<212> TYPE: PRT
<213> ORGANISM: Salinispora arenicola

<400> SEQUENCE: 74

Met Ser Asn Gln His Glu Thr Tyr Asp Leu Val Gly Ile Gly Phe Gly
1 5 10 15

Pro Ser Asn Leu Ser Leu Ala Ile Ala Leu Lys Glu Tyr Glu Ala Asn
20 25 30

Gly Gln Glu Asn Gly Ile Ser Thr Leu Phe Phe Glu Arg Gln Ser Ser
35 40 45

```
Phe Gly Trp His Arg Asn Met Leu Leu Pro Ser Thr Thr Met Gln Ile
    50                  55                  60

Ser Phe Leu Lys Asp Leu Val Thr Phe Arg Asn Pro Thr Ser Gly Phe
65                  70                  75                  80

Ser Phe Ile Ser Tyr Leu His Ala Ser Gly Arg Leu Pro Gln Phe Val
                85                  90                  95

Asn Asn Gln Asp Phe Phe Pro Thr Arg Gln Glu Phe His Gln Tyr Leu
            100                 105                 110

Glu Trp Ala Glu Glu Arg Met Ala Gly Arg Val Ala Tyr Gly Ser Glu
        115                 120                 125

Val Thr Ser Ile Arg Leu Pro Ser Gly Thr Val Pro Glu Leu Ser Asp
    130                 135                 140

Arg Leu Arg Leu Glu Val Thr Asp Ala Ala Gly Arg Val Gly Arg Val
145                 150                 155                 160

Val Glu Ala Arg Asn Val Val Ile Ser Thr Gly Leu Val Pro Arg Met
                165                 170                 175

Pro Glu Gly Ile Glu Arg Asp Glu Arg Val Trp His Ser Ser Glu Phe
            180                 185                 190

Leu Gln Lys Tyr Arg Arg Met Asn Pro Gly Asp Leu Arg Arg Val Ala
        195                 200                 205

Val Val Gly Ala Gly Gln Ser Ala Ala Glu Ile Thr Arg Phe Leu His
    210                 215                 220

Asp Glu Leu Pro His Ala Glu Val Trp Val Val Ile Pro Ser Tyr Gly
225                 230                 235                 240

Tyr Ser Val Ala Asp Asp Thr Pro Phe Ala Asn Gln Ile Phe Asp Pro
                245                 250                 255

Glu Ala Val Asp Asp Tyr Tyr Phe Gly Thr Glu Gln Thr Arg Asp Ala
            260                 265                 270

Phe Trp Arg Tyr His Arg Asn Thr Asn Tyr Ser Val Val Asp Asp Glu
        275                 280                 285

Val Ile Arg Asp Leu Tyr Arg Arg Val Tyr Asp Ala Glu Val Arg Gly
    290                 295                 300

Ile Lys Arg Leu Gln Ile Leu Asn Leu Thr Arg Ile Thr Gly Val Lys
305                 310                 315                 320

Arg Ala Ala Ala Glu Thr Arg Val Glu Leu Gln Val Gly Pro Asp Ser
                325                 330                 335

Glu Val Arg Glu Leu Asp Val Asp Ala Leu Val Cys Ala Thr Gly Tyr
            340                 345                 350

Asp Gly Met Glu Pro Thr His Leu Leu Gly Asp Leu Asp Arg Leu Cys
        355                 360                 365

Leu Arg Asp Lys Ala Gly Arg His Gln Ile Glu Arg Asp Tyr Arg Ile
    370                 375                 380

Ala Thr Ala Pro Glu Met Arg Cys Gly Ile Tyr Leu Gln Gly Gly Thr
385                 390                 395                 400

Glu His Thr His Gly Leu Ser Ser Ser Leu Leu Ser Asn Ile Ala Val
                405                 410                 415

Arg Ser Gly Glu Ile Ala Asp Ser Ile Val Ser Arg Arg Ala Arg His
            420                 425                 430

Asn Ser Glu Tyr Ala Leu Ala Ala Gly Ala Glu Gly Asp Thr Cys
        435                 440                 445
```

<210> SEQ ID NO 75
<211> LENGTH: 447
<212> TYPE: PRT

<213> ORGANISM: Salinispora arenicola

<400> SEQUENCE: 75

Met Ser Asn Gln His Glu Thr Tyr Asp Leu Val Gly Ile Gly Phe Gly
1 5 10 15

Pro Ser Asn Leu Ser Leu Ala Ile Ala Leu Lys Glu Tyr Glu Ala Asn
20 25 30

Gly Gln Glu Asn Gly Ile Ser Thr Leu Phe Phe Glu Arg Gln Ser Ser
35 40 45

Phe Gly Trp His Arg Asn Met Leu Leu Pro Ser Thr Thr Met Gln Ile
50 55 60

Ser Phe Leu Lys Asp Leu Val Thr Phe Arg Asn Pro Thr Ser Gly Phe
65 70 75 80

Ser Phe Ile Ser Tyr Leu His Ala Ser Gly Arg Leu Pro Gln Phe Val
85 90 95

Asn Asn Gln Asp Phe Phe Pro Thr Arg Gln Glu Phe His Gln Tyr Leu
100 105 110

Glu Trp Ala Glu Glu Arg Met Ala Gly Arg Val Ala Tyr Gly Ser Glu
115 120 125

Val Thr Ser Ile Arg Leu Pro Ser Gly Thr Val Pro Glu Leu Ser Asp
130 135 140

Arg Leu Arg Leu Glu Val Thr Asp Ala Ala Gly Arg Val Gly Arg Val
145 150 155 160

Val Glu Ala Arg Asn Val Val Ile Ser Thr Gly Leu Val Pro Arg Met
165 170 175

Pro Glu Gly Ile Glu Arg Asp Glu Arg Val Trp His Ser Ser Glu Phe
180 185 190

Leu Gln Lys Tyr Arg Arg Met Asn Pro Gly Asp Leu Arg Arg Val Ala
195 200 205

Val Val Gly Ala Gly Gln Ser Ala Ala Glu Ile Thr Arg Phe Leu His
210 215 220

Asp Glu Leu Pro His Ala Glu Val Trp Val Val Ile Pro Ser Tyr Gly
225 230 235 240

Tyr Ser Val Ala Asp Asp Thr Pro Phe Ala Asn Gln Ile Phe Asp Pro
245 250 255

Glu Ala Val Asp Asp Tyr Tyr Phe Gly Thr Glu Gln Thr Arg Asp Ala
260 265 270

Phe Trp Arg Tyr His Arg Asn Thr Asn Tyr Ser Val Val Asp Asp Glu
275 280 285

Val Ile Arg Asp Leu Tyr Arg Arg Val Tyr Asp Ala Glu Val Arg Gly
290 295 300

Ile Lys Arg Leu Gln Ile Leu Asn Leu Thr Arg Ile Thr Gly Val Lys
305 310 315 320

Arg Ala Ala Ala Glu Thr Arg Val Glu Leu Gln Val Gly Pro Asp Ser
325 330 335

Glu Val Arg Glu Leu Asp Val Asp Ala Leu Val Cys Ala Thr Gly Tyr
340 345 350

Asp Gly Met Glu Pro Thr His Leu Leu Gly Asp Leu Asp Arg Leu Cys
355 360 365

Leu Arg Asp Lys Ala Gly Arg His Gln Ile Glu Arg Asp Tyr Arg Ile
370 375 380

Ala Thr Ala Pro Glu Met Arg Cys Gly Ile Tyr Leu Gln Gly Gly Thr
385 390 395 400

Glu His Thr His Gly Leu Ser Ser Ser Leu Leu Ser Asn Ile Ala Val
405 410 415

Arg Ser Gly Glu Ile Ala Asp Ser Ile Val Ser Arg Arg Ala Arg His
420 425 430

Asn Ser Glu Tyr Ala Leu Ala Ala Gly Ala Glu Gly Asp Thr Cys
435 440 445

<210> SEQ ID NO 76
<211> LENGTH: 447
<212> TYPE: PRT
<213> ORGANISM: Salinispora arenicola

<400> SEQUENCE: 76

Met Ser Asn Gln His Glu Thr Tyr Asp Leu Val Gly Ile Gly Phe Gly
1 5 10 15

Pro Ser Asn Leu Ser Leu Ala Ile Ala Leu Lys Glu Tyr Glu Ala Asn
20 25 30

Gly Gln Glu Asn Gly Ile Ser Thr Leu Phe Phe Glu Arg Gln Ser Ser
35 40 45

Phe Gly Trp His Arg Asn Met Leu Leu Pro Ser Thr Thr Met Gln Ile
50 55 60

Ser Phe Leu Lys Asp Leu Val Thr Phe Arg Asn Pro Thr Ser Gly Phe
65 70 75 80

Ser Phe Ile Ser Tyr Leu His Ala Ser Gly Arg Leu Pro Gln Phe Val
85 90 95

Asn Asn Gln Asp Phe Phe Pro Thr Arg Gln Glu Phe His Gln Tyr Leu
100 105 110

Glu Trp Ala Glu Glu Arg Met Ala Gly Arg Val Ala Tyr Cys Ser Glu
115 120 125

Val Thr Ser Ile Arg Leu Pro Ser Gly Thr Val Pro Glu Leu Ser Asp
130 135 140

Arg Leu Arg Leu Glu Val Thr Asp Ala Ala Gly Arg Val Gly Arg Val
145 150 155 160

Val Glu Ala Arg Asn Val Val Ile Ser Thr Gly Leu Val Pro Arg Met
165 170 175

Pro Glu Gly Ile Glu Arg Asp Glu Arg Val Trp His Ser Ser Glu Phe
180 185 190

Leu Gln Lys Tyr Arg Arg Met Asn Pro Gly Asp Leu Arg Arg Val Ala
195 200 205

Val Val Gly Ala Gly Gln Ser Ala Ala Glu Ile Thr Arg Phe Leu His
210 215 220

Asp Glu Leu Pro His Ala Glu Val Trp Val Val Ile Pro Ser Tyr Gly
225 230 235 240

Tyr Ser Val Ala Asp Asp Thr Pro Phe Ala Asn Gln Ile Phe Asp Pro
245 250 255

Glu Ala Val Asp Asp Tyr Tyr Phe Gly Thr Glu Gln Thr Arg Asp Ala
260 265 270

Phe Trp Arg Tyr His Arg Asn Thr Asn Tyr Ser Val Val Asp Asp Glu
275 280 285

Val Ile Arg Asp Leu Tyr Arg Arg Val Tyr Asp Ala Glu Val Arg Gly
290 295 300

Ile Lys Arg Leu Gln Ile Leu Asn Leu Thr Arg Ile Thr Gly Val Lys
305 310 315 320

Arg Ala Ala Ala Glu Thr Arg Val Glu Leu Gln Val Gly Pro Asp Ser
325 330 335

```
Glu Val Arg Glu Leu Asp Val Asp Ala Leu Val Cys Ala Thr Gly Tyr
            340                 345                 350

Asp Gly Met Glu Pro Thr His Leu Leu Gly Asp Leu Asp Arg Leu Cys
        355                 360                 365

Leu Arg Asp Lys Ala Gly Arg His Gln Ile Glu Arg Asp Tyr Arg Ile
    370                 375                 380

Ala Thr Ala Pro Glu Met Arg Cys Gly Ile Tyr Leu Gln Gly Gly Thr
385                 390                 395                 400

Glu His Thr His Gly Leu Ser Ser Ser Leu Leu Ser Asn Ile Ala Val
                405                 410                 415

Arg Ser Gly Glu Ile Ala Asp Ser Ile Val Ser Arg Arg Ala Arg His
            420                 425                 430

Asn Ser Glu Tyr Ala Leu Ala Ala Gly Ala Glu Gly Asp Thr Cys
        435                 440                 445


<210> SEQ ID NO 77
<211> LENGTH: 447
<212> TYPE: PRT
<213> ORGANISM: Salinispora arenicola

<400> SEQUENCE: 77

Met Ser Asn Gln His Glu Thr Tyr Asp Leu Val Gly Ile Gly Phe Gly
1               5                   10                  15

Pro Ser Asn Leu Ser Leu Ala Ile Ala Leu Lys Glu Tyr Glu Ala Asn
            20                  25                  30

Gly Gln Glu Asn Gly Ile Ser Thr Leu Phe Phe Glu Arg Gln Ser Ser
        35                  40                  45

Phe Gly Trp His Arg Asn Met Leu Leu Pro Ser Thr Thr Met Gln Ile
    50                  55                  60

Ser Phe Leu Lys Asp Leu Val Thr Phe Arg Asn Pro Thr Ser Gly Phe
65                  70                  75                  80

Ser Phe Ile Ser Tyr Leu His Ala Ser Gly Arg Leu Pro Gln Phe Val
                85                  90                  95

Asn Asn Gln Asp Phe Phe Pro Thr Arg Gln Glu Phe His Gln Tyr Leu
            100                 105                 110

Glu Trp Ala Glu Glu Arg Met Ala Gly Arg Val Ala Tyr Cys Ser Glu
        115                 120                 125

Val Thr Ser Ile Arg Leu Pro Ser Gly Thr Val Pro Glu Leu Ser Asp
    130                 135                 140

Arg Leu Arg Leu Glu Val Thr Asp Ala Ala Gly Arg Val Gly Arg Val
145                 150                 155                 160

Val Glu Ala Arg Asn Val Val Ile Ser Thr Gly Leu Val Pro Arg Met
                165                 170                 175

Pro Glu Gly Ile Glu Arg Asp Glu Arg Val Trp His Ser Ser Glu Phe
            180                 185                 190

Leu Gln Lys Tyr Arg Arg Met Asn Pro Gly Asp Leu Arg Arg Val Ala
        195                 200                 205

Val Val Gly Ala Gly Gln Ser Ala Ala Glu Ile Thr Arg Phe Leu His
    210                 215                 220

Asp Glu Leu Pro His Ala Glu Val Trp Val Val Ile Pro Ser Tyr Gly
225                 230                 235                 240

Tyr Ser Val Ala Asp Asp Thr Pro Phe Ala Asn Gln Ile Phe Asp Pro
                245                 250                 255

Glu Ala Val Asp Asp Tyr Tyr Phe Gly Thr Glu Gln Thr Arg Asp Ala
```

```
            260                 265                 270

Phe Trp Arg Tyr His Arg Asn Thr Asn Tyr Ser Val Val Asp Asp Glu
        275                 280                 285

Val Ile Arg Asp Leu Tyr Arg Arg Val Tyr Asp Ala Glu Val Arg Gly
    290                 295                 300

Ile Lys Arg Leu Gln Ile Leu Asn Leu Thr Arg Ile Thr Gly Val Lys
305                 310                 315                 320

Arg Ala Ala Ala Glu Thr Arg Val Glu Leu Gln Val Gly Pro Asp Ser
                325                 330                 335

Glu Val Arg Glu Leu Asp Val Asp Ala Leu Val Cys Ala Thr Gly Tyr
            340                 345                 350

Asp Gly Met Glu Pro Thr His Leu Leu Gly Asp Leu Asp Arg Leu Cys
        355                 360                 365

Leu Arg Asp Lys Ala Gly Arg His Gln Ile Glu Arg Asp Tyr Arg Ile
    370                 375                 380

Ala Thr Ala Pro Glu Met Arg Cys Gly Ile Tyr Leu Gln Gly Gly Thr
385                 390                 395                 400

Glu His Thr His Gly Leu Ser Ser Ser Leu Leu Ser Asn Ile Ala Val
                405                 410                 415

Arg Ser Gly Glu Ile Ala Asp Ser Ile Val Ser Arg Arg Ala Arg His
            420                 425                 430

Asn Ser Glu Tyr Ala Leu Ala Ala Gly Ala Glu Gly Asp Thr Cys
        435                 440                 445


<210> SEQ ID NO 78
<211> LENGTH: 447
<212> TYPE: PRT
<213> ORGANISM: Salinispora pacifica

<400> SEQUENCE: 78

Met Ser Asn Gln His Glu Thr Tyr Asp Leu Val Gly Ile Gly Phe Gly
1               5                   10                  15

Pro Ser Asn Leu Ser Leu Ala Ile Ala Leu Lys Glu Tyr Glu Ala Asn
            20                  25                  30

Gly Gln Glu Asn Gly Ile Ser Thr Leu Phe Phe Glu Arg Gln Ser Ser
        35                  40                  45

Phe Gly Trp His Arg Asn Met Leu Leu Pro Ser Thr Thr Met Gln Ile
    50                  55                  60

Ser Phe Leu Lys Asp Leu Val Thr Phe Arg Asn Pro Thr Ser Gly Phe
65                  70                  75                  80

Ser Phe Ile Ser Tyr Leu His Ala Ser Gly Arg Leu Pro Gln Phe Val
                85                  90                  95

Asn Asn Gln Asp Phe Phe Pro Thr Arg Gln Glu Phe His Gln Tyr Leu
            100                 105                 110

Glu Trp Ala Glu Glu Arg Met Ala Gly Arg Val Ala Tyr Cys Ser Glu
        115                 120                 125

Val Thr Ser Ile Arg Leu Pro Ser Gly Thr Val Pro Glu Leu Ser Asp
    130                 135                 140

Arg Leu Arg Leu Glu Val Thr Asp Ala Ala Gly Arg Val Gly Arg Val
145                 150                 155                 160

Val Glu Ala Arg Asn Val Val Ile Ser Thr Gly Leu Val Pro Arg Met
                165                 170                 175

Pro Glu Gly Ile Glu Arg Asp Glu Arg Val Trp His Ser Ser Glu Phe
            180                 185                 190
```

-continued

```
Leu Gln Lys Tyr Arg Arg Met Asn Pro Gly Asp Leu Arg Arg Val Ala
        195                 200                 205

Val Val Gly Ala Gly Gln Ser Ala Ala Glu Ile Thr Arg Phe Leu His
    210                 215                 220

Asp Glu Leu Pro His Ala Glu Val Trp Val Val Ile Pro Ser Tyr Gly
225                 230                 235                 240

Tyr Ser Val Ala Asp Asp Thr Pro Phe Ala Asn Gln Ile Phe Asp Pro
                245                 250                 255

Glu Ala Val Asp Asp Tyr Tyr Phe Gly Thr Glu Gln Thr Arg Asp Ala
            260                 265                 270

Phe Trp Arg Tyr His Arg Asn Thr Asn Tyr Ser Val Val Asp Asp Glu
        275                 280                 285

Val Ile Arg Asp Leu Tyr Arg Arg Val Tyr Asp Ala Glu Val Arg Gly
    290                 295                 300

Ile Lys Arg Leu Gln Ile Leu Asn Leu Thr Arg Ile Thr Gly Val Lys
305                 310                 315                 320

Arg Ala Ala Ala Glu Thr Arg Val Glu Leu Gln Val Gly Pro Asp Ser
                325                 330                 335

Glu Val Arg Glu Leu Asp Val Asp Ala Leu Val Cys Ala Thr Gly Tyr
            340                 345                 350

Asp Gly Met Glu Pro Thr His Leu Leu Gly Asp Leu Asp Arg Leu Cys
        355                 360                 365

Leu Arg Asp Lys Ala Gly Arg His Gln Ile Glu Arg Asp Tyr Arg Ile
    370                 375                 380

Ala Thr Ala Pro Glu Met Arg Cys Gly Ile Tyr Leu Gln Gly Gly Thr
385                 390                 395                 400

Glu His Thr His Gly Leu Ser Ser Ser Leu Leu Ser Asn Ile Ala Val
                405                 410                 415

Arg Ser Gly Glu Ile Ala Asp Ser Ile Val Ser Arg Arg Ala Arg His
            420                 425                 430

Asn Ser Glu Tyr Ala Leu Ala Ala Gly Ala Glu Gly Asp Thr Cys
        435                 440                 445


<210> SEQ ID NO 79
<211> LENGTH: 433
<212> TYPE: PRT
<213> ORGANISM: Streptomyces aureofaciens

<400> SEQUENCE: 79

Val Gly Glu Arg Gln Arg Ser Gly Val Val Ala Gly Thr Gly Ile Val
1               5                   10                  15

Asp Val Ala Gly Ile Gly Phe Gly Pro Ser Asn Leu Ala Leu Ala Ala
            20                  25                  30

Ala Ile Ala Glu Ile Ala Gly Glu Ala Pro Val Ser Ala Arg Phe Phe
        35                  40                  45

Glu Ala Gln Pro Arg Phe Gly Trp His Arg Gly Met Leu Ile Glu Gly
    50                  55                  60

Ala Thr Met Gln Val Ser Tyr Leu Lys Asp Leu Val Thr Met Arg Asn
65                  70                  75                  80

Pro Thr Ser Pro Tyr Ser Phe Leu Cys Tyr Leu Gln Ala Arg Gly Arg
                85                  90                  95

Leu Ala Asp Phe Ile Asn Thr Lys Ser Pro Tyr Pro Leu Arg Val Glu
            100                 105                 110

Phe His Asp Tyr Leu Glu Trp Val Ala Glu Ser Phe Ala Asp Leu Val
        115                 120                 125
```

Ser Tyr Gly Ala Arg Val Val Ser Val Glu Pro Val Ser Ala Glu Gln
130 135 140

Gly Val Glu Phe Leu Asp Val His Phe Val Ala Pro Asp Gly Thr Arg
145 150 155 160

Gln Val Gln Arg Ala Arg Asn Leu Val Ile Ala Ala Gly Ile Glu Pro
165 170 175

Arg Leu Pro Ala Gly Leu Pro Ala Ser Pro Arg Ile Trp His Thr Ala
180 185 190

Lys Phe Leu Pro Glu Val Asp Arg Ile Ala Arg Gln Asp Pro Arg Ser
195 200 205

Phe Val Val Leu Gly Ser Gly Gln Ser Ala Ala Glu Ala Ile Glu His
210 215 220

Leu His Ala Arg Phe Pro Arg Ala Gln Val His Ser Val His Ala Arg
225 230 235 240

Tyr Gly Phe Ser Val Ala Asp Asp Ser Pro Phe Ala Asn Gln Val Phe
245 250 255

Asn Pro Glu Ala Val Asp Arg Phe His Thr Ala Pro Asp Asp Val Arg
260 265 270

Gln Arg Leu Ile Asp Tyr His Ala Ser Thr Asn Tyr Ser Val Val Asp
275 280 285

Ala Asp Leu Leu His Ser Leu Phe Gln Gln Ala Tyr Leu Glu Lys Val
290 295 300

Ala Gly Asn Pro Arg Leu Asn Phe His Asn Val Ser Arg Val Ser Glu
305 310 315 320

Val Thr Glu Thr Pro Asp Gly Leu Arg Ile Asp Val Glu Ser Leu Ser
325 330 335

Ser Gly Thr Ser Thr Val Ile Glu Ala Gln Ala Leu Val Cys Ala Thr
340 345 350

Gly Tyr Thr Arg Thr Asp Pro Ala Val Phe Leu Asp Gly Leu Leu Pro
355 360 365

His Cys Pro Leu Asp Asp Gln Gly Arg Leu Arg Leu Asp Arg Glu His
370 375 380

Arg Val Val Thr Asp Glu Ser Val Arg Cys Gly Ile Tyr Val Gln Gly
385 390 395 400

Phe Gly Glu His Ser His Gly Leu Ser Glu Thr Leu Leu Ser Leu Ser
405 410 415

Ala Val Arg Ala Gly Glu Ile Gly Asp Met Leu Val Lys Ala Leu Ser
420 425 430

Gly

<210> SEQ ID NO 80
<211> LENGTH: 447
<212> TYPE: PRT
<213> ORGANISM: Streptomyces sp. OK885

<400> SEQUENCE: 80

Met Gly Ala Arg Glu Thr Glu Val Tyr Asp Val Val Gly Val Gly Phe
1 5 10 15

Gly Pro Ser Asn Leu Ser Leu Ala Val Ala Ile Gln Glu His Asn Ser
20 25 30

Ser Thr Ser Asp Arg Pro Leu Thr Ala Ala Phe Phe Glu Arg Gln Glu
35 40 45

Ala Phe Gly Trp His Arg Asn Met Leu Leu Pro Ala Ala Thr Met Gln
50 55 60

-continued

Ile Pro Phe Leu Lys Asp Ile Ala Thr Phe Arg Asn Pro Ala Ser Arg
65 70 75 80

Tyr Ser Phe Val Ala Tyr Leu His Ala Ser Gly Arg Leu Ala Gly Phe
85 90 95

Val Asn Asn Gln Thr Phe Phe Pro Thr Arg Arg Glu Phe His Arg Tyr
100 105 110

Leu Glu Trp Val Ala Ala Asn Phe Thr Asp Gln Val Ser Tyr Gly Cys
115 120 125

Glu Val Val Gly Leu Arg Leu Ser Gly Gln Gly Thr Gly Ala Gly Ala
130 135 140

Pro Ala His Leu Glu Ile Glu Val Ala Gly Gly Ala Gly Arg Gln Arg
145 150 155 160

Ser Ser Val Arg Ala Arg Asn Val Val Val Ser Thr Gly Leu Val Pro
165 170 175

Arg Met Pro Glu Gly Val Leu Gly Asp Asp Arg Val Trp His Ser Ser
180 185 190

Glu Phe Leu Thr Arg Phe Arg Gly Leu Lys Pro Val Asp Leu Arg Ala
195 200 205

Val Ala Val Val Gly Ala Gly Gln Ser Ala Ala Glu Ile Thr Arg Phe
210 215 220

Val His Asp Ala Ala Pro His Ala Gln Val Tyr Ser Val Ile Pro Ser
225 230 235 240

Tyr Gly Tyr Ala Leu Ala Asp Asp Thr Pro Phe Ala Asn Gln Val Phe
245 250 255

Asp Pro Ala Ala Val Asp Asp Tyr Phe Phe Gly Thr Asp Arg Ala Arg
260 265 270

Gln Ala Phe Trp Asp Tyr His Lys Asn Thr Asn Tyr Ser Val Val Asp
275 280 285

Asp Asp Val Ile Arg Asp Leu Tyr Arg Arg Ser Tyr Asp Glu Glu Val
290 295 300

Asn Gly Ala Arg Arg Leu His Phe Leu Asn Leu Thr Arg Val Gly Glu
305 310 315 320

Val Lys Arg Ala Gly Asp Glu Thr Arg Val Leu Leu Met Asn Gly Glu
325 330 335

Arg Arg Glu Leu Glu Val Asp Leu Cys Val Phe Ala Thr Gly Tyr His
340 345 350

Gly Met Glu Pro Ala Gly Val Leu Gly Asp Leu Ala Pro Tyr Cys Leu
355 360 365

Arg Asp Glu Ala Gly Arg Leu Arg Val Glu Arg Asp Tyr Arg Leu Val
370 375 380

Thr Gly Pro Glu Leu Pro Gly Gly Ile Tyr Leu Gln Gly Gly Thr Glu
385 390 395 400

His Thr His Gly Leu Ser Ser Ser Leu Leu Ser Asn Ile Ala Val Arg
405 410 415

Ser Gly Glu Ile Ala Glu Ser Ile Val Ser Arg His Arg Ile Glu Arg
420 425 430

Glu Leu Gly Gln Val His Pro Ala Glu Pro Ala Gly Lys Ile Arg
435 440 445

<210> SEQ ID NO 81
<211> LENGTH: 441
<212> TYPE: PRT
<213> ORGANISM: Pseudonocardia sp. AL041005-10

<400> SEQUENCE: 81

Met Asp Thr Asp Asp Met Gly Thr Tyr Asp Phe Val Gly Ile Gly Phe
1               5                   10                  15

Gly Pro Ser Asn Leu Ser Leu Ala Ala Ala Leu Arg Asp Ala Ser Ser
            20                  25                  30

Ser Asp Ala Ser Pro Val Arg Gly His Phe Phe Glu Ala Gln Pro Ser
        35                  40                  45

Phe Gly Trp His Arg Asn Met Leu Leu Pro Ser Ala Lys Met Gln Val
    50                  55                  60

Ser Phe Leu Lys Asp Leu Val Thr Phe Arg Asn Pro His Ser Arg Phe
65                  70                  75                  80

Ser Phe Val Ser Tyr Leu His Glu Met Asn Arg Leu Pro Gln Phe Ala
                85                  90                  95

Asn Asn Asn Asp Phe Phe Pro Thr Arg Arg Glu Phe His Gln Tyr Leu
            100                 105                 110

Glu Trp Val Ala Gly His Phe Ala Asp Ser Val Thr Tyr Gly Ala Arg
        115                 120                 125

Val Thr Gly Ile Glu Pro Ile Cys Gly Gly Ala Thr Ala Gly Pro His
    130                 135                 140

Asp Arg Phe Arg Ile Thr Ile Ala Ser Gly Lys Asp Ala Leu Ala Thr
145                 150                 155                 160

Thr Arg Val Glu Ala Tyr Asn Val Val Leu Ala Thr Gly Leu Thr Pro
                165                 170                 175

Arg Met Pro Glu Gly Ser Val Arg Asp Asp Arg Val Trp His Ser Ser
            180                 185                 190

Glu Phe Leu Glu Arg Phe Gly Ser Cys Ser Ser Ala Ser Leu Arg Arg
        195                 200                 205

Val Ala Val Val Gly Ala Gly Gln Ser Ala Ala Glu Ile Ala Arg Phe
    210                 215                 220

Cys Tyr Asp His Ala Pro Asn Ala Thr Ile Ser Ala Ile Leu Pro Ser
225                 230                 235                 240

Tyr Gly Tyr Ser Ile Ala Asp Asn Thr Pro Phe Ala Asn Arg Val Phe
                245                 250                 255

Asp Pro Gly Ala Val Asp Asp Tyr Tyr Phe Ser Asp Pro Leu Gly Lys
            260                 265                 270

Asp Arg Leu Trp Glu Ser His Arg Asn Thr Asn Tyr Ser Val Val Asp
        275                 280                 285

Asp Glu Val Ile Arg Ser Leu Phe Gln Arg Gln Tyr Asp Asp Glu Val
    290                 295                 300

Arg Gly Val Glu Arg Leu Gln Ile Ile Asn Leu Ala Arg Val Ala Asn
305                 310                 315                 320

Ile Lys Arg Ser Gly Asp Glu Thr Arg Val Thr Ile His Ser Leu Ala
                325                 330                 335

Arg Asp Glu His Phe Asp Leu Asp Val Asp Val Val Val Cys Ala Thr
            340                 345                 350

Gly Tyr Glu Ala Met Gly Ala Asp Gly Val Leu Ala Gly Leu Asp Ala
        355                 360                 365

Phe Cys Pro Arg Asp Asp Arg Gly Arg His Arg Val Glu Arg Asp Tyr
    370                 375                 380

Arg Leu Ile Thr Thr Asp Asp Leu Thr Ala Gly Ile Tyr Leu Gln Gly
385                 390                 395                 400

Gly Thr Glu His Thr His Gly Leu Thr Ser Ser Leu Leu Ser Asn Leu
                405                 410                 415

Ala Thr Arg Ser Gly Glu Ile Ala Ser Ser Leu Arg Ser Ser Arg Arg
420 425 430

Val Gly Ser Ala Gly Gly Asp Arg Trp
435 440

<210> SEQ ID NO 82
<211> LENGTH: 224
<212> TYPE: PRT
<213> ORGANISM: Mycobacterium marinum

<400> SEQUENCE: 82

Met Tyr Glu Arg Pro Gly Tyr Ser Ala Ile Glu Pro Ala Ala Val Leu
1 5 10 15

Asp Leu Leu Thr Ala Asn Pro Leu Gly Leu Val Val Thr Ile Asp Gly
20 25 30

Ala Arg Pro Leu Ala Thr His Ala Pro Val Leu Phe Ser Gln Gly Pro
35 40 45

Asn Gly Val Ala Gln Ala Glu Val Ala Ser Gly Asp Ala Pro Leu Val
50 55 60

Gly Ser Leu Leu Val Gly His Met Asn Ala Asp Asn Pro Gln Trp Arg
65 70 75 80

Gly Met Gln Lys Gly Gly Arg Val Leu Val Ala Phe Gln Gly Pro His
85 90 95

Gly Tyr Val Ser Pro Ser Val Tyr Gly Val Thr Pro Ala Ser Pro Thr
100 105 110

Trp Asn Phe Thr Ala Val His Ile Ala Gly Thr Leu Glu Pro Ile Ala
115 120 125

Asp Pro Glu Ser Thr Phe Glu Leu Val Cys Asp Thr Ala Arg Arg Leu
130 135 140

Glu Ala Arg Phe Gly His Gly Trp Arg Gln Glu Pro Ser Leu Asp Tyr
145 150 155 160

Phe Arg Arg Ile Val Ser Gly Val Gly Ala Phe Glu Ile Gln Val Glu
165 170 175

Ser Val Gln Thr Met Phe Lys Leu Ser Gln Glu Gln Pro Pro Val Leu
180 185 190

Arg Arg Arg Val Ala Glu His Phe Glu Ser Ser Asp Ser Val Leu His
195 200 205

Gln Glu Leu Ala Asp Leu Met Arg Lys His Val Phe Pro Lys Pro Ile
210 215 220

<210> SEQ ID NO 83
<211> LENGTH: 218
<212> TYPE: PRT
<213> ORGANISM: Lentzea flaviverrucosa

<400> SEQUENCE: 83

Met Phe Val Pro Ala Gln Tyr Arg Glu Pro His Gly His Trp Ile Thr
1 5 10 15

Asp Leu Val Arg Gly His Pro Leu Ala Gln Leu Val Ser Asn Gly Pro
20 25 30

Ala Gly Ser Ser Pro Tyr Val Thr His Ala Pro Ile Ile Leu Asp Pro
35 40 45

Gly His Pro Asp Pro His Pro Asp Asp Leu His Gly Ala Val Leu Trp
50 55 60

Gly His Leu Asn Arg Ala Asn Pro His Trp Ala Ala Leu Gly Asp Gly
65 70 75 80

```
Thr Glu Val Thr Ala Val Phe Thr Gly Pro Gly Ser Tyr Val Ser Pro
                85                  90                  95

Thr Val Tyr Glu Arg Thr Pro Ala Ala Pro Thr Trp Asp Phe Thr Ala
            100                 105                 110

Val His Val Arg Gly Thr Leu Arg Arg Val Leu Asp Ala Glu Gln Thr
        115                 120                 125

Leu Ala Thr Val Thr Ala Thr Val Arg Ala Phe Glu Ala Asp His Gly
    130                 135                 140

Thr Gly Trp Ser Met Glu Ser Ser Leu Asp Tyr Phe Asp Gln Leu Leu
145                 150                 155                 160

Pro Gly Val Gly Ala Phe Arg Leu Ala Val Thr Gly Val Asp Ala Met
                165                 170                 175

Phe Lys Leu Ser Gln Glu Gln Pro Pro Glu Val Arg Leu Arg Val Arg
            180                 185                 190

Asp His Phe Ala Gly Ser Glu Arg Thr His His Cys Leu Ile Ala Glu
        195                 200                 205

Met Met Asp Arg Leu Pro Val Ala Glu His
    210                 215
```

<210> SEQ ID NO 84
<211> LENGTH: 217
<212> TYPE: PRT
<213> ORGANISM: Streptomyces aureofaciens

<400> SEQUENCE: 84

```
Val Phe Thr Pro Lys Leu Tyr Gln Val Asp Gly Asp Asp Trp Pro Leu
1               5                   10                  15

Arg Ile Ile Glu Arg His Pro Leu Ala Val Leu Val Ser Asn Gly Asp
            20                  25                  30

Pro Val Pro Asn Ala Thr His Val Pro Val Ile Ala Pro Pro Asp Ala
        35                  40                  45

Ala Pro Glu Asp Ala Leu Ser Gly Met Arg Leu Trp Ala His Leu Thr
    50                  55                  60

Arg Ala Asn Pro His Trp Gln Gln Leu Ala Ala Ala Gly Gly Gly Pro
65                  70                  75                  80

Ala Lys Leu Val Phe His Gly Pro Asn Gly Tyr Val Thr Pro Ser Leu
                85                  90                  95

Tyr Ser Ala Asp Met Val Ala Pro Thr Trp Asn Tyr Val Ala Val His
            100                 105                 110

Leu Glu Gly Thr Val Glu Leu Ala Gly Asp Asp Glu Thr Leu Ala Ile
        115                 120                 125

Val His Thr Thr Ala Gln Thr Leu Glu Asp Arg Phe Gly Asp Gly Met
    130                 135                 140

Ala Leu Ala Pro Ser Leu Glu Tyr His Arg Gln Ile Val Gly Ala Val
145                 150                 155                 160

Gly Gly Leu Phe Phe Thr Val Thr Lys Val Asp Val Met Phe Lys Leu
                165                 170                 175

Ser Gln Glu Lys Asp Pro Glu Val Gln Gln Arg Val Leu Asp Arg Phe
            180                 185                 190

Ala Ala Ser Gly Ser Gly Leu His Arg Glu Val Ala Asp Thr Met Arg
        195                 200                 205

Ala Leu Arg Leu Gly Gly Ser Ala Gly
    210                 215
```

-continued

<210> SEQ ID NO 85
<211> LENGTH: 224
<212> TYPE: PRT
<213> ORGANISM: Streptomyces diastatochromogenes

<400> SEQUENCE: 85

```
Val Tyr Ile Pro Asp Leu Tyr Arg Thr Asp Asp Lys Glu Trp Pro Val
1               5                   10                  15

Arg Ile Leu Glu Glu Asn Pro Leu Gly Leu Leu Thr Thr His Ala Ser
            20                  25                  30

Ser Ser Ala Pro Pro Phe Ala Thr His Leu Pro Val Ile Ile Pro Ser
        35                  40                  45

Gly Ser Arg Asp Ala Leu Leu Gln Asp Glu Lys Trp Arg Gly Ala Thr
    50                  55                  60

Leu Leu Gly His Met Asn Arg Ala Asn Pro His Trp Gln Ser Leu Ala
65                  70                  75                  80

Asp Gly Thr Pro Ala Arg Ile Val Phe Gln Gly Pro Gly Ala Tyr Val
                85                  90                  95

Ser Pro Ser Val Tyr His Thr Asp Pro Ala Ala Pro Thr Trp Asp Phe
            100                 105                 110

Thr Ala Val His Val Gln Gly Thr Leu Trp Pro Val Arg Asp Glu Ala
        115                 120                 125

Glu Thr Leu Ala Ile Val Thr Ala Thr Ala Thr Glu Leu Glu Arg Lys
    130                 135                 140

Phe Gly Thr Gly Trp Cys Pro His Ser Ser Thr Glu Tyr Phe Arg Gln
145                 150                 155                 160

Leu Leu Ala Gly Val Gly Ala Phe Glu Leu Arg Val Asp Thr Met Asp
                165                 170                 175

Ala Met Phe Lys Leu Ser Gln Glu Lys Ser His Glu Ile Arg Asn Gly
            180                 185                 190

Val Val Asp Trp Phe Val Gln Gly Gln His Gly Arg Ser Arg Glu Leu
        195                 200                 205

Ala Ser Leu Met Ala Glu Phe Tyr Lys Asp Asp Arg Gly Thr Gly Ala
    210                 215                 220
```

<210> SEQ ID NO 86
<211> LENGTH: 215
<212> TYPE: PRT
<213> ORGANISM: Streptomyces sp. DvalAA-43

<400> SEQUENCE: 86

```
Met Phe Val Pro Ser His Tyr Arg Glu Pro Asp Gly Ser Trp Met Ile
1               5                   10                  15

Asp Leu Ile Arg Ala Asn Pro Met Ala Ile Met Ala Ile Asn Gly Ser
            20                  25                  30

Ser Ala Asp Gly Pro Phe Ala Thr His Leu Pro Val Ile Pro Asp Pro
        35                  40                  45

Ala Ala Thr Gly Arg Arg Ser Ala Asp Leu Ser Gly Ala Thr Leu Leu
    50                  55                  60

Gly His Met Asn Arg Ala Asn Pro Gln Trp Ala Ala Leu Glu Ser Gly
65                  70                  75                  80

Gly Val Ala Leu Leu Ile Phe Thr Gly Pro His Gly Tyr Val Ser Pro
                85                  90                  95

Thr Val Tyr Glu Met Ala Pro Ala Ala Pro Thr Trp Asn Phe Thr Ser
            100                 105                 110

Val His Val His Gly Met Val Glu Lys Ile Asp Ser Thr Glu Glu Thr
```

-continued

```
        115                 120                 125

Leu Gly Val Val Lys Ser Thr Val Thr Ala Leu Glu Thr Asp Phe Gly
    130                 135                 140

Thr Asp Trp Asp Met Ser Gly Ser Val Asp Tyr Phe Arg Lys Ile Val
145                 150                 155                 160

Pro Ala Val Gly Ala Phe Arg Phe Thr Val Ser Gly Ala Glu Gly Met
                165                 170                 175

Phe Lys Leu Ser Gln Glu Gln Pro Ala Glu Val Arg Asp Arg Val Gln
            180                 185                 190

Thr Ser Phe Ser Cys Arg Glu Gln Gly Arg Tyr Arg Glu Thr Ala Glu
        195                 200                 205

Leu Met Gly Arg Leu Pro Gly
    210                 215


<210> SEQ ID NO 87
<211> LENGTH: 218
<212> TYPE: PRT
<213> ORGANISM: Collimonas fungivorans

<400> SEQUENCE: 87

Met Tyr Val Pro Glu Tyr Tyr Arg Val Asp Glu Asn Thr Ala Arg Glu
1               5                   10                  15

Leu Val Tyr Arg His Pro Leu Ala Leu Leu Val Cys Asn Gly Asn Asn
            20                  25                  30

Gly Leu Pro Trp Ala Thr His Leu Pro Ala Ile Phe Pro Pro Glu Thr
        35                  40                  45

Arg Lys Leu Leu Asp Gln Gly Glu Ser Ile Ile Gly Lys Thr Met Tyr
    50                  55                  60

Gly His Met Asn Arg Ile Asn Pro His Trp Asn Ala Leu Gln Ala Gly
65                  70                  75                  80

Ser Ala Leu Leu Ile Phe Gln Gly Pro Asn Ser Tyr Val Ser Pro Thr
                85                  90                  95

Val Tyr Glu Val Thr Pro Ala Ala Pro Thr Trp Asn Phe Thr Ser Thr
            100                 105                 110

His Leu Arg Gly Thr Leu Arg Pro Ile Asp Glu Arg Asp Gln Ile Leu
        115                 120                 125

Glu Ile Val Arg Trp Thr Val Ala Thr Phe Glu Lys Glu Phe Cys Thr
    130                 135                 140

Asn Trp Asp Leu Thr Glu Ser Ile Pro Tyr Phe Glu Arg Ile Val His
145                 150                 155                 160

Gly Val Gly Ala Phe Ala Phe Glu Val Glu Ser Phe Asp Ser Met Phe
                165                 170                 175

Lys Leu Ser Gln Glu Gln Pro Ala Ala Ile Gln Glu Arg Val Val Asn
            180                 185                 190

Ser Phe Ala Ser Ser Ser His Cys Pro His Lys Glu Ile Ala Asp Leu
        195                 200                 205

Met Gln Arg Thr Asn Ser Lys Asn Lys Lys
    210                 215


<210> SEQ ID NO 88
<211> LENGTH: 231
<212> TYPE: PRT
<213> ORGANISM: Streptomyces reticuli

<400> SEQUENCE: 88

Val Tyr Glu Arg Pro Leu Tyr Arg Glu Asp Arg Asp Gly Val Val Leu
```

-continued

```
1               5                   10                  15

Ala Phe Leu His His His Pro Leu Ala Leu Val Val Thr Ala His Glu
            20                  25                  30

Gly Val Pro Val Ala Thr His Ala Pro Val Leu Phe Arg His Gly Pro
        35                  40                  45

Asp Gly Ala Asp Ala Glu Ala Val Ala Ala Gly Thr Val Pro Leu Ala
    50                  55                  60

Gly Ser Thr Leu Ile Gly His Met Asn Val Glu Asn Pro Gln Trp Arg
65                  70                  75                  80

Arg Met Arg Ser Gly Asp Gln Ala Leu Ile Val Phe Gln Gly Pro His
                85                  90                  95

Gly Tyr Val Ser Pro Thr Val Tyr Asp Val Thr Pro Ala Ala Pro Thr
            100                 105                 110

Trp Asn Phe Thr Ala Val His Val Thr Gly Thr Val Glu Pro Thr Ala
        115                 120                 125

Glu Pro Ala Asp Val Leu Asp Ile Val Ser Asp Thr Ala Arg Arg Leu
    130                 135                 140

Glu Gly Arg Phe Gly Arg Gly Trp Asp Gln Glu Ser Ser Leu Asp Tyr
145                 150                 155                 160

Phe Arg Gln Ile Ala Pro Gly Val Gly Ala Phe Thr Leu Arg Val Glu
                165                 170                 175

Ser Val Gln Thr Met Phe Lys Leu Ser Gln Glu Lys Pro Thr Pro Met
            180                 185                 190

Arg Arg Arg Val Ala Glu Gln Phe Glu Ala Ser Glu Ser Gly Thr His
        195                 200                 205

Arg Ala Leu Ala Gly Met Met Arg Ala His Gly Leu Thr Asp Ala Asp
    210                 215                 220

Glu Glu Arg Glu Thr Ala Gly
225                 230
```

<210> SEQ ID NO 89
<211> LENGTH: 231
<212> TYPE: PRT
<213> ORGANISM: Streptomyces scabies

<400> SEQUENCE: 89

```
Met Phe Val Pro Asp Pro Tyr Arg Glu Pro Asp Gly Ser Trp Met Thr
1               5                   10                  15

Glu Leu Ile Arg Leu Asn Pro Phe Ala Leu Leu Val Ser Asn Gly Pro
            20                  25                  30

Ala Asp Ala Asp Pro Tyr Ala Thr His Leu Pro Val Leu Arg Asp Pro
        35                  40                  45

Glu Trp Thr Gly Glu Trp Thr Glu Asp Leu Ala Gly Gly Arg Leu Val
    50                  55                  60

Gly His Met Asn Arg Glu Asn Pro His Trp Thr Ala Leu Glu Thr Gly
65                  70                  75                  80

Thr Pro Val Leu Ile Thr Phe Thr Gly Pro His Ala Tyr Val Ser Pro
                85                  90                  95

Thr Val Tyr Asp Ile Thr Pro Ala Ala Pro Thr Trp Asp Phe Thr Ser
            100                 105                 110

Val His Val His Gly Val Phe His Lys Ile Glu Ala Ala Ala Pro Gly
        115                 120                 125

Glu Asp Thr Leu Glu Val Cys Lys Asp Thr Val Lys Ala Tyr Glu Arg
    130                 135                 140
```

```
Asp Phe Gly Ala Ala Lys Ala Trp Asp Met Ser Arg Ser Ile Asp Tyr
145                 150                 155                 160

Phe Ala Thr Ile Leu Pro Ala Val Gly Ala Phe Arg Val Glu Ile Thr
                165                 170                 175

Gly Ala Glu Gly Met Phe Lys Leu Ser Gln Glu Gln Asp Gln Glu Ile
            180                 185                 190

Arg Glu Arg Val Gln Lys Asp Phe Ala Leu Arg Asp Ser Thr Gln Tyr
        195                 200                 205

Arg Glu Thr Ala Asp Leu Met Asp Arg Met Glu Lys Thr Gly Thr Val
    210                 215                 220

Gln Gly Cys Pro Val His His
225                 230


<210> SEQ ID NO 90
<211> LENGTH: 214
<212> TYPE: PRT
<213> ORGANISM: Kutzneria albida

<400> SEQUENCE: 90

Met Phe Val Pro Ser His Tyr Arg Glu Pro Asp Val Ser Trp Met Val
1               5                   10                  15

Asp Leu Met Arg Gln Asn Pro Leu Ala Leu Leu Ala Ser Asn Gly Asn
            20                  25                  30

Pro Ala Asp Gly Pro Phe Ala Thr His Leu Pro Val Ile Thr Asp Pro
        35                  40                  45

Ala Trp Asp Gly Pro Pro Ala Glu Lys Leu Ala Gly Trp Pro Leu Leu
    50                  55                  60

Gly His Met Asn Arg Ala Asn Pro Gln Trp Thr Ala Leu Glu Asn Gly
65                  70                  75                  80

Ala Thr Val Leu Leu Thr Phe Thr Gly Pro His Ala Tyr Val Ser Pro
                85                  90                  95

Thr Val Tyr Glu Ile Ser Pro Ala Ala Pro Thr Trp Asn Phe Thr Ser
            100                 105                 110

Val His Ala His Gly Val Val Glu Lys Ile Glu Ser Ile Glu Glu Thr
        115                 120                 125

Leu Glu Val Val Gln Ala Thr Val Lys Val Phe Glu Lys Phe Phe Gly
    130                 135                 140

Asp Ser Trp Asp Met Thr Glu Ser Leu Gly Tyr Phe Arg Lys Ile Val
145                 150                 155                 160

Pro Ala Val Gly Ala Phe Arg Ile Arg Val Thr Arg Ala Asp Gly Met
                165                 170                 175

Phe Lys Leu Ser Gln Glu Gln Lys Pro Glu Val Arg Lys Arg Val Val
            180                 185                 190

Thr Ser Phe Ser Glu Arg Gly Cys Gly Arg His Ala Gln Thr Ala Ala
        195                 200                 205

Leu Met Thr Gln Leu Pro
    210


<210> SEQ ID NO 91
<211> LENGTH: 216
<212> TYPE: PRT
<213> ORGANISM: Streptomyces albus

<400> SEQUENCE: 91

Met Phe Val Pro Pro Glu Tyr Arg Pro Asp Asp Pro Glu Trp Leu Ile
1               5                   10                  15
```

```
Glu Val Ile Arg Ser His Pro Leu Ala Cys Leu Val Thr Asn Gly Pro
            20                  25                  30

Asp Gly Pro Arg Ala Ser His Val Pro Val Ile Pro Asp Pro Glu Gln
        35                  40                  45

Phe Pro Ser Gly Met Pro Ala Arg Glu Gly Glu Val Ala Gly Arg Arg
    50                  55                  60

Leu Phe Gly His Met Asn Arg Leu Asn Pro His Trp Ala Ala Leu Gln
65                  70                  75                  80

Gly Gly Ala Gln Ala Leu Leu Val Phe Gln Gly Pro Asn Gly Tyr Val
                85                  90                  95

Ser Pro Thr Val Tyr Glu Tyr Thr Pro Ala Ala Pro Thr Trp Asp Phe
            100                 105                 110

Thr Ala Val His Val Arg Gly Trp Leu Glu Pro Val Gly Asp Arg Glu
        115                 120                 125

Ser Ser Leu Gln Ile Ile Thr Glu Thr Val Ala Ala Tyr Glu Arg Asp
    130                 135                 140

Leu Gly Thr Gly Trp Asp Met Thr Glu Ser Leu Gly Tyr Phe Arg Gln
145                 150                 155                 160

Leu Leu Pro Gly Val Gly Ala Phe Arg Leu Ala Ile Asp Thr Val Asp
                165                 170                 175

Gly Met Phe Lys Leu Ser Gln Glu Gln Ser Pro Glu Val Arg Glu Arg
            180                 185                 190

Val Ala Cys Glu Phe Ala Ala Arg Ala Glu Ala Arg Gly Thr Ala Leu
        195                 200                 205

Ala Glu His Ile Gln Arg Thr Lys
    210                 215


<210> SEQ ID NO 92
<211> LENGTH: 218
<212> TYPE: PRT
<213> ORGANISM: Rhodococcus fascians

<400> SEQUENCE: 92

Met Tyr Val Pro Arg Ile Tyr Lys Ala Ser Asp Arg Thr Trp Leu Arg
1               5                   10                  15

Arg Val Val Ala Gln Tyr Pro Phe Ala Ala Leu Ile Ser Asn Gly Pro
            20                  25                  30

Lys Ala Pro Tyr Ala Thr His Leu Pro Val Ile Cys Ala Pro Cys Ala
        35                  40                  45

Pro Ser Glu Ser Glu Asp Leu Glu Gly Ser Thr Leu Phe Gly His Met
    50                  55                  60

Asn Arg Ala Asn Pro His Trp Asp Ser Leu Val Asp Gly Ala Asp Ala
65                  70                  75                  80

Gln Leu Ile Phe Thr Gly Pro His Gly Tyr Val Thr Pro Ser Val Tyr
                85                  90                  95

Gln Arg Asp Ser Val Ala Pro Thr Trp Asn Tyr Val Ser Val His Leu
            100                 105                 110

Arg Gly Lys Leu Gln Pro Val Ala Asp Phe Glu Glu Thr Leu Lys Val
        115                 120                 125

Val Gln Leu Thr Val Ser Thr Tyr Glu Gln Lys Phe Gly Ser Gly Trp
    130                 135                 140

Glu Met Asp Ser Ser Leu Asp His Tyr Arg Arg Ile Gly Pro Ala Val
145                 150                 155                 160

Gly Ala Phe Ser Phe Glu Val Glu Ser Ala Asp Gly Met Phe Lys Leu
                165                 170                 175
```

```
Ser Gln Glu Gln Asn Leu Glu Thr Arg Arg Arg Val Ala Asp His Phe
            180                 185                 190

Ser Ala Asn His Ala Gly Arg Gly Lys Glu Leu Ala Ser Phe Met Arg
        195                 200                 205

Glu Tyr Ser His Gly Asp Tyr Asn Asn Phe
    210                 215
```

<210> SEQ ID NO 93
<211> LENGTH: 231
<212> TYPE: PRT
<213> ORGANISM: Streptomyces neyagawaensis

<400> SEQUENCE: 93

```
Met Phe Val Pro Asp Pro Tyr Arg Glu Pro Asp Gly Ser Trp Met Thr
1               5                   10                  15

Glu Leu Ile Arg Leu Asn Pro Phe Ala Leu Leu Val Ser Asn Gly Pro
            20                  25                  30

Ala Asp Ala Asp Pro Tyr Ala Thr His Leu Pro Val Ile Arg Asp Pro
        35                  40                  45

Glu Trp Thr Gly Ala Trp Thr Glu Asn Leu Ala Gly Gly Arg Leu Ile
    50                  55                  60

Gly His Met Asn Arg Glu Asn Pro His Trp Thr Ala Leu Glu Asn Gly
65                  70                  75                  80

Thr Pro Val Leu Ile Thr Phe Thr Gly Pro His Ala Tyr Val Ser Pro
                85                  90                  95

Thr Val Tyr Asp Ile Thr Pro Ala Ala Pro Thr Trp Asp Phe Thr Ser
            100                 105                 110

Val His Val His Gly Val Phe Glu Lys Ile Glu Ala Ala Ala Pro Gly
        115                 120                 125

Glu Asp Ser Leu Glu Val Cys Lys Asp Thr Val Lys Ala Tyr Glu Arg
    130                 135                 140

Asp Phe Gly Ala Ala Lys Ala Trp Asp Met Ser Arg Ser Ile Asp Tyr
145                 150                 155                 160

Phe Ala Thr Ile Leu Pro Ala Val Gly Ala Phe Arg Val Glu Ile Thr
                165                 170                 175

Gly Ala Glu Gly Met Phe Lys Leu Ser Gln Glu Gln Asp Glu Glu Ile
            180                 185                 190

Arg Glu Arg Val Arg Glu Asp Phe Ala Leu Arg Asp Ser Ser Gln Tyr
        195                 200                 205

Arg Glu Thr Ala Glu Leu Met Asp Arg Met Glu Lys Thr Gly Thr Ile
    210                 215                 220

Lys Gly Cys Pro Val His His
225                 230
```

<210> SEQ ID NO 94
<211> LENGTH: 220
<212> TYPE: PRT
<213> ORGANISM: Kutzneria buriramensis

<400> SEQUENCE: 94

```
Met Phe Val Pro His His Tyr His Glu Pro Asn Glu Ser Trp Met Thr
1               5                   10                  15

Asp Leu Ile Arg Glu Asn Pro Leu Ala Glu Leu Val Ser Asn Gly Asn
            20                  25                  30

Gly Pro Ala Gly Pro Phe Ala Thr His Val Pro Val Ile Pro Asp Pro
        35                  40                  45
```

```
His Asp Pro Asp Arg Pro Pro Gly Glu Ile Val Gly Ala Thr Leu Trp
    50                  55                  60

Gly His Met Asn Arg Ser Asn Pro His Trp Ala Ala Leu Glu Ser Glu
65                  70                  75                  80

Thr Pro Val Val Ile Val Phe Thr Gly Pro His Ala Tyr Val Ser Pro
                85                  90                  95

Thr Leu Tyr Gln Arg Thr Pro Ala Ala Pro Thr Trp Asn Phe Thr Ala
            100                 105                 110

Val His Ala Arg Gly Leu Leu Arg Arg Val Asp Ala Glu Ala Ala Gly
        115                 120                 125

Asp Glu Thr Leu Glu Thr Val Met Ala Thr Val Arg Ala Phe Glu Ala
    130                 135                 140

Arg Phe Gly Ala Gly Trp Ala Met Ser Glu Ser Val Glu Tyr Phe Arg
145                 150                 155                 160

Arg Ile Val Pro Ala Val Gly Ala Phe Arg Val Thr Val Ser His Val
                165                 170                 175

Asp Gly Met Phe Lys Leu Ser Gln Glu Gln Asp Ala Asp Val Arg Ala
            180                 185                 190

Arg Val Arg Glu Ser Phe Ala Glu Arg Glu Ser Ser Asn His Lys Ala
        195                 200                 205

Ile Ala Ala Met Met Gly Arg Leu Ala Asp Ala Glu
    210                 215                 220


<210> SEQ ID NO 95
<211> LENGTH: 214
<212> TYPE: PRT
<213> ORGANISM: Streptomyces yanglinensis

<400> SEQUENCE: 95

Met Phe Val Pro Ser Gln Tyr Arg Glu Pro Asp Val Ser Trp Met Val
1               5                   10                  15

Asp Leu Met Arg Asp Asn Pro Leu Ala Leu Met Ala Ser Asn Gly Thr
            20                  25                  30

Ala Ala Asp Gly Pro Tyr Ala Thr His Leu Pro Val Ile Thr Asp Pro
        35                  40                  45

Gly Trp Glu Gly Pro Pro Ala Ala Asp Leu Ala Gly Met Leu Leu Leu
    50                  55                  60

Gly His Met Asn Arg Ala Asn Pro His Trp Ser Ala Leu Glu Asp Gly
65                  70                  75                  80

Gln Thr Ile Leu Leu Thr Phe Thr Gly Pro His Ala Tyr Val Ser Pro
                85                  90                  95

Thr Val Tyr Asp Ile Thr Pro Ala Ala Pro Thr Trp Asn Phe Thr Ser
            100                 105                 110

Val His Val Arg Gly Thr Val Glu Lys Ile Ala Thr Thr Glu Glu Thr
        115                 120                 125

Leu Glu Val Val Lys Ser Thr Val Arg Ala Tyr Glu Lys Glu Phe Gly
    130                 135                 140

Asp Ser Trp Asp Met Asn Ala Ser Leu Asp Tyr Phe Arg Lys Ile Val
145                 150                 155                 160

Pro Gly Val Gly Ala Phe His Val Arg Val Thr Arg Ala Glu Ala Met
                165                 170                 175

Phe Lys Leu Ser Gln Glu Gln Ser Pro Glu Val Arg Asp Arg Val Val
            180                 185                 190

Arg Ser Phe Ala Gly Arg Gly Cys Thr Arg His Ala Gln Ala Ala Asp
```

```
        195                 200                 205

Leu Met Thr Arg Leu Pro
    210


<210> SEQ ID NO 96
<211> LENGTH: 214
<212> TYPE: PRT
<213> ORGANISM: Streptomyces griseochromogenes

<400> SEQUENCE: 96

Met Phe Val Pro Ser His Tyr Arg Glu Pro Asp Val Ser Trp Met Val
1               5                   10                  15

Asp Leu Met Arg Gly Asn Pro Leu Ala Leu Met Ala Ser Asn Gly Thr
            20                  25                  30

Pro Ala Asp Gly Pro Phe Ala Thr His Leu Pro Val Ile Thr Asp Pro
        35                  40                  45

Gln Trp Glu Gly Ser Pro Thr Ala Asp Leu Ala Gly Met Pro Leu Leu
    50                  55                  60

Gly His Met Asn Arg Ala Asn Pro His Trp Ala Ala Leu Glu Thr Gly
65                  70                  75                  80

Ser Ala Ile Leu Leu Thr Phe Thr Gly Pro His Ala Tyr Val Ser Pro
                85                  90                  95

Thr Val Tyr Asp Val Thr Pro Ala Ala Pro Thr Trp Asn Phe Thr Ser
            100                 105                 110

Val His Val His Gly Val Val Glu Lys Ile Glu Ser Thr Glu Glu Thr
        115                 120                 125

Leu Asp Val Val Gln Ala Thr Val Gln Ala Phe Glu Gly Glu Phe Gly
    130                 135                 140

Asp Ser Trp Asp Met Ser Glu Ser Val Asp Tyr Phe Arg Lys Ile Val
145                 150                 155                 160

Thr Gly Val Gly Ala Phe Arg Val Arg Val Thr Lys Ala Glu Gly Met
                165                 170                 175

Phe Lys Leu Ser Gln Glu Gln Arg Pro Glu Ile Arg Glu Arg Val Val
            180                 185                 190

Gln Ser Phe Ala Gly Arg Glu Cys Thr Arg His Val Gln Thr Ala Asp
        195                 200                 205

Leu Met Asn Arg Leu Pro
    210


<210> SEQ ID NO 97
<211> LENGTH: 215
<212> TYPE: PRT
<213> ORGANISM: Frankia sp. AvcI
<220> FEATURE:
<221> NAME/KEY: misc_feature
<222> LOCATION: (75)..(75)
<223> OTHER INFORMATION: Xaa can be any naturally occurring amino acid

<400> SEQUENCE: 97

Met Phe Val Pro Cys His Tyr Arg Ala Pro Asn Val Ser Met Met Val
1               5                   10                  15

Asp Leu Met Arg Glu Asn Pro Leu Ala Leu Met Val Ser Asn Gly Ala
            20                  25                  30

Pro Gly Ala Val Pro Phe Ala Thr His Leu Pro Val Ile Thr Asp Pro
        35                  40                  45

Cys Trp Asp Gly Gln Ala Gly Pro Asp Leu Gly Gly Met Val Leu Leu
    50                  55                  60
```

-continued

```
Gly His Leu Asn Arg Ala Asn Pro His Trp Xaa Ala Leu Glu Thr Gly
65                  70                  75                  80

Ser Met Ile Leu Leu Thr Phe Thr Gly Pro His Ala Tyr Val Ser Pro
                85                  90                  95

Thr Val Tyr Gly Leu Thr Pro Ala Ala Pro Thr Trp Asp Phe Thr Ser
            100                 105                 110

Val His Val His Gly Val Val Glu Lys Leu Thr Thr Thr Glu Glu Thr
        115                 120                 125

Leu Glu Val Val Arg Ala Thr Val Leu Ala Phe Glu Gln Glu Phe Gly
    130                 135                 140

Asp Gly Trp Asp Met Thr Asp Ser Leu Gly Tyr Phe Arg Arg Ile Val
145                 150                 155                 160

Pro Arg Val Gly Ala Phe Arg Leu Arg Val Thr Gly Ala Gln Gly Met
                165                 170                 175

Phe Lys Leu Ser Gln Glu Gln Thr Pro Glu Ile Arg Glu Arg Val Ala
            180                 185                 190

Arg Ser Phe Ala Ala His Gly Ser Thr Arg His Ala Gln Thr Ala Glu
        195                 200                 205

Leu Ile Ser Arg Leu Pro His
    210                 215


<210> SEQ ID NO 98
<211> LENGTH: 214
<212> TYPE: PRT
<213> ORGANISM: Streptomyces incarnatus

<400> SEQUENCE: 98

Met Phe Val Pro Ser Phe Tyr Arg Glu Pro Asp Ser Ala Trp Met Val
1               5                   10                  15

Asp Leu Ile Arg Gly Asn Pro Leu Ala Leu Ala Val Thr Asn Gly Ser
            20                  25                  30

Pro Glu Asp Gly Pro Phe Ala Thr His Leu Pro Val Ile Phe Asp Pro
        35                  40                  45

Glu Thr Ser Gly Asp Trp Ser Gly Glu Leu Pro Gly Ala Thr Leu Leu
    50                  55                  60

Gly His Met Asn Arg Ala Asn Pro His Trp Ala Ala Leu Glu Thr Gly
65                  70                  75                  80

Ser Val Leu Leu Leu Thr Phe Thr Gly Pro His Ser Tyr Val Ser Pro
                85                  90                  95

Thr Val Tyr Glu Thr Thr Pro Ala Ala Pro Thr Trp Asn Phe Thr Ala
            100                 105                 110

Val His Val Arg Gly Val Val Glu Lys Ile Ser Ser Thr Glu Glu Thr
        115                 120                 125

Leu Gly Val Val Gln Ser Thr Val Arg Ala Tyr Glu Gly Ala Phe Gly
    130                 135                 140

Asp Gly Trp Asp Met Ser Glu Ser Leu Asp Tyr Phe Arg Lys Ile Val
145                 150                 155                 160

Pro Ala Val Gly Ala Phe Arg Phe Thr Val Thr Gly Ala Glu Gly Met
                165                 170                 175

Phe Lys Leu Ser Gln Glu Gln Pro Gly Glu Val Arg Glu Arg Val Arg
            180                 185                 190

Asp Ala Phe Gly Gln Ser Gly Cys Ala Tyr Arg Arg Glu Val Ala Gly
        195                 200                 205

Leu Met Ser Arg Leu Pro
    210
```

<210> SEQ ID NO 99
<211> LENGTH: 214
<212> TYPE: PRT
<213> ORGANISM: Streptomyces sp. MUSC136T

<400> SEQUENCE: 99

```
Met Phe Val Pro Pro Gln Tyr Arg Glu Pro Asp Gly Ser Trp Met Val
1               5                   10                  15

Asp Leu Met Arg Arg Asn Pro Leu Ala Leu Cys Val Thr Asn Gly Asp
            20                  25                  30

Ala Ala Asp Gly Pro Tyr Ala Thr His Leu Pro Val Ile Arg Asp Pro
        35                  40                  45

Gly Met Thr Gly Glu Trp Ala Glu Asp Leu Ser Gly Gly Thr Leu Leu
    50                  55                  60

Gly His Met Asn Leu Gln Asn Pro His Trp Ala Ala Leu Arg Asp Gly
65                  70                  75                  80

Gln Ser Val Leu Leu Val Phe Thr Gly Pro His Ala Tyr Val Ser Pro
                85                  90                  95

Thr Val Tyr Glu Lys Ser Pro Ala Ala Pro Thr Trp Asp Phe Thr Ala
            100                 105                 110

Val His Val His Gly Thr Val Glu Lys Leu Thr Ser Ala Gln Asp Thr
        115                 120                 125

Leu Asp Val Val Lys Ser Thr Val Arg Ala Phe Glu Ser Asp Leu Gly
    130                 135                 140

Thr Gly Trp Asp Met Thr Glu Ser Glu Ala Tyr Phe Asp Gln Leu Leu
145                 150                 155                 160

Pro Gly Val Gly Ala Phe Arg Val Glu Val Thr Gly Ala Glu Gly Met
                165                 170                 175

Phe Lys Leu Ser Gln Glu Gln Gln Pro His Val Arg Asp Arg Val His
            180                 185                 190

Asp Ala Phe Ala Glu Arg Pro Cys Gly Arg His Arg Glu Thr Ala Glu
        195                 200                 205

Leu Met Ala Arg Leu Pro
    210
```

<210> SEQ ID NO 100
<211> LENGTH: 216
<212> TYPE: PRT
<213> ORGANISM: Streptomyces albulus

<400> SEQUENCE: 100

```
Met Phe Val Pro Pro Glu Tyr Arg Pro Asp Asp Pro Glu Trp Leu Ile
1               5                   10                  15

Glu Val Ile Arg Ser His Pro Leu Ala Cys Leu Val Thr Asn Gly Pro
            20                  25                  30

Asp Gly Pro Arg Ala Ser His Val Pro Val Ile Pro Asp Pro Glu Gln
        35                  40                  45

Phe Pro Ser Gly Met Pro Ala Arg Glu Gly Glu Val Ala Gly Arg Arg
    50                  55                  60

Leu Phe Gly His Met Asn Arg Leu Asn Pro His Trp Ala Ala Leu Gln
65                  70                  75                  80

Gly Gly Ala Gln Ala Leu Leu Val Phe Gln Gly Pro Asn Gly Tyr Val
                85                  90                  95

Ser Pro Thr Val Tyr Glu Tyr Thr Pro Ala Ala Pro Thr Trp Asp Phe
            100                 105                 110
```

```
Thr Ala Val His Val Arg Gly Trp Leu Glu Pro Val Gly Asp Arg Glu
        115                 120                 125

Ser Ser Leu Gln Ile Ile Thr Glu Thr Val Ala Ala Tyr Glu Arg Asp
    130                 135                 140

Leu Gly Thr Gly Trp Asp Met Thr Glu Ser Leu Gly Tyr Phe Arg Gln
145                 150                 155                 160

Leu Leu Pro Gly Val Gly Ala Phe Arg Leu Ala Ile Asp Thr Val Asp
                165                 170                 175

Gly Met Phe Lys Leu Ser Gln Glu Gln Ser Pro Glu Val Arg Glu Arg
            180                 185                 190

Val Ala Cys Glu Phe Ala Ala Arg Ala Glu Ala Arg Gly Thr Ala Leu
        195                 200                 205

Ala Glu His Ile Gln Arg Thr Lys
    210                 215


<210> SEQ ID NO 101
<211> LENGTH: 214
<212> TYPE: PRT
<213> ORGANISM: Streptomyces tsukubaensis

<400> SEQUENCE: 101

Met Phe Val Pro Ser Met Tyr Arg Ala Pro Asp Ser Ser Trp Met Val
1               5                   10                  15

Asn Leu Ile Arg Glu Asn Pro Leu Ala Leu Ala Val Ala Asn Gly Ser
            20                  25                  30

Pro Glu Asn Gly Pro Phe Ala Thr His Leu Pro Val Val Phe Asp Pro
        35                  40                  45

Glu Thr Ser Ala Asp Pro Ala Gly Glu Leu Pro Gly Thr Thr Leu Leu
    50                  55                  60

Gly His Met Asn Arg Ala Asn Pro His Trp Ala Ala Leu Glu Thr Gly
65                  70                  75                  80

Ser Val Leu Leu Leu Thr Phe Thr Gly Pro Asn Ser Tyr Val Ser Pro
                85                  90                  95

Ser Val Tyr Gly Val Thr Pro Ala Ala Pro Thr Trp Asn Phe Thr Ala
            100                 105                 110

Val His Val Arg Gly Val Val Glu Lys Ile Ser Ser Leu Glu Glu Ser
        115                 120                 125

Leu Asp Val Val Gln Ser Thr Val Arg Ala Phe Glu Gly Ala Phe Gly
    130                 135                 140

Asn Gly Trp Asp Met Thr Glu Ser Leu Gly Tyr Phe Arg Arg Ile Ala
145                 150                 155                 160

Pro Ala Val Gly Ala Phe Arg Leu Thr Val Thr Gly Ala Glu Gly Met
                165                 170                 175

Phe Lys Leu Ser Gln Glu Gln Pro Gly Asp Val Arg Arg Arg Val Arg
            180                 185                 190

Glu Ser Phe Gly Gln Ser Ala Cys Arg Tyr Arg Arg Glu Thr Ala Gly
        195                 200                 205

Leu Met Ser Arg Leu Pro
    210


<210> SEQ ID NO 102
<211> LENGTH: 214
<212> TYPE: PRT
<213> ORGANISM: Streptomyces himastatinicus

<400> SEQUENCE: 102
```

Met Phe Val Pro Ser His Tyr Arg Glu Pro Asp Ser Ser Trp Met Val
1 5 10 15

Asp Ile Ile Arg Gly Asn Pro Leu Ala Leu Met Met Ser Asn Gly Ala
20 25 30

Ala Gly Glu Pro Pro Phe Ala Thr His Leu Pro Val Ile Pro Asp Pro
35 40 45

Ala Met Thr Gly Asp Trp Ser Glu Arg Leu Ser Glu Ala Thr Leu Leu
50 55 60

Gly His Met Asn Arg Asp Asn Pro Gln Trp Gln Ala Leu Glu Asp Gly
65 70 75 80

Ala Val Val Arg Ile Ala Phe Ser Gly Pro His Ala Tyr Val Ser Pro
85 90 95

Thr Leu Tyr Gly Val Thr Pro Ala Ala Pro Thr Trp Asn Phe Thr Ser
100 105 110

Val His Val Arg Gly Val Val Glu Arg Ile Pro Ser Thr Glu Glu Thr
115 120 125

Leu Glu Val Val Lys Ser Thr Val Arg Ala Phe Glu Ala Asp Phe Gly
130 135 140

Glu Gly Trp Asp Met Ala Ala Ser Ile Asp Tyr Phe Arg Lys Ile Val
145 150 155 160

Pro Gly Val Gly Ala Phe Arg Ile Met Val Arg Asn Val Asp Gly Met
165 170 175

Phe Lys Leu Ser Gln Glu Gln Gln Pro Glu Val Arg Asp Arg Val Arg
180 185 190

Lys Ser Phe Ala Gly Arg Glu Cys Gly Arg His Gln Glu Thr Ala Ala
195 200 205

Tyr Met Ser Arg Leu Pro
210

<210> SEQ ID NO 103
<211> LENGTH: 231
<212> TYPE: PRT
<213> ORGANISM: Streptomyces flaveolus

<400> SEQUENCE: 103

Met Tyr Glu Arg Pro Leu Tyr Arg Glu Asp Cys Asp Gly Val Val Leu
1 5 10 15

Ala Phe Leu Arg His Asn Pro Leu Ala Met Val Val Thr Ser His Asp
20 25 30

Asp Val Pro Val Ala Thr His Ala Pro Val Leu Phe Arg His Gly Pro
35 40 45

Asp Gly Ala Asp Ala Glu Ala Val Ala Ala Gly Thr Val Pro Leu Ala
50 55 60

Gly Ser Thr Leu Ile Gly His Met Asn Val Glu Asn Pro Gln Trp Arg
65 70 75 80

Arg Met Arg Ser Gly Asp Arg Ala Leu Ile Val Phe Gln Gly Pro His
85 90 95

Gly Tyr Val Ser Pro Thr Val Tyr Gly Val Thr Pro Ala Ala Pro Thr
100 105 110

Trp Asp Phe Ile Ala Val His Val Asn Gly Thr Val Glu Pro Thr Ala
115 120 125

Asp Pro Ala Ala Val Leu Asp Ile Val Ser Asp Thr Ala Arg Arg Leu
130 135 140

Glu Ser Gly Phe Gly Arg Gly Trp Asp Gln Glu Ser Ser Leu Asp Tyr

```
145                 150                 155                 160

Phe Arg Gln Ile Ala Pro Gly Val Gly Ala Phe Thr Leu Arg Val Asp
                165                 170                 175

Ser Val Gln Thr Met Phe Lys Leu Ser Gln Glu Lys Pro Ala Pro Met
            180                 185                 190

Arg Arg Arg Val Val Glu Gln Phe Glu Ala Ser Glu Ser Gly Thr His
        195                 200                 205

Arg Ala Leu Ala Ser Val Met Arg Asp Arg Gly Leu Thr Glu Ala Asp
    210                 215                 220

Glu Glu Arg Glu Thr Ala Gly
225                 230


<210> SEQ ID NO 104
<211> LENGTH: 214
<212> TYPE: PRT
<213> ORGANISM: Streptomyces auranticaus

<400> SEQUENCE: 104

Met Phe Val Pro Ser Gln Tyr Arg Gln Pro Asp Ser Ser Trp Met Leu
1               5                   10                  15

Asp Leu Ile His Gly Asn Pro Leu Ala Leu Phe Val Ser Asn Gly Ser
            20                  25                  30

Pro Glu Ala Gly Pro Phe Ala Thr His Leu Pro Val Ile Gln Asp Pro
        35                  40                  45

Glu Trp Thr Gly Glu Trp Ser Asp Asp Leu Ser Gly Gly Arg Leu Leu
    50                  55                  60

Gly His Met Asn Arg Ala Asn Pro His Trp Lys Ala Leu Glu Ser Gly
65                  70                  75                  80

Thr Val Asn Leu Leu Thr Phe Thr Gly Pro His Gly Tyr Val Ser Pro
                85                  90                  95

Thr Val Tyr Arg Thr Thr Pro Ala Ala Pro Thr Trp Asn Phe Thr Ser
            100                 105                 110

Val His Val His Gly Val Val Glu Lys Ile Asp Gly Ile Glu Asn Thr
        115                 120                 125

Leu Glu Val Val Lys Ala Thr Val Arg Ala Tyr Glu Gly Ala Phe Gly
    130                 135                 140

Ala Gly Trp Asp Met Thr Glu Ser Leu Asp Tyr Phe Arg Lys Ile Val
145                 150                 155                 160

Pro Ala Val Gly Ala Phe Gln Phe Arg Val Thr Gly Ala Glu Gly Met
                165                 170                 175

Phe Lys Leu Ser Gln Glu Gln Pro Asp Asp Val Gln Glu Arg Val Arg
            180                 185                 190

Glu Ser Phe Gly Gly Arg Glu Cys Thr Arg His Gln Ala Ala Ala Gln
        195                 200                 205

Leu Met Asp Lys Leu Arg
    210


<210> SEQ ID NO 105
<211> LENGTH: 223
<212> TYPE: PRT
<213> ORGANISM: Streptomyces sp. RJA2928

<400> SEQUENCE: 105

Met Phe Val Pro Gln His Tyr Arg Thr Asp Asp Arg Arg Trp Pro Val
1               5                   10                  15

Arg Ile Val Gln Asp Asn Pro Leu Ala Leu Leu Met Ser Thr Arg Asp
```

-continued

```
            20                  25                  30

Gly Arg Ala Pro Phe Ala Ser His Val Pro Val Ile Val Leu Pro Arg
        35                  40                  45

Gln Arg Glu Glu Leu Glu Arg Thr Gly Arg Trp Gln Gly Ala Val Leu
    50                  55                  60

His Gly His Met Asn Arg Ala Asn Pro His Trp Lys Ser Leu Ala Asp
65                  70                  75                  80

Gly Gln Pro Ala Gly Leu Val Phe Gln Gly Pro Ala Gly Tyr Val Ser
                85                  90                  95

Pro Ala Val Tyr Asn Thr Ser Pro Ala Val Pro Thr Trp Asn Phe Thr
            100                 105                 110

Ala Val His Val Gln Gly Arg Leu Lys Leu Val Ala Asp Glu Glu Ala
        115                 120                 125

Thr Leu Gly Val Val Ser Ala Thr Ala Arg Gln Leu Glu Glu Arg Phe
    130                 135                 140

Gly Ala Arg Trp Thr Val Glu Pro Ser Val Asp His Phe Arg Gln Ile
145                 150                 155                 160

Leu Pro Gly Val Gly Ala Phe Glu Leu Arg Val Glu Glu Cys Asp Ser
                165                 170                 175

Met Phe Lys Leu Ser Gln Glu Lys Glu His Glu Val Arg His Ala Val
            180                 185                 190

Met Asp Trp Cys Ala Arg Ser Pro Arg Gly Arg Ser Asn Asp Leu Ala
        195                 200                 205

Ala Val Met Arg Asp Tyr Tyr Pro Pro Thr Thr Thr Trp Pro Ser
    210                 215                 220


<210> SEQ ID NO 106
<211> LENGTH: 215
<212> TYPE: PRT
<213> ORGANISM: Frankia alni str. ACN14A

<400> SEQUENCE: 106

Met Phe Val Pro Cys His Tyr Arg Ala Pro Asn Val Ser Met Met Val
1               5                   10                  15

Asp Leu Met Arg Glu Asn Pro Leu Ala Leu Met Val Ser Asn Gly Ala
            20                  25                  30

Pro Gly Ala Val Pro Phe Ala Thr His Leu Pro Val Ile Thr Asp Pro
        35                  40                  45

Cys Trp Asp Gly Gln Ala Gly Pro Asp Leu Gly Gly Met Val Leu Leu
    50                  55                  60

Gly His Leu Asn Arg Ala Asn Pro His Trp Ala Ala Leu Glu Thr Gly
65                  70                  75                  80

Ser Met Ile Leu Leu Thr Phe Thr Gly Pro His Ala Tyr Val Ser Pro
                85                  90                  95

Thr Val Tyr Gly Leu Thr Pro Ala Ala Pro Thr Trp Asp Phe Thr Ser
            100                 105                 110

Val His Val His Gly Val Val Glu Lys Leu Thr Thr Thr Glu Glu Thr
        115                 120                 125

Leu Glu Val Val Arg Ala Thr Val Leu Ala Phe Glu Gln Glu Phe Gly
    130                 135                 140

Asp Gly Trp Asp Met Thr Asp Ser Leu Gly Tyr Phe Arg Arg Ile Val
145                 150                 155                 160

Pro Arg Val Gly Ala Phe Arg Leu Arg Val Thr Gly Ala Gln Gly Met
                165                 170                 175
```

Phe Lys Leu Ser Gln Glu Gln Thr Pro Glu Ile Arg Glu Arg Val Ala
180 185 190

Arg Ser Phe Ala Ala His Gly Ser Thr Arg His Ala Gln Thr Ala Glu
195 200 205

Leu Ile Ser Arg Leu Pro His
210 215

<210> SEQ ID NO 107
<211> LENGTH: 218
<212> TYPE: PRT
<213> ORGANISM: Actinosynnema mirum

<400> SEQUENCE: 107

Met His Val Pro Pro Met Tyr Arg Ala Asp Asp Glu Asp Arg Ala Arg
1 5 10 15

Gln Val Val His Asp Tyr Pro Leu Ala Thr Leu Val Ser Asn Gly Pro
20 25 30

Arg Val Pro His Ala Thr His Leu Pro Val Val Ala Ala Pro Gly Ala
35 40 45

Pro Gln Val Gly Gly Leu Ala Gly Ser Thr Leu Trp Gly His Leu Asn
50 55 60

Arg Ala Asn Ala His Trp Arg Ala Leu Ala Gly Gly Val Pro Ala Val
65 70 75 80

Leu Val Phe Thr Gly Pro His Ala Tyr Ile Thr Pro Ala Ile Tyr Arg
85 90 95

Thr Thr Pro Ala Val Pro Thr Trp Asp Phe Val Ser Val His Leu His
100 105 110

Gly Arg Val Glu Pro Ile Asp Gly Glu Ala Gly Thr Leu Glu Val Val
115 120 125

Lys Arg Thr Ala Glu Leu Phe Glu Ser Ala Phe Gly Ala Gly Trp Ala
130 135 140

Ala Glu Pro Ser His Gly His Phe Ala Arg Ile Val Ser Gly Val Gly
145 150 155 160

Ala Phe Arg Phe His Val Glu Ser Val Asp Ser Met Phe Lys Leu Ser
165 170 175

Gln Glu Lys Asp Arg Asp Val Arg Val Arg Ile Ile Ala Ser Leu Arg
180 185 190

Glu Ala Ser Gly Pro Ala Ala Glu Leu Gly Arg Ile Met His Glu His
195 200 205

Gly Leu Gly Gly Arg Gly Ala Glu Gly Ala
210 215

<210> SEQ ID NO 108
<211> LENGTH: 213
<212> TYPE: PRT
<213> ORGANISM: Kutzneria sp. 744

<400> SEQUENCE: 108

Met Phe Val Pro Gly Pro Tyr His Ala Pro Glu Asp Arg Trp Leu Val
1 5 10 15

Asp Leu Val Arg Gly His Pro Leu Ala Gln Leu Ala Ser Asn Gly Ala
20 25 30

Gly Gly Ala Ala Pro His Ile Thr His Val Pro Ile Ile Val Asp Pro
35 40 45

Glu Leu Asp Gly Pro Val Asp Arg Leu Val Gly Ile Thr Leu Trp Gly
50 55 60

-continued

```
His Met Asn Arg Ala Asn Pro His Trp Ala Ala Leu Gly Gly Ala Ala
65                  70                  75                  80

Asn Val Val Ala Thr Phe Ala Gly Pro Asn Ala Tyr Val Ser Pro Ala
                85                  90                  95

Val Tyr Arg Thr Ala Pro Ala Ala Pro Thr Trp Asn Phe Thr Ser Val
            100                 105                 110

Gln Val Arg Gly Glu Leu Arg Lys Val Glu Ser Ala Asp Asp Thr Leu
        115                 120                 125

Ala Thr Val Arg Ala Thr Val Ala Ala Leu Glu Ser Arg Phe Gly Ala
    130                 135                 140

Gly Trp Asp Met Thr Gly Ser Leu Asp Tyr Phe Arg Arg Ile Leu Pro
145                 150                 155                 160

Gly Val Gly Ala Phe Arg Leu Arg Val Ala Glu Ala Asp Gly Met Phe
                165                 170                 175

Lys Leu Ser Gln Glu Gln Gln Pro Ala Ile Arg Arg Arg Val Arg His
            180                 185                 190

Ser Phe Gly Gly Cys Glu Ala Thr Arg Ala Val Ala Gly Leu Met Asp
        195                 200                 205

Arg Leu Pro Thr Glu
    210


<210> SEQ ID NO 109
<211> LENGTH: 214
<212> TYPE: PRT
<213> ORGANISM: Kibdelosporangium sp. MJ126-NF4

<400> SEQUENCE: 109

Met His Val Pro Pro Met Tyr Glu Ala Pro Asp Pro Ala Trp Ile Pro
1               5                   10                  15

Ala Leu Ile Arg Ala His Pro Leu Ala Thr Leu Val Thr Ala Pro Asp
            20                  25                  30

Gly Ile Pro Ala Ala Ser His Val Pro Met Ile Ile Arg Arg Thr Pro
        35                  40                  45

Asp Asp Glu Arg Leu Thr Leu Val Gly His Met Asn Arg Met Asn Pro
    50                  55                  60

Gln Phe Lys Ala Ile Gly Asp Gly Cys Pro Ala Leu Leu Val Phe Thr
65                  70                  75                  80

Gly Pro His Gly Tyr Val Ser Pro Thr Val Tyr Gly Phe Thr Pro Ala
                85                  90                  95

Ala Pro Thr Trp Asn Phe Ala Val Val His Ala Ser Gly Thr Leu Ser
            100                 105                 110

Pro Leu Pro Ala Gly Pro Asp Thr Leu Glu Val Ile Ile Asp Thr Val
        115                 120                 125

Thr Ala Leu Glu Gly Gln Leu Gly Asn Gly Trp Gln Met Arg Asp Ser
    130                 135                 140

Leu Glu Tyr Phe Asp Gln Leu Leu Pro Gly Val Gly Ala Phe Ser Val
145                 150                 155                 160

Gln Val Asp Arg Val Glu Ala Met Tyr Lys Leu Ser Gln Glu Gln Glu
                165                 170                 175

Pro Thr Thr Arg Glu Thr Val Ala Ala Ala Phe Glu Ala Arg Ser Ser
            180                 185                 190

Asp Leu Ala Ala Met Met Arg Val Cys Leu Asp Val Glu Arg Ser Thr
        195                 200                 205

Leu Gly Asn Arg Val Gly
    210
```

<210> SEQ ID NO 110
<211> LENGTH: 252
<212> TYPE: PRT
<213> ORGANISM: Mycobacterium xenopi

<400> SEQUENCE: 110

Met Leu Ser Leu Leu Pro Phe Arg Ala Gln Ala Ile Ala Gln Glu Ile
1 5 10 15

Ala Ala Ser Arg His Arg Asp Ala Val Thr Val Arg Gln Arg Pro Val
20 25 30

Gly Asp Tyr Pro Pro Lys Arg Tyr Leu Glu Thr Asp Pro Asp Arg Leu
35 40 45

Arg Ala Val Ile Glu Arg Tyr Arg Phe Ala Thr Leu Ile Ser Ala Arg
50 55 60

Ala Thr Asp Glu Pro Val Val Thr Gln Leu Pro Leu Thr Leu Asp Thr
65 70 75 80

Ser Arg Gly Ser His Gly Val Leu Phe Gly His Met Asp Leu Ala Asn
85 90 95

Pro His Ala Glu Leu Leu Asp Gly Arg Pro Val Leu Ala Leu Phe His
100 105 110

Gly Pro Asn Gly Tyr Ile Pro Pro His Gln Ser Asn Gln Leu Pro Thr
115 120 125

Trp Asn Ser Ile Thr Val Glu Val Arg Gly Arg Ala Arg Ile Leu Arg
130 135 140

Asp Lys Asp Ala Val Val Asp Gly Leu Arg Gly Ile Ala Ala Ala Ala
145 150 155 160

Asp Pro Ser Pro Gly Gly Phe Arg Leu Thr Arg Glu Ala Ala Ser Asp
165 170 175

Glu Arg Leu Phe Pro Phe Leu Val Gly Phe Glu Ile Asp Ile Asp Glu
180 185 190

Met Val Gly Arg Phe Lys Leu Ser Gln Asp Arg Asp Asp Arg Asp Arg
195 200 205

Trp Leu Ala Ala Arg Thr Leu Ala His Gly Leu Glu Gln Asp Asp Arg
210 215 220

Asp Leu Ile Ala Ser Ile Val Glu Leu Pro Leu Asp Arg Asp Asp Asp
225 230 235 240

Pro Ile Pro Leu Arg Arg Ala Arg Thr Ser Gly Thr
245 250

<210> SEQ ID NO 111
<211> LENGTH: 214
<212> TYPE: PRT
<213> ORGANISM: Streptomyces mirabilis

<400> SEQUENCE: 111

Met Phe Val Pro Ser Phe Tyr Arg Glu Pro Asp Ser Ser Trp Met Val
1 5 10 15

Asp Leu Ile Arg Gly Asn Pro Leu Ala Leu Ala Ala Ala Asn Gly Ser
20 25 30

Pro Glu Glu Gly Pro Phe Ala Thr His Leu Pro Val Ile Phe Asp Pro
35 40 45

Glu Thr Ser Gly Asp Trp Ser Gly Glu Leu Pro Gly Ala Thr Leu Leu
50 55 60

Gly His Met Asn Arg Ala Asn Pro His Trp Ala Ala Leu Ala Thr Gly
65 70 75 80

```
Ser Val Leu Leu Leu Thr Phe Thr Gly Pro His Ser Tyr Val Ser Pro
                85                  90                  95

Thr Val Tyr Glu Val Thr Pro Ala Ala Pro Thr Trp Asn Phe Thr Ala
            100                 105                 110

Val His Val Arg Gly Val Val Glu Lys Ile Asp Ser Ile Glu Glu Thr
        115                 120                 125

Leu Gly Val Val Gln Ser Thr Val Arg Ala Phe Glu Gly Ala Phe Gly
    130                 135                 140

Asp Gly Trp Asp Met Thr Glu Ser Leu Gly Tyr Phe Arg Lys Ile Val
145                 150                 155                 160

Pro Asp Val Gly Ala Phe Arg Phe Thr Val Thr Gly Ala Glu Gly Met
                165                 170                 175

Phe Lys Leu Ser Gln Glu Gln Pro Gly Glu Val Arg Glu Arg Val Arg
            180                 185                 190

Glu Ser Phe Gly His Ser Ala Cys Ala Tyr Lys Arg Glu Thr Ala Gly
        195                 200                 205

Leu Met Ser Arg Leu Pro
    210


<210> SEQ ID NO 112
<211> LENGTH: 214
<212> TYPE: PRT
<213> ORGANISM: Streptomyces scabrisporus

<400> SEQUENCE: 112

Met Phe Val Pro Arg His Tyr Arg Glu Pro Asp Ser Ser Trp Met Val
1               5                   10                  15

Asp Leu Ile Arg Ala Asn Pro Leu Ala Leu Ala Val Met Asn Gly Asp
            20                  25                  30

Pro Ser Ala Gly Pro Phe Ala Thr His Leu Pro Val Ile Pro Asp Pro
        35                  40                  45

Gln Met Thr Pro Ser Trp Ser Asp Asp Leu Ser Gly Ala Thr Leu Leu
    50                  55                  60

Gly His Met Asn Arg Ala Asn Pro His Trp Lys Ala Leu Glu Thr Gly
65                  70                  75                  80

Thr Val Leu Leu Leu Thr Phe Thr Gly Pro His Gly Tyr Val Ser Pro
                85                  90                  95

Thr Val Tyr Glu Val Thr Pro Ala Ala Pro Thr Trp Asn Phe Thr Ser
            100                 105                 110

Val His Val Arg Gly Val Val Glu Arg Ile Asp Ser Leu Glu Glu Thr
        115                 120                 125

Leu Gly Val Val Arg Ala Thr Ala Leu Ala Phe Glu Ser Glu Phe Gly
    130                 135                 140

Ala Gly Trp Asp Gln Thr Glu Ser Val Asp Tyr Phe Arg Lys Ile Val
145                 150                 155                 160

Pro Gly Val Gly Ala Phe Arg Val Thr Val Thr Gly Ala Glu Gly Met
                165                 170                 175

Phe Lys Leu Ser Gln Glu Gln Pro Ala Glu Val Arg Glu Arg Val Arg
            180                 185                 190

Gln Ser Phe Ser Thr Arg Ala Cys Ser Leu Gln Arg Glu Thr Ala Glu
        195                 200                 205

Leu Met Thr Arg Leu Pro
    210
```

<210> SEQ ID NO 113
<211> LENGTH: 224
<212> TYPE: PRT
<213> ORGANISM: Streptomyces sp. TAA040

<400> SEQUENCE: 113

```
Val Phe Val Pro Thr His Tyr Arg Glu Pro Asp Gly Ser Trp Met Ala
1               5                   10                  15

Asp Leu Met Arg Glu Asn Pro Leu Ala Leu Ala Val Thr Asp Gly Gly
            20                  25                  30

Ala Gly Asp Gly Pro Phe Ala Thr His Leu Pro Val Val Pro Asp Pro
        35                  40                  45

Gly Thr Thr Gly Asp Trp Pro Asn Gly Leu Lys Gly Ala Thr Leu Leu
    50                  55                  60

Gly His Met Asn Arg Ala Asn Pro His Trp Arg Ala Leu Glu Thr Gly
65                  70                  75                  80

Gly Val Val Leu Leu Ala Phe Thr Gly Pro His Ala Tyr Val Ser Pro
                85                  90                  95

Thr Val Tyr Glu Val Thr Pro Ala Ala Pro Thr Trp Asn Phe Thr Ser
            100                 105                 110

Val His Val Arg Gly Val Val Asp Arg Ile Asp Ser Pro Glu Glu Thr
        115                 120                 125

Leu Asp Val Val Arg Thr Thr Ala Leu Val Tyr Glu Ala Arg Phe Gly
    130                 135                 140

Ala Gly Trp Asp Gln Ala Ala Ser Leu Asp Tyr Phe Arg Arg Ile Val
145                 150                 155                 160

Pro Ala Val Gly Ala Phe Arg Ile Ala Val Thr Ser Ala Glu Gly Met
                165                 170                 175

Phe Lys Leu Ser Gln Glu Gln Pro Ala Glu Val Arg Glu Arg Val His
            180                 185                 190

Arg Ser Phe Ser Gly Arg Glu Cys Gly Arg His Arg Asp Thr Ala Ala
        195                 200                 205

Leu Met Glu Arg Leu Pro Arg Thr Gly Ala Glu Pro Pro Val Gly Arg
    210                 215                 220
```

<210> SEQ ID NO 114
<211> LENGTH: 243
<212> TYPE: PRT
<213> ORGANISM: Actinoalloteichus cyanogriseus

<400> SEQUENCE: 114

```
Met Phe Val Pro His Gln Tyr Arg Ala Ala Asp Thr Arg Pro Leu Val
1               5                   10                  15

Glu Leu Ile Arg Ser Phe Pro Leu Ala Thr Leu Val Ser His Ala Asp
            20                  25                  30

Gly Ala Leu Phe Ala Thr His Val Pro Val Leu Leu Ala Ala Asp Ala
        35                  40                  45

Asp Ala Gly Arg Asp Val Pro Asp Pro Ala Asp Leu Thr Ile Leu Gly
    50                  55                  60

His Leu Asn Arg Leu Asn Pro His Arg Asp Ala Leu Ala Gly Gly Gly
65                  70                  75                  80

Ala Cys Leu Leu Thr Phe Thr Gly Pro His Ser Tyr Val Ser Pro Ala
                85                  90                  95

His Tyr Gly Arg Asp Thr Ala Ala Pro Thr Trp Asn Phe Thr Ser Val
            100                 105                 110

His Val His Gly His Leu Thr Pro Leu Asp Ser Thr Glu Asp Thr Arg
```

```
        115                 120                 125

His Val Val Arg Ser Thr Ala Leu Leu Tyr Glu Arg Arg Phe Gly Ala
    130                 135                 140

Gly Trp Asp Met Thr Gly Ser Leu Asp Tyr Phe Glu Gln Leu Leu Pro
145                 150                 155                 160

Gly Val Ser Ala Phe Arg Val Asp Val Gly Thr Val Glu Gly Met Phe
                165                 170                 175

Lys Leu Gly Gln Glu Gln Pro Gly His Ala Arg Gln Gly Val Leu Ala
            180                 185                 190

Ala Phe Thr Ser Pro Gly Ala Pro Pro His Gln Arg Ala Val Ala Glu
        195                 200                 205

Leu Met Arg Arg Phe Pro Pro Asp Ala Ala Gly Gly Val Pro Gly Cys
    210                 215                 220

Pro Ala Gln Ser Ala Ala Arg Met Ser Pro Pro Ala Asp Ala Ile Arg
225                 230                 235                 240

Gly Glu His


<210> SEQ ID NO 115
<211> LENGTH: 214
<212> TYPE: PRT
<213> ORGANISM: Streptomyces sp. HNS054

<400> SEQUENCE: 115

Met Phe Val Pro Asn Phe Tyr Arg Glu Pro Asp Ala Ser Trp Met Val
1               5                   10                  15

Asp Leu Val Arg Gly Asn Pro Leu Ala Leu Ala Val Ser Asn Gly Cys
            20                  25                  30

Pro Glu Asp Gly Pro Phe Ala Thr His Leu Pro Val Ile Phe Asp Pro
        35                  40                  45

Ala Arg Tyr Gly Asp Leu Pro Gly Glu Leu Ala Gly Ala Thr Leu Leu
    50                  55                  60

Gly His Met Asn Arg Ala Asn Pro His Trp Pro Ala Leu Gln Thr Gly
65                  70                  75                  80

Gly Ile Leu Leu Leu Thr Phe Thr Gly Pro His Ser Tyr Val Ser Pro
                85                  90                  95

Thr Ala Tyr Gly Thr Thr Pro Ala Ala Pro Thr Trp Asn Phe Thr Ala
            100                 105                 110

Val His Ala Arg Gly Val Val Glu Lys Ile Asp Ser Thr Glu Glu Thr
        115                 120                 125

Leu Asp Val Val Lys Ala Thr Val Arg Ala Tyr Glu Gly Glu Phe Gly
    130                 135                 140

Asp Gly Trp Asp Met Thr Glu Ser Leu Gly Tyr Phe Arg Lys Ile Val
145                 150                 155                 160

Pro Ala Val Gly Ala Phe Arg Leu Thr Val Thr Arg Ala Glu Gly Met
                165                 170                 175

Phe Lys Leu Ser Gln Glu Gln Pro Ala Glu Val Arg Glu Arg Val Arg
            180                 185                 190

Glu Ser Phe Glu Gln Ser Ala Cys Arg Tyr Lys Arg Glu Thr Ala Gly
        195                 200                 205

Leu Met Ser Arg Leu Pro
    210


<210> SEQ ID NO 116
<211> LENGTH: 238
<212> TYPE: PRT
```

<213> ORGANISM: Streptomyces sp. AW19M42

<400> SEQUENCE: 116

```
Met Tyr Val Pro Asp His Tyr Gln Gly Ser Pro Glu Ala Ala Leu Thr
1               5                   10                  15

Val Val Arg Ala Gly Pro Leu Ala Thr Leu Val Thr Gly Ala Asp Pro
            20                  25                  30

Trp Pro Leu Ala Thr His Leu Pro Val Val Val Pro Ala Asp Val Glu
        35                  40                  45

Ala Ala Leu Glu His Gly Pro Val Asp Leu Arg Gly His Arg Leu Ile
    50                  55                  60

Gly His Leu Asn Arg Ala Asn Pro His Trp Arg Gln Leu Ser Ala Gly
65                  70                  75                  80

Glu Gln Pro Ser Leu Leu Ile Phe Arg Gly Pro His Gly Tyr Ile Ser
                85                  90                  95

Pro Val Val Tyr Glu Ser Thr Pro Ala Ala Pro Thr Trp Asn Phe Thr
            100                 105                 110

Ala Val His Val His Gly Thr Ile Arg Pro Leu Pro Ala Gly Lys Glu
        115                 120                 125

Thr Leu Asp Val Ile His Arg Thr Val Glu Val Leu Glu Gly Gly Phe
    130                 135                 140

Gly His Gly Trp Asp Met Arg Gly Ser Leu Glu Tyr Phe Glu Lys Ile
145                 150                 155                 160

Val Pro His Val Gly Ala Phe Glu Phe Gln Val Ala Glu Val Asp Gly
                165                 170                 175

Met Phe Lys Leu Ser Gln Glu Leu Asp Glu Glu Thr Arg Glu Arg Thr
            180                 185                 190

Thr His His Phe Ala Thr Ser Ala His Gly Thr His Arg Glu Leu Ala
        195                 200                 205

Cys Glu Met Ala Arg Leu Ser Thr Ala Ala Glu Thr Lys Asp Gly Ala
    210                 215                 220

Ser Glu Gly Ala Ser Gly Ser Ser Ser Lys Arg Gly Thr Ala
225                 230                 235
```

<210> SEQ ID NO 117
<211> LENGTH: 221
<212> TYPE: PRT
<213> ORGANISM: Salinispora pacifica

<400> SEQUENCE: 117

```
Met Phe Val Pro Ser Pro Tyr Arg Glu Pro Asp Gly Ser Trp Thr Val
1               5                   10                  15

Asp Leu Met Arg Arg Asn Pro Leu Ala Leu Leu Val Thr Ser Ser Asp
            20                  25                  30

Lys Thr Asp Val Pro Tyr Ala Thr His Leu Pro Val Ile Phe Asp Pro
        35                  40                  45

Cys Met Pro Glu Glu Asp Tyr Ser Asp Pro Ala Arg Phe Val Leu Leu
    50                  55                  60

Gly His Met Asn Arg Ala Asn Pro His Trp Lys Ala Leu Ala Thr Gly
65                  70                  75                  80

Met Pro Thr Leu Val Val Phe Ser Gly Ser His Ala Tyr Val Ser Pro
                85                  90                  95

Thr Val Tyr Asp Lys Ser Pro Ala Ala Pro Thr Trp Asn Phe Thr Ala
            100                 105                 110

Ala His Ala Arg Gly Val Leu Glu Lys Ile Glu Ser Ala Glu Glu Thr
```

```
        115                 120                 125

Leu Gly Val Ile Gly Ser Thr Val Arg Ala Phe Glu Ala Asp Phe Gly
    130                 135                 140

Thr Asp Trp Asp Met Thr Gln Ser Val Gly Tyr Phe Arg Lys Ile Leu
145                 150                 155                 160

Pro Gly Val Gly Ala Phe Arg Ile Ala Val Ser Ser Ile Asp Ser Met
                165                 170                 175

Phe Lys Leu Ser Gln Glu Gln Pro Pro Glu Val Arg Asp Arg Val Gly
            180                 185                 190

Cys Ala Phe Ala Glu Ser Ala Ser Thr Arg His Arg Glu Val Ala Gly
        195                 200                 205

Leu Met Asn Arg Leu Ala Val Pro Lys Gln Val Thr Val
    210                 215                 220


<210> SEQ ID NO 118
<211> LENGTH: 221
<212> TYPE: PRT
<213> ORGANISM: Salinispora pacifica

<400> SEQUENCE: 118

Met Phe Val Pro Ser Pro Tyr Arg Glu Pro Asp Gly Ser Trp Thr Val
1               5                   10                  15

Asp Leu Met Arg Arg Asn Pro Leu Ala Leu Leu Val Thr Ser Ser Asp
            20                  25                  30

Lys Thr Asp Val Pro Tyr Ala Thr His Leu Pro Val Ile Phe Asp Pro
        35                  40                  45

Cys Met Pro Glu Glu Asp Tyr Ser Asp Pro Ala Arg Phe Val Leu Leu
    50                  55                  60

Gly His Met Asn Arg Ala Asn Pro His Trp Lys Ala Leu Ala Thr Gly
65                  70                  75                  80

Met Pro Thr Leu Val Val Phe Ser Gly Ser His Ala Tyr Val Ser Pro
                85                  90                  95

Thr Val Tyr Asp Lys Ser Pro Ala Ala Pro Thr Trp Asn Phe Thr Ala
            100                 105                 110

Ala His Ala Arg Gly Val Leu Glu Lys Ile Glu Ser Ala Glu Glu Thr
        115                 120                 125

Leu Gly Val Ile Gly Ser Thr Val Arg Ala Phe Glu Ala Asp Phe Gly
    130                 135                 140

Thr Asp Trp Asp Met Thr Gln Ser Val Gly Tyr Phe Arg Lys Ile Leu
145                 150                 155                 160

Pro Gly Val Gly Ala Phe Arg Ile Ala Val Ser Ser Ile Asp Ser Met
                165                 170                 175

Phe Lys Leu Ser Gln Glu Gln Pro Pro Glu Val Arg Asp Arg Val Gly
            180                 185                 190

Cys Ala Phe Ala Glu Ser Ala Ser Thr Arg His Arg Glu Val Ala Gly
        195                 200                 205

Leu Met Asn Arg Leu Ala Val Pro Lys Gln Val Thr Val
    210                 215                 220


<210> SEQ ID NO 119
<211> LENGTH: 221
<212> TYPE: PRT
<213> ORGANISM: Salinispora tropica

<400> SEQUENCE: 119

Met Phe Val Pro Ser Pro Tyr Arg Glu Pro Asp Gly Ser Trp Thr Val
```

-continued

```
1               5                   10                  15

Asp Leu Met Arg Arg Asn Pro Leu Ala Leu Leu Val Thr Ser Ser Asp
            20                  25                  30

Lys Thr Asp Ile Pro Tyr Ala Thr His Leu Pro Val Ile Phe Asp Pro
        35                  40                  45

Arg Met Pro Glu Glu Asp Tyr Ser Asp Pro Ala Arg Phe Val Leu Leu
    50                  55                  60

Gly His Met Asn Arg Ala Asn Pro His Trp Lys Ala Leu Ala Thr Gly
65                  70                  75                  80

Met Pro Thr Leu Val Val Phe Ser Gly Ser His Ala Tyr Val Ser Pro
                85                  90                  95

Thr Val Tyr Asp Lys Ser Pro Ala Ala Pro Thr Trp Asn Phe Thr Ala
            100                 105                 110

Ala His Ala Arg Gly Val Leu Glu Lys Ile Glu Ser Ala Glu Glu Thr
        115                 120                 125

Leu Gly Val Ile Gly Ser Thr Val Arg Ala Phe Glu Ala Asp Phe Gly
    130                 135                 140

Ala Asp Trp Asp Met Ala Gln Ser Val Gly Tyr Phe Arg Lys Ile Leu
145                 150                 155                 160

Pro Gly Val Gly Ala Phe Arg Ile Ala Val Ser Ser Ile Asp Ser Met
                165                 170                 175

Phe Lys Leu Ser Gln Glu Gln Ser Pro Glu Val Arg Asp Arg Val Gly
            180                 185                 190

Cys Ala Phe Ala Glu Ser Ala Ser Thr Arg His Arg Glu Val Ala Asp
        195                 200                 205

Leu Met Asn Arg Leu Ala Val Pro Lys Gln Val Thr Val
    210                 215                 220


<210> SEQ ID NO 120
<211> LENGTH: 221
<212> TYPE: PRT
<213> ORGANISM: Salinispora arenicola

<400> SEQUENCE: 120

Met Phe Val Pro Ser Pro Tyr Arg Glu Pro Asp Gly Ser Trp Thr Val
1               5                   10                  15

Asp Leu Met Arg Arg Asn Pro Leu Ala Leu Leu Val Thr Ser Ser Asp
            20                  25                  30

Lys Thr Asp Val Pro Tyr Ala Thr His Leu Pro Val Ile Phe Asp Pro
        35                  40                  45

Cys Met Pro Glu Glu Asp Tyr Ser Asp Pro Ala Arg Phe Val Leu Leu
    50                  55                  60

Gly His Met Asn Arg Ala Asn Pro His Trp Lys Ala Leu Ala Thr Gly
65                  70                  75                  80

Met Pro Thr Leu Val Val Phe Ser Gly Ser His Ala Tyr Val Ser Pro
                85                  90                  95

Thr Val Tyr Asp Lys Ser Pro Ala Ala Pro Thr Trp Asn Phe Thr Ala
            100                 105                 110

Ala His Ala Arg Gly Val Leu Glu Lys Ile Glu Ser Ala Glu Glu Ala
        115                 120                 125

Leu Gly Val Ile Gly Ser Thr Val Arg Ala Phe Glu Ala Asp Phe Gly
    130                 135                 140

Thr Asp Trp Asp Met Thr Gln Ser Val Gly Tyr Phe Arg Lys Ile Leu
145                 150                 155                 160
```

-continued

```
Pro Gly Val Gly Ala Phe Arg Ile Ala Val Ser Ser Ile Asp Ser Met
                165                 170                 175

Phe Lys Leu Ser Gln Glu Gln Pro Pro Glu Val Arg Asp Arg Val Gly
            180                 185                 190

Cys Ala Phe Ala Glu Ser Ala Ser Thr Arg His Arg Glu Val Ala Gly
        195                 200                 205

Leu Met Asn Arg Leu Ala Val Pro Lys Arg Val Thr Val
    210                 215                 220
```

<210> SEQ ID NO 121
<211> LENGTH: 221
<212> TYPE: PRT
<213> ORGANISM: Salinispora arenicola

<400> SEQUENCE: 121

```
Met Phe Val Pro Ser Pro Tyr Arg Glu Pro Asp Gly Ser Trp Thr Val
1               5                   10                  15

Asp Leu Met Arg Arg Asn Pro Leu Ala Leu Leu Val Thr Ser Ser Asp
            20                  25                  30

Lys Thr Asp Val Pro Tyr Ala Thr His Leu Pro Val Ile Phe Asp Pro
        35                  40                  45

Cys Met Pro Glu Glu Asp Tyr Ser Asp Pro Ala Arg Phe Val Leu Leu
    50                  55                  60

Gly His Met Asn Arg Ala Asn Pro His Trp Lys Ala Leu Ala Thr Gly
65                  70                  75                  80

Met Pro Thr Leu Val Val Phe Ser Gly Ser His Ala Tyr Val Ser Pro
                85                  90                  95

Thr Val Tyr Asp Lys Ser Pro Ala Ala Pro Thr Trp Asn Phe Thr Ala
            100                 105                 110

Ala His Ala Arg Gly Val Leu Glu Lys Ile Glu Ser Ala Glu Glu Ala
        115                 120                 125

Leu Gly Val Ile Gly Ser Thr Val Arg Ala Phe Glu Ala Asp Phe Gly
    130                 135                 140

Thr Asp Trp Asp Met Thr Gln Ser Val Gly Tyr Phe Arg Lys Ile Leu
145                 150                 155                 160

Pro Gly Val Gly Ala Phe Arg Ile Ala Val Ser Ser Ile Asp Ser Met
                165                 170                 175

Phe Lys Leu Ser Gln Glu Gln Pro Pro Glu Val Arg Asp Arg Val Gly
            180                 185                 190

Cys Ala Phe Ala Glu Ser Ala Ser Thr Arg His Arg Glu Val Ala Gly
        195                 200                 205

Leu Met Asn Arg Leu Ala Val Pro Lys Arg Val Thr Val
    210                 215                 220
```

<210> SEQ ID NO 122
<211> LENGTH: 221
<212> TYPE: PRT
<213> ORGANISM: Salinispora tropica

<400> SEQUENCE: 122

```
Met Phe Val Pro Ser Pro Tyr Arg Glu Pro Asp Gly Ser Trp Thr Val
1               5                   10                  15

Asp Leu Met Arg Arg Asn Pro Leu Ala Leu Leu Val Thr Ser Ser Asp
            20                  25                  30

Lys Thr Asp Ile Pro Tyr Ala Thr His Leu Pro Val Ile Phe Asp Pro
        35                  40                  45
```

-continued

```
Arg Met Pro Glu Glu Asp Tyr Ser Asp Pro Ala Arg Phe Val Leu Leu
    50                  55                  60

Gly His Met Asn Arg Ala Asn Pro His Trp Lys Ala Leu Ala Thr Gly
65                  70                  75                  80

Met Pro Thr Leu Val Val Phe Ser Gly Ser His Ala Tyr Val Ser Pro
                85                  90                  95

Thr Val Tyr Asp Lys Ser Pro Ala Ala Pro Thr Trp Asn Phe Thr Ala
            100                 105                 110

Ala His Ala Arg Gly Val Leu Glu Lys Ile Glu Ser Ala Glu Glu Thr
        115                 120                 125

Leu Gly Val Ile Gly Ser Thr Val Arg Ala Phe Glu Ala Asp Phe Gly
    130                 135                 140

Thr Asp Trp Asp Met Ala Gln Ser Val Gly Tyr Phe Arg Lys Ile Leu
145                 150                 155                 160

Pro Gly Val Gly Ala Phe Arg Ile Ala Val Ser Ser Ile Asp Ser Met
                165                 170                 175

Phe Lys Leu Ser Gln Glu Gln Ser Pro Glu Val Arg Asp Arg Val Gly
            180                 185                 190

Cys Ala Phe Ala Glu Ser Ala Ser Thr Arg His Arg Glu Val Ala Asp
        195                 200                 205

Leu Met Asn Arg Leu Ala Val Pro Lys Gln Val Thr Val
    210                 215                 220


<210> SEQ ID NO 123
<211> LENGTH: 221
<212> TYPE: PRT
<213> ORGANISM: Salinispora tropica

<400> SEQUENCE: 123

Met Phe Val Pro Ser Pro Tyr Arg Glu Pro Asp Gly Ser Trp Thr Val
1               5                   10                  15

Asp Leu Met Arg Arg Asn Pro Leu Ala Leu Leu Val Thr Ser Ser Asp
            20                  25                  30

Lys Thr Asp Ile Pro Tyr Ala Thr His Leu Pro Val Ile Phe Asp Pro
        35                  40                  45

Arg Met Pro Glu Glu Asp Tyr Ser Asp Pro Ala Arg Phe Val Leu Leu
    50                  55                  60

Gly His Met Asn Arg Ala Asn Pro His Trp Lys Ala Leu Ala Thr Gly
65                  70                  75                  80

Met Pro Thr Leu Val Val Phe Ser Gly Ser His Ala Tyr Val Ser Pro
                85                  90                  95

Thr Val Tyr Asp Lys Ser Pro Ala Ala Pro Thr Trp Asn Phe Thr Ala
            100                 105                 110

Ala His Ala Arg Gly Val Leu Glu Lys Ile Glu Ser Ala Glu Glu Thr
        115                 120                 125

Leu Gly Val Ile Gly Ser Thr Val Arg Ala Phe Glu Ala Asp Phe Gly
    130                 135                 140

Thr Asp Trp Asp Met Ala Gln Ser Val Gly Tyr Phe Arg Lys Ile Leu
145                 150                 155                 160

Pro Gly Val Gly Ala Phe Arg Ile Ala Val Ser Ser Ile Asp Ser Met
                165                 170                 175

Phe Lys Leu Ser Gln Glu Gln Ser Pro Glu Val Arg Asp Arg Val Gly
            180                 185                 190

Cys Ala Phe Ala Glu Ser Ala Ser Thr Arg His Arg Glu Val Ala Asp
        195                 200                 205
```

```
Leu Met Asn Arg Leu Ala Val Pro Lys Gln Val Thr Val
    210                 215                 220


<210> SEQ ID NO 124
<211> LENGTH: 221
<212> TYPE: PRT
<213> ORGANISM: Salinispora tropica

<400> SEQUENCE: 124

Met Phe Val Pro Ser Pro Tyr Arg Glu Pro Asp Gly Ser Trp Thr Val
1               5                   10                  15

Asp Leu Met Arg Arg Asn Pro Leu Ala Leu Leu Val Thr Ser Ser Asp
            20                  25                  30

Lys Thr Asp Ile Pro Tyr Ala Thr His Leu Pro Val Ile Phe Asp Pro
        35                  40                  45

Arg Met Pro Glu Glu Asp Tyr Ser Asp Pro Ala Arg Phe Val Leu Leu
    50                  55                  60

Gly His Met Asn Arg Ala Asn Pro His Trp Lys Ala Leu Val Thr Gly
65                  70                  75                  80

Met Pro Thr Leu Val Val Phe Ser Gly Ser His Ala Tyr Val Ser Pro
                85                  90                  95

Thr Val Tyr Asp Lys Ser Pro Ala Ala Pro Thr Trp Asn Phe Thr Ala
            100                 105                 110

Ala His Ala Arg Gly Val Leu Glu Lys Ile Glu Ser Ala Glu Glu Thr
        115                 120                 125

Leu Gly Val Ile Gly Ser Thr Val Arg Ala Phe Glu Ala Asp Phe Gly
    130                 135                 140

Thr Asp Trp Asp Met Ala Gln Ser Val Gly Tyr Phe Arg Lys Ile Leu
145                 150                 155                 160

Pro Gly Val Gly Ala Phe Arg Ile Ala Val Ser Ser Ile Asp Ser Met
                165                 170                 175

Phe Lys Leu Ser Gln Glu Gln Ser Pro Glu Val Arg Asp Arg Val Gly
            180                 185                 190

Cys Ala Phe Ala Glu Ser Ala Ser Thr Arg His Arg Glu Val Ala Asp
        195                 200                 205

Leu Met Asn Arg Leu Ala Val Pro Lys Gln Val Thr Val
    210                 215                 220


<210> SEQ ID NO 125
<211> LENGTH: 225
<212> TYPE: PRT
<213> ORGANISM: Streptomyces sp. PsTaAH-137

<400> SEQUENCE: 125

Met Phe Val Pro Ser Phe Tyr Arg Glu Pro Asp Ser Ser Trp Met Val
1               5                   10                  15

Asp Leu Ile Arg Gly Asn Pro Leu Ala Leu Ala Val Ala Asn Gly Pro
            20                  25                  30

Ala Glu Asp Gly Pro Phe Ala Thr His Leu Pro Val Ile Phe Asp Pro
        35                  40                  45

Glu Thr Ser Ala Asp Val Ser Gly Glu Leu Pro Gly Val Thr Leu Leu
    50                  55                  60

Gly His Met Asn Arg Ala Asn Pro His Trp Ser Ala Leu Gln Asp Gly
65                  70                  75                  80

Gly Val Leu Leu Leu Thr Phe Thr Gly Pro His Ser Tyr Val Ser Pro
                85                  90                  95
```

```
Thr Val Tyr Glu Lys Ser Pro Ala Ala Pro Thr Trp Asn Phe Thr Ser
            100                 105                 110

Val His Val Arg Gly Val Val Glu Lys Ile Ser Ser Ile Glu Glu Thr
        115                 120                 125

Leu Glu Val Val Gln Ala Thr Val Arg Ala Phe Glu Gly Ala Phe Gly
    130                 135                 140

Asp Gly Trp Asp Met Thr Gly Ser Leu Asp Tyr Phe Arg Lys Ile Val
145                 150                 155                 160

Pro Ala Val Gly Ala Phe Arg Phe Thr Val Thr Gly Ala Glu Gly Met
                165                 170                 175

Phe Lys Leu Ser Gln Glu Gln Pro Gly Glu Val Arg Glu Arg Val Arg
            180                 185                 190

Glu Ser Phe Gly Gln Ser Ala Cys Thr Tyr Lys Arg Glu Thr Ala Gly
        195                 200                 205

Leu Met Asn Arg Leu Ala Gln Thr Glu Asp Val Thr Val Ser Ser Gly
    210                 215                 220

Ala
225


<210> SEQ ID NO 126
<211> LENGTH: 213
<212> TYPE: PRT
<213> ORGANISM: Salinispora arenicola

<400> SEQUENCE: 126

Met Leu Val Pro His Met Tyr Glu Ala Pro Ser Ala Ala Gln Val Asp
1               5                   10                  15

Ala Val Ile Thr Gly His Pro Met Ala Val Leu Val Thr Asn Gly Pro
            20                  25                  30

Asp Val Pro His Ala Thr His Leu Pro Val Ile Arg Thr Val Asp Thr
        35                  40                  45

Glu Gln Thr Gly Pro Gly Ser Val Leu Leu Gly His Met Asn Arg Thr
    50                  55                  60

Asn Pro His Trp Ser Ala Leu Thr Ser Gly Thr Pro Gly Lys Leu Ile
65                  70                  75                  80

Phe Thr Gly Pro Asn Thr Tyr Val Cys Pro Val Leu Tyr Gln Thr Glu
                85                  90                  95

Pro Ala Ala Pro Thr Trp Asp Phe Val Val Val His Val Ser Gly Arg
            100                 105                 110

Val Met Pro Leu Asp Ala Gly Glu Pro Thr Leu Ala Val Val Gln Arg
        115                 120                 125

Thr Ala Ala Thr Leu Glu Gly Ala Phe Gly Ala Gly Trp Asp His Thr
    130                 135                 140

Gly Ser Ile Asp Tyr Phe Arg Ser Ile Val Gly Gly Val Gly Ala Phe
145                 150                 155                 160

Glu Phe Val Val Glu Gln Val Glu Ser Met Phe Lys Leu Ser Gln Glu
                165                 170                 175

Lys Asp His Thr Val Arg Gln Arg Leu Ile Asp Asp Phe Thr Ser Ala
            180                 185                 190

Pro Arg Asn Gly Ser Ala Gln Val Gly Gln Leu Met Ser Asp Leu Asn
        195                 200                 205

Leu Gly Val Ala Pro
    210
```

<210> SEQ ID NO 127
<211> LENGTH: 213
<212> TYPE: PRT
<213> ORGANISM: Salinispora arenicola

<400> SEQUENCE: 127

```
Met Leu Val Pro His Met Tyr Glu Ala Pro Ser Ala Ala Gln Val Asp
1               5                   10                  15

Ala Val Ile Thr Gly His Pro Met Ala Val Leu Val Thr Asn Gly Pro
            20                  25                  30

Asp Val Pro His Ala Thr His Leu Pro Val Ile Arg Thr Val Asp Thr
        35                  40                  45

Glu Gln Thr Gly Pro Gly Ser Val Leu Leu Gly His Met Asn Arg Thr
    50                  55                  60

Asn Pro His Trp Ser Ala Leu Thr Ser Gly Thr Pro Gly Lys Leu Ile
65                  70                  75                  80

Phe Thr Gly Pro Asn Thr Tyr Val Cys Pro Val Leu Tyr Gln Thr Glu
                85                  90                  95

Pro Ala Ala Pro Thr Trp Asp Phe Val Val Val His Val Ser Gly Arg
            100                 105                 110

Val Met Pro Leu Asp Ala Gly Glu Pro Thr Leu Ala Val Val Gln Arg
        115                 120                 125

Thr Ala Ala Thr Leu Glu Gly Ala Phe Gly Ala Gly Trp Asp His Thr
    130                 135                 140

Gly Ser Ile Asp Tyr Phe Arg Ser Ile Val Gly Gly Val Gly Ala Phe
145                 150                 155                 160

Glu Phe Val Val Glu Gln Val Glu Ser Met Phe Lys Leu Ser Gln Glu
                165                 170                 175

Lys Asp His Thr Val Arg Gln Arg Leu Ile Asp Asp Phe Thr Ser Ala
            180                 185                 190

Pro Arg Asn Gly Ser Ala Gln Val Gly Gln Leu Met Ser Asp Leu Asn
        195                 200                 205

Leu Gly Val Ala Pro
    210
```

<210> SEQ ID NO 128
<211> LENGTH: 213
<212> TYPE: PRT
<213> ORGANISM: Salinispora pacifica

<400> SEQUENCE: 128

```
Met Leu Val Pro His Met Tyr Glu Ala Pro Ser Ala Ala Gln Val Asp
1               5                   10                  15

Ala Val Ile Thr Gly His Pro Met Ala Val Leu Val Thr Asn Gly Pro
            20                  25                  30

Asp Val Pro His Ala Thr His Leu Pro Val Ile Arg Thr Val Asp Thr
        35                  40                  45

Glu Gln Thr Gly Pro Gly Ser Val Leu Leu Gly His Met Asn Arg Thr
    50                  55                  60

Asn Pro His Trp Ser Ala Leu Thr Ser Gly Thr Pro Gly Lys Leu Ile
65                  70                  75                  80

Phe Thr Gly Pro Asn Thr Tyr Val Cys Pro Val Leu Tyr Gln Thr Glu
                85                  90                  95

Pro Ala Ala Pro Thr Trp Asp Phe Val Val Val His Val Ser Gly Arg
            100                 105                 110

Val Met Pro Leu Asp Ala Gly Glu Pro Thr Leu Ala Val Val Gln Arg
```

```
        115                 120                 125

Thr Ala Ala Thr Leu Glu Gly Ala Phe Gly Ala Gly Trp Asp His Thr
    130                 135                 140

Gly Ser Ile Asp Tyr Phe Arg Ser Ile Val Gly Gly Val Gly Ala Phe
145                 150                 155                 160

Glu Phe Val Val Glu Gln Val Glu Ser Met Phe Lys Leu Ser Gln Glu
                165                 170                 175

Lys Asp His Thr Val Arg Gln Arg Leu Ile Asp Asp Phe Thr Ser Ala
            180                 185                 190

Pro Arg Asn Gly Ser Thr Gln Val Gly Gln Leu Met Ser Asp Leu Asn
        195                 200                 205

Leu Gly Val Ala Pro
    210


<210> SEQ ID NO 129
<211> LENGTH: 232
<212> TYPE: PRT
<213> ORGANISM: Actinomadura atramentaria

<400> SEQUENCE: 129

Val Phe Val Pro Pro Gln Tyr Arg Pro Arg Gly Arg Ser Trp Thr Leu
1               5                   10                  15

Glu Thr Val Arg Ser Asn Pro Leu Ala Met Leu Val Thr Arg Gly Glu
            20                  25                  30

Arg Ala Leu Pro Trp Ile Thr His Leu Pro Val Ile Thr His Pro Glu
        35                  40                  45

Arg Pro Pro Ala Glu Leu Pro Gly Ala Thr Leu Leu Gly His Met Asn
    50                  55                  60

Ala Ala Asn Pro His Trp Ala Ala Val Ala Ser Gly Gly Pro Gly Thr
65                  70                  75                  80

Leu Val Phe Thr Gly Pro His Gly Tyr Val Ser Pro Thr Val Tyr Glu
                85                  90                  95

Leu Pro Val Ala Ala Pro Thr Trp Asp Phe Val Ala Val His Val His
            100                 105                 110

Gly Thr Leu Arg Pro Leu Asp Thr Pro Glu Asp Ala Arg Arg Val Val
        115                 120                 125

Arg Trp Thr Val Glu Ala Tyr Glu Gly Thr His Gly Thr Gly Trp Asp
    130                 135                 140

Pro Glu Gly Ser Leu Asp Tyr Phe Asp Lys Ile Leu Pro Gly Val Arg
145                 150                 155                 160

Ala Phe Glu Phe His Val Glu Ser Val Asp Gly Met Tyr Lys Leu Ser
                165                 170                 175

Gln Glu Gln Glu Pro Glu Thr Arg Arg Arg Val Val Arg Ser Phe Ala
            180                 185                 190

Ala Ser Gly Arg Gly Ala His Ala Glu Leu Ser Ala Leu Ile Asp Arg
        195                 200                 205

Phe Gly Asp Pro Gly Pro Gly Ala Pro Ala Thr Gly Cys Pro Ala Ala
    210                 215                 220

Arg Glu Ala Gly Asp Gly Ala Arg
225                 230


<210> SEQ ID NO 130
<211> LENGTH: 218
<212> TYPE: PRT
<213> ORGANISM: Streptomyces drozdowiczii
```

<400> SEQUENCE: 130

Met Phe Val Pro Pro Met Tyr Arg Thr Glu Asn Glu Gly Arg Leu Arg
1 5 10 15

Gln Val Met Glu Arg Tyr Pro Leu Ala Met Leu Val Thr Asn Gly Glu
20 25 30

Pro Thr Pro Tyr Ala Thr His Leu Pro Val Ile Phe Asp Gln Asn Gly
35 40 45

Ala Pro Gly Thr Asp Gly Pro Val Gly Ala Thr Leu Leu Gly His Leu
50 55 60

Asn Arg Asn Asn Pro His Trp Arg Thr Leu Thr Asp Gly Leu Ala Ala
65 70 75 80

Lys Leu Val Phe Thr Gly Pro His Ser Tyr Ile Thr Pro Thr Leu Tyr
85 90 95

Glu Thr Thr Pro Ala Ala Pro Thr Trp Asn Phe Val Thr Val His Leu
100 105 110

Glu Gly Thr Leu His Pro Val Thr Asp Leu Glu Glu Thr Leu Gly Val
115 120 125

Leu Gln Ala Thr Val Glu Thr Phe Glu Ser Ala Phe Gly Asn Lys Trp
130 135 140

Glu Met Asp Ser Ser Leu Asp Tyr Phe Arg His Ile Gly Pro Ala Val
145 150 155 160

Gly Ala Phe Arg Phe Val Val Thr Ser Ala Asp Gly Met Phe Lys Leu
165 170 175

Ser Gln Glu Lys Thr Pro Glu Ile Gln His Arg Ile Ala Asp Arg Leu
180 185 190

Ile Gly Thr Glu Thr Gly Thr Arg His Glu Leu Gly Ala Leu Met Ala
195 200 205

Glu Leu Thr Leu Gly Asp Arg Asp Gly Val
210 215

<210> SEQ ID NO 131
<211> LENGTH: 200
<212> TYPE: PRT
<213> ORGANISM: Streptomyces sp. RSD-27

<400> SEQUENCE: 131

Met Val Asp Leu Val Arg Gly His Pro Met Ala Leu Ala Val Ala Asn
1 5 10 15

Gly Ser Pro Glu Asp Gly Pro Phe Ala Thr His Leu Pro Val Ile Phe
20 25 30

Asp Pro Val Thr Ser Gly Gln Trp Thr Gly Glu Leu Pro Gly Ala Thr
35 40 45

Leu Leu Gly His Met Asn Arg Ala Asn Pro His Trp Ala Ala Leu Glu
50 55 60

Thr Gly Gly Val Leu Leu Leu Thr Phe Thr Gly Pro His Ser Tyr Val
65 70 75 80

Ser Pro Thr Val Tyr Ala Lys Ser Pro Ala Ala Pro Thr Trp Asn Phe
85 90 95

Thr Ser Val His Val Arg Gly Val Val Glu Lys Ile Asp Ser Ile Glu
100 105 110

Glu Thr Leu Glu Val Val Gln Ser Thr Val Arg Ala Phe Glu Gly Ala
115 120 125

Phe Gly Asp Gly Trp Asp Met Thr Gly Ser Leu Asp Tyr Phe Arg Lys
130 135 140

```
Ile Val Pro Asp Val Gly Ala Phe Arg Leu Thr Val Thr Gly Ala Glu
145                 150                 155                 160

Gly Met Phe Lys Leu Ser Gln Glu Gln Pro Gly Glu Val Arg Glu Arg
                165                 170                 175

Val Arg Glu Ser Phe Gly Gln Ser Ala Cys Thr Tyr Arg Arg Glu Thr
            180                 185                 190

Ala Gly Leu Met Gly Arg Leu Pro
        195                 200
```

<210> SEQ ID NO 132
<211> LENGTH: 200
<212> TYPE: PRT
<213> ORGANISM: Streptomyces sp. YR375

<400> SEQUENCE: 132

```
Met Val Asp Leu Leu Arg Asn Asn Pro Leu Ala Leu Met Val Ser Asn
1               5                   10                  15

Gly Asp Ala Ala Ala Ala Pro Phe Ala Thr His Leu Pro Val Ile Pro
            20                  25                  30

Asp Pro Ala Met Thr Asp Glu Trp Ser Ala Asp Leu Ser Gly Ala Thr
        35                  40                  45

Leu Leu Gly His Met Asn Arg Gly Asn Pro His Trp Lys Ala Leu Glu
    50                  55                  60

Thr Gly Asp Val Val Leu Leu Thr Phe Thr Gly Pro His Ala Tyr Val
65                  70                  75                  80

Ser Pro Thr Val Tyr Glu Val Thr Pro Ala Ala Pro Thr Trp Asn Phe
                85                  90                  95

Thr Ser Val His Val Arg Gly Val Val Glu Lys Ile Asp Ser Ala Glu
            100                 105                 110

Glu Thr Leu Glu Val Val Gln Ser Thr Val Arg Ala Phe Glu Ala Asp
        115                 120                 125

Phe Gly Asp Asp Trp Asp Met Thr Glu Ser Leu Gly Tyr Phe Arg Arg
    130                 135                 140

Ile Val Pro Ala Val Gly Ala Phe Arg Leu Thr Val Ser Gly Ala Glu
145                 150                 155                 160

Gly Met Phe Lys Leu Ser Gln Glu Gln Lys Pro Glu Val Arg Glu Arg
                165                 170                 175

Val Gln Lys Ala Phe Ser Gly Arg Glu Cys Gly Arg His Arg Glu Thr
            180                 185                 190

Ala Ser Phe Met Ser Arg Leu Pro
        195                 200
```

<210> SEQ ID NO 133
<211> LENGTH: 241
<212> TYPE: PRT
<213> ORGANISM: Actinoalloteichus spitiensis

<400> SEQUENCE: 133

```
Met Phe Val Pro Asp Gln Tyr Arg Ala Ala Asp Asn Arg Pro Leu Val
1               5                   10                  15

Glu Leu Ile Arg Ser Phe Pro Leu Ala Thr Leu Val Ser His Ala Glu
            20                  25                  30

Gly Thr Leu Phe Ala Thr His Val Pro Val Leu Leu Ala Ala Asp Ala
        35                  40                  45

Asp Ala Gly Arg Asp Val Pro Glu Pro Ala Asp Leu Thr Ile Leu Gly
    50                  55                  60
```

-continued

His Leu Asp Arg Arg Asn Pro His Arg Ala Ala Leu Ala Ala Gly Gly
65 70 75 80

Pro Cys Leu Leu Thr Phe Thr Gly Pro His Ser Tyr Val Ser Pro Ala
85 90 95

His Tyr Gly Arg Glu Thr Ala Ala Pro Thr Trp Asn Phe Thr Ala Val
100 105 110

His Val His Gly Arg Leu Thr Pro Leu Asp Gly Ala Glu Asp Thr Arg
115 120 125

His Val Val Arg Ser Thr Ala Leu Leu Tyr Glu Arg Arg Phe Gly Ala
130 135 140

Gly Trp Asp Thr Thr Gly Ser Leu Asp Tyr Phe Glu Gln Leu Leu Pro
145 150 155 160

Gly Val Ser Ala Phe Arg Val Asp Val Ser Thr Val Glu Gly Met Phe
165 170 175

Lys Leu Gly Gln Glu Gln Pro Gly Tyr Ala Arg Gln Gly Val Val Ala
180 185 190

Ala Phe Thr Ser Pro Gly Ala Pro Pro His Gln Arg Ala Val Ala Glu
195 200 205

Leu Met Arg Arg Phe Ala Pro Asp Ser Pro Asp Asp Gly Gly Pro Gly
210 215 220

Cys Pro Val Arg Ala Pro Ala Lys Pro Glu Pro Ala Thr Arg Gly Glu
225 230 235 240

Arg

<210> SEQ ID NO 134
<211> LENGTH: 200
<212> TYPE: PRT
<213> ORGANISM: Streptomyces sp. Ncost-T6T-1

<400> SEQUENCE: 134

Met Val Asp Leu Met Arg Ser Asn Pro Leu Ala Leu Met Val Ser Asn
1 5 10 15

Gly Ser Pro Glu Ala Ser Pro Phe Ala Thr His Leu Pro Val Ile Phe
20 25 30

Asp Pro Gly Asp Ala Ala Asp Leu Ala Glu Asp Leu Ala Arg Leu Pro
35 40 45

Leu Leu Gly His Met Asn Arg Ala Asn Pro His Trp Ser Ala Leu Gln
50 55 60

Asp Asp Ala Val Val Leu Leu Ser Phe Thr Gly Pro His Ala Tyr Val
65 70 75 80

Ser Pro Thr Val Tyr Asp Val Thr Pro Ala Ala Pro Thr Trp Asn Phe
85 90 95

Thr Ser Val His Val His Gly Val Val Glu Lys Phe Asp Ser Thr Glu
100 105 110

Glu Thr Leu Glu Val Val Gln Ala Thr Val Arg Ala Phe Glu Glu Lys
115 120 125

Phe Gly Asn Asn Trp Asp Met Thr Asp Ser Ile Asp Tyr Phe Arg Lys
130 135 140

Ile Val His Asp Val Gly Ala Phe Arg Ile Arg Val Thr Lys Ala Glu
145 150 155 160

Gly Met Phe Lys Leu Ser Gln Glu Gln Glu Pro Glu Ile Arg Asp Arg
165 170 175

Val Val Gln Ser Phe Thr Gly Arg Gly Cys Thr Arg His Ala Gln Thr
180 185 190

```
Ala Thr Leu Met Ser Arg Leu Pro
        195                 200


<210> SEQ ID NO 135
<211> LENGTH: 231
<212> TYPE: PRT
<213> ORGANISM: Streptomyces sp. PBH53

<400> SEQUENCE: 135

Val Tyr Glu Arg Pro Leu Tyr Arg Glu Asp Arg Asp Gly Val Val Leu
1               5                   10                  15

Ala Phe Leu His His His Pro Leu Ala Leu Val Val Thr Ala His Glu
            20                  25                  30

Gly Val Pro Val Ala Thr His Ala Pro Val Leu Phe Arg His Gly Pro
        35                  40                  45

Asp Gly Ala Asp Ala Glu Ala Val Ala Ala Gly Thr Val Pro Leu Ala
    50                  55                  60

Gly Ser Thr Leu Ile Gly His Met Asn Val Glu Asn Pro Gln Trp Arg
65                  70                  75                  80

Arg Met Arg Ser Gly Asp Arg Ala Leu Ile Val Phe Gln Gly Pro His
                85                  90                  95

Gly Tyr Val Ser Pro Thr Val Tyr Asp Val Thr Pro Ala Ala Pro Thr
            100                 105                 110

Trp Asn Phe Thr Ala Val His Val Thr Gly Thr Val Glu Pro Thr Ala
        115                 120                 125

Glu Pro Ala Asp Val Leu Asp Ile Val Ser Asp Thr Ala Arg Arg Leu
    130                 135                 140

Glu Gly Arg Phe Gly Arg Gly Trp Asp Gln Glu Ser Ser Leu Asp Tyr
145                 150                 155                 160

Phe Arg Gln Ile Ala Pro Gly Val Gly Ala Phe Thr Leu Arg Val Glu
                165                 170                 175

Ser Val Gln Thr Met Phe Lys Leu Ser Gln Glu Lys Pro Thr Pro Met
            180                 185                 190

Arg Arg Arg Val Ala Glu Gln Phe Glu Ala Ser Glu Ser Gly Thr His
        195                 200                 205

Arg Ala Leu Ala Gly Met Met Arg Ala His Gly Leu Thr Asp Ala Asp
    210                 215                 220

Glu Glu Arg Glu Thr Ala Gly
225                 230


<210> SEQ ID NO 136
<211> LENGTH: 213
<212> TYPE: PRT
<213> ORGANISM: Salinispora arenicola

<400> SEQUENCE: 136

Met Leu Val Pro His Met Tyr Glu Ala Pro Ser Ala Ala Gln Val Asp
1               5                   10                  15

Ala Val Ile Thr Gly His Pro Met Ala Val Leu Val Thr Asn Gly Pro
            20                  25                  30

Asp Val Pro His Ala Thr His Leu Pro Val Ile Arg Thr Val Asp Thr
        35                  40                  45

Glu Gln Thr Gly Pro Gly Ser Val Leu Leu Gly His Met Asn Arg Thr
    50                  55                  60

Asn Pro His Trp Ser Ala Leu Thr Ser Gly Thr Pro Gly Lys Leu Ile
65                  70                  75                  80
```

```
Phe Thr Gly Pro Asn Thr Tyr Val Cys Pro Val Leu Tyr Gln Thr Glu
                85                  90                  95

Pro Ala Ala Pro Thr Trp Asp Phe Val Val Val His Val Ser Gly Arg
            100                 105                 110

Val Met Pro Leu Asp Ala Gly Glu Pro Thr Leu Ala Val Val Gln Arg
        115                 120                 125

Thr Ala Ala Thr Leu Glu Gly Ala Phe Gly Ala Gly Trp Asp His Thr
    130                 135                 140

Gly Ser Ile Asp Tyr Phe Arg Ser Ile Val Gly Gly Val Gly Ala Phe
145                 150                 155                 160

Glu Phe Val Val Glu Gln Val Glu Ser Met Phe Lys Leu Ser Gln Glu
                165                 170                 175

Lys Asp His Thr Val Arg Gln Arg Leu Ile Asp Asp Phe Thr Ser Ala
            180                 185                 190

Pro Arg Asn Gly Ser Ala Gln Val Gly Gln Leu Met Ser Asp Leu Asn
        195                 200                 205

Leu Gly Val Ala Pro
    210


<210> SEQ ID NO 137
<211> LENGTH: 219
<212> TYPE: PRT
<213> ORGANISM: Streptomyces sp. MNU77

<400> SEQUENCE: 137

Met Phe Val Pro Arg Ile Tyr Gln Val Asp Gly Glu His Trp Pro Ser
1               5                   10                  15

Glu Ile Ile Asp Arg His Pro Leu Ala Leu Leu Thr Thr Asn Gly Asp
            20                  25                  30

Asp Val Pro His Ala Thr His Val Pro Val Ile Arg Pro Pro His Asp
        35                  40                  45

Glu Gln Leu Val Gly Ser Glu Leu Leu Val His Met Asn Arg Ala Asn
    50                  55                  60

Pro His Trp Ala Ala Leu Ser Asp His Asp Ala Ala Lys Leu Val Phe
65                  70                  75                  80

Gln Gly Pro Asp Gly Tyr Val Thr Pro Ser Val Tyr His Val Glu Pro
                85                  90                  95

Ala Val Pro Thr Trp Asp Phe Val Thr Val His Leu Thr Gly Thr Leu
            100                 105                 110

Arg Ile Ser Glu Asp Val Asp Glu Val Leu Ser Ile Val Thr Ala Thr
        115                 120                 125

Ala Arg Thr Leu Glu Arg Arg Phe Gly Ala Gly Phe Asp Val Asp Arg
    130                 135                 140

Ala Ala Asp His His Ala Arg Ile Ala Ser Gly Val Gly Ala Ile Arg
145                 150                 155                 160

Phe Arg Val Thr Lys Ala Glu Ala Met Phe Lys Phe Ser Gln Glu Lys
                165                 170                 175

Asp Ala Glu Ile Arg Asp Arg Val Met Gln Trp Phe Glu Asp Ser Asp
            180                 185                 190

Ile Gly Glu Tyr Ala Asp Leu Gly Arg Leu Met Arg Gln Phe Leu Asp
        195                 200                 205

Arg Pro Asp Ile Thr Ala Pro Ala Ala Ala Gly
    210                 215


<210> SEQ ID NO 138
```

<211> LENGTH: 217
<212> TYPE: PRT
<213> ORGANISM: Micromonospora halophytica

<400> SEQUENCE: 138

Met Phe Val Pro Arg Ser Phe Ala Val Glu Asp Ala Gly Pro Val Val
1 5 10 15

Glu Leu Met Arg Ser Asn Pro Leu Ala Cys Phe Val Leu Gly Gly Glu
20 25 30

Ser Pro Ser Val Ser His Leu Pro Val Val Phe Ala Asp Asp Asp Glu
35 40 45

Arg Asp Asp Leu Ala Gly Ile Thr Leu Leu Thr His Met Asn Arg Gln
50 55 60

Asn Pro Leu Trp Gly Ser Leu Ser Asp Gly Ala Arg Val Leu Val Val
65 70 75 80

Phe Gln Gly Pro His Gly Tyr Val Ser Pro Thr Val Tyr Gly Val Ser
85 90 95

Pro Ala Ala Pro Thr Trp Asn Phe Thr Val Val His Ala His Gly Val
100 105 110

Val Arg Leu Leu Gly Ala Gly Glu Pro Ala Leu Arg Val Val Lys Arg
115 120 125

Thr Val Gln Val Leu Glu Gly Arg Phe Gly Ala Gly Trp Asp Met Thr
130 135 140

Gly Ser Leu Gly Tyr Phe Glu Arg Ile Val His Ala Val Gly Ala Leu
145 150 155 160

Glu Ile His Val Asp Ala Val Gln Ser Met Phe Lys Leu Ser Gln Asp
165 170 175

Gln Pro Val Glu Leu Gln Ser Lys Val Ala Ala Ala Phe Ala Gly Ser
180 185 190

Gly Arg Gly Thr His Arg Glu Leu Ala Glu Gln Met Tyr Thr His Leu
195 200 205

Arg Leu Lys Ala Asp Val Asp Gly Phe
210 215

<210> SEQ ID NO 139
<211> LENGTH: 214
<212> TYPE: PRT
<213> ORGANISM: Streptacidiphilus carbonis

<400> SEQUENCE: 139

Met Phe Val Pro Pro Pro Tyr Arg Pro Pro Asp Gly Ser Trp Thr Ala
1 5 10 15

Glu Leu Ile Arg Ser Asn Pro Leu Ala Ile Leu Ala Ser Asn Gly Ser
20 25 30

Thr Ala Asp Gly Pro Phe Ala Thr His Leu Pro Val Ile Pro Asp Pro
35 40 45

Gly Thr Pro Asp Leu Leu Ser Ala Glu Leu Thr Gly Ala Val Leu Leu
50 55 60

Gly His Met Asn Arg Ala Asn Pro His Trp Ala Ala Leu Ala Glu Gly
65 70 75 80

Gly Thr Ser Leu Leu Thr Phe Thr Gly Pro His Ala Tyr Val Ser Pro
85 90 95

Thr Val Tyr Gly Val Thr Pro Ala Ala Pro Thr Trp Asn Phe Thr Ser
100 105 110

Val His Ala Arg Gly Thr Ile Glu Arg Ile Glu Ser Ser Glu Glu Thr
115 120 125

```
Leu Glu Val Val Lys Ala Thr Val Arg Ala Phe Glu Glu Arg Phe Gly
    130                 135                 140

Ala Glu Trp Asp Met Ser Glu Ser Ile Ser Tyr Phe Arg Gln Ile Leu
145                 150                 155                 160

Pro Gly Val Gly Gly Phe Arg Phe Thr Val Thr Gly Thr Asp Gly Met
                165                 170                 175

Phe Lys Leu Ser Gln Glu Gln Ala Pro Glu Ile Arg Cys Arg Val Gln
            180                 185                 190

Arg Ser Phe Thr Gly Arg Glu Cys Ser Arg His Arg Glu Thr Ala Ala
        195                 200                 205

Leu Met Gly Ser Leu Pro
    210


<210> SEQ ID NO 140
<211> LENGTH: 223
<212> TYPE: PRT
<213> ORGANISM: Streptomyces sp. MnatMP-M27

<400> SEQUENCE: 140

Met Phe Val Pro Gln His Tyr Arg Thr Asp Asp Arg Arg Trp Pro Val
1               5                   10                  15

Arg Ile Val Gln Asp Asn Pro Leu Ala Leu Leu Met Ser Thr Arg Asp
            20                  25                  30

Gly Arg Ala Pro Phe Ala Ser His Val Pro Val Ile Val Leu Pro Arg
        35                  40                  45

Gln Arg Glu Glu Leu Glu Arg Thr Gly Arg Trp Gln Gly Ala Val Leu
    50                  55                  60

His Gly His Met Asn Arg Ala Asn Pro His Trp Lys Ser Leu Ala Asp
65                  70                  75                  80

Gly Gln Pro Ala Gly Leu Val Phe Gln Gly Pro Ala Gly Tyr Val Ser
                85                  90                  95

Pro Ala Val Tyr Asn Thr Ser Pro Ala Val Pro Thr Trp Asn Phe Thr
            100                 105                 110

Ala Val His Val Gln Gly Arg Leu Lys Leu Val Ala Asp Glu Glu Ala
        115                 120                 125

Thr Leu Gly Val Val Ser Ala Thr Ala Arg Gln Leu Glu Glu Arg Phe
    130                 135                 140

Gly Ala Arg Trp Thr Val Glu Pro Ser Val Asp His Phe Arg Gln Ile
145                 150                 155                 160

Leu Pro Gly Val Gly Ala Phe Glu Leu Arg Val Glu Glu Cys Asp Ser
                165                 170                 175

Met Phe Lys Leu Ser Gln Glu Lys Glu His Glu Val Arg His Ala Val
            180                 185                 190

Met Asp Trp Cys Ala Arg Ser Pro Arg Gly Arg Ser Asn Asp Leu Ala
        195                 200                 205

Ala Val Met Arg Asp Tyr Tyr Pro Pro Thr Thr Ala Trp Pro Ser
    210                 215                 220


<210> SEQ ID NO 141
<211> LENGTH: 220
<212> TYPE: PRT
<213> ORGANISM: Pseudonocardia sp. EC080625-04

<400> SEQUENCE: 141

Met Phe Val Pro Glu Gln Tyr Arg Glu Gln Asp Ser Asn Trp Met Leu
1               5                   10                  15
```

```
Asp Ile Val Arg Ser Asn Pro Leu Ala Leu Met Ala Ser Asp Gly Thr
            20                  25                  30

Pro Glu Gly Cys Gly Pro Ala Ala Thr His Leu Pro Cys Ile Pro Asp
        35                  40                  45

Pro Ser Ala Pro His Asp Trp Ser Asp Gly Pro Arg Gly Ala Val Leu
    50                  55                  60

Leu Gly His Met Asn Arg Ala Asn Pro Gln Trp Arg His Leu His Asp
65                  70                  75                  80

Gly Gln Thr Val Leu Leu Val Phe Thr Gly Pro His Ala Tyr Val Ser
                85                  90                  95

Pro Ala Val Tyr Asp Thr Thr Pro Ala Ala Pro Thr Trp Asp Phe Thr
            100                 105                 110

Ala Val His Val His Gly Val Val Thr Lys Leu Glu Pro His Lys Ala
        115                 120                 125

Glu Arg Thr Thr Leu Asp Val Val Thr Asp Thr Val Thr Ala Leu Glu
    130                 135                 140

Gly Arg Phe Gly Ala Gly Trp Asp Met Thr Asp Ser Ile Glu Tyr Phe
145                 150                 155                 160

His Arg Leu Leu Pro Gly Val Gly Ala Phe Arg Val Arg Val Gly Ser
                165                 170                 175

Ala Glu Gly Met Phe Lys Leu Ser Gln Glu Gln Pro Ser Asp Ile Arg
            180                 185                 190

Asp Arg Val Arg Cys His Phe Ala Ala Ala Gln His Gly Arg Ser Ser
        195                 200                 205

Glu Ile Ala His Leu Met Thr Thr Leu Asp Gly His
    210                 215                 220


<210> SEQ ID NO 142
<211> LENGTH: 220
<212> TYPE: PRT
<213> ORGANISM: Pseudonocardia sp. HH130629-09

<400> SEQUENCE: 142

Met Phe Val Pro Glu Gln Tyr Arg Glu Gln Asp Ser Asn Trp Met Leu
1               5                   10                  15

Asp Ile Val Arg Ser Asn Pro Leu Ala Leu Met Ala Ser Asp Gly Thr
            20                  25                  30

Pro Glu Gly Cys Gly Pro Ala Ala Thr His Leu Pro Cys Ile Pro Asp
        35                  40                  45

Pro Ser Ala Pro His Asp Trp Ser Asp Gly Pro Arg Gly Ala Val Leu
    50                  55                  60

Leu Gly His Met Asn Arg Ala Asn Pro Gln Trp Arg His Leu His Asp
65                  70                  75                  80

Gly Gln Thr Val Leu Leu Val Phe Thr Gly Pro His Ala Tyr Val Ser
                85                  90                  95

Pro Ala Val Tyr Asp Thr Thr Pro Ala Ala Pro Thr Trp Asp Phe Thr
            100                 105                 110

Ala Val His Val His Gly Val Val Thr Lys Leu Glu Pro His Lys Ala
        115                 120                 125

Glu Arg Thr Thr Leu Asp Val Val Thr Asp Thr Val Thr Ala Leu Glu
    130                 135                 140

Gly Arg Phe Gly Ala Gly Trp Asp Met Thr Asp Ser Ile Glu Tyr Phe
145                 150                 155                 160

His Arg Leu Leu Pro Gly Val Gly Ala Phe Arg Val Arg Val Gly Ser
```

```
                165                 170                 175

Ala Glu Gly Met Phe Lys Leu Ser Gln Glu Gln Pro Ser Asp Ile Arg
            180                 185                 190

Asp Arg Val Arg Cys His Phe Ala Ala Ala Gln His Gly Arg Ser Ser
        195                 200                 205

Glu Ile Ala His Leu Met Thr Thr Leu Asp Gly His
    210                 215                 220


<210> SEQ ID NO 143
<211> LENGTH: 214
<212> TYPE: PRT
<213> ORGANISM: Streptomyces parvulus

<400> SEQUENCE: 143

Met Phe Val Pro Ser Phe Tyr Arg Glu Pro Ser Asn Ser Trp Met Val
1               5                   10                  15

Asp Leu Ile Arg Gly Asn Pro Leu Ala Leu Ala Val Ala Asn Gly Gln
            20                  25                  30

Pro Asp Glu Gly Pro Phe Ala Thr His Leu Pro Val Ile Phe Asp Pro
        35                  40                  45

Asp His Pro Leu Asp Arg Asp Asp Asp Leu Thr Gly Ala Thr Leu Leu
    50                  55                  60

Gly His Met Asn Arg Ala Asn Pro His Trp Gly Ser Leu Glu Thr Gly
65                  70                  75                  80

Gly Val Leu Leu Leu Thr Phe Thr Gly Pro His Ser Tyr Val Ser Pro
                85                  90                  95

Thr Val Tyr Glu Val Thr Pro Ala Ala Pro Thr Trp Asn Phe Thr Ala
            100                 105                 110

Val His Val Arg Gly Val Val Glu Lys Leu Asp Ser Thr Asp Glu Thr
        115                 120                 125

Leu Ala Val Val Gln Ser Thr Val Arg Ala Phe Glu Gly Glu Phe Gly
    130                 135                 140

Asn Gly Trp Asp Met Thr Asp Ser Leu Gly Tyr Phe Arg Lys Ile Ala
145                 150                 155                 160

Pro Gly Val Gly Ala Phe Arg Phe Thr Val Thr Gly Ala Glu Gly Met
                165                 170                 175

Phe Lys Leu Ser Gln Glu Gln Pro Gly Glu Val Arg Asp Arg Val Arg
            180                 185                 190

Glu Ser Phe Gly Gln Ser Gly Cys Val His Lys Arg Gly Thr Ala Gly
        195                 200                 205

Leu Met Ser Arg Leu Pro
    210


<210> SEQ ID NO 144
<211> LENGTH: 214
<212> TYPE: PRT
<213> ORGANISM: Streptomyces sp. OK885

<400> SEQUENCE: 144

Met Phe Val Pro Asp Pro Tyr Arg Glu Pro Asn Thr Thr Trp Met Val
1               5                   10                  15

Asp Leu Ile Arg Arg Asn Pro Leu Ala Leu Leu Thr Thr Asn Gly Pro
            20                  25                  30

Ala Glu Cys Gly Pro Phe Ala Thr His Leu Pro Val Ile Gln Asp Pro
        35                  40                  45

Gly Met Thr Ala Glu Trp Ser Ala Asp Leu Ser Gly Ser Leu Leu Leu
```

```
    50                  55                  60

Gly His Met Asn Ala Gln Asn Pro His Trp Ser Ala Leu Arg Asp Gly
65                  70                  75                  80

Asp Ser Val Leu Leu Ala Phe Thr Gly Pro His Ala Tyr Val Ser Pro
                85                  90                  95

Thr Val Tyr Gln Lys Ile Pro Ala Ala Pro Thr Trp Asn Phe Thr Ser
            100                 105                 110

Val His Val His Gly Val Ile Glu Lys Ile Glu Ser Glu Glu Glu Thr
        115                 120                 125

Leu Thr Val Val Arg Ser Thr Val Arg Ala Phe Glu Glu Glu Phe Gly
    130                 135                 140

Thr Asp Trp Asn Met Glu Gly Ser Val Asp Tyr Phe Arg Lys Ile Leu
145                 150                 155                 160

Pro Gly Val Gly Ala Phe Arg Ile Thr Val Ser Arg Ala Asp Gly Met
                165                 170                 175

Phe Lys Leu Ser Gln Glu Gln Glu Pro Gln Ile Arg Asp Arg Val Arg
            180                 185                 190

Gln Ser Phe Ala Gln Arg Lys Cys Ser Leu His Arg Glu Thr Ala Asp
        195                 200                 205

Leu Met Gly Arg Leu Pro
    210


<210> SEQ ID NO 145
<211> LENGTH: 218
<212> TYPE: PRT
<213> ORGANISM: Streptomyces sp. CFMR 7

<400> SEQUENCE: 145

Met Tyr Val Pro Ser Ile Tyr Gln Ala Glu Asp Arg Ala Trp Leu Arg
1               5                   10                  15

His Val Val Glu Arg Tyr Pro Leu Ala Thr Val Ile Thr Asn Gly Pro
            20                  25                  30

Gln Ala Pro Tyr Ala Thr His Val Pro Val Ile Pro Ala Pro Asp Thr
        35                  40                  45

Thr Ser Trp Asn Asp Gly Pro Glu Gly Ala Thr Leu Leu Gly His Met
    50                  55                  60

Asn Arg Ala Asn Ser His Trp Gly Ser Leu Thr Asp Gly Thr His Ala
65                  70                  75                  80

Gln Leu Val Phe Thr Gly Pro Asn Gly Tyr Val Ser Pro Thr Val Tyr
                85                  90                  95

Glu Thr Ser Pro Ala Ala Pro Thr Trp Asn Phe Val Ser Val His Leu
            100                 105                 110

Arg Gly Arg Leu Arg Pro Ile Ser Asp Phe Glu Glu Thr Leu Glu Val
        115                 120                 125

Val Arg Leu Thr Val Glu Ala Tyr Glu Lys Asn Phe Gly Asp Gly Trp
    130                 135                 140

Glu Met Asp Ser Ser Leu Glu Tyr Phe Arg Asn Ile Gly Pro Ala Val
145                 150                 155                 160

Gly Gly Phe Arg Phe Asp Val Glu Ser Ala Asp Gly Met Phe Lys Leu
                165                 170                 175

Ser Gln Glu Lys His Pro Glu Thr Arg Arg Arg Ile Ala Asp Arg Phe
            180                 185                 190

Gly Gly Arg Arg Ser Gly Arg Ala Thr Glu Leu Ala Phe Phe Met Arg
        195                 200                 205
```

```
Gln Phe Thr Ser Ala Asp His His Ala Ser
    210                 215


<210> SEQ ID NO 146
<211> LENGTH: 218
<212> TYPE: PRT
<213> ORGANISM: Streptomyces sp. DvalAA-19

<400> SEQUENCE: 146

Met Tyr Val Pro Ser Ile Tyr Gln Ala Glu Asp Arg Ala Trp Leu Arg
1               5                   10                  15

His Val Val Glu Arg Tyr Pro Leu Ala Thr Val Ile Thr Asn Gly Pro
            20                  25                  30

Gln Ala Pro Tyr Ala Thr His Val Pro Val Ile Pro Ala Pro Asp Thr
        35                  40                  45

Thr Ser Trp Asn Asp Gly Pro Glu Gly Ala Thr Leu Leu Gly His Met
    50                  55                  60

Asn Arg Ala Asn Ser His Trp Gly Ser Leu Thr Asp Gly Thr His Ala
65                  70                  75                  80

Gln Leu Val Phe Thr Gly Pro Asn Gly Tyr Val Ser Pro Thr Ile Tyr
                85                  90                  95

Glu Thr Ser Pro Ala Ala Pro Thr Trp Asn Phe Val Ser Val His Leu
            100                 105                 110

Arg Gly Arg Leu Arg Pro Ile Ser Asp Phe Glu Glu Thr Leu Glu Val
        115                 120                 125

Val Arg Leu Thr Val Glu Ala Tyr Glu Lys Asn Phe Gly Asp Gly Trp
    130                 135                 140

Glu Met Asp Ser Ser Leu Glu Tyr Phe Arg Asn Ile Gly Pro Ala Val
145                 150                 155                 160

Gly Gly Phe Arg Phe Asp Val Glu Ser Ala Asp Gly Met Phe Lys Leu
                165                 170                 175

Ser Gln Glu Lys His Pro Glu Thr Arg Arg Arg Ile Ala Asp Arg Phe
            180                 185                 190

Gly Gly Arg Arg Ser Gly Arg Ala Thr Glu Leu Ala Phe Phe Met Arg
        195                 200                 205

Gln Phe Thr Ser Ala Asp Arg His Ala Ser
    210                 215


<210> SEQ ID NO 147
<211> LENGTH: 218
<212> TYPE: PRT
<213> ORGANISM: Rhodococcus fascians

<400> SEQUENCE: 147

Met Tyr Val Pro Arg Ile Tyr Lys Ala Ser Asp Arg Thr Trp Leu Arg
1               5                   10                  15

Arg Val Val Ala Gln Tyr Pro Phe Ala Ala Leu Ile Ser Asn Gly Pro
            20                  25                  30

Lys Ala Pro Tyr Ala Thr His Leu Pro Val Ile Cys Ala Pro Cys Ala
        35                  40                  45

Pro Ser Glu Ser Glu Asp Leu Glu Gly Ser Thr Leu Phe Gly His Met
    50                  55                  60

Asn Arg Ala Asn Pro His Trp Asp Ser Leu Val Asp Gly Ala Asp Ala
65                  70                  75                  80

Gln Leu Ile Phe Thr Gly Pro His Gly Tyr Val Thr Pro Ser Val Tyr
                85                  90                  95
```

-continued

```
Gln Arg Asp Ser Val Ala Pro Thr Trp Asn Tyr Val Ser Val His Leu
            100                 105                 110

Arg Gly Lys Leu Gln Pro Val Ala Asp Phe Glu Glu Thr Leu Lys Val
        115                 120                 125

Val Gln Leu Thr Val Ser Thr Tyr Glu Gln Lys Phe Gly Ser Gly Trp
    130                 135                 140

Glu Met Asp Ser Ser Leu Asp His Tyr Arg Arg Ile Gly Pro Ala Val
145                 150                 155                 160

Gly Ala Phe Ser Phe Glu Val Glu Ser Ala Asp Gly Met Phe Lys Leu
                165                 170                 175

Ser Gln Glu Gln Asn Leu Glu Thr Arg Arg Arg Val Ala Asp His Phe
            180                 185                 190

Ser Ala Asn His Ala Gly Arg Gly Lys Glu Leu Ala Ser Phe Met Arg
        195                 200                 205

Glu Tyr Ser His Gly Asp Tyr Asn Asn Phe
    210                 215


<210> SEQ ID NO 148
<211> LENGTH: 218
<212> TYPE: PRT
<213> ORGANISM: Rhodococcus fascians

<400> SEQUENCE: 148

Met Tyr Val Pro Arg Ile Tyr Lys Ala Ser Asp Arg Thr Trp Leu Arg
1               5                   10                  15

Arg Val Val Ala Gln Tyr Pro Phe Ala Ala Leu Ile Ser Asn Gly Pro
            20                  25                  30

Lys Ala Pro Tyr Ala Thr His Leu Pro Val Ile Cys Ala Pro Cys Ala
        35                  40                  45

Pro Ser Glu Ser Glu Asp Leu Glu Gly Ser Thr Leu Phe Gly His Met
    50                  55                  60

Asn Arg Ala Asn Pro His Trp Asp Ser Leu Val Asp Gly Ala Asp Ala
65                  70                  75                  80

Gln Leu Ile Phe Thr Gly Pro His Gly Tyr Val Thr Pro Ser Val Tyr
                85                  90                  95

Gln Arg Asp Ser Val Ala Pro Thr Trp Asn Tyr Val Ser Val His Leu
            100                 105                 110

Arg Gly Lys Leu Gln Pro Val Ala Asp Phe Glu Glu Thr Leu Lys Val
        115                 120                 125

Val Gln Leu Thr Val Ser Thr Tyr Glu Gln Lys Phe Gly Ser Gly Trp
    130                 135                 140

Glu Met Asp Ser Ser Leu Asp His Tyr Arg Arg Ile Gly Pro Ala Val
145                 150                 155                 160

Gly Ala Phe Ser Phe Glu Val Glu Ser Ala Asp Gly Met Phe Lys Leu
                165                 170                 175

Ser Gln Glu Gln Asn Leu Glu Thr Arg Arg Arg Val Ala Asp His Phe
            180                 185                 190

Ser Ala Asn His Ala Gly Arg Gly Lys Glu Leu Ala Ser Phe Met Arg
        195                 200                 205

Glu Tyr Ser His Gly Asp Tyr Asn Asn Phe
    210                 215


<210> SEQ ID NO 149
<211> LENGTH: 218
<212> TYPE: PRT
<213> ORGANISM: Rhodococcus fascians
```

<400> SEQUENCE: 149

Met Tyr Val Pro Arg Ile Tyr Lys Ala Ser Asp Arg Thr Trp Leu Arg
1               5                   10                  15

Arg Val Val Ala Gln Tyr Pro Phe Ala Ala Leu Ile Ser Asn Gly Pro
            20                  25                  30

Lys Ala Pro Tyr Ala Thr His Leu Pro Val Ile Cys Ala Pro Cys Ala
        35                  40                  45

Pro Ser Glu Ser Glu Asp Leu Glu Gly Ser Thr Leu Phe Gly His Met
    50                  55                  60

Asn Arg Ala Asn Pro His Trp Asp Ser Leu Val Asp Gly Ala Asp Ala
65                  70                  75                  80

Gln Leu Ile Phe Thr Gly Pro His Gly Tyr Val Thr Pro Ser Val Tyr
                85                  90                  95

Gln Arg Asp Ser Val Ala Pro Thr Trp Asn Tyr Val Ser Val His Leu
            100                 105                 110

Arg Gly Lys Leu Gln Pro Val Ala Asp Phe Glu Glu Thr Leu Lys Val
        115                 120                 125

Val Gln Leu Thr Val Ser Thr Tyr Glu Gln Lys Phe Gly Ser Gly Trp
    130                 135                 140

Glu Met Asp Ser Ser Leu Asp His Tyr Arg Arg Ile Gly Pro Ala Val
145                 150                 155                 160

Gly Ala Phe Ser Phe Glu Val Glu Ser Ala Asp Gly Met Phe Lys Leu
                165                 170                 175

Ser Gln Glu Gln Asn Leu Glu Thr Arg Arg Arg Val Ala Asp His Phe
            180                 185                 190

Ser Ala Asn His Ala Gly Arg Gly Lys Glu Leu Ala Ser Phe Met Arg
        195                 200                 205

Glu Tyr Ser His Gly Asp Tyr Asn Asn Phe
    210                 215

<210> SEQ ID NO 150
<211> LENGTH: 218
<212> TYPE: PRT
<213> ORGANISM: Rhodococcus fascians

<400> SEQUENCE: 150

Met Tyr Val Pro Arg Ile Tyr Lys Ala Ser Asp Arg Thr Trp Leu Arg
1               5                   10                  15

Arg Val Val Ala Gln Tyr Pro Phe Ala Ala Leu Ile Ser Asn Gly Pro
            20                  25                  30

Lys Ala Pro Tyr Ala Thr His Leu Pro Val Ile Cys Ala Pro Cys Ala
        35                  40                  45

Pro Ser Glu Ser Glu Asp Leu Glu Gly Ser Thr Leu Phe Gly His Met
    50                  55                  60

Asn Arg Ala Asn Pro His Trp Asp Ser Leu Val Asp Gly Ala Asp Ala
65                  70                  75                  80

Gln Leu Ile Phe Thr Gly Pro His Gly Tyr Val Thr Pro Ser Val Tyr
                85                  90                  95

Gln Arg Asp Ser Val Ala Pro Thr Trp Asn Tyr Val Ser Val His Leu
            100                 105                 110

Arg Gly Lys Leu Gln Pro Val Ala Asp Phe Glu Glu Thr Leu Lys Val
        115                 120                 125

Val Gln Leu Thr Val Ser Thr Tyr Glu Gln Lys Phe Gly Ser Gly Trp
    130                 135                 140

```
Glu Met Asp Ser Ser Leu Asp His Tyr Arg Arg Ile Gly Pro Ala Val
145                 150                 155                 160

Gly Ala Phe Ser Phe Glu Val Glu Ser Ala Asp Gly Met Phe Lys Leu
                165                 170                 175

Ser Gln Glu Gln Asn Leu Glu Thr Arg Arg Arg Val Ala Asp His Phe
            180                 185                 190

Ser Ala Asn His Ala Gly Arg Gly Lys Glu Leu Ala Ser Phe Met Arg
        195                 200                 205

Glu Tyr Ser His Gly Asp Tyr Asn Asn Phe
    210                 215


<210> SEQ ID NO 151
<211> LENGTH: 218
<212> TYPE: PRT
<213> ORGANISM: Rhodococcus fascians

<400> SEQUENCE: 151

Met Tyr Val Pro Arg Ile Tyr Lys Ala Ser Asp Arg Thr Trp Leu Arg
1               5                   10                  15

Arg Val Val Ala Gln Tyr Pro Phe Ala Ala Leu Ile Ser Asn Gly Pro
            20                  25                  30

Lys Ala Pro Tyr Ala Thr His Leu Pro Val Ile Cys Ala Pro Cys Ala
        35                  40                  45

Pro Ser Glu Ser Glu Asp Leu Glu Gly Ser Thr Leu Phe Gly His Met
    50                  55                  60

Asn Arg Ala Asn Pro His Trp Asp Ser Leu Val Asp Gly Ala Asp Ala
65                  70                  75                  80

Gln Leu Ile Phe Thr Gly Pro His Gly Tyr Val Thr Pro Ser Val Tyr
                85                  90                  95

Gln Arg Asp Ser Val Ala Pro Thr Trp Asn Tyr Val Ser Val His Leu
            100                 105                 110

Arg Gly Lys Leu Gln Pro Val Ala Asp Phe Glu Glu Thr Leu Lys Val
        115                 120                 125

Val Gln Leu Thr Val Ser Thr Tyr Glu Gln Lys Phe Gly Ser Gly Trp
    130                 135                 140

Glu Met Asp Ser Ser Leu Asp His Tyr Arg Arg Ile Gly Pro Ala Val
145                 150                 155                 160

Gly Ala Phe Ser Phe Glu Val Glu Ser Ala Asp Gly Met Phe Lys Leu
                165                 170                 175

Ser Gln Glu Gln Asn Leu Glu Thr Arg Arg Arg Val Ala Asp His Phe
            180                 185                 190

Ser Ala Asn His Ala Gly Arg Gly Lys Glu Leu Ala Ser Phe Met Arg
        195                 200                 205

Glu Tyr Ser His Gly Asp Tyr Asn Asn Phe
    210                 215


<210> SEQ ID NO 152
<211> LENGTH: 218
<212> TYPE: PRT
<213> ORGANISM: Rhodococcus fascians

<400> SEQUENCE: 152

Met Tyr Val Pro Arg Ile Tyr Lys Ala Ser Asp Arg Thr Trp Leu Arg
1               5                   10                  15

Arg Val Val Ala Gln Tyr Pro Phe Ala Ala Leu Ile Ser Asn Gly Pro
            20                  25                  30
```

```
Lys Ala Pro Tyr Ala Thr His Leu Pro Val Ile Cys Ala Pro Cys Ala
        35                  40                  45

Pro Ser Glu Ser Glu Asp Leu Glu Gly Ser Thr Leu Phe Gly His Met
    50                  55                  60

Asn Arg Ala Asn Pro His Trp Asp Ser Leu Val Asp Gly Ala Asp Ala
65                  70                  75                  80

Gln Leu Ile Phe Thr Gly Pro His Gly Tyr Val Thr Pro Ser Val Tyr
                85                  90                  95

Gln Arg Asp Ser Val Ala Pro Thr Trp Asn Tyr Val Ser Val His Leu
            100                 105                 110

Arg Gly Lys Leu Gln Pro Val Ala Asp Phe Glu Glu Thr Leu Lys Val
        115                 120                 125

Val Gln Leu Thr Val Ser Thr Tyr Glu Gln Lys Phe Gly Ser Gly Trp
    130                 135                 140

Glu Met Asp Ser Ser Leu Asp His Tyr Arg Arg Ile Gly Pro Ala Val
145                 150                 155                 160

Gly Ala Phe Ser Phe Glu Val Glu Ser Ala Asp Gly Met Phe Lys Leu
                165                 170                 175

Ser Gln Glu Gln Asn Leu Glu Thr Arg Arg Arg Val Ala Asp His Phe
            180                 185                 190

Ser Ala Asn His Ala Gly Arg Gly Lys Glu Leu Ala Ser Phe Met Arg
        195                 200                 205

Glu Tyr Ser His Gly Asp Tyr Asn Asn Phe
    210                 215


<210> SEQ ID NO 153
<211> LENGTH: 218
<212> TYPE: PRT
<213> ORGANISM: Rhodococcus fascians

<400> SEQUENCE: 153

Met Tyr Val Pro Arg Ile Tyr Lys Ala Ser Asp Arg Thr Trp Leu Arg
1               5                   10                  15

Arg Val Val Ala Gln Tyr Pro Phe Ala Ala Leu Ile Ser Asn Gly Pro
            20                  25                  30

Lys Ala Pro Tyr Ala Thr His Leu Pro Val Ile Cys Ala Pro Cys Ala
        35                  40                  45

Pro Ser Glu Ser Glu Asp Leu Glu Gly Ser Thr Leu Phe Gly His Met
    50                  55                  60

Asn Arg Ala Asn Pro His Trp Asp Ser Leu Val Asp Gly Ala Asp Ala
65                  70                  75                  80

Gln Leu Ile Phe Thr Gly Pro His Gly Tyr Val Thr Pro Ser Val Tyr
                85                  90                  95

Gln Arg Asp Ser Val Ala Pro Thr Trp Asn Tyr Val Ser Val His Leu
            100                 105                 110

Arg Gly Lys Leu Gln Pro Val Ala Asp Phe Glu Glu Thr Leu Lys Val
        115                 120                 125

Val Gln Leu Thr Val Ser Thr Tyr Glu Gln Lys Phe Gly Ser Gly Trp
    130                 135                 140

Glu Met Asp Ser Ser Leu Asp His Tyr Arg Arg Ile Gly Pro Ala Val
145                 150                 155                 160

Gly Ala Phe Ser Phe Glu Val Glu Ser Ala Asp Gly Met Phe Lys Leu
                165                 170                 175

Ser Gln Glu Gln Asn Leu Glu Thr Arg Arg Arg Val Ala Asp His Phe
```

```
            180                 185                 190

Ser Ala Asn His Ala Gly Arg Gly Lys Glu Leu Ala Ser Phe Met Arg
        195                 200                 205

Glu Tyr Ser His Gly Asp Tyr Asn Asn Phe
    210                 215


<210> SEQ ID NO 154
<211> LENGTH: 218
<212> TYPE: PRT
<213> ORGANISM: Rhodococcus fascians

<400> SEQUENCE: 154

Met Tyr Val Pro Arg Ile Tyr Lys Ala Ser Asp Arg Thr Trp Leu Arg
1               5                   10                  15

Arg Val Val Ala Gln Tyr Pro Phe Ala Ala Leu Ile Ser Asn Gly Pro
            20                  25                  30

Lys Ala Pro Tyr Ala Thr His Leu Pro Val Ile Cys Ala Pro Cys Ala
        35                  40                  45

Pro Ser Glu Ser Glu Asp Leu Glu Gly Ser Thr Leu Phe Gly His Met
    50                  55                  60

Asn Arg Ala Asn Pro His Trp Asp Ser Leu Val Asp Gly Ala Asp Ala
65                  70                  75                  80

Gln Leu Ile Phe Thr Gly Pro His Gly Tyr Val Thr Pro Ser Val Tyr
                85                  90                  95

Gln Arg Asp Ser Val Ala Pro Thr Trp Asn Tyr Val Ser Val His Leu
            100                 105                 110

Arg Gly Lys Leu Gln Pro Val Ala Asp Phe Glu Glu Thr Leu Lys Val
        115                 120                 125

Val Gln Leu Thr Val Ser Thr Tyr Glu Gln Lys Phe Gly Ser Gly Trp
    130                 135                 140

Glu Met Asp Ser Ser Leu Asp His Tyr Arg Arg Ile Gly Pro Ala Val
145                 150                 155                 160

Gly Ala Phe Ser Phe Glu Val Glu Ser Ala Asp Gly Met Phe Lys Leu
                165                 170                 175

Ser Gln Glu Gln Asn Leu Glu Thr Arg Arg Arg Val Ala Asp His Phe
            180                 185                 190

Ser Ala Asn His Ala Gly Arg Gly Lys Glu Leu Ala Ser Phe Met Arg
        195                 200                 205

Glu Tyr Ser His Gly Asp Tyr Asn Asn Phe
    210                 215


<210> SEQ ID NO 155
<211> LENGTH: 218
<212> TYPE: PRT
<213> ORGANISM: Rhodococcus fascians

<400> SEQUENCE: 155

Met Tyr Val Pro Arg Ile Tyr Lys Ala Ser Asp Arg Thr Trp Leu Arg
1               5                   10                  15

Arg Val Val Ala Gln Tyr Pro Phe Ala Ala Leu Ile Ser Asn Gly Pro
            20                  25                  30

Lys Ala Pro Tyr Ala Thr His Leu Pro Val Ile Cys Ala Pro Cys Ala
        35                  40                  45

Pro Ser Glu Ser Glu Asp Leu Glu Gly Ser Thr Leu Phe Gly His Met
    50                  55                  60

Asn Arg Ala Asn Pro His Trp Asp Ser Leu Val Asp Gly Ala Asp Ala
```

-continued

```
65                  70                  75                  80

Gln Leu Ile Phe Thr Gly Pro His Gly Tyr Val Thr Pro Ser Val Tyr
                85                  90                  95

Gln Arg Asp Ser Val Ala Pro Thr Trp Asn Tyr Val Ser Val His Leu
            100                 105                 110

Arg Gly Lys Leu Gln Pro Val Ala Asp Phe Glu Glu Thr Leu Lys Val
        115                 120                 125

Val Gln Leu Thr Val Ser Thr Tyr Glu Gln Lys Phe Gly Ser Gly Trp
    130                 135                 140

Glu Met Asp Ser Ser Leu Asp His Tyr Arg Arg Ile Gly Pro Ala Val
145                 150                 155                 160

Gly Ala Phe Ser Phe Glu Val Glu Ser Ala Asp Gly Met Phe Lys Leu
                165                 170                 175

Ser Gln Glu Gln Asn Leu Glu Thr Arg Arg Arg Val Ala Asp His Phe
            180                 185                 190

Ser Ala Asn His Ala Gly Arg Gly Lys Glu Leu Ala Ser Phe Met Arg
        195                 200                 205

Glu Tyr Ser His Gly Asp Tyr Asn Asn Phe
    210                 215


<210> SEQ ID NO 156
<211> LENGTH: 218
<212> TYPE: PRT
<213> ORGANISM: Rhodococcus fascians

<400> SEQUENCE: 156

Met Tyr Val Pro Arg Ile Tyr Lys Ala Ser Asp Arg Thr Trp Leu Arg
1               5                   10                  15

Arg Val Val Ala Gln Tyr Pro Phe Ala Ala Leu Ile Ser Asn Gly Pro
            20                  25                  30

Lys Ala Pro Tyr Ala Thr His Leu Pro Val Ile Cys Ala Pro Cys Ala
        35                  40                  45

Pro Ser Glu Ser Glu Asp Leu Glu Gly Ser Thr Leu Phe Gly His Met
    50                  55                  60

Asn Arg Ala Asn Pro His Trp Asp Ser Leu Val Asp Gly Ala Asp Ala
65                  70                  75                  80

Gln Leu Ile Phe Thr Gly Pro His Gly Tyr Val Thr Pro Ser Val Tyr
                85                  90                  95

Gln Arg Asp Ser Val Ala Pro Thr Trp Asn Tyr Val Ser Val His Leu
            100                 105                 110

Arg Gly Lys Leu Gln Pro Val Ala Asp Phe Glu Glu Thr Leu Lys Val
        115                 120                 125

Val Gln Leu Thr Val Ser Thr Tyr Glu Gln Lys Phe Gly Ser Gly Trp
    130                 135                 140

Glu Met Asp Ser Ser Leu Asp His Tyr Arg Arg Ile Gly Pro Ala Val
145                 150                 155                 160

Gly Ala Phe Ser Phe Glu Val Glu Ser Ala Asp Gly Met Phe Lys Leu
                165                 170                 175

Ser Gln Glu Gln Asn Leu Glu Thr Arg Arg Arg Val Ala Asp His Phe
            180                 185                 190

Ser Ala Asn His Ala Gly Arg Gly Lys Glu Leu Ala Ser Phe Met Arg
        195                 200                 205

Glu Tyr Ser His Gly Asp Tyr Asn Asn Phe
    210                 215
```

<210> SEQ ID NO 157
<211> LENGTH: 218
<212> TYPE: PRT
<213> ORGANISM: Rhodococcus fascians

<400> SEQUENCE: 157

Met Tyr Val Pro Arg Ile Tyr Lys Ala Ser Asp Arg Thr Trp Leu Arg
1 5 10 15

Arg Val Val Ala Gln Tyr Pro Phe Ala Ala Leu Ile Ser Asn Gly Pro
20 25 30

Lys Ala Pro Tyr Ala Thr His Leu Pro Val Ile Cys Ala Pro Cys Ala
35 40 45

Pro Ser Glu Ser Glu Asp Leu Glu Gly Ser Thr Leu Phe Gly His Met
50 55 60

Asn Arg Ala Asn Pro His Trp Asp Ser Leu Val Asp Gly Ala Asp Ala
65 70 75 80

Gln Leu Ile Phe Thr Gly Pro His Gly Tyr Val Thr Pro Ser Val Tyr
85 90 95

Gln Arg Asp Ser Val Ala Pro Thr Trp Asn Tyr Val Ser Val His Leu
100 105 110

Arg Gly Lys Leu Gln Pro Val Ala Asp Phe Glu Glu Thr Leu Lys Val
115 120 125

Val Gln Leu Thr Val Ser Thr Tyr Glu Gln Lys Phe Gly Ser Gly Trp
130 135 140

Glu Met Asp Ser Ser Leu Asp His Tyr Arg Arg Ile Gly Pro Ala Val
145 150 155 160

Gly Ala Phe Ser Phe Glu Val Glu Ser Ala Asp Gly Met Phe Lys Leu
165 170 175

Ser Gln Glu Gln Asn Leu Glu Thr Arg Arg Arg Val Ala Asp His Phe
180 185 190

Ser Ala Asn His Ala Gly Arg Gly Lys Glu Leu Ala Ser Phe Met Arg
195 200 205

Glu Tyr Ser His Gly Asp Tyr Asn Asn Phe
210 215

<210> SEQ ID NO 158
<211> LENGTH: 227
<212> TYPE: PRT
<213> ORGANISM: Streptomyces sp. CNT360

<400> SEQUENCE: 158

Met Tyr Val Pro Gln His Phe Ala Val Asp Glu Thr Glu Pro Val Val
1 5 10 15

Glu Leu Ile Arg Ala Asn Pro Leu Ala Val Phe Val Thr Thr Gln Gly
20 25 30

Gly Val Pro Val Ala Ser His Ile Pro Val Val Phe Ala Ser Glu Asp
35 40 45

Glu Ala Glu Gln Ala Asp Asp Leu Val Gly Val Thr Leu Phe Gly His
50 55 60

Leu Asn Val Gln Asn Pro Gln Tyr Gly Val Leu Ala Asp Gly Asp Arg
65 70 75 80

Val Leu Val Val Phe Gln Gly Ser His Gly Tyr Ile Ser Pro Thr Val
85 90 95

Tyr Asp Thr Val Pro Ala Ala Pro Thr Trp Asn Phe Ser Ala Val His
100 105 110

```
Val Thr Gly Thr Val Arg Leu Leu Gly Pro Gly Glu Pro Ala Leu Lys
        115                 120                 125

Val Val Arg Arg Thr Val Thr Ala Leu Glu Arg Arg Phe Gly Ala Gly
    130                 135                 140

Trp Asp Met Thr Glu Ser Leu Pro Tyr Phe Glu Arg Ile Val Pro Gly
145                 150                 155                 160

Val Gly Ala Phe Glu Ile Ala Val Glu Ala Val Asp Ser Ile Phe Lys
                165                 170                 175

Leu Ser Gln Asp Gln Pro Ala Glu Leu Arg Asp Lys Ala Glu Cys Ala
            180                 185                 190

Phe Arg Asn Ser Asp Ala Gly Val His Arg Glu Leu Ala Ala Gln Met
        195                 200                 205

Arg Arg His Asn Gly Ala Ala Cys Ser His Gln Glu Arg Thr Ala Arg
    210                 215                 220

Asp Gly Asp
225


<210> SEQ ID NO 159
<211> LENGTH: 213
<212> TYPE: PRT
<213> ORGANISM: Salinispora arenicola

<400> SEQUENCE: 159

Met Leu Val Pro His Met Tyr Glu Ala Pro Ser Ala Ala Gln Val Asp
1               5                   10                  15

Ala Val Ile Thr Gly His Pro Met Ala Val Leu Val Thr Asn Gly Pro
            20                  25                  30

Asp Val Pro His Ala Thr His Leu Pro Val Ile Arg Thr Val Asp Thr
        35                  40                  45

Glu Gln Thr Gly Pro Gly Ser Val Leu Leu Gly His Met Asn Arg Thr
    50                  55                  60

Asn Pro His Trp Ser Ala Leu Thr Ser Gly Thr Pro Gly Lys Leu Ile
65                  70                  75                  80

Phe Thr Gly Pro Asn Thr Tyr Val Cys Pro Val Leu Tyr Gln Thr Glu
                85                  90                  95

Pro Ala Ala Pro Thr Trp Asp Phe Val Val Val His Val Ser Gly Arg
            100                 105                 110

Val Met Pro Leu Asp Ala Gly Glu Pro Thr Leu Ala Val Val Gln Arg
        115                 120                 125

Thr Ala Ala Thr Leu Glu Gly Ala Phe Gly Ala Gly Trp Asp His Thr
    130                 135                 140

Gly Ser Ile Asp Tyr Phe Arg Ser Ile Val Gly Gly Val Gly Ala Phe
145                 150                 155                 160

Glu Phe Val Val Glu Gln Val Glu Ser Met Phe Lys Leu Ser Gln Glu
                165                 170                 175

Lys Asp His Thr Val Arg Gln Arg Leu Ile Asp Asp Phe Thr Ser Ala
            180                 185                 190

Pro Arg Asn Gly Ser Ala Gln Val Gly Gln Leu Met Ser Asp Leu Asn
        195                 200                 205

Leu Gly Val Ala Pro
    210


<210> SEQ ID NO 160
<211> LENGTH: 213
<212> TYPE: PRT
<213> ORGANISM: Salinispora arenicola
```

<400> SEQUENCE: 160

Met Leu Val Pro His Met Tyr Glu Ala Pro Ser Ala Ala Gln Val Asp
1 5 10 15

Ala Val Ile Thr Gly His Pro Met Ala Val Leu Val Thr Asn Gly Pro
20 25 30

Asp Val Pro His Ala Thr His Leu Pro Val Ile Arg Thr Val Asp Thr
35 40 45

Glu Gln Thr Gly Pro Gly Ser Val Leu Leu Gly His Met Asn Arg Thr
50 55 60

Asn Pro His Trp Ser Ala Leu Thr Ser Gly Thr Pro Gly Lys Leu Ile
65 70 75 80

Phe Thr Gly Pro Asn Thr Tyr Val Cys Pro Val Leu Tyr Gln Thr Glu
85 90 95

Pro Ala Ala Pro Thr Trp Asp Phe Val Val Val His Val Ser Gly Arg
100 105 110

Val Met Pro Leu Asp Ala Gly Glu Pro Thr Leu Ala Val Val Gln Arg
115 120 125

Thr Ala Ala Thr Leu Glu Gly Ala Phe Gly Ala Gly Trp Asp His Thr
130 135 140

Gly Ser Ile Asp Tyr Phe Arg Ser Ile Val Gly Gly Val Gly Ala Phe
145 150 155 160

Glu Phe Val Val Glu Gln Val Glu Ser Met Phe Lys Leu Ser Gln Glu
165 170 175

Lys Asp His Thr Val Arg Gln Arg Leu Ile Asp Asp Phe Thr Ser Ala
180 185 190

Pro Arg Asn Gly Ser Ala Gln Val Gly Gln Leu Met Ser Asp Leu Asn
195 200 205

Leu Gly Val Ala Pro
210

<210> SEQ ID NO 161
<211> LENGTH: 213
<212> TYPE: PRT
<213> ORGANISM: Salinispora arenicola

<400> SEQUENCE: 161

Met Leu Val Pro His Met Tyr Glu Ala Pro Ser Ala Ala Gln Val Asp
1 5 10 15

Ala Val Ile Thr Gly His Pro Met Ala Val Leu Val Thr Asn Gly Pro
20 25 30

Asp Val Pro His Ala Thr His Leu Pro Val Ile Arg Thr Val Asp Thr
35 40 45

Glu Gln Thr Gly Pro Gly Ser Val Leu Leu Gly His Met Asn Arg Thr
50 55 60

Asn Pro His Trp Ser Ala Leu Thr Ser Gly Thr Pro Gly Lys Leu Ile
65 70 75 80

Phe Thr Gly Pro Asn Thr Tyr Val Cys Pro Val Leu Tyr Gln Thr Glu
85 90 95

Pro Ala Ala Pro Thr Trp Asp Phe Val Val Val His Val Ser Gly Arg
100 105 110

Val Met Pro Leu Asp Ala Gly Glu Pro Thr Leu Ala Val Val Gln Arg
115 120 125

Thr Ala Ala Thr Leu Glu Gly Ala Phe Gly Ala Gly Trp Asp His Thr
130 135 140

```
Gly Ser Ile Asp Tyr Phe Arg Ser Ile Val Gly Gly Val Gly Ala Phe
145                 150                 155                 160

Glu Phe Val Val Glu Gln Val Glu Ser Met Phe Lys Leu Ser Gln Glu
                165                 170                 175

Lys Asp His Thr Val Arg Gln Arg Leu Ile Asp Asp Phe Thr Ser Ala
            180                 185                 190

Pro Arg Asn Gly Ser Ala Gln Val Gly Gln Leu Met Ser Asp Leu Asn
        195                 200                 205

Leu Gly Val Ala Pro
    210


<210> SEQ ID NO 162
<211> LENGTH: 213
<212> TYPE: PRT
<213> ORGANISM: Salinispora arenicola

<400> SEQUENCE: 162

Met Leu Val Pro His Met Tyr Glu Ala Pro Ser Ala Ala Gln Val Asp
1               5                   10                  15

Ala Val Ile Thr Gly His Pro Met Ala Val Leu Val Thr Asn Gly Pro
            20                  25                  30

Asp Val Pro His Ala Thr His Leu Pro Val Ile Arg Thr Val Asp Thr
        35                  40                  45

Glu Gln Thr Gly Pro Gly Ser Val Leu Leu Gly His Met Asn Arg Thr
    50                  55                  60

Asn Pro His Trp Ser Ala Leu Thr Ser Gly Thr Pro Gly Lys Leu Ile
65                  70                  75                  80

Phe Thr Gly Pro Asn Thr Tyr Val Cys Pro Val Leu Tyr Gln Thr Glu
                85                  90                  95

Pro Ala Ala Pro Thr Trp Asp Phe Val Val Val His Val Ser Gly Arg
            100                 105                 110

Val Met Pro Leu Asp Ala Gly Glu Pro Thr Leu Ala Val Val Gln Arg
        115                 120                 125

Thr Ala Ala Thr Leu Glu Gly Ala Phe Gly Ala Gly Trp Asp His Thr
    130                 135                 140

Gly Ser Ile Asp Tyr Phe Arg Ser Ile Val Gly Gly Val Gly Ala Phe
145                 150                 155                 160

Glu Phe Val Val Glu Gln Val Glu Ser Met Phe Lys Leu Ser Gln Glu
                165                 170                 175

Lys Asp His Thr Val Arg Gln Arg Leu Ile Asp Asp Phe Thr Ser Ala
            180                 185                 190

Pro Arg Asn Gly Ser Ala Gln Val Gly Gln Leu Met Ser Asp Leu Asn
        195                 200                 205

Leu Gly Val Ala Pro
    210


<210> SEQ ID NO 163
<211> LENGTH: 213
<212> TYPE: PRT
<213> ORGANISM: Salinispora arenicola

<400> SEQUENCE: 163

Met Leu Val Pro His Met Tyr Glu Ala Pro Ser Ala Ala Gln Val Asp
1               5                   10                  15

Ala Val Ile Thr Gly His Pro Met Ala Val Leu Val Thr Asn Gly Pro
            20                  25                  30
```

```
Asp Val Pro His Ala Thr His Leu Pro Val Ile Arg Thr Val Asp Thr
        35                  40                  45

Glu Gln Thr Gly Pro Gly Ser Val Leu Leu Gly His Met Asn Arg Thr
    50                  55                  60

Asn Pro His Trp Ser Ala Leu Thr Ser Gly Thr Pro Gly Lys Leu Ile
65                  70                  75                  80

Phe Thr Gly Pro Asn Thr Tyr Val Cys Pro Val Leu Tyr Gln Thr Glu
                85                  90                  95

Pro Ala Ala Pro Thr Trp Asp Phe Val Val Val His Val Ser Gly Arg
            100                 105                 110

Val Met Pro Leu Asp Ala Gly Glu Pro Thr Leu Ala Val Val Gln Arg
        115                 120                 125

Thr Ala Ala Thr Leu Glu Gly Ala Phe Gly Ala Gly Trp Asp His Thr
    130                 135                 140

Gly Ser Ile Asp Tyr Phe Arg Ser Ile Val Gly Gly Val Gly Ala Phe
145                 150                 155                 160

Glu Phe Val Val Glu Gln Val Glu Ser Met Phe Lys Leu Ser Gln Glu
                165                 170                 175

Lys Asp His Thr Val Arg Gln Arg Leu Ile Asp Asp Phe Thr Ser Ala
            180                 185                 190

Pro Arg Asn Gly Ser Thr Gln Val Gly Gln Leu Met Ser Asp Leu Asn
        195                 200                 205

Leu Gly Val Ala Pro
    210


<210> SEQ ID NO 164
<211> LENGTH: 213
<212> TYPE: PRT
<213> ORGANISM: Salinispora arenicola

<400> SEQUENCE: 164

Met Leu Val Pro His Met Tyr Glu Ala Pro Ser Ala Ala Gln Val Asp
1               5                   10                  15

Ala Val Ile Thr Gly His Pro Met Ala Val Leu Val Thr Asn Gly Pro
            20                  25                  30

Asp Val Pro His Ala Thr His Leu Pro Val Ile Arg Thr Val Asp Thr
        35                  40                  45

Glu Gln Thr Gly Pro Gly Ser Val Leu Leu Gly His Met Asn Arg Thr
    50                  55                  60

Asn Pro His Trp Ser Ala Leu Thr Ser Gly Thr Pro Gly Lys Leu Ile
65                  70                  75                  80

Phe Thr Gly Pro Asn Thr Tyr Val Cys Pro Val Leu Tyr Gln Thr Glu
                85                  90                  95

Pro Ala Ala Pro Thr Trp Asp Phe Val Val Val His Val Ser Gly Arg
            100                 105                 110

Val Met Pro Leu Asp Ala Gly Glu Pro Thr Leu Ala Val Val Gln Arg
        115                 120                 125

Thr Ala Ala Thr Leu Glu Gly Ala Phe Gly Ala Gly Trp Asp His Thr
    130                 135                 140

Gly Ser Ile Asp Tyr Phe Arg Ser Ile Val Gly Gly Val Gly Ala Phe
145                 150                 155                 160

Glu Phe Val Val Glu Gln Val Glu Ser Met Phe Lys Leu Ser Gln Glu
                165                 170                 175

Lys Asp His Thr Val Arg Gln Arg Leu Ile Asp Asp Phe Thr Ser Ala
```

```
            180                 185                 190

Pro Arg Asn Gly Ser Thr Gln Val Gly Gln Leu Met Ser Asp Leu Asn
        195                 200                 205

Leu Gly Val Ala Pro
    210


<210> SEQ ID NO 165
<211> LENGTH: 213
<212> TYPE: PRT
<213> ORGANISM: Salinispora pacifica

<400> SEQUENCE: 165

Met Leu Val Pro His Met Tyr Glu Ala Pro Ser Ala Ala Gln Val Asp
1               5                   10                  15

Ala Val Ile Thr Gly His Pro Met Ala Val Leu Val Thr Asn Gly Pro
            20                  25                  30

Asp Val Pro His Ala Thr His Leu Pro Val Ile Arg Thr Val Asp Thr
        35                  40                  45

Glu Gln Thr Gly Pro Gly Ser Val Leu Leu Gly His Met Asn Arg Thr
    50                  55                  60

Asn Pro His Trp Ser Ala Leu Thr Ser Gly Thr Pro Gly Lys Leu Ile
65                  70                  75                  80

Phe Thr Gly Pro Asn Thr Tyr Val Cys Pro Val Leu Tyr Gln Thr Glu
                85                  90                  95

Pro Ala Ala Pro Thr Trp Asp Phe Val Val Val His Val Ser Gly Arg
            100                 105                 110

Val Met Pro Leu Asp Ala Gly Glu Pro Thr Leu Ala Val Val Gln Arg
        115                 120                 125

Thr Ala Ala Thr Leu Glu Gly Ala Phe Gly Ala Gly Trp Asp His Thr
    130                 135                 140

Gly Ser Ile Asp Tyr Phe Arg Ser Ile Val Gly Gly Val Gly Ala Phe
145                 150                 155                 160

Glu Phe Val Val Glu Gln Val Glu Ser Met Phe Lys Leu Ser Gln Glu
                165                 170                 175

Lys Asp His Thr Val Arg Gln Arg Leu Ile Asp Asp Phe Thr Ser Ala
            180                 185                 190

Pro Arg Asn Gly Ser Thr Gln Val Gly Gln Leu Met Ser Asp Leu Asn
        195                 200                 205

Leu Gly Val Ala Pro
    210


<210> SEQ ID NO 166
<211> LENGTH: 217
<212> TYPE: PRT
<213> ORGANISM: Streptomyces aureofaciens

<400> SEQUENCE: 166

Val Phe Thr Pro Lys Leu Tyr Gln Val Asp Gly Asp Asp Trp Pro Leu
1               5                   10                  15

Arg Ile Ile Glu Arg His Pro Leu Ala Val Leu Val Ser Asn Gly Asp
            20                  25                  30

Pro Val Pro Asn Ala Thr His Val Pro Val Ile Ala Pro Pro Asp Ala
        35                  40                  45

Ala Pro Glu Asp Ala Leu Ser Gly Met Arg Leu Trp Ala His Leu Thr
    50                  55                  60

Arg Ala Asn Pro His Trp Gln Gln Leu Ala Ala Ala Gly Gly Gly Pro
```

```
65                  70                  75                  80

Ala Lys Leu Val Phe His Gly Pro Asn Gly Tyr Val Thr Pro Ser Leu
                85                  90                  95

Tyr Ser Ala Asp Met Val Ala Pro Thr Trp Asn Tyr Val Ala Val His
            100                 105                 110

Leu Glu Gly Thr Val Glu Leu Ala Gly Asp Asp Glu Thr Leu Ala Ile
        115                 120                 125

Val His Thr Thr Ala Gln Thr Leu Glu Asp Arg Phe Gly Asp Gly Met
    130                 135                 140

Ala Leu Ala Pro Ser Leu Glu Tyr His Arg Gln Ile Val Gly Ala Val
145                 150                 155                 160

Gly Gly Leu Phe Phe Thr Val Thr Lys Val Asp Val Met Phe Lys Leu
                165                 170                 175

Ser Gln Glu Lys Asp Pro Glu Val Gln Gln Arg Val Leu Asp Arg Phe
            180                 185                 190

Ala Ala Ser Gly Ser Gly Leu His Arg Glu Val Ala Asp Thr Met Arg
        195                 200                 205

Ala Leu Arg Leu Gly Gly Ser Ala Gly
    210                 215
```

<210> SEQ ID NO 167
<211> LENGTH: 700
<212> TYPE: PRT
<213> ORGANISM: Streptomyces sp. CFMR 7

<400> SEQUENCE: 167

```
Val Arg Asn Ala His Ala Thr His Pro Asp Asp Asp Pro Val Gly Thr
1               5                   10                  15

Thr Thr Glu Arg Pro Tyr Asp Leu Leu Gly Ile Gly Phe Gly Pro Ser
            20                  25                  30

Asn Leu Ala Leu Ala Val Cys Ala Arg Glu Gln Lys Leu Pro Leu Ser
        35                  40                  45

Cys Leu Phe Val Glu Arg Gln Asp Thr Val Ala Trp His Pro Gly Met
    50                  55                  60

Leu Ile Asp Gly Ala Arg Met Gln Ile Ser Phe Leu Lys Asp Leu Val
65                  70                  75                  80

Ser Leu Arg Asn Pro Ser Ser Pro Tyr Ser Phe Leu Gln Tyr Thr Lys
                85                  90                  95

Ala Lys Gly Arg Leu Glu Arg Phe Val Asn Leu Asn Glu Ser Arg Pro
            100                 105                 110

Thr Arg Ile Glu Tyr Asp Asp Tyr Leu Lys Trp Val Ala Gln Asp Phe
        115                 120                 125

Ala Asp Gln Val Arg Phe Gly Ser Gln Val Asp Arg Val Thr Pro Val
    130                 135                 140

Gln Gly Pro Asp Gly Gly Asp Leu Ser Leu Phe Arg Val Glu Thr Gln
145                 150                 155                 160

Asp Val Ala Thr Gly Arg His Ser Val His Tyr Ala Arg Asn Val Val
                165                 170                 175

His Ala Gly Gly Gly Arg Pro Pro Ala Arg Thr Ala Gly Val Ala Glu
            180                 185                 190

Val Ser Ser Val Val His Ser Ser Glu Phe Leu Thr Arg Phe Pro Asp
        195                 200                 205

Gln Phe Lys Asp His Asp Gly Ala Tyr Arg Phe Val Val Val Gly Gly
    210                 215                 220
```

-continued

```
Gly Gln Ser Ala Gly Glu Ile Ser Glu Tyr Leu Leu Asp His Tyr Asp
225                 230                 235                 240

Arg Ala Glu Val His Val Val Val Ser Gly Tyr Thr Leu Leu Pro Thr
                245                 250                 255

Asp Asn Ser Pro Phe Val Asn Glu Gln Phe Tyr Ser Gly Asn Ala Asp
            260                 265                 270

Ala Phe Tyr Arg Met Arg Pro Glu Gln Arg Ala Ala Val Ser Gly Arg
        275                 280                 285

Leu Arg Ala Ala Asn Tyr Gly Val Val Arg Glu Asp Leu Leu Glu Arg
    290                 295                 300

Leu Phe Asn Thr Asp Tyr Leu Asp Gln Val Lys Gly Arg Lys Arg Leu
305                 310                 315                 320

His Ile His Pro Phe Ser Arg Leu Ser Glu Val Arg Glu Asn Gly Asp
                325                 330                 335

Ala Leu Ala Val Thr Leu Arg Gln His Leu Asp Glu Gly Pro Glu Glu
            340                 345                 350

Pro Leu Arg Cys Asp Gly Val Val Leu Ala Thr Gly Tyr Asp Arg Ser
        355                 360                 365

Leu Asp Pro Ala Val Phe Gly Asp Val Leu Pro His Leu Thr Ala Gly
    370                 375                 380

Glu Gly Glu Gly Val Gly Gly Val Ala Leu Ser Arg His Tyr Arg Ala
385                 390                 395                 400

Arg Thr Ser Pro Glu Leu Arg Ala Gly Leu Tyr Leu Gln Gly Phe Gly
                405                 410                 415

Glu Ala Gln Phe Gly Leu Gly Asp Thr Leu Leu Ser Leu Leu Pro Phe
            420                 425                 430

Arg Ser Gln Glu Ile Val Glu Asp Ile Ala Asp Arg Val Pro Val Ala
        435                 440                 445

Gly Val Gly Gly Cys Pro Val Met Ser Pro Tyr Gly Ser Gly Val Val
    450                 455                 460

Ser Thr Ser Pro His Gly Pro Ala Arg Ser Ala Val Tyr Pro Pro Lys
465                 470                 475                 480

Trp Tyr Leu Glu His Asp Arg Glu Lys Leu Tyr Gly Leu Met Glu Arg
                485                 490                 495

Phe Arg Phe Ala Thr Leu Ile Ser Ala Arg Ser Gly Asp Gln Pro Phe
            500                 505                 510

Ala Thr His Leu Pro Leu Ile Leu Asp Arg Ser Arg Gly Ala Asn Gly
        515                 520                 525

Val Leu Phe Gly His Leu Asp Arg Gly Asn Glu His Ala Asp Leu Ile
    530                 535                 540

Asp Gly Arg His Met Leu Ala Val Phe His Gly Pro Asn Ala Tyr Met
545                 550                 555                 560

Pro Pro Gly Val Phe Glu Ser Asp Pro Leu Pro Thr Trp Asn Ser Met
                565                 570                 575

Ser Val His Val Arg Gly Arg Val Arg Val Val Arg Asp Arg Asp Ala
            580                 585                 590

Leu Val His Gly Leu Ile Gly Ile Ala Glu Arg Ser Gln Pro Asp Asn
        595                 600                 605

Arg Leu Ala Ala Asp Asp Pro Arg Ile Asp Arg Ile Ile Gly Ser Ile
    610                 615                 620

Val Gly Phe Glu Phe Glu Val Glu Glu Leu Val Gly Arg Phe Lys Leu
625                 630                 635                 640

Ser Gln Asp Arg Asp Glu Thr Asp Arg Arg His Ala Ala Val Ala Leu
```

```
                645                 650                 655

Ala Arg Ala Thr Glu Arg Gly Glu Arg Asp Phe Ile Glu Tyr Val Val
            660                 665                 670

Gly Leu Ser Leu Ile Thr Glu Asp Asp Pro Arg Asp Leu Ala Gly Arg
        675                 680                 685

Pro Leu Ser Pro Leu Ala Ile Gly Gly Val His Glu
    690                 695                 700


<210> SEQ ID NO 168
<211> LENGTH: 672
<212> TYPE: PRT
<213> ORGANISM: Micromonospora tulbaghiae

<400> SEQUENCE: 168

Met Arg Asn Asp Pro Ala Pro Asp Ala Arg Ser Ser Glu Pro Gly Ser
1               5                   10                  15

Glu Gln Asn Pro Tyr Asp Leu Ile Gly Val Gly Phe Gly Pro Ser Asn
            20                  25                  30

Leu Ala Leu Ala Ile Ala Ala Glu Glu Leu Asp Gly Glu Arg Thr Cys
        35                  40                  45

Leu Phe Phe Glu Arg Ser Pro Ser Leu Gln Trp His Pro Gly Met Leu
    50                  55                  60

Leu Glu Gly Ser Arg Met Gln Ile Ser Phe Leu Lys Asp Leu Val Ser
65                  70                  75                  80

Leu Arg Asn Pro Ala Ser Pro Tyr Thr Phe Leu Gln Tyr Ala Lys Ala
                85                  90                  95

Lys Asp Arg Leu Glu Arg Phe Val Asn Leu Ser Glu Phe Arg Pro Thr
            100                 105                 110

Arg Leu Glu Tyr Gln Asp Tyr Leu Arg Trp Val Ala Glu Phe Phe Ala
        115                 120                 125

Gly Gln Val Arg Tyr His Thr Glu Val Thr Arg Val Ser Pro Val Arg
    130                 135                 140

Arg Pro Gly Glu Asp Val His Arg Leu Phe Arg Val Glu Ala Arg Asp
145                 150                 155                 160

Ile Arg Thr Gly Glu Thr Thr Val His His Ala Ala Asn Val Val His
                165                 170                 175

Ala Ala Gly Gly Arg Pro Arg Leu Pro Pro Gly Gly Val Cys Ala Ser
            180                 185                 190

Pro Ala Val Ile His Ser Ser Asp Phe Leu Pro His Phe Pro Glu Arg
        195                 200                 205

Phe Ala Asp Arg Ser Arg Pro Tyr Glu Phe Ala Val Ala Gly Asp Gly
    210                 215                 220

Gln Ser Ala Gly Glu Val Ala Leu Tyr Leu Met Arg Thr Tyr Pro Glu
225                 230                 235                 240

Ser Arg Val His Leu Phe Leu Ser Gly Gln Ala Leu Arg Ala Thr Asp
                245                 250                 255

Asn Ser Pro Phe Val Asn Glu Gln Phe Phe Glu Ser Ser Ala Asn Ala
            260                 265                 270

Phe Ser Ala Arg Pro Arg Asp Glu Arg Thr Ala Leu Arg Ala Glu Leu
        275                 280                 285

Arg Asn Thr Asn Tyr Gly Val Val Glu Ala Gly Thr Leu Asp Asp Leu
    290                 295                 300

Tyr Arg Thr Val Tyr Asp Asp Glu Val Arg Gly Arg His Arg Leu Ile
305                 310                 315                 320
```

-continued

```
Val His Pro Ala Thr Arg Val Val Ala Val Arg Glu Gly Asp Glu Gly
                325                 330                 335

Pro Leu Val Ala Ile Leu Asp Arg Arg Ser Gly Ala Glu Gly Glu Ile
            340                 345                 350

Arg Cys Asp Gly Val Val Leu Ala Thr Gly Tyr Val Arg Ala Leu Asp
        355                 360                 365

Glu Ser Ile Phe Ser Glu Leu Thr Pro Phe Leu Arg Thr Glu Ser Asp
    370                 375                 380

Lys Leu Leu Leu Ser Gly Tyr Arg Val Arg Thr Thr Ala Glu Val Ala
385                 390                 395                 400

Gly Gly Phe Tyr Val Gln Gly Tyr Gly Glu Gln His Phe Gly Leu Gly
                405                 410                 415

Asp Thr Leu Leu Ser Leu Leu Pro Phe Arg Ser Arg Gln Ile Phe Thr
            420                 425                 430

Asp Ile Cys Arg Arg Thr Pro Pro Pro Arg Gln Ala Val Ala Val Ser
        435                 440                 445

Asp Ala Ser Ala Tyr Pro Pro Pro His Tyr Leu Glu His Asp Pro Glu
    450                 455                 460

Lys Leu Tyr Ala Val Met Glu Arg Phe Asn Phe Ala Thr Val Ile Ser
465                 470                 475                 480

Ala Arg Ala Ala Glu Asp Pro Val Val Thr His Val Pro Leu Thr Leu
                485                 490                 495

Asp Arg Ser Arg Gly Ala His Gly Val Leu Phe Gly His Leu Asp Arg
            500                 505                 510

Ala Asn Pro His Ala Gln Leu Ile Asp Gly Lys Gln Val Thr Val Val
        515                 520                 525

Phe His Gly Pro Asn Thr Tyr Leu Ser Pro Tyr Ala Leu Glu Thr Asp
    530                 535                 540

Ala Leu Pro Thr Trp Asn Ser Met Asn Val His Val Gly Gly Arg Gly
545                 550                 555                 560

Arg Leu Leu Ala Asp Arg Ala Ala Leu Val Thr Gly Leu Ser Gly Ile
                565                 570                 575

Cys Glu Lys Ser Asp Pro Gly Val Asp Ser Tyr Arg Leu Asp Pro Asp
            580                 585                 590

Asp Pro Arg Ile Asp Arg Leu Val Asp Tyr Val Val Gly Phe Glu Ile
        595                 600                 605

Glu Ile Gln Ala Leu Val Gly Arg Phe Lys Leu Ser Gln Glu Leu Asp
    610                 615                 620

Asp Arg Asn Arg Arg Leu Ala Ala Ser Ala Leu Met Ala Thr Ala Arg
625                 630                 635                 640

Arg Asp Glu Ser Glu Val Ile Gly Lys Val Phe Gly Met Ser Pro Val
                645                 650                 655

Asn Gly Arg Gln Asn Gly Ser Ser Ala Leu Trp Ser Ala His Ser Arg
            660                 665                 670


<210> SEQ ID NO 169
<211> LENGTH: 661
<212> TYPE: PRT
<213> ORGANISM: Amycolatopsis alba

<400> SEQUENCE: 169

Met Arg Asn Asp Ala Pro Pro Asn Pro Leu Thr Ala Glu Leu Gly Ala
1               5                   10                  15

Glu Gly Asn Pro Tyr Asp Leu Ile Gly Val Gly Phe Gly Pro Ser Asn
            20                  25                  30
```

-continued

```
Leu Ala Leu Ala Ile Ala Ala Glu Glu Leu Asp Ser Glu Arg Asn Cys
        35                  40                  45

Leu Phe Phe Glu Arg Ser Ser Arg Leu Arg Trp His Pro Gly Met Leu
    50                  55                  60

Ile Asp Gly Ser Arg Met Gln Ile Ser Phe Leu Lys Asp Leu Val Ser
65                  70                  75                  80

Leu Arg Asn Leu Ala Ser Pro Tyr Thr Phe Leu Gln Tyr Thr Lys Ala
                85                  90                  95

Lys Gly Arg Leu Glu Gln Phe Val Asn Leu Asn Asp Phe Arg Pro Thr
            100                 105                 110

Arg Leu Glu Tyr Gln Asp Tyr Leu Glu Trp Val Ala Glu Ser Phe Ser
        115                 120                 125

Gly Gln Val Arg Tyr Asn Ser Glu Val Thr Arg Val Thr Pro Val Arg
    130                 135                 140

Arg Thr Gly Glu Asp Ala His Arg Leu Phe Arg Val Glu Ala Arg Asp
145                 150                 155                 160

Val Val Thr Gly Gln Thr Thr Val Arg Tyr Ala Ala Asn Val Val His
                165                 170                 175

Ala Ala Gly Gly Arg Pro Arg Leu Pro Asp Gly Gly Val Cys Asp Ser
            180                 185                 190

Pro Ala Val Val His Ser Ser Asp Phe Leu Pro Arg Phe Pro Gly His
        195                 200                 205

Phe Ala Asp Arg Ser Arg Pro Tyr Glu Phe Gly Val Ala Gly Asp Gly
    210                 215                 220

Gln Ser Ala Gly Glu Ile Ala Ala Tyr Leu Leu Ser Arg Tyr Pro Ala
225                 230                 235                 240

Ser Arg Val His Leu Leu Leu Ser Gly Ser Ala Leu Arg Ala Ala Asp
                245                 250                 255

Ser Asn Pro Phe Val Asn Glu Gln Phe Phe Glu Gly Arg Ala Asn His
            260                 265                 270

Phe His Ala Arg Thr Lys Pro Asp Arg Thr Gly Leu Leu Ala Glu Leu
        275                 280                 285

Arg Asn Thr Asn Tyr Ala Val Val Glu Pro Gly Phe Leu Asp Asp Leu
    290                 295                 300

Tyr Arg Leu Val Tyr Asp Asp Glu Val Arg Gly Thr Arg Arg Leu Ile
305                 310                 315                 320

Val His Pro Gly Thr Lys Val Thr Ala Val Gly Ala Asp Gly Ala Ser
                325                 330                 335

Leu Arg Val Ala Val Thr Asp Arg Arg Gly Gly Asp Glu Glu Met Arg
            340                 345                 350

Cys Asp Gly Val Val Leu Ala Thr Gly Tyr Val Arg Ala Leu Asp Glu
        355                 360                 365

Ser Met Phe Ala Asp Leu Leu Pro Phe Leu Arg Glu Glu Ser Gly Asp
    370                 375                 380

Leu Val Leu Ser Pro Asp Tyr Arg Val Gly Thr Thr Ala Glu Leu Glu
385                 390                 395                 400

Gly Gly Phe Tyr Val Gln Gly Tyr Gly Glu Ser Ser Phe Gly Leu Gly
                405                 410                 415

Asp Thr Leu Leu Ser Leu Leu Pro Phe Arg Ala Lys Gln Ile Phe Thr
            420                 425                 430

Asp Ile Cys Lys Gln Thr Pro Pro Pro Val Arg Thr Arg Arg Pro Val
        435                 440                 445
```

-continued

```
Glu Val Ser Lys Ala Ser Ala Tyr Pro Pro Pro His Tyr Val Glu Thr
    450                 455                 460

Asp Pro Lys Lys Ile Tyr Ala Val Met Glu Arg Phe Ser Phe Ala Thr
465                 470                 475                 480

Leu Ile Ser Ala Arg Gly Ala Glu Asp Pro Val Val Thr His Leu Pro
                485                 490                 495

Leu Thr Leu Asp Arg Ala Arg Gly Ala His Gly Val Leu Phe Gly His
            500                 505                 510

Leu Asp Arg Ala Asn Pro His Val Gln Leu Ile Asp Gly His Gln Leu
        515                 520                 525

Thr Val Leu Phe His Gly Pro Asn Ala Tyr Leu Ser Pro Gln Val Phe
    530                 535                 540

Glu Thr Ser Val Leu Pro Thr Trp Asn Ser Met Asn Val His Val Arg
545                 550                 555                 560

Gly Arg Gly Arg Leu Leu Pro Asp Arg Ala Ala Leu Leu Ala Gly Leu
                565                 570                 575

Ser Gly Ile Cys Val Lys Ser Asp Pro Gly Asp Asp Ser Tyr Arg Leu
            580                 585                 590

Asp Leu Asp Asp Pro Arg Ile Asp Arg Met Ile Glu His Ile Val Gly
        595                 600                 605

Phe Glu Ile Glu Ile His Glu Leu Val Gly Arg Phe Lys Leu Ser Gln
    610                 615                 620

Glu Leu Asp Asp Gln Asn Arg Met Leu Ala Ala Ser Ala Leu Ser Ala
625                 630                 635                 640

Thr Ala Arg Arg Gly Glu Leu Glu Leu Ile Glu Glu Val Val Gly Leu
                645                 650                 655

Asn Val Val Gln Gly
            660


<210> SEQ ID NO 170
<211> LENGTH: 682
<212> TYPE: PRT
<213> ORGANISM: Mycobacterium sp. IS-1556

<400> SEQUENCE: 170

Met Thr Ser Met Pro Pro Gly Glu Gly His Asp Ser Asp Leu Asp Phe
1               5                   10                  15

Ile Gly Ile Gly Phe Gly Pro Ser Asn Leu Ala Leu Ala Val Ala Ala
            20                  25                  30

Asp Glu Ile Val Pro Asp Arg Lys Gly Leu Phe Phe Glu Arg Ser Gly
        35                  40                  45

Thr Phe Gln Trp His Pro Gly Met Leu Leu Asp Gly Thr Lys Met Gln
    50                  55                  60

Ile Ser Phe Leu Lys Asp Leu Ala Thr Leu Arg Asn Pro Ala Ser Arg
65                  70                  75                  80

Tyr Thr Phe Leu Gln Tyr Ala Lys Ala Arg Gly Arg Leu Glu Gln Phe
                85                  90                  95

Val Asn Leu His Glu Phe His Pro Ser Arg Leu Glu Tyr Asn Asp Tyr
            100                 105                 110

Leu Arg Trp Val Ala Glu Phe Phe Thr Asp Arg Val Cys Tyr Asn Thr
        115                 120                 125

Ile Val Thr Ala Val Val Pro Val Gly His Ser Pro Ser Ser Asn Gly
    130                 135                 140

His Leu Thr Arg Phe Arg Val His Val Arg Asp Met Ala Thr Gly Ala
145                 150                 155                 160
```

-continued

```
Glu Ser Cys Phe Phe Thr Ala Asn Val Ile Phe Gly Gly Gly Gly Val
                165                 170                 175

Pro Arg Leu Leu Gly Ala Arg Ala Asp Ala Ser Ala Val Leu His Ser
            180                 185                 190

Ser Ala Phe Leu Pro Asn Phe Thr Asn Arg Phe Asn Glu Ser Gln Lys
        195                 200                 205

Pro Tyr Arg Phe Ala Val Ile Gly Asn Gly Gln Ser Ala Ala Glu Ile
    210                 215                 220

Val Asp Tyr Leu Leu Asn His Tyr Pro Gly Ala Thr Ile His Leu Phe
225                 230                 235                 240

Ile Ser Asp Cys Thr Leu Arg Ala Thr Asp His Ser Pro Phe Ile Asn
                245                 250                 255

Glu His Phe Phe Ser Thr Ser Ala Ala Asp Phe Tyr Asn His Pro Pro
            260                 265                 270

Ala Gln Arg Val Ala Leu Arg Ser Ala Leu Arg Ser Thr Asn Tyr Gly
        275                 280                 285

Val Val Asp Ala Asp Leu Leu Gln Lys Leu Tyr Gln Ile Thr Tyr Leu
    290                 295                 300

Asp Glu Val Lys Gly Cys Arg Arg Leu Leu Leu His Arg Glu Ser Arg
305                 310                 315                 320

Leu Ser Gln Ile Glu Glu Ile Asp Asp Gln Val Val Ala Ser Phe Glu
                325                 330                 335

Asp Arg Phe Ser Gly Asp Ser Ser Glu Phe His Phe Asp Gly Ala Val
            340                 345                 350

Leu Ala Thr Gly Tyr Glu Arg Val Leu Asp Ala Glu Val Phe Arg His
        355                 360                 365

Val Leu Pro His Val Leu Trp Asp Glu Ser Gly Ala Ile Ser Leu Thr
    370                 375                 380

Arg Ser Cys Arg Val Asn Thr Val Pro Ala Val Thr Ala Arg Leu Phe
385                 390                 395                 400

Leu Gln Gly Tyr Gly Glu Ala Trp Phe Gly Ile Gly Asp Thr Leu Leu
                405                 410                 415

Ser Leu Leu Pro Phe Arg Ala Gln Ala Ile Ala Gln Glu Ile Gly Asn
            420                 425                 430

Ala Pro Ser Gly Ala Pro Ile Arg Arg Lys Gln Arg Val His Gly Glu
        435                 440                 445

Tyr Pro Pro Lys Arg Tyr Leu Glu Thr Asp Pro Asp Arg Leu His Asp
    450                 455                 460

Val Ile Asn Arg Tyr Arg Phe Ala Thr Leu Val Ser Ala Ser Gly Val
465                 470                 475                 480

Asp Glu Pro Val Val Thr Gln Leu Pro Leu Thr Leu Asp Thr Ser Arg
                485                 490                 495

Gly Ser Leu Gly Val Leu Phe Gly His Met Asp Phe Ala Asn Pro His
            500                 505                 510

Thr Glu Leu Leu Asp Gly Arg Arg Val Leu Val Leu Phe His Gly Pro
        515                 520                 525

Asn Gly Tyr Ile Ser Pro His Val Tyr Glu Ser Ala Gln Leu Pro Thr
    530                 535                 540

Trp Asn Ser Ile Thr Val Glu Val Arg Gly Arg Ala Arg Ile Leu Arg
545                 550                 555                 560

Asp Lys Asp Ala Val Val Asn Gly Leu Arg Gly Ile Ala Ala Ala Ala
                565                 570                 575
```

-continued

Asp Pro Thr Pro Gly Gly Phe Arg Leu Thr Arg Glu Ala Ala Ser Asp
580 585 590

Gln Arg Leu Phe Pro Leu Leu Val Gly Phe Glu Ile Asp Ile Asp Asp
595 600 605

Met Arg Gly Arg Phe Lys Leu Ser Gln Glu Arg Asp Asp Arg Asp Arg
610 615 620

Trp His Ala Ala His Ala Leu Ala Asn Gly Val Glu Gln Asp Asp Arg
625 630 635 640

Asp Leu Ile Ser Ser Ile Val Gly Leu Pro Leu Asp Val Asp Glu Glu
645 650 655

Pro Lys Pro Gln Gln Gln Ala Gln Ile His Gln Tyr Gly Asn Ala Pro
660 665 670

Ala Asp Thr Ala Tyr Arg Arg Val Asp Gly
675 680

<210> SEQ ID NO 171
<211> LENGTH: 710
<212> TYPE: PRT
<213> ORGANISM: Streptomyces sp. Root55

<400> SEQUENCE: 171

Met Ser Ser Glu Ala Gly Ala Val Phe Pro Cys Ala Asn Gly Arg Pro
1 5 10 15

Ala Ala Glu Val Ala Pro Gly Pro Ser Arg Gly Ser His Pro Ala Asp
20 25 30

Pro Tyr Asp Leu Ile Gly Val Gly Phe Gly Pro Ser Asn Met Ala Leu
35 40 45

Ala Ile Ala Val Glu Glu Leu Asp Pro Gly Arg Ser Cys Leu Phe Leu
50 55 60

Glu Arg Asn Thr Gly Val Arg Trp His Pro Gly Met Leu Ile Glu Gly
65 70 75 80

Ala Arg Met Gln Ile Ser Tyr Leu Lys Asp Leu Val Ser Leu Arg Asn
85 90 95

Leu Ala Ser Pro Tyr Thr Phe Leu Ser Tyr Leu Lys Ala Lys Gly Arg
100 105 110

Leu Glu Lys Phe Ile Asn Val Gly Ala Ser Arg Pro Thr Arg Leu Glu
115 120 125

Tyr Gln Asp Tyr Leu Ser Trp Val Ala Glu Asp Phe Gly His Val Val
130 135 140

Arg Tyr Glu Ser Glu Val Val Ala Val Val Pro Val Ala Gly Pro Gly
145 150 155 160

Ser Glu Thr Leu Asp Leu Leu Arg Val Arg Val Arg Asp Ala Gly Ser
165 170 175

Ala Glu Phe His Asp Leu Tyr Ala Arg Asn Val Val His Ala Gly Gly
180 185 190

Gly Thr Pro Arg Arg Gly Ala Pro Gly Gln Ile Cys Asp Ala Ser Ser
195 200 205

Val Ile His Ser Ser Thr Phe Leu Asp Ala Phe Pro Ala Arg Phe Pro
210 215 220

Asp His Asp Ala Ala Leu Asp Leu Gly Val Val Gly Asp Gly Gln Ser
225 230 235 240

Ala Ala Glu Ile Thr Ser His Val Leu Lys Gly Tyr Pro Asn Ala Arg
245 250 255

Val His Leu Phe Val Pro Gly Tyr Ala Leu Arg Ala Thr Asp Asn Asn
260 265 270

-continued

```
Pro Phe Ala Asn Glu Gln Phe Tyr Gln Arg Asn Ala Gly Glu Phe Tyr
        275                 280                 285

Ala Ser Gly Ala Arg Arg Arg Thr Ile Leu Arg Thr Glu Leu Arg Asn
    290                 295                 300

Thr Asn Tyr Gly Ala Val Glu Ala Gly His Leu Asp Glu Leu Tyr Asp
305                 310                 315                 320

Ile Thr Tyr Ala Asp Glu Val Arg Gly Ala Pro Arg Leu Val Val His
                325                 330                 335

Arg Ala Ser His Val Ser Arg Val Val Glu Asp Gly Glu Arg Leu Ser
            340                 345                 350

Val Glu Val Arg Asp Arg Thr Asp Gly Pro Asp Arg Thr Met Val Cys
        355                 360                 365

Asp Gly Leu Val Leu Ala Thr Gly Tyr Thr Arg Glu Leu His Pro Ala
    370                 375                 380

Val Phe Gly Glu Leu Thr Pro Leu Leu Ser Arg Asp Asp Ser Gly Glu
385                 390                 395                 400

Leu Leu Val Thr Ala Asp Cys Arg Val Arg Thr Asp Glu Arg Val Thr
                405                 410                 415

Ala Gly Phe Tyr Val Gln Gly Tyr Ala Glu Ser Ala Tyr Gly Ile Gly
            420                 425                 430

Asp Thr Leu Leu Ser Leu Leu Pro Phe Arg Ser Gln Gln Ile Val Asp
        435                 440                 445

Asp Ile Arg Gly Arg Leu Pro Ala Gly Arg Pro Val Ala Val Glu Glu
    450                 455                 460

Ser Ala Pro Tyr Pro Pro Ser His Tyr Val Glu Thr Asp Leu Asp Arg
465                 470                 475                 480

Ile Arg Ser Leu Met Glu Arg Phe Asn Phe Ala Thr Val Ile Ser Val
                485                 490                 495

Ala Arg Asp Ala Arg Val Leu Val Thr His Val Pro Leu Val Val Glu
            500                 505                 510

Arg Asp Arg Gly Gly Glu His Gly Met Leu Ile Gly His Leu Asp Arg
        515                 520                 525

Ser Asn Pro Gln Val Glu Leu Leu Arg Asp Arg Pro Val Thr Val Val
    530                 535                 540

Phe His Gly Pro Asp Ala Tyr Leu Ser Pro Asp Val Leu Lys Thr Asp
545                 550                 555                 560

Arg Leu Pro Thr Trp Asn Ser Met Ser Val His Val Arg Gly His Ala
                565                 570                 575

Arg Leu Phe Ser Gly Arg Asp Glu Leu Met Arg Val Phe Asn Gly Leu
            580                 585                 590

Cys Glu Gln Ala Glu Gly Glu Ser Gly Ser Tyr Trp Leu Arg Pro Asp
        595                 600                 605

Asp Thr Arg Ile Glu Gln Leu Arg Gly Gln Val Val Gly Phe Glu Val
    610                 615                 620

Asp Ile His Glu Leu Thr Gly Arg Phe Lys Leu Ser Gln Glu Leu Asp
625                 630                 635                 640

Glu Ala Asn Arg Glu Leu Ala Ala Ala Asp Met Ala Arg Gly Thr Ser
                645                 650                 655

Ala Glu Arg Gln Ala Phe Ile Glu Arg Ala Phe Asp Leu Gln Pro Arg
            660                 665                 670

Pro Asp Val Leu Gly Pro Pro Gly Gly Pro Gly Val Gly Gly Cys Pro
        675                 680                 685
```

Val Gly Gly Ala Arg Ala Ala Gly Gly Thr Thr Ala Val Ala Asp Asn
690 695 700

Glu Arg Glu Thr Ala Arg
705 710

<210> SEQ ID NO 172
<211> LENGTH: 627
<212> TYPE: PRT
<213> ORGANISM: Streptomyces sp. 2AW

<400> SEQUENCE: 172

Met Leu Asp Leu Leu Gly Ile Gly Phe Gly Pro Ser Asn Val Ala Leu
1 5 10 15

Ala Ala Ala Met Ala Glu Gly Gly Lys Pro Pro Arg Ala Leu Phe Leu
20 25 30

Glu Ala Lys Glu Arg Phe Gly Trp His Pro Gly Met Leu Leu Asp Gly
35 40 45

Ala Arg Met Gln Ile Ser Phe Leu Lys Asp Leu Val Thr Leu Arg Asn
50 55 60

Pro Glu Ser Pro Tyr Ser Phe Leu Ala Tyr Leu Lys Ala Lys Gly Arg
65 70 75 80

Leu Glu Glu Phe Ala Asn Leu Arg Glu Phe Tyr Pro Ser Arg Ile Glu
85 90 95

Phe Gln Asp Tyr Leu Arg Trp Val Ala Gly His Phe Glu His Gln Ala
100 105 110

Val Phe Gly Ala Arg Val Ala Ser Val Ser Pro Asp Phe Gly Ile Asp
115 120 125

Gly Met Ala Arg Ser Phe Thr Val Arg Ala Glu Leu Ala Asp Ser Gly
130 135 140

Glu Tyr Val Thr Tyr Gln Ala Arg Asn Val Val Tyr Ala Pro Gly Gly
145 150 155 160

Thr Pro Asn Arg Val Ala Gly Val Ala Pro Arg Asp Glu Arg Val Ile
165 170 175

His Thr Ala Glu Phe Leu Glu Arg Phe Pro Lys Ser Phe Pro Asp His
180 185 190

Ser Ala Asp Leu Ser Phe Ala Val Val Gly Gly Gly Gln Ser Ala Ala
195 200 205

Glu Ile Ile Glu Tyr Ile Leu Ala Lys Tyr Pro Leu Ser Arg Val His
210 215 220

Ala Ile Leu Pro Gly Tyr Ser Phe Arg Pro Ala Asp Asp Ser Pro Tyr
225 230 235 240

Ser Asn Glu Val Phe Phe Ser Ala Glu Val Asp Asp His Phe Thr Ala
245 250 255

His Asp Gln Ala Ala Arg Leu Ala Glu Ala Arg Ser Thr Asn Tyr Gly
260 265 270

Val Val Asp Leu Asp Leu Ile Glu Asp Leu Tyr Arg Met Gly Tyr Glu
275 280 285

Asp Gln Val Arg Gly Asn Val Pro Arg Leu Thr Phe Cys Arg Ser Ser
290 295 300

Arg Leu Leu Ser Ala Asp Ala Gly Pro Ser Gly Ile Glu Val Thr Val
305 310 315 320

Gly Gly Pro Glu Gly Ser Arg Ser Leu Asn Leu Asp Gly Leu Val Leu
325 330 335

Ala Thr Gly Tyr His Arg Glu Leu Asp Pro Glu Met Phe Arg Asp Val
340 345 350

Ile Pro His Leu Gln Arg Asn Glu Ser Gly Asn Phe Leu Val Ser Arg
        355                 360                 365

Ala Tyr Arg Ala Asp Ser Val Pro Glu Leu Thr Ala Gly Ile Tyr Phe
    370                 375                 380

Gln Gly Leu Thr Glu Leu Ser His Gly Ile Gly Asp Thr Leu Leu Ser
385                 390                 395                 400

Leu Leu Ser Phe Arg Ser Ala Glu Ile Ala Glu Asp Val Arg Lys Arg
                405                 410                 415

Ser Glu Val Pro Ser Ala Asp Glu Val Glu Tyr Pro Pro Ala Arg His
            420                 425                 430

Ile Glu Pro Tyr Arg Ala Ala Ile Leu Glu Thr Leu Gln Arg Phe Pro
        435                 440                 445

Leu Ala Thr Leu Ile Ser Ser Asp Asp Glu Ser Glu Val Phe Ala Thr
    450                 455                 460

His Leu Pro Leu Ile Leu Asp Arg Glu Arg Gly Glu Gln Gly Val Leu
465                 470                 475                 480

Phe Gly His Leu Asp Val Gly Asn Pro Gln Val Pro Asn Leu Asn Gly
                485                 490                 495

Arg Arg Val Leu Ala Val Phe His Gly Pro Asn Ser Tyr Ile Ser Pro
            500                 505                 510

Arg Thr Tyr Thr Thr Asp Gln Leu Pro Thr Trp Asn Tyr Val Ala Val
        515                 520                 525

His Val Arg Gly His Val Arg Val Leu Glu Asn Gln Asp Gln Val Val
    530                 535                 540

Ser Gly Leu Ala Ser Ile Ser Glu Lys Ala Asp Arg Ser Asp Gly Ala
545                 550                 555                 560

Tyr Arg Leu Asp Glu Asn Asp Ser Arg Ile Glu Lys Leu Ile Gly Gly
                565                 570                 575

Ile Val Gly Phe Glu Leu Asp Ile Glu Ser Leu Thr Gly Arg Phe Lys
            580                 585                 590

Leu Ser Gln Asp Arg Ser Asp Glu Asp Arg Lys Arg Ala Met Ala Val
        595                 600                 605

Leu Arg Glu Gly Ala Gly Asp Glu His His Asp Phe Val Ala Arg Ile
    610                 615                 620

His Gln Gln
625

<210> SEQ ID NO 173
<211> LENGTH: 703
<212> TYPE: PRT
<213> ORGANISM: Streptomyces sp. SolWspMP-5a-2

<400> SEQUENCE: 173

Met Pro Lys Lys Gly Gly Ala Val Thr Pro Arg Ala Gln Gly Leu Pro
1               5                   10                  15

Ser Gly Glu Ala Gly Pro Ala Pro Arg Arg Gly Thr Asp Pro Ala Asp
            20                  25                  30

Pro Leu Asp Leu Ile Gly Ile Gly Phe Gly Pro Ser Asn Leu Ala Leu
        35                  40                  45

Ala Ile Ala Ala Glu Glu Leu Asp Pro Ala Ala Asp Arg Leu Phe Leu
    50                  55                  60

Glu Arg Asn Ala Gly Val His Trp His Pro Gly Met Leu Leu Glu Gly
65                  70                  75                  80

Ala Arg Met Gln Ile Ser Tyr Leu Lys Asp Leu Val Ser Leu Arg Asn

-continued

```
                85                  90                  95

Leu Ala Ser Pro Tyr Thr Phe Leu Ser Tyr Leu Lys Ala Lys Gly Arg
            100                 105                 110

Leu Glu Lys Phe Ile Asn Ile Gly Val Thr Arg Pro Thr Arg Leu Glu
        115                 120                 125

Tyr Gln Asp Tyr Leu Thr Trp Val Ala Gly His Phe Ala Asp Val Val
    130                 135                 140

Arg Tyr Arg Ser Glu Val Val Ser Val Thr Pro Val Ser Gly Pro Gly
145                 150                 155                 160

Ser Thr Ala Leu Asp Leu Leu His Val Arg Val Arg Asp Thr Ala Thr
                165                 170                 175

Gly Thr Pro Tyr Ser Leu Tyr Ala Arg Asn Val Val His Ala Gly Gly
            180                 185                 190

Gly Thr Pro Arg Arg Gly Thr Pro Asp Arg Ile Cys Asp Thr Pro Ser
        195                 200                 205

Val Ile His Ser Ser Arg Phe Leu Pro Ala Phe Pro Arg Arg Phe Pro
    210                 215                 220

Asp His Asp Ala Ala Leu Asp Leu Gly Val Val Gly Asp Gly Gln Ser
225                 230                 235                 240

Ala Ala Glu Ile Ala Ala His Met Leu Thr His Tyr Pro Asp Ala Thr
                245                 250                 255

Val His Leu Phe Val Pro Gly Tyr Ala Leu Arg Ala Thr Asp Asn Asn
            260                 265                 270

Pro Phe Val Asn Glu Gln Phe Tyr Arg His Asn Ala Asp Ala Phe Tyr
        275                 280                 285

Ala Asp Glu Pro His Arg Arg Ala Leu Leu Arg Thr Glu Leu Arg Asn
    290                 295                 300

Thr Asn Tyr Gly Ala Val Glu Ala Gly Tyr Leu Asp Thr Leu Tyr Asp
305                 310                 315                 320

Ile Thr Tyr Ala Asp Glu Val Arg Gly Ala Pro Arg Leu Leu Val His
                325                 330                 335

Arg Gly Cys Asp Val Thr Arg Ile Thr Glu Asp Gly Pro Arg Leu Asp
            340                 345                 350

Val Leu Val Arg Asp Arg Thr Gly Gly Pro Asp Arg Thr Val Arg Cys
        355                 360                 365

Asp Gly Val Val Leu Ala Thr Gly Tyr Thr Arg Ala Leu Asp Pro Ala
    370                 375                 380

Val Phe Ala Gly Leu Asp Pro Leu Leu Arg Arg Asp Glu Ser Gly Ala
385                 390                 395                 400

Leu Leu Val Ser Ala Asp Cys Arg Val Asp Ala Glu Ala Pro Leu Thr
                405                 410                 415

Ala Gly Phe Tyr Val Gln Gly Tyr Ala Glu Gly Ala Tyr Gly Ile Gly
            420                 425                 430

Asp Thr Leu Leu Ser Leu Leu Pro Phe Arg Ser Gln Arg Ile Ile Asp
        435                 440                 445

Asp Leu Arg Ala Arg Arg Pro Glu Asp Leu Pro Ser Gly Gly Pro Tyr
    450                 455                 460

Pro Pro Asp His Tyr Val Glu Lys Asp Leu Glu Arg Val Arg Ala Val
465                 470                 475                 480

Met Glu Arg Phe Asn Phe Ala Thr Val Ile Ser Ala Asp Arg Asp Ala
                485                 490                 495

Arg Val Leu Val Thr His Val Pro Leu Val Val Glu Arg Asp Arg Gly
            500                 505                 510
```

```
Gly Glu His Gly Thr Leu Ile Gly His Leu Asp Arg Ser Asn Pro Gln
        515                 520                 525

Val Glu Leu Leu Arg Asp Arg Pro Val Thr Val Val Phe His Gly Pro
    530                 535                 540

Asn Ser Tyr Leu Ser Pro Asp Val Leu Thr Thr Asp Lys Leu Pro Thr
545                 550                 555                 560

Trp Asn Ser Met Ser Val His Val Arg Gly His Ala Arg Leu Phe Ser
                565                 570                 575

Gly Arg Asp Glu Leu Met Arg Val Phe Asn Gly Leu Cys Glu Gln Ala
            580                 585                 590

Glu Pro Gly Pro Gly Ser Tyr Arg Leu Arg Pro Asp Asp Glu Arg Ile
        595                 600                 605

Asp Gln Leu Leu Gly His Val Val Gly Phe Glu Val Asp Ile Gln Glu
    610                 615                 620

Val Thr Gly Arg Phe Lys Leu Ser Gln Asp Leu Asp Glu Asp Asn Arg
625                 630                 635                 640

Ala Leu Ala Ala Ala Asp Met Gln Arg Asp Leu Gly Glu Glu Arg Arg
                645                 650                 655

Thr Phe Val Ala Asp Val Phe Asp Leu Ala Pro Arg Pro Asp Gly Pro
            660                 665                 670

Glu Ala Gly Pro Arg Ala Cys Gly Cys Pro Leu Gly Gly Pro Pro Ala
        675                 680                 685

Gly Thr Gly Ala Ala Leu Ala Glu Glu Ala Gly Gln Thr Val Arg
    690                 695                 700


<210> SEQ ID NO 174
<211> LENGTH: 694
<212> TYPE: PRT
<213> ORGANISM: Streptomyces sp. ScaeMP-e83

<400> SEQUENCE: 174

Val Arg Asn Ala His Ala Thr His Pro Asp Asp Asp Pro Val Gly Thr
1               5                   10                  15

Thr Thr Glu Arg Pro Tyr Asp Leu Leu Gly Ile Gly Phe Gly Pro Ser
            20                  25                  30

Asn Leu Ala Leu Ala Val Cys Ala Arg Glu Gln Lys Leu Pro Leu Ser
        35                  40                  45

Cys Leu Phe Val Glu Arg Gln Asp Thr Val Ala Trp His Pro Gly Met
    50                  55                  60

Leu Ile Asp Gly Ala Arg Met Gln Ile Ser Phe Leu Lys Asp Leu Val
65                  70                  75                  80

Ser Leu Arg Asp Pro Ser Ser Pro Tyr Ser Phe Leu Arg Tyr Thr Lys
                85                  90                  95

Ala Lys Gly Arg Leu Glu Arg Phe Val Asn Leu Asn Glu Ser Arg Pro
            100                 105                 110

Thr Arg Ile Glu Tyr Asp Asp Tyr Leu Lys Trp Val Ala Gln Asp Phe
        115                 120                 125

Ala Asp Gln Val Arg Phe Gly Ser Gln Val Asp Arg Val Thr Pro Val
    130                 135                 140

Gln Gly Pro Asp Gly Gly Asp Leu Ser Leu Phe Arg Val Glu Thr Glu
145                 150                 155                 160

Asp Val Ala Thr Gly Arg Arg Ser Val His Tyr Ala Arg Asn Val Val
                165                 170                 175

His Ala Gly Gly Gly Arg Pro Pro Thr Arg Thr Ala Gly Val Ala Glu
```

```
            180                 185                 190

Val Pro Ser Val Val His Ser Ser Glu Phe Leu Thr Arg Phe Pro Gly
        195                 200                 205

Gln Phe Lys Asp His Asp Gly Ala Tyr Arg Phe Val Val Val Gly Gly
    210                 215                 220

Gly Gln Ser Ala Gly Glu Ile Ser Glu Tyr Leu Leu Asp His Tyr Asp
225                 230                 235                 240

Arg Ala Glu Val His Val Val Val Pro Gly Tyr Thr Leu Leu Pro Thr
                245                 250                 255

Asp Asn Ser Pro Phe Val Asn Glu Gln Phe Tyr Ser Gly Asn Ala Asp
            260                 265                 270

Ala Phe Tyr Arg Met Arg Pro Glu Gln Arg Ala Ala Val Ser Gly Arg
        275                 280                 285

Leu Arg Ala Ala Asn Tyr Gly Val Val Arg Glu Asp Leu Leu Glu Arg
    290                 295                 300

Leu Phe Asn Thr Asp Tyr Leu Asp Gln Val Lys Gly Arg Lys Arg Leu
305                 310                 315                 320

His Ile His Ser Phe Ser Arg Leu Ser Glu Val Arg Glu Asp Gly Glu
                325                 330                 335

Ala Leu Ala Val Thr Leu Gln Pro Arg Leu Asp Glu Gly Pro Glu Glu
            340                 345                 350

Ser Leu Arg Cys Asp Gly Val Val Leu Ala Thr Gly Tyr Asp Arg Ser
        355                 360                 365

Leu Asp Pro Ala Val Phe Gly Asp Val Leu Pro His Leu Thr Pro Gly
    370                 375                 380

Glu Gly Glu Gly Ala Ala Gly Val Val Leu Ser Arg His Tyr Arg Ala
385                 390                 395                 400

Arg Thr Ser Pro Glu Leu Arg Ala Gly Leu Tyr Leu Gln Gly Phe Gly
                405                 410                 415

Glu Ala Gln Phe Gly Leu Gly Asp Thr Leu Leu Ser Leu Leu Pro Phe
            420                 425                 430

Arg Ser Gln Glu Ile Val Glu Asp Ile Ala Asp Arg Val Pro Ala Ala
        435                 440                 445

Gly Val Gly Gly Cys Pro Val Met Ser Pro Tyr Gly Ser Gly Val Val
    450                 455                 460

Ser Thr Ser Pro His Gly Pro Val Pro Ser Ala Val Tyr Pro Pro Lys
465                 470                 475                 480

Trp Tyr Leu Glu His Asp Arg Glu Lys Leu Tyr Gly Leu Met Glu Arg
                485                 490                 495

Phe Arg Phe Ala Thr Leu Ile Ser Ala Arg Ser Gly Asp Glu Pro Phe
            500                 505                 510

Ala Thr His Leu Pro Leu Ile Leu Asp Arg Ser Arg Gly Ala Asn Gly
        515                 520                 525

Val Leu Phe Gly His Leu Asp Arg Gly Asn Glu His Ala Glu Leu Ile
    530                 535                 540

Asp Gly Arg His Met Leu Ala Val Phe His Gly Pro Asn Ala Tyr Met
545                 550                 555                 560

Pro Pro Gly Val Phe Glu Ser Asp Pro Leu Pro Thr Trp Asn Ser Met
                565                 570                 575

Ser Val His Val Arg Gly Arg Val Arg Ala Val Arg Asp Gln Asp Ala
            580                 585                 590

Leu Val Arg Gly Leu Ile Gly Ile Ala Glu Arg Ser Gln Pro Asp Asn
        595                 600                 605
```

Arg Leu Ala Ala Asp Asp Pro Arg Ile Asp Arg Ile Ile Gly Ser Ile
610 615 620

Val Gly Phe Glu Phe Glu Val Glu Glu Leu Val Gly Arg Phe Lys Leu
625 630 635 640

Ser Gln Asp Arg Asp Glu Thr Asp Arg Arg His Ala Ala Val Ala Leu
645 650 655

Ala Arg Ala Thr Glu Arg Gly Glu Arg Asp Phe Ile Glu Tyr Val Val
660 665 670

Gly Leu Ser Leu Ile Thr Glu Asp Asp Pro Arg Asp Leu Ala Gly Arg
675 680 685

Pro Leu Ser Pro Ser Pro
690

<210> SEQ ID NO 175
<211> LENGTH: 682
<212> TYPE: PRT
<213> ORGANISM: Mycobacterium sp. GA-0227b

<400> SEQUENCE: 175

Met Thr Ser Met Pro Pro Gly Glu Gly His Asp Ser Asp Leu Asp Phe
1 5 10 15

Ile Gly Ile Gly Phe Gly Pro Ser Asn Leu Ala Leu Ala Val Ala Ala
20 25 30

Asp Glu Ile Val Pro Asp Arg Lys Gly Leu Phe Phe Glu Arg Ser Gly
35 40 45

Thr Phe Gln Trp His Pro Gly Met Leu Leu Asp Gly Thr Lys Met Gln
50 55 60

Ile Ser Phe Leu Lys Asp Leu Ala Thr Leu Arg Asn Pro Ala Ser Arg
65 70 75 80

Tyr Thr Phe Leu Gln Tyr Ala Lys Ala Arg Gly Arg Leu Glu Gln Phe
85 90 95

Val Asn Leu His Glu Phe His Pro Ser Arg Leu Glu Tyr Asn Asp Tyr
100 105 110

Leu Arg Trp Val Ala Glu Phe Phe Thr Asp Arg Val Cys Tyr Asn Thr
115 120 125

Ile Val Thr Ala Val Val Pro Val Gly His Ser Pro Ser Ser Asn Gly
130 135 140

His Leu Thr Arg Phe Arg Val His Val Arg Asp Met Ala Thr Gly Ala
145 150 155 160

Glu Ser Cys Phe Phe Thr Ala Asn Val Ile Phe Gly Gly Gly Gly Val
165 170 175

Pro Arg Leu Leu Gly Ala Arg Ala Asp Ala Ser Ala Val Leu His Ser
180 185 190

Ser Ala Phe Leu Pro Asn Phe Thr Asn Arg Phe Asn Glu Ser Gln Lys
195 200 205

Pro Tyr Arg Phe Ala Val Ile Gly Asn Gly Gln Ser Ala Ala Glu Ile
210 215 220

Val Asp Tyr Leu Leu Asn His Tyr Pro Gly Ala Thr Ile His Leu Phe
225 230 235 240

Ile Ser Asp Cys Thr Leu Arg Ala Thr Asp His Ser Pro Phe Ile Asn
245 250 255

Glu His Phe Phe Ser Thr Ser Ala Ala Asp Phe Tyr Asn His Pro Pro
260 265 270

Ala Gln Arg Val Ala Leu Arg Ser Ala Leu Arg Ser Thr Asn Tyr Gly

-continued

```
        275                 280                 285

Val Val Asp Ala Asp Leu Leu Gln Lys Leu Tyr Gln Ile Thr Tyr Leu
    290                 295                 300

Asp Glu Val Lys Gly Cys Arg Arg Leu Leu Leu His Arg Glu Ser Arg
305                 310                 315                 320

Leu Ser Gln Ile Glu Glu Ile Asp Asp Gln Val Val Ala Ser Phe Glu
                325                 330                 335

Asp Arg Phe Ser Gly Asp Ser Ser Glu Phe His Phe Asp Gly Ala Val
            340                 345                 350

Leu Ala Thr Gly Tyr Glu Arg Val Leu Asp Ala Glu Val Phe Arg His
        355                 360                 365

Val Leu Pro His Val Leu Trp Asp Glu Ser Gly Ala Ile Ser Leu Thr
    370                 375                 380

Arg Ser Cys Arg Val Asn Thr Val Pro Ala Val Thr Ala Arg Leu Phe
385                 390                 395                 400

Leu Gln Gly Tyr Gly Glu Ala Trp Phe Gly Ile Gly Asp Thr Leu Leu
                405                 410                 415

Ser Leu Leu Pro Phe Arg Ala Gln Ala Ile Ala Gln Glu Ile Gly Asn
            420                 425                 430

Ala Pro Ser Gly Ala Pro Ile Arg Arg Lys Gln Arg Val His Gly Glu
        435                 440                 445

Tyr Pro Pro Lys Arg Tyr Leu Glu Thr Asp Pro Asp Arg Leu His Asp
    450                 455                 460

Val Ile Asn Arg Tyr Arg Phe Ala Thr Leu Val Ser Ala Ser Gly Val
465                 470                 475                 480

Asp Glu Pro Val Val Thr Gln Leu Pro Leu Thr Leu Asp Thr Ser Arg
                485                 490                 495

Gly Ser Leu Gly Val Leu Phe Gly His Met Asp Phe Ala Asn Pro His
            500                 505                 510

Thr Glu Leu Leu Asp Gly Arg Arg Val Leu Val Leu Phe His Gly Pro
        515                 520                 525

Asn Gly Tyr Ile Ser Pro His Val Tyr Glu Ser Ala Gln Leu Pro Thr
    530                 535                 540

Trp Asn Ser Ile Thr Val Glu Val Arg Gly Arg Ala Arg Ile Leu Arg
545                 550                 555                 560

Asp Lys Asp Ala Val Val Asn Gly Leu Arg Gly Ile Ala Ala Ala Ala
                565                 570                 575

Asp Pro Thr Pro Gly Gly Phe Arg Leu Thr Arg Glu Ala Ala Ser Asp
            580                 585                 590

Gln Arg Leu Phe Pro Leu Leu Val Gly Phe Glu Ile Asp Ile Asp Asp
        595                 600                 605

Met Arg Gly Arg Phe Lys Leu Ser Gln Glu Arg Asp Asp Arg Asp Arg
    610                 615                 620

Trp His Ala Ala His Ala Leu Ala Asn Gly Val Glu Gln Asp Asp Arg
625                 630                 635                 640

Asp Leu Ile Ser Ser Ile Val Gly Leu Pro Leu Asp Val Asp Glu Glu
                645                 650                 655

Pro Lys Pro Gln Gln Gln Ala Gln Ile His Gln Tyr Gly Asn Ala Pro
            660                 665                 670

Ala Asp Thr Ala Tyr Arg Arg Val Asp Gly
        675                 680
```

<210> SEQ ID NO 176

<211> LENGTH: 682
<212> TYPE: PRT
<213> ORGANISM: Mycobacterium sp. GA-1999

<400> SEQUENCE: 176

Met Thr Ser Met Pro Pro Gly Glu Gly His Asp Ser Asp Leu Asp Phe
1               5                   10                  15

Ile Gly Ile Gly Phe Gly Pro Ser Asn Leu Ala Leu Ala Val Ala Ala
            20                  25                  30

Asp Glu Ile Val Pro Asp Arg Lys Gly Leu Phe Phe Glu Arg Ser Gly
        35                  40                  45

Thr Phe Gln Trp His Pro Gly Met Leu Leu Asp Gly Thr Lys Met Gln
    50                  55                  60

Ile Ser Phe Leu Lys Asp Leu Ala Thr Leu Arg Asn Pro Ala Ser Arg
65                  70                  75                  80

Tyr Thr Phe Leu Gln Tyr Ala Lys Ala Arg Gly Arg Leu Glu Gln Phe
                85                  90                  95

Val Asn Leu His Glu Phe His Pro Ser Arg Leu Glu Tyr Asn Asp Tyr
            100                 105                 110

Leu Arg Trp Val Ala Glu Phe Phe Thr Asp Arg Val Cys Tyr Asn Thr
        115                 120                 125

Ile Val Thr Ala Val Val Pro Val Gly His Ser Pro Ser Ser Asn Gly
    130                 135                 140

His Leu Thr Arg Phe Arg Val His Val Arg Asp Met Ala Thr Gly Ala
145                 150                 155                 160

Glu Ser Cys Phe Phe Thr Ala Asn Val Ile Phe Gly Gly Gly Gly Val
                165                 170                 175

Pro Arg Leu Leu Gly Ala Arg Ala Asp Ala Ser Ala Val Leu His Ser
            180                 185                 190

Ser Ala Phe Leu Pro Asn Phe Thr Asn Arg Phe Asn Glu Ser Gln Lys
        195                 200                 205

Pro Tyr Arg Phe Ala Val Ile Gly Asn Gly Gln Ser Ala Ala Glu Ile
    210                 215                 220

Val Asp Tyr Leu Leu Asn His Tyr Pro Gly Ala Thr Ile His Leu Phe
225                 230                 235                 240

Ile Ser Asp Cys Thr Leu Arg Ala Thr Asp His Ser Pro Phe Ile Asn
                245                 250                 255

Glu His Phe Phe Ser Thr Ser Ala Ala Asp Phe Tyr Asn His Pro Pro
            260                 265                 270

Ala Gln Arg Val Ala Leu Arg Ser Ala Leu Arg Ser Thr Asn Tyr Gly
        275                 280                 285

Val Val Asp Ala Asp Leu Leu Gln Lys Leu Tyr Gln Ile Thr Tyr Leu
    290                 295                 300

Asp Glu Val Lys Gly Cys Arg Arg Leu Leu Leu His Arg Glu Ser Arg
305                 310                 315                 320

Leu Ser Gln Ile Glu Glu Ile Asp Asp Gln Val Val Ala Ser Phe Glu
                325                 330                 335

Asp Arg Phe Ser Gly Asp Ser Ser Glu Phe His Phe Asp Gly Ala Val
            340                 345                 350

Leu Ala Thr Gly Tyr Glu Arg Val Leu Asp Ala Glu Val Phe Arg His
        355                 360                 365

Val Leu Pro His Val Leu Trp Asp Glu Ser Gly Ala Ile Ser Leu Thr
    370                 375                 380

Arg Ser Cys Arg Val Asn Thr Val Pro Ala Val Thr Ala Arg Leu Phe

-continued

```
385                 390                 395                 400

Leu Gln Gly Tyr Gly Glu Ala Trp Phe Gly Ile Gly Asp Thr Leu Leu
                405                 410                 415

Ser Leu Leu Pro Phe Arg Ala Gln Ala Ile Ala Gln Glu Ile Gly Asn
            420                 425                 430

Ala Pro Ser Gly Ala Pro Ile Arg Arg Lys Gln Arg Val His Gly Glu
        435                 440                 445

Tyr Pro Pro Lys Arg Tyr Leu Glu Thr Asp Pro Asp Arg Leu His Asp
    450                 455                 460

Val Ile Asn Arg Tyr Arg Phe Ala Thr Leu Val Ser Ala Ser Gly Val
465                 470                 475                 480

Asp Glu Pro Val Val Thr Gln Leu Pro Leu Thr Leu Asp Thr Ser Arg
                485                 490                 495

Gly Ser Leu Gly Val Leu Phe Gly His Met Asp Phe Ala Asn Pro His
            500                 505                 510

Thr Glu Leu Leu Asp Gly Arg Arg Val Leu Val Leu Phe His Gly Pro
        515                 520                 525

Asn Gly Tyr Ile Ser Pro His Val Tyr Glu Ser Ala Gln Leu Pro Thr
    530                 535                 540

Trp Asn Ser Ile Thr Val Glu Val Arg Gly Arg Ala Arg Ile Leu Arg
545                 550                 555                 560

Asp Lys Asp Ala Val Val Asn Gly Leu Arg Gly Ile Ala Ala Ala Ala
                565                 570                 575

Asp Pro Thr Pro Gly Gly Phe Arg Leu Thr Arg Glu Ala Ala Ser Asp
            580                 585                 590

Gln Arg Leu Phe Pro Leu Leu Val Gly Phe Glu Ile Asp Ile Asp Asp
        595                 600                 605

Met Arg Gly Arg Phe Lys Leu Ser Gln Glu Arg Asp Asp Arg Asp Arg
    610                 615                 620

Trp His Ala Ala His Ala Leu Ala Asn Gly Val Glu Gln Asp Asp Arg
625                 630                 635                 640

Asp Leu Ile Ser Ser Ile Val Gly Leu Pro Leu Asp Val Asp Glu Glu
                645                 650                 655

Pro Lys Pro Gln Gln Gln Ala Gln Ile His Gln Tyr Gly Asn Ala Pro
            660                 665                 670

Ala Asp Thr Ala Tyr Arg Arg Val Asp Gly
        675                 680
```

<210> SEQ ID NO 177
<211> LENGTH: 7041
<212> TYPE: DNA
<213> ORGANISM: Artificial Sequence
<220> FEATURE:
<223> OTHER INFORMATION: Synthetic plasmid

<400> SEQUENCE: 177

```
tatggctgcc gcgcggcacc aggccgctgc tgtgatgatg atgatgatgg ctgctgccca     60

tggtatatct ccttcttaaa gttaaacaaa attatttcta gaggggaatt gttatccgct    120

cacaattccc ctatagtgag tcgtattaat ttcgcgggat cgagatctcg atcctctacg    180

ccggacgcat cgtggccggc atcaccggcg ccacaggtgc ggttgctggc gcctatatcg    240

ccgacatcac cgatggggaa gatcgggctc gccacttcgg gctcatgagc gcttgtttcg    300

gcgtgggtat ggtggcaggc cccgtggccg ggggactgtt gggcgccatc tccttgcatg    360

caccattcct tgcggcggcg gtgctcaacg gcctcaacct actactgggc tgcttcctaa    420
```

```
tgcaggagtc gcataaggga gagcgtcgag atcccggaca ccatcgaatg gcgcaaaacc    480
tttcgcggta tggcatgata gcgcccggaa gagagtcaat tcagggtggt gaatgtgaaa    540
ccagtaacgt tatacgatgt cgcagagtat gccggtgtct cttatcagac cgtttcccgc    600
gtggtgaacc aggccagcca cgtttctgcg aaaacgcggg aaaaagtgga agcggcgatg    660
gcggagctga attacattcc caaccgcgtg gcacaacaac tggcgggcaa acagtcgttg    720
ctgattggcg ttgccacctc cagtctggcc ctgcacgcgc cgtcgcaaat tgtcgcggcg    780
attaaatctc gcgccgatca actgggtgcc agcgtggtgg tgtcgatggt agaacgaagc    840
ggcgtcgaag cctgtaaagc ggcggtgcac aatcttctcg cgcaacgcgt cagtgggctg    900
atcattaact atccgctgga tgaccaggat gccattgctg tggaagctgc ctgcactaat    960
gttccggcgt tatttcttga tgtctctgac cagacaccca tcaacagtat tattttctcc   1020
catgaagacg gtacgcgact gggcgtggag catctggtcg cattgggtca ccagcaaatc   1080
gcgctgttag cgggcccatt aagttctgtc tcggcgcgtc tgcgtctggc tggctggcat   1140
aaatatctca ctcgcaatca aattcagccg atagcggaac gggaaggcga ctggagtgcc   1200
atgtccggtt ttcaacaaac catgcaaatg ctgaatgagg gcatcgttcc cactgcgatg   1260
ctggttgcca acgatcagat ggcgctgggc gcaatgcgcg ccattaccga gtccgggctg   1320
cgcgttggtg cggatatctc ggtagtggga tacgacgata ccgaagacag ctcatgttat   1380
atcccgccgt taaccaccat caaacaggat tttcgcctgc tggggcaaac cagcgtggac   1440
cgcttgctgc aactctctca gggccaggcg gtgaagggca atcagctgtt gcccgtctca   1500
ctggtgaaaa gaaaaaccac cctggcgccc aatacgcaaa ccgcctctcc ccgcgcgttg   1560
gccgattcat taatgcagct ggcacgacag gtttcccgac tggaaagcgg gcagtgagcg   1620
caacgcaatt aatgtaagtt agctcactca ttaggcaccg ggatctcgac cgatgccctt   1680
gagagccttc aacccagtca gctccttccg gtgggcgcgg ggcatgacta tcgtcgccgc   1740
acttatgact gtcttcttta tcatgcaact cgtaggacag gtgccggcag cgctctgggt   1800
cattttcggc gaggaccgct ttcgctggag cgcgacgatg atcggcctgt cgcttgcggt   1860
attcggaatc ttgcacgccc tcgctcaagc cttcgtcact ggtcccgcca ccaaacgttt   1920
cggcgagaag caggccatta tcgccggcat ggcggccgac gcgctgggct acgtcttgct   1980
ggcgttcgcg acgcgaggct ggatggcctt ccccattatg attcttctcg cttccggcgg   2040
catcgggatg cccgcgttgc aggccatgct gtccaggcag gtagatgacg accatcaggg   2100
acagcttcaa ggatcgctcg cggctcttac cagcctaact tcgatcactg gaccgctgat   2160
cgtcacggcg atttatgccg cctcggcgag cacatggaac gggttggcat ggattgtagg   2220
cgccgcccta taccttgtct gcctccccgc gttgcgtcgc ggtgcatgga gccgggccac   2280
ctcgacctga atggaagccg gcggcacctc gctaacggat tcaccactcc aagaattgga   2340
gccaatcaat tcttgcggag aactgtgaat gcgcaaacca acccttggca gaacatatcc   2400
atcgcgtccg ccatctccag cagccgcacg cggcgcatct cgggcagcgt tgggtcctgg   2460
ccacgggtgc gcatgatcgt gctcctgtcg ttgaggaccc ggctaggctg gcggggttgc   2520
cttactggtt agcagaatga atcaccgata cgcgagcgaa cgtgaagcga ctgctgctgc   2580
aaaacgtctg cgacctgagc aacaacatga atggtcttcg gtttccgtgt ttcgtaaagt   2640
ctggaaacgc ggaagtcagc gccctgcacc attatgttcc ggatctgcat cgcaggatgc   2700
tgctggctac cctgtggaac acctacatct gtattaacga agcgctggca ttgaccctga   2760
```

-continued

```
gtgatttttc tctggtcccg ccgcatccat accgccagtt gtttaccctc acaacgttcc   2820
agtaaccggg catgttcatc atcagtaacc cgtatcgtga gcatcctctc tcgtttcatc   2880
ggtatcatta cccccatgaa cagaaatccc ccttacacgg aggcatcagt gaccaaacag   2940
gaaaaaaccg cccttaacat ggcccgcttt atcagaagcc agacattaac gcttctggag   3000
aaactcaacg agctggacgc ggatgaacag gcagacatct gtgaatcgct tcacgaccac   3060
gctgatgagc tttaccgcag ctgcctcgcg cgtttcggtg atgacggtga aaacctctga   3120
cacatgcagc tcccggagac ggtcacagct tgtctgtaag cggatgccgg gagcagacaa   3180
gcccgtcagg gcgcgtcagc gggtgttggc gggtgtcggg gcgcagccat gacccagtca   3240
cgtagcgata gcggagtgta tactggctta actatgcggc atcagagcag attgtactga   3300
gagtgcacca tatatgcggt gtgaaatacc gcacagatgc gtaaggagaa aataccgcat   3360
caggcgctct tccgcttcct cgctcactga ctcgctgcgc tcggtcgttc ggctgcggcg   3420
agcggtatca gctcactcaa aggcggtaat acggttatcc acagaatcag gggataacgc   3480
aggaaagaac atgtgagcaa aaggccagca aaaggccagg aaccgtaaaa aggccgcgtt   3540
gctggcgttt ttccataggc tccgcccccc tgacgagcat cacaaaaatc gacgctcaag   3600
tcagaggtgg cgaaacccga caggactata aagataccag gcgtttcccc ctggaagctc   3660
cctcgtgcgc tctcctgttc cgaccctgcc gcttaccgga tacctgtccg cctttctccc   3720
ttcgggaagc gtggcgcttt ctcatagctc acgctgtagg tatctcagtt cggtgtaggt   3780
cgttcgctcc aagctgggct gtgtgcacga accccccgtt cagcccgacc gctgcgcctt   3840
atccggtaac tatcgtcttg agtccaaccc ggtaagacac gacttatcgc cactggcagc   3900
agccactggt aacaggatta gcagagcgag gtatgtaggc ggtgctacag agttcttgaa   3960
gtggtggcct aactacggct acactagaag gacagtattt ggtatctgcg ctctgctgaa   4020
gccagttacc ttcggaaaaa gagttggtag ctcttgatcc ggcaaacaaa ccaccgctgg   4080
tagcggtggt ttttttgttt gcaagcagca gattacgcgc agaaaaaaag gatctcaaga   4140
agatcctttg atcttttcta cggggtctga cgctcagtgg aacgaaaact cacgttaagg   4200
gattttggtc atgagattat caaaaaggat cttcacctag atccttttaa attaaaaatg   4260
aagttttaaa tcaatctaaa gtatatatga gtaaacttgg tctgacagtt accaatgctt   4320
aatcagtgag gcacctatct cagcgatctg tctatttcgt tcatccatag ttgcctgact   4380
ccccgtcgtg tagataacta cgatacggga gggcttacca tctggcccca gtgctgcaat   4440
gataccgcga gacccacgct caccggctcc agatttatca gcaataaacc agccagccgg   4500
aagggccgag cgcagaagtg gtcctgcaac tttatccgcc tccatccagt ctattaattg   4560
ttgccgggaa gctagagtaa gtagttcgcc agttaatagt ttgcgcaacg ttgttgccat   4620
tgctgcaggc atcgtggtgt cacgctcgtc gtttggtatg gcttcattca gctccggttc   4680
ccaacgatca aggcgagtta catgatcccc catgttgtgc aaaaaagcgg ttagctcctt   4740
cggtcctccg atcgttgtca gaagtaagtt ggccgcagtg ttatcactca tggttatggc   4800
agcactgcat aattctctta ctgtcatgcc atccgtaaga tgcttttctg tgactggtga   4860
gtactcaacc aagtcattct gagaatagtg tatgcggcga ccgagttgct cttgcccggc   4920
gtcaacacgg gataataccg cgccacatag cagaacttta aaagtgctca tcattggaaa   4980
acgttcttcg gggcgaaaac tctcaaggat cttaccgctg ttgagatcca gttcgatgta   5040
acccactcgt gcacccaact gatcttcagc atcttttact ttcaccagcg tttctgggtg   5100
agcaaaaaca ggaaggcaaa atgccgcaaa aaagggaata agggcgacac ggaaatgttg   5160
```

-continued aatactcata ctcttccttt ttcaatatta ttgaagcatt tatcagggtt attgtctcat 5220
gagcggatac atatttgaat gtatttagaa aaataaacaa ataggggttc cgcgcacatt 5280
tccccgaaaa gtgccacctg acgtctaaga aaccattatt atcatgacat taacctataa 5340
aaataggcgt atcacgaggc cctttcgtct tcaagaattc tcatgtttga cagcttatca 5400
tcgataagct ttaatgcggt agtttatcac agttaaattg ctaacgcagt caggcaccgt 5460
gtatgaaatc taacaatgcg ctcatcgtca tcctcggcac cgtcaccctg gatgctgtag 5520
gcataggctt ggttatgccg gtactgccgg gcctcttgcg ggatatccgg atatagttcc 5580
tcctttcagc aaaaaacccc tcaagacccg tttagaggcc ccaaggggtt atgctagtta 5640
ttgctcagcg gtggcagcag ccaactcagc ttcctttcgg gctttgttag cagccggatc 5700
ctcagcccct gttccccgct gctgccttgc ttccggtgga gcggtccggg tcgcaccggc 5760
cgccggtgat cgaccgggcg atctcgcccg cgcggaccgc caccatggac agcagggtgg 5820
aggcgatgcc gtgggtcgcc tcggtggcgc cctggacgta gatgccgcac cggaaatccc 5880
cggtggtgcc gagccggtag tcgcggccga tcagcaactc cccgcctcg tcccggcgga 5940 gggcgccgga gacgccgccg agcagttcgg ccgggtcggt ggagtcgtac ccggtggcgt 6000
acacgaccag gtcggcgtcc aggtcggtgt gttcgcccgt gggcaggaac tccacgcgta 6060
cggcggcgga ttcctggcgc ggttcgacgg acaccaggcg ggaggcgttc atcacccgca 6120
gccgcggggc gccggacacc ttctgctcgt actggcggcg gtagaggccc tggaggacgt 6180
cctcgtcgac gacggcgtag ttggtgccgc cgtggtagcg catgatggcc tgcttgacct 6240
cgggcggggc gaagtagaag tcgtccacgg cggccgggtc gaagacgcgg ttggcgaacg 6300
ggctggagtc ggcgacgctg tagccgtagc gggcgaacac cgcgcacacc tcggcctgcg 6360
ggtagcggtc catgaggtgc gcggcgacct cggccgcgct ctggccggcg ccgaccacga 6420
cggcccggcg gggcgggcgt tcgtcgaacg cgggcagccg gtgcagcaac tgggagctgt 6480
gccagacgcg ttcgccggtc tccgcgccct cgggcagccg gggcgcaggg ccggaggcga 6540
ggacgaggtt tctggtccgg gcgaccaccc ggtccccggc gagcacgtcg agcgcgacga 6600
cctcaccggc ttcggtcacc ggccgcacac cggtggcctc cacgccgtac tcgaccaggt 6660
ggttcagccg gtcggcggcc cactggaggt agtcgtggta ctcgatccgg gagggcagca 6720
gggtgtgctg gttgatgaag tcgaccagcc ggtccttctc ctggagatag gacaggaatc 6780
cgaaatcact ggtgggattg cgcatcgtgg cgatgtcctt gagaaaggac acctggagcg 6840
aggagccccc caggagcatc cccgatgcc agccgaattc cttctgcttc tccaggaaaa 6900
gggccttccc ggcggcttcg gattcatgga gcgccaccgc cagggcgaga ttcgcggcac 6960
cgaatccgat tccggtgacg tccagtactt ctgattccgg gctctgctgc gcagtggatg 7020
attgctctgc gagccgggtc a 7041

<210> SEQ ID NO 178
<211> LENGTH: 7426
<212> TYPE: DNA
<213> ORGANISM: Artificial Sequence
<220> FEATURE:
<223> OTHER INFORMATION: Synthetic plasmid

<400> SEQUENCE: 178
gtaggagggc gtggatatgt cctgcgggta aactatagtc gttgagagga ggagtctgac 60
tcctgttgat agatccagta atgacctcag aactccatct ggatttgttc agaacgctcg 120

-continued gttgccgccg ggcgtttttt attggtgaga ataggtcttg acggctggcg agaggtgcgg 180
ggaggatctg accgacgcgg tccacacgtg gcaccgcgat gctgttgtgg gcacaatcgt 240
gccggttggt aggatccggt taattaagca gtaccagatc tgactgagtg accaaaggag 300
gcggacatat gacccggctc gcagagcaat catccactgc gcagcagagc ccggaatcag 360
aagtactgga cgtcaccgga atcggattcg gtgccgcgaa tctcgccctg gcggtggcgc 420
tccatgaatc cgaagccgcc gggaaggccc ttttcctgga gaagcagaag gaattcggct 480
ggcatcgggg gatgctcctg gggggctcct cgctccaggt gtcctttctc aaggacatcg 540
ccacgatgcg caatcccacc agtgatttcg gattcctgtc ctatctccag gagaaggacc 600
ggctggtcga cttcatcaac cagcacaccc tgctgccctc ccggatcgag taccacgact 660
acctccagtg ggccgccgac cggctgaacc acctggtcga gtacggcgtg gaggccaccg 720
gtgtgcggcc ggtgaccgaa gccggtgagg tcgtcgcgct cgacgtgctc gccggggacc 780
gggtggtcgc ccggaccaga aacctcgtcc tcgcctccgg cctgcgcccc cggctgcccg 840
agggcgcgga gaccggcgaa cgcgtctggc acagctccca gttgctgcac cggctgcccg 900
cgttcgacga acgcccgccc cgccgggccg tcgtggtcgg cgccggccag agcgcggccg 960
aggtcgccgc gcacctcatg gaccgctacc cgcaggccga ggtgtgcgcg gtgttcgccc 1020
gctacggcta cagcgtcgcc gactccagcc cgttcgccaa ccgcgtcttc gacccggccg 1080
ccgtggacga cttctacttc gccccgcccg aggtcaagca ggccatcatg cgctaccacg 1140
gcggcaccaa ctacgccgtc gtcgacgagg acgtcctcca gggcctctac cgccgccagt 1200
acgagcagaa ggtgtccggc gccccgcggc tgcgggtgat gaacgcctcc cgcctggtgt 1260
ccgtcgaacc gcgccaggaa tccgccgccg tacgcgtgga gttcctgccc acgggcgaac 1320
acaccgacct ggacgccgac ctggtcgtgt acgccaccgg gtacgactcc accgacccgg 1380
ccgaactgct cggcggcgtc tccggcgccc tccgccggga cgaggcgggg gagttgctga 1440
tcggccgcga ctaccggctc ggcaccaccg ggatttccgg gtgcggcatc tacgtccagg 1500
gcgccaccga ggcgacccac ggcatcgcct ccaccctgct gtccatggtg gcggtccgcg 1560
cgggcgagat cgcccggtcg atcaccggcg gccggtgcga cccggaccgc tccaccggaa 1620
gcaaggcagc agcggggaac aggggctgag gatccccggg taccttcgaa aaaaaaaggc 1680
tccaaaagga gcctttaatt gttcctccag accttacttg accggcgctc actgcccgct 1740
ttccagtcgg gaaacctgtc gtgccagctg cattaatgaa tcggccaacg cgcggggaga 1800
ggcggtttgc gtattgggcg ctcttccgct tcctcgctca ctgactcgct gcgctcggtc 1860
gttcggctgc ggcgagcggt atcagctcac tcaaaggcgg taatacggtt atccacagaa 1920
tcaggggata acgcaggaaa gaacatgtga gcaaaaggcc agcaaaaggc caggaaccgt 1980
aaaaaggccg cgttgctggc gtttttccat aggctccgcc cccctgacga gcatcacaaa 2040
aatcgacgct caagtcagag gtggcgaaac ccgacaggac tataaagata ccaggcgttt 2100
ccccctggaa gctccctcgt gcgctctcct gttccgaccc tgccgcttac cggatacctg 2160
tccgcctttc tcccttcggg aagcgtggcg ctttctcata gctcacgctg taggtatctc 2220
agttcggtgt aggtcgttcg ctccaagctg ggctgtgtgc acgaaccccc cgttcagccc 2280
gaccgctgcg ccttatccgg taactatcgt cttgagtcca acccggtaag acacgactta 2340
tcgccactgg cagcagccac tggtaacagg attagcagag cgaggtatgt aggcggtgct 2400
acagagttct tgaagtggtg gcctaactac ggctacacta gaagaacagt atttggtatc 2460
tgcgctctgc tgaagccagt taccttcgga aaaagagttg gtagctcttg atccggcaaa 2520

-continued caaaccaccg ctggtagcgg tggttttttt gtttgcaagc agcagattac gcgcagaaaa 2580
aaaggatctc aagaagatcc tttgatcttt tctacggggt ctgacgctca gtggaacgaa 2640
aactcacgtt aagggatttt ggtcatgaga ttatcaaaaa ggatcttcac ctagatcctt 2700
ttggttcatg tgcagctcca ctgctttaga ctctacatct gtatgaagtc ttcagatcct 2760
ctacgccgga cgcatcgtgg ccggatctaa aaaaaagccc gctcattagg cgggctgaca 2820
gttaccaatg cttaatcagt gaggcaccta tctcagcgat ctgtctattt cgttcatcca 2880
tagttgcctg actccccgtc gtgtagataa ctacgatacg ggagggctta ccatctggcc 2940
ccagtgctgc aatgataccg cgagacccac gctcaccggc tccagattta tcagcaataa 3000
accagccagc cggaagggcc gagcgcagaa gtggtcctgc aactttatcc gcctccatcc 3060
agtctattaa ttgttgccgg gaagctagag taagtagttc gccagttaat agtttgcgca 3120
acgttgttgc cattgctaca ggcatcgtgg tgtcacgctc gtcgtttggt atggcttcat 3180
tcagctccgg ttcccaacga tcaaggcgag ttacatgatc ccccatgttg tgcaaaaaag 3240
cggttagctc cttcggtcct ccgatcgttg tcagaagtaa gttggccgca gtgttatcac 3300
tcatggttat ggcagcactg cataattctc ttactgtcat gccatccgta agatgctttt 3360
ctgtgactgg tgagtactca accaagtcat tctgagaata gtgtatgcgg cgaccgagtt 3420
gctcttgccc ggcgtcaata cgggataata ccgcgccaca tagcagaact ttaaaagtgc 3480
tcatcattgg aaaacgttct tcggggcgaa aactctcaag gatcttaccg ctgttgagat 3540
ccagttcgat gtaacccact cgtgcaccca actgatcttc agcatctttt actttcacca 3600
gcgtttctgg gtgagcaaaa acaggaaggc aaaatgccgc aaaaaaggga ataagggcga 3660
cacggaaatg ttgaatactc atactcttcc tttttcaata ttattgaagc atttatcagg 3720
gttattgtct catgagcgga tacatatttg aatgtattta gaaaaataaa caaatagggg 3780
ttccgcgcac atttccccga aaagtgccac ctggcgcgcc acaaaacagc agggaagcag 3840
cgcttttccg ctgcataacc ctgcttcggg gtcattatag cgatttttc ggtatatcca 3900 tcctttttcg cacgatatac aggattttgc caaagggttc gtgtagactt tccttggtgt 3960
atccaacggc gtcagccggg caggataggt gaagtaggcc cacccgcgag cgggtgttcc 4020
ttcttcactg tcccttattc gcacctggcg gtgctcaacg ggaatcctgc tctgcgaggc 4080
tggccggcta ccgccggcgt aacagatgag ggcaagcgga tggctgatga aaccaagcca 4140
accaggaagg gcagcccacc tatcaaggtg tactgccttc cagacgaacg aagagcgatt 4200
gaggaaaagg cggcggcggc cggcatgagc ctgtcggcct acctgctggc cgtcggccag 4260
ggctacaaaa tcacgggcgt cgtggactat gagcacgtcg gcgcgcctct agtatgcagg 4320
agtggggagg cacgatggcc gctttggtcg acctcaacga gacgatgaag ccgtggaacg 4380
acaccacccc ggcggccctg ctggaccaca cccggcacta caccttcgac gtctgatcat 4440
cactgacgaa tcgaggtcga ggaaccgagc gtccgaggaa cagaggcgct tatcggttgg 4500
ccgcgagatt cctgtcgatc ctctcgtgca gcgcgattcc gagggaaacg gaaacgttga 4560
gagactcggt ctggctcatc atggggatgg aaaccgaggc ggaagacgcc tcctcgaaca 4620
ggtcggaagg cccacccttt tcgctgccga acagcaaggc cagccgatcc ggattgtccc 4680
cgagttcctt cacggaaatg tcgccatccg ccttgagcgt catcagctgc ataccgctgt 4740
cccgaatgaa ggcgatggcc tcctcgcgac cggagagaac gacgggaagg gagaagacgt 4800
aacctcggct ggccctttgg agacgccggt ccgcgatgct ggtgatgtca ctgtcgacca 4860

-continued

```
ggatgatccc cgacgctccg agcgcgagcg acgtgcgtac tatcgcgccg atgttcccga   4920
cgatcttcac cccgtcgaga acgacgacgt ccccacgccg gctcgcgata tcgccgaacc   4980
tggccgggcg agggacgcgg gcgatgccga atgtcttggc cttccgctcc cccttgaaca   5040
actggttgac gatcgaggag tcgatgaggc ggaccggtat gttctgccgc ccgcacagat   5100
ccagcaactc agatggaaaa ggactgctgt cgctgccgta gacctcgatg aactccaccc   5160
cggccgcgat gctgtgcatg aggggctcga cgtcctcgat caacgttgtc tttatgttgg   5220
atcgcgacgg cttggtgaca tcgatgatcc gctgcaccgc gggatcggac ggatttgcga   5280
tggtgtccaa ctcagtcatg gtcgtcctac cggctgctgt gttcagtgac gcgattcctg   5340
gggtgtgaca ccctacgcga cgatggcgga tggctgccct gaccggcaat caccaacgca   5400
aggggaagac tacgccttcc actagaccgg tcgacctgca ggcctgctgg cgccggacgg   5460
ggcttcagac gtttcgggtg ctgggttgtt gtctctggac agtgatccat gggaaactac   5520
tcagcaccac caatgttccc aaaagaaagc gcaggtcagc gcccatgagc caatatctag   5580
gcatgtcgcc cttcatcgct cccgaggtcc ctgagcacct tctcgacact gttcgcgtct   5640
tcctgtacgc gcgtcagtct aagggccggt ccgacggctc agacgtgtcg accgaagcac   5700
agctcgcggc cggtcgtgcg ttggtcgcgt ctcgcaacgc ccagggggt gcgcgctggg    5760
tcgtggcagg tgagttcgtg gacgtcgggc gctccggctg ggacccgaac gtgacccgtg   5820
ccgacttcga gcgcatgatg ggcgaagtcc gcgccggcga aggtgacgtt gtcgttgtga   5880
atgagctttc ccggctcact cgcaagggcg cccatgacgc gctcgaaatc gacaacgaat   5940
tgaagaagca cggcgtgcgc ttcatgtcgg ttcttgagcc gttccttgac acgtctaccc   6000
ctatcggcgt cgccattttc gcgctgatcg ctgcccttgc gaaacaggac agtgacctga   6060
aggcggagcg cctgaagggt gcgaaagacg agattgccgc gctgggtggc gttcactcgt   6120
cttccgcccc gttcggaatg cgcgccgtgc gcaagaaggt cgataatctc gtgatctccg   6180
ttcttgagcc ggacgaagac aacccggatc acgtcgagct agttgagcgc atggcgaaaa   6240
tgtcgttcga gggcgtgtcc gacaacgcca ttgcaacgac cttcgagaag gaaaagatcc   6300
cgtcgcccgg aatggctgag agacgcgcca cggaaaagcg tcttgcgtcc atcaaggcac   6360
gtcgcctgaa cggcgctgaa aagccgatca tgtggcgcgc tcaaacggtc cgatggattc   6420
tcaaccatcc cgcaatcggc ggtttcgcat tcgagcgtgt gaagcacggt aaggcgcaca   6480
tcaacgtcat acggcgcgac cccggcggca agccgctaac gccccacacg ggcattctca   6540
gcggctcgaa gtggcttgag cttcaagaga agcgttccgg gaagaatctc agcgaccgga   6600
agcctggggc cgaagtcgaa ccgacgcttc tgagcgggtg gcgtttcctg ggtgccgaa    6660
tctgcggcgg ctcaatgggt cagtcccagg gtggccgtaa gcgcaacggc gaccttgccg   6720
aaggcaatta catgtgcgcc aacccgaagg ggcacggcgg cttgtcggtc aagcgcagcg   6780
aactggacga gttcgttgct tcgagggtgt gggcacggct ccgcacagcc gacatggaag   6840
atgaacacga tcaggcatgg attgccgccg ctgcggagcg cttcgccctt cagcacgacc   6900
tagcgggggt ggccgatgag cggcgcgaac aacaggcgca cctagacaac gtgcggcgct   6960
ccatcaagga ccttcaggcg gaccgtaagg ccggtctgta cgtcgggcgt gaagagctgg   7020
aaacgtggcg ctcaacggtg ctgcaatacc ggtcctacga agcggagtgc acgacccgac   7080
tcgctgagct tgacgagaag atgaacggca gcacccgcgt tccgtctgag tggttcagcg   7140
gcgaagaccc gacggccgaa gggggcatct gggcaagctg ggacgtgtac gagcgtcggg   7200
agttcctgag cttcttcctt gactccgtca tggtcgaccg gggcgccac cctgagacga    7260
```

agaaatacat ccccctgaag gaccgtgtga cgctcaagtg ggcggagctg ctgaaggagg 7320
aagacgaagc gagcgaagcc actgagcggg agcttgcggc gctgtaggta caatcataat 7380
gaggctagac tacagacgcg aagaatctcg tgctttcagc ttcgat 7426

<210> SEQ ID NO 179
<211> LENGTH: 6396
<212> TYPE: DNA
<213> ORGANISM: Artificial Sequence
<220> FEATURE:
<223> OTHER INFORMATION: Synthetic plasmid

<400> SEQUENCE: 179
tatgtacgaa cgtccgctgt accgggagga ttgcgacggc gtcgtcctgg cgtttctgcg 60
acacaaccca ctggcaatgg tcgtcacctc gcacgacgac gtcccggtgg ccacccacgc 120
gccggtgctg ttccggcacg gacccgacgg cgccgacgcc gaggccgtcg ccgcgggcac 180
cgtcccgctc gccggctcca ccctgatcgg ccacatgaac gtcgagaacc cgcagtggcg 240
ccggatgcgc tccggcgacc gggcgctcat cgtcttccag ggcccgcacg gctatgtctc 300
gccgacggtc tacggggtca cgcccgcggc ccccacctgg gacttcatcg ccgtccacgt 360
gaacggcaca gtggagccca ccgccgaccc cgccgccgtg ctggacatcg tctccgacac 420
cgcccggcgg ctggagtccg gcttcgggcg cggctgggac caggagtcct ccctcgacta 480
cttccgccag atcgcgcccg gcgtgggcgc cttcaccctg cgggtcgatt ccgtgcagac 540
gatgttcaag ctcagccagg agaagcccgc cccgatgcgg cggcgcgtgg tcgagcagtt 600
cgaagcaagc gagtccggca cccaccgcgc cctggccagc gtgatgcgcg accgcggact 660
caccgaagcc gacgaggagc gggagacagc cggatgagga tccggctgct aacaaagccc 720
gaaaggaagc tgagttggct gctgccaccg ctgagcaata actagcataa ccccttgggg 780
cctctaaacg ggtcttgagg ggttttttgc tgaaaggagg aactatatcc ggatatcccg 840
caagaggccc ggcagtaccg gcataaccaa gcctatgcct acagcatcca gggtgacggt 900
gccgaggatg acgatgagcg cattgttaga tttcatacac ggtgcctgac tgcgttagca 960
atttaactgt gataaactac cgcattaaag cttatcgatg ataagctgtc aaacatgaga 1020
attcttgaag acgaaagggc ctcgtgatac gcctattttt ataggttaat gtcatgataa 1080
taatggtttc ttagacgtca ggtggcactt ttcggggaaa tgtgcgcgga acccctattt 1140
gtttattttt ctaaatacat tcaaatatgt atccgctcat gagacaataa ccctgataaa 1200
tgcttcaata atattgaaaa aggaagagta tgagtattca acatttccgt gtcgccctta 1260
ttcccttttt tgcggcattt tgccttcctg tttttgctca cccagaaacg ctggtgaaag 1320
taaaagatgc tgaagatcag ttgggtgcac gagtgggtta catcgaactg gatctcaaca 1380
gcggtaagat ccttgagagt tttcgccccg aagaacgttt tccaatgatg agcactttta 1440
aagttctgct atgtggcgcg gtattatccc gtgttgacgc cgggcaagag caactcggtc 1500
gccgcataca ctattctcag aatgacttgg ttgagtactc accagtcaca gaaaagcatc 1560
ttacggatgg catgacagta agagaattat gcagtgctgc cataaccatg agtgataaca 1620
ctgcggccaa cttacttctg acaacgatcg gaggaccgaa ggagctaacc gcttttttgc 1680
acaacatggg ggatcatgta actcgccttg atcgttggga accggagctg aatgaagcca 1740
taccaaacga cgagcgtgac accacgatgc ctgcagcaat ggcaacaacg ttgcgcaaac 1800
tattaactgg cgaactactt actctagctt cccggcaaca attaatagac tggatggagg 1860

-continued

```
cggataaagt tgcaggacca cttctgcgct cggcccttcc ggctggctgg tttattgctg   1920
ataaatctgg agccggtgag cgtgggtctc gcggtatcat tgcagcactg gggccagatg   1980
gtaagccctc ccgtatcgta gttatctaca cgacggggag tcaggcaact atggatgaac   2040
gaaatagaca gatcgctgag ataggtgcct cactgattaa gcattggtaa ctgtcagacc   2100
aagtttactc atatatactt tagattgatt taaaacttca tttttaattt aaaaggatct   2160
aggtgaagat cctttttgat aatctcatga ccaaaatccc ttaacgtgag ttttcgttcc   2220
actgagcgtc agaccccgta gaaaagatca aaggatcttc ttgagatcct ttttttctgc   2280
gcgtaatctg ctgcttgcaa acaaaaaaac caccgctacc agcggtggtt tgtttgccgg   2340
atcaagagct accaactctt tttccgaagg taactggctt cagcagagcg cagataccaa   2400
atactgtcct tctagtgtag ccgtagttag gccaccactt caagaactct gtagcaccgc   2460
ctacatacct cgctctgcta atcctgttac cagtggctgc tgccagtggc gataagtcgt   2520
gtcttaccgg gttggactca agacgatagt taccggataa ggcgcagcgg tcgggctgaa   2580
cggggggttc gtgcacacag cccagcttgg agcgaacgac ctacaccgaa ctgagatacc   2640
tacagcgtga gctatgagaa agcgccacgc ttcccgaagg gagaaaggcg gacaggtatc   2700
cggtaagcgg cagggtcgga acaggagagc gcacgaggga gcttccaggg ggaaacgcct   2760
ggtatcttta tagtcctgtc gggtttcgcc acctctgact tgagcgtcga tttttgtgat   2820
gctcgtcagg ggggcggagc ctatggaaaa acgccagcaa cgcggccttt ttacggttcc   2880
tggccttttg ctggcctttt gctcacatgt tctttcctgc gttatcccct gattctgtgg   2940
ataaccgtat taccgccttt gagtgagctg ataccgctcg ccgcagccga acgaccgagc   3000
gcagcgagtc agtgagcgag gaagcggaag agcgcctgat gcggtatttt ctccttacgc   3060
atctgtgcgg tatttcacac cgcatatatg gtgcactctc agtacaatct gctctgatgc   3120
cgcatagtta agccagtata cactccgcta tcgctacgtg actgggtcat ggctgcgccc   3180
cgacacccgc caacacccgc tgacgcgccc tgacgggctt gtctgctccc ggcatccgct   3240
tacagacaag ctgtgaccgt ctccgggagc tgcatgtgtc agaggttttc accgtcatca   3300
ccgaaacgcg cgaggcagct gcggtaaagc tcatcagcgt ggtcgtgaag cgattcacag   3360
atgtctgcct gttcatccgc gtccagctcg ttgagtttct ccagaagcgt taatgtctgg   3420
cttctgataa agcgggccat gttaagggcg gttttttcct gtttggtcac tgatgcctcc   3480
gtgtaagggg gatttctgtt catgggggta atgataccga tgaaacgaga gaggatgctc   3540
acgatacggg ttactgatga tgaacatgcc cggttactgg aacgttgtga gggtaaacaa   3600
ctggcggtat ggatgcggcg ggaccagaga aaaatcactc agggtcaatg ccagcgcttc   3660
gttaatacag atgtaggtgt tccacagggt agccagcagc atcctgcgat gcagatccgg   3720
aacataatgg tgcagggcgc tgacttccgc gtttccagac tttacgaaac acggaaaccg   3780
aagaccattc atgttgttgc tcaggtcgca gacgttttgc agcagcagtc gcttcacgtt   3840
cgctcgcgta tcggtgattc attctgctaa ccagtaaggc aaccccgcca gcctagccgg   3900
gtcctcaacg acaggagcac gatcatgcgc acccgtggcc aggacccaac gctgcccgag   3960
atgcgccgcg tgcggctgct ggagatggcg gacgcgatgg atatgttctg ccaagggttg   4020
gtttgcgcat tcacagttct ccgcaagaat tgattggctc caattcttgg agtggtgaat   4080
ccgttagcga ggtgccgccg gcttccattc aggtcgaggt ggcccggctc catgcaccgc   4140
gacgcaacgc ggggaggcag acaaggtata gggcggcgcc tacaatccat gccaacccgt   4200
tccatgtgct cgccgaggcg gcataaatcg ccgtgacgat cagcggtcca gtgatcgaag   4260
```

-continued

```
ttaggctggt aagagccgcg agcgatcctt gaagctgtcc ctgatggtcg tcatctacct   4320

gcctggacag catggcctgc aacgcgggca tcccgatgcc gccggaagcg agaagaatca   4380

taatggggaa ggccatccag cctcgcgtcg cgaacgccag caagacgtag cccagcgcgt   4440

cggccgccat gccggcgata atggcctgct tctcgccgaa acgtttggtg gcgggaccag   4500

tgacgaaggc ttgagcgagg gcgtgcaaga ttccgaatac cgcaagcgac aggccgatca   4560

tcgtcgcgct ccagcgaaag cggtcctcgc cgaaaatgac ccagagcgct gccggcacct   4620

gtcctacgag ttgcatgata aagaagacag tcataagtgc ggcgacgata gtcatgcccc   4680

gcgcccaccg gaaggagctg actgggttga aggctctcaa gggcatcggt cgagatcccg   4740

gtgcctaatg agtgagctaa cttacattaa ttgcgttgcg ctcactgccc gctttccagt   4800

cgggaaacct gtcgtgccag ctgcattaat gaatcggcca acgcgcgggg agaggcggtt   4860

tgcgtattgg gcgccagggt ggtttttctt ttcaccagtg agacgggcaa cagctgattg   4920

cccttcaccg cctggccctg agagagttgc agcaagcggt ccacgctggt ttgccccagc   4980

aggcgaaaat cctgtttgat ggtggttaac ggcgggatat aacatgagct gtcttcggta   5040

tcgtcgtatc ccactaccga gatatccgca ccaacgcgca gcccggactc ggtaatggcg   5100

cgcattgcgc ccagcgccat ctgatcgttg gcaaccagca tcgcagtggg aacgatgccc   5160

tcattcagca tttgcatggt ttgttgaaaa ccggacatgg cactccagtc gccttcccgt   5220

tccgctatcg gctgaatttg attgcgagtg agatatttat gccagccagc cagacgcaga   5280

cgcgccgaga cagaacttaa tgggcccgct aacagcgcga tttgctggtg acccaatgcg   5340

accagatgct ccacgcccag tcgcgtaccg tcttcatggg agaaaataat actgttgatg   5400

ggtgtctggt cagagacatc aagaaataac gccggaacat tagtgcaggc agcttccaca   5460

gcaatggcat cctggtcatc cagcggatag ttaatgatca gcccactgac gcgttgcgcg   5520

agaagattgt gcaccgccgc tttacaggct tcgacgccgc ttcgttctac catcgacacc   5580

accacgctgg cacccagttg atcggcgcga gatttaatcg ccgcgacaat ttgcgacggc   5640

gcgtgcaggg ccagactgga ggtggcaacg ccaatcagca acgactgttt gcccgccagt   5700

tgttgtgcca cgcggttggg aatgtaattc agctccgcca tcgccgcttc cactttttcc   5760

cgcgttttcg cagaaacgtg gctggcctgg ttcaccacgc gggaaacggt ctgataagag   5820

acaccggcat actctgcgac atcgtataac gttactggtt tcacattcac caccctgaat   5880

tgactctctt ccgggcgcta tcatgccata ccgcgaaagg ttttgcgcca ttcgatggtg   5940

tccgggatct cgacgctctc ccttatgcga ctcctgcatt aggaagcagc ccagtagtag   6000

gttgaggccg ttgagcaccg ccgccgcaag gaatggtgca tgcaaggaga tggcgcccaa   6060

cagtcccccg gccacggggc ctgccaccat acccacgccg aaacaagcgc tcatgagccc   6120

gaagtggcga gcccgatctt ccccatcggt gatgtcggcg atataggcgc cagcaaccgc   6180

acctgtggcg ccggtgatgc cggccacgat gcgtccggcg tagaggatcg agatctcgat   6240

cccgcgaaat taatacgact cactataggg gaattgtgag cggataacaa ttcccctcta   6300

gaaataattt tgtttaactt taagaaggag atataccatg ggcagcagcc atcatcatca   6360

tcatcacagc agcggcctgg tgccgcgcgg cagcca                             6396
```

<210> SEQ ID NO 180
<211> LENGTH: 6781
<212> TYPE: DNA
<213> ORGANISM: Artificial Sequence
<220> FEATURE:

-continued

<223> OTHER INFORMATION: Synthetic plasmid

<400> SEQUENCE: 180
gtaggagggc gtggatatgt cctgcgggta aactatagtc gttgagagga ggagtctgac 60
tcctgttgat agatccagta atgacctcag aactccatct ggatttgttc agaacgctcg 120
gttgccgccg ggcgtttttt attggtgaga ataggtcttg acggctggcg agaggtgcgg 180
ggaggatctg accgacgcgg tccacacgtg gcaccgcgat gctgttgtgg gcacaatcgt 240
gccggttggt aggatccggt taattaagca gtaccagatc tgactgagtg accaaaggag 300
gcggacatat gtacgaacgt ccgctgtacc gggaggattg cgacggcgtc gtcctggcgt 360
ttctgcgaca caacccactg gcaatggtcg tcacctcgca cgacgacgtc ccggtggcca 420
cccacgcgcc ggtgctgttc cggcacggac ccgacggcgc cgacgccgag gccgtcgccg 480
cgggcaccgt cccgctcgcc ggctccaccc tgatcggcca catgaacgtc gagaacccgc 540
agtggcgccg gatgcgctcc ggcgaccggg cgctcatcgt cttccagggc ccgcacggct 600
atgtctcgcc gacggtctac ggggtcacgc ccgcggcccc cacctgggac ttcatcgccg 660
tccacgtgaa cggcacagtg gagcccaccg ccgaccccgc cgccgtgctg gacatcgtct 720
ccgacaccgc ccggcggctg gagtccggct tcgggcgcgg ctgggaccag gagtcctccc 780
tcgactactt ccgccagatc gcgcccggcg tgggcgcctt caccctgcgg gtcgattccg 840
tgcagacgat gttcaagctc agccaggaga agcccgcccc gatgcggcgg cgcgtggtcg 900
agcagttcga agcaagcgag tccggcaccc accgcgccct ggccagcgtg atgcgcgacc 960
gcggactcac cgaagccgac gaggagcggg agacagccgg atgaggatcc ccgggtacct 1020
tcgaaaaaaa aaggctccaa aaggagcctt taattgttcc tccagacctt acttgaccgg 1080
cgctcactgc ccgctttcca gtcgggaaac ctgtcgtgcc agctgcatta atgaatcggc 1140
caacgcgcgg ggagaggcgg tttgcgtatt gggcgctctt ccgcttcctc gctcactgac 1200
tcgctgcgct cggtcgttcg gctgcggcga gcggtatcag ctcactcaaa ggcggtaata 1260
cggttatcca cagaatcagg ggataacgca ggaaagaaca tgtgagcaaa aggccagcaa 1320
aaggccagga accgtaaaaa ggccgcgttg ctggcgtttt tccataggct ccgcccccct 1380
gacgagcatc acaaaaatcg acgctcaagt cagaggtggc gaaacccgac aggactataa 1440
agataccagg cgtttccccc tggaagctcc ctcgtgcgct ctcctgttcc gaccctgccg 1500
cttaccggat acctgtccgc ctttctccct tcgggaagcg tggcgctttc tcatagctca 1560
cgctgtaggt atctcagttc ggtgtaggtc gttcgctcca agctgggctg tgtgcacgaa 1620
ccccccgttc agcccgaccg ctgcgcctta tccggtaact atcgtcttga gtccaacccg 1680
gtaagacacg acttatcgcc actggcagca gccactggta acaggattag cagagcgagg 1740
tatgtaggcg gtgctacaga gttcttgaag tggtggccta actacggcta cactagaaga 1800
acagtatttg gtatctgcgc tctgctgaag ccagttacct tcggaaaaag agttggtagc 1860
tcttgatccg gcaaacaaac caccgctggt agcggtggtt tttttgtttg caagcagcag 1920
attacgcgca gaaaaaaagg atctcaagaa gatcctttga tcttttctac ggggtctgac 1980
gctcagtgga acgaaaactc acgttaaggg attttggtca tgagattatc aaaaaggatc 2040
ttcacctaga tccttttggt tcatgtgcag ctccactgct ttagactcta catctgtatg 2100
aagtcttcag atcctctacg ccggacgcat cgtggccgga tctaaaaaaa agcccgctca 2160
ttaggcgggc tgacagttac caatgcttaa tcagtgaggc acctatctca gcgatctgtc 2220
tatttcgttc atccatagtt gcctgactcc ccgtcgtgta gataactacg atacgggagg 2280

-continued

```
gcttaccatc tggccccagt gctgcaatga taccgcgaga cccacgctca ccggctccag   2340
atttatcagc aataaaccag ccagccggaa gggccgagcg cagaagtggt cctgcaactt   2400
tatccgcctc catccagtct attaattgtt gccgggaagc tagagtaagt agttcgccag   2460
ttaatagttt gcgcaacgtt gttgccattg ctacaggcat cgtggtgtca cgctcgtcgt   2520
ttggtatggc ttcattcagc tccggttccc aacgatcaag gcgagttaca tgatccccca   2580
tgttgtgcaa aaaagcggtt agctccttcg gtcctccgat cgttgtcaga agtaagttgg   2640
ccgcagtgtt atcactcatg gttatggcag cactgcataa ttctcttact gtcatgccat   2700
ccgtaagatg cttttctgtg actggtgagt actcaaccaa gtcattctga gaatagtgta   2760
tgcggcgacc gagttgctct tgcccggcgt caatacggga taataccgcg ccacatagca   2820
gaactttaaa agtgctcatc attggaaaac gttcttcggg gcgaaaactc tcaaggatct   2880
taccgctgtt gagatccagt tcgatgtaac ccactcgtgc acccaactga tcttcagcat   2940
cttttacttt caccagcgtt tctgggtgag caaaaacagg aaggcaaagt gccgcaaaaa   3000
agggaataag ggcgacacgg aaatgttgaa tactcatact cttccttttt caatattatt   3060
gaagcattta tcagggttat tgtctcatga gcggatacat atttgaatgt atttagaaaa   3120
ataaacaaat aggggttccg cgcacatttc cccgaaaagt gccacctggc gcgccacaaa   3180
acagcaggga agcagcgctt ttccgctgca taaccctgct tcggggtcat tatagcgatt   3240
ttttcggtat atccatcctt tttcgcacga tatacaggat tttgccaaag ggttcgtgta   3300
gactttcctt ggtgtatcca acggcgtcag ccgggcagga taggtgaagt aggcccaccc   3360
gcgagcgggt gttccttctt cactgtccct tattcgcacc tggcggtgct caacgggaat   3420
cctgctctgc gaggctggcc ggctaccgcc ggcgtaacag atgagggcaa gcggatggct   3480
gatgaaacca agccaaccag gaagggcagc ccacctatca aggtgtactg ccttccagac   3540
gaacgaagag cgattgagga aaaggcggcg gcggccggca tgagcctgtc ggcctacctg   3600
ctggccgtcg gccagggcta caaaatcacg ggcgtcgtgg actatgagca cgtcggcgcg   3660
cctctagtat gcaggagtgg ggaggcacga tggccgcttt ggtcgacctc aacgagacga   3720
tgaagccgtg gaacgacacc accccggcgg ccctgctgga ccacacccgg cactacacct   3780
tcgacgtctg atcatcactg acgaatcgag gtcgaggaac cgagcgtccg aggaacagag   3840
gcgcttatcg gttggccgcg agattcctgt cgatcctctc gtgcagcgcg attccgaggg   3900
aaacggaaac gttgagagac tcggtctggc tcatcatggg gatggaaacc gaggcggaag   3960
acgcctcctc gaacaggtcg gaaggcccac ccttttcgct gccgaacagc aaggccagcc   4020
gatccggatt gtccccgagt tccttcacgg aaatgtcgcc atccgccttg agcgtcatca   4080
gctgcatacc gctgtcccga atgaaggcga tggcctcctc gcgaccggag agaacgacgg   4140
gaagggagaa gacgtaacct cggctggccc tttggagacg ccggtccgcg atgctggtga   4200
tgtcactgtc gaccaggatg atccccgacg ctccgagcgc gagcgacgtg cgtactatcg   4260
cgccgatgtt cccgacgatc ttcaccccgt cgagaacgac gacgtcccca cgccggctcg   4320
cgatatcgcc gaacctggcc gggcgaggga cgcgggcgat gccgaatgtc ttggccttcc   4380
gctccccctt gaacaactgg ttgacgatcg aggagtcgat gaggcggacc ggtatgttct   4440
gccgcccgca cagatccagc aactcagatg gaaaaggact gctgtcgctg ccgtagacct   4500
cgatgaactc caccccggcc gcgatgctgt gcatgagggg ctcgacgtcc tcgatcaacg   4560
ttgtctttat gttggatcgc gacggcttgg tgacatcgat gatccgctgc accgcgggat   4620
```

cggacggatt tgcgatggtg tccaactcag tcatggtcgt cctaccggct gctgtgttca 4680
gtgacgcgat tcctggggtg tgacacccta cgcgacgatg gcggatggct gccctgaccg 4740
gcaatcacca acgcaagggg aagactacgc cttccactag accggtcgac ctgcaggcct 4800
gctggcgccg gacggggctt cagacgtttc gggtgctggg ttgttgtctc tggacagtga 4860
tccatgggaa actactcagc accaccaatg ttcccaaaag aaagcgcagg tcagcgccca 4920
tgagccaata tctaggcatg tcgcccttca tcgctcccga ggtccctgag caccttctcg 4980
acactgttcg cgtcttcctg tacgcgcgtc agtctaaggg ccggtccgac ggctcagacg 5040
tgtcgaccga agcacagctc gcggccggtc gtgcgttggt cgcgtctcgc aacgcccagg 5100
ggggtgcgcg ctgggtcgtg gcaggtgagt tcgtggacgt cgggcgctcc ggctgggacc 5160
cgaacgtgac ccgtgccgac ttcgagcgca tgatgggcga agtccgcgcc ggcgaaggtg 5220
acgttgtcgt tgtgaatgag ctttcccggc tcactcgcaa gggcgcccat gacgcgctcg 5280
aaatcgacaa cgaattgaag aagcacggcg tgcgcttcat gtcggttctt gagccgttcc 5340
ttgacacgtc taccoctatc ggcgtcgcca ttttcgcgct gatcgctgcc cttgcgaaac 5400
aggacagtga cctgaaggcg gagcgcctga agggtgcgaa agacgagatt gccgcgctgg 5460
gtggcgttca ctcgtcttcc gccccgttcg gaatgcgcgc cgtgcgcaag aaggtcgata 5520
atctcgtgat ctccgttctt gagccggacg aagacaaccc ggatcacgtc gagctagttg 5580
agcgcatggc gaaaatgtcg ttcgagggcg tgtccgacaa cgccattgca acgaccttcg 5640
agaaggaaaa gatcccgtcg cccggaatgg ctgagagacg cgccacggaa aagcgtcttg 5700
cgtccatcaa ggcacgtcgc ctgaacggcg ctgaaaagcc gatcatgtgg cgcgctcaaa 5760
cggtccgatg gattctcaac catcccgcaa tcggcggttt cgcattcgag cgtgtgaagc 5820
acggtaaggc gcacatcaac gtcatacggc gcgaccccgg cggcaagccg ctaacgcccc 5880
acacgggcat tctcagcggc tcgaagtggc ttgagcttca agagaagcgt tccgggaaga 5940
atctcagcga ccggaagcct ggggccgaag tcgaaccgac gcttctgagc gggtggcgtt 6000
tcctggggtg ccgaatctgc ggcggctcaa tgggtcagtc ccagggtggc cgtaagcgca 6060
acggcgacct tgccgaaggc aattacatgt gcgccaaccc gaaggggcac ggcggcttgt 6120
cggtcaagcg cagcgaactg gacgagttcg ttgcttcgag ggtgtgggca cggctccgca 6180
cagccgacat ggaagatgaa cacgatcagg catggattgc cgccgctgcg gagcgcttcg 6240
cccttcagca cgacctagcg gggtggccg atgagcggcg cgaacaacag gcgcacctag 6300
acaacgtgcg gcgctccatc aaggaccttc aggcggaccg taaggccggt ctgtacgtcg 6360
ggcgtgaaga gctggaaacg tggcgctcaa cggtgctgca ataccggtcc tacgaagcgg 6420
agtgcacgac ccgactcgct gagcttgacg agaagatgaa cggcagcacc cgcgttccgt 6480
ctgagtggtt cagcggcgaa gacccgacgg ccgaaggggg catctgggca agctgggacg 6540
tgtacgagcg tcgggagttc ctgagcttct tccttgactc cgtcatggtc gaccgggggc 6600
gccaccctga gacgaagaaa tacatccccc tgaaggaccg tgtgacgctc aagtgggcgg 6660
agctgctgaa ggaggaagac gaagcgagcg aagccactga gcgggagctt gcggcgctgt 6720
aggtacaatc ataatgaggc tagactacag acgcgaagaa tctcgtgctt tcagcttcga 6780
t 6781

<210> SEQ ID NO 181
<211> LENGTH: 6264
<212> TYPE: DNA
<213> ORGANISM: Artificial Sequence
<220> FEATURE:
<223> OTHER INFORMATION: Synthetic plasmid

<400> SEQUENCE: 181

```
atctacgtct gtcgagaagt ttctgatcga aaagttcgac agcgtctccg acctgatgca     60
gctctcgcag ggcgaagaat ctcgtgcttt cagcttcgat gtaggagggc gtggatatgt    120
cctgcgggta aactatagtc gttgagagga ggagtctgac tcctgttgat agatccagta    180
atgacctcag aactccatct ggatttgttc agaacgctcg gttgccgccg ggcgtttttt    240
attggtgaga ataggtcttg acggctggcg agaggtgcgg ggaggatctg accgacgcgg    300
tccacacgtg gcaccgcgat gctgttgtgg gcacaatcgt gccggttggt aggatccggt    360
taattaagca gtaccagatc tgactgagtg accaaaggag gcggacatat gtacgaacgt    420
ccgctgtacc gggaggattg cgacggcgtc gtcctggcgt ttctgcgaca caacccactg    480
gcaatggtcg tcacctcgca cgacgacgtc ccggtggcca cccacgcgcc ggtgctgttc    540
cggcacggac ccgacggcgc cgacgccgag gccgtcgccg cgggcaccgt cccgctcgcc    600
ggctccaccc tgatcggcca catgaacgtc gagaacccgc agtggcgccg gatgcgctcc    660
ggcgaccggg cgctcatcgt cttccagggc ccgcacggct atgtctcgcc gacggtctac    720
ggggtcacgc ccgcggcccc cacctgggac ttcatcgccg tccacgtgaa cggcacagtg    780
gagcccaccg ccgaccccgc cgccgtgctg gacatcgtct ccgacaccgc ccggcggctg    840
gagtccggct tcgggcgcgg ctgggaccag gagtcctccc tcgactactt ccgccagatc    900
gcgcccggcg tgggcgcctt caccctgcgg gtcgattccg tgcagacgat gttcaagctc    960
agccaggaga agcccgcccc gatgcggcgg cgcgtggtcg agcagttcga agcaagcgag   1020
tccggcaccc accgcgccct ggccagcgtg atgcgcgacc gcggactcac cgaagccgac   1080
gaggagcggg agacagccgg atgaggatcc ccgggtacct tcgaaaaaaa aaggctccaa   1140
aaggagcctt taattgttcc tccagacctt acttgaccgg cgctcactgc ccgctttcca   1200
gtcgggaaac ctgtcgtgcc agctgcatta atgaatcggc caacgcgcgg ggagaggcgg   1260
tttgcgtatt gggcgctctt ccgcttcctc gctcactgac tcgctgcgct cggtcgttcg   1320
gctgcggcga gcggtatcag ctcactcaaa ggcggtaata cggttatcca cagaatcagg   1380
ggataacgca ggaaagaaca tgtgagcaaa aggccagcaa aaggccagga accgtaaaaa   1440
ggccgcgttg ctggcgtttt tccataggct ccgcccccct gacgagcatc acaaaaatcg   1500
acgctcaagt cagaggtggc gaaacccgac aggactataa agataccagg cgtttccccc   1560
tggaagctcc ctcgtgcgct ctcctgttcc gaccctgccg cttaccggat acctgtccgc   1620
ctttctccct tcgggaagcg tggcgctttc tcatagctca cgctgtaggt atctcagttc   1680
ggtgtaggtc gttcgctcca agctgggctg tgtgcacgaa ccccccgttc agcccgaccg   1740
ctgcgcctta tccggtaact atcgtcttga gtccaacccg gtaagacacg acttatcgcc   1800
actggcagca gccactggta acaggattag cagagcgagg tatgtaggcg gtgctacaga   1860
gttcttgaag tggtggccta actacggcta cactagaaga acagtatttg gtatctgcgc   1920
tctgctgaag ccagttacct tcggaaaaag agttggtagc tcttgatccg gcaaacaaac   1980
caccgctggt agcggtggtt tttttgtttg caagcagcag attacgcgca gaaaaaaagg   2040
atctcaagaa gatcctttga tcttttctac ggggtctgac gctcagtgga acgaaaactc   2100
acgttaaggg attttggtca tgagattatc aaaaaggatc ttcacctaga tccttttggt   2160
tcatgtgcag ctccatcagc aaaaggggat gataagttta tcaccaccga ctatttgcaa   2220
```

-continued

```
cagtgccgtt gatcgtgcta tgatcgactg atgtcatcag cggtggagtg caatgtcgtg   2280
caatacgaat ggcgaaaagc cgagctcatc ggtcagcttc tcaaccttgg ggttaccccc   2340
ggcggtgtgc tgctggtcca cagctccttc cgtagcgtcc ggcccctcga agatgggcca   2400
cttggactga tcgaggccct gcgtgctgcg ctgggtccgg gagggacgct cgtcatgccc   2460
tcgtggtcag gtctggacga cgagccgttc gatcctgcca cgtcgcccgt tacaccggac   2520
cttggagttg tctctgacac attctggcgc ctgccaaatg taaagcgcag cgcccatcca   2580
tttgcctttg cggcagcggg gccacaggca gagcagatca tctctgatcc attgcccctg   2640
ccacctcact cgcctgcaag cccggtcgcc cgtgtccatg aactcgatgg gcaggtactt   2700
ctcctcggcg tgggacacga tgccaacacg acgctgcatc ttgccgagtt gatggcaaag   2760
gttccctatg ggtgccgag acactgcacc attcttcagg atggcaagtt ggtacgcgtc   2820
gattatctcg agaatgacca ctgctgtgag cgctttgcct tggcggacag gtggctcaag   2880
gagaagagcc ttcagaagga aggtccagtc ggtcatgcct ttgctcggtt gatccgctcc   2940
cgcgacattg tggcgacagc cctgggtcaa ctgggccgag atccgttgat cttcctgcat   3000
ccgccagagg cgggatgcga agaatgcgat gccgctcgcc agtcgattgg ctgagctcat   3060
gagcggagaa cgagatgacg ttggaggggc aaggtcgcgc tgattgctgg ggcaacacgt   3120
ggagcggatc ggggattgtc tttcttcagc tcgctgatga tatgctgacg ctcaatgccg   3180
tttggcctcc gactaacgaa aatcccgcat ttggacggct gatccgattg gcacggcgga   3240
cggcgaatgg cggagcagac gctcgtccgg gggcaatgag atatgaaaaa gcctgaactc   3300
accgcgacgt atcgggccct ggccagctag ctagagtcga cctgcaggtc cccggggatc   3360
ggtcttgcct tgctcgtcgg tgatgtactt caccagctcc gcgaagtcgc tcttcttgat   3420
ggagcgcatg gggacgtgct tggcaatcac gcgcaccccc cggccgtttt agcggctaaa   3480
aaagtcatgg ctctgccctc gggcggacca cgcccatcat gaccttgcca agctcgtcct   3540
gcttctcttc gatcttcgcc agcagggcga ggatcgtggc atcaccgaac cgcgccgtgc   3600
gcgggtcgtc ggtgagccag agtttcagca ggccgcccag gcggcccagg tcgccattga   3660
tgcgggccag ctcgcggacg tgctcatagt ccacgacgcc cgtgattttg tagccctggc   3720
cgacggccag caggtaggcc gacaggctca tgccggccgc cgccgccttt tcctcaatcg   3780
ctcttcgttc gtctggaagg cagtacacct tgataggtgg gctgcccttc ctggttggct   3840
tggtttcatc agccatccgc ttgccctcat ctgttacgcc ggcggtagcc ggccagcctc   3900
gcagagcagg attcccgttg agcaccgcca ggtgcgaata agggacagtg aagaaggaac   3960
acccgctcgc gggtgggcct acttcaccta tcctgcccgg ctgacgccgt tggatacacc   4020
aaggaaagtc tacacgaacc ctttggcaaa atcctgtata tcgtgcgaaa aaggatggat   4080
ataccgaaaa aatcgctata atgaccccga agcagggtta tgcagcggaa aagatccgtc   4140
gacctgcagg catgcaagct ctagcgattc cagacgtccc gaaggcgtgg cgcggcttcc   4200
ccgtgccgga gcaatcgccc tgggtgggtt acacgacgcc cctctatggc ccgtactgac   4260
ggacacaccg aagccccggc ggcaaccctc agcggatgcc ccggggcttc acgttttccc   4320
aggtcagaag cggttttcgg gagtagtgcc ccaactgggg taacctttga gttctctcag   4380
ttgggggcgt agggtcgccg acatgacaca aggggttgtg accggggtgg acacgtacgc   4440
gggtgcttac gaccgtcagt cgcgcgagcg cgaaaattcg agcgcagcaa gcccagcgac   4500
acagcgtagc gccaacgaag acaaggcggc cgaccttcag cgcgaagtcg agcgcgacgg   4560
gggccggttc aggttcgtcg ggcatttcag cgaagcgccg ggcacgtcgg cgttcgggac   4620
```

-continued

```
ggcggagcgc ccggagttcg aacgcatcct gaacgaatgc cgcgccgggc ggctcaacat   4680

gatcattgtc tatgacgtgt cgcgcttctc gcgcctgaag gtcatggacg cgattccgat   4740

tgtctcggaa ttgctcgccc tgggcgtgac gattgtttcc actcaggaag gcgtcttccg   4800

gcagggaaac gtcatggacc tgattcacct gattatgcgg ctcgacgcgt cgcacaaaga   4860

atcttcgctg aagtcggcga agattctcga cacgaagaac cttcagcgcg aattgggcgg   4920

gtacgtcggc gggaaggcgc cttacggctt cgagcttgtt tcggagacga aggagatcac   4980

gcgcaacggc cgaatggtca atgtcgtcat caacaagctt gcgcactcga ccactcccct   5040

taccggaccc ttcgagttcg agcccgacgt aatccggtgg tggtggcgtg agatcaagac   5100

gcacaaacac cttcccttca agccgggcag tcaagccgcc attcacccgg gcagcatcac   5160

ggggctttgt aagcgcatgg acgctgacgc cgtgccgacc cggggcgaga cgattgggaa   5220

gaagaccgct tcaagcgcct gggacccggc aaccgttatg cgaatccttc gggacccgcg   5280

tattgcgggc ttcgccgctg aggtgatcta caagaagaag ccggacggca cgccgaccac   5340

gaagattgag ggttaccgca ttcagcgcga cccgatcacg ctccggccgg tcgagcttga   5400

ttgcggaccg atcatcgagc ccgctgagtg gtatgagctt caggcgtggt tggacggcag   5460

ggggcgcggc aaggggcttt cccgggggca agccattctg tccgccatgg acaagctgta   5520

ctgcgagtgt ggcgccgtca tgacttcgaa gcgcggggaa gaatcgatca aggactctta   5580

ccgctgccgt cgccggaagg tggtcgaccc gtccgcacct gggcagcacg aaggcacgtg   5640

caacgtcagc atggcggcac tcgacaagtt cgttgcggaa cgcatcttca acaagatcag   5700

gcacgccgaa ggcgacgaag agacgttggc gcttctgtgg gaagccgccc gacgcttcgg   5760

caagctcact gaggcgcctg agaagagcgg cgaacgggcg aaccttgttg cggagcgcgc   5820

cgacgccctg aacgcccttg aagagctgta cgaagaccgc gcggcaggcg cgtacgacgg   5880

acccgttggc aggaagcact tccggaagca acaggcagcg ctgacgctcc ggcagcaagg   5940

ggcggaagag cggcttgccg aacttgaagc cgccgaagcc ccgaagcttc cccttgacca   6000

atggttcccc gaagacgccg acgctgaccc gaccggccct aagtcgtggt gggggcgcgc   6060

gtcagtagac gacaagcgcg tgttcgtcgg gctcttcgta gacaagatcg ttgtcacgaa   6120

gtcgactacg ggcagggggc agggaacgcc catcgagaag cgcgcttcga tcacgtgggc   6180

gaagccgccg accgacgacg acgaagacga cgcccaggac ggcacggaag acgtagcggc   6240

gtagcgagac acccgggaag cctg                                          6264
```

TRANSGENIC MICROORGANISMS AND SYNTHESIS OF PIPERAZIC ACID, PIPERAZIC ACID CONTAINING PRODUCTS, AND DERIVATIVES THEREOF

CROSS-REFERENCE TO RELATED APPLICATIONS

This application is a Continuation of U.S. Nonprovisional application Ser. No. 16/024,077 filed on 29 Jun. 2018, now abandoned, which claims priority from U.S. Provisional Application Ser. No. 62/527,586 filed on 30 Jun. 2017, which is incorporated herein by reference in its entirety.

STATEMENT REGARDING FEDERALLY SPONSORED RESEARCH OR DEVELOPMENT

Not Applicable.

MATERIAL INCORPORATED-BY-REFERENCE

The Sequence Listing, which is a part of the present disclosure, includes a computer readable form (named "017073-US-NP_Sequence_Listing_ST25.txt", created on 6 Sep. 2018; 572,928 bytes) comprising nucleotide and/or amino acid sequences of the present invention. The subject matter of the Sequence Listing is incorporated herein by reference in its entirety.

FIELD OF THE INVENTION

The present disclosure generally relates to the synthesis of piperazic acid.

BACKGROUND OF THE INVENTION

Piperazic acid (Piz) is a nonproteinogenic amino acid that contains a characteristic and biochemically unusual N—N bond. Piz is a proline structural mimic, and Piz-containing compounds are of significant interest for drug discovery. Piz itself is not bioactive, but peptidic compounds incorporating Piz as a building block include antibacterial, antiviral, immunomodulatory, and anticancer drug leads. Intriguingly, all naturally-occurring Piz containing compounds discovered thus far have been bioactive.

SUMMARY OF THE INVENTION

Among the various aspects of the present disclosure is the provision of a biological and biochemical production of enantiopure piperazic acid derived from the newly discovered production pathway for L-piperazic acid. For example, the present disclosure provides for a transgenic microorganism for the synthesis of L-piperazic acid and derivatives thereof and additional biosynthetic processes for the production of L-piperazic acid and derivatives thereof.

Briefly, therefore, the present disclosure is directed to methods of producing piperazic acid, especially L-piperazic acid and derivatives thereof. Synthesis of enantiopure L-Piz has been elusive and expensive. The methods and transgenic organisms as described herein have overcome many of the challenges currently faced regarding the synthesis of enantiopure L-Piz. L-Piz and derivatives thereof can be used as a starting material for a large range of bioactive molecules, including many currently known therapeutics and can be isotopically labeled for use in drug discovery analyses and imaging modalities. The new synthetic routes can give access to isotope (e.g., $^{15}N$, $^{13}C$, $^{2}H$) or radioisotopically-labeled piperazic acid for which no synthetic pathways are currently reported.

One aspect of the present disclosure includes transgenic microorganisms (e.g., bacteria) engineered to accumulate piperazic acid and derivatives thereof, including a piperazic acid (Piz)-containing product.

Another aspect of the present disclosure includes biochemical and biological methods for producing piperazic acid and derivatives thereof, including a piperazic acid (Piz)-containing product.

Another aspect of the present disclosure includes compositions and methods of using isotopically labeled piperazic acid and derivatives thereof, including a piperazic acid (Piz)-containing product.

Another aspect of the present disclosure provides for a method for preparing a piperazic acid (Piz)-containing product. In some embodiments, the method comprises: (i) providing $N^5$—OH-Ornithine or derivative thereof; (ii) providing a suitable enzyme comprising a $N^5$—OH Ornithine cyclase/dehydratase; or (iii) optionally, buffer salts, a NADPH cofactor, $Fe^{+2}$ salts, and a catalytic Flavin Adenine Dinucleotide (FAD) cofactor.

In some embodiments, the method further comprises: (i) providing an ornithine or a derivative thereof; or (ii) providing a suitable enzyme comprising an ornithine $N^5$ hydroxylase.

In some embodiments, the (i) the $N^5$—OH-Ornithine or derivative thereof is an enantiopure L-Ornithine or derivative thereof; (ii) the enzyme comprising $N^5$—OH Ornithine cyclase/dehydratase is a L—$N^5$—OH Ornithine cyclase/dehydratase or a PzbB enzyme; or (iii) the enzyme comprising ornithine $N^5$ hydroxylase is an L-ornithine $N^5$—OHase or a PzbA enzyme.

In some embodiments, the method is carried out in the absence of $O_2$, substantially no $O_2$, or in the presence of low $O_2$.

In some embodiments, the method comprises a coupled enzyme assay.

In some embodiments, the piperazic acid (Piz)-containing product comprises a compound of formula:

(I)

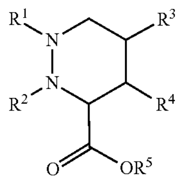

where $R^5$ is a hydrogen, an alkyl, a piperazic acid, an acetyl, ora carboxyl protecting group; each $R^1$ and $R^2$ are independently selected from hydrogen or an amino protecting group, wherein $R^1$ and $R^2$ may be taken together to form a fused bicyclic or tricyclic amino protecting group; or each $R^3$ and $R^4$ are independently selected from a hydrogen, a halo (e.g., a chloro, a fluoro, a bromo, a iodo), or a hydroxyl. In some embodiments, $R^1$ and $R^2$ are not simultaneously hydrogen.

In some embodiments, the piperazic acid (Piz)-containing product is used as a starting material in a synthetic method of making a bioactive Piz-containing composition selected from the group consisting of: (i) an antibacterial agent, an antibiotic agent, an antitumor agent, an antiviral agent, an immunomodulatory agent, or an anti-inflammatory agent; (ii) a molecular probe, anticancer drug, or drug lead; (ii) a metalloprotease inhibitor, a caspase inhibitor, an angiotensin converting enzyme (ACE) inhibitor, an inflammatory peptide C5a antagonist, an oxytocin receptor antagonist, or a matylastin type-IV collagenase inhibitor; (iii) a dehydropiperazic acid; a chloropiperazic acid; a hydroxypiperazic acid; a monamycin, an aurantimycin, an antrimycin, an azinothricin, a luzopeptin, a kettapeptin, a quinoxapeptin, a lydiamycin, a piperazimycin, or a sangamide; or (iv) sanglifehrin A, pandanamide A, azinothricin, Sch392583, luzopeptin A, kutzernide 2, piperazic acid, L-piperazic acid, antrimycin, kettapeptin, GE3, A83586C, chloptosin, himastatin, luzopeptin, quinoxapeptin, lydiamycin, piperazimycin, sanglifehrin, sangamide NVP018, sangamide NVP019, sanglifehrin, Sch 382583; chloptosin, himastatin, verucopeptin, luzopeptin A, L-156,602, aurantimycin A, or L-156,373.

Another aspect of the present disclosure provides for a transgenic microorganism comprising an artificial DNA construct. In some embodiments, the transgenic microorganism comprises, as operably associated components in the 5' to 3' direction of transcription: (I)(a) a promoter functional in the microorganism; (b)(i) a first polynucleotide comprising a nucleotide sequence encoding a first polypeptide having a L-Ornithine $N^5$ hydroxylase activity; (ii) a second polynucleotide comprising a nucleotide sequence encoding a second polypeptide having a L-Ornithine $N^5$ cyclase activity or L-Ornithine $N^5$ dehydratase activity; or (iii) a third polynucleotide comprising a nucleotide sequence encoding a third polypeptide having a L-Ornithine $N^5$ hydroxylase activity and a L-Ornithine $N^5$ cyclase activity or L-Ornithine $N^5$ dehydratase activity; or (c) a transcriptional termination sequence; or (II)(a) a promoter functional in the microorganism; (b)(i) a first polynucleotide comprising a nucleotide sequence encoding a first polypeptide having PzbA activity; (ii) a second polynucleotide comprising a nucleotide sequence encoding a second polypeptide having PzbB activity; or (iii) a third polynucleotide comprising a nucleotide sequence encoding a first polypeptide having PzbA activity and PzbB activity; or (c) a transcriptional termination sequence. In some embodiments, the transgenic microorganism accumulates increased levels of a piperazic acid (Piz)-containing product, optionally L-Piz, compared to a microorganism not comprising the DNA construct.

In some embodiments, the microorganism comprises (a) (i) a nucleotide sequence encoding a polypeptide selected from SEQ ID NO: 1-SEQ ID NO: 81 or SEQ ID NO: 167-SEQ ID NO: 176 or a sequence at least 25% identical thereto having L-Ornithine $N^5$ hydroxylase activity; or (ii) a nucleotide sequence encoding a polypeptide selected from SEQ ID NO: 82-SEQ ID NO: 166 or SEQ ID NO: 167-SEQ ID NO: 176 ora sequence at least 25% identical thereto having L-Ornithine $N^5$ cyclase activity and L-Ornithine $N^5$ dehydratase activity; or (b) a nucleotide sequence encoding a polypeptide selected from SEQ ID NO: 167-SEQ ID NO: 176 or a sequence at least 25% identical thereto having L-Ornithine $N^5$ hydroxylase activity, L-Ornithine $N^5$ cyclase activity, and L-Ornithine $N^5$ dehydratase activity.

In some embodiments, the microorganism comprises: (i) a PzbA ortholog with at least about 25% identity to SEQ ID NO: 1-SEQ ID NO: 81 or SEQ ID NO: 167-SEQ ID NO: 176 and has PzbA activity to produce a piperazic acid (Piz)-containing product; (ii) a PzbB ortholog with at least about 25% identity to SEQ ID NO: 82-SEQ ID NO: 166 or SEQ ID NO: 167-SEQ ID NO: 176 and has PzbB activity to produce a piperazic acid (Piz)-containing product; or (iii) a PzbAB ortholog with at least about 25% identity to or SEQ ID NO: 167-SEQ ID NO: 176 and has PzbA and PzbB activity to produce a piperazic acid (Piz)-containing product.

In some embodiments, the microorganism is an Actinobacteria selected from the group consisting of *Streptomyces, Corynebacterium, Kutzneria*, and *Actinomadura*; is a heterologous population of microorganisms; is an Actinobacteria (optionally, an actinomycete); or is selected from the group consisting of *Streptomyces lividans* or *Corynebacterium glutamicum*, optionally carrying one or more copies of a native or non-native pzbA and optionally carrying one or more copies of pzbB.

In some embodiments, the transgenic microorganism overproduces L-Ornithine; the pzbA or the pzbB are cloned from a sanglifehrin biosynthetic locus of *Streptomyces flaveolus*; or a piperazic acid (Piz)-containing product accumulates within the microorganism.

Another aspect of the present disclosure provides for a method for producing a piperazic acid (Piz)-containing product. In some embodiments, the method comprises: (i) providing a transgenic microorganism capable of accumulating a piperazic acid (Piz)-containing product; (ii) cultivating the microorganism; or (iii) isolating accumulated piperazic acid (Piz)-containing product.

In some embodiments, the method comprises providing a transgenic microorganism and providing a feedstock, wherein the transgenic microorganism comprises at least one copy of pzbA and at least one copy of pzbB under a constitutive promoter; or the at least one pzbA is optionally a native copy.

In some embodiments, the transgenic microorganism is (i) a heterologous population of microorganisms; (ii) an Actinobacteria (optionally, an actinomycete); or (ii) selected from the group consisting of *Streptomyces lividans* or *Corynebacterium glutamicum*, optionally carrying one or more copies of a native or non-native pzbA and optionally carrying one or more copies of pzbB.

In some embodiments, the pzbA or pzbB are cloned from a sanglifehrin biosynthetic locus of *Streptomyces flaveolus*; or a piperazic acid (Piz)-containing product accumulates within the microorganism.

In some embodiments, the method is carried out in the absence of $O_2$, substantially no $O_2$, or in the presence of low $O_2$.

In some embodiments, the piperazic acid (Piz)-containing product comprises a compound of formula:

(I)

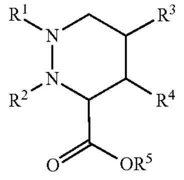

where: $R^5$ is a hydrogen, an alkyl, a piperazic acid, an acetyl, or a carboxyl protecting group; each $R^1$ and $R^2$ are independently selected from hydrogen or an amino protecting group, wherein $R^1$ and $R^2$ may be taken together to form a fused bicyclic or tricyclic amino protecting group; or each $R^3$ and $R^4$ are independently selected from a hydrogen, a halo (e.g., a chloro, a fluoro, a bromo, a iodo), or hydroxyl. In some embodiments, $R^1$ and $R^2$ are not simultaneously hydrogen.

In some embodiments, the piperazic acid (Piz)-containing product is used as a starting material in the synthesis of a bioactive Piz-containing composition selected from the group consisting of: (i) an antibacterial agent, an antibiotic agent, an antitumor agent, an antiviral agent, an immunomodulatory agent, or an anti-inflammatory agent; (ii) a molecular probe, anticancer drug, or drug lead; (iii) a metalloprotease inhibitor, a caspase inhibitor, an angiotensin converting enzyme (ACE) inhibitor, an inflammatory peptide C5a antagonist, an oxytocin receptor antagonist, or a matylastin type-IV collagenase inhibitor; (iv) a dehydropiperazic acid; a chloropiperazic acid; a hydroxypiperazic acid; a monamycin, an aurantimycin, an antrimycin, an azinothricin, a luzopeptin, a kettapeptin, a quinoxapeptin, a lydiamycin, a piperazimycin, or a sangamide; or (v) sanglifehrin A, pandanamide A, azinothricin, Sch392583, luzopeptin A, kutzernide 2, piperazic acid, L-piperazic acid, antrimycin, kettapeptin, GE3, A83586C, chloptosin, himastatin, luzopeptin, quinoxapeptin, lydiamycin, piperazimycin, sanglifehrin, sangamide NVP018, sangamide NVP019, sanglifehrin, Sch 382583; chloptosin, himastatin, verucopeptin, luzopeptin A, L-156,602, aurantimycin A, or L-156,373.

Another aspect of the present disclosure provides for a composition comprising a radiolabeled piperazic acid-containing product or a pharmaceutically acceptable salt, solvate, or polymorph thereof, including all tautomers and stereoisomers thereof, optionally in combination with one or more pharmaceutically acceptable excipients.

Another aspect of the present disclosure provides for a method comprising a process for preparation of a radiolabeled piperazic acid-containing product comprising: (i) providing a radiolabeled $N^5$—OH-Ornithine or derivative thereof; (ii) providing a suitable $N^5$—OH Ornithine cyclase/dehydratase; or (iii) optionally, buffer salts, a NADPH cofactor, $Fe^{+2}$ salts, and a catalytic Flavin Adenine Dinucleotide (FAD) cofactor.

In some embodiments, the method comprises: (i) providing a radiolabeled ornithine or a derivative thereof; or (ii) providing a suitable ornithine $N^5$ hydroxylase.

In some embodiments, (i) the radiolabeled $N^5$—OH-Ornithine or derivative thereof is an enantiopure radiolabeled L-Ornithine or derivative thereof; (ii) the enzyme comprising $N^5$—OH Ornithine cyclase/dehydratase is L-$N^5$—OH Ornithine cyclase/dehydratase or the enzyme PzbB; or (iii) the enzyme comprising ornithine $N^5$ hydroxylase is a L-ornithine $N^5$—OHase or the enzyme PzbA.

In some embodiments, the method comprises a coupled enzyme assay.

Another aspect of the present disclosure provides for a method of detecting radiolabeled piperazic acid-containing product. In some embodiments, the method comprises: (i) providing a microorganism; (ii) contacting the microorganism with a radiolabeled piperazic acid-containing product; or (iii) detecting a radiolabeled natural product, a radiolabeled biocatalysis product, or a radiolabeled metabolite.

Another aspect of the present disclosure provides for a the radiolabeled piperazic acid-containing product is: (i) labeled for use as a biologically active molecular probe as a drug discovery agent; or (ii) labeled for use in detecting a natural product drug lead compound.

Another aspect of the present disclosure provides for a piperazic acid (Piz)-containing product comprises: (i) a single radiolabel; (ii) a radiolabel selected from the group consisting of $^2H$ (D or deuterium), $^3H$ (T or tritium), $^{11}C$, $^{13}C$, $^{14}C$, $^{13}N$, $^{15}N$, $^{15}O$, $^{17}O$, $^{18}O$, $^{18}F$, $^{35}S$, $^{36}Cl$, $^{82}Sr$, $^{75}Br$, $^{78}Br$, $^{77}Br$, $^{123}I$, $^{124}$, $^{125}I$, and $^{131}I$; (iii) a radiolabel selected from the group consisting of $^{15}N$, $^{13}C$, and $^2H$; or (iv) a radiolabeled L-Piz or L-Piz derivative.

In some embodiments, the composition can be used in mass spectrometry, gamma imaging, magnetic resonance imaging, magnetic resonance spectroscopy, or fluorescence spectroscopy.

Other objects and features will be in part apparent and in part pointed out hereinafter.

DESCRIPTION OF THE DRAWINGS

Those of skill in the art will understand that the drawings, described below, are for illustrative purposes only. The drawings are not intended to limit the scope of the present teachings in any way.

DETAILED DESCRIPTION OF THE INVENTION

Figure 1A:
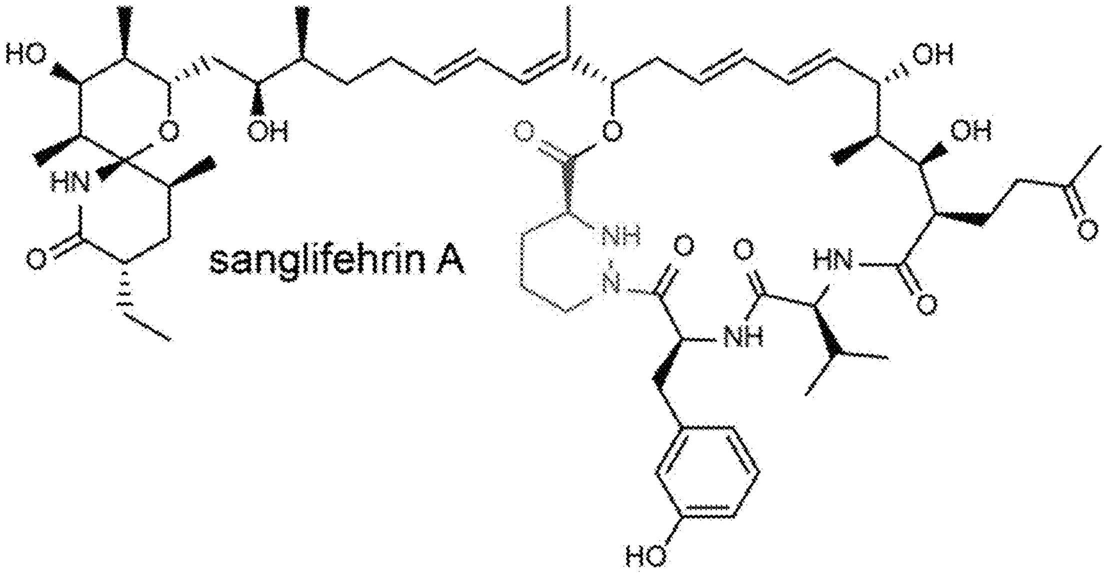
FIG. 1A-FIG. 1C is a series of chemical structures showing examples of piperazic acid (Piz) family natural products sanglifehrin and padanamide A (FIG. 1A), luzopeptin A and Sch392583 (FIG. 1B), and azinthricin and kutzneride 2 (FIG. 1C). Piz and modified Piz (dehydropiperazic, chloropiperazic and hydroxypiperazic acid) molecular components are shown. All of these molecules are bioactive, with sanglifehrin under consideration as an immunosuppressant and Hepatitis-C antiviral. The small molecule in Sch 382583 is a member of an emerging group of Piz containing metalloprotease inhibitors with clinical relevance as metastatic cancer and antibacterial antibiotic leads. All of these molecules are currently thought to be exclusively produced by actinobacteria.
Figure 1A:
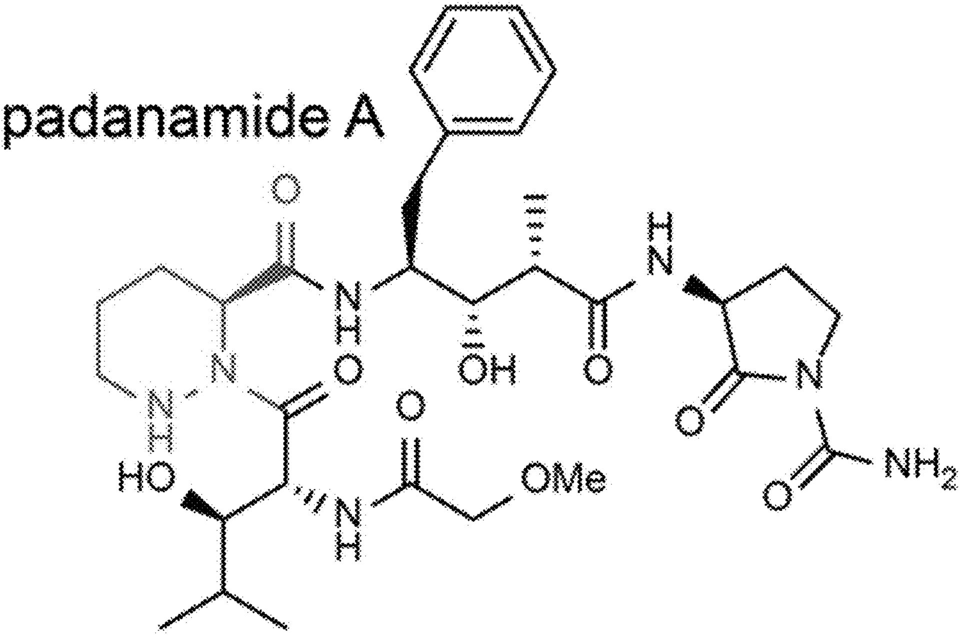

The present disclosure is based, at least in part, on the discovery of a complete biosynthetic pathway to L-Piz from the central metabolite L-Orn (the complete biosynthetic pathway not previously known). As shown herein, the present disclosure provides for biological and biochemical production of enantiopure L-piperazic acid. For example, the present disclosure provides for in vitro coupled enzyme assay furnished L-Piz or $d_7$-L-Piz. As another example, the present disclosure provides for in vivo L-Piz production using genetically engineered *S. lividans* (natively containing pzbA-gene, pzbB engineered), and data indicating incorporation of L-Piz in L-Piz containing sanglifehrin.

Advantages of the methods as described herein include a more cost-effective method of producing L-Piz; the methods as described herein avoid the multi-step synthetic processes currently known in the art; the enzyme catalysts are typically stereospecific providing enantiopure products.

One aspect of the present disclosure provides for green biocatalysis of L-Piz in vitro, where no organic solvents and fewer reagents are used (see e.g., Example 2). Another aspect of the present disclosure provides an enzymatic route to heavy isotope-labelled Piz (see e.g., Example 3). Another aspect of the present disclosure provides green biocatalysis of L-Piz in vivo (see e.g., Example 4). Another aspect of the present disclosure provides Directed discovery of drugs and drug-like compounds using heavy isotope L-Piz (see e.g., Example 5). The processes as described herein enable a more efficient and less expensive means to produce L-Piz or isotopically labeled L-Piz. Also provided herein are genes or enzymes encoding Piz production.

Piperazic Acid-Containing Products

As described herein, piperazic acid (Piz)-containing products can be produced using a biochemical or biological approach.

A piperazic acid (Piz)-containing product can be piperazic acid or a derivative thereof (e.g., L-piperazic acid (L-Piz)).

Piperazic acid (Piz) (aka hexahydropyridazine-3-carboxylic acid) is a nonproteinogenic amino acid that contains a characteristic and biochemically unusual N—N bond.

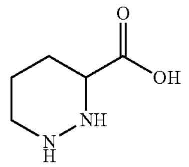

hexahydropyridazine-3-carboxylic acid

Piz is a proline structural mimic, and Piz-containing compounds are of significant interest for drug discovery. Piz itself is not bioactive, but peptidic compounds incorporating Piz as a building block include antibacterial, antiviral, immunomodulatory, and anticancer drug leads (see e.g., Oelke et al. 2011 Nat. Prod. Rep. (28) 1445-1471. Especially therapeutically interesting are Piz-containing metalloprotease inhibitors for drugging bacterial N-formylpeptidases, validated targets for antibiotic development. Intriguingly, all known naturally-occurring Piz containing compounds discovered thus far are bioactive. Beyond Piz natural products (i.e., naturally occurring compounds produced by live organisms), synthetic chemists are attracted to Piz as a synthetic building block for incorporation into drug-like compounds, molecular probes, and the like. As described herein, there are many bioactive piperazic acid-containing products.

For example, a piperazic acid-containing product can be any product comprising a piperazic acid, piperazic acid moiety, a piperazic acid dipeptide fragment, or a derivative thereof.

In some embodiments, a piperazic acid-containing product can be Piz, L-Piz, a Piz derivative, a modified Piz, or a Piz-containing compound. For example, a Piz-containing compound or Piz derivative-containing compound can be:

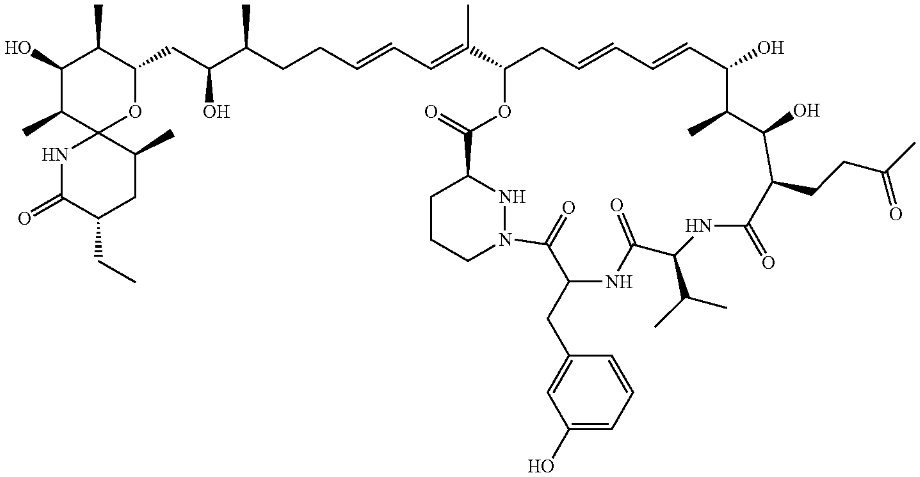

Sanglifehrin A

-continued
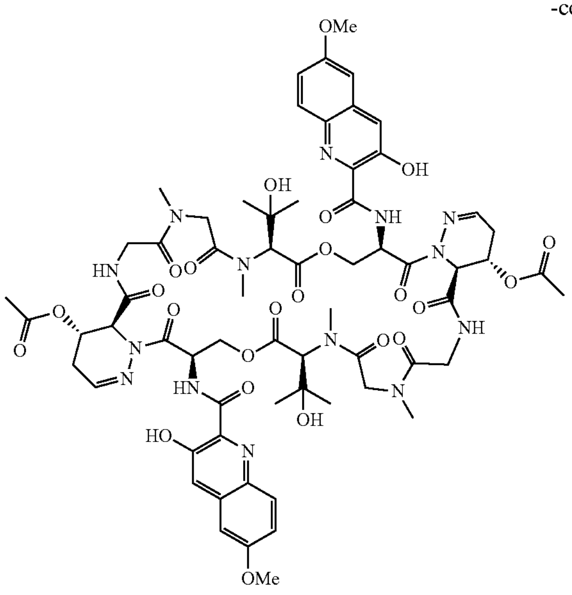
luzopeptin A
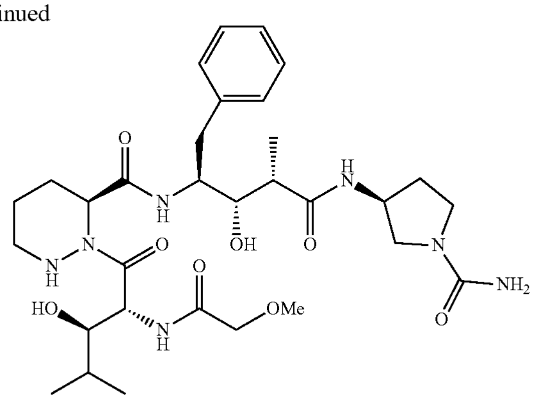
padanamide A
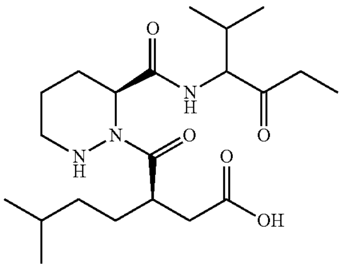
Sch392583
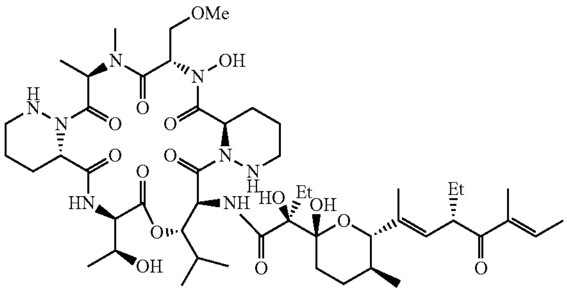
azinothricin
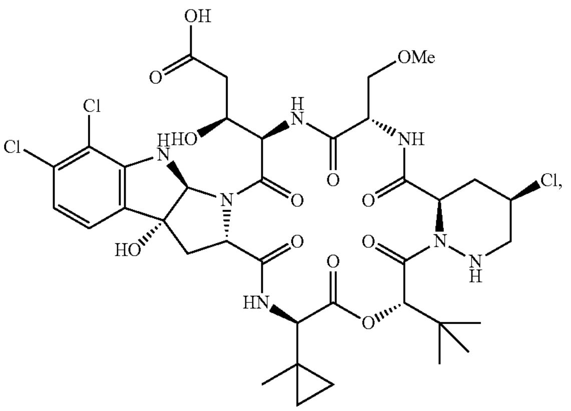
kutzneride 2
As another example, a Piz derivative can be a dehydropiperazic acid, a chloropiperazic acid, or a hydroxypiperazic acid. As another example, a Piz derivative can be sanglifehrin or Sch 382583.

As another example, a Piz derivative can be:

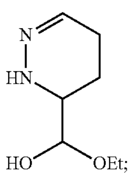
;
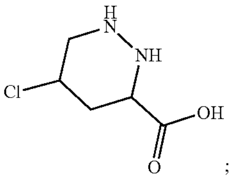
;
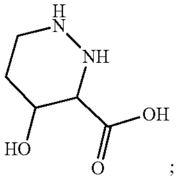
;

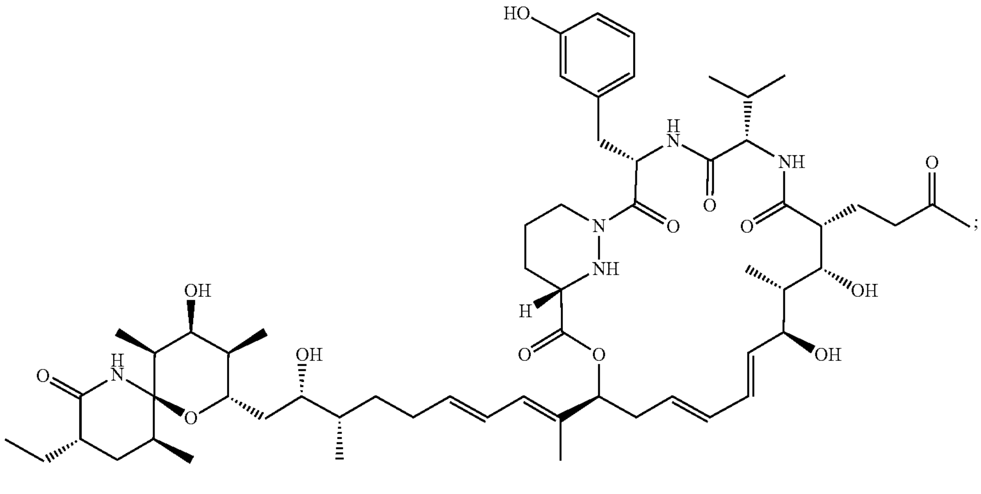
;

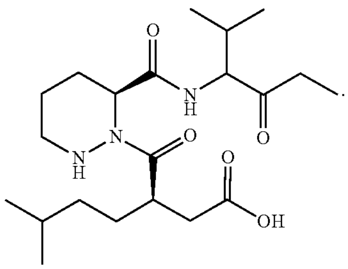
.

or

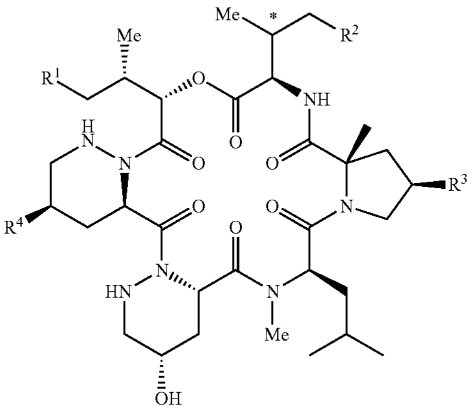

A starting material comprising Piz or a Pi-z derivative (e.g., L-Piz) can be a useful reagent for expanding chemical space in small molecule library, molecular analog construction, and molecular probes.

Previous synthetic routes (see e.g., U.S. Pat. No. 6,632,942, incorporated herein by reference) have a lower yield (~80%) than the processes as described herein (~100%). Furthermore, the previous methods require multi-step synthetic procedures (6 steps).

As an example, a Piz-containing product can be a monamycin. Exemplary monomycins are shown below.

| Compound | $R^1$ | $R^2$ | $R^3$ | $R^4$ |
|---|---|---|---|---|
| Monamycin A | H | H | Me | H |
| Monamycin $B_1$ | H | H | Me | H |
| Monamycin $B_2$ | H | Me | H | H |
| Monamycin $B_3$ | Me | H | H | H |
| Monamycin C | Me | H | Me | H |
| Monamycin $D_1$ | Me | H | Me | H |
| Monamycin $D_2$ | H | Me | Me | H |
| Monamycin E | Me | Me | Me | H |
| Monamycin F | Me | Me | Me | H |
| Monamycin $G_1$ | H | H | Me | Cl |

-continued

| Compound | $R^1$ | $R^2$ | $R^3$ | $R^4$ |
|---|---|---|---|---|
| Monamycin $G_2$ | H | Me | H | Cl |
| Monamycin $G_3$ | Me | H | H | Cl |
| Monamycin $H_1$ | Me | H | Me | Cl |
| Monamycin $H_2$ | H | Me | Me | Cl |
| Monamycin I | Me | Me | Me | Cl |

As another example, a Piz-containing product can be an antrimycin. Exemplary antrimycins are shown below.

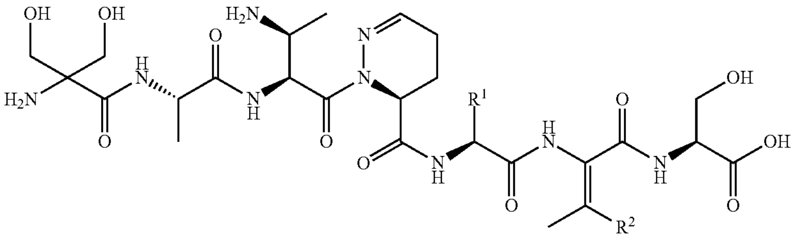

| Compound | $R^1$ | $R^2$ |
|---|---|---|
| Antrimycin A | Me | Et |
| Antrimycin B | Et | Et |
| Antrimycin C | n-Pr | Et |
| Antrimycin D | i-Bu | Et |
| Antrimycin Av | Me | Me |
| Antrimycin Bv | Et | Me |
| Antrimycin Cv | n-Pr | Me |
| Antrimycin Dv | i-Bu | Me |

As another example, a Piz-containing product can be an azinothricin. Exemplary azinothricins are shown below.

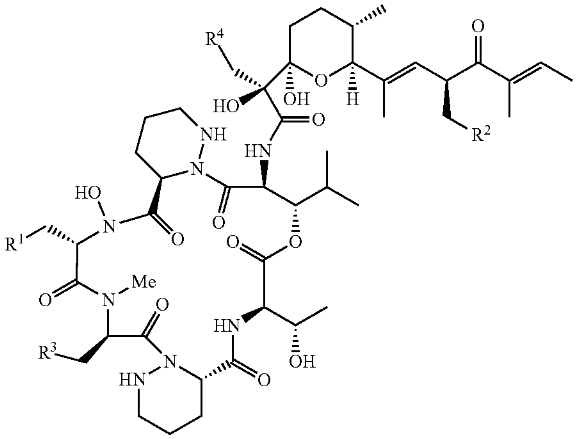

| Compound | $R^1$ | $R^2$ | $R^3$ | $R^4$ |
|---|---|---|---|---|
| Azinothricin | OMe | Me | H | Me |
| Kettapeptin | OMe | H | H | Me |
| A38586C | H | H | H | Me |
| GE3 | H | H | i-Pr | H |

As another example, a Piz-containing product can be chloptosin or himastatin.

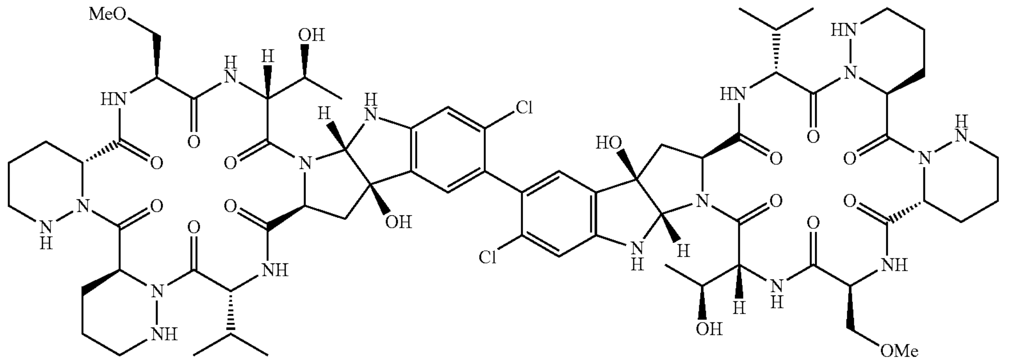
Chloptosin
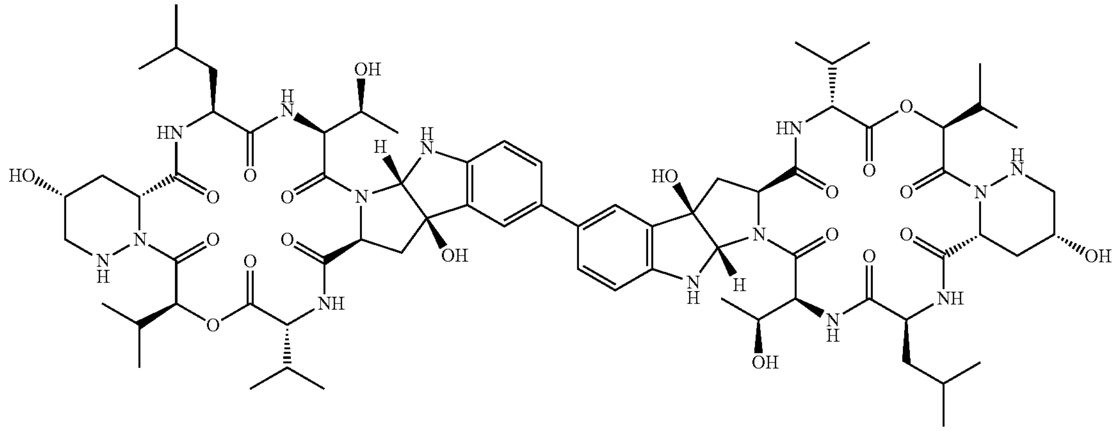
Himastatin
As another example, a Piz-containing product can be a luzopeptin or a quinoxapeptin. Exemplary luzopeptins and quinoxapeptins are shown below.
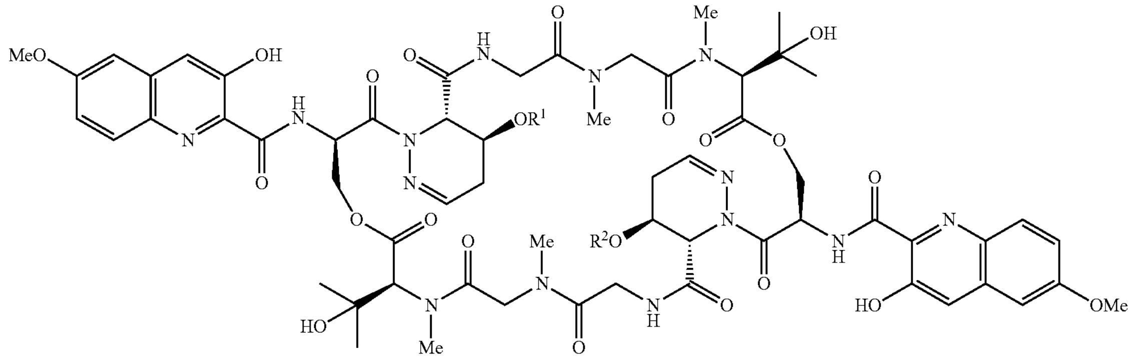
| Compound | $R^1$ | $R^2$ |
|---|---|---|
| Luzopeptin A | Ac | Ac |
| Luzopeptin B | H | Ac |
| Luzopeptin C | H | H |

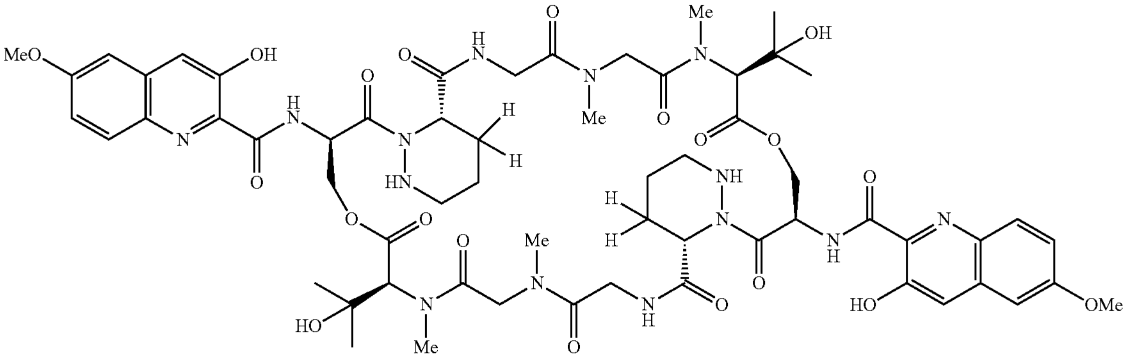

Luzopeptin E2

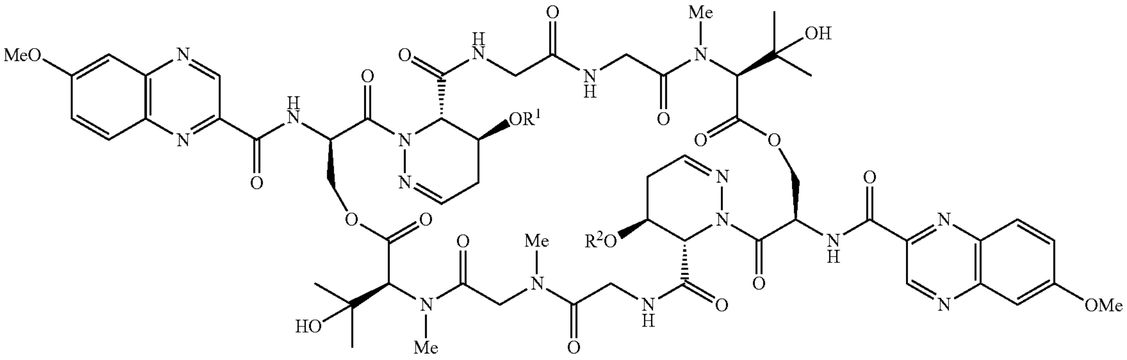

| Compound | $R^1$ | $R^2$ |
|---|---|---|
| Quinoxapeptin A | 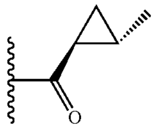 [SMILES: *C(=O)[C@H]1C[C@@H]1C] | 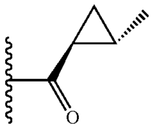 [SMILES: *C(=O)[C@H]1C[C@@H]1C] |
| Quinoxapeptin B | Ac | 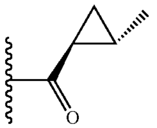 [SMILES: *C(=O)[C@H]1C[C@@H]1C] |
| Quinoxapeptin C | H | H |

As another example, a Piz-containing product can be a lydiamycin. Exemplary lydiamycins are shown below.

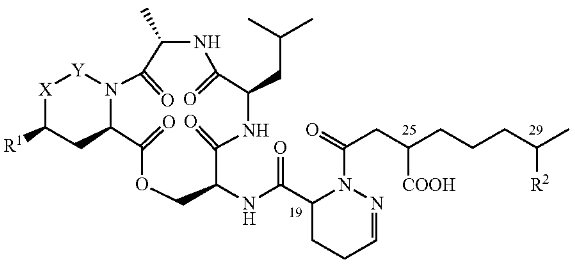

| Compound | $R^1$ | $R^2$ | X—Y |
|---|---|---|---|
| Lydiamycin A | H | H | $CH_2$—NH |
| Lydiamycin B | OH | H | $CH_2$—NH |
| Lydiamycin C | H | H | CH = N |
| Lydiamycin D | OH | OH | $CH_2$—NH |

As another example, a Piz-containing product can be a piperazimycin. Exemplary piperazimycins are shown below.

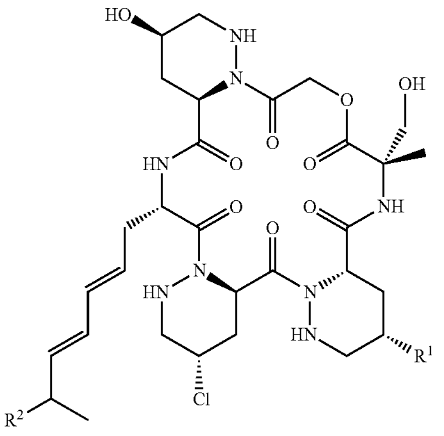
| Compound | $R^1$ | $R^2$ |
|---|---|---|
| Piperazimycin A | OH | Me |
| Piperazimycin B | H | Me |
| Piperazimycin C | OH | Et |
As another example, a Piz-containing product can be a sanglifehrin. Exemplary sanglifehrins are shown below.
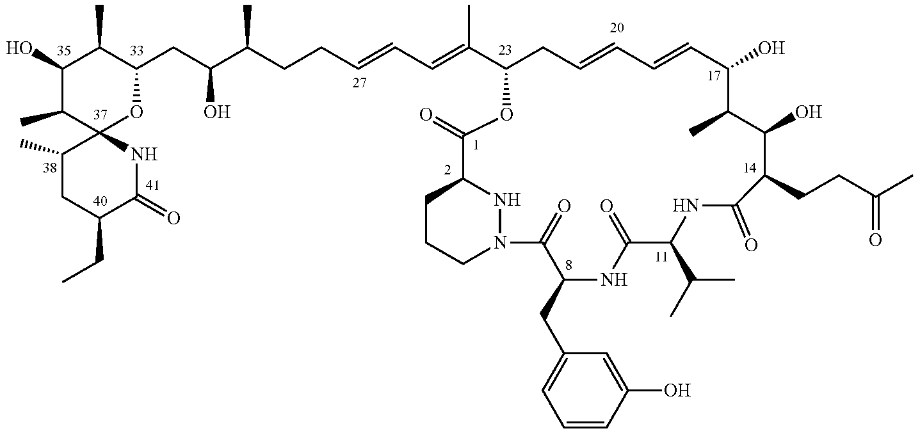
Sanglifehrin A
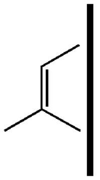
Sanglifehrin B: C35/C36
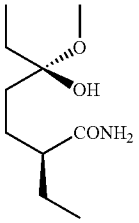
Sanglifehrin E: C38/C42

-continued

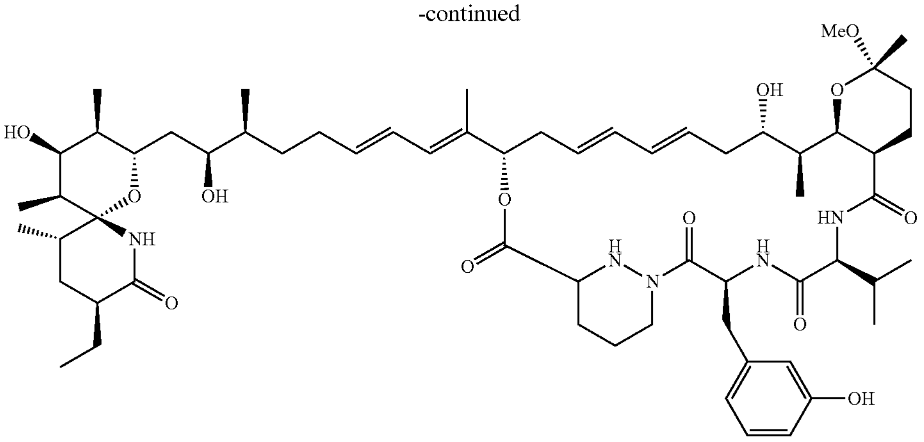

Sanglifehrin C

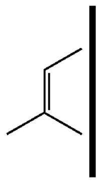

Sanglifehrin D: C35/C36

Piperazic acid-containing products can be antibacterial, antiviral, immunomodulatory, or anticancer drug leads. Piperazic acid-containing products can be caspase (apoptosis, cytokine activation) inhibitors, angiotensin converting enzyme (ACE) inhibitors, anti-inflammatory agents (e.g., sanglifehrin), antitumor antibiotics (e.g., azinothricin, verucopeptin, himastatin, luzopeptin A, immunosuppressants (e.g., L-156,602 an inflammatory peptide C5a antagonist), antibiotics (e.g., Aurantimycin A (inhibits Gram-positive bacteria growth), monamycins), oxytocin receptor antagonist (e.g., L-156,373) (modulate behaviors), or Matylastin type-IV collagenase inhibitors. Piperazic acid-containing products can be antivirals (e.g., sangamides NVP018, NVP019 against chronic Hepatitis B).

In some embodiments the Piz-containing product can have the formula:

(I)

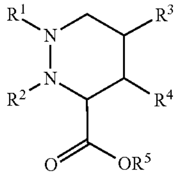

wherein: $R^5$ is a hydrogen, alkyl, a piperazic acid, acetyl, or carboxyl protecting group; and each $R^1$ and $R^2$ are independently selected from hydrogen or an amino protecting group, wherein $R^1$ and $R^2$ may be taken together to form a fused bicyclic or tricyclic amino protecting group; and each $R^3$ and $R^4$ are independently selected from hydrogen, halo (e.g., chloro, fluoro, etc.), or hydroxyl.

R groups (e.g., $R^1$, $R^2$, $R^3$, $R^4$, $R^5$) or formula (I) can be optionally substituted with one or more groups independently selected from the group consisting of hydroxyl; hydroxyl; amine; $C_{1-10}$carboxylic acid; $C_{1-10}$carboxyl; straight chain or branched $C_{1-10}$alkyl, optionally containing unsaturation; a $C_{2-6}$ cycloalkyl optionally containing unsaturation or one oxygen or nitrogen atom; straight chain or branched $C_{1-10}$alkyl amine; heterocyclyl; heterocyclic amine; and aryl comprising a phenyl; heteroaryl containing from 1 to 4 N, O, or S atoms; unsubstituted phenyl ring; substituted phenyl ring; unsubstituted heterocyclyl; and substituted heterocyclyl, wherein the unsubstituted phenyl ring or substituted phenyl ring can be optionally substituted with one or more groups independently selected from the group consisting of hydroxyl; $C_{1-10}$alkyl hydroxyl; amine; $C_{1-10}$carboxylic acid; $C_{1-10}$carboxyl, straight chain or branched $C_{1-10}$alkyl, optionally containing unsaturation; straight chain or branched $C_{1-10}$alkyl amine, optionally containing unsaturation; a $C_{2-6}$ cycloalkyl optionally containing unsaturation or one oxygen or nitrogen atom; straight chain or branched $C_{1-10}$alkyl amine; heterocyclyl; heterocyclic amine; aryl comprising a phenyl; and heteroaryl containing from 1 to 4 N, O, or S atoms; and the unsubstituted heterocyclyl or substituted heterocyclyl can be optionally substituted with one or more groups independently selected from the group consisting of hydroxyl; $C_{1-10}$alkyl hydroxyl; amine; $C_{1-10}$carboxylic acid; $C_{1-10}$carboxyl, straight chain or branched $C_{1-10}$alkyl, optionally containing unsaturation; straight chain or branched $C_{1-10}$alkyl amine, optionally containing unsaturation; a $C_{2-6}$cycloalkyl optionally containing unsaturation or one oxygen or nitrogen atom; heterocyclyl; straight chain or branched $C_{1-10}$alkyl amine; heterocyclic amine; and aryl comprising a phenyl; and heteroaryl containing from 1 to 4 N, O, or S atoms.

The term "imine" or "imino", as used herein, unless otherwise indicated, includes a functional group or chemical compound containing a carbon-nitrogen double bond. The expression "imino compound", as used herein, unless otherwise indicated, refers to a compound that includes an "imine" or an "imino" group as defined herein.

The term "hydroxyl", as used herein, unless otherwise indicated, includes —OH.

The terms "halogen" and "halo", as used herein, unless otherwise indicated, include a chlorine, chloro, Cl; fluorine, fluoro, F; bromine, bromo, Br; or iodine, iodo, or I.

The term "aryl", as used herein, unless otherwise indicated, include a carbocyclic aromatic group. Examples of aryl groups include, but are not limited to, phenyl, benzyl, naphthyl, or anthracenyl.

The terms "amine" and "amino", as used herein, unless otherwise indicated, include a functional group that contains a nitrogen atom with a lone pair of electrons and wherein one or more hydrogen atoms have been replaced by a substituent such as, but not limited to, an alkyl group or an aryl group.

The term "alkyl", as used herein, unless otherwise indicated, includes saturated monovalent hydrocarbon radicals having straight or branched moieties, such as but not limited to, methyl, ethyl, propyl, butyl, pentyl, hexyl, octyl groups, etc. Representative straight-chain lower alkyl groups include, but are not limited to, -methyl, -ethyl, -n-propyl, -n-butyl, -n-pentyl, -n-hexyl, -n-heptyl and -n-octyl; while branched lower alkyl groups include, but are not limited to, -isopropyl, -sec-butyl, -isobutyl, -tert-butyl, -isopentyl, 2-methylbutyl, 2-methylpentyl, 3-methylpentyl, 2,2-dimethylbutyl, 2,3-dimethylbutyl, 2,2-dimethylpentyl, 2,3-dimethylpentyl, 3,3-dimethylpentyl, 2,3,4-trimethylpentyl, 3-methylhexyl, 2,2-dimethylhexyl, 2,4-dimethylhexyl, 2,5-dimethylhexyl, 3,5-dimethylhexyl, 2,4-dimethylpentyl, 2-methylheptyl, 3-methylheptyl, unsaturated $C_1$-$C_8$alkyls include, but are not limited to, -vinyl, -allyl, -1-butenyl, -2-butenyl, -isobutylenyl, -1-pentenyl, -2-pentenyl, -3-methyl-1-butenyl, -2-methyl-2-butenyl, -2,3-dimethyl-2-butenyl, 1-hexyl, 2-hexyl, 3-hexyl, -acetylenyl, -propynyl, -1-butynyl, -2-butynyl, -1-pentynyl, -2-pentynyl, or -3-methyl-1 butynyl. An alkyl can be saturated, partially saturated, or unsaturated.

The term "carboxyl", as used herein, unless otherwise indicated, includes a functional group consisting of a carbon atom double bonded to an oxygen atom and single bonded to a hydroxyl group (—COOH).

The term "alkenyl", as used herein, unless otherwise indicated, includes alkyl moieties having at least one carbon-carbon double bond wherein alkyl is as defined above and including E and Z isomers of said alkenyl moiety. An alkenyl can be partially saturated or unsaturated.

The term "alkynyl", as used herein, unless otherwise indicated, includes alkyl moieties having at least one carbon-carbon triple bond wherein alkyl is as defined above. An alkynyl can be partially saturated or unsaturated.

The term "acyl", as used herein, unless otherwise indicated, includes a functional group derived from an aliphatic carboxylic acid, by removal of the hydroxyl (—OH) group.

The term "alkoxyl", as used herein, unless otherwise indicated, includes O-alkyl groups wherein alkyl is as defined above and 0 represents oxygen. Representative alkoxyl groups include, but are not limited to, —O-methyl, —O-ethyl, —O-n-propyl, —O-n-butyl, —O-n-pentyl, —O-n-hexyl, —O-n-heptyl, —O-n-octyl, —O-isopropyl, —O-sec-butyl, —O-isobutyl, —O-tert-butyl, —O-isopentyl, —O-2-methylbutyl, —O-2-methylpentyl, —O-3-methylpentyl, —O-2,2-dimethylbutyl, —O-2,3-dimethylbutyl, —O-2,2-dimethylpentyl, —O-2,3-dimethylpentyl, —O-3,3-dimethylpentyl, —O-2,3,4-trimethyl pentyl, —O-3-methylhexyl, —O-2,2-dimethylhexyl, —O-2,4-dimethylhexyl, —O-2,5-dimethylhexyl, —O-3,5-dimethylhexyl, —O-2,4dimethylpentyl, —O-2-methylheptyl, —O-3-methylheptyl, —O-vinyl, —O-allyl, —O-1-butenyl, —O-2-butenyl, —O-isobutylenyl, —O-1-pentenyl, —O-2-pentenyl, —O-3-methyl-1-butenyl, —O-2-methyl-2-butenyl, —O-2,3-dimethyl-2-butenyl, —O-1-hexyl, —O-2-hexyl, —O-3-hexyl, —O-acetylenyl, —O-propynyl, —O-1-butynyl, —O-2-butynyl, —O-1-pentynyl, —O-2-pentynyl and —O-3-methyl-1-butynyl, —O-cyclopropyl, —O-cyclobutyl, —O-cyclopentyl, —O-cyclohexyl, —O-cycloheptyl, —O-cyclooctyl, —O-cyclononyl and —O-cyclodecyl, —O—$CH_2$-cyclopropyl, —O—$CH_2$-cyclobutyl, —O—$CH_2$-cyclopentyl, —O—$CH_2$-cyclohexyl, —O—$CH_2$-cycloheptyl, —O—$CH_2$-cyclooctyl, —O—$CH_2$-cyclononyl, —O—$CH_2$-cyclodecyl, —O—$(CH_2)_2$-cyclopropyl, —O—$(CH_2)_2$-cyclobutyl, —O—$(CH_2)_2$-cyclopentyl, —O—$(CH_2)_2$-cyclohexyl, —O—$(CH_2)_2$-cycloheptyl, —O—$(CH_2)_2$-cyclooctyl, —O—$(CH_2)_2$-cyclononyl, or —O—$(CH_2)_2$-cyclodecyl. An alkoxyl can be saturated, partially saturated, or unsaturated.

The term "cycloalkyl", as used herein, unless otherwise indicated, includes a non-aromatic, saturated, partially saturated, or unsaturated, monocyclic or fused, spiro or unfused bicyclic or tricyclic hydrocarbon referred to herein containing a total of from 3 to 10 carbon atoms, preferably 3 to 8 ring carbon atoms. Examples of cycloalkyls include, but are not limited to, $C_3$-$C_8$ cycloalkyl groups include, but are not limited to, -cyclopropyl, -cyclobutyl, -cyclopentyl, -cyclopentadienyl, -cyclohexyl, -cyclohexenyl, -1,3-cyclohexadienyl, -1,4-cyclohexadienyl, -cycloheptyl, -1,3-cycloheptadienyl, -1,3,5-cycloheptatrienyl, -cyclooctyl, and -cyclooctadienyl.

The term "cycloalkyl" also includes -lower alkyl-cycloalkyl, wherein lower alkyl and cycloalkyl are as defined herein. Examples of -lower alkyl-cycloalkyl groups include, but are not limited to, —$CH_2$-cyclopropyl, —$CH_2$-cyclobutyl, —$CH_2$-cyclopentyl, —$CH_2$-cyclopentadienyl, —$CH_2$-cyclohexyl, —$CH_2$-cycloheptyl, or —$CH_2$-cyclooctyl.

The term "heterocyclic", as used herein, unless otherwise indicated, includes an aromatic or non-aromatic cycloalkyl in which one to four of the ring carbon atoms are independently replaced with a heteroatom from the group consisting of O, S and N. Representative examples of a heterocycle include, but are not limited to, benzofuranyl, benzothiophene, indolyl, benzopyrazolyl, coumarinyl, isoquinolinyl, pyrrolyl, pyrrolidinyl, thiophenyl, furanyl, thiazolyl, imidazolyl, pyrazolyl, triazolyl, quinolinyl, pyrimidinyl, pyridinyl, pyridonyl, pyrazinyl, pyridazinyl, isothiazolyl, isoxazolyl, (1,4)-dioxane, (1,3)-dioxolane, 4,5-dihydro-1H-imidazolyl, or tetrazolyl. Heterocycles can be substituted or unsubstituted. Heterocycles can also be bonded at any ring atom (i.e., at any carbon atom or heteroatom of the heterocyclic ring). A heterocyclic can be saturated, partially saturated, or unsaturated.

The term "cyano", as used herein, unless otherwise indicated, includes a —CN group.

The term "alcohol", as used herein, unless otherwise indicated, includes a compound in which the hydroxyl functional group (—OH) is bound to a carbon atom. In particular, this carbon center should be saturated, having single bonds to three other atoms.

The term "solvate" is intended to mean a solvate form of a specified compound that retains the effectiveness of such compound. Examples of solvates include compounds of the invention in combination with, for example: water, isopropanol, ethanol, methanol, dimethylsulfoxide (DMSO), ethyl acetate, acetic acid, or ethanolamine.

The term "mmol", as used herein, is intended to mean millimole. The term "equiv", as used herein, is intended to mean equivalent. The term "mL", as used herein, is intended to mean milliliter. The term "g", as used herein, is intended to mean gram. The term "kg", as used herein, is intended to mean kilogram. The term "μg", as used herein, is intended to mean micrograms. The term "h", as used herein, is intended to mean hour. The term "min", as used herein, is intended to mean minute. The term "M", as used herein, is intended to mean molar. The term "μL", as used herein, is intended to mean microliter. The term "μM", as used herein, is intended to mean micromolar. The term "nM", as used herein, is intended to mean nanomolar. The term "N", as used herein, is intended to mean normal. The term "amu", as used herein, is intended to mean atomic mass unit. The term "° C.", as used herein, is intended to mean degree Celsius. The term "wt/wt", as used herein, is intended to mean weight/weight. The term "v/v", as used herein, is intended to mean volume/volume. The term "MS", as used herein, is intended to mean mass spectroscopy. The term "HPLC", as used herein, is intended to mean high performance liquid chromatograph. The term "RT", as used herein, is intended to mean room temperature. The term "e.g.", as used herein, is intended to mean example. The term "N/A", as used herein, is intended to mean not tested.

As used herein, the expression "pharmaceutically acceptable salt" refers to pharmaceutically acceptable organic or inorganic salts of a compound of the invention. Preferred salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, or pamoate (i.e., 1,1'-methylene-bis-(2-hydroxy-3-naphthoate)) salts. A pharmaceutically acceptable salt may involve the inclusion of another molecule such as an acetate ion, a succinate ion or other counterion. The counterion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counterions. Hence, a pharmaceutically acceptable salt can have one or more charged atoms and/or one or more counterion. As used herein, the expression "pharmaceutically acceptable solvate" refers to an association of one or more solvent molecules and a compound of the invention. Examples of solvents that form pharmaceutically acceptable solvates include, but are not limited to, water, isopropanol, ethanol, methanol, DMSO, ethyl acetate, acetic acid, and ethanolamine. As used herein, the expression "pharmaceutically acceptable hydrate" refers to a compound of the invention, or a salt thereof, that further includes a stoichiometric or non-stoichiometric amount of water bound by non-covalent intermolecular forces.

Host

The host genetically engineered to accumulate a Piz compound can be any microorganism. One aspect of the present disclosure is directed to a transgenic microorganism engineered to accumulate L-piperazic acid (L-Piz). As described herein, a microorganism can be used in the biosynthesis of piperazic acid and piperazic acid derivatives. Exemplary microorganisms that can be engineered to accumulate Piz or Piz containing compounds include, but are not limited to, bacteria (e.g., actinobacteria, proteobacteria) or fungi (e.g., yeast).

As described herein, the microorganism can be a bacterium. In some embodiments, the microorganism can be in the Phylum, Actinobacteria or Proteobacteria. Any actinobacteria or proteiobacteria with native pzBA or pzbB genes can be suitable for use as a heterologous host.

Exemplary Proteobacteria that can be used in the biosynthesis of piperazic acid or piperazic acid derivatives can be *Collimonas* (a divergent member of the gram negative Burkholderiales). As an example, the *Collimonas* can be of the species *Collimonas arenas; Collimonas fungivorans+, Collimonas pratensis; Collimonas* sp. 16.2.3; *Collimonas* sp. 16.2.7; *Collimonas* sp. 16.3.1; *Collimonas* sp. 5.15; *Collimonas* sp. 8.2.7; *Collimonas* sp. A6AGF; *Collimonas* sp. A6ATD5, *Collimonas* sp. A9 1b-26a, *Collimonas* sp. AASATF; *Collimonas* sp. AD101, *Collimonas* sp. AD102, *Collimonas* sp. AD103, *Collimonas* sp. AD137; *Collimonas* sp. AD19; *Collimonas* sp. AD23; *Collimonas* sp. AD33; *Collimonas* sp. AD58; *Collimonas* sp. AD59; *Collimonas* sp. AD60, *Collimonas* sp. AD61; *Collimonas* sp. AD62; *Collimonas* sp. AD63; *Collimonas* sp. AD64; *Collimonas* sp. AD65; *Collimonas* sp. AD66; *Collimonas* sp. AD67; *Collimonas* sp. AD68; *Collimonas* sp. AD69; *Collimonas* sp. AD70, *Collimonas* sp. AD71; *Collimonas* sp. AD76; *Collimonas* sp. AD77; *Collimonas* sp. AD88; *Collimonas* sp. AD89; *Collimonas* sp. AD95; *Collimonas* sp. AD97; *Collimonas* sp. AD98; *Collimonas* sp. AD99; *Collimonas* sp. AR5(10), *Collimonas* sp. AR5(11), *Collimonas* sp. AR5(6), *Collimonas* sp. AS3(2), *Collimonas* sp. AS3(5), *Collimonas* sp. BJC15-A11; *Collimonas* sp. BJC15-A32; *Collimonas* sp. BPN72; *Collimonas* sp. BPN73; *Collimonas* sp. C2PN21; *Collimonas* sp. CB13, *Collimonas* sp. CB20, *Collimonas* sp. CT; *Collimonas* sp. CT_MP11E6, *Collimonas* sp. CT_MP11E8, *Collimonas* sp. CTO 113 b214; *Collimonas* sp. DEC-B5; *Collimonas* sp. ES3-61, *Collimonas* sp. F11, *Collimonas* sp. F14; *Collimonas* sp. GCM11, *Collimonas* sp. HPML71; *Collimonas* sp. HPN72; *Collimonas* sp. HPN73; *Collimonas* sp. III-15, *Collimonas* sp. III-27; *Collimonas* sp. III-32, *Collimonas* sp. III-35, *Collimonas* sp. III-47, *Collimonas* sp. III-48; *Collimonas* sp. III-5, *Collimonas* sp. III-9, *Collimonas* sp. IS343, *Collimonas* sp. ISO468_OTU1303; *Collimonas* sp. ISO613_OTU1303; *Collimonas* sp. IS0615_OTU1303; *Collimonas* sp. ISO616_OTU1303, *Collimonas* sp. 150644_OTU1303; *Collimonas* sp. ISO648_OTU1303; *Collimonas* sp. KN-1; *Collimonas* sp. KW19; *Collimonas* sp. M1Ju29; *Collimonas* sp. M1U16; *Collimonas* sp. M1U8, *Collimonas* sp. M1U9, *Collimonas* sp. MF3_1; *Collimonas* sp. MH6; *Collimonas* sp. MPS11E8, *Collimonas* sp. NAR2(8); *Collimonas* sp. NAR7(1); *Collimonas* sp. NAR7(12); *Collimonas* sp. NAR7(15); *Collimonas* sp. NAS7(14); *Collimonas* sp. NAS9(14); *Collimonas* sp. NBRC 3740; *Collimonas* sp. NCCB 100027; *Collimonas* sp. RE1; *Collimonas* sp. RX265; *Collimonas* sp. S2U21, *Collimonas* sp. S2U31, *Collimonas* sp. S3.TSA.015, *Collimonas* sp. S5.ACT.019, *Collimonas* sp. S5.CEL.014, *Collimonas* sp. S5.TSA.011, *Collimonas* sp. S5.TSA.20, *Collimonas* sp. UR 9-06; *Collimonas* sp. wged101, *Collimonas* sp. wged148; *Collimonas* sp. wged41, *Collimonas* sp. wged45; *Collimonas* sp. wged84; *Collimonas* sp. wged96; or *Collimonas* sp. ZL261.

Exemplary Actinomycetes that can be used in the biosynthesis of piperazic acid or piperazic acid derivatives can be *Actinoalloteichus, Actinomadura, Actinosynnema, Amycolatopsis, Frankia, Kibdelosporangium, Kutzneria, Lentzea,*

*Mycobacterium, Pseudonocardia, Rhodococcus, Salinispora, Streptacidiphilus*, or *Streptomyces*. These exemplary Actinomycetes are known to have strains with native pzbB, which would indicate that they can be heterologous hosts for Piz or Piz derivative production.

As described herein, an Actinobacteria that can be used in the biosynthesis of piperazic acid or piperazic acid derivatives can be of the genus *Actinoalloteichus*. As an example, the *Actinoalloteichus* can be of the species *Actinoalloteichus alkalophilus; Actinoalloteichus cyanogriseus* F, *Actinoalloteichus hymeniacidonis; Actinoalloteichus nanshanensis; Actinoalloteichus* sp. 10-82; *Actinoalloteichus* sp. 2216-6; *Actinoalloteichus* sp. 3BG8; *Actinoalloteichus* sp. AH97; *Actinoalloteichus* sp. CA; *Actinoalloteichus* sp. CA1, *Actinoalloteichus* sp. FXJ7.260; *Actinoalloteichus* sp. JAJ70, *Actinoalloteichus* sp. JAJ71; *Actinoalloteichus* sp. L2004; *Actinoalloteichus* sp. MA-32; *Actinoalloteichus* sp. MHA15, *Actinoalloteichus* sp. NPS-702; *Actinoalloteichus* sp. QA116; *Actinoalloteichus* sp. SH18(2011), *Actinoalloteichus* sp. SHA6; *Actinoalloteichus* sp. TRM46408; *Actinoalloteichus* sp. TS1127-17, *Actinoalloteichus* sp. WH1-2216-6; or *Actinoalloteichus spitiensis*+.

As described herein, an Actinobacteria that can be used in the biosynthesis of piperazic acid or piperazic acid derivatives can be of the genus *Actinomadura*. As an example, the *Actinomadura* can be of the species *Actinomadura alba; Actinomadura apis; Actinomadura atramentaria+; Actinomadura bangladeshensis; Actinomadura catellatispora; Actinomadura chibensis+; Actinomadura chokoriensis; Actinomadura citrea; Actinomadura coerulea; Actinomadura cremea+; Actinomadura echinospora; Actinomadura fibrosa; Actinomadura flavalba+; Actinomadura formosensis+; Actinomadura fulvescens; Actinomadura geliboluensis; Actinomadura glauciflava+; Actinomadura hallensis; Actinomadura hibisca+; Actinomadura keratinilytica; Actinomadura kijaniata+; Actinomadura latina+; Actinomadura livida; Actinomadura luteofluorescens; Actinomadura macra+; Actinomadura madurae+; Actinomadura maheshkhaliensis; Actinomadura melliaura; Actinomadura meridians; Actinomadura mexicana; Actinomadura meyerae; Actinomadura miaoliensis; Actinomadura namibiensis; Actinomadura napierensis; Actinomadura nitritigenes; Actinomadura ochracea; Actinomadura oligospora+; Actinomadura pelletieri+; Actinomadura rifamycini+; Actinomadura rubrobrunea+; Actinomadura rudentiformis; Actinomadura rugatobispora; Actinomadura rupiterrae; Actinomadura scrupuli; Actinomadura sediminis; Actinomadura* sp.; *Actinomadura* sp. 10-124; *Actinomadura* sp. 10-44; *Actinomadura* sp. 13670A; *Actinomadura* sp. 13679C; *Actinomadura* sp. 171712; *Actinomadura* sp. 171810; *Actinomadura* sp. 171812; *Actinomadura* sp. 171817; *Actinomadura* sp. 171824; *Actinomadura* sp. 171828; *Actinomadura* sp. 171839; *Actinomadura* sp. 171848; *Actinomadura* sp. 171849; *Actinomadura* sp. 172301; *Actinomadura* sp. 172301y, *Actinomadura* sp. 172302a, *Actinomadura* sp. 172315; *Actinomadura* sp. 172320; *Actinomadura* sp. 172512; *Actinomadura* sp. 1A01698; *Actinomadura* sp. 1g12710, *Actinomadura* sp. 21G792, *Actinomadura* sp. 2602GPT1-42; *Actinomadura* sp. 28a-59-3; *Actinomadura* sp. 28a-77-2; *Actinomadura* sp. 2EPS; *Actinomadura* sp. 3-196; *Actinomadura* sp. 306D04; *Actinomadura* sp. 3196; *Actinomadura* sp. 322C06; *Actinomadura* sp. 322G01; *Actinomadura* sp. 334D05; *Actinomadura* sp. 334E07; *Actinomadura* sp. 337H02; *Actinomadura* sp. 387B311; *Actinomadura* sp. 387H07; *Actinomadura* sp. 392-1; *Actinomadura* sp. 40007; *Actinomadura* sp. 40008; *Actinomadura* sp. 413D10; *Actinomadura* sp. 413F04; *Actinomadura* sp. 413G02; *Actinomadura* sp. 415A12; *Actinomadura* sp. 418H03; *Actinomadura* sp. 419B09; *Actinomadura* sp. 428G07; *Actinomadura* sp. 43-45-3; *Actinomadura* sp. 431D03; *Actinomadura* sp. 431D09, *Actinomadura* sp. 6192; *Actinomadura* sp. 8-104; *Actinomadura* sp. A16; *Actinomadura* sp. A17; *Actinomadura* sp. AC104; *Actinomadura* sp. AF-555; *Actinomadura* sp. AML286; *Actinomadura* sp. AML34; *Actinomadura* sp. AML691; *Actinomadura* sp. AMS667; *Actinomadura* sp. ANSum10; *Actinomadura* sp. ART34; *Actinomadura* sp. ART64; *Actinomadura* sp. AV1; *Actinomadura* sp. AW310; *Actinomadura* sp. BK148; *Actinomadura* sp. CAP 48; *Actinomadura* sp. CC 0580; *Actinomadura* sp. CNQ-052_SD01; *Actinomadura* sp. CNT-075_SF06; *Actinomadura* sp. CNU-125 PL04; *Actinomadura* sp. CNU125 PL04; *Actinomadura* sp. CPCC201357; *Actinomadura* sp. CPCC202697; *Actinomadura* sp. DLS-42; *Actinomadura* sp. DLS-70; *Actinomadura* sp. DNK540; *Actinomadura* sp. E6; *Actinomadura* sp. EGI 80046; *Actinomadura* sp. EGI 80170; *Actinomadura* sp. EHA-2; *Actinomadura* sp. ERI-11; *Actinomadura* sp. EXM-24-2; *Actinomadura* sp. EXM-7-1; *Actinomadura* sp. EYN-10-1; *Actinomadura* sp. EYN-4-5; *Actinomadura* sp. FIM95-F26; *Actinomadura* sp. FXJ1.340; *Actinomadura* sp. FXJ6.213; *Actinomadura* sp. FXJ6.337; *Actinomadura* sp. FXJ7.135; *Actinomadura* sp. FXJ7.250; *Actinomadura* sp. FZ04; *Actinomadura* sp. G08C011; *Actinomadura* sp. GD15; *Actinomadura* sp. GKU 128; *Actinomadura* sp. GKU 147; *Actinomadura* sp. GKU 154; *Actinomadura* sp. GKU 157; *Actinomadura* sp. GKU 505; *Actinomadura* sp. GKU 822; *Actinomadura* sp. GMKU359; *Actinomadura* sp. H590; *Actinomadura* sp. I43-1; *Actinomadura* sp. ID05-A0321; *Actinomadura* sp. IM-1232; *Actinomadura* sp. IM-1290; *Actinomadura* sp. IM-2953; *Actinomadura* sp. IM-3046; *Actinomadura* sp. IM-3889; *Actinomadura* sp. IM-5243; *Actinomadura* sp. IM-5508; *Actinomadura* sp. IM-5556; *Actinomadura* sp. IM-5929; *Actinomadura* sp. IM-6226; *Actinomadura* sp. IM-6793; *Actinomadura* sp. IM-6830; *Actinomadura* sp. IM-6847; *Actinomadura* sp. IM-6849; *Actinomadura* sp. IM-6891; *Actinomadura* sp. IM-6895; *Actinomadura* sp. IM-6933; *Actinomadura* sp. IM-6993; *Actinomadura* sp. IM-7012; *Actinomadura* sp. IM-7044; *Actinomadura* sp. IM-7045; *Actinomadura* sp. IM-7056; *Actinomadura* sp. IM-7057; *Actinomadura* sp. IM-7092; *Actinomadura* sp. IM-7177; *Actinomadura* sp. IM-7187; *Actinomadura* sp. IM-7212; *Actinomadura* sp. IM-7213; *Actinomadura* sp. IM-7214; *Actinomadura* sp. IM-7222; *Actinomadura* sp. IM-7258; *Actinomadura* sp. IM-7397; *Actinomadura* sp. IM-7435; *Actinomadura* sp. IM-8473; *Actinomadura* sp. J4S16; *Actinomadura* sp. J4S4; *Actinomadura* sp. J5S1, *Actinomadura* sp. J5S10, *Actinomadura* sp. J5S17; *Actinomadura* sp. JCM 4674; *Actinomadura* sp. JSM 082016; *Actinomadura* sp. K22T, *Actinomadura* sp. KC-IT-F8; *Actinomadura* sp. KC-IT-H5; *Actinomadura* sp. L1958; *Actinomadura* sp. L2003; *Actinomadura* sp. L2097; *Actinomadura* sp. L2187; *Actinomadura* sp. LZ95; *Actinomadura* sp. M23; *Actinomadura* sp. M9; *Actinomadura* sp. MD49; *Actinomadura* sp. MNPostmon14; *Actinomadura* sp. MSSRFDF8; *Actinomadura* sp. NEAU-Jh1-3; *Actinomadura* sp. NEAU-Jh2-5; *Actinomadura* sp. new-30-5s-4-2; *Actinomadura* sp. new-30-5s-4-5; *Actinomadura* sp. NN236; *Actinomadura* sp. NN242; *Actinomadura* sp. NTRHn4; *Actinomadura* sp. OS1-43; *Actinomadura* sp. OS3-82; *Actinomadura* sp. OS3-83; *Actinomadura* sp. OS3-87; *Actinomadura* sp. OS3-89; *Actinomadura* sp. P3829; *Actinomadura* sp. P3842; *Actinomadura* sp. P3874; *Actinomadura* sp. PM2091; *Actinomadura* sp. PMPostmon12;

*Actinomadura* sp. PN409; *Actinomadura* sp. PN414; *Actinomadura* sp. PN4221; *Actinomadura* sp. PN4222; *Actinomadura* sp. PN4223; *Actinomadura* sp. PN4226; *Actinomadura* sp. PN425; *Actinomadura* sp. Postmonl3; *Actinomadura* sp. QAP 98-328-1842; *Actinomadura* sp. R-Ac152; *Actinomadura* sp. R10-32; *Actinomadura* sp. R16-14; *Actinomadura* sp. R17-27; *Actinomadura* sp. R39; *Actinomadura* sp. RD001933; *Actinomadura* sp. RK2_75; *Actinomadura* sp. RK59; *Actinomadura* sp. RK75; *Actinomadura* sp. RK79; *Actinomadura* sp. RS-52; *Actinomadura* sp. RtIII23; *Actinomadura* sp. RtIII29; *Actinomadura* sp. RtIV13; *Actinomadura* sp. RtIV2; *Actinomadura* sp. RY35-68; *Actinomadura* sp. S14; *Actinomadura* sp. S19-10; *Actinomadura* sp. 519-13; *Actinomadura* sp. S2; *Actinomadura* sp. S20-30; *Actinomadura* sp. SBMs009; *Actinomadura* sp. SBSK-502; *Actinomadura* sp. Shinshu-MS-02; *Actinomadura* sp. Shinshu-MS-03; *Actinomadura* sp. SK74; *Actinomadura* sp. SpB081030SC-15; *Actinomadura* sp. SpC090624GE_01; *Actinomadura* sp. SR-43; *Actinomadura* sp. T16-1; *Actinomadura* sp. T355; *Actinomadura* sp. T5513; *Actinomadura* sp. T555; *Actinomadura* sp. TCA62003; *Actinomadura* sp. TF1; *Actinomadura* sp. TFS 1144; *Actinomadura* sp. TFS 1200; *Actinomadura* sp. TFS 455; *Actinomadura* sp. TP-A0878; *Actinomadura* sp. UKMCC_L29; *Actinomadura* sp. VAN305; *Actinomadura* sp. WMMB 441; *Actinomadura* sp. WMMB 499; *Actinomadura* sp. WMMB 616; *Actinomadura* sp. XM-11-5; *Actinomadura* sp. XM-17-1; *Actinomadura* sp. XM-17-10; *Actinomadura* sp. XM-17-11; *Actinomadura* sp. XM-17-12; *Actinomadura* sp. XM-17-13; *Actinomadura* sp. XM-17-2; *Actinomadura* sp. XM-17-3; *Actinomadura* sp. XM-17-4; *Actinomadura* sp. XM-17-5; *Actinomadura* sp. XM-17-6; *Actinomadura* sp. XM-17-7; *Actinomadura* sp. XM-17-8; *Actinomadura* sp. XM-18-9; *Actinomadura* sp. XM-24-1; *Actinomadura* sp. XM-24-10; *Actinomadura* sp. XM-24-11, *Actinomadura* sp. XM-24-12; *Actinomadura* sp. XM-24-13; *Actinomadura* sp. XM-24-14; *Actinomadura* sp. XM-24-15; *Actinomadura* sp. XM-24-2; *Actinomadura* sp. XM-24-3; *Actinomadura* sp. XM-24-4; *Actinomadura* sp. XM-24-5; *Actinomadura* sp. XM-24-7; *Actinomadura* sp. XM-24-8; *Actinomadura* sp. XM-24-9; *Actinomadura* sp. XM-4-3; *Actinomadura* sp. XM-4-4; *Actinomadura* sp. XM-7-1; *Actinomadura* sp. XM-7-2; *Actinomadura* sp. XMU188; *Actinomadura* sp. Y218; *Actinomadura* sp. YIM 48842; *Actinomadura* sp. YIM 61608; *Actinomadura* sp. YIM 65605; *Actinomadura* sp. YIM 65650; *Actinomadura* sp. YIM 65655; *Actinomadura* sp. YIM 65659; *Actinomadura* sp. YIM 65663; *Actinomadura* sp. YIM 65810; *Actinomadura* sp. YIM 75700; *Actinomadura* sp. YIM 77502; *Actinomadura* sp. YIM 77510; *Actinomadura* sp. YIM M 10855; *Actinomadura* sp. YIM M 11143; *Actinomadura* sp. YIM M 11219; *Actinomadura* sp. YIM M11072; *Actinomadura* sp. YIM M11327; *Actinomadura* sp. YN-10-4; *Actinomadura* sp. YN-5-3; *Actinomadura* sp. YN-5-4; *Actinomadura* sp. YN-6-4; *Actinomadura* sp. YN-7-1; *Actinomadura* sp. YN-7-10; *Actinomadura* sp. YN-7-11; *Actinomadura* sp. YN-7-12; *Actinomadura* sp. YN-7-13; *Actinomadura* sp. YN-7-2; *Actinomadura* sp. YN-7-3; *Actinomadura* sp. YN-7-6; *Actinomadura* sp. YN-7-7; *Actinomadura* sp. YN-7-8; *Actinomadura* sp. YN-7-9; *Actinomadura* sp. YN-8-11; *Actinomadura* sp. ZZY-2013; *Actinomadura sputi+; Actinomadura umbrina; Actinomadura verrucosospora; Actinomadura vinacea; Actinomadura viridilutea; Actinomadura viridis; Actinomadura vulgaris+; Actinomadura xylanilytica; Actinomadura yumaensis*+; or *Excellospora japonica.*

As described herein, an *Actinobacteria* that can be used in the biosynthesis of piperazic acid or piperazic acid derivatives can be of the genus *Actinosynnema*. As an example, the *Actinosynnema* can be of the species *Actinosynnema mirum* or *Actinosynnema pretiosum.*

As described herein, an Actinobacteria that can be used in the biosynthesis of piperazic acid or piperazic acid derivatives can be of the genus *Amycolatopsis*. As an example, the *Amycolatopsis* can be of the species *Amycolatopsis alba; Amycolatopsis albidoflavus; Amycolatopsis azures; Amycolatopsis balhimycina; Amycolatopsis coloradensis; Amycolatopsis decaplanina; Amycolatopsis eurytherma; Amycolatopsis fastidiosa; Amycolatopsis japonica; Amycolatopsis kentuckyensis; Amycolatopsis keratiniphila; Amycolatopsis lexingtonensis; Amycolatopsis lurida; Amycolatopsis mediterranei; Amycolatopsis methanolica; Amycolatopsis orientalis; Amycolatopsis palatopharyngis; Amycolatopsis pretoriensis; Amycolatopsis rubida; Amycolatopsis rugosa; Amycolatopsis sacchari; Amycolatopsis sulphurea; Amycolatopsis thermoflava; Amycolatopsis tolypomycina*; or *Amycolatopsis vancoresmycina.*

As described herein, an Actinobacteria that can be used in the biosynthesis of piperazic acid or piperazic acid derivatives can be of the genus *Frankia*. As an example, the *Frankia* can be of the species *Frankia brunchorstii* or *Frankia subtilis.*

As described herein, an Actinobacteria that can be used in the biosynthesis of piperazic acid or piperazic acid derivatives can be of the genus *Kibdelosporangium*. As an example, the *Kibdelosporangium* can be of the species *Kibdelosporangium albatum, Kibdelosporangium aridum*; or *Kibdelosporangium philippinense.*

As described herein, an Actinobacteria that can be used in the biosynthesis of piperazic acid or piperazic acid derivatives can be of the genus *Lentzea*. As an example, the *Lentzea* can be of the species *Lentzea albida; Lentzea albidocapillata; Lentzea californiensis; Lentzea flaviverrucosa; Lentzea jiangxiensis; Lentzea kentuckyensis; Lentzea* sp. 132; *Lentzea* sp. 173316; *Lentzea* sp. 173591; *Lentzea* sp. 173892; *Lentzea* sp. 18-3; *Lentzea* sp. 4_C7_44; *Lentzea* sp. 4_C7_58; *Lentzea* sp. 7887; *Lentzea* sp. 84741; *Lentzea* sp. ACT-0091; *Lentzea* sp. BJ36; *Lentzea* sp. DHS C013; *Lentzea* sp. G-MN-1; *Lentzea* sp. GP0204; *Lentzea* sp. 108A-00410; *Lentzea* sp. IMER-B1-1; *Lentzea* sp. IR11-RCA120; *Lentzea* sp. KLBMP 1096; *Lentzea* sp. LM 058; *Lentzea* sp. LM 121; *Lentzea* sp. mCFU23; *Lentzea* sp. ML457-mF8; *Lentzea* sp. MS-15; *Lentzea* sp. MS-20; *Lentzea* sp. MS-5; *Lentzea* sp. MS6, *Lentzea* sp. SAUK6214; *Lentzea* sp. YIM 48827; *Lentzea* sp. YIM 48828; *Lentzea* sp. YIM 65117; *Lentzea* sp. YIM 75756; *Lentzea* sp. YIM 75760; *Lentzea* sp. YIM 75761; *Lentzea* sp. YIM 75778; *Lentzea* sp. YIM 75796; *Lentzea* sp. YM-11; *Lentzea* sp. YN-8-6; *Lentzea violacea*; or *Lentzea waywayandensis.*

As described herein, an Actinobacteria that can be used in the biosynthesis of piperazic acid or piperazic acid derivatives can be of the genus *Mycobacterium*. As an example, the *Mycobacterium* can be of the species *Mycobacterium abscessus; Mycobacterium africanum; Mycobacterium agri; Mycobacterium aichiense; Mycobacterium alvei; Mycobacterium arupense; Mycobacterium asiaticum; Mycobacterium aubagnense; Mycobacterium aurum; Mycobacterium austroafricanum; Mycobacterium avium+, Mycobacterium boenickei; Mycobacterium bohemicum, Mycobacterium bolletii; Mycobacterium botniense; Mycobacterium bovis+; Mycobacterium branded; Mycobacterium brisbanense; Mycobacterium brumae; Mycobacterium canariasense; Mycobacterium caprae; Mycobacterium celatum; Mycobacterium chelonae+; Mycobacterium*

*chimaera; Mycobacterium chitae; Mycobacterium chlorophenolicum; Mycobacterium chubuense; Mycobacterium colombiense; Mycobacterium conceptionense; Mycobacterium confluentis; Mycobacterium conspicuum; Mycobacterium cookie; Mycobacterium cosmeticum; Mycobacterium diernhoferi; Mycobacterium doricum; Mycobacterium duvalii; Mycobacterium elephantis; Mycobacterium; Mycobacterium farcinogenes; Mycobacterium flavescens; Mycobacterium florentinum; Mycobacterium fluoranthenivorans; Mycobacterium fortuitum+; Mycobacterium frederiksbergense; Mycobacterium gadium; Mycobacterium gastri; Mycobacterium genavense; Mycobacterium gilvum; Mycobacterium goodie; Mycobacterium gordonae; Mycobacterium haemophilum; Mycobacterium hassiacum; Mycobacterium heckeshornense; Mycobacterium heidelbergense; Mycobacterium hiberniae; Mycobacterium hodleri; Mycobacterium holsaticum; Mycobacterium houstonense; Mycobacterium immunogenum; Mycobacterium interjectum; Mycobacterium intermedium; Mycobacterium intracellulare; Mycobacterium kansasii; Mycobacterium komossense; Mycobacterium kubicae; Mycobacterium lacus; Mycobacterium lentiflavum; Mycobacterium leprae; Mycobacterium lepraemurium; Mycobacterium madagascariense; Mycobacterium mageritense; Mycobacterium malmoense; Mycobacterium marinum; Mycobacterium massiliense; Mycobacterium microti; Mycobacterium montefiorense; Mycobacterium moriokaense; Mycobacterium mucogenicum; Mycobacterium murale; Mycobacterium nebraskense; Mycobacterium neoaurum; Mycobacterium neworleansense; Mycobacterium nonchromogenicum; Mycobacterium novocastrense; Mycobacterium obuense; Mycobacterium palustre; Mycobacterium parafortuitum; Mycobacterium parascrofulaceum; Mycobacterium parmense; Mycobacterium peregrinum; Mycobacterium phlei; Mycobacterium phocaicum; Mycobacterium pinnipedii; Mycobacterium porcinum; Mycobacterium poriferae; Mycobacterium pseudoshottsii; Mycobacterium psychrotolerans; Mycobacterium pulveris; Mycobacterium pyrenivorans; Mycobacterium rhodesiae; Mycobacterium saskatchewanense; Mycobacterium scrofulaceurium, Mycobacterium senegalense; Mycobacterium septicum; Mycobacterium shimoidei; Mycobacterium shottsii; Mycobacterium simiae; Mycobacterium smegmatis; Mycobacterium sphagni; Mycobacterium szulgai; Mycobacterium terrae; Mycobacterium thermoresistibile; Mycobacterium tokaiense; Mycobacterium triplex; Mycobacterium triviale; Mycobacterium tuberculosis+; Mycobacterium tusciae; Mycobacterium ulcerans; Mycobacterium vaccae; Mycobacterium vanbaalenii; Mycobacterium wolinskyi*; or *Mycobacterium xenopi.*

As described herein, an Actinobacteria that can be used in the biosynthesis of piperazic acid or piperazic acid derivatives can be of the genus *Pseudonocardia*. As an example, the *Pseudonocardia* can be of the species *Pseudonocardia alaniniphila; Pseudonocardia alni; Pseudonocardia asaccharolytica; Pseudonocardia aurantiaca; Pseudonocardia autotrophica; Pseudonocardia azures; Pseudonocardia benzenivorans; Pseudonocardia chloroethenivorans; Pseudonocardia compacta; Pseudonocardia halophobica; Pseudonocardia hydrocarbonoxydans; Pseudonocardia kongjuensis; Pseudonocardia nitrificans; Pseudonocardia petroleophila; Pseudonocardia saturnea; Pseudonocardia spinosa; Pseudonocardia spinosispora; Pseudonocardia sulfidoxydans; Pseudonocardia thermophile; Pseudonocardia xinjiangensis; Pseudonocardia yunnanensis*; or *Pseudonocardia zijingensis.*

As described herein, an Actinobacteria that can be used in the biosynthesis of piperazic acid or piperazic acid derivatives can be of the genus *Rhodococcus*. As an example, the *Rhodococcus* can be of the species *Rhodococcus luberonensis; Rhodococcus marchali; Rhodococcus perornatus; Rhodococcus rosaeluteae; Rhodococcus sariuoni; Rhodococcus spiraeae*; or *Rhodococcus turanicus.*

As described herein, an Actinobacteria that can be used in the biosynthesis of piperazic acid or piperazic acid derivatives can be of the genus *Salinispora*. As an example, the *Salinispora* can be of the species *Actinocatenispora; Actinoplanes; Amorphosporangium; Ampullariella; Asanoa; Catellatospora; Catenuloplanes; Couchioplanes; Dactylosporangium; Krasilnikovia; Longispora; Luedemannella; Micromonospora; Myceliochytrium; Pilimelia; Planopolyspora; Planosporangium; Polymorphospora; Salinispora; Spirilliplanes; Verrucosispora; Virgisporangium corrig.*

As described herein, an Actinobacteria that can be used in the biosynthesis of piperazic acid or piperazic acid derivatives can be of the genus *Streptacidiphilus*. As an example, the *Streptacidiphilus* can be of the species *Streptacidiphilus albus, Streptacidiphilus carbonis, Streptacidiphilus neutrinimicus, Streptacidiphilus anmyonensis, Streptacidiphilus durhamensis, Streptacidiphilus hamsterleyensis, Streptacidiphilus jiangxiensis, Streptacidiphilus melanogenes, Streptacidiphilus oryzae*, or *Streptacidiphilus rugosus.*

As described herein, an Actinobacteria that can be used in the biosynthesis of piperazic acid or piperazic acid derivatives can be of the genus *Streptomyces*. As an example, the *Streptomyces* can be of the species *Streptomyces coelicolor, S. lividans, S. albicans, S. griseus*, or *S. plicatosporus*. As another example, the Streptomyces can be of the species *Streptomyces abietis; Streptomyces abikoensis; Streptomyces aburaviensis; Streptomyces achromogenes, Streptomyces acidiscabies; Streptomyces actinomycinicus; Streptomyces acrimycini; Streptomyces actuosus; Streptomyces aculeolatus; Streptomyces abyssalis; Streptomyces afghaniensis; Streptomyces aidingensis; Streptomyces africanus; Streptomyces alanosinicus; Streptomyces albaduncus; Streptomyces albiaxialis; Streptomyces albidochromogenes, Streptomyces albiflavescens, Streptomyces albiflaviniger, Streptomyces albidoflavus; Streptomyces albofaciens; Streptomyces alboflavus; Streptomyces albogriseolus; Streptomyces albolongus; Streptomyces alboniger, Streptomyces albospinus; Streptomyces albulus; Streptomyces albus, Streptomyces aldersoniae Streptomyces alfalfae, Streptomyces alkaliphilus, Streptomyces alkalithermotolerans, Streptomyces almquistii, Streptomyces alni, Streptomyces althioticus, Streptomyces amakusaensis; Streptomyces ambofaciens; Streptomyces amritsarensis; Streptomyces anandii; Streptomyces angustmyceticus; Streptomyces anthocyanicus; Streptomyces antibioticus; Streptomyces antimycoticus; Streptomyces anulatus, Streptomyces aomiensis, Streptomyces araujoniae; Streptomyces ardus; Streptomyces arenae; Streptomyces armeniacus; Streptomyces artemisiae; Streptomyces arcticus; Streptomyces ascomycinicus; Streptomyces asiaticus; Streptomyces asterosporus; Streptomyces atacamensis; Streptomyces atratus; Streptomyces atriruber, Streptomyces atroolivaceus; Streptomyces atrovirens; Streptomyces aurantiacus; Streptomyces aurantiogriseus; Streptomyces auratus; Streptomyces aureocirculatus; Streptomyces aureofaciens; Streptomyces aureorectus; Streptomyces a ureoverticillatus; Streptomyces aureus; Streptomyces avellaneus; Streptomyces avermitilis; Streptomyces avicenniae; Streptomyces avidinii; Streptomyces axinellae; Streptomyces azureus; Streptomyces bacillaris; Streptomyces badius; Streptomyces*

*bambergiensis; Streptomyces bangladeshensis; Streptomyces baliensis; Streptomyces barkulensis; Streptomyces beijiangensis; Streptomyces bellus; Streptomyces bikiniensis; Streptomyces blastmyceticus; Streptomyces bluensis; Streptomyces bobili; Streptomyces bohaiensis; Streptomyces bottropensis; Streptomyces brasiliensis; Streptomyces brevispora; Streptomyces bullii, Streptomyces bungoensis; Streptomyces burgazadensis; Streptomyces cacaoi; Streptomyces caelestis; Streptomyces caeruleatus; Streptomyces calidiresistens; Streptomyces calvus; Streptomyces canarius; Streptomyces canchipurensis; Streptomyces candidus; Streptomyces cangkringensis; Streptomyces caniferus; Streptomyces canus; Streptomyces capillispiralis; Streptomyces capoamus; Streptomyces carpaticus; Streptomyces carpinensis; Streptomyces castelarensis; Streptomyces catbensis; Streptomyces catenulae; Streptomyces cavourensis; Streptomyces cellostaticus; Streptomyces celluloflavus; Streptomyces cellulolyticus; Streptomyces cellulosae; Streptomyces chartreusis; Streptomyces chattanoogensis; Streptomyces cheonanensis; Streptomyces chiangmaiensis; Streptomyces chrestomyceticus; Streptomyces chromofuscus; Streptomyces chryseus; Streptomyces chilikensis; Streptomyces chlorus; Streptomyces chumphonensis; Streptomyces cinereorectus; Streptomyces cinereoruber; Streptomyces cinereospinus; Streptomyces cinereus; Streptomyces cinerochromogenes; Streptomyces cinnabarinus; Streptomyces cinnamonensis; Streptomyces cinnamoneus; Streptomyces cirratus; Streptomyces ciscaucasicus; Streptomyces clavifer, Streptomyces clavuligerus; Streptomyces coacervatus; Streptomyces cocklensis; Streptomyces coelescens; Streptomyces coelicoflavus; Streptomyces coelicolor, Streptomyces coeruleoflavus; Streptomyces coeruleofuscus; Streptomyces coeruleoprunus; Streptomyces coeruleorubidus; Streptomyces coerulescens; Streptomyces collinus; Streptomyces colombiensis; Streptomyces corchorusii; Streptomyces costaricanus; Streptomyces cremeus; Streptomyces crystallinus; Streptomyces cuspidosporus; Streptomyces cyaneofuscatus; Streptomyces cyaneus; Streptomyces cyanoalbus; Streptomyces cyslabdanicus; Streptomyces daghestanicus; Streptomyces daliensi; Streptomyces deccanensis; Streptomyces decoyicus; Streptomyces demainii; Streptomyces deserti; Streptomyces diastaticus; Streptomyces diastatochromogenes; Streptomyces djakartensis; Streptomyces drozdowiczii; Streptomyces durhamensis; Streptomyces durmitorensis; Streptomyces echinatus; Streptomyces echinoruber, Streptomyces ederensis; Streptomyces emeiensis; Streptomyces endophyticus; Streptomyces endus; Streptomyces enissocaesilis; Streptomyces erythrogriseus; Streptomyces erringtonii; Streptomyces eurocidicus; Streptomyces europaeiscabiei; Streptomyces eurythermus; Streptomyces exfoliatus; Streptomyces fabs; Streptomyces fenghuangensis; Streptomyces ferralitis; Streptomyces filamentosus; Streptomyces fildesensis; Streptomyces filipinensis; Streptomyces fimbriatus; Streptomyces finlayi; Streptomyces flaveolus; Streptomyces flaveus; Streptomyces flavofungini; Streptomyces flavotricini; Streptomyces flavovariabilis; Streptomyces flavovirens; Streptomyces flavoviridis; Streptomyces fradiae; Streptomyces fragilis; Streptomyces fukangensis; Streptomyces fulvissimus; Streptomyces fulvorobeus; Streptomyces fumanus; Streptomyces fumigatiscleroticus; Streptomyces galbus; Streptomyces galilaeus; Streptomyces gancidicus; Streptomyces gardneri; Streptomyces gelaticus; Streptomyces geldanamycininus; Streptomyces geysiriensis; Streptomyces ghanaensis; Streptomyces gilvifuscus; Streptomyces glaucescens; Streptomyces glauciniger, Streptomyces glaucosporus; Streptomyces glaucus; Streptomyces globisporus; Streptomyces globosus; Streptomyces glomeratus; Streptomyces glomeroaurantiacus; Streptomyces glycovorans; Streptomyces Streptomyces goshikiensis; Streptomyces gougerotii; Streptomyces graminearus; Streptomyces gramineus; Streptomyces graminifolii; Streptomyces graminilatus; Streptomyces graminisoli; Streptomyces griseiniger, Streptomyces griseoaurantiacus; Streptomyces griseocarneus; Streptomyces griseochromogenes; Streptomyces griseoflavus; Streptomyces griseofuscus; Streptomyces griseoincarnatus; Streptomyces griseoloalbus; Streptomyces griseolus; Streptomyces griseoluteus; Streptomyces griseomycini; Streptomyces griseoplanus; Streptomyces griseorubens; Streptomyces griseoruber, Streptomyces griseorubiginosus; Streptomyces griseosporeus; Streptomyces griseostramineus; Streptomyces griseoviridis; Streptomyces griseus; Streptomyces guanduensis; Streptomyces gulbargensis; Streptomyces hainanensis; Streptomyces haliclonae; Streptomyces halophytocola; Streptomyces halstedii; Streptomyces harbinensis; Streptomyces hawaiiensis; Streptomyces hebeiensis; Streptomyces heilongjiangensis; Streptomyces heliomycini; Streptomyces helvaticus; Streptomyces herbaceus; Streptomyces herbaricolor; Streptomyces himastatinicus; Streptomyces hiroshimensis; Streptomyces hirsutus; Streptomyces hokutonensis; Streptomyces hoynatensis; Streptomyces humidus; Streptomyces humiferus; Streptomyces hundungensis; Streptomyces hyderabadensis; Streptomyces hygroscopicus; Streptomyces hypolithicus; Streptomyces iakyrus; Streptomyces iconiensis; Streptomyces incanus; Streptomyces indiaensis; Streptomyces indigoferus; Streptomyces indicus; Streptomyces indonesiensis; Streptomyces intermedius; Streptomyces inusitatus; Streptomyces Ipomoeae; Streptomyces iranensis; Streptomyces janthinus; Streptomyces jamaicensis; Streptomyces javensis; Streptomyces jietaisiensis; Streptomyces jiujiangensis; Streptomyces kaempferi; Streptomyces kanamyceticus; Streptomyces karpasiensis; Streptomyces kasugaensis; Streptomyces katrae; Streptomyces kebangsaanensis; Streptomyces klenkii; Streptomyces koyangensis; Streptomyces kunmingensis; Streptomyces kurssanovii; Streptomyces labedae; Streptomyces lacrimifluminis; Streptomyces lacticiproducens; Streptomyces laculatispora; Streptomyces lanatus; Streptomyces lannensis; Streptomyces lateritius; Streptomyces laurentii; Streptomyces lavendofoliae; Streptomyces lavendulae; Streptomyces lavenduligriseus; Streptomyces leeuwenhoekii; Streptomyces lavendulocolor, Streptomyces levis; Streptomyces libani; Streptomyces lienomycini; Streptomyces lilacinus; Streptomyces lincolnensis; Streptomyces litmocidini; Streptomyces litoralis; Streptomyces lomondensis; Streptomyces longisporoflavus; Streptomyces longispororuber, Streptomyces lopnurensis; Streptomyces longisporus; Streptomyces longwoodensis; Streptomyces lucensis; Streptomyces lunaelactis; Streptomyces lunalinharesii; Streptomyces luridiscabiei; Streptomyces luridus; Streptomyces lusitanus; Streptomyces lushanensis; Streptomyces luteireticuli; Streptomyces luteogriseus; Streptomyces luteosporeus; Streptomyces lydicus; Streptomyces macrosporus; Streptomyces malachitofuscus; Streptomyces malachitospinus; Streptomyces malaysiensis; Streptomyces mangrovi; Streptomyces murinus; Streptomyces marokkonensis; Streptomyces mashuensis; Streptomyces massasporeus; Streptomyces matensis; Streptomyces mayteni; Streptomyces mauvecolor, Streptomyces megasporus; Streptomyces melanogenes; Streptomyces melanosporofaciens; Streptomyces mexicanus; Streptomyces michiganensis; Streptomyces microflavus; Streptomyces milbemycinicus; Streptomyces minutiscleroticus; Streptomyces mirabilis; Streptomyces misakiensis; Streptomyces misionensis; Streptomyces moba-* raensis; Streptomyces monomycini; Streptomyces mordarskii; Streptomyces morookaense; Streptomyces muensis; Streptomyces murinus; Streptomyces mutabilis; Streptomyces mutomycini; Streptomyces naganishii; Streptomyces nanhaiensis; Streptomyces nanshensis; Streptomyces narbonensis; Streptomyces nashvillensis; Streptomyces netropsis; Streptomyces neyagawaensis; Streptomyces niger, Streptomyces nigrescens; Streptomyces nitrosporeus; Streptomyces niveiciscabiei; Streptomyces niveiscabiei; Streptomyces niveoruber, Streptomyces niveus; Streptomyces noboritoensis; Streptomyces nodosus; Streptomyces nogalater, Streptomyces nojiriensis; Streptomyces noursei; Streptomyces novaecaesareae; Streptomyces ochraceiscleroticus; Streptomyces olivaceiscleroticus; Streptomyces olivaceoviridis; Streptomyces olivaceus; Streptomyces olivicoloratus; Streptomyces olivochromogenes; Streptomyces olivomycini; Streptomyces olivoverticillatus; Streptomyces omiyaensis; Streptomyces osmaniensis; Streptomyces orinoci; Streptomyces pactum; Streptomyces panacagri; Streptomyces panaciradicis; Streptomyces paradoxus; Streptomyces parvulus; Streptomyces parvus; Streptomyces pathocidins; Streptomyces paucisporeus; Streptomyces peucetius; Streptomyces phaeochromogenes; Streptomyces phaeofaciens; Streptomyces phaeogriseichromatogenes; Streptomyces phaeoluteichromatogenes; Streptomyces phaeoluteigriseus; Streptomyces phaeopurpureus; Streptomyces pharetrae; Streptomyces pharmamarensis; Streptomyces phytohabitans; Streptomyces pilosus; Streptomyces platensis; Streptomyces plicatus; Streptomyces plumbiresistens; Streptomyces pluricolorescens; Streptomyces pluripotens; Streptomyces polyantibioticus; Streptomyces polychromogenes; Streptomyces polygonati; Streptomyces polymachus; Streptomyces poonensis; Streptomyces prasinopilosus; Streptomyces prasinosporus; Streptomyces prasinus; Streptomyces pratens; Streptomyces pratensis; Streptomyces prunicolor, Streptomyces psammoticus; Streptomyces pseudoechinosporeus; Streptomyces pseudogriseolus; Streptomyces pseudovenezuelae; Streptomyces pulveraceus; Streptomyces puniceus; Streptomyces puniciscabiei; Streptomyces purpeofuscus; Streptomyces purpurascens; Streptomyces purpureus; Streptomyces purpurogeneiscleroticus; Streptomyces qinglanensis; Streptomyces racemochromogenes; Streptomyces radiopugnans; Streptomyces rameus; Streptomyces ramulosus; Streptomyces rapamycinicus; Streptomyces recifensis; Streptomyces rectiviolaceus; Streptomyces regensis; Streptomyces resistomycificus; Streptomyces reticuliscabiei; Streptomyces rhizophilus; Streptomyces rhizosphaericus; Streptomyces rimosus; Streptomyces rishiriensis; Streptomyces rochei; Streptomyces rosealbus; Streptomyces roseiscleroticus; Streptomyces roseofulvus; Streptomyces roseolilacinus; Streptomyces roseolus; Streptomyces roseosporus; Streptomyces roseoviolaceus; Streptomyces roseoviridis; Streptomyces ruber, Streptomyces rubidus; Streptomyces rubiginosohelvolus; Streptomyces rubiginosus; Streptomyces rubrisoli; Streptomyces rubrogriseus; Streptomyces rubrus; Streptomyces rutgersensis; Streptomyces samsunensis; Streptomyces sanglieri; Streptomyces sannanensis; Streptomyces sanyensis; Streptomyces sasae; Streptomyces scabiei; Streptomyces scabrisporus; Streptomyces sclerotialus; Streptomyces scopiformis; Streptomyces scopuliridis; Streptomyces sedi; Streptomyces seoulensis; Streptomyces seranimatus; Streptomyces seymenliensis; Streptomyces shaanxiensis; Streptomyces shenzhenensis; Streptomyces showdoensis; Streptomyces silaceus; Streptomyces sindenensis; Streptomyces sioyaensis; Streptomyces smyrnaeus; Streptomyces sodiiphilus; Streptomyces somaliensis; Streptomyces sudanensis; Streptomyces sparsogenes; Streptomyces sparsus; Streptomyces specialis; Streptomyces spectabilis; Streptomyces speibonae; Streptomyces speleomycini; Streptomyces spinoverrucosus; Streptomyces spiralis; Streptomyces spiroverticillatus; Streptomyces spongiae; Streptomyces spongficola; Streptomyces sporocinereus; Streptomyces sporoclivatus; Streptomyces spororaveus; Streptomyces sporoverrucosus; Streptomyces staurosporininus; Streptomyces stelliscabiei; Streptomyces stramineus; Streptomyces subrutilus; Streptomyces sulfonofaciens; Streptomyces sulphureus; Streptomyces sundarbansensis; Streptomyces synnematoformans; Streptomyces tacrolimicus; Streptomyces tanashiensis; Streptomyces tateyamensis; Streptomyces tauricus; Streptomyces tendae; Streptomyces termitum; Streptomyces thermoalcalitolerans; Streptomyces thermoautotrophicus; Streptomyces thermocarboxydovorans; Streptomyces thermocarboxydus; Streptomyces thermocoprophilus; Streptomyces thermodiastaticus; Streptomyces thermogriseus; Streptomyces thermolineatus; Streptomyces thermospinosisporus; Streptomyces thermoviolaceus; Streptomyces thermovulgaris; Streptomyces thinghirensis; Streptomyces thioluteus; Streptomyces torulosus; Streptomyces toxytricini; Streptomyces tremellae; Streptomyces tritolerans; Streptomyces tricolor Streptomyces tsukubensis; Streptomyces tubercidicus; Streptomyces tuirus; Streptomyces tunisiensis; Streptomyces turgidiscabies; Streptomyces tyrosinilyticus; Streptomyces umbrinus; Streptomyces variabilis; Streptomyces variegatus; Streptomyces varsoviensis; Streptomyces verticillus; Streptomyces vastus; Streptomyces venezuelae; Streptomyces vietnamensis; Streptomyces vinaceus; Streptomyces vinaceusdrappus; Streptomyces violaceochromogenes; Streptomyces violaceolatus; Streptomyces violaceorectus; Streptomyces violaceoruber, Streptomyces violaceorubidus; Streptomyces violaceus; Streptomyces violaceusniger, Streptomyces violarus; Streptomyces violascens; Streptomyces violens; Streptomyces virens; Streptomyces virginiae; Streptomyces viridis; Streptomyces viridiviolaceus; Streptomyces viridobrunneus; Streptomyces viridochromogenes; Streptomyces viridodiastaticus; Streptomyces viridosporus; Streptomyces vitaminophilus; Streptomyces wedmorensis; Streptomyces wellingtoniae; Streptomyces werraensis; Streptomyces wuyuanensis; Streptomyces xanthochromogenes; Streptomyces xanthocidicus; Streptomyces xantholiticus; Streptomyces xanthophaeus; Streptomyces xiamenensis; Streptomyces xinghaiensis; Streptomyces xishensis; Streptomyces yaanensis; Streptomyces yanglinensis; Streptomyces yangpuensis; Streptomyces yanii; Streptomyces yatensis; Streptomyces yeochonensis; Streptomyces yerevanensis; Streptomyces yogyakartensis; Streptomyces yokosukanensis; Streptomyces youssoufiensis; Streptomyces yunnanensis; Streptomyces zagrosensis; Streptomyces zaomyceticus; Streptomyces zhaozhouensis; Streptomyces zincíresistens; or *Streptomyces ziwulingensis*. As another example, the microorganism can be a *streptomyces* species with azinothricin as the founding member, *Steptomyces flaveolus* DSM 9954, *Streptomyces* MK498-98F14 strain, *Steptomyces* sp. RJA2928, *Streptomyces hygroscopicus* strain ATCC 53653, *Streptomyces lycidus* (strain HKI0343), *Streptomyces* strain CNQ-593, *Streptomyces* sp. (A92-308110), or *Streptomyces himastatinicus* ATCC 53653. As another example, the microorganism can be a *Streptomyces* strain BB10EC, ES09EC, LM04EC, CS08EC, CM04EC, PF8EC, MRY08EC, LM08EC, JM05EC, BB04EC, PF1EC, PF5EC, N594, or dV596.

As another example, an Actinobacteria that can be used in the biosynthesis of piperazic acid or piperazic acid derivatives can be of the genus, *Corynebacterium*. As another example, the *Corynebacterium* can be of the species *Corynebacterium glutamicum*. As another example, the *Corynebacterium* can be of the species *Corynebacterium efficiens, Corynebacterium diphtheriae* group, *Corynebacterium xerosis, Corynebacterium striatum, Corynebacterium minutissimum, Corynebacterium amycolatum, Corynebacterium glucuronolyticum, Corynebacterium argentoratense, Corynebacterium matruchotii, Corynebacterium glutamicum, Corynebacterium* sp., Non fermentative corynebacteria, *Corynebacterium afermentans* subsp. *Afermentans, Corynebacterium auris, Corynebacterium pseudodiphtheriticum, Corynebacterium propinquum, Corynebacterium uropygiale, Corynebacterium jeikeium, Corynebacterium urealyticum, Corynebacterium afermentans* subsp. lipophilum, *Corynebacterium accolens, Corynebacterium macginleyi*, CDC coryneform groups F-1 and G, *Corynebacterium bovis*, or *Corynebacterium kroppenstedtii.*

As another example, an Actinobacteria that can be used in the biosynthesis of piperazic acid or piperazic acid derivatives can be of the genus, *Kutzneria*. As another example, the *Kutzneria* can be of the species *Kutzneria* spp. 744, *Kutzneria albida, Kutzneria kofuensis, Kutzneria viridogrisea*), (see e.g., Neuman et al. 2012 13(7) 972-976). Kutzneria were previously known to be in the family of Streptosporangiaceae (suborder Streptosporangineae) and were known as *Streptosporangium albidum, Streptosporangium viridogriseum* (subspecies kofuense), or *Streptosporangium viridogriseum.*

As described herein, an Actinobacteria that can be used in the biosynthesis of piperazic acid or piperazic acid derivatives can be of the genus *Actinomadura*. As an example, the *Actinomadura* can be of the species *Actinomadura luzonensis, Actinomadura dassonvillei, Actinomadura madurae, Actinomadura pelletieri, Actinomadura sputi, Actinomadura meyerae, Actinomadura hibisca, Actinomadura pusilla, A. fastidiosa, A. ferruoinea, A. helvata, A. kijaniata, A. libanotica, A. roseola, A. roseoviolacea, A. rubra., A. salmonea*, or *A. spiralis.*

As described herein, the microorganism can be a fungi. For example, the gene can be refactored and insterted into eukaryal vectors for yeast or fungal expression. In fact, some fungi also encode functionally orthologous PzbA enzymes (SidA). In some embodiments, the microorganism can be in the *Phylum, Ascomycota* or the genus, *Aspergillus*. As an example, the species can be *Aspergillus caesiellus, Aspergillus candidus, Aspergillus carneus, Aspergillus clavatus, Aspergillus deflectus, Aspergillus flavus, Aspergillus fumigatus, Aspergillus glaucus, Aspergillus israelii, Aspergillus nidulans, Aspergillus niger, Aspergillus ochraceus, Aspergillus oryzae, Aspergillus parasiticus, Aspergillus penicilloides, Aspergillus restrictus, Aspergillus sojae, Aspergillus sydowi, Aspergillus tamari, Aspergillus terreus, Aspergillus ustus*, or *Aspergillus versicolor.*

In some embodiments, transformed microorganisms, as described herein, can accumulate at least about 1 μM to at least about 1 M L-Piz. For example, in some embodiments, transformed microorganisms can accumulate about 1 μM; about 10 μM; about 20 μM; about 30 μM; about 40 μM; about 50 μM; about 60 μM; about 70 μM; about 80 μM; about 90 μM; about 100 μM; about 110 μM; about 120 μM; about 130 μM; about 140 μM; about 150 μM; about 160 μM; about 170 μM; about 180 μM; about 190 μM; about 200 μM; about 210 μM; about 220 μM; about 230 μM; about 240 μM; about 250 μM; about 260 μM; about 270 μM; about 280 μM; about 290 μM; about 300 μM; about 310 μM; about 320 μM; about 330 μM; about 340 μM; about 350 μM; about 360 μM; about 370 μM; about 380 μM; about 390 μM; about 400 μM; about 410 μM; about 420 μM; about 430 μM; about 440 μM; about 450 μM; about 460 μM; about 470 μM; about 480 μM; about 490 μM; about 500 μM; about 510 μM; about 520 μM; about 530 μM; about 540 μM; about 550 μM; about 560 μM; about 570 μM; about 580 μM; about 590 μM; about 600 μM; about 610 μM; about 620 μM; about 630 μM; about 640 μM; about 650 μM; about 660 μM; about 670 μM; about 680 μM; about 690 μM; about 700 μM; about 710 μM; about 720 μM; about 730 μM; about 740 μM; about 750 μM; about 760 μM; about 770 μM; about 780 μM; about 790 μM; about 800 μM; about 810 μM; about 820 μM; about 830 μM; about 840 μM; about 850 μM; about 860 μM; about 870 μM; about 880 μM; about 890 μM; about 900 μM; about 910 μM; about 920 μM; about 930 μM; about 940 μM; about 950 μM; about 960 μM; about 970 μM; about 980 μM; about 990 μM; or about 1000 μM. Recitation of each of these discrete values is understood to include ranges between each value. Recitation of each of a range is understood to include discrete values within the range.

In some embodiments, transformed microorganisms, as described herein, can accumulate between at least about 1 mg and at least about 3 mg of Piz or Piz derivatives (e.g., L-Piz, see e.g., Examples 4 or 14) per liter in about 3 days (or at least about 14 μg/L per hour or at least about 0.2 μg/L per minute). In some embodiments, transformed microorganisms can accumulate at least about 0.1 μg up to about 10 μg of a Piz or Piz derivatives (e.g., L-Piz) per minute per L. For example, transformed microorganisms can accumulate at least about 0.1 μg, at least about 0.2 μg, at least about 0.3 μg, at least about 0.4 μg, at least about 0.5 μg, at least about 0.6 μg, at least about 0.7 μg, at least about 0.8 μg, at least about 0.9 μg, or at least about 1 μg of Piz or Piz derivatives (e.g., L-Piz) per minute per L. In other embodiments, various transformed microorganisms accumulate similar amounts of Piz or Piz derivatives (e.g., L-Piz). Recitation of each of these discrete values is understood to include ranges between each value. Recitation of each of a range is understood to include discrete values within the range.

Hydroxylase, Cyclase, and Dehydratase

A microorganism (e.g., the bacteria, *Streptomyces lividans*) can be transformed so as to have hydroxylase, cyclase, or dehydratase activity (e.g., L-Ornithine $N^5$-hydroxylase, L-Ornithine cyclase, L-Ornithine dehydratase activity).

Hydroxylase (e.g., L-Ornithine $N^5$-hydroxylase) activity can be engineered into a microorganism by way of one or more individual genes encoding a polypeptide having hydroxylase (e.g., L-Ornithine $N^5$-hydroxylase) activity. It is contemplated these activities can likewise be engineered in other microorganisms.

Cyclase (e.g., L-Ornithine $N^5$-cyclase) activity or dehydratase (e.g., L-Ornithine $N^5$-dehydratase) activity can be engineered into a microorganism by way of one or more of the individual genes. For example, cyclase (e.g., L-Ornithine $N^5$-cyclase) activity or dehydratase (e.g., L-Ornithine $N^5$-dehydratase) activity can be engineered into a microorganism by way of one or more genes encoding a polypeptide having cyclase (e.g., L-Ornithine $N^5$-cyclase) activity or encoding a polypeptide having dehydratase (e.g., L-Ornithine $N^5$-dehydratase) activity; or by one gene encoding both cyclase (e.g., L-Ornithine $N^5$-cyclase) and dehydratase (e.g., L-Ornithine $N^5$-dehydratase). For example, L-Ornithine $N^5$-cyclase activity and L-Ornithine $N^5$-dehydratase activity can be present in a polypeptide or a fusion polypeptide. It is contemplated these activities can likewise be engineered in other microorganisms.

The Piz (e.g., L-Piz) can be endogenous or exogenous to the microorganism. Where the Piz is endogenous, the microorganism can be engineered to produce increased levels of Piz. Where Piz is exogenous, the microorganism can be engineered to produce such exogenous Piz.

The microorganism can be engineered to synthesize and accumulate the desired Piz continuously, after some developmental state, or upon being induced to do so. Induction of Piz synthesis can be according to the actions of an inducible promoter associated with the encoded hydroxylase, cyclase, or dehydratase and an inducing agent, as discussed in further detail herein. Also, the promoters as recited herein are only as examples of useful promoters. It is contemplated to adjust copy number (e.g., plasmid as self replicating high copy, low copy, or chromosomally insertional), in conjunction with promoters driving high, medium, or low expression of pzbA and pzbB combinations.

Radiolabeled

One embodiment of the present disclosure provides for a radiolabeled compound. The composition can be Piz, a Piz derivative, or a Piz-containing compound. According to another embodiment, the radiolabeled compound can be for use as a drug discovery agent or an imaging agent.

References herein to "radiolabeled" include a compound where one or more atoms are replaced or substituted by an atom having an atomic mass or mass number different from the atomic mass or mass number typically found in nature (i.e., naturally occurring). One non-limiting exception is $^{19}F$, which allows detection of a molecule which contains this element without enrichment to a higher degree than what is naturally occurring. Compounds carrying the substituent $^{19}F$ may thus also be referred to as "labelled" or the like. The term radiolabeled may be interchangeably used with "isotopically-labelled", "labelled", "isotopic tracer group", "isotopic marker", "isotopic label", "detectable isotope", or "radioligand".

In one embodiment, the compound comprises a single radiolabeled group.

Examples of suitable, non-limiting radiolabel groups can include: $^{2}H$ (D or deuterium), $^{3}H$ (T or tritium), $^{11}C$, $^{13}C$, $^{14}C$, $^{13}N$, $^{15}N$, $^{15}C$, $^{17}C$, $^{18}O$, $^{18}F$, $^{35}S$, $^{36}Cl$, $^{82}Br$, $^{75}Br$, $^{76}Br$, $^{77}Br$, $^{123}I$, $^{124}I$, $^{125}I$, or $^{131}I$. It is to be understood that an isotopically labeled compound needs only to be enriched with a detectable isotope to, or above, the degree which allows detection with a technique suitable for the particular application, e.g., in a detectable compound labeled with $^{11}C$, the carbon-atom of the labeled group of the labeled compound may be constituted by $^{12}C$ or other carbon-isotopes in a fraction of the molecules. The radionuclide that is incorporated in the radiolabeled compounds will depend on the specific application of that radiolabeled compound. For example, "heavy" isotope-labeled compounds (e.g., compounds containing deuterons/heavy hydrogen, heavy nitrogen, heavy oxygen, heavy carbon) can be useful for mass spectrometric and NMR based studies. As another example, for in vitro labelling or in competition assays, compounds that incorporate $^{3}H$, $^{14}C$, or $^{125}I$ can be useful. For in vivo imaging applications $^{11}C$, $^{13}C$, $^{18}F$, $^{19}F$, $^{120}I$, $^{123}I$, $^{131}I$, $^{75}Br$, or $^{76}Br$ can generally be useful. In one embodiment, the radiolabel is $^{11}C$. In an alternative embodiment, the radiolabel is $^{14}C$. In a yet further alternative embodiment, the radiolabel is $^{13}C$.

Molecular Engineering

A gene of particular interest for engineering a microorganism to accumulate Piz or Piz derivative is the active pzbB gene from *Streptomyces flaveolus* (see e.g., Example 3). Another gene of interest for engineering a microorganism to accumulate Piz is the active pzbA gene. As shown herein, pzbA is natively encoded on the *S. lividans* chromosome. But pzbA or pzbB can be expressed in another host that does not natively express the pzbA or pzbB gene or the host can be engineered to carry more than one copy of the a non-natively expressed pzbA or pzbB gene.

In some embodiments, an pzbA- or pzbB-encoding nucleotide sequence is cloned from its native source (e.g., *Streptomyces flaveolus, S. lividans*) and inserted into a host microorganism (see e.g., Example 3). In some embodiments, a transformed host microorganism comprises a pzbA or pzbB polynucleotide of SEQ ID NO: 177-SEQ ID NO: 178 (pzbA) or SEQ ID NO: 179-SEQ ID NO: 181 (pzbB). In some embodiments, a microorganism is transformed with a nucleotide sequence encoding pzbA or pzbB polypeptide of SEQ ID NO: 1-SEQ ID NO: 81 or SEQ ID NO: 82-SEQ ID NO: 166. In some embodiments, a transformed host microorganism comprises a pzbA and pzbB polynucleotides of SEQ ID NO: 167-SEQ ID NO: 176.

In some embodiments, a transformed host microorganism comprises a nucleotide sequence having at least about 25% sequence identity to SEQ ID NO: 177-SEQ ID NO: 178 ora nucleotide sequence encoding a polypeptide having L-Ornithine $N^5$ hydroxylase activity and at least about 80% sequence identity to SEQ ID NO: 1-SEQ ID NO: 81. As an example, a transformed host microorganism, such as a bacterium, can comprise a nucleotide sequence having at least about 85%, at least about 90%, at least about 95%, or at least about 99% sequence identity to SEQ ID NO: 177-SEQ ID NO: 178, wherein the transformed host exhibits L-Ornithine $N^5$ hydroxylase activity, pzbA activity, and/or accumulation of Piz. As an example, a transformed host microorganism can comprise a nucleotide sequence encoding a polypeptide having at least about 85%, at least about 90%, at least about 95%, or at least about 99% sequence identity to SEQ ID NO: 1-SEQ ID NO: 81, wherein the transformed host exhibits L-Ornithine $N^5$ hydroxylase activity, pzbA activity and/or accumulation of Piz. As another example, a transformed host microorganism can comprise a nucleotide sequence that hybridizes under stringent conditions to SEQ ID NO: 177-SEQ ID NO: 178 over the entire length of SEQ ID NO: 177-SEQ ID NO: 178, and which encodes an active pzbA polypeptide. As a further example, a transformed host microorganism can comprise the complement to any of the above sequences.

In some embodiments, a transformed host microorganism comprises a nucleotide sequence having at least about 80% sequence identity to SEQ ID NO: 179-SEQ ID NO: 181 ora nucleotide sequence encoding a polypeptide having L-Ornithine $N^5$ cyclase activity or L-Ornithine $N^5$ dehydratase activity and at least about 80% sequence identity to SEQ ID NO: 82-SEQ ID NO: 166. As an example, a transformed host microorganism, such as a bacterium, can comprise a nucleotide sequence having at least about 85%, at least about 90%, at least about 95%, or at least about 99% sequence identity to SEQ ID NO: 179-SEQ ID NO: 181, wherein the transformed host exhibits L-Ornithine $N^5$ cyclase activity or L-Ornithine $N^5$ dehydratase activity, or pzbB activity and/or accumulation of Piz. As an example, a transformed host microorganism can comprise a nucleotide sequence encoding a polypeptide having at least about 85%, at least about 90%, at least about 95%, or at least about 99% sequence identity to SEQ ID NO: 82-SEQ ID NO: 166, wherein the transformed host exhibits L-Ornithine $N^5$ cyclase activity or L-Ornithine $N^5$ dehydratase activity, or pzbB activity and/or accumulation of Piz. As another example, a transformed host microorganism can comprise a nucleotide sequence that hybridizes under stringent conditions to SEQ ID NO: 179-SEQ ID NO: 181 over the entire length of SEQ ID NO: 179-SEQ ID NO: 181, and which encodes an active pzbB polypeptide. As a further example, a transformed host microorganism can comprise the complement to any of the above sequences.

In some embodiments, L-Ornithine $N^5$ hydroxylase (see e.g., SEQ ID NO: 177-SEQ ID NO: 178 encoding pzbA gene and SEQ ID NO: 1-SEQ ID NO: 81 encoding pzbA polypeptide), or homologue thereof, is engineered to be expressed or overexpressed in a transformed microorganism. For example, a microorganism can be transformed with a nucleotide having a sequence of 1SEQ ID NO: 177-SEQ ID NO: 178 so as to express L-Ornithine $N^5$ hydroxylase. As another example, a microorganism can be transformed with a nucleotide having at least about 80%, at least about 85%, at least about 90%, at least about 95%, or at least about 99% percent identity to SEQ ID NO: 177-SEQ ID NO: 178 encoding a polypeptide having L-Ornithine $N^5$ hydroxylase activity. As another example, a transformed host microorganism can comprise a nucleotide sequence encoding a polypeptide having at least about 85%, at least about 90%, at least about 95%, or at least about 99% sequence identity to SEQ ID NO: 1-SEQ ID NO: 81, wherein the transformed host exhibits L-Ornithine $N^5$ hydroxylase activity, pzbA activity, and/or accumulation of Piz.

In some embodiments, L-Ornithine $N^5$ cyclase or L-Ornithine $N^5$ dehydratase (see e.g., SEQ ID NO: 179-SEQ ID NO: 181 encoding pzbB gene and SEQ ID NO: 82-SEQ ID NO: 166 encoding pzbB polypeptide), or homologue thereof, is engineered to be expressed or overexpressed in a transformed microorganism. For example, a microorganism can be transformed with a nucleotide having a sequence of SEQ ID NO: 179-SEQ ID NO: 181 so as to express L-Ornithine $N^5$ cyclase or L-Ornithine $N^5$ dehydratase. As another example, a microorganism can be transformed with a nucleotide having at least about 80%, at least about 85%, at least about 90%, at least about 95%, or at least about 99% percent identity to SEQ ID NO: 179-SEQ ID NO: 181 encoding a polypeptide having L-Ornithine $N^5$ hydroxylase activity. As another example, a transformed host microorganism can comprise a nucleotide sequence encoding a polypeptide having at least about 85%, at least about 90%, at least about 95%, or at least about 99% sequence identity to SEQ ID NO: 82-SEQ ID NO: 166, wherein the transformed host exhibits L-Ornithine $N^5$ cyclase activity, L-Ornithine $N^5$ dehydratase activity, pzbB activity, and/or accumulation of Piz.

In some embodiments, a microorganism (e.g., a bacterium) is engineered to express one or more of pzbA, pzbB, L-Ornithine $N^5$ hydroxylase, L-Ornithine $N^5$ cyclase, or L-Ornithine $N^5$ dehydratase.

Design, generation, and testing of the variant nucleotides, and their encoded polypeptides, having the above required percent identities to an pzbA or pzbB sequence and retaining a required activity of the expressed protein and/or Piz accumulation phenotype is within the skill of the art.

The following definitions and methods are provided to better define the present invention and to guide those of ordinary skill in the art in the practice of the present invention. Unless otherwise noted, terms are to be understood according to conventional usage by those of ordinary skill in the relevant art.

The terms "heterologous DNA sequence", "exogenous DNA segment" or "heterologous nucleic acid," as used herein, each refer to a sequence that originates from a source foreign to the particular host cell or, if from the same source, is modified from its original form. Thus, a heterologous gene in a host cell includes a gene that is endogenous to the particular host cell but has been modified through, for example, the use of DNA shuffling. The terms also include non-naturally occurring multiple copies of a naturally occurring DNA sequence. Thus, the terms refer to a DNA segment that is foreign or heterologous to the cell, or homologous to the cell but in a position within the host cell nucleic acid in which the element is not ordinarily found. Exogenous DNA segments are expressed to yield exogenous polypeptides. A "homologous" DNA sequence is a DNA sequence that is naturally associated with a host cell into which it is introduced.

Expression vector, expression construct, plasmid, or recombinant DNA construct is generally understood to refer to a nucleic acid that has been generated via human intervention, including by recombinant means or direct chemical synthesis, with a series of specified nucleic acid elements that permit transcription or translation of a particular nucleic acid in, for example, a host cell. The expression vector can be part of a plasmid, virus, or nucleic acid fragment. Typically, the expression vector can include a nucleic acid to be transcribed operably linked to a promoter.

A "promoter" is generally understood as a nucleic acid control sequence that directs transcription of a nucleic acid. An inducible promoter is generally understood as a promoter that mediates transcription of an operably linked gene in response to a particular stimulus. In some embodiments, the promoter is iducible by an agent selected from the group consisting of temperature, pH, a metabolite, light, an osmotic agent, a heavy metal, and an antibiotic. In some embodiments, the promoter is selected from the group consisting of a constitutive promoter to produce L-Piz.

A promoter can include necessary nucleic acid sequences near the start site of transcription, such as, in the case of a polymerase II type promoter, a TATA element. A promoter can optionally include distal enhancer or repressor elements, which can be located as much as several thousand base pairs from the start site of transcription.

A "transcribable nucleic acid molecule" as used herein refers to any nucleic acid molecule capable of being transcribed into a RNA molecule. Methods are known for introducing constructs into a cell in such a manner that the transcribable nucleic acid molecule is transcribed into a functional mRNA molecule that is translated and therefore expressed as a protein product. Constructs may also be constructed to be capable of expressing antisense RNA molecules, in order to inhibit translation of a specific RNA molecule of interest. For the practice of the present disclosure, conventional compositions and methods for preparing and using constructs and host cells are well known to one skilled in the art (see e.g., Sambrook and Russel (2006) Condensed Protocols from Molecular Cloning: A Laboratory Manual, Cold Spring Harbor Laboratory Press, ISBN-10: 0879697717; Ausubel et al. (2002) Short Protocols in Molecular Biology, 5th ed., Current Protocols, ISBN-10: 0471250929; Sambrook and Russel (2001) Molecular Cloning: A Laboratory Manual, 3d ed., Cold Spring Harbor Laboratory Press, ISBN-10: 0879695773; Elhai, J. and Wolk, C. P. 1988. Methods in Enzymology 167, 747-754).

The "transcription start site" or "initiation site" is the position surrounding the first nucleotide that is part of the transcribed sequence, which is also defined as position+1. With respect to this site all other sequences of the gene and its controlling regions can be numbered. Downstream sequences (i.e., further protein encoding sequences in the 3' direction) can be denominated positive, while upstream sequences (mostly of the controlling regions in the 5' direction) are denominated negative.

"Operably-linked" or "functionally linked" refers preferably to the association of nucleic acid sequences on a single nucleic acid fragment so that the function of one is affected by the other. For example, a regulatory DNA sequence is said to be "operably linked to" or "associated with" a DNA sequence that codes for an RNA or a polypeptide if the two sequences are situated such that the regulatory DNA sequence affects expression of the coding DNA sequence (i.e., that the coding sequence or functional RNA is under the transcriptional control of the promoter). Coding sequences can be operably-linked to regulatory sequences in sense or antisense orientation. The two nucleic acid molecules may be part of a single contiguous nucleic acid molecule and may be adjacent. For example, a promoter is operably linked to a gene of interest if the promoter regulates or mediates transcription of the gene of interest in a cell.

A "construct" is generally understood as any recombinant nucleic acid molecule such as a plasmid, cosmid, virus, autonomously replicating nucleic acid molecule, phage, or linear or circular single-stranded or double-stranded DNA or RNA nucleic acid molecule, derived from any source, capable of genomic integration or autonomous replication, comprising a nucleic acid molecule where one or more nucleic acid molecule has been operably linked.

A constructs of the present disclosure can contain a promoter operably linked to a transcribable nucleic acid molecule operably linked to a 3' transcription termination nucleic acid molecule. In addition, constructs can include but are not limited to additional regulatory nucleic acid molecules from, e.g., the 3'-untranslated region (3' UTR). Constructs can include but are not limited to the 5' untranslated regions (5' UTR) of an mRNA nucleic acid molecule which can play an important role in translation initiation and can also be a genetic component in an expression construct. These additional upstream and downstream regulatory nucleic acid molecules may be derived from a source that is native or heterologous with respect to the other elements present on the promoter construct.

The term "transformation" refers to the transfer of a nucleic acid fragment into the genome of a host cell, resulting in genetically stable inheritance. Host cells containing the transformed nucleic acid fragments are referred to as "transgenic" cells, and organisms comprising transgenic cells are referred to as "transgenic organisms".

"Transformed," "transgenic," and "recombinant" refer to a host cell or organism such as a bacterium, cyanobacterium, animal or a plant into which a heterologous nucleic acid molecule has been introduced. The nucleic acid molecule can be stably integrated into the genome as generally known in the art and disclosed (Sambrook 1989; Innis 1995; Gelfand 1995; Innis & Gelfand 1999). Known methods of PCR include, but are not limited to, methods using paired primers, nested primers, single specific primers, degenerate primers, gene-specific primers, vector-specific primers, partially mismatched primers, and the like. The term "untransformed" refers to normal cells that have not been through the transformation process.

"Wild-type" refers to a virus or organism found in nature without any known mutation.

Design, generation, and testing of the variant nucleotides, and their encoded polypeptides, having the above required percent identities and retaining a required activity of the expressed protein is within the skill of the art. For example, directed evolution and rapid isolation of mutants can be according to methods described in references including, but not limited to, Link et al. (2007) Nature Reviews 5(9), 680-688; Sanger et al. (1991) Gene 97(1), 119-123; Ghadessy et al. (2001) Proc Natl Acad Sci USA 98(8) 4552-4557. Thus, one skilled in the art could generate a large number of nucleotide (e.g. pzbA, pzbB) and/or polypeptide (e.g., pzbA, pzbB) variants having, for example, at least 95%-99% identity to the reference sequence described herein and screen such for desired phenotypes according to methods routine in the art.

Nucleotide and/or amino acid sequence identity percent (%) is understood as the percentage of nucleotide or amino acid residues that are identical with nucleotide or amino acid residues in a candidate sequence in comparison to a reference sequence when the two sequences are aligned. To determine percent identity, sequences are aligned and if necessary, gaps are introduced to achieve the maximum percent sequence identity. Sequence alignment procedures to determine percent identity are well known to those of skill in the art. Often publicly available computer software such as BLAST, BLAST2, ALIGN2 or Megalign (DNASTAR) software is used to align sequences. Those skilled in the art can determine appropriate parameters for measuring alignment, including any algorithms needed to achieve maximal alignment over the full-length of the sequences being compared. When sequences are aligned, the percent sequence identity of a given sequence A to, with, or against a given sequence B (which can alternatively be phrased as a given sequence A that has or comprises a certain percent sequence identity to, with, or against a given sequence B) can be calculated as: percent sequence identity=X/Y100, where X is the number of residues scored as identical matches by the sequence alignment program's or algorithm's alignment of A and B and Y is the total number of residues in B. If the length of sequence A is not equal to the length of sequence B, the percent sequence identity of A to B will not equal the percent sequence identity of B to A.

Generally, conservative substitutions can be made at any position so long as the required activity is retained. So-called conservative exchanges can be carried out in which the amino acid which is replaced has a similar property as the original amino acid, for example the exchange of Glu by Asp, Gln by Asn, Val by Ile, Leu by Ile, and Ser by Thr. For example, amino acids with similar properties can be Aliphatic amino acids (e.g., Glycine, Alanine, Valine, Leucine, Isoleucine); Hydroxyl or sulfur/selenium-containing amino acids (e.g., Serine, Cysteine, Selenocysteine, Threonine, Methionine); Cyclic amino acids (e.g., Proline); Aromatic amino acids (e.g., Phenylalanine, Tyrosine, Tryptophan); Basic amino acids (e.g., Histidine, Lysine, Arginine); or Acidic and their Amide (e.g., Aspartate, Glutamate, Asparagine, Glutamine). Deletion is the replacement of an amino acid by a direct bond. Positions for deletions include the termini of a polypeptide and linkages between individual protein domains. Insertions are introductions of amino acids into the polypeptide chain, a direct bond formally being replaced by one or more amino acids. Amino acid sequence can be modulated with the help of art-known computer simulation programs that can produce a polypeptide with, for example, improved activity or altered regulation. On the basis of this artificially generated polypeptide sequences, a corresponding nucleic acid molecule coding for such a modulated polypeptide can be synthesized in-vitro using the specific codon-usage of the desired host cell.

"Highly stringent hybridization conditions" are defined as hybridization at 65° C. in a 6×SSC buffer (i.e., 0.9 M sodium chloride and 0.09 M sodium citrate). Given these conditions, a determination can be made as to whether a given set of sequences will hybridize by calculating the melting temperature ($T_m$) of a DNA duplex between the two sequences. If a particular duplex has a melting temperature lower than 65° C. in the salt conditions of a 6×SSC, then the two sequences will not hybridize. On the other hand, if the melting temperature is above 65° C. in the same salt conditions, then the sequences will hybridize. In general, the melting temperature for any hybridized DNA:DNA sequence can be determined using the following formula: $T_m$=81.5° C.+16.6(logio[$Na^+$])+0.41(fraction G/C content)−0.63(% formamide)−(600/l). Furthermore, the $T_m$ of a DNA:DNA hybrid is decreased by 1-1.5° C. for every 1% decrease in nucleotide identity (see e.g., Sambrook and Russel, 2006).

Host cells can be transformed using a variety of standard techniques known to the art (see, e.g., Sambrook and Russel (2006) Condensed Protocols from Molecular Cloning: A Laboratory Manual, Cold Spring Harbor Laboratory Press, ISBN-10: 0879697717; Ausubel et al. (2002) Short Protocols in Molecular Biology, 5th ed., Current Protocols, ISBN-10: 0471250929; Sambrook and Russel (2001) Molecular Cloning: A Laboratory Manual, 3d ed., Cold Spring Harbor Laboratory Press, ISBN-10: 0879695773; Elhai, J. and Wolk, C. P. 1988. Methods in Enzymology 167, 747-754). Such techniques include, but are not limited to, viral infection, calcium phosphate transfection, liposome-mediated transfection, microprojectile-mediated delivery, receptor-mediated uptake, cell fusion, electroporation, and the like. The transfected cells can be selected and propagated to provide recombinant host cells that comprise the expression vector stably integrated in the host cell genome.

Exemplary nucleic acids which may be introduced to a host cell include, for example, DNA sequences or genes from another species, or even genes or sequences which originate with or are present in the same species, but are incorporated into recipient cells by genetic engineering methods. The term "exogenous" is also intended to refer to genes that are not normally present in the cell being transformed, or perhaps simply not present in the form, structure, etc., as found in the transforming DNA segment or gene, or genes which are normally present and that one desires to express in a manner that differs from the natural expression pattern, e.g., to over-express. Thus, the term "exogenous" gene or DNA is intended to refer to any gene or DNA segment that is introduced into a recipient cell, regardless of whether a similar gene may already be present in such a cell. The type of DNA included in the exogenous DNA can include DNA which is already present in the cell, DNA from another individual of the same type of organism, DNA from a different organism, or a DNA generated externally, such as a DNA sequence containing an antisense message of a gene, or a DNA sequence encoding a synthetic or modified version of a gene.

Host strains developed according to the approaches described herein can be evaluated by a number of means known in the art (see e.g., Studier (2005) Protein Expr Purif. 41(1), 207-234; Gellissen, ed. (2005) Production of Recombinant Proteins: Novel Microbial and Eukaryotic Expression Systems, Wiley-VCH, ISBN-10: 3527310363; Baneyx (2004) Protein Expression Technologies, Taylor & Francis, ISBN-10: 0954523253).

Methods of down-regulation or silencing genes are known in the art. For example, expressed protein activity can be down-regulated or eliminated using antisense oligonucleotides, protein aptamers, nucleotide aptamers, and RNA interference (RNAi) (e.g., small interfering RNAs (siRNA), short hairpin RNA (shRNA), and micro RNAs (miRNA) (see e.g., Fanning and Symonds (2006) Handb Exp Pharmacol. 173, 289-303G, describing hammerhead ribozymes and small hairpin RNA; Helene, C., et al. (1992) Ann. N.Y. Acad. Sci. 660, 27-36; Maher (1992) Bioassays 14(12): 807-15, describing targeting deoxyribonucleotide sequences; Lee et al. (2006) Curr Opin Chem Biol. 10, 1-8, describing aptamers; Reynolds et al. (2004) Nature Biotechnology 22(3), 326-330, describing RNAi; Pushparaj and Melendez (2006) Clinical and Experimental Pharmacology and Physiology 33(5-6), 504-510, describing RNAi; Dillon et al. (2005) Annual Review of Physiology 67, 147-173, describing RNAi; Dykxhoorn and Lieberman (2005) Annual Review of Medicine 56, 401-423, describing RNAi). RNAi molecules are commercially available from a variety of sources (e.g., Ambion, TEX; Sigma Aldrich, MO; Invitrogen). Several siRNA molecule design programs using a variety of algorithms are known to the art (see e.g., Cenix algorithm, Ambion; BLOCK-iT™ RNAi Designer, Invitrogen; siRNA Whitehead Institute Design Tools, Bioinofrmatics & Research Computing). Traits influential in defining optimal siRNA sequences include G/C content at the termini of the siRNAs, Tm of specific internal domains of the siRNA, siRNA length, position of the target sequence within the CDS (coding region), and nucleotide content of the 3' overhangs.

Definitions and methods described herein are provided to better define the present disclosure and to guide those of ordinary skill in the art in the practice of the present disclosure. Unless otherwise noted, terms are to be understood according to conventional usage by those of ordinary skill in the relevant art.

In some embodiments, numbers expressing quantities of ingredients, properties such as molecular weight, reaction conditions, and so forth, used to describe and claim certain embodiments of the present disclosure are to be understood as being modified in some instances by the term "about." In some embodiments, the term "about" is used to indicate that a value includes the standard deviation of the mean for the device or method being employed to determine the value. In some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the present disclosure are approximations, the numerical values set forth in the specific examples are reported as precisely as practicable. The numerical values presented in some embodiments of the present disclosure may contain certain errors necessarily resulting from the standard deviation found in their respective testing measurements. The recitation of ranges of values herein is merely intended to serve as a shorthand method of referring individually to each separate value falling within the range. Unless otherwise indicated herein, each individual value is incorporated into the specification as if it were individually recited herein.

In some embodiments, the terms "a" and "an" and "the" and similar references used in the context of describing a particular embodiment (especially in the context of certain of the following claims) can be construed to cover both the singular and the plural, unless specifically noted otherwise. In some embodiments, the term "or" as used herein, including the claims, is used to mean "and/or" unless explicitly indicated to refer to alternatives only or the alternatives are mutually exclusive.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and can also cover other unlisted steps. Similarly, any composition or device that "comprises," "has" or "includes" one or more features is not limited to possessing only those one or more features and can cover other unlisted features.

All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the present disclosure and does not pose a limitation on the scope of the present disclosure otherwise claimed. No language in the specification should be construed as indicating any non-claimed element essential to the practice of the present disclosure.

Groupings of alternative elements or embodiments of the present disclosure disclosed herein are not to be construed as limitations. Each group member can be referred to and claimed individually or in any combination with other members of the group or other elements found herein. One or more members of a group can be included in, or deleted from, a group for reasons of convenience or patentability. When any such inclusion or deletion occurs, the specification is herein deemed to contain the group as modified thus fulfilling the written description of all Markush groups used in the appended claims.

Citation of a reference herein shall not be construed as an admission that such is prior art to the present disclosure.

Having described the present disclosure in detail, it will be apparent that modifications, variations, and equivalent embodiments are possible without departing the scope of the present disclosure defined in the appended claims. Furthermore, it should be appreciated that all examples in the present disclosure are provided as non-limiting examples.

EXAMPLES

The following non-limiting examples are provided to further illustrate the present disclosure. It should be appreciated by those of skill in the art that the techniques disclosed in the examples that follow represent approaches the inventors have found function well in the practice of the present disclosure, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the present disclosure.

Example 1

Discovery of the Complete Biosynthetic Pathway to L-Piz from the Central Metabolite L-Orn The following example describes the discovery of the complete biosynthetic pathway to L-Piz from the central metabolite, L-Orn.

Figure 1B:
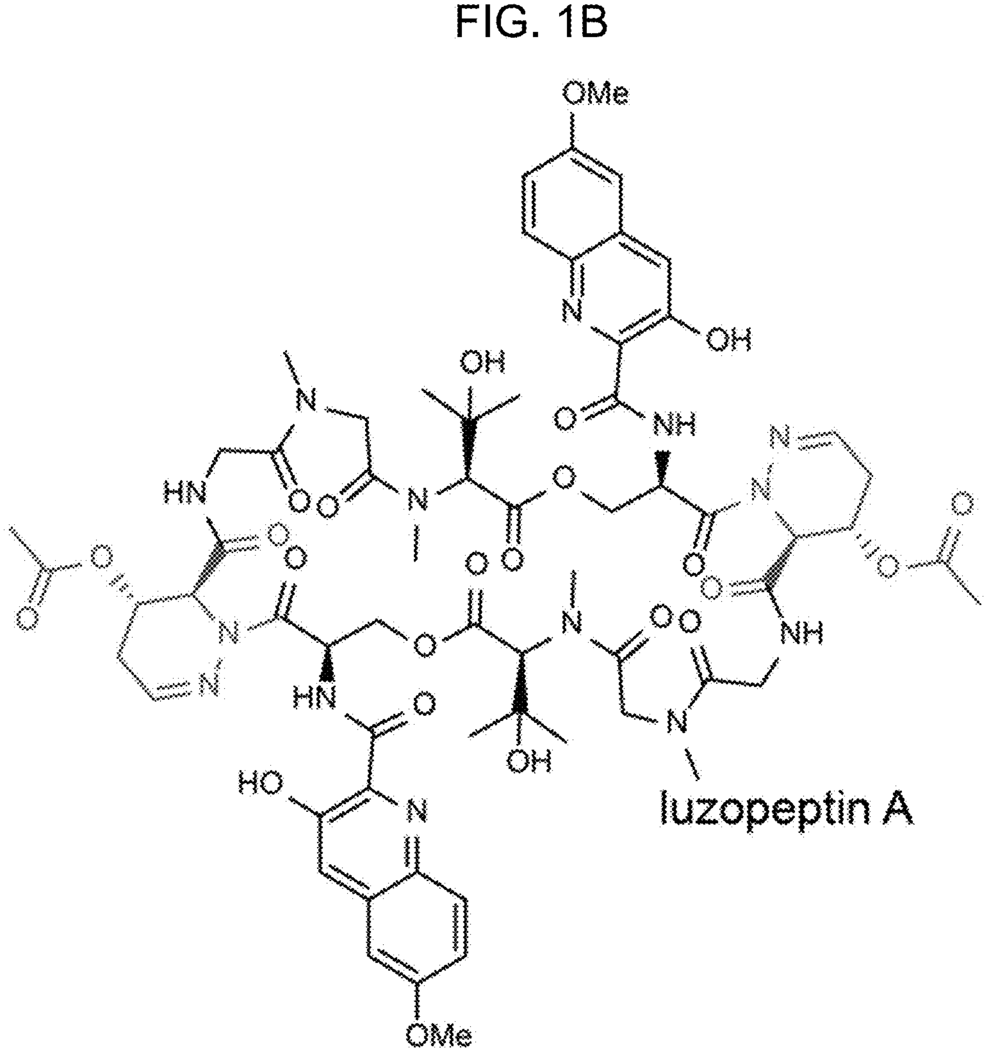
Figure 1B:
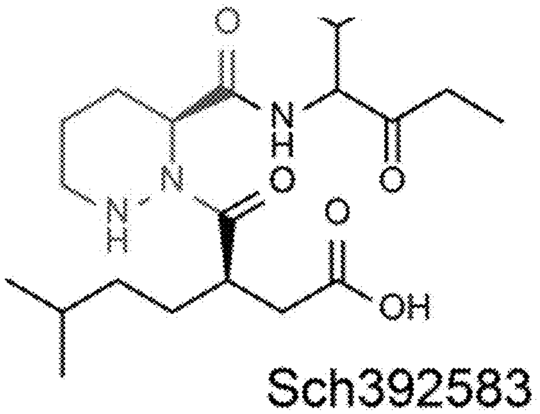
Figure 1C:
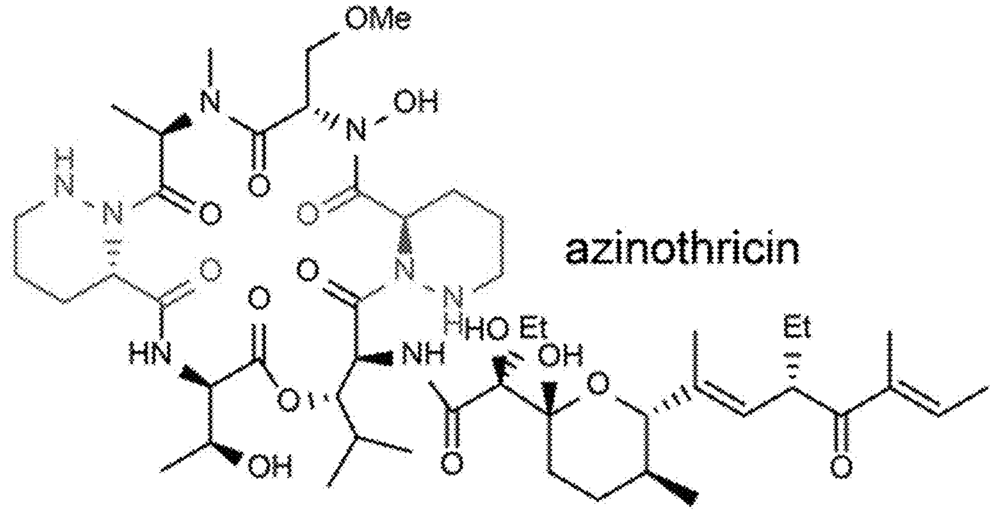
Figure 1C:
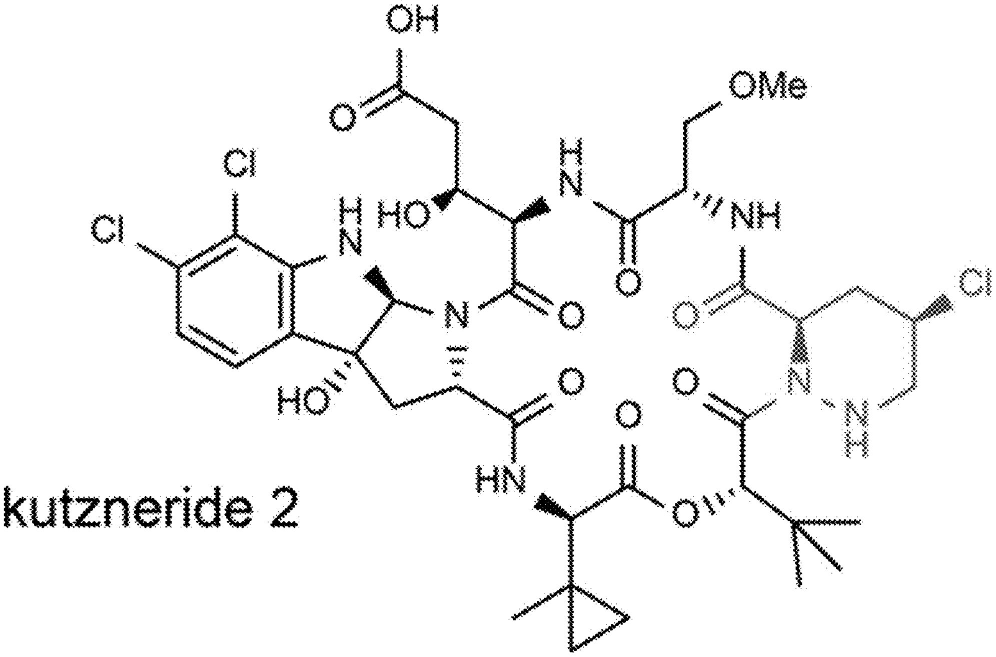

Select examples of piperazic acid (Piz) family of natural products are shown in FIG. 1A, FIG. 1B, and FIG. 1C. Piz and modified Piz (e.g., dehydropiperazic, chloropiperazic, hydroxypiperazic acid) molecular components are shaded as shown in FIG. 1A, FIG. 1B, and FIG. 1C. All of these molecules are bioactive, with sanglifehrin under consideration as an immunosuppressant and Hepatitis-C antiviral. The small molecule Sch 382583 is a 5 member of an emerging group of Piz containing metalloprotease inhibitors with clinical relevance as metastatic cancer and antibacterial antibiotic leads. All of these molecules are exclusively produced by actinobacteria.

Scheme 1. Summary of prior knowledge regarding the incorporation of Ornithine into Piz via the activity of an Ornithine $N^5$ hydroxylase (PzbA). Conversion of $N^5$—OH-Orn into piperazic acid, and responsible enzyme(s) were previously unknown.

1.

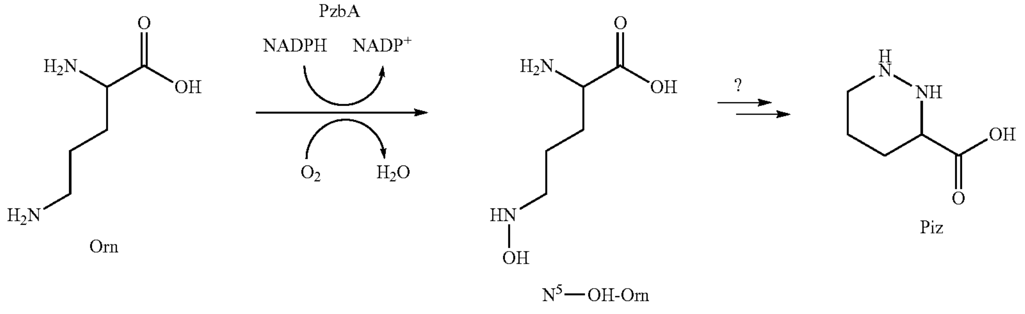

Scheme 2. Refined model for Piz production from Orn supported by the present data. The newly recognized enzyme PzbB is necessary and sufficient for the production of Piz directly from $N^5$—OH-Orn.

2.

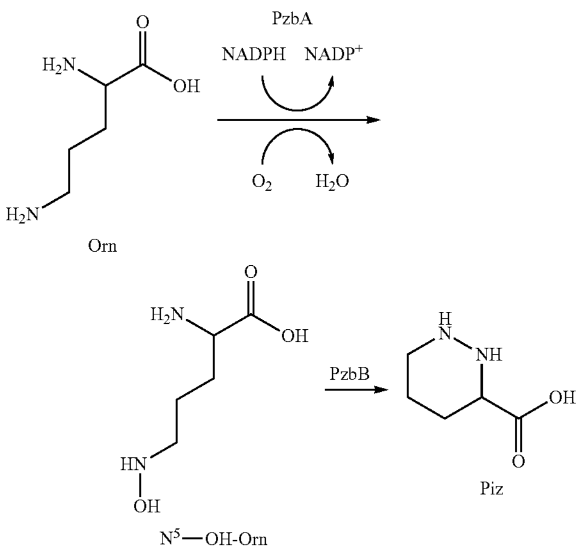

Orn $N^5$—OH-Orn

Piz

Figure 2:
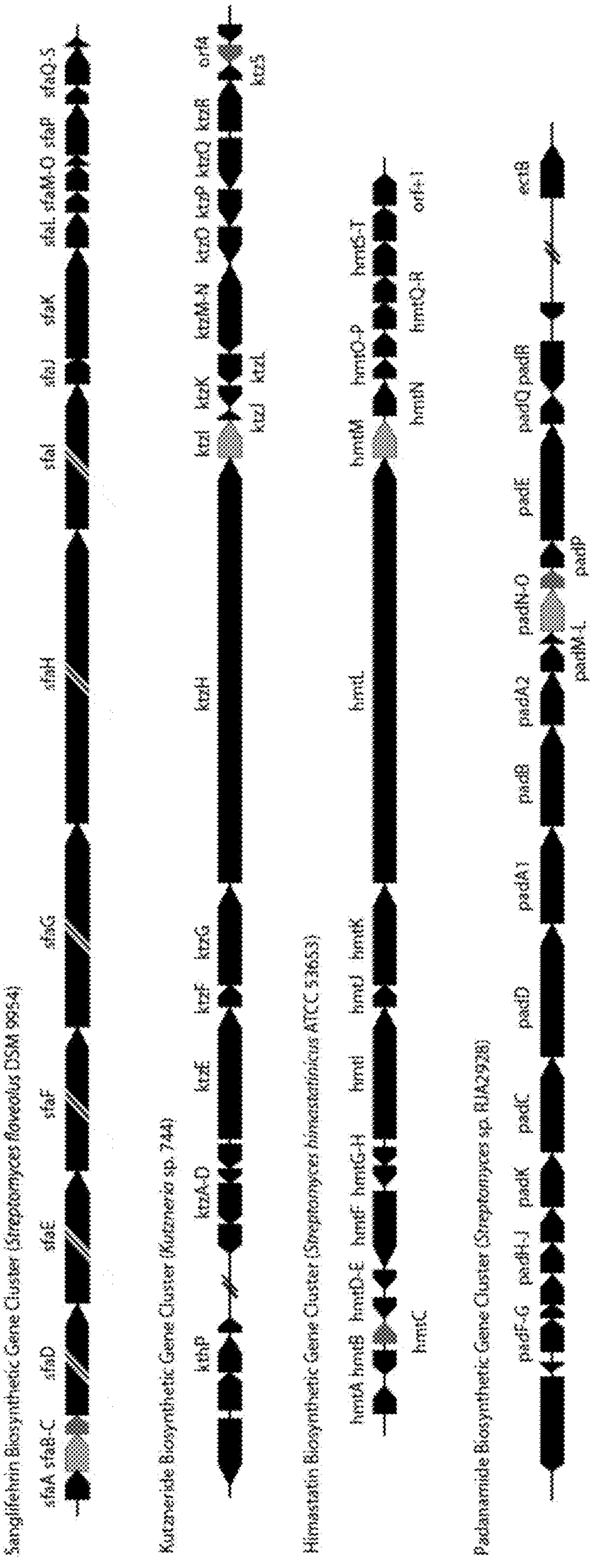
FIG. 2 shows orthologs of both PzbA and PzbB are found within biosynthetic gene clusters for known Piz-containing antibiotics. As these clusters encode molecules that are structurally dissimilar except for the incorporation of Piz, parsimony suggests both pzbA and pzbB (previously unrecognized) are involved in Piz biosynthesis.

Orthologs of both PzbA (yellow) and PzbB (red) were found within biosynthetic gene clusters for known Piz-containing antibiotics (see e.g., FIG. 2). As these clusters encode molecules that are structurally dissimilar except for the incorporation of Piz, parsimony suggests both pzbA (previously known) and pzbB (previously unrecognized) are involved in Piz biosynthesis.

In vitro reconstitution of L-Piz production from L-Orn in a coupled enzymatic reaction containing purified PzbA, PzbB, buffer salts, NADPH cofactor, $Fe^{+2}$ salts, and catalytic FAD (Flavin Adenine Dinucleotide) cofactor according to Scheme 2.

FIG. 2 shows the HPLC-ESI-MS detection of products and substrates with assay time points at time 0 min, 15 min, and 30 min showing the consumption of L-Orn, accumulation of the known intermediate $N^5$—OH-Orn, and the concomitant formation of Piz. Data (not shown) in the same assay lacking PzbB, the enzyme product is $N^5$—OH-Orn and no Piz is formed.

Example 2

Green Biocatalysis of L-Piz In Vitro

Figure 3:
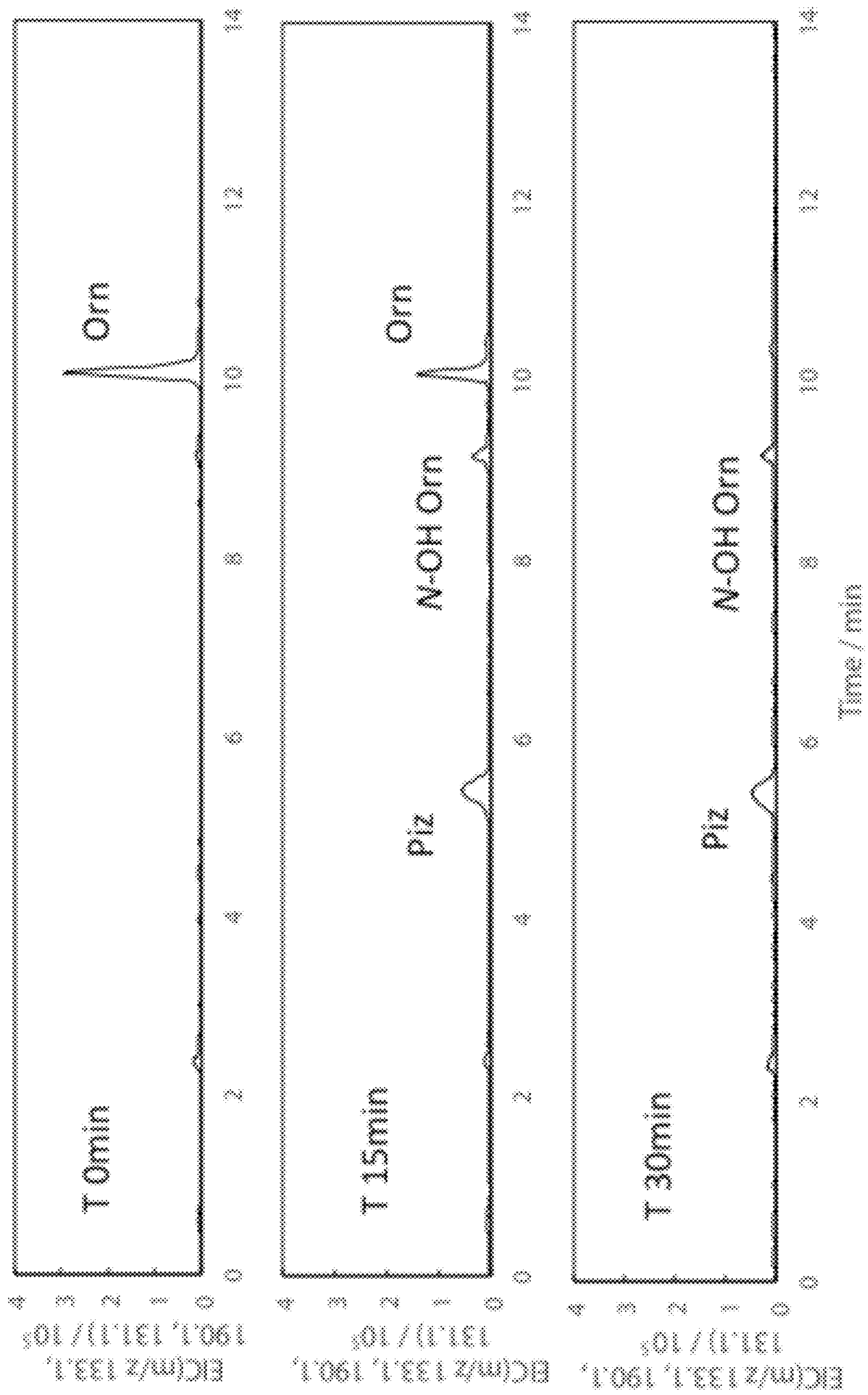
FIG. 3 shows HPLC-ESI-MS detection of products and substrates with assay time points at time 0 min, 15 min, and 30 min showing the consumption of L-Orn, accumulation of the known intermediate $N^5$—OH-Orn, and the concomitant formation of Piz. In vitro reconstitution of L-Piz production from L-Orn in a coupled enzymatic reaction containing purified PzbA, PzbB buffer salts, NADPH cofactor, $Fe^{+2}$ salts, and catalytic FAD (Flavin Adenine Dinucleotide) cofactor according to Scheme 2. Not shown: In the same assay lacking PzbB, the enzyme product is $N^5$—OH-Orn and no Piz is formed.

L-Piz can be synthesized chemically, but to date a fermentative pathway to the amino acid has eluded researchers. Enantiopure synthetic L-Piz is expensive: ($2800/gram, 95% pure). DL-Piz synthesized as a mix of isomers, which is significantly less chemically desirable, is less expensive ($800/gram, 95% pure), but still of significant cost. Using a coupled enzyme assay containing a suitable L-Ornithine $N^5$—OHase (PzbA), and a suitable PzbB (L—$N^5$—OH Orn cyclase/dehydratase), enantiopure (as currently understood) L-Piz can be made from the inexpensive feedstock enantiopure L-Ornithine ($1.40/gram, >99% pure, Sigma-Aldrich), buffer salts, NADPH cofactor, $Fe^{+2}$ salts, and catalytic FAD (Flavin Adenine Dinucleotide) cofactor (see e.g., FIG. 3).

Example 3

An Enzymatic Route to Heavy Isotope-Labelled Piz

Heavy isotope-labeled compounds (e.g., compounds containing deuterons/heavy hydrogen, heavy nitrogen, heavy oxygen, heavy carbon) are valuable tools for mass spectrometric and NMR based studies. Currently, no vendors, custom or otherwise, that offer L-Piz having any combination of these isotopes. Using $d_7$-L-Orn, the feasible production of $d_7$ L-Piz using the reaction described in Example 2 above has been demonstrated. In principle, any heavy isotope labeled L-Orn could yield similarly labeled L-Piz. Coupled PzbA/PzbB enzymatic reactions could be scaled to produce and market variously heavy isotopically labeled or radioisotopically labeled versions of L-Piz, for which there are current no known synthetic paths.

Example 4

Green Biocatalysis of L-Piz In Vivo

This example shows a greener production of L-Piz (no organic solvents and fewer reagents than conventional methods).

Micro-organisms such as bacteria and fungi are preferred producers of amino acids in the biotechnology industry. This is because the cellular enzyme catalysts of life are typically stereospecific, giving enantiopure products. Enantiopurity can be more difficult to achieve in synthetic chemistry. Also, inexpensive feedstocks are provided for growth, significantly reducing the cost of amino acid production in contrast to fine chemical starting points often required for synthetic chemistry. Here, L-Piz fermentation in a heterologous, genetically engineered host (*Streptomyces lividans*) grown on standard lab media, and with no investment in yield optimization (see e.g., FIG. 4) has been demonstrated.

Figure 4:
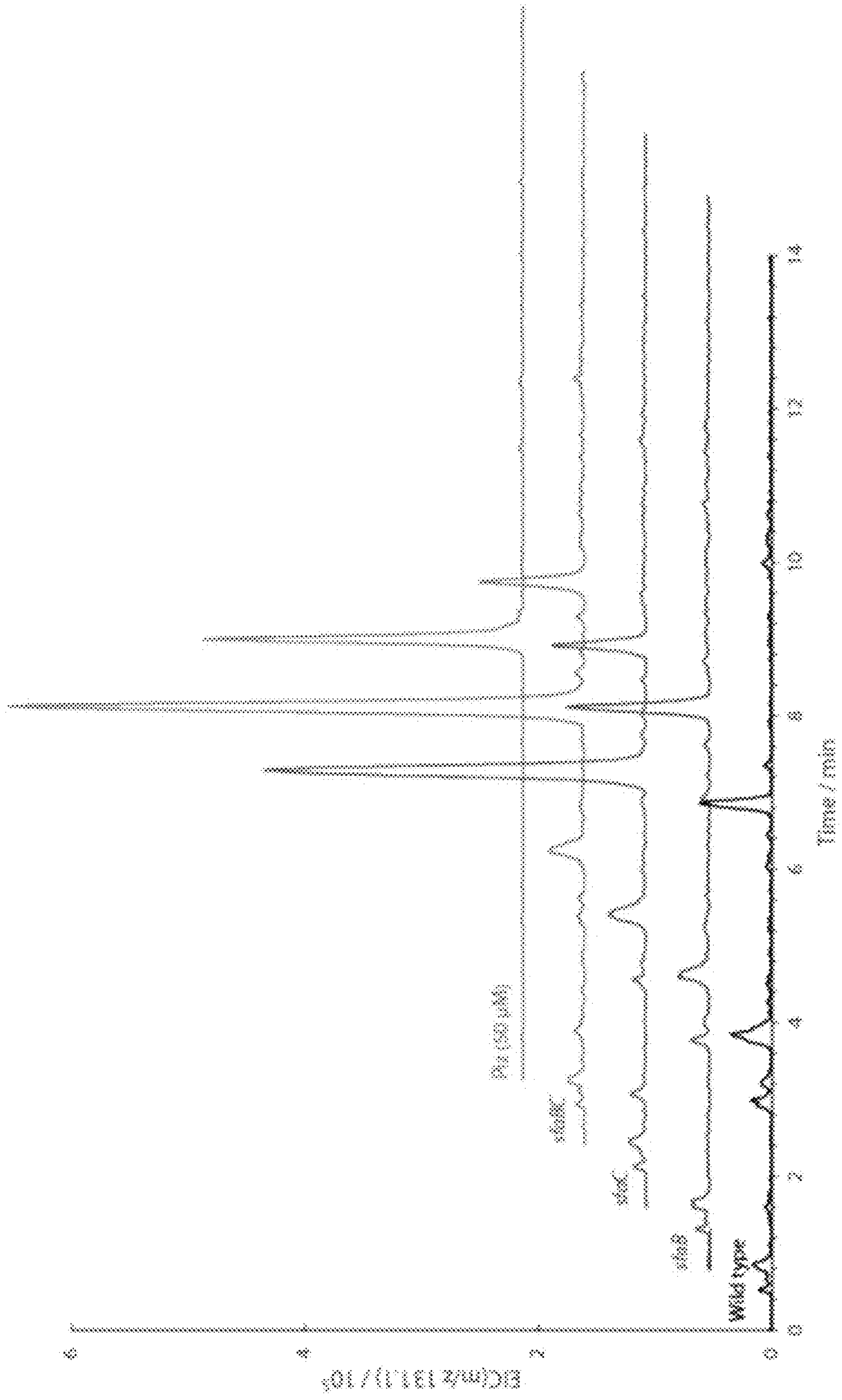
FIG. 4 is a series of LC/MS spectra of biosynthetic Piz compared against an authentic L-Piz standard (top row) showing in vivo production of L-Piz in a heterologous bacterial host, *Streptomyces lividans*. *S. lividans* (WT parent, no Piz production) is compared against *S. lividans* harboring a single copy of pzbA (sfaB) alone, pzbB (sfaC) alone, or co-expressing pzbA and pzbB (sfaBC) cloned from the sanglifehrin biosynthetic locus of *Streptomyces flaveolus*. LC/MS detection of biosynthetic Piz was compared against an authentic L-Piz standard (top row). In contrast with the in vitro data above, pzbA is dispensable in the heterologous system because *S. lividans* encodes a native copy of the gene as part of a siderophore biosynthetic pathway unrelated to Piz production. Thus, pzbA remains required for Piz production, but its role in bacteria is not limited to Piz anabolism. In contrast, it is currently thought that pzbB is only found associated with Piz production.

*S. lividans* (WT parent, no Piz production) is compared against *S. lividans* harboring a single copy of pzbA (sfaB) alone, pzbB (sfaC) alone, or co-expressing pzbA and pzbB (sfaBC) cloned from the sanglifehrin biosynthetic locus of *Streptomyces flaveolus* in FIG. 4. LC/MS detection of biosynthetic Piz was compared against an authentic L-Piz standard (top row, FIG. 4). In contrast with the in vitro data in FIG. 4, pzbA is dispensable in the heterologous system because *S. lividans* encodes a native copy of the gene as part of a siderophore biosynthetic pathway unrelated to Piz production. Thus, pzbA remains required for Piz production, but its role in bacteria is not limited to Piz anabolism. In contrast, to our knowledge, pzbB is only found associated with Piz production.

Using a mass-spectrometric (MS/MS) method for sensitive quantification, it was estimated that *S. lividans* is carrying at minimum a single copy of a suitable pzbB gene (one or more native pzbA's are natively encoded on the *S. lividans* chromosome, and therefore is not absolutely required for heterologous expression) under a constitutive promoter to produce micromolar L-Piz. Measurably higher (~1 mM) L-Piz titers can be achieved using a heterologous *S. lividans* producer carrying one or more copies of a non-native pzbA in conjunction with heterologous pzbB. *S. lividans* serves as a proof of concept host, not necessarily an industrial endpoint. Much higher L-Piz production can likely be achieved by expressing suitable pzbA and pzbB genes in a heterologous host that overproduces the critical feedstock L-Ornithine. One such candidate host is the actinobacterial industrial producer of L-Orn, *Corynebacterium*

*glutamicum* (20.8-51.5 grams/liter). Importantly, at least one such industrial L-Orn producing strain is publicly available through the American Type Culture Collection (ATCC), making strain engineering from a high producer feasible.

L-Piz Fermentation Production Rate.

The following describes the the rate of fermented L-Piz in heterologous hosts (*Streptomyces lividans*), plated in 1 L. *S. lividans* makes at least 1 mg/L plates in 3 days. This translates to ~14 μg/L per hour or 0.2 μg/L per minute.

Example 5

Directed Discovery of Drugs and Drug-Like Compounds Using Heavy Isotope L-PIZ

This example shows how newfound ability to recognize biosynthetic genes encoding Piz-derived small molecules (e.g., isotopically labeled Piz compound) can facilitate genomic discovery of new natural products that can be used as drug leads.

Current technologies can only enable a rough estimate what the final chemical structures encoded by these biosynthetic genes are. To link biosynthetic genes to the compounds they produce, especially in the case of L-Piz containing compounds, supplying $d_7$-L-Orn to microorganisms of interest can link the biosynthetic compounds to the produced compounds. Some percentage of this labeled compound is expected to become $d_7$ L-Piz in cellulo, and consequently become incorporated into the natural products that will be discovered.

Differential mass spectrometry allows for the detection of the labeled compounds in a much more specific way than absence of such a technology. However, L-Orn can be incorporated into many natural compounds, confusing the analyses. Isotopically labeled L-Piz would be a much more useful molecular probe for the specific and directed discovery of L-Piz—containing drug leads compared to labeled L-Orn for the reasons above.

Figure 5:
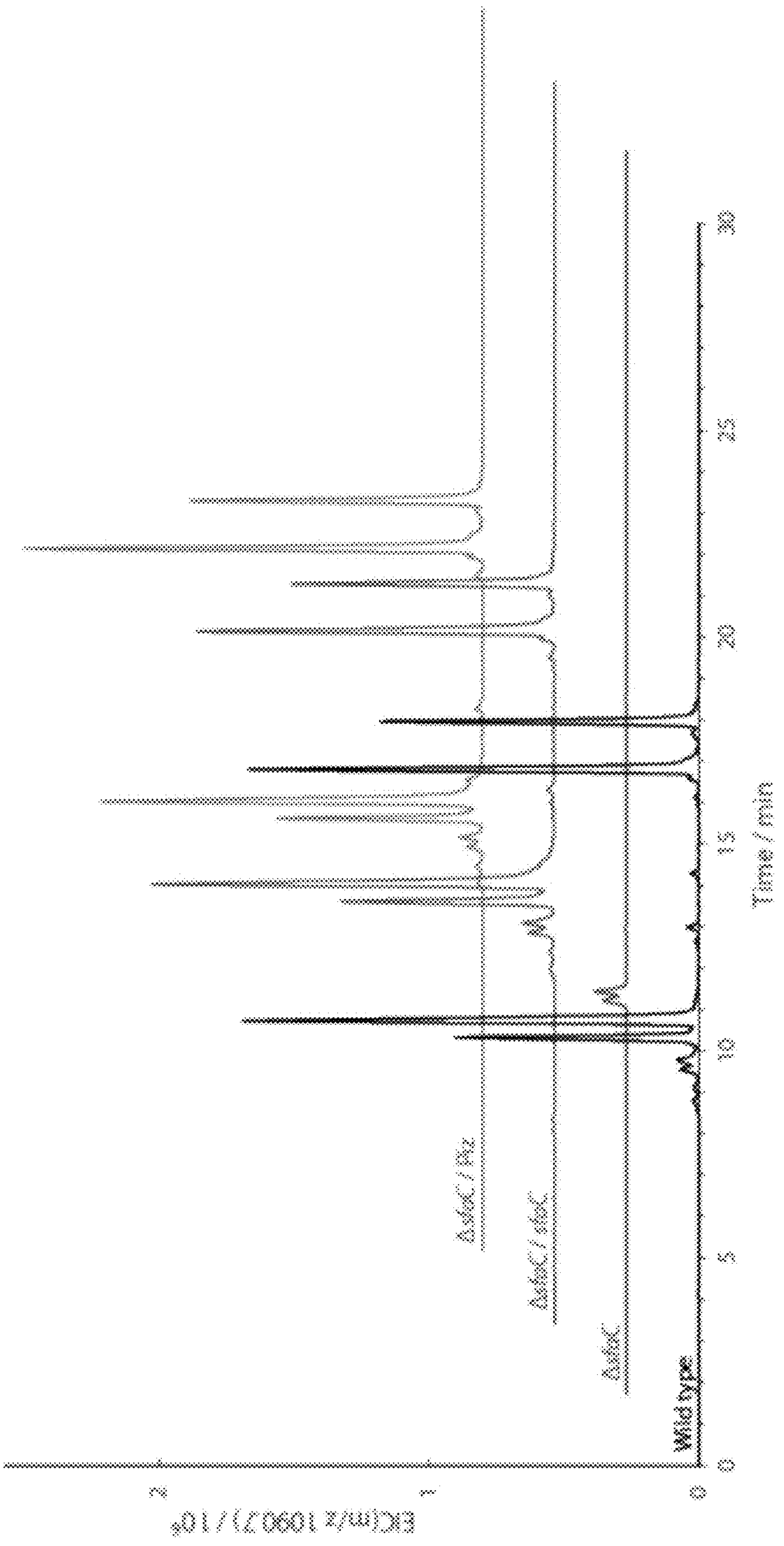
FIG. 5 is a series of LC/MS spectra showing the detection of sanglifehrin, a Piz—containing compound produced by *Streptomyces flaveolus*. Four major isobaric isomers of sanglifehrin A detected in WT *S. flaveolus* fermentation extracts. As expected from the results above, an unmarked gene deletion of pzbB (sfaC) from *S. flaveolus* abrogates sanglifehrin production. Genetic complementation of this mutant with an additional copy of pzbB, or exogenously supplied 50 μM authentic L-Piz (top), restored the production of the four sanglifehrin A isobars. L-Piz is therefore cell penetrant and qualitatively nontoxic. These data additionally link pzbB function with Piz production in vivo, which agrees with the in vitro assay data.

Data indicating L-Piz successfully penetrates at least one Piz-compound producing actinomycete was obtained, followed by subsequent incorporation into a Piz drug-like compound sanglifehrin (see e.g., FIG. 5). FIG. 5 shows LC/MS detection of sanglifehrin, a Piz—containing compound produced by *Streptomyces flaveolus*. Four major isobaric isomers of sanglifehrin A detected in WT *S. flaveolus* fermentation extracts. As expected from the results in FIG. 5, an unmarked gene deletion of pzbB (sfaC) from *S. flaveolus* abrogates sanglifehrin production. Genetic complementation of this mutant with an additional copy of pzbB, or exogenously supplied 50 μM authentic L-Piz (top, FIG. 5), restore the production of the four sanglifehrin A isobars. L-Piz is therefore cell penetrant and qualitatively nontoxic. These data (see e.g., FIG. 5) additionally link pzbB function with Piz production in vivo, which agrees with the in vitro assay data.

Thus, it is expected that isotopically labeled L-Piz will penetrate cells and label Piz compounds without significant complications from poor cell penetrance, transport, or toxicity.

Example 6

Characterization of L-Piperazic Acid Sterochemistry

The following example describes the characterization of the synthesized piperazic acid compound. It was shown that the product is an L-Piz and is enantiomerically pure.

Figure 6:
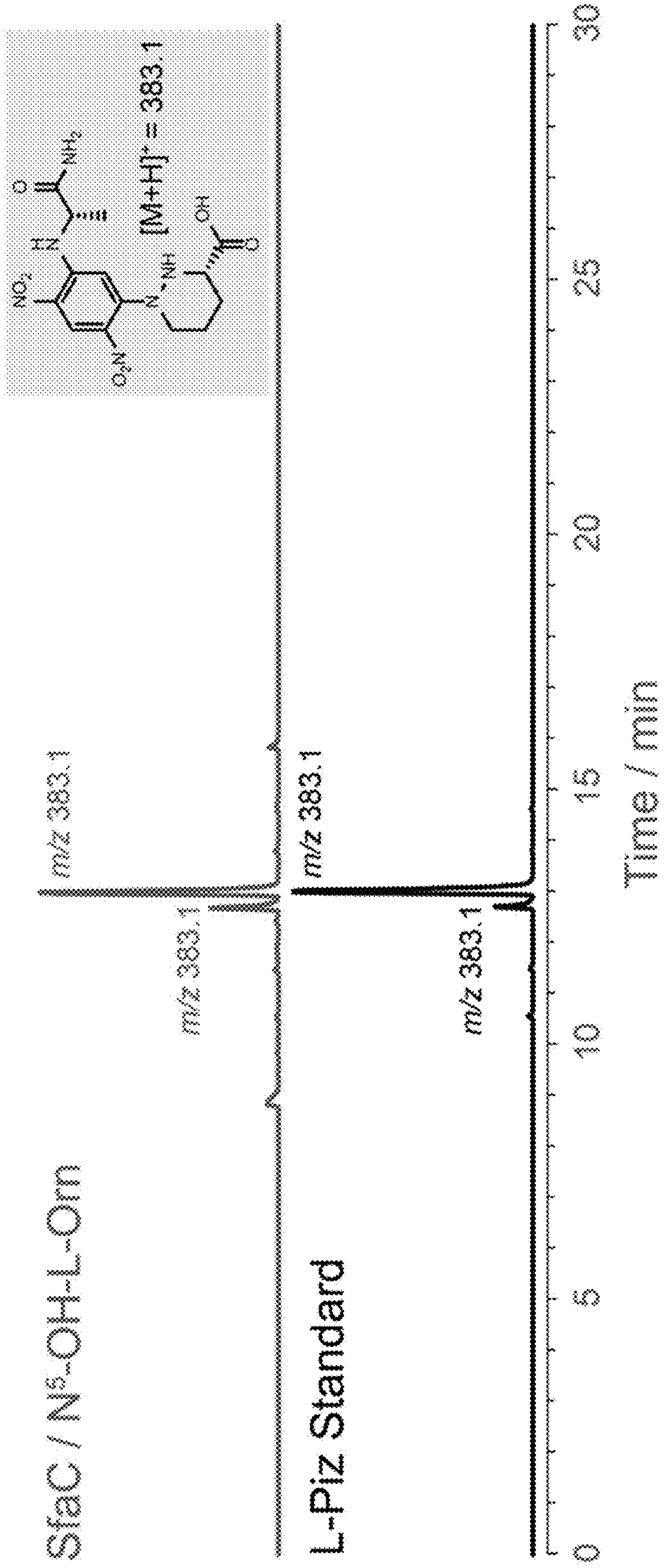
FIG. 6 is a Marfey's derivatization analysis of the product of PzbB in an assay with L-N5 hydroxy Ornithine substrate (the product of PzbA) showing that the synthesized compound is enantiopure L-Piz.

FIG. 6 shows the Marfey's derivatization analysis of the product of PzbB in an assay with L-N5 hydroxy Ornithine substrate (the product of PzbA). This conclusively shows the product of PzbB has the same stereochemistry (L) and mass as the same derivative produced using L-Piz authentic standard (see e.g., FIG. 6).

Example 7

PzBB Ortholog Identity with PzBB Activity

The following example shows that a PzbB ortholog can have as little as around 25% sequence identity to another PzbB ortholog and still produce L-Piz or retain PzbB activity.

Bioinformatic data showed PzbB orthologs that can be used to produce L-Piz have an estimated protein identity (functional cutoff) to be around 25% (some predicted PzbB orthologs have identity scores in the 30% range and most have 45% or above.

Example 8

SFABC (Co-Expressing PZBA and PZBB) Combined Ornithine in Vitro Assay Method

100 μL of reaction in 50 mM Tris.HCl at pH 8.0 was set up with L-orn (500 μM), FAD (50 μM), $His_6$-SfaB (10 μM), SfaC-$His_6$ (135 μM), NADPH (2 mM), and $FeSO_4$ (10 mM). 30 μL aliquots were removed at 0 min, 15 min, and 30 min, and combined with 30 μL acetonitrile. The cloudy mixture was centrifuged, and 30 μL of the supernatant was acidified with 3 μL 2 M HCl. Sample was analyzed for piperazic acid by HPLC/MS. Analysis was performed using an lmtakt Intrada Amino Acid column (50×3 mm, 3 μm pore size) installed on an Agilent 1260 Infinity HPLC connected to an Agilent 6420 Triple-Quad mass spectrometer using the following method: T=0, 0% B; T=2, 0% B; T=8, 100% B; T=14, 100% B; A: water (30%)/methanol (70%)+0.3% formic acid, B: water+100 mM ammonium formate; 0.4 mL/min. A novel peak at T=5.4 min eluted with a $[M+H]^+$ of 131, corresponding to piperazic acid.

Example 9

SFABC (Co-Expressing PZBA and PZBB) Combined $D^7$-Ornithine In Vitro Assay Method 100 μL of reaction in 50 mM Tris.HCl at pH 8.0 was set up with $d^7$-L-orn (500 μM), FAD (50 μM), $His_6$-SfaB (10 μM), SfaC-$His_6$ (135 μM), NADPH (2 mM), and $FeSO_4$ (10 mM). 30 μL aliquots were removed at 0 min, 15 min, and 30 min, and combined with 30 μL acetonitrile. The cloudy mixture was centrifuged, and 30 μL of the supernatant was acidified with 3 μL 2 M HCl. Sample was analyzed for piperazic acid by HPLC/MS. Analysis was performed using an lmtakt Intrada Amino Acid column (50×3 mm, 3 μm pore size) installed on an Agilent 1260 Infinity HPLC connected to an Agilent 6420 Triple-Quad mass spectrometer using the following method: T=0, 0% B; T=2, 0% B; T=8, 100% B; T=14, 100% B; A: water (30%)/methanol (70%)+0.3% formic acid, B: water+100 mM ammonium formate; 0.4 mL/min. A novel peak at T=5.4 min eluted with a $[M+H]^+$ of 138, corresponding to piperazic acid.

Example 10

PmAB (*Amycolatopsis Alba*) Ornithine In Vitro Assay

100 μL of reaction in 50 mM Tris.HCl at pH 7.0 was set up with L-orn (500 μM), FAD (50 μM), PzbAB(*Amycolatopsis alba*) (14 μM), NADPH (2 mM), and $FeSO_4$ (10 mM). 30 μL aliquots were removed at 0 min, 15 min, and 30 min, and combined with 30 μL acetonitrile. The cloudy mixture was centrifuged, and 30 μL of the supernatant was acidified with 3 μL 2 M HCl. Sample was analyzed for piperazic acid by HPLC/MS. Analysis was performed using an lmtakt Intrada Amino Acid column (50×3 mm, 3 μm pore size) installed on an Agilent 1260 Infinity HPLC connected to an Agilent 6420 Triple-Quad mass spectrometer using the following method: T=0, 0% B; T=2, 0% B; T=8, 100% B; T=14, 100% B; A: water (30%)/methanol (70%)+0.3% formic acid, B: water+100 mM ammonium formate; 0.4 mL/min. A novel peak at T=5.4 min eluted with a $[M+H]^+$ of 131, corresponding to piperazic acid.

Example 11

SFAC (Expressing PZBB) $N^5$—OH-L-ORNITHINE In Vitro Assay

100 μL of reaction in 50 mM Tris.HCl at pH 8.0 was set up with $N^5$—OH-L-orn (1 mM), $His_6$-SfaC (18 μM). 30 μL aliquots were removed at 0 min, 10 min, and 20 min, and combined with 30 μL 6% 5-sulfosalicylic acid. The cloudy mixture was centrifuged, and the supernatant was used for analysis. Sample was analyzed for piperazic acid by HPLC/MS. Analysis was performed using an lmtakt Intrada Amino Acid column (50×3 mm, 3 μm pore size) installed on an Agilent 1260 Infinity HPLC connected to an Agilent 6420 Triple-Quad mass spectrometer using the following method: T=0.86% B; T=3, 86% B; T=10, 0% B; T=11, 0% B; T=12, 86% B; T=14, 86% B; A: water+100 mM ammonium formate, B: acetonitrile+0.1% formic acid; 0.6 mL/min. A peak at 5.6 min with a $[M+H]^+$ of 131, corresponded to piperazic acid.

Example 12

Marfey'S Analysis of SFAC (Expressing PZBB) Product

The following example confirms that the product of PzbAB from L-Orn is actually L-Piz. Marfey's analysis was performed on the PzbAB reaction product and compared the results with synthetic L-Piz standard. The data so far are consistent with the PzbAB reaction yielding an enantiopure L-Piz.

100 μL of reaction in 50 mM Tris.HCl at pH 8.0 was set up with $N^5$—OH-L-orn (1 mM), $His_6$-SfaC (20 μM), hemin (20 μM). Reaction was allowed to proceed for a few minutes. A control was also set up in 50 mM Tris.HCl at pH 8.0 with L-Piz (0.25 mg/mL) and hemin (20 μM). To 100 μL of aqueous reaction or control was added 50 μL of 1% FDAA in acetone. The reaction was incubated at 50° C. for 1 hour. 100 μL of 1 M HCl was then added. Finally, 300 μL of water/MeCN (50:50) was added to dissolve the precipitate. The supernatant was filtered (Agilent Captiva Econo Filter, 0.2 μL) into HPLC vials for HPLC/MS analysis.

Analysis was performed using a Phenomenex Luna C18 column (75×3 mm, 3 μm pore size) installed on an Agilent 1260 Infinity HPLC connected to an Agilent 6420 Triple-Quad mass spectrometer using the following method: T=0, 10% B; T=5, 10% B; T=25, 100% B; T=27, 100% B, T=29, 10% B, T=30, 10% B; A: water+0.1% formic acid, B: acetonitrile+0.1% formic acid; 0.6 mL/min. 10 μL of the sample was injected per run, and a total ion count chromatogram was obtained for each sample. An extracted ion count chromatogram at m/z 383.1 (monoisotopic mass of protonated FDAA-derivatized piz) was used to detect derivatization. The UV response at 340 nm was also monitored.

Example 13

Hemin Influence on SFAC (Expressing PZBB)

This example shows that the PzbB's cofactor is now confirmed to be $Fe^{+3}$-protoporphryin IX (aka hemin). As expected for a bona fide cofactor, adding hemin increases the rate of turnover.

100 μL of reaction in 50 mM Tris.HCl at pH 8.0 was set up with $N^5$—OH-L-orn (1 mM), SfaC-$His_6$ (2 μM), and either hemin in DMSO (10 μM) or just DMSO. The two reactions were incubated at 4° C. for 7 hours. Then, 30 μL aliquots were removed at 30, 60, and 90 sec, and combined with 30 μL 6% 5-sulfosalicylic acid. The cloudy mixture was centrifuged, and the supernatant was used for analysis. Sample was analyzed for piperazic acid by HPLC/MS. Analysis was performed using an lmtakt Intrada Amino Acid column (50×3 mm, 3 μm pore size) installed on an Agilent 1260 Infinity HPLC connected to an Agilent 6420 Triple-Quad mass spectrometer using the following method: T=0, 86% B; T=3, 86% B; T=10, 0% B; T=11, 0% B; T=12, 86% B; T=14, 86% B; A: water+100 mM ammonium formate, B: acetonitrile+0.1% formic acid; 0.6 mL/min. An extracted ion count chromatogram at m/z 131.1 (monoisotopic mass of protonated piperazic acid) was used to detect piperazic acid. For quantification, an SRM transition (m/z 131.1=>56.3; source voltage, 86 V; collision energy, 37 V) was monitored, and a standard curve (second order polynomial, R2=0.9996) was generated between 0.1 μM and 100 μM using a chemically synthesized L-piperazic acid dihydrochloride standard. The concentrations in time were plotted, and fitted to a line. The slope of the line was used as the rate of the reaction. Hemin increased the slope by 14.4 times.

Example 14

Fermentative L-Piz Production from Various *Streptomyces* Strains

Figure 7:
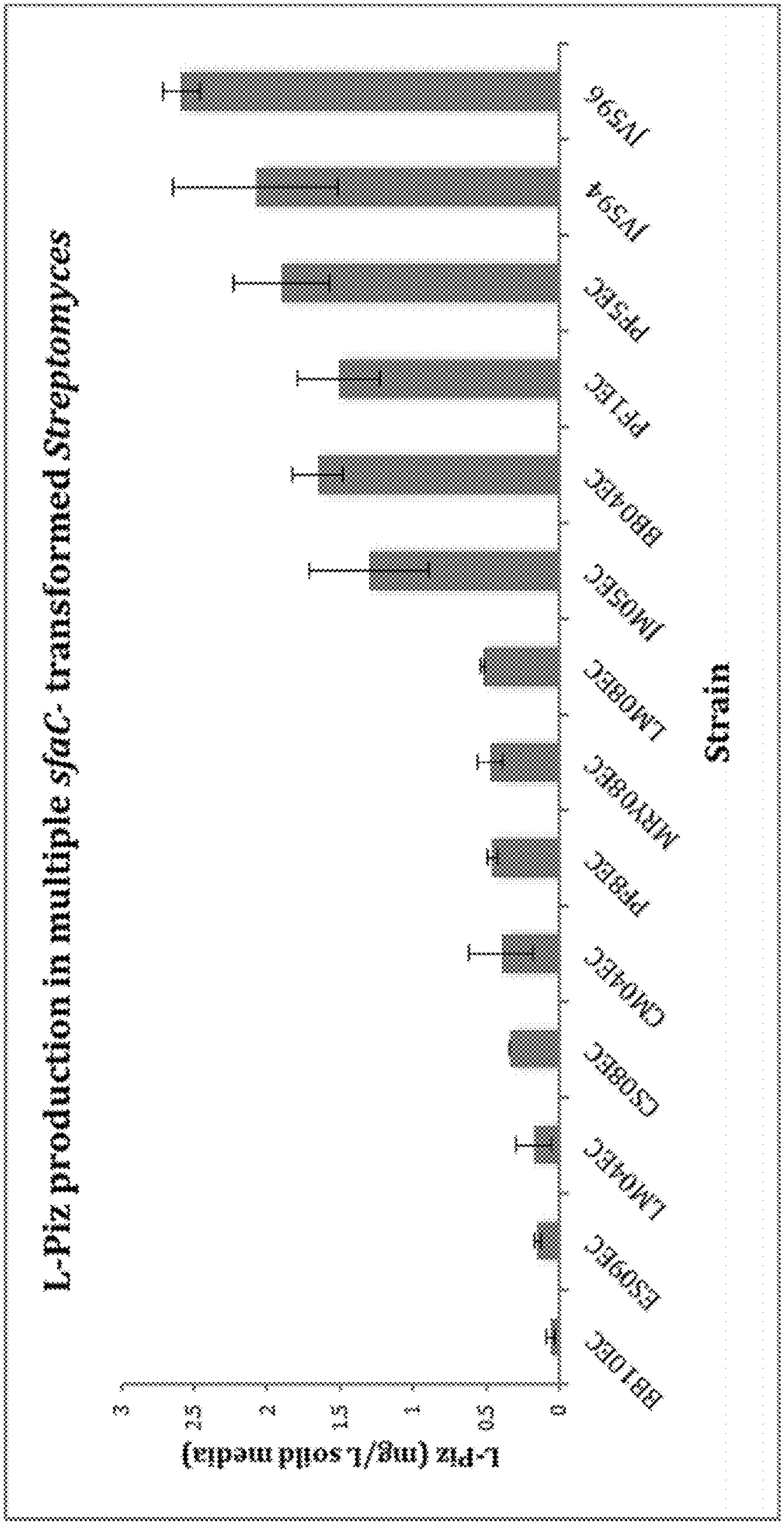
FIG. 7 is a graph showing L-Piz production from various *Streptomyces* strains. Randomly selected environmental *Streptomyces* isolates were transformed with pYH015 via intergeneric conjugation as described for *S. lividans.*

This example describes L-Piz production from various *Streptomyces* strains (see e.g., FIG. 7) (methods are as described above unless stated otherwise). Randomly selected environmental *Streptomyces* isolates were transformed with pYHO15 via intergeneric conjugation as described for *S. lividans*. L-Piz production was quantified via SRM LC/MS from triplicate growths essentially as noted for the *S. lividans* transformants. Resulting strain to strain Piz production is variable, ranging from very low to nearly the same as *S. lividans* carrying pYH015 (JV594). Note *S. lividans* JV 596 expressing both sfaB and sfaC produces more L-Piz, with less titer variability, than all sfaC-alone strains in the panel. L-Piz was not detected in any non-transformed parent strains (not shown).

It is noted that the value reported here for for JV596 (~2.5 mg/L) is higher that what we previously reported (~1 mg/L).

SEQUENCE LISTING

PzbA
SEQ ID NO: 1 >*Mycobacterium_marinum*_M
MQQRLTMWSATGLIFGHALCMNTCRTMVVPRGKPLCIERVPPLPCQPKMGESTMPSGGIA
DPELALVDRTLSVVGVGFGVTGLALAAALHEAEMTEDALFLESRPKFGWHDDMLIEGSSM
QVSFLKDIVTMRNPTSRFSFISYLHAMGRLTNFINHGVLTPSRREFADYLRWVARQLDHL
VRYDVHVTDVRPVYEGATVSALDIVAGENAVVRTRNLVLGTGLRPRMPQGVIPNRRVWHS
SELLSRLAECGDYLARQIVVVGAGQSAAEIALYLLDRYPDSQVCPVFARYGYSAVDASPF
ANRIFDPSGVDDFYAASPSVKASLLRYHGNTNYSVVSSDVLGALYRRQYEQSVIGDPRLR
IFHASRLHLVSFNDDSVVADIEFLPTGEVTRLDTDLVVIYATGYESRDPKHLLTSLAGYL
RTDELGALRLDRRYRVKTVEGFRCGIFVQGATESTHGIASTLLSVAAVRAGEISQSLMET
SQARPPAGSVTHRH SEQ ID NO: 2 >*Lentzea_flaviverrucosa*_DSM_44664
VTSEPYDVVGIGFGPSNLSLAIALEETGGLSAAFFEKQDSLRWHSGMLVPGAKMQVSFLK
DLATPRNPVSSYSFVSYLHDRGRFARFVNNSDFFPTRREFQDYLRWAEARLSPPVHYRAE
VVSVRRAEGVLRVHVRDTESGATRTVDTRNIVISTGLVPRMPVGLEAGESVWHSSQFLHR
FHALGDRDVRRVAVVGAGQSAAELVRYLHENLPSAQVFAVLPSYGYAIADSTPFANEVFD
ADAVDVFYDASDKAKAAIWRYHRNTNYSVVDDEVIRDLYQRAYDDEVRGEPRLRFLPLTR
VVGAKQDRDGITLLTHSTVDDQARDLPLDLVVCATGYDPMDPGELLAGLGCSVAYDELGR
HLVGRDHRLVTEPDQDCGIYLQGGTEHTHGLTSSLLSNIAVRGGEITQSILRRRAEQRNG
APA SEQ ID NO: 3 >*Streptomyces_aureofaciens*_ATCC_10762
VGERQRSGVVAGTGIVDVAGIGFGPSNLALAAAIAEIAGEAPVSARFFEA
QPRFGWHRGMLIEGATMQVSYLKDLVTMRNPTSPYSFLCYLQARGRLADF
INTKSPYPLRVEFHDYLEWVAESFADLVSYGARVVSVEPVSAEQGVEFLD
VHFVAPDGTRQVQRARNLVIAAGIEPRLPAGLPASPRIWHTAKFLPEVDR
IARQDPRSFVVLGSGQSAAEAIEHLHARFPRAQVHSVHARYGFSVADDSP
FANQVFNPEAVDRFHTAPDDVRQRLIDYHASTNYSVVDADLLHSLFQQAY
LEKVAGNPRLNFHNVSRVSEVTETPDGLRIDVESLSSGTSTVIEAQALVC
ATGYTRTDPAVFLDGLLPHCPLDDQGRLRLDREHRVVTDESVRCGIYVQG
FGEHSHGLSETLLSLSAVRAGEIGDMLVKALSG SEQ ID NO: 4 >*Streptomyces_diastatochromogenes*_NRRL_B-1698
VNVSEPGSDQVVDVVGIGFGPSNLALAVALGEGGRKASEKPVTSVFFERK
ERFTWHGGMLIDGATMQISFLKDLVTLRDPRSPYTFLHYLHQVGRLPDFI
NHKLLFPSRIEFHDYLCWVAESFDHQVRYGADVVDVRPVHSDGAVNHLDV
VVRHEGPEGERISVQRTRNVVVGTGLEAHMPAGAAPGDRVWHTSELLHKV
AALKEEPRRIVVVGAGQSAAEATEYLHRRFEAAEICPVFTRYGYSPADDS
PFANRIFDPLAVDDYYAATPEVKRMLLGYHRNTNYSVVDAELIDELYRRV
YQEKVQGRHRLKVFNASRLAEVKAGAEGVQVTVESVISRCRTVLDADCVV
YATGYRPTDVRRLIGGMAGLCKADEMGRLHADRDYRVVTEGDVHCGIYLQ
GATEHSHGISSSLLSNTAVRAGEIADSIVAGVVGATASE SEQ ID NO: 5 >*Streptomyces*_sp._DvalAA-43
MDASARETYDVVGIGFGPSNLSLAIALEEHEANVPARPISAAFFERQPSF
GWHRNMLLPAATMQISFLKDLATFRNPVSRYSFIAYLHAADRLVQFVNNQ
TFFPTRQEFHQYLEWAESSFSDRVSYNSEVTAIRRATGTGPGEPDCLQIE
VRDGIGGGCRLVHARNVAISTGLVPRMPAGVERDDRVWHSSEFLEKYGQV
DPNALKSVAVVGAGQSAAEITRFLHDALPHARVFAVVPSYGYSVADDTPF
ANRVFDPSAVDDYYFGTEQTREAFWRYHRNTNYSVVDDEIIRDLHQRSYD
EDVRNDRRLHFLNLTRVDDVQRIGTEIRVGLRSLIDVEAQTLDVDALVFA
TGYGAMQPTGLLGDLDRHCLRDAAGRHRAERDYRLVTTPELSCGIYLQGG
TEHTHGLTSSLLSNVAVRSGEIADSIVRRRAEEHEPVASLGTSGRTS SEQ ID NO: 6 >*Collimonas_fungivorans*_Ter6
MQVCFLKDLAMLRNPTSPFTFLSYLHDKNRLVDFVNHKILFSSRVEFHDY
LEWAAAKLKRLVQYDAEVVEVSPVICDGVVKWLDVVVQRDGNPSHHEIYR
THNLVIAPGLEPTMPPGISRSERVWHSSEVLDRIAHLTEEPQQFTVVGAG
QSAAEITAYLHDHFKYAKVRSIFSRYGYSAADDSPFTNRIFDPLAVDEYY
QARDDVKKMLLNFHRNTNYSVVDADLLEDLYRRHYQEMVRGESRLEFMNV
SKVFGAVADRDSVDLSVEFLPTGDMRKLRSDIVVFGSGYKIADPIRYFSD
FAGKCIRDSFGQLRVARNYRICTSEDVECGIYLQGTTEHTHGLSSTLLSN
TAVRAGEILEAMTWERDNKKISSHA SEQ ID NO: 7 >*Streptomyces_reticuli*_TUE45
MTRLAGQAPTAQHSPESEVRDVTGIGFGAANLALAVALHESGAGDRALFL
EKQKEFGWHRGMLIEGSSLQVSFLKDIATMRNPTSDFGFLSYLQEKGRLV
DFINQHTLLPSRIEYHDYLQWAADRLGHMVEYGVEATGVRPVTDAGEVVA
LDVLAGDRVVTRTRNLVIASGLRPRLPEGAETGERVWHSSQLLHRLPAFD
ERPPRRAVVVGAGQSAAEVAAHLMERYPQAEVCAVFSRYGYSVADSSPFA
NRVFDPAAVDDFYFAPPEVKQAIMRYHGGTNYAVVDEDVLQGLYRRQYEQ
KVTGTPRLRVMNASRLVSVEPRGETAAVRVEFLPTGEHADLDADLVVYAT
GYRSADPAELLGGVAGSLRRDAAGQVLIGRDYRLSTTGDFRCGIYVQGAT
EATHGIASTLLSMVAVRAGEIAQSIIGGRRDPDRTAGTKAVAGNRG SEQ ID NO: 8 >*Streptomyces_scabiei*_NCPPB_4086
MEAHTDAYEVVGIGFGPSNLSLAIALEEQRGKDEKPLTAAFFEKQASLGW
HRNMLLPDTKMQISFLKDLATFRNPASQWSFIAYLHAAGRLAQFVNNQNF -continued

SEQUENCE LISTING

FPTRNEFHDYLDWAESSFSDRVTYNCEVNAVHLPDGYTGGPVDTVRVEVK
DNTPRGGTRLVEARNLVISTGLVPTMPTGIERGERVWHSSEFLGRFGTLD
RDRVRRFAVVGAGQSAAEITRYVYDIVPNAEVYAIMPSYGYSIADDTPYA
NRIFDADAVDDYYGGTDHTRESFWRYHRNTNYGVADDEVIRDLYQRAYDD
EVARIKRLHLLNLSRVRTVEQTVDGARLTMHSVRDDSTYGLDVDAIVFAT
GYDSMDPTALLGDLAPHCLRDEEGRLRVERDYRLVTSPDLNVGIYLQGGT
EHTHGLASALLSNIAIRSGEIADAIAIDLAARQHTTARSTIG

SEQ ID NO: 9 >*Kutzneria_albida*_DSM_43870
MQRDYRVVTVPEMRCGIYLQGGTEHTHGLTSSLLSNIVIRTGEITDSIIT
RRAELNVGERRTVNG SEQ ID NO: 10 >*Streptomyces_albus*_ZpM
MTGPEVYDIVGVGFGPANLALAVALTERGSSTPLRALFLDRNESFSWHPG
MLIHDATMQVNFLKDLITLRNPASDFSFLSYLKARGRLVDFINHKTFFPT
RVEFHDYLEWAAGRVGDVVEYGTEVVDVRPVERDGEVVYFDVVGHQQVGG
VSQAVVCRARNVVVAPGLVPRLPGEASQSERVWHSSELLHRVGDLPTDKR
MQFVVVGAGQSAAEVVGYLHARYECADVHAVHSRYGYSPADDTPFANRVF
DPAAVEHFFHAPPSVKDKFFEYHANTNYSVVDVELIEDLYARVYRESVTE
RRRLHIHGMSELTEVADGPEGLRVSVRFLPDGTTTVLEPDHVVYATGYKP
ADVNRVIGVVAELCKRDSSGNLRLLHDYRVDMASHVRCGIYLQGGTEHSH
GITSSLLSNLADRAAEILDSVLAHGGQLSADAAAWEVAS SEQ ID NO: 11 >*Rhodococcus_fascians*_02-815
MGAQSGSSVADVVGVGFGPSNLALAIALQESIQPGPVPAKFSMKFYELQP
RFGWHRGMLMEDATMQVSFLKDLATMRNPMSRYTFVSYLREKERIAEFIN
SKTLYPLRVEFHDYLEWAASQFQSNVSYGSEIKDIRPVVENGVVEYVDVV
GPDDVVQRARNIVIGMGLTPRLPDGVNRSERIWHSSQLLGRAAAVTYVPQ
NFVVVGSGQSAAEVADYLHRTFPRANVHTVLSRYGYSVADDSPYANGIFD
PEGVDRFFSAPTDEKQRLLEYHANTNYSVVDLDISQSLYLKSYQEKVLGK
QRLRMINTSRVTSVDEDTDGVRVEVTSSATGLTHTIEADVIVYATGYRPS
DPAPLLQGLMRECKHDEQGRLSVGRDYRVTTSDAVRAGIYVHGASTEHSH
GLSAGLLSNTAVRSGEIAQSILRR SEQ ID NO: 12 >Streptomyces_neyagawaensis_NRRL_B-3092
MEANTEAYEVVGIGFGPANLSLAIALEEQRGKDEKQLTAAFFEKQPSLGW
HRNMLLPDTKMQISFLKDLATFRNPASQWSFIAYLHAAGRLAQFVNNQNF
FPTRNEFHDYLEWAESSFSDRVTYNSEVNAVHLPDGHDGGPVDTVRVEVK
DNGPRGGTRLVEARNLVISTGLVPKMPDGVDRGERVWHSSEFLGRFHTLD
PSRVRRFAVVGAGQSAAEITRYVYDTIPDAEVYAIMPSYGYSIADDTPYA
NRIFDADAVDDYYGGTDRTRESFWRYHRNTNYGVADDEVIRDLYQRAYDD
EVARIKRLHLLNLSRVQRVDQRADGARLTMHSVRDDSVYDLDVDAIVFAT
GYDSMDPTALLGDLAPYCLRDDEGRLRVERDYRLVTKPELNVGIYLQGGT
EHTHGLASSLLSNIAIRSGEIADAIAIAIDLASRRHTTV SEQ ID NO: 13 >*Kutzneria_buriramensis*_DSM_45791
MDTRGSETYDVVGIGFGPANLSLAIALEESPQRLTSAFFERQPSLGWHRG
MLVPAAKMQVAFLKDLVTFRNPTSTFSFVSYLHDRGRLARFVNNQDFFPT
RREFHDYLEWAESRVSHRVSYQSEVTAMRLPCAQRPGEDDHVEVEVRDRT
APSGSRTVAARNVVISTGLVPRMPAGLQTDEFVWHSSEFLHKFSRADHSG
LKRVAVVGAGQSAAEIVRFLYDMLPDANVFAIIPSYGYSIADNTPFANQI
FDPAAVDDFYAGSDQAKDAIWRYHRNTNYSVVDDEVIKDLYRRQYDDDLG
RPGRLAFLNLSRVLDVKRVGEDTRVTVHSTATEQAADLDVDVLVCATGYS
PMEPADLLGDLARYCVYDGDGRYQVDRDYRLVTPDLDCGIYLQGGTEHTH
GLSSSLLSNIAVRSGEIAASIARRRLSTNGNGVHA SEQ ID NO: 14 >*Streptomyces_yanglinensis*_CGMCC_4.2023
MSNREQTYDVVGIGFGPSNLSLAIALEEFGAHGMENEISSLFLERQPSFG
WHRNMLLPSATMQISFLKDLVTFRNPTSGFSFIAYLHASGRLPQFVNNQD
FFPTRQEFHQYLEWAQAQVAGRIEYGAEVTSIRLPSGTAPQEGADRLVLE
VAEGAGRTGRAVEARNVVISTGLVPSMPAGAERDERVWHSSEFLDKYRRT
DHRELRRVAVVGAGQSAAEIARFLYDELPHAQVSAIIPSYGYAVADDTPF
ANRIFDPSAVDDYYFGTEQTRESFWRYHRNTNYSVVDDEVIRDLYRRSYD
DEVRGVTRLQLLNLTRVTGVKRAGAETRVSLQVGPDAELRELDFDLLVCA
TGYDGMEPTGLLGELDRYCLRDEAGRYRVERDYRIVTTPELRCGIYLQGG
TEHTHGLTSSLLSNLAVRSGEIADSIIARRAGYGAEREVLAKIGGDIA SEQ ID NO: 15 >*Streptomyces_griseochromogenes*_ATCC_14511
MSDREHETYDVVGIGFGPSNLSLAIALEEYRANGPENEISALFLERQSAF
GWHRNMLLPSTTMQISFLKDLVTFRNPTSSFSFIAYLHASGRLPQFVNNQ
DFFPTRQEFHQYLEWAQARVADRVAYGSEVTSIRLPPGADPERSDRLRLE
VADATGRNGRVVEARNVVISTGLVPSMPVGTERDERVWHSSEFLEKYRRM
NPAELRRVAVVGAGQSAAEITRFLYDELPHAEVCAVIPSYGYSVADDTPF
ANQIFDPGAVDDYYFGTEQTREAFWRYHRNTNYSVVDDEVIRDLYRRSYD
DEVRGVRRLQFLNLTRVTSVKRVGAETRVSLQVGPDDEVRELDFDALVCA
TGYSTMEPTDLLGDLDRHCLRDEAGRYRVERDYRIVTAPEMRCGIYLQGG
TEHTHGLTSSLLSNIAVRSGEIADSIVAGRAGRNAERALLAEVGGDTR -continued

SEQUENCE LISTING

SEQ ID NO: 16 >*Streptomyces_incarnatus*_NRRL_8089
MDIAGRPSQEIYDVVGIGFGPSNMSLAIALEEHEASSPQHPLKCHFFERQ
PTFGWHRNMLLPSTTMQISFLKDLATFRNPTSRFSFISYLHAADRLVQFV
NNQDFFPTRQEFHQYLEWAAAGLRDRVTYGAEVTSIRPAGEAGSGTSDIL
EIEVRGGDGTTSVVSARNVVISTGLVPRLPEGVTSDERVWHSSEFLSRFH
AQAPGDLKSVAVVGAGQSAAEITRFLYDSLPHAQVTAVIPSYGYSVADDT
PFANQVFDPSAVDEYYFGTERARDSFWRYHRNTNYSVVDADVIRALYQRS
YDEQVRGSQRLHFRNLTRVDEVERVGSGARVVVRSVLDDRTEELALDALV
FATGYDGLDPARLLGDFDRHFLRDAAGRHRVERDYRLVPASGLTAGVYLQ
GGTEHTHGLSSALLSNIAVRSGEIADSIVLRRTERELGSGRPVQAARSAA SEQ ID NO: 17 >*Streptomyces_albulus*_PD-1
MESHRMTGPEVYDIVGVGFGPANLALAVALTERGSSTPLRALFLDRNESFSWHPGMLIHD
ATMQVNFLKDLITLRNPASDFSFLSYLKARGRLVDFINHKTFFPTRVEFHDYLEWAAGRV
GDVVEYGTEVVDVRPVERDGEVVYFDVVGHQQVGGVSQAVVCRARNVVVAPGLVPRLPGE
ASQSERVWHSSELLHRVGDLPTDKRMQFVVVGAGQSAAEVVGYLHARYECADVHAVHSRY
GYSPADDTPFANRVFDPAAVEHFFHAPPSVKDKFFEYHANTNYSVVDVELIEDLYARVYR
ESVTERRRLHIHGMSELTEVADGPEGLRVSVRFLPDGTTTVLEPDHVVYATGYKPADVNR
VIGVVAELCKRDSSGNLRLLHDYRVDMASHVRCGIYLQGGTEHSHGITSSLLSNLADRAA
EILDSVLAHGGQLSADAAAWEVAS SEQ ID NO: 18 >*Streptomyces_tsukubaensis*_NRRL_18488
MGITGRGKHEVLDLVGIGFGPSNLALAIALDEHGASAPQHPVTSHFFERQPAFGWHRNML
LPSTTMQISFLKDLATFRNPMSRFSFVSYLHASNRLVQFVNNQDFYPTRQEFHQYLEWAA
AALGDRVTYGAEVASIRPRTGPGSRTADLLEIEVRRGDGTTGTVTARNVAISTGLVPRLP
KGVTSGPRVWHSSEFLGRFGAQTPADLRHVAVVGAGQSAAEITRFLHDSLPHAQVSAVIP
SYGYSIADDTPFANQVFDPGAVDEYYYGTQRARDAFWRYHGNTNYSVVDADVIRDLYRRS
YDEEVRGGRRLHFRNLTRVVEVEGSASGAWVMLRSLLDDRREELAVDALVFATGYDGMDP
ARLLGDFDRHFQRDAAGRHRLERDYRLVSASGLTCGVYLQGGTEHSHGLSSSLLSNTAVR
SGEIADSIVMRRTRQELGRSRSVAESPSAA SEQ ID NO: 19 >*Streptomyces_himastatinicus*_ATCC_53653_hmtM
MAHETEIYDVVGIGFGPSNLSLAIALEESPDPVTSLFFERQPTLGWHRGMLLPSAKMQVS
FLKDLATFRNPASGFGFISYLHDMGRLTRFVNNQDFFPTRREFHDYLEWAASKLTGRVSY
DSEVTAVSAVAAAGEGPADRVRVTVRGADGAPRQVEARNVVISTGLVPRMPVNLEAGERV
WHSSEFLHRFRQREGELTRVAVVGAGQSAAEIVRFLYDTLPEVRVSAVIPSFGYAIADDT
PFANQVFDPDAVDSYYHGTQASKDAVWQYHKNTNYSVVDDEVIRGLYERAYEDELSGHGR
LDFRNLARVLDAEPTGDGTRITVYSLVDDASYDLDVDVLICATGYDPMNPARVLGELDKY
CVHDTEGRHRVDRDYRLVTTSDLTCGIYLQGGTEHTHGLGSSLLSNIAVRSGDIAQSITA
RCAGAPKKGLTA SEQ ID NO: 20 >*Streptomyces_flaveolus*_DSM_9954_sfaB
MTRLAEQSSTAQQSPESEVLDVTGIGFGAANLALAVALHESEAAGKALFLEKQKEFGWHR
GMLLGGSSLQVSFLKDIATMRNPTSDFGFLSYLQEKDRLVDFINQHTLLPSRIEYHDYLQ
WAADRLNHLVEYGVEATGVRPVTEAGEVVALDVLAGDRVVARTRNLVLASGLRPRLPEGA
ETGERVWHSSQLLHRLPAFDERPPRRAVVVGAGQSAAEVAAHLMDRYPQAEVCAVFARYG
YSVADSSPFANRVFDPAAVDDFYFAPPEVKQAIMRYHGGTNYAVVDEDVLQGLYRRQYEQ
KVSGAPRLRVMNASRLVSVEPRQESAAVRVEFLPTGEHTDLDADLVVYATGYDSTDPAEL
LGGVSGALRRDEAGELLIGRDYRLGTTGDFRCGIYVQGATEATHGIASTLLSMVAVRAGE
IARSITGGRCDPDRSTGSKAAAGNRG SEQ ID NO: 21 >*Streptomyces_aurantiacus*_JA_4570
MGTREHEIYDIVGIGFGPSNLSLAIALEEHQANSSQQPVRAAFFERQPSFGWHRNMLLPQ
ATMQISFLKDLATFRNPLSRYSFVSYLHASDRLVQFVNNQDFFPTRQEFHQYLEWAESGF
RDRVTYNSEVTEIRVSDEGSGGEQLLEIVVRDTVGGGTRVVQARNVTVSTGLVPRMPDGM
LRDERVWHSSEFLAKYGRMRPEDLKNVAVVGAGQSAAEITKYLHDKLPHAQVSAILPSYG
YSVADDTPFANQVFDPTAVDHYYFGTENTRDAFWRYHKNTNYSVVDDDVIRELFRRSYEE
EVAGEKRLHFLNLTRVKEVKRSGNDTRVVLHSLLDGESEQEMDVDALVFATGYSTMDATR
LLGDLDRFCERDEEGRHRVERDYRVVTSGELSCGIYLQGGTEHTHGLTSSLLSNIAVRSG
EIADSIVERRGAGQRV SEQ ID NO: 22 >*Streptomyces*_sp._RJA2928_padN
MTDSAPEDRTVDVTGIGFGPSNLALATALAEPSATGPGRPLEAVYFERKNRFSWHGGMLL
DGATMQISFLKDLVTLRDPRSPYSFLSYLHHAGRLSDFINHKLLFPSRIEFHDYLEWVAG
FFEEQVVYGSEVVDVRPVAREDAVEHMDVVVRQRTAAGERTVVQRTRDLVVATGLEPSLP
PGTVCSDRVWHSSELLYRVERLPPTPRRIVVVGAGQSAAEAAEFLHSRFPSTDICAVFSR
YGYSPSDDSPFANRIFDPAAVDDYCAAAPETRRMLLDYHRNTNYSVVDPELIDELYRRVY
QEKVRGRPRLNILGASRLMAAEPAGDGVDVVVESLVTGERTPMRADCVVYATGYRPTDAR
GLLGSMAGLCKADELGRLEADRRYRVITEGDVRCAIYLQGATEHSHGISSSLLSNTAVRA
GEIADAIRADAVRAGARATTRSQPQPQT SEQ ID NO: 23 >*Frankia_alni*_str._ACN14A
MSAREFDIYDVVGIGFGPSNLSLAVALDEFRVNGMGNVFSNIFFERRSSFAWHPSMLLPS
ATMQISFLKDLVTFRNPTSSFSFVAYLHESGRLPRFVNNQDFFPTREEFHQYLEWAQARV
AHRVAYGSEARSLRLPAGVGPERADRLCLQVADAASGTSRMVEARNVVISTGLVPTMPTG
VERGERVWHSSEFLERFRRTSPARIRRVAVVGAGQSAAEITRFLYDELPHAEVSAIIPSY -continued

SEQUENCE LISTING

GYCVADDTPFANEVFDPEAIDDYYYATERTREALWRYHSNTNYSVVDDSVIRDLYRRSYE
DDLRDVGRLRFLRLTRVAGVRSVGAQTRVSLRAGIDGDLRDLDVDVLVCATGYAAMEPTG
LLGDLDQYCLRDEAGRYRIERDYRIVTAPEMQCGIYLQGGTEHTHGLSSSLLSNIAVRSG
EIIDSIVARSAERTAPCAVLAEA

SEQ ID NO: 24 >*Actinosynnema_mirum*_DSM_43827
MTAVVQGADAPRDVVGVGFGPSNLALAVALAERDGPSSAFFERQPRFGWH
RGMLLDGATMQVSFLKDLVSMRNPTSPYSFVSYLHARGRMPEFVNAKTLY
PLRVEFHDYLEWVAGHFAGSVSYGSEITALEPVAEDGVVGHLDVVARRDG
RTTTTRARNVVVATGLEPRLPDGVTGGERVWHSGELLHRVPWLRERRVRK
VAVVGAGQSAAEVTEYLHRTLPGAEVIAVFSRFGYSVADDTPFVNEVFDP
DSVDLFYGSPPSVRQALLAHHGNTNYSVVDADLSLELYRRRYQERVTGSS
RLRVVNVSRVRSVRERPDGVALQVEYLPTGVVGTLAADAVVCATGYRPAD
PTPLLRGLAKLDGAGRPVLDRDHRVVTSGSVRAGIYLQGAVTEPTHGLSA
GLLSTTAVRAGEIVRAILDEGR SEQ ID NO: 25 >*Kutzneria*_sp._744_ktzl
MTVAHAGESPTHDVVGVGFGPANLSLAVALEESPAALTSAFFERRASISWHQGMLLPAAK
MQVSFLKDLATFRNPASRFSFVSFLHERGRLVRFANNHDFPPTRREFHDYLEWAESKLAH
EVSYDSEVTAIRPGPGRPVDSVLVDVSTPEATRTVEARNIVISTGLVPRMPAGVQSDEFV
WHSSRFLDHFRDRDPRSLRRVAVAGGGQSAAEIVRFLHDNRPDTVVHAIMPSYGYVVADN
TPFANQIFDPAAVDDYFDGSKQAKDAFWRYHRNTNYSVVDDEVIRDLYRRGYDDEVAGAP
RLNFVNLAHVVGAKRIADDTRVTVYSMAREESYDLDVDVLVCATGYDPMDPGDLLGELAE
HCVQDAEGRWQVDRDYRMVTTPDLRCGIYLQGGTEHTHGLSSSLLSNLATRSGEIVSSIE
RRKS SEQ ID NO: 26 >*Kibdelosporangium*_sp._MJ126-NF4
VTDIHDLVGVGFGPSNLALSIAAAEADVPLRAVFLERSERFGWHRDMLIDDATMQVAFLK
DLATPRNPVSRFGFVPYLWARDRLSAFINQKTLFPTRVEFHDYLEWAAAQVDDVVEYAAE
VVDIRPVHDNGEVAFLDVVSVRPDGQARVRRTRNVVLALGLQPVVPPGVHPSPRVWHSAD
LLGRAATLDRAKPLRFAVVGAGQSAAECVSYLHRAFEQAEVHAVFGRYGYSPADDSPFAN
RIFDPAAVDDYFVSPDQVKQRFFDYHANTNYSAVDTELLEELSHRVYRESLSGRQRLFTH
HLSAITDLADTDDGVSVSVEFLPTGERTMLRVDHVIHATGYRPTDPIPLLGTTAELCHKD
TLGRLRVERDYRVVTKPDVRTGIYLQGGTEHSHGISSSLLSNVAVRAGEILASIQERPQR
RDGDQDERTARAGDDPARRAAALPRR SEQ ID NO: 27 >*Mycobacterium_xenopi*_RIVM700367
MLPGEDDSDLDFIGIGFGPSNLALAVAAEELIPNWRGLFLERSQSFQWHPGMMLEGARMQ
ISFLKDLATLRNPASRYTFLQYAKARGRLEQFVNINEFRPTRLEYNDYLKWVAESFADRV
RYGAVVTAVVPLRDSPSPAGRFGRLRVYVRDESTGVETCFSSPNVVYGGGGVPRLLGARN
TSAVVHSSAFLPNFPNRFNEPDKAYRFAVVGNGQSAAEIAEYLLSHYRRATTHLFISDHT
LRATDHSPFINEHFFSVNAAEFYDYPPAKRAALRNELRLTNYGVVDADVLQKLYQIAYLD
EVRGCRRLFLHGESRLSRVEEIDGRVVARFEDRFSGESHEFDFDGAVLATGYDRVLDAEI
FREVLPHVLRDESGEISLSRSCRVNTGPALTAGLFLQG SEQ ID NO: 28 >*Streptomyces_mirabilis*_YR139
MGITGRRSQEIYDVVGIGFGPSNLSLAIALEEHGASAPQHPVKSLFFERQSRFGWHRNML
LPSTTMQISFLKDLATYRNPTSRFSFISYLHASNRLVQFVNNQDFYPTRQEFHQYLEWAA
AGLRDRVTYGAEVTSIRPGTEAGSRTPDLLEVEVRTGDGTTSVVTARNVVISTGLVPRLP
QGVTSDERVWHSSEFLSRFNAQAPGDLKSVAVVGAGQSAAEITRFLHDSLPHAQVCAVIP
SYGYSVADDTPFANQVFDPGAVDEYYFGTEQAQDAFWRYHRNTNYAVVDADVIRALYQRS
YDEQVHGSRRLHFRNLTRVAEVKRTGSGTRVVLRSLLEDRTEELAVDALVFATGYDGLDP
AHLLGDFDQHFLRDAAGRHRVERDYSLVTASGLTCGVYLQGGTEHSHGLSSSLLSNIAVR
SGEIADSIVLRRTERELGSTCPVKVASSAA SEQ ID NO: 29 >*Streptomyces_scabrisporus*_DSM_41855
MGMFGHEIHDVVGIGFGPSNLSLAIALEEHQANESARPVTAAFFERQPAFGWHRNMLLPS
TTMQISFLKDLATFRNPVSRFGFISYLHASGRLPQFVNAQDFFPTRQEFHQYLEWAESSV
TDRVSYGSDVTSIRPPQGIAARDAKHLEIEVEDLVSGATRLVKARNVTVSTGLVPRLPQG
IERDERVWHSSEFLEKFGRMDAAGLGSVAVVGAGQSAAEITRFLYDTLPHARVSAILPAY
GYSVADDTPFANQVFDPGAVDEYYFGSDRTREAFWRYHKNTNYSVVDDEVIRDLYRRSYE
EEVRGVRRLNFLNLTRVDQVKRSGDETRVSLRSLLDDRVRELDVDALVFATGYDSPEPSG
LLGDLDRYCLRDEAGRHRVGRDYRLVTSPELSCGIYLQGGTEHTHGLTSSLLSNIAIRSG
EIADSVIRRRVEHELELERNAALEVARETR SEQ ID NO: 30 >*Streptomyces*_sp._TAA040
MHDLVVVGAGPYGLSIAAHAAAAGLQPRVLGTPMASWRDHMPQGMYLKSEPWSSDLSDPA
GAHTLAAYCATRGLVAEHGNPLPIEVFTDYGCWFAGRAAPPVEERIVVAVRPHGDGYRVE
TAEGERITTRTVALAVGVMPFVHHPSALAALPAELATHSSDHRDLARFRGRDVTVVGAGQ
AALETATLLTEHGARARVLARADRINWNTPPQPLERGLWKSLRDPHCGLGTGWSSWLWSE
RPSAVRRLPAGLRAAIAGSALGPAGAWWLRERFEQAVPVLLGHRLLAAEQVGGRVRLDVR
LADGTARNLHTDHVVAATGFTPELDRLGLLALSLTGTLRRVPGTGAPELGRCFESSRPGL
FFGGLLTAPSFGPAMRFVHGAGFTAGRLVEGVRRRLGSGAASRTRAVPQAAGSVGRAAAE
RPPG SEQ ID NO: 31 >*Actinoalloteichus_cyanogriseus*_DSM_43889
MYGSVPVDGNQVSDVVGVGFGPSNLALAVAIAEHNETAPPKTRLRAQFLERQPVFGWHRG -continued

SEQUENCE LISTING

MLLPDTTLQVSFLKDLVTLRNPRSSFGFVSYLHDRNRLVDFVNHQSFFPSRREYHDYLEW
VAGRFTGSVHYGHEVVDVLPVNEGPDVVAFDVVAAHGGVGATRRVRTRNVVLAPGLEPVL
PQGITPSDRVWHSSELLHRLDGVRELLPSRPRFVVVGAGQSAAEVMAHLHDAFPTATVRS
VCSRYGFAPADDSPFVNQLFDPAGVDEFFEAALPARENLLRTHAGTNYSAVDGGLINELY
RRSYQERVAGEPRLLFERLSRVVATEEGDDEVSVAVRSLADGRVTNRRCDVVVLATGYRP
RDALRPLGELAALCKLDANGWPRVERDYRITTTETVRAGIYLQGGTEHSHGLSSTLLSNL
AVRSGEITRALVSR

SEQ ID NO: 32 >*Streptomyces*_sp._HNS054
MGITGRRHQEIYDVIGIGFGPSNMSLAIALEEHEASAPQQPLRYHFFERQPTFGWHRNML
LPSTTMQISFLKDLATFRNPLSRFSFISFLHSSNRLVQFVNNQDFFPTRQEFHQYLEWAA
AGLSDRVTYGTEVVSIRPGTEGGTLTPDLLEIEVRDGDGTTSVVVTRNVVISTGLVPRLP
EGVTADERVWHSSQFLSKFHARDPRELKRVAVVGAGQSAAEITRFFYDSLPHAEVLAVIP
SYGYSVADDTPFANQVFDPGAVDEYYYGTDRARDAFWRYHRNTNYSVVDTDVIRALYQRS
YDEQVRGTQRLHFRNLTRVVEVGSTGEGTRVVLRSLLDDRREDLAVDALVFATGYDGVDP
ARLLGDGFDAHFERDAAGRHRVERDYRLVSSSGLTCGVYLQGGTEHSHGLTSSLLSNMAV
RSGEIADSIVLGRTGRELDRTHSVEEASSAA SEQ ID NO: 33 >*Streptomyces*_sp._AW19M42
VCRGAATFLETTLTTPLETARSAAPHDPADGAPLDVLGVGFGPSNLALAIALSEVERPRP
RVHFYDRSSRFSWHGGMLLKGATMQVHFLKDLVTLRNPGSPYSFLSYLHDRERLVDFINH
KALFPSRVEFHDYLEWAAQACSDRVTYGSEVSRIEPEWVDGEVHRFRVHLTHSEPGERGV
RHEVRSARNVVLAPGLRPHLPEGTAESEHVWHSSRLLSRLEDIPKDAPVRFTVVGAGQSG
AEVTAYLHGRFPQAQVRAVFSPYGYNPADDSPFANRIFDPAAVDEFFGAPQAVREMLVDR
HGNTNYSVVDQDLIAELYRIWYQEKVTDERRLIIDNVSRLVGVREASGLRLTIESLATRE
RHEVDSDYLVYATGYRPVAPDDLVDPEIMKLCRRDAAGGLRVNRDYRVQTEDMVRCGLYV
QGATEHTHGLSSTLLSNTAVRAGEIASSLLGRM SEQ ID NO: 34 >*Salinispora_pacifica*_DSM_45549
VFDEPSVYDVLGIGFGPSNLSLAIALHEMGDVEGRPLAARFFEQQPSFGWHRNMLLPSAK
MQVSFLKDLVTFRNPHSRFTFVSYLHEMNRLARFINNCDFFPTREEFHGYLEWAAANFAD
QVTYGATITSISVPPDSGPGDPIDRVRVNLASGPTGAESSSVEARNVVLGTGLVPRFPAG
LTSDDRVWHSSEFLGKFQRCDTTKLKRVLVVGGGQSAAEIAHFVYDNVPGVTVTAVIPSY
GYSIADATPFANRVFDPSAIDDYYYGDENSKDAFWRYHRNTNYAVVDSNLISDLNRKAYD
EAVTGETRLRFAELSRLSGVRRRDDGVVVSIHSMLSNRTSEVDADIVICATGYEPMEIGD
MLGPLDRFCIRDEQGRYRVERDYRLATTEHLRCGIYLQGGMEHTHGLSSSLLSNLAVRNG
DISTSVARRAQSQSHDDGRVLQGLVPTGS SEQ ID NO: 35 >*Salinispora_pacifica*_CNT150
VFDEPSVYDVLGIGFGPSNLSLAIALHEMGDVEGRPLAARFFEQQPSFGW
HRNMLLPSAKMQVSFLKDLVTFRNPHSRFTFVSYLHEMNRLARFINNCDF
FPTREEFHGYLEWAAANFADQVTYGATITSISVPPDSGPGDPIDRVRVNL
ASGPTGAESSSVEARNVVLGTGLVPRFPAGLTSDDRVWHSSEFLGKFQRC
DTTKLKRVLVVGGGQSAAEIAHFVYDNVPGVIVTAVIPSYGYSIADATPF
ANRVFDPSAIDDYYYGDENSKDAFWRYHRNTNYAVVDSNLISDLNRKAYD
EAVTGETRLRFAELSRLSGVRRRDDGVVVSIHSMLSNRTSEVDADIVICA
TGYEPMEIGDMLGPLDRFCIRDEQGRYRVERDYRLATTEHLRCGIYLQGG
MEHTHGLSSSLLSNLAVRNGDISTSVARRAQSQSHDDGRVLQGLVPTGS SEQ ID NO: 36 >*Salinispora_tropica*_CNB536
VTGKVHIVFDEPSVYDVLGIGFGPSNLSLAIALHEMGDVEGRPLAARFFEQQPSFGWHRN
MLLPSAKMQVSFLKDLVTFRNPHSRFTFVSYLHEMNRLARFVNNCDFFPTREEFHGYLEW
AATNFADQVTYGATITSISVPPDSGPGDPIDRVRVHLASGPTGTESSSVEARNVVLGTGL
VPRFPAGLTSDDRVWHSSEFLGKFQRCDTTKLKRVLVVGGGQSAAEIAHFVYENVPGATV
TAVIPSYGYSIADATPFANRVFDPSAIDDYYYGDENSRDAFWRYHRNTNYAVVDSDLISD
LNRKAYDEAVTGEIRLRFAELSRLSGVRRRDDGVVVSIHSMLSNRTSEVDADIVICATGY
EPMEIGDMLGPLDRFCIRDEHGRYRVERDYRLATTEHLRCGIYLQGGMEHTHGLSSSLLS
NLAVRNGDISTSVARRAQSQPHGDGRVLQGLVPTGS SEQ ID NO: 37 >*Salinispora_arenicola*_CNH996
VFDEPSVYDVLGIGFGPSNLSLAIALHEMGDVEGRPLAARFFEQQPSFGWHRNMLLPSAK
MQVSFLKDLVTFRNPHSRFTFVSYLHEMNRLARFINNCDFFPTREEFHGYLEWAAATFAD
QVTYGATITSISVPPDSGPGDPIDRVRVHLASGPTGTESSSVEARNVVLGTGLVPRFPAG
LTSDDRVWHSSEFLGKFQRCDTTKLKRVLVVGGGQSAAEIAHFVYENVPGATVTAVIPSY
GYSIADATPFANRVFDPSAIDDYYYGDENSKDAFWRYHRNTNYAVVDSDLISDLNRKAYD
EAVTGETRLRFAELSRLSGVRRRDDGVVVSIHSMLSNRTSEVDADIVICATGYEPMEIGD
MLGPLDRFCIRDEQGRYRVERDYRLATTEHLRCGIYLQGGMEHTHGLSSSLLSNLAVRNG
DISTSVARRAQSQPHDDGRVLQGLVPTGS SEQ ID NO: 38 >*Salinispora_arenicola*_CNH996B
VFDEPSVYDVLGIGFGPSNLSLAIALHEMGDVEGRPLAARFFEQQPSFGW
HRNMLLPSAKMQVSFLKDLVTFRNPHSRFTFVSYLHEMNRLARFINNCDF
FPTREEFHGYLEWAAATFADQVTYGATITSISVPPDSGPGDPIDRVRVHL
ASGPTGTESSSVEARNVVLGTGLVPRFPAGLTSDDRVWHSSEFLGKFQRC
DTTKLKRVLVVGGGQSAAEIAHFVYENVPGATVTAVIPSYGYSIADATPF
ANRVFDPSAIDDYYYGDENSKDAFWRYHRNTNYAVVDSDLISDLNRKAYD
EAVTGETRLRFAELSRLSGVRRRDDGVVVSIHSMLSNRTSEVDADIVICA -continued

SEQUENCE LISTING

TGYEPMEIGDMLGPLDRFCIRDEQGRYRVERDYRLATTEHLRCGIYLQGG
MEHTHGLSSSLLSNLAVRNGDISTSVARRAQSQPHDDGRVLQGLVPTGS

SEQ ID NO: 39 >*Salinispora_tropica*_CNY012
VTGKVHIVFDEPSVYDVLGIGFGPSNLSLAIALHEMGDVEGRPLAARFFEQQPSFGWHRN
MLLPSAKMQVSFLKDLVTFRNPHSRFTFVSYLHEMNRLARFVNNCDFFPTREEFHGYLEW
AATNFADQVTYGATITSISVPPDSGPGDPIDRVRVHLASGPTGTESSSVEARNVVLGTGL
VPRFPAGLTSDDRVWHSSEFLGKFQRCDTTKLKRVLVVGGGQSAAEIAHFVYENVPGATV
TAVIPSYGYSIADATPFANRVFDPSAIDDYYYGDENSRDAFWRYHRNTNYAVVDSDLISD
LNRKAYDEAVTGEIRLRFAELSRLSGVRRRDDGVVVSIHSMLSNRTSEVDADIVICATGY
EPMEIGDMLGPLDRFCIRDEHGRYRVERDYRLATTEHLRCGIYLQGGMEHTHGLSSSLLS
NLAVRNGDISTSVARRAQSQPHGDGRVLQGLVPTGS SEQ ID NO: 40 >*Salinispora_tropica*_CNT261
VTGKVHIVFDEPSVYDVLGIGFGPSNLSLAIALHEMGDVEGRPLAARFFEQQPSFGWHRN
MLLPSAKMQVSFLKDLVTFRNPHSRFTFVSYLHEMNRLARFVNNCDFFPTREEFHGYLEW
AATNFADQVTYGATITSISVPPDSGPGDPIDRVRVHLASGPTGTESSSVEARNVVLGTGL
VPRFPAGLTSDDRVWHSSEFLGKFQRCDTTKLKRVLVVGGGQSAAEIAHFVYENVPGATV
TAVIPSYGYSIADATPFANRVFDPSAIDDYYYGDENSRDAFWRYHRNTNYAVVDSDLISD
LNRKAYDEAVTGEIRLRFAELSRLSGVRRRDDGVVVSIHSMLSNRTSEVDADIVICATGY
EPMEIGDMLGPLDRFCIRDEHGRYRVERDYRLATTEHLRCGIYLQGGMEHTHGLSSSLLS
NLAVRNGDISTSVARRAQSQPHGDGRVLQGLVPTGS SEQ ID NO: 41 >*Salinispora_tropica*_CNH898
VTGKVHIVFDEPSVYDVLGIGFGPSNLSLAIALHEMGDVEGRPLAARFFEQQPSFGWHRN
MLLPSAKMQVSFLKDLVTFRNPHSRFTFVSYLHEMNRLARFVNNCDFFPTREEFHGYLEW
AATNFADQVTYGATITSISVPPDSGPGDPIDRVRVHLASGPTGTESSSVEARNVVLGTGL
VPRFPAGLTSDDRVWHSSEFLGKFQRCDTTKLKRVLVVGGGQSAAEIAHFVYENVPGATV
TAVIPSYGYSIADATPFANRVFDPSAIDDYYYGDENSRDAFWRYHRNTNYAVVDSDLISD
LNRKAYDEAVTGETRLRFAELSRLSGVRRRDDGVVVSIHSMLSNRTSEVDADIVICATGY
EPMEIGDMLGPLDRFCIRDEHGRYRVERDYRLATTEHLRCGIYLQGGMEHTHGLSSSLLS
NLAVRNGDISTSVARRAQSQPHGDGRVLQGLVPTGS SEQ ID NO: 42 >*Streptomyces*_sp._PsTaAH-137
MDTPGSLSQEIYDVVGIGFGPSNLSLAVALEEQGASSAQHPV SEQ ID NO: 43 >*Salinispora_arenicola*_CNS296
MSNQHETYDLVGIGFGPSNLSLAIALKEYEANGQENGISTLFFERQSSFGWHRNMLLPST
TMQISFLKDLVTFRNPTSGFSFISYLHASGRLPQFVNNQDFFPTRQEFHQYLEWAEERMA
GRVAYGSEVTSIRLPSGTVPELSDRLRLEVTDAAGRVGRVVEARNVVISTGLVPRMPEGI
ERDERVWHSSEFLQKYRRMNPGDLRRVAVVGAGQSAAEITRFLHDELPHAEVWVVIPSYG
YSVADDTPFANQIFDPEAVDDYYFGTEQTRDAFWRYHRNTNYSVVDDEVIRDLYRRVYDA
EVRGIKRLQILNLTRITGVKRAAAETRVELQVGPDSEVRELDVDALVCATGYDGMEPTHL
LGDLDRLCLRDKAGRHQIERDYRIATAPEMRCGIYLQGGTEHTHGLSSSLLSNIAVRSGE
IADSIVSRRARHNSEYALAAGAEGDTC SEQ ID NO: 44 >*Salinispora_arenicola*_CNS299
MSNQHETYDLVGIGFGPSNLSLAIALKEYEANGQENGISTLFFERQSSFGWHRNMLLPST
TMQISFLKDLVTFRNPTSGFSFISYLHASGRLPQFVNNQDFFPTRQEFHQYLEWAEERMA
GRVAYGSEVTSIRLPSGTVPELSDRLRLEVTDAAGRVGRVVEARNVVISTGLVPRMPEGI
ERDERVWHSSEFLQKYRRMNPGDLRRVAVVGAGQSAAEITRFLHDELPHAEVWVVIPSYG
YSVADDTPFANQIFDPEAVDDYYFGTEQTRDAFWRYHRNTNYSVVDDEVIRDLYRRVYDA
EVRGIKRLQILNLTRITGVKRAAAETRVELQVGPDSEVRELDVDALVCATGYDGMEPTHL
LGDLDRLCLRDKAGRHQIERDYRIATAPEMRCGIYLQGGTEHTHGLSSSLLSNIAVRSGE
IADSIVSRRARHNSEYALAAGAEGDTC SEQ ID NO: 45 >*Salinispora_pacifica*_CNY363
MSNQHETYDLVGIGFGPSNLSLAIALKEYEANGQENGISTLFFERQSSFGWHRNMLLPST
TMQISFLKDLVTFRNPTSGFSFISYLHASGRLPQFVNNQDFFPTRQEFHQYLEWAEERMA
GRVAYCSEVTSIRLPSGIVPELSDRLRLEVTDAAGRVGRVVEARNVVISTGLVPRMPEGI
ERDERVWHSSEFLQKYRRMNPGDLRRVAVVGAGQSAAEITRFLHDELPHAEVWVVIPSYG
YSVADDTPFANQIFDPEAVDDYYFGTEQTRDAFWRYHRNTNYSVVDDEVIRDLYRRVYDA
EVRGIKRLQILNLTRITGVKRAAAETRVELQVGPDSEVRELDVDALVCATGYDGMEPTHL
LGDLDRLCLRDKAGRHQIERDYRIATAPEMRCGIYLQGGTEHTHGLSSSLLSNIAVRSGE
IADSIVSRRARHNSEYALAAGAEGDTC SEQ ID NO: 46 >*Actinomadura_atramentaria*_DSM_43919
VTGPATDADDILDIVGVGFGPSNLALAVAVREHNADRPAAEHLTQVYFEKQPAFGWHRGM
LIDGATMQVSFIKDLVTMRNPASEYGFLSYLHDNDRLADFINHKSLFPSRVEFHDYLEWV
ARRFQDVARYGSEVVAMRPGPGGDHIEVIVRRGGEHRVQRARNVVVAVGQEPALPDDIEL
GDRIWHCAQLLERVERLTEEPRRAVVVGAGQSAAETTEFLHRRFENAEVSAIFLRYGYSV
ADDTPFANRIFDPESVDVFYGAPENVKRMLFDYHRNTNYSVVDQELADELYRRVYQERVR
GVERLRILNASRLHAVRRDVTGDGLRVDVEHLPTGEKRSFGVDLVVYATGYRPIDPANVL
GEVAEYCRRDAGKRPAITRDYRLETDDRLRAGIYLQGGTEQTHGISAQLLSNTAVRAGEI
VRSIAGARVGAV -continued

SEQUENCE LISTING

SEQ ID NO: 47 >*Streptomyces_drozdowiczii*_SCSII_10141
MTVNLGSTSVLEVAGIGFGPSNMALAIALEEMHGARANSPGPAMEFFEKQPAFGWHRGML
MEDATMQVSFLKDLATMRDPQSRYTFMAYLKAKGRIARFINSKTLFPLRVEFHDYLEWVA
DLLAPVVSYGSDVLAIRPVVEDGVMECLDVVVRTSAGDGEPIVRRARNVVIGTGLTPRLP
DGTEESARVWHSSRLMDRAASIAAAPRGFVVVGAGQSAAEATEYLHRSFPGTPVSAVFAR
YGYSVADDSPFTNGIFDPEAVDEFYAASRDVKQDLLDYHGNTNYAVVDLSLTEELYRRAY
QEEVLGRERLRFHNASRVLKVEEHPDRVRVIVEHLPDRTVETLDADAVVYATGYRPSDPT
PLLQNLLPECKLDDAGRITLDRDYRIVTSGDVRCGIYLHGASAECTHGLSAGLLSNTAVR
SGEIADSIIKR SEQ ID NO: 48 >*Streptomyces*_sp._RSD-27
MGITGRRDEEIYDVIGIGFGPSNMSLAIALQEHGAGVPLHPVRSHFFERQ
PTFGWHRNMLLPSTTMQISFLKDLATFRNPMSRFSFVSYLHASNRLVQFV
NNQSFIPTRQEFHQYLEWAAAGLRDQVTYGAEVTSVRPVTAAGSRTPDLL
EVEVRTGDEVSVVTARNVVVSTGLVPRMPEGVPAGERVWHSSEFLARFNA
QDPAELKSVAVVGAGQSAAEVTRFLYDSLPHAEVSAVIPSYGYSVADDTP
FANQVFDPDTVDEYYFGTEGARDAFWRYHRNTNYSVVDADVIRSLYQRWY
DEQVRGVQRLRFRNLTRVDGVEGSGSGARMVLRSLLDDSREELAVDAVVF
ASGYDGLDPARLLGEDFDRHFQRDAAGRHRVERDYRLVSTSGLTCGVYLQ
GGTEHSHGLTSALLSNIAIRSGEIADSIVLRRTERELGRHAEEAPSAA SEQ ID NO: 49 >*Actinoalloteichus_spitiensis*_RMV-1378
MDGSFPVDGNQVSDVVGVGFGPSNLALAVAVAEHNEAVGPEERLRARFLERQPDFGWHRG
MLLPDTTLQVSFLKDLVSLRNPRSSFSFISYLHDRNRLVDFVNHQCFFPSRREYHDYLEW
VAGRFVDSVHYDHDVVDVLPVHEGPDVVAFDVVAVQGGAGATRRLRTRNVVLAPGLEPVL
PQGITPSDRVWHSSELLHRLDGFRDRLPDRPRFVVVGAGQSAAEVMAHLHGVFPKATVRS
VCSRYGFAPADDSPFVNQLFDPAAVDEFFEAALPARENILRVHAGTNYSAVDGDLISELY
RRSYQERVSGEPRLHFERLARVVATEERDEEVSVSVLSLTDGRVTDRGCDVVVLATGYRP
RDALRPLGQLAALCKLDANGWPRVERNYRITTTETVRAGIYLQGGTEHSHGLSSTLLSNL
AVRSGEITRALAAP SEQ ID NO: 50 >*Streptomyces*_sp._PBH53
MTRLAGQAPTAQHSPESEVRDVTGIGFGAANLALAVALHESGAGGRALFLEKQKEFGWHR
GMLIEGSSLQVSFLKDIATMRNPTSDFGFLSYLQEKGRLVDFINQHTLLPSRIEYHDYLQ
WAADRLGHMVEYGVEATGVRPVTDAGEVVALDVLAGDRVVTRTRNLVIASGLRPRLPEGA
ETGERVWHSSQLLHRLPAFDERPPRRAVVVGAGQSAAEVAAHLMERYPQAEVCAVFSRYG
YSVADSSPFANRVFDPAAVDDFYFAPPEVKQAIMRYHGGTNYAVVDEDVLQGLYRRQYEQ
KVTGTPRLRVMNASRLVSVEPRGETAAVRVEFLPTGEHADLDADLVVYATGYRSADPAEL
LGGVAGSLRRDAAGQVLIGRDYRLSTTGDFRCGIYVQGATEATHGIASTLLSMVAVRAGE
IAQSIIGGRRDPDRTAGTKAVAGNRG SEQ ID NO: 51 >*Salinispora_arenicola*_CNS-991_DSM_45545
MSNQHETYDLVGIGFGPSNLSLAIALKEYEANGQENGISTLFFERQSSFGWHRNMLLPST
TMQISFLKDLVTFRNPTSGFSFISYLHASGRLPQFVNNQDFFPTRQEFHQYLEWAEERMA
GRVAYGSEVTSIRLPSGTVPELSDRLRLEVTDAAGRVGRVVEARNVVISTGLVPRMPEGI
ERDERVWHSSEFLQKYRRMNPGDLRRVAVVGAGQSAAEITRFLHDELPHAEVWVVIPSYG
YSVADDTPFANQIFDPEAVDDYYFGTEQTRDAFWRYHRNTNYSVVDDEVIRDLYRRVYDA
EVRGIKRLQILNLTRITGVKRAAAETRVELQVGPDSEVRELDVDALVCATGYDGMEPTHL
LGDLDRLCLRDKAGRHQIERDYRIATAPEMRCGIYLQGGTEHTHGLSSSLLSNIAVRSGE
IADSIVSRRARHNSEYALAAGAEGDTC SEQ ID NO: 52 >*Streptomyces*_sp._MNU77
VEASASVTDVVGVGFGPANLALAIALRELGAGPPGGDGLTAAFLEAQPQFGWHSGMLIED
STMQVSFLKDLVTPRNPVSPFSFVAYLHAVGRLGRFMDSKMMYPLRIEFHNYLEWVAGHF
ANQVAYSRRVTALRPVHGQDGVEALDVVARDADGTERVLRARSVVLACGLRPRLPEGLTG
SDRVWHTADLLPRARRLLESGAAPTSFVVLGAGQSSAEAAHYLHRTFTRSSVSVVHSRYG
FSVSDDSPFANAVFGAKAVDEFYGAPDEVKRMVLDYHANTNYAVVDEDLIHRLYGDVYRE
SLTGDDRLRFHHLSRLSTVTPGEDAVRVEVEALHDGRRTVIDADALVCATGYRPSDPADL
MGDLLPLCARDEQDRLVLDRDRRLVTREPLAGGVYVTGYGEHTHGIAESLLSLTAQRAGE
LTEALAKTFVT SEQ ID NO: 53 >*Micromonospora_pattaloongensis*_DSM_45245
MSETDSATVRQVVGVGFGPANLALAIAAGEVAGPDGRTLLDECVFLERQP
SFGWHRGMLLDGATMQVSFLKDLATLRSPSSRYTFTSYLHDVGRLTDFIN
SKTLYPYRTDFHTYLEWAADRLPADVRYGTEVVSVTPERTDDVVRELLVR
TGDGRTFRTRNLVIGTGMTPCFPDGVQRGPRVWHSAELLTRLAAPAPTRP
RTFAVVGAGQSAAEVVEHLHATHPEADVHAIFGRFGYSMSDDSPFANQIF
DPDSVDEFYHAPGEVRDALMGYHANTNYSVVDLDLIRSLHGTAYREHIAG
RRRLHFHHASRITRQTVTGEGVHLDVEFLPTGTIRQIDADAIVYATGYRP
SDPRQLLGDLADECKTDDRGRLALARDYRVITSDGVRCGIYVHGAAAERT
HGLSAGLLSNVAVRAGEILAAIRSL SEQ ID NO: 54 >*Streptacidiphilus_carbonis*_NBRC_100919
MGARENATYDVVGIGFGPSNLSLAIALEERCANVLTNSITSAFFERQSSF
GWHRNMLLPSATMQISFLKDLVTFRNPVSRFSFVAFLHAKGRLGQFVNRK
DFFPTRQEFHQYLEWAAAKMADAVTYDSTVTSVQLPPDHGSGGDGYVQLE -continued

SEQUENCE LISTING

VRDTAAGSTRRVNTRNVVVSTGLVPRMPDGIARDDRVWHSSEFLTRYGRT
DPEVLRSVAVVGAGQSAAEITQFFHGRLPHAQVHAIMPSYGYSVADDTPF
ANQVFDADAVEDYYDGDEPARDAFWRYHRNTNYGVVDSADIQALYQTQYD
EGVAGAKRLHFHNLTKVRAVERNGSARRVTLQSLRHHEVRQLDVDAIVFA
TGYASMDPTQLLGDLDRYCLRDESGHHRVTRDYRLVTTPELSCGIYLQGG
TEHTHGLTSSLLSNIAVRSGEIADSIICRRAESELATIAAEVREAVAERL

SEQ ID NO: 55 >*Streptomyces*_sp._MnatMP-M27
MTDSAPGDRTVDVTGIGFGPSNLALATALAEPSATGPGRPLEAVYFERKN
RFSWHGGMLLDGATMQISFLKDLVTLRDPRSPYSFLSYLHHAGRLSDFIN
HKLLFPSRIEFHDYLEWVAGFFEEQVVYGSEVVDVRPVAREDAVEHMDVV
VRQRTAAGERTVVQRTRDLVVATGLEPSLPPGTVCSDRVWHSSELLYRVE
RLPPTPRRIVVVGAGQSAAEAAEFLHSRFPSTDICAVFSRYGYSPSDDSP
FANRIFDPAAVDDYCAAAPETRRMLLDYHRNTNYSVVDPELIDELYRRVY
QEKVRGRPRLNILGASRLTAAEPAGDGVDVVVESLVTGERTPMRADCVVY
ATGYRPTDARGLLGSMAGLCKADELGRLEADRRYRVITEGDVRCAIYLQG
ATEHSHGISSSLLSNTAVRAGEIADAIRADAVRAGARATTRSQPQPQT SEQ ID NO: 56 >*Pseudonocardia*_sp._EC080625-04
MCTCKSDVYDVVGIGFGPSNLSLAIALGEHQGNRAGHPVKAAFFERQQSF
GWHRNMLLPETTMQISFMKDLVTFRNPRSRFSFVNYLHESGRLTQFCNNQ
DFFPTRQEFHRYLEWVGSSFDDQVSYDSEVLGVTLAPEPCECAQRYLKLE
ISNGAIGATEIVNARNISISTGLVPKVPDNVATGDRIWHSSQFLEKLRDV
DPADLRNVAVVGGGQSAAEIARYLHATLPEAQIYAIVPSYGYSVADDTPF
ANQVFDPEAVDDYYFGSDETRDAFWRYHRNTNYSVVDDDIIRDLHRASYA
EQVTGERRLHFLNLTRVRAVTRNGATNRVSLHSLIDRETRELDIDALVLA
TGYTEMTPTGLIGDVDHFCHRDPEGRYRIERDYRLMTDPEFPCGIYLQGG
TEHTHGLTSSLLSNVAVRGGEIADSVITRTRADAPTMQRSTRRIEQAWER
AG SEQ ID NO: 57 >*Pseudonocardia*_sp._HH130629-09
MCTCKSDVYDVVGIGFGPSNLSLAIALGEHQGNRAGHPVKAAFFERQQSF
GWHRNMLLPETTMQISFMKDLVTFRNPRSRFSFVNYLHESGRLTQFCNNQ
DFFPTRQEFHRYLEWVGSSFDDQVSYDSEVLGVTLAPEPCECAQLYLKLE
ISNGAIGATEIVNARNISISTGLVPKVPDNVPTGDRIWHSSQFLEKLRDV
DPADLRNVAVVGGGQSAAEIARYLHATLPEAQIYAIVPSYGYSVADDTPF
ANQVFDPEAVDDYYFGSDETRDAFWRYHRNTNYSVVDDDIIRDLHRASYA
EQVTGERRLHFLNLTRVRAVTRNGATNRVSLHSLIDRETRELDIDALVLA
TGYTEMTPTGLIGDVDHFCHRDPEGRYRIERDYRLMTDPEFPCGIYLQGG
TEHTHGLTSSLLSNVAVRGGEIADSVITRTRADAPTMQRSTRRIEQAWER
AG SEQ ID NO: 58 >*Streptomyces_parvulus*_2297
MGITGRRNEEILDVVGIGFGPSNLSLAIALEEHGASAPRHPVTSHFFERQ
PTFGWHRNMLLPSTTMQISFLKDLATFRNPMSRFSFISYLHASDRLVQFV
NNQDFFPTRQEFHQYLEWAASGLSDRVTYGAEVTAIRPGSDGNGLSPDLL
EVEARTADGTTRVVTARNVAISTGLVPRLPEGVTADERVWHSSQFLSRFN
AQSPDDLKSVAVVGAGQSAAEITRFLHDALPHAQVCAVVPSYGYSVADDT
PFANQVFDPAAVDDYYFGTDRGRDAFWRYHRNTNYSVVDADVIRDLHQRT
YDEEVRGTRRLHFRNLTRVAEVERSGSTTRVVLRSLLDDRTEDLSVDALV
FATGYDGLDPVRLLGDFDRHFRRDAAGRHRLERDYRLVPATDLTCGVYLQ
GGTEHSHGLSSSLLSNIAVRSGEIADSIVLRRTERELERDRPVEVAPPVA SEQ ID NO: 59 >*Streptomyces*_sp._CFMR_7
MAIRAGSHILDVVGIGFGPSNLALAIALQEMIKADTGRTEYAMAFHERQP
RFGWHRGMLMEDATMQVSFLKDLATMRNATSRYTFVAYLQEQGRVAEFIN
SKTLYPLRVEFHDYLEWAAQQFDASVSYGSEIVAVRPVIESGSVEYVDVV
ARSASGGSSTVVQRARNVVIGMGLTPRLPDGIEESERIWHSSQLLHRADS
LPYRPRNFVVVGSGQSAAEVADYLHRTFSDANVHTVLSRYGYSVADDSPF
ANGVFDPEAVDRFYTSSADAKQRLLDYHGNTNYSVVDLEVSQDLYRRSYQ
EKVLGKQRLRMLNSSRVTSAEEHADGVRVIVEAMDSGSVRTMDADVIVYA
TGYRPSDAAPLLSELAGECKRDEEGRLAVERDYRVITSEAVRCGIYVHGA
VTEHSHGLSAGLLSNTAVRSGEIARSILRR SEQ ID NO: 60 >*Streptomyces*_sp._DvalAA-19
MAIRAGSHISDVVGIGFGPSNLALAIALQEMIKADTGRTEYAMAFHERQP
RFGWHRGMLMEDATMQVSFLKDLATMRNATSRYTFVAYLQEKGRVAEFIN
SKTLYPLRVEFHDYLEWAAQQFDASVSYGSEIVAVRPVIESGSVEYVDVV
ARSASGGSSTVVQRARNVVIGMGLTPRLPDGIEESERIWHSSQLLHRADS
LPYRPRNFVVVGSGQSAAEVADYLHRTFSDANVHTVLSRYGYSVADDSPF
ANGVFDPEAVDRFYTSSADAKQRLLDYHGNTNYSVVDLEVSQDLYRRSYQ
EKVLGKQRLRMLNSSRVTSAEEHADGVRVIVEAMDSGSVRTMDADVIVYA
TGYRPSDAAPLLSELAGECKRDEEGRLAVERDYRVITSEAVRCGIYVHGA
VTEHSHGLSAGLLSNTAVRSGEIARSILRR SEQ ID NO: 61 >*Rhodococcus_fascians*_A3b
MGAQSGSSVADVVGVGFGPSNLALAIALQESIQPGPVPAKFSMKFYELQP -continued

SEQUENCE LISTING

RFGWHRGMLMEDATMQVSFLKDLATMRNPMSRYTFVSYLREKERIAEFIN
SKTLYPLRVEFHDYLEWAASQFQSNVSYGSEIKDIRPVVENGVVEYVDVV
GPDDVVQRARNIVIGMGLTPRLPDGVNRSERIWHSSQLLGRAAAVTYVPQ
NFVVVGSGQSAAEVADYLHRTFPRANVHTVLSRYGYSVADDSPYANGIFD
PEGVDRFFSAPTDEKQRLLEYHANTNYSVVDLDISQSLYLKSYQEKVLGK
QRLRMINTSRVTSVDEDTDGVRVEVTSSATGLTHTIEADVIVYATGYRPS
DPAPLLQGLMRECKHDEQGRLSVGRDYRVTTSDAVRAGIYVHGASTEHSH
GLSAGLLSNTAVRSGEIAQSILRR

SEQ ID NO: 62 >*Rhodococcus_fascians*_A73a
MGAQSGSSVADVVGVGFGPSNLALAIALQESIQPGPVPAKFSMKFYELQP
RFGWHRGMLMEDATMQVSFLKDLATMRNPMSRYTFVSYLREKERIAEFIN
SKTLYPLRVEFHDYLEWAASQFQSNVSYGSEIKDIRPVVENGVVEYVDVV
GPDDVVQRARNIVIGMGLTPRLPDGVNRSERIWHSSQLLGRAAAVTYVPQ
NFVVVGSGQSAAEVADYLHRTFPRANVHTVLSRYGYSVADDSPYANGIFD
PEGVDRFFSAPTDEKQRLLEYHANTNYSVVDLDISQSLYLKSYQEKVLGK
QRLRMINTSRVTSVDEDTDGVRVEVTSSATGLTHTIEADVIVYATGYRPS
DPAPLLQGLMRECKHDEQGRLSVGRDYRVTTSDAVRAGIYVHGASTEHSH
GLSAGLLSNTAVRSGEIAQSILRR SEQ ID NO: 63 >*Rhodococcus_fascians*_A76
MGAQSGSSVADVVGVGFGPSNLALAIALQESIQPGPVPAKFSMKFYELQP
RFGWHRGMLMEDATMQVSFLKDLATMRNPMSRYTFVSYLREKERIAEFIN
SKTLYPLRVEFHDYLEWAASQFQSNVSYGSEIKDIRPVVENGVVEYVDVV
GPDDVVQRARNIVIGMGLTPRLPDGVNRSERIWHSSQLLGRAAAVTYVPQ
NFVVVGSGQSAAEVADYLHRTFPRANVHTVLSRYGYSVADDSPYANGIFD
PEGVDRFFSAPTDEKQRLLEYHANTNYSVVDLDISQSLYLKSYQEKVLGK
QRLRMINTSRVTSVDEDTDGVRVEVTSSATGLTHTIEADVIVYATGYRPS
DPAPLLQGLMRECKHDEQGRLSVGRDYRVTTSDAVRAGIYVHGASTEHSH
GLSAGLLSNTAVRSGEIAQSILRR SEQ ID NO: 64 >*Rhodococcus_fascians*_A78
MGAQSGSSVADVVGVGFGPSNLALAIALQESIQPGPVPAKFSMKFYELQP
RFGWHRGMLMEDATMQVSFLKDLATMRNPMSRYTFVSYLREKERIAEFIN
SKTLYPLRVEFHDYLEWAASQFQSNVSYGSEIKDIRPVVENGVVEYVDVV
GPDDVVQRARNIVIGMGLTPRLPDGVNRSERIWHSSQLLGRAAAVTYVPQ
NFVVVGSGQSAAEVADYLHRTFPRANVHTVLSRYGYSVADDSPYANGIFD
PEGVDRFFSAPTDEKQRLLEYHANTNYSVVDLDISQSLYLKSYQEKVLGK
QRLRMINTSRVTSVDEDTDGVRVEVTSSATGLTHTIEADVIVYATGYRPS
DPAPLLQGLMRECKHDEQGRLSVGRDYRVTTSDAVRAGIYVHGASTEHSH
GLSAGLLSNTAVRSGEIAQSILRR SEQ ID NO: 65 >*Rhodococcus_fascians*_D188
MGAQSGSSVADVVGVGFGPSNLALAIALQESIQPGPVPAKFSMKFYELQP
RFGWHRGMLMEDATMQVSFLKDLATMRNPMSRYTFVSYLREKERIAEFIN
SKTLYPLRVEFHDYLEWAASQFQSNVSYGSEIKDIRPVVENGVVEYVDVV
GPDDVVQRARNIVIGMGLTPRLPDGVNRSERIWHSSQLLGRAAAVTYVPQ
NFVVVGSGQSAAEVADYLHRTFPRANVHTVLSRYGYSVADDSPYANGIFD
PEGVDRFFSAPTDEKQRLLEYHANTNYSVVDLDISQSLYLKSYQEKVLGK
QRLRMINTSRVTSVDEDTDGVRVEVTSSATGLTHTIEADVIVYATGYRPS
DPAPLLQGLMRECKHDEQGRLSVGRDYRVTTSDAVRAGIYVHGASTEHSH
GLSAGLLSNTAVRSGEIAQSILRR SEQ ID NO: 66 >*Rhodococcus_fascians*_02-816c
MGAQSGSSVADVVGVGFGPSNLALAIALQESIQPGPVPAKFSMKFYELQP
RFGWHRGMLMEDATMQVSFLKDLATMRNPMSRYTFVSYLREKERIAEFIN
SKTLYPLRVEFHDYLEWAASQFQSNVSYGSEIKDIRPVVENGVVEYVDVV
GPDDVVQRARNIVIGMGLTPRLPDGVNRSERIWHSSQLLGRAAAVTYVPQ
NFVVVGSGQSAAEVADYLHRTFPRANVHTVLSRYGYSVADDSPYANGIFD
PEGVDRFFSAPTDEKQRLLEYHANTNYSVVDLDISQSLYLKSYQEKVLGK
QRLRMINTSRVTSVDEDTDGVRVEVTSSATGLTHTIEADVIVYATGYRPS
DPAPLLQGLMRECKHDEQGRLSVGRDYRVTTSDAVRAGIYVHGASTEHSH
GLSAGLLSNTAVRSGEIAQSILRR SEQ ID NO: 67 >*Rhodococcus_fascians*_05-339-1
MGAQSGSSVADVVGVGFGPSNLALAIALQESIQPGPVPAKFSMKFYELQP
RFGWHRGMLMEDATMQVSFLKDLATMRNPMSRYTFVSYLREKERIAEFIN
SKTLYPLRVEFHDYLEWAASQFQSNVSYGSEIKDIRPVVENGVVEYVDVV
GPDDVVQRARNIVIGMGLTPRLPDGVNRSERIWHSSQLLGRAAAVTYVPQ
NFVVVGSGQSAAEVADYLHRTFPRANVHTVLSRYGYSVADDSPYANGIFD
PEGVDRFFSAPTDEKQRLLEYHANTNYSVVDLDISQSLYLKSYQEKVLGK
QRLRMINTSRVTSVDEDTDGVRVEVTSSATGLTHTIEADVIVYATGYRPS
DPAPLLQGLMRECKHDEQGRLSVGRDYRVTTSDAVRAGIYVHGASTEHSH
GLSAGLLSNTAVRSGEIAQSILRR SEQ ID NO: 68 >*Rhodococcus_fascians*_LMG_3605
MGAQSGSSVADVVGVGFGPSNLALAIALQESIQPGPVPAKFSMKFYELQP -continued

SEQUENCE LISTING

RFGWHRGMLMEDATMQVSFLKDLATMRNPMSRYTFVSYLREKERIAEFIN
SKTLYPLRVEFHDYLEWAASQFQSNVSYGSEIKDIRPVVENGVVEYVDVV
GPDDVVQRARNIVIGMGLTPRLPDGVNRSERIWHSSQLLGRAAAVTYVPQ
NFVVVGSGQSAAEVADYLHRTFPRANVHTVLSRYGYSVADDSPYANGIFD
PEGVDRFFSAPTDEKQRLLEYHANTNYSVVDLDISQSLYLKSYQEKVLGK
QRLRMINTSRVTSVDEDTDGVRVEVTSSATGLTHTIEADVIVYATGYRPS
DPAPLLQGLMRECKHDEQGRLSVGRDYRVTTSDAVRAGIYVHGASTEHSH
GLSAGLLSNTAVRSGEIAQSILRR

SEQ ID NO: 69 >*Rhodococcus_fascians*_LMG_3616
MGAQSGSSVADVVGVGFGPSNLALAIALQESIQPGPVPAKFSMKFYELQP
RFGWHRGMLMEDATMQVSFLKDLATMRNPMSRYTFVSYLREKERIAEFIN
SKTLYPLRVEFHDYLEWAASQFQSNVSYGSEIKDIRPVVENGVVEYVDVV
GPDDVVQRARNIVIGMGLTPRLPDGVNRSERIWHSSQLLGRAAAVTYVPQ
NFVVVGSGQSAAEVADYLHRTFPRANVHTVLSRYGYSVADDSPYANGIFD
PEGVDRFFSAPTDEKQRLLEYHANTNYSVVDLDISQSLYLKSYQEKVLGK
QRLRMINTSRVTSVDEDTDGVRVEVTSSATGLTHTIEADVIVYATGYRPS
DPAPLLQGLMRECKHDEQGRLSVGRDYRVTTSDAVRAGIYVHGASTEHSH
GLSAGLLSNTAVRSGEIAQSILRR SEQ ID NO: 70 >*Rhodococcus_fascians*_LMG_3623
MGAQSGSSVADVVGVGFGPSNLALAIALQESIQPGPVPAKFSMKFYELQP
RFGWHRGMLMEDATMQVSFLKDLATMRNPMSRYTFVSYLREKERIAEFIN
SKTLYPLRVEFHDYLEWAASQFQSNVSYGSEIKDIRPVVENGVVEYVDVV
GPDDVVQRARNIVIGMGLTPRLPDGVNRSERIWHSSQLLGRAAAVTYVPQ
NFVVVGSGQSAAEVADYLHRTFPRANVHTVLSRYGYSVADDSPYANGIFD
PEGVDRFFSAPTDEKQRLLEYHANTNYSVVDLDISQSLYLKSYQEKVLGK
QRLRMINTSRVTSVDEDTDGVRVEVTSSATGLTHTIEADVIVYATGYRPS
DPAPLLQGLMRECKHDEQGRLSVGRDYRVTTSDAVRAGIYVHGASTEHSH
GLSAGLLSNTAVRSGEIAQSILRR SEQ ID NO: 71 >*Rhodococcus_fascians*_A22b
MGAQSGSSVADVVGVGFGPSNLALAIALQESIQPGPVPAKFSMKFYELQP
RFGWHRGMLMEDATMQVSFLKDLATMRNPMSRYTFVSYLREKERIAEFIN
SKTLYPLRVEFHDYLEWAASQFQSNVSYGSEIKDIRPVVENGVVEYVDVV
GPDDVVQRARNIVIGMGLTPRLPDGVNRSERIWHSSQLLGRAAAVTYVPQ
NFVVVGSGQSAAEVADYLHRTFPRANVHTVLSRYGYSVADDSPYANGIFD
PEGVDRFFSAPTDEKQRLLEYHANTNYSVVDLDISQSLYLKSYQEKVLGK
QRLRMINTSRVTSVDEDTDGVRVEVTSSATGLTHTIEADVIVYATGYRPS
DPAPLLQGLMRECKHDEQGRLSVGRDYRVTTSDAVRAGIYVHGASTEHSH
GLSAGLLSNTAVRSGEIAQSILRR SEQ ID NO: 72 >*Salinispora_arenicola*_CNS848
MSNQHETYDLVGIGFGPSNLSLAIALKEYEANGQENGISTLFFERQSSFG
WHRNMLLPSTTMQISFLKDLVTFRNPTSGFSFISYLHASGRLPQFVNNQD
FFPTRQEFHQYLEWAEERMAGRVAYGSEVTSIRLPSGTVPELSDRLRLEV
TDAAGRVGRVVEARNVVISTGLVPRMPEGIERDERVWHSSEFLQKYRRMN
PGDLRRVAVVGAGQSAAEITRFLHDELPHAEVWVVIPSYGYSVADDTPFA
NQIFDPEAVDDYYFGTEQTRDAFWRYHRNTNYSVVDDEVIRDLYRRVYDA
EVRGIKRLQILNLTRITGVKRAAAETRVELQVGPDSEVRELDVDALVCAT
GYDGMEPTHLLGDLDRLCLRDKAGRHQIERDYRIATAPEMRCGIYLQGGT
EHTHGLSSSLLSNIAVRSGEIADSIVSRRARHNSEYALAAGAEGDTC SEQ ID NO: 73 >*Salinispora_arenicola*_CNY231
MSNQHETYDLVGIGFGPSNLSLAIALKEYEANGQENGISTLFFERQSSFG
WHRNMLLPSTTMQISFLKDLVTFRNPTSGFSFISYLHASGRLPQFVNNQD
FFPTRQEFHQYLEWAEERMAGRVAYGSEVTSIRLPSGTVPELSDRLRLEV
TDAAGRVGRVVEARNVVISTGLVPRMPEGIERDERVWHSSEFLQKYRRMN
PGDLRRVAVVGAGQSAAEITRFLHDELPHAEVWVVIPSYGYSVADDTPFA
NQIFDPEAVDDYYFGTEQTRDAFWRYHRNTNYSVVDDEVIRDLYRRVYDA
EVRGIKRLQILNLTRITGVKRAAAETRVELQVGPDSEVRELDVDALVCAT
GYDGMEPTHLLGDLDRLCLRDKAGRHQIERDYRIATAPEMRCGIYLQGGT
EHTHGLSSSLLSNIAVRSGEIADSIVSRRARHNSEYALAAGAEGDTC SEQ ID NO: 74 >*Salinispora_arenicola*_CNY280
MSNQHETYDLVGIGFGPSNLSLAIALKEYEANGQENGISTLFFERQSSFG
WHRNMLLPSTTMQISFLKDLVTFRNPTSGFSFISYLHASGRLPQFVNNQD
FFPTRQEFHQYLEWAEERMAGRVAYGSEVTSIRLPSGTVPELSDRLRLEV
TDAAGRVGRVVEARNVVISTGLVPRMPEGIERDERVWHSSEFLQKYRRMN
PGDLRRVAVVGAGQSAAEITRFLHDELPHAEVWVVIPSYGYSVADDTPFA
NQIFDPEAVDDYYFGTEQTRDAFWRYHRNTNYSVVDDEVIRDLYRRVYDA
EVRGIKRLQILNLTRITGVKRAAAETRVELQVGPDSEVRELDVDALVCAT
GYDGMEPTHLLGDLDRLCLRDKAGRHQIERDYRIATAPEMRCGIYLQGGT
EHTHGLSSSLLSNIAVRSGEIADSIVSRRARHNSEYALAAGAEGDTC SEQ ID NO: 75 >*Salinispora_arenicola*_CNT005
MSNQHETYDLVGIGFGPSNLSLAIALKEYEANGQENGISTLFFERQSSFG -continued

SEQUENCE LISTING

WHRNMLLPSTTMQISFLKDLVTFRNPTSGFSFISYLHASGRLPQFVNNQD
FFPTRQEFHQYLEWAEERMAGRVAYGSEVTSIRLPSGTVPELSDRLRLEV
TDAAGRVGRVVEARNVVISTGLVPRMPEGIERDERVWHSSEFLQKYRRMN
PGDLRRVAVVGAGQSAAEITRFLHDELPHAEVWVVIPSYGYSVADDTPFA
NQIFDPEAVDDYYFGTEQTRDAFWRYHRNTNYSVVDDEVIRDLYRRVYDA
EVRGIKRLQILNLTRITGVKRAAAETRVELQVGPDSEVRELDVDALVCAT
GYDGMEPTHLLGDLDRLCLRDKAGRHQIERDYRIATAPEMRCGIYLQGGT
EHTHGLSSSLLSNIAVRSGEIADSIVSRRARHNSEYALAAGAEGDTC

SEQ ID NO: 76 >*Salinispora_arenicola*_CNY230
MSNQHETYDLVGIGFGPSNLSLAIALKEYEANGQENGISTLFFERQSSFG
WHRNMLLPSTTMQISFLKDLVTFRNPTSGFSFISYLHASGRLPQFVNNQD
FFPTRQEFHQYLEWAEERMAGRVAYCSEVTSIRLPSGTVPELSDRLRLEV
TDAAGRVGRVVEARNVVISTGLVPRMPEGIERDERVWHSSEFLQKYRRMN
PGDLRRVAVVGAGQSAAEITRFLHDELPHAEVWVVIPSYGYSVADDTPFA
NQIFDPEAVDDYYFGTEQTRDAFWRYHRNTNYSVVDDEVIRDLYRRVYDA
EVRGIKRLQILNLTRITGVKRAAAETRVELQVGPDSEVRELDVDALVCAT
GYDGMEPTHLLGDLDRLCLRDKAGRHQIERDYRIATAPEMRCGIYLQGGT
EHTHGLSSSLLSNIAVRSGEIADSIVSRRARHNSEYALAAGAEGDTC SEQ ID NO: 77 >*Salinispora_arenicola*_CNY486
MSNQHETYDLVGIGFGPSNLSLAIALKEYEANGQENGISTLFFERQSSFG
WHRNMLLPSTTMQISFLKDLVTFRNPTSGFSFISYLHASGRLPQFVNNQD
FFPTRQEFHQYLEWAEERMAGRVAYCSEVTSIRLPSGTVPELSDRLRLEV
TDAAGRVGRVVEARNVVISTGLVPRMPEGIERDERVWHSSEFLQKYRRMN
PGDLRRVAVVGAGQSAAEITRFLHDELPHAEVWVVIPSYGYSVADDTPFA
NQIFDPEAVDDYYFGTEQTRDAFWRYHRNTNYSVVDDEVIRDLYRRVYDA
EVRGIKRLQILNLTRITGVKRAAAETRVELQVGPDSEVRELDVDALVCAT
GYDGMEPTHLLGDLDRLCLRDKAGRHQIERDYRIATAPEMRCGIYLQGGT
EHTHGLSSSLLSNIAVRSGEIADSIVSRRARHNSEYALAAGAEGDTC SEQ ID NO: 78 >*Salinispora_pacifica*_CNY331
MSNQHETYDLVGIGFGPSNLSLAIALKEYEANGQENGISTLFFERQSSFG
WHRNMLLPSTTMQISFLKDLVTFRNPTSGFSFISYLHASGRLPQFVNNQD
FFPTRQEFHQYLEWAEERMAGRVAYCSEVTSIRLPSGTVPELSDRLRLEV
TDAAGRVGRVVEARNVVISTGLVPRMPEGIERDERVWHSSEFLQKYRRMN
PGDLRRVAVVGAGQSAAEITRFLHDELPHAEVWVVIPSYGYSVADDTPFA
NQIFDPEAVDDYYFGTEQTRDAFWRYHRNTNYSVVDDEVIRDLYRRVYDA
EVRGIKRLQILNLTRITGVKRAAAETRVELQVGPDSEVRELDVDALVCAT
GYDGMEPTHLLGDLDRLCLRDKAGRHQIERDYRIATAPEMRCGIYLQGGT
EHTHGLSSSLLSNIAVRSGEIADSIVSRRARHNSEYALAAGAEGDTC SEQ ID NO: 79 >*Streptomyces_aureofaciens*_NRRL_2209
VGERQRSGVVAGTGIVDVAGIGFGPSNLALAAAIAEIAGEAPVSARFFEA
QPRFGWHRGMLIEGATMQVSYLKDLVTMRNPTSPYSFLCYLQARGRLADF
INTKSPYPLRVEFHDYLEWVAESFADLVSYGARVVSVEPVSAEQGVEFLD
VHFVAPDGTRQVQRARNLVIAAGIEPRLPAGLPASPRIWHTAKFLPEVDR
IARQDPRSFVVLGSGQSAAEAIEHLHARFPRAQVHSVHARYGFSVADDSP
FANQVFNPEAVDRFHTAPDDVRQRLIDYHASTNYSVVDADLLHSLFQQAY
LEKVAGNPRLNFHNVSRVSEVTETPDGLRIDVESLSSGTSTVIEAQALVC
ATGYTRTDPAVFLDGLLPHCPLDDQGRLRLDREHRVVTDESVRCGIYVQG
FGEHSHGLSETLLSLSAVRAGEIGDMLVKALSG SEQ ID NO: 80 >*Streptomyces*_sp._OK885
MGARETEVYDVVGVGFGPSNLSLAVAIQEHNSSTSDRPLTAAFFERQEAF
GWHRNMLLPAATMQIPFLKDIATFRNPASRYSFVAYLHASGRLAGFVNNQ
TFFPTRREFHRYLEWVAANFTDQVSYGCEVVGLRLSGQGTGAGAPAHLEI
EVAGGAGRQRSSVRARNVVVSTGLVPRMPEGVLGDDRVWHSSEFLTRFRG
LKPVDLRAVAVVGAGQSAAEITRFVHDAAPHAQVYSVIPSYGYALADDTP
FANQVFDPAAVDDYFFGTDRARQAFWDYHKNTNYSVVDDDVIRDLYRRSY
DEEVNGARRLHFLNLTRVGEVKRAGDETRVLLMNGERRELEVDLCVFATG
YHGMEPAGVLGDLAPYCLRDEAGRLRVERDYRLVTGPELPGGIYLQGGTE
HTHGLSSSLLSNIAVRSGEIAESIVSRHRIERELGQVHPAEPAGKIR SEQ ID NO: 81 >*Pseudonocardia*_sp._AL041005-10
MDTDDMGTYDFVGIGFGPSNLSLAAALRDASSSDASPVRGHFFEAQPSFG
WHRNMLLPSAKMQVSFLKDLVTFRNPHSRFSFVSYLHEMNRLPQFANNND
FFPTRREFHQYLEWVAGHFADSVTYGARVTGIEPICGGATAGPHDRFRIT
IASGKDALATTRVEAYNVVLATGLTPRMPEGSVRDDRVWHSSEFLERFGS
CSSASLRRVAVVGAGQSAAEIARFCYDHAPNATISAILPSYGYSIADNTP
FANRVFDPGAVDDYYFSDPLGKDRLWESHRNTNYSVVDDEVIRSLFQRQY
DDEVRGVERLQIINLARVANIKRSGDETRVTIHSLARDEHFDLDVDVVVC
ATGYEAMGADGVLAGLDAFCPRDDRGRHRVERDYRLITTDDLTAGIYLQG
GTEHTHGLTSSLLSNLATRSGEIASSLRSSRRVGSAGGDRW PzbB
SEQ ID NO: 82 >*Mycobacterium_marinum*_M -continued

SEQUENCE LISTING

MYERPGYSAIEPAAVLDLLTANPLGLVVTIDGARPLATHAPVLFSQGPNGVAQAEVASGD
APLVGSLLVGHMNADNPQWRGMQKGGRVLVAFQGPHGYVSPSVYGVTPASPTWNFTAVHI
AGTLEPIADPESTFELVCDTARRLEARFGHGWRQEPSLDYFRRIVSGVGAFEIQVESVQT
MFKLSQEQPPVLRRRVAEHFESSDSVLHQELADLMRKHVFPKPI

SEQ ID NO: 83 >*Lentzea_flaviverrucosa*_DSM_44664
MFVPAQYREPHGHWITDLVRGHPLAQLVSNGPAGSSPYVTHAPIILDPGHPDPHPDDLHG
AVLWGHLNRANPHWAALGDGTEVTAVFTGPGSYVSPIVYERTPAAPTWDFTAVHVRGTLR
RVLDAEQTLATVTATVRAFEADHGTGWSMESSLDYFDQLLPGVGAFRLAVTGVDAMFKLS
QEQPPEVRLRVRDHFAGSERTHHCLIAEMMDRLPVAEH SEQ ID NO: 84 >*Streptomyces_aureofaciens*_ATCC_10762
VFTPKLYQVDGDDWPLRIIERHPLAVLVSNGDPVPNATHVPVIAPPDAAPEDALSGMRLW
AHLTRANPHWQQLAAAGGGPAKLVFHGPNGYVTPSLYSADMVAPTWNYVAVHLEGTVELA
GDDETLAIVHTTAQTLEDRFGDGMALAPSLEYHRQIVGAVGGLFFTVTKVDVMFKLSQEK
DPEVQQRVLDRFAASGSGLHREVADTMRALRLGGSAG SEQ ID NO: 85 >*Streptomyces_diastatochromogenes*_NRRL_B-1698
VYIPDLYRTDDKEWPVRILEENPLGLLTTHASSSAPPFATHLPVIIPSGSRDALLQDEKW
RGATLLGHMNRANPHWQSLADGTPARIVFQGPGAYVSPSVYHTDPAAPTWDFTAVHVQGT
LWPVRDEAETLAIVTATATELERKFGTGWCPHSSTEYFRQLLAGVGAFELRVDTMDAMFK
LSQEKSHEIRNGVVDWFVQGQHGRSRELASLMAEFYKDDRGTGA SEQ ID NO: 86 >*Streptomyces*_sp._DvalAA-43
MFVPSHYREPDGSWMIDLIRANPMAIMAINGSSADGPFATHLPVIPDPAATGRRSADLSG
ATLLGHMNRANPQWAALESGGVALLIFTGPHGYVSPTVYEMAPAAPTWNFTSVHVHGMVE
KIDSTEETLGVVKSTVTALETDFGTDWDMSGSVDYFRKIVPAVGAFRFTVSGAEGMFKLS
QEQPAEVRDRVQTSFSCREQGRYRETAELMGRLPG SEQ ID NO: 87 >*Collimonas_fungivorans*_Ter6
MYVPEYYRVDENTARELVYRHPLALLVCNGNNGLPWATHLPAIFPPETRKLLDQGESIIG
KTMYGHMNRINPHWNALQAGSALLIFQGPNSYVSPTVYEVTPAAPTWNFTSTHLRGTLRP
IDERDQILEIVRWTVATFEKEFCTNWDLTESIPYFERIVHGVGAFAFEVESFDSMFKLSQ
EQPAAIQERVVNSFASSSHCPHKEIADLMQRTNSKNKK SEQ ID NO: 88 >*Streptomyces_reticuli*_TUE45
VYERPLYREDRDGVVLAFLHHHPLALVVTAHEGVPVATHAPVLFRHGPDGADAEAVAAGT
VPLAGSTLIGHMNVENPQWRRMRSGDQALIVFQGPHGYVSPTVYDVTPAAPTWNFTAVHV
TGTVEPTAEPADVLDIVSDTARRLEGRFGRGWDQESSLDYFRQIAPGVGAFTLRVESVQT
MFKLSQEKPTPMRRRVAEQFEASESGTHRALAGMMRAHGLTDADEERETAG SEQ ID NO: 89 >*Streptomyces_scabiei*_NCPPB_4086
MFVPDPYREPDGSWMTELIRLNPFALLVSNGPADADPYATHLPVLRDPEWTGEWTEDLAG
GRLVGHMNRENPHWTALETGTPVLITFTGPHAYVSPIVYDITPAAPTWDFTSVHVHGVFH
KIEAAAPGEDTLEVCKDTVKAYERDFGAAKAWDMSRSIDYFATILPAVGAFRVEITGAEG
MFKLSQEQDQEIRERVQKDFALRDSTQYRETADLMDRMEKTGTVQGCPVHH SEQ ID NO: 90 >*Kutzneria_albida*_DSM_43870
MFVPSHYREPDVSWMVDLMRQNPLALLASNGNPADGPFATHLPVITDPAWDGPPAEKLAG
WPLLGHMNRANPQWTALENGATVLLTFTGPHAYVSPTVYEISPAAPTWNFTSVHAHGVVE
KIESIEETLEVVQATVKVFEKFFGDSWDMTESLGYFRKIVPAVGAFRIRVTRADGMFKLS
QEQKPEVRKRVVTSFSERGCGRHAQTAALMTQLP SEQ ID NO: 91 >*Streptomyces_albus*_ZpM
MFVPPEYRPDDPEWLIEVIRSHPLACLVTNGPDGPRASHVPVIPDPEQFPSGMPAREGEV
AGRRLFGHMNRLNPHWAALQGGAQALLVFQGPNGYVSPTVYEYTPAAPTWDFTAVHVRGW
LEPVGDRESSLQIITETVAAYERDLGTGWDMTESLGYFRQLLPGVGAFRLAIDTVDGMFK
LSQEQSPEVRERVACEFAARAEARGTALAEHIQRTK SEQ ID NO: 92 >*Rhodococcus_fascians*_02-815
MYVPRIYKASDRTWLRRVVAQYPFAALISNGPKAPYATHLPVICAPCAPSESEDLEGSTL
FGHMNRANPHWDSLVDGADAQLIFTGPHGYVTPSVYQRDSVAPTWNYVSVHLRGKLQPVA
DFEETLKVVQLTVSTYEQKFGSGWEMDSSLDHYRRIGPAVGAFSFEVESADGMFKLSQEQ
NLETRRRVADHFSANHAGRGKELASFMREYSHGDYNNF SEQ ID NO: 93 >*Streptomyces_neyagawaensis*_NRRL_B-3092
MFVPDPYREPDGSWMTELIRLNPFALLVSNGPADADPYATHLPVIRDPEWTGAWTENLAG
GRLIGHMNRENPHWTALENGTPVLITFTGPHAYVSPTVYDITPAAPTWDFTSVHVHGVFE
KIEAAAPGEDSLEVCKDTVKAYERDFGAAKAWDMSRSIDYFATILPAVGAFRVEITGAEG
MFKLSQEQDEEIRERVREDFALRDSSQYRETAELMDRMEKTGTIKGCPVHH SEQ ID NO: 94 >*Kutzneria_buriramensis*_DSM_45791
MFVPHHYHEPNESWMTDLIRENPLAELVSNGNGPAGPFATHVPVIPDPHDPDRPPGEIVG
ATLWGHMNRSNPHWAALESETPVVIVFTGPHAYVSPTLYQRTPAAPTWNFTAVHARGLLR
RVDAEAAGDETLETVMATVRAFEARFGAGWAMSESVEYFRRIVPAVGAFRVTVSHVDGMF
KLSQEQDADVRARVRESFAERESSNHKAIAAMMGRLADAE -continued

SEQUENCE LISTING

SEQ ID NO: 95 >*Streptomyces_yanglinensis*_CGMCC_4.2023
MFVPSQYREPDVSWMVDLMRDNPLALMASNGTAADGPYATHLPVITDPGWEGPPAADLAG
MLLLGHMNRANPHWSALEDGQTILLTFTGPHAYVSPTVYDITPAAPTWNFTSVHVRGTVE
KIATTEETLEVVKSTVRAYEKEFGDSWDMNASLDYFRKIVPGVGAFHVRVTRAEAMFKLS
QEQSPEVRDRVVRSFAGRGCTRHAQAADLMTRLP SEQ ID NO: 96 >*Streptomyces_griseochromogenes*_ATCC_14511
MFVPSHYREPDVSWMVDLMRGNPLALMASNGTPADGPFATHLPVITDPQWEGSPTADLAG
MPLLGHMNRANPHWAALETGSAILLTFTGPHAYVSPTVYDVTPAAPTWNFTSVHVHGVVE
KIESTEETLDVVQATVQAFEGEFGDSWDMSESVDYFRKIVTGVGAFRVRVTKAEGMFKLS
QEQRPEIRERVVQSFAGRECTRHVQTADLMNRLP SEQ ID NO: 97 >*Frankia*_sp._Avcl.1
MFVPCHYRAPNVSMMVDLMRENPLALMVSNGAPGAVPFATHLPVITDPCWDGQAGPDLGG
MVLLGHLNRANPHWXALETGSMILLTFTGPHAYVSPTVYGLTPAAPTWDFTSVHVHGVVE
KLTTTEETLEVVRATVLAFEQEFGDGWDMTDSLGYFRRIVPRVGAFRLRVTGAQGMFKLS
QEQTPEIRERVARSFAAHGSTRHAQTAELISRLPH SEQ ID NO: 98 >*Streptomyces_incarnatus*_NRRL_8089
MFVPSFYREPDSAWMVDLIRGNPLALAVTNGSPEDGPFATHLPVIFDPETSGDWSGELPG
ATLLGHMNRANPHWAALETGSVLLLTFTGPHSYVSPTVYETTPAAPTWNFTAVHVRGVVE
KISSTEETLGVVQSTVRAYEGAFGDGWDMSESLDYFRKIVPAVGAFRFTVTGAEGMFKLS
QEQPGEVRERVRDAFGQSGCAYRREVAGLMSRLP SEQ ID NO: 99 >*Streptomyces*_sp._MUSC136T
MFVPPQYREPDGSWMVDLMRRNPLALCVTNGDAADGPYATHLPVIRDPGMTGEWAEDLSG
GTLLGHMNLQNPHWAALRDGQSVLLVFTGPHAYVSPTVYEKSPAAPTWDFTAVHVHGTVE
KLTSAQDTLDVVKSTVRAFESDLGTGWDMTESEAYFDQLLPGVGAFRVEVTGAEGMFKLS
QEQQPHVRDRVHDAFAERPCGRHRETAELMARLP SEQ ID NO: 100 >*Streptomyces_albulus*_PD-1
MFVPPEYRPDDPEWLIEVIRSHPLACLVTNGPDGPRASHVPVIPDPEQFPSGMPAREGEV
AGRRLFGHMNRLNPHWAALQGGAQALLVFQGPNGYVSPTVYEYTPAAPTWDFTAVHVRGW
LEPVGDRESSLQIITETVAAYERDLGTGWDMTESLGYFRQLLPGVGAFRLAIDTVDGMFK
LSQEQSPEVRERVACEFAARAEARGTALAEHIQRTK SEQ ID NO: 101 >*Streptomyces_tsukubaensis*_NRRL_18488
MFVPSMYRAPDSSWMVNLIRENPLALAVANGSPENGPFATHLPVVFDPETSADPAGELPG
TTLLGHMNRANPHWAALETGSVLLLTFTGPNSYVSPSVYGVTPAAPTWNFTAVHVRGVVE
KISSLEESLDVVQSTVRAFEGAFGNGWDMTESLGYFRRIAPAVGAFRLTVTGAEGMFKLS
QEQPGDVRRRVRESFGQSACRYRRETAGLMSRLP SEQ ID NO: 102 >*Streptomyces_himastatinicus*_ATCC_53653_hmtC
MFVPSHYREPDSSWMVDIIRGNPLALMMSNGAAGEPPFATHLPVIPDPAMTGDWSERLSE
ATLLGHMNRDNPQWQALEDGAVVRIAFSGPHAYVSPTLYGVTPAAPTWNFTSVHVRGVVE
RIPSTEETLEVVKSTVRAFEADFGEGWDMAASIDYFRKIVPGVGAFRIMVRNVDGMFKLS
QEQQPEVRDRVRKSFAGRECGRHQETAAYMSRLP SEQ ID NO: 103 >*Streptomyces_flaveolus*_DSM_9954_sfaC
MYERPLYREDCDGVVLAFLRHNPLAMVVTSHDDVPVATHAPVLFRHGPDGADAEAVAAGT
VPLAGSTLIGHMNVENPQWRRMRSGDRALIVFQGPHGYVSPTVYGVTPAAPTWDFIAVHV
NGTVEPTADPAAVLDIVSDTARRLESGFGRGWDQESSLDYFRQIAPGVGAFTLRVDSVQT
MFKLSQEKPAPMRRRVVEQFEASESGTHRALASVMRDRGLTEADEERETAG SEQ ID NO: 104 >*Streptomyces_auranticaus*_JA_4570
MFVPSQYRQPDSSWMLDLIHGNPLALFVSNGSPEAGPFATHLPVIQDPEWTGEWSDDLSG
GRLLGHMNRANPHWKALESGTVNLLTFTGPHGYVSPTVYRTTPAAPTWNFTSVHVHGVVE
KIDGIENTLEVVKATVRAYEGAFGAGWDMTESLDYFRKIVPAVGAFQFRVTGAEGMFKLS
QEQPDDVQERVRESFGGRECTRHQAAAQLMDKLR SEQ ID NO: 105 >*Streptomyces*_sp._RJA2928_padO
MFVPQHYRTDDRRWPVRIVQDNPLALLMSTRDGRAPFASHVPVIVLPRQREELERTGRWQ
GAVLHGHMNRANPHWKSLADGQPAGLVFQGPAGYVSPAVYNTSPAVPTWNFTAVHVQGRL
KLVADEEATLGVVSATARQLEERFGARWTVEPSVDHFRQILPGVGAFELRVEECDSMFKL
SQEKEHEVRHAVMDWCARSPRGRSNDLAAVMRDYYPPTTTWPS SEQ ID NO: 106 >*Frankia_alni*_str._ACN14A
MFVPCHYRAPNVSMMVDLMRENPLALMVSNGAPGAVPFATHLPVITDPCWDGQAGPDLGG
MVLLGHLNRANPHWAALETGSMILLTFTGPHAYVSPTVYGLTPAAPTWDFTSVHVHGVVE
KLTTTEETLEVVRATVLAFEQEFGDGWDMTDSLGYFRRIVPRVGAFRLRVTGAQGMFKLS
QEQTPEIRERVARSFAAHGSTRHAQTAELISRLPH SEQ ID NO: 107 >*Actinosynnema_mirum*_DSM_43827
MHVPPMYRADDEDRARQVVHDYPLATLVSNGPRVPHATHLPVVAAPGAPQVGGLAGSTLW
GHLNRANAHWRALAGGVPAVLVFTGPHAYITPAIYRTTPAVPTWDFVSVHLHGRVEPIDG
EAGTLEVVKRTAELFESAFGAGWAAEPSHGHFARIVSGVGAFRFHVESVDSMFKLSQEKD
RDVRVRIIASLREASGPAAELGRIMHEHGLGGRGAEGA -continued

SEQUENCE LISTING

SEQ ID NO: 108 >*Kutzneria*_sp._744_orf4
MFVPGPYHAPEDRWLVDLVRGHPLAQLASNGAGGAAPHITHVPIIVDPELDGPVDRLVGI
TLWGHMNRANPHWAALGGAANVVATFAGPNAYVSPAVYRTAPAAPTWNFTSVQVRGELRK
VESADDTLATVRATVAALESRFGAGWDMTGSLDYFRRILPGVGAFRLRVAEADGMFKLSQ
EQQPAIRRRVRHSFGGCEATRAVAGLMDRLPTE SEQ ID NO: 109 >*Kibdelosporangium*_sp._MJ126-NF4
MHVPPMYEAPDPAWIPALIRAHPLATLVTAPDGIPAASHVPMIIRRTPDDERLTLVGHMN
RMNPQFKAIGDGCPALLVFTGPHGYVSPTVYGFTPAAPTWNFAVVHASGTLSPLPAGPDT
LEVIIDTVTALEGQLGNGWQMRDSLEYFDQLLPGVGAFSVQVDRVEAMYKLSQEQEPTTR
ETVAAAFEARSSDLAAMMRVCLDVERSTLGNRVG SEQ ID NO: 110 >*Mycobacterium_xenopi*_RIVM700367
MLSLLPFRAQAIAQEIAASRHRDAVTVRQRPVGDYPPKRYLETDPDRLRAVIERYRFATL
ISARATDEPVVTQLPLTLDTSRGSHGVLFGHMDLANPHAELLDGRPVLALFHGPNGYIPP
HQSNQLPTWNSITVEVRGRARILRDKDAVVDGLRGIAAAADPSPGGFRLTREAASDERLF
PFLVGFEIDIDEMVGRFKLSQDRDDRDRWLAARTLAHGLEQDDRDLIASIVELPLDRDDD
PIPLRRARTSGT SEQ ID NO: 111 >*Streptomyces_mirabilis*_YR139
MFVPSFYREPDSSWMVDLIRGNPLALAAANGSPEEGPFATHLPVIFDPETSGDWSGELPG
ATLLGHMNRANPHWAALATGSVLLLTFTGPHSYVSPTVYEVTPAAPTWNFTAVHVRGVVE
KIDSIEETLGVVQSTVRAFEGAFGDGWDMTESLGYFRKIVPDVGAFRFTVTGAEGMFKLS
QEQPGEVRERVRESFGHSACAYKRETAGLMSRLP SEQ ID NO: 112 >*Streptomyces_scabrisporus*_DSM_41855
MFVPRHYREPDSSWMVDLIRANPLALAVMNGDPSAGPFATHLPVIPDPQMTPSWSDDLSG
ATLLGHMNRANPHWKALETGTVLLLTFTGPHGYVSPTVYEVTPAAPTWNFTSVHVRGVVE
RIDSLEETLGVVRATALAFESEFGAGWDQTESVDYFRKIVPGVGAFRVTVTGAEGMFKLS
QEQPAEVRERVRQSFSTRACSLQRETAELMTRLP SEQ ID NO: 113 >*Streptomyces*_sp._TAA040
VFVPTHYREPDGSWMADLMRENPLALAVTDGGAGDGPFATHLPVVPDPGTTGDWPNGLKG
ATLLGHMNRANPHWRALETGGVVLLAFTGPHAYVSPTVYEVTPAAPTWNFTSVHVRGVVD
RIDSPEETLDVVRTTALVYEARFGAGWDQAASLDYFRRIVPAVGAFRIAVTSAEGMFKLS
QEQPAEVRERVHRSFSGRECGRHRDTAALMERLPRTGAEPPVGR SEQ ID NO: 114 >*Actinoalloteichus_cyanogriseus*_DSM_43889
MFVPHQYRAADTRPLVELIRSFPLATLVSHADGALFATHVPVLLAADADAGRDVPDPADL
TILGHLNRLNPHRDALAGGGACLLTFTGPHSYVSPAHYGRDTAAPTWNFTSVHVHGHLTP
LDSTEDTRHVVRSTALLYERRFGAGWDMTGSLDYFEQLLPGVSAFRVDVGTVEGMFKLGQ
EQPGHARQGVLAAFTSPGAPPHQRAVAELMRRFPPDAAGGVPGCPAQSAARMSPPADAIR
GEH SEQ ID NO: 115 >*Streptomyces*_sp._HNS054
MFVPNFYREPDASWMVDLVRGNPLALAVSNGCPEDGPFATHLPVIFDPARYGDLPGELAG
ATLLGHMNRANPHWPALQTGGILLLTFTGPHSYVSPTAYGTTPAAPTWNFTAVHARGVVE
KIDSTEETLDVVKATVRAYEGEFGDGWDMTESLGYFRKIVPAVGAFRLTVTRAEGMFKLS
QEQPAEVRERVRESFEQSACRYKRETAGLMSRLP SEQ ID NO: 116 >*Streptomyces*_sp._AW19M42
MYVPDHYQGSPEAALTVVRAGPLATLVTGADPWPLATHLPVVVPADVEAALEHGPVDLRG
HRLIGHLNRANPHWRQLSAGEQPSLLIFRGPHGYISPVVYESTPAAPTWNFTAVHVHGTI
RPLPAGKETLDVIHRTVEVLEGGFGHGWDMRGSLEYFEKIVPHVGAFEFQVAEVDGMFKL
SQELDEETRERTTHHFATSAHGTHRELACEMARLSTAAETKDGASEGASGSSSKRGTA SEQ ID NO: 117 >*Salinispora_pacifica*_DSM_45549
MFVPSPYREPDGSWTVDLMRRNPLALLVTSSDKTDVPYATHLPVIFDPCMPEEDYSDPAR
FVLLGHMNRANPHWKALATGMPTLVVFSGSHAYVSPTVYDKSPAAPTWNFTAAHARGVLE
KIESAEETLGVIGSTVRAFEADFGTDWDMTQSVGYFRKILPGVGAFRIAVSSIDSMFKLS
QEQPPEVRDRVGCAFAESASTRHREVAGLMNRLAVPKQVTV SEQ ID NO: 118 >*Salinispora_pacifica*_CNT150
MFVPSPYREPDGSWTVDLMRRNPLALLVTSSDKTDVPYATHLPVIFDPCM
PEEDYSDPARFVLLGHMNRANPHWKALATGMPTLVVFSGSHAYVSPTVYD
KSPAAPTWNFTAAHARGVLEKIESAEETLGVIGSTVRAFEADFGTDWDMT
QSVGYFRKILPGVGAFRIAVSSIDSMFKLSQEQPPEVRDRVGCAFAESAS
TRHREVAGLMNRLAVPKQVTV SEQ ID NO: 119 >*Salinispora_tropica*_CNB536
MFVPSPYREPDGSWTVDLMRRNPLALLVTSSDKTDIPYATHLPVIFDPRMPEEDYSDPAR
FVLLGHMNRANPHWKALATGMPTLVVFSGSHAYVSPTVYDKSPAAPTWNFTAAHARGVLE
KIESAEETLGVIGSTVRAFEADFGADWDMAQSVGYFRKILPGVGAFRIAVSSIDSMFKLS
QEQSPEVRDRVGCAFAESASTRHREVADLMNRLAVPKQVTV -continued

SEQUENCE LISTING

SEQ ID NO: 120 >*Salinispora_arenicola*_CNH996B
MFVPSPYREPDGSWTVDLMRRNPLALLVTSSDKTDVPYATHLPVIFDPCM
PEEDYSDPARFVLLGHMNRANPHWKALATGMPTLVVFSGSHAYVSPTVYD
KSPAAPTWNFTAAHARGVLEKIESAEEALGVIGSTVRAFEADFGTDWDMT
QSVGYFRKILPGVGAFRIAVSSIDSMFKLSQEQPPEVRDRVGCAFAESAS
TRHREVAGLMNRLAVPKRVIV SEQ ID NO: 121 >*Salinispora_arenicola*_CNH996
MFVPSPYREPDGSWTVDLMRRNPLALLVTSSDKTDVPYATHLPVIFDPCMPEEDYSDPAR
FVLLGHMNRANPHWKALATGMPTLVVFSGSHAYVSPTVYDKSPAAPTWNFTAAHARGVLE
KIESAEEALGVIGSTVRAFEADFGTDWDMTQSVGYFRKILPGVGAFRIAVSSIDSMFKLS
QEQPPEVRDRVGCAFAESASTRHREVAGLMNRLAVPKRVTV SEQ ID NO: 122 >*Salinispora_tropica*_CNY012
MFVPSPYREPDGSWTVDLMRRNPLALLVTSSDKTDIPYATHLPVIFDPRMPEEDYSDPAR
FVLLGHMNRANPHWKALATGMPTLVVFSGSHAYVSPTVYDKSPAAPTWNFTAAHARGVLE
KIESAEETLGVIGSTVRAFEADFGTDWDMAQSVGYFRKILPGVGAFRIAVSSIDSMFKLS
QEQSPEVRDRVGCAFAESASTRHREVADLMNRLAVPKQVTV SEQ ID NO: 123 >*Salinispora_tropica*_CNT261
MFVPSPYREPDGSWTVDLMRRNPLALLVTSSDKTDIPYATHLPVIFDPRMPEEDYSDPAR
FVLLGHMNRANPHWKALATGMPTLVVFSGSHAYVSPTVYDKSPAAPTWNFTAAHARGVLE
KIESAEETLGVIGSTVRAFEADFGTDWDMAQSVGYFRKILPGVGAFRIAVSSIDSMFKLS
QEQSPEVRDRVGCAFAESASTRHREVADLMNRLAVPKQVTV SEQ ID NO: 124 >*Salinispora_tropica*_CNH898
MFVPSPYREPDGSWTVDLMRRNPLALLVTSSDKTDIPYATHLPVIFDPRMPEEDYSDPAR
FVLLGHMNRANPHWKALVTGMPTLVVFSGSHAYVSPTVYDKSPAAPTWNFTAAHARGVLE
KIESAEETLGVIGSTVRAFEADFGTDWDMAQSVGYFRKILPGVGAFRIAVSSIDSMFKLS
QEQSPEVRDRVGCAFAESASTRHREVADLMNRLAVPKQVTV SEQ ID NO: 125 >*Streptomyces*_sp._PsTaAH-137
MFVPSFYREPDSSWMVDLIRGNPLALAVANGPAEDGPFATHLPVIFDPETSADVSGELPG
VTLLGHMNRANPHWSALQDGGVLLLTFTGPHSYVSPTVYEKSPAAPTWNFTSVHVRGVVE
KISSIEETLEVVQATVRAFEGAFGDGWDMTGSLDYFRKIVPAVGAFRFTVTGAEGMFKLS
QEQPGEVRERVRESFGQSACTYKRETAGLMNRLAQTEDVTVSSGA SEQ ID NO: 126 >*Salinispora_arenicola*_CNS296
MLVPHMYEAPSAAQVDAVITGHPMAVLVTNGPDVPHATHLPVIRTVDTEQTGPGSVLLGH
MNRTNPHWSALTSGTPGKLIFTGPNTYVCPVLYQTEPAAPTWDFVVVHVSGRVMPLDAGE
PTLAVVQRTAATLEGAFGAGWDHTGSIDYFRSIVGGVGAFEFVVEQVESMFKLSQEKDHT
VRQRLIDDFTSAPRNGSAQVGQLMSDLNLGVAP SEQ ID NO: 127 >*Salinispora_arenicola*_CNS299
MLVPHMYEAPSAAQVDAVITGHPMAVLVTNGPDVPHATHLPVIRTVDTEQTGPGSVLLGH
MNRTNPHWSALTSGTPGKLIFTGPNTYVCPVLYQTEPAAPTWDFVVVHVSGRVMPLDAGE
PTLAVVQRTAATLEGAFGAGWDHTGSIDYFRSIVGGVGAFEFVVEQVESMFKLSQEKDHT
VRQRLIDDFTSAPRNGSAQVGQLMSDLNLGVAP SEQ ID NO: 128 >*Salinispora_pacifica*_CNY363
MLVPHMYEAPSAAQVDAVITGHPMAVLVTNGPDVPHATHLPVIRTVDTEQTGPGSVLLGH
MNRTNPHWSALTSGTPGKLIFTGPNTYVCPVLYQTEPAAPTWDFVVVHVSGRVMPLDAGE
PTLAVVQRTAATLEGAFGAGWDHTGSIDYFRSIVGGVGAFEFVVEQVESMFKLSQEKDHT
VRQRLIDDFTSAPRNGSTQVGQLMSDLNLGVAP SEQ ID NO: 129 >*Actinomadura_atramentaria*_DSM_43919
VFVPPQYRPRGRSWTLETVRSNPLAMLVTRGERALPWITHLPVITHPERPPAELPGATLL
GHMNAANPHWAAVASGGPGTLVFTGPHGYVSPTVYELPVAAPTWDFVAVHVHGTLRPLDT
PEDARRVVRWTVEAYEGTHGTGWDPEGSLDYFDKILPGVRAFEFHVESVDGMYKLSQEQE
PETRRRVVRSFAASGRGAHAELSALIDRFGDPGPGAPATGCPAAREAGDGAR SEQ ID NO: 130 >*Streptomyces_drozdowiczii*_SCSIO_10141
MFVPPMYRTENEGRLRQVMERYPLAMLVTNGEPTPYATHLPVIFDQNGAPGTDGPVGATL
LGHLNRNNPHWRTLTDGLAAKLVFTGPHSYITPTLYETTPAAPTWNFVTVHLEGTLHPVT
DLEETLGVLQATVETFESAFGNKWEMDSSLDYFRHIGPAVGAFRFVVTSADGMFKLSQEK
TPEIQHRIADRLIGTETGTRHELGALMAELTLGDRDGV SEQ ID NO: 131 >*Streptomyces*_sp._RSD-27
MVDLVRGHPMALAVANGSPEDGPFATHLPVIFDPVTSGQWTGELPGATLLGHMNRANPHW
AALETGGVLLLTFTGPHSYVSPTVYAKSPAAPTWNFTSVHVRGVVEKIDSIEETLEVVQS
TVRAFEGAFGDGWDMTGSLDYFRKIVPDVGAFRLTVTGAEGMFKLSQEQPGEVRERVRES
FGQSACTYRRETAGLMGRLP SEQ ID NO: 132 >*Streptomyces*_sp._YR375
MVDLLRNNPLALMVSNGDAAAAPFATHLPVIPDPAMTDEWSADLSGATLLGHMNRGNPHW
KALETGDVVLLTFTGPHAYVSPTVYEVTPAAPTWNFTSVHVRGVVEKIDSAEETLEVVQS -continued

SEQUENCE LISTING

TVRAFEADFGDDWDMTESLGYFRRIVPAVGAFRLTVSGAEGMFKLSQEQKPEVRERVQKA
FSGRECGRHRETASFMSRLP

SEQ ID NO: 133 >*Actinoalloteichus_spitiensis*_RMV-1378
MFVPDQYRAADNRPLVELIRSFPLATLVSHAEGTLFATHVPVLLAADADAGRDVPEPADL
TILGHLDRRNPHRAALAAGGPCLLTFTGPHSYVSPAHYGRETAAPTWNFTAVHVHGRLTP
LDGAEDTRHVVRSTALLYERRFGAGWDTTGSLDYFEQLLPGVSAFRVDVSTVEGMFKLGQ
EQPGYARQGVVAAFTSPGAPPHQRAVAELMRRFAPDSPDDGGPGCPVRAPAKPEPATRGE
R SEQ ID NO: 134 >*Streptomyces*_sp._Ncost-T6T-1
MVDLMRSNPLALMVSNGSPEASPFATHLPVIFDPGDAADLAEDLARLPLLGHMNRANPHW
SALQDDAVVLLSFTGPHAYVSPTVYDVTPAAPTWNFTSVHVHGVVEKFDSTEETLEVVQA
TVRAFEEKFGNNWDMTDSIDYFRKIVHDVGAFRIRVTKAEGMFKLSQEQEPEIRDRVVQS
FTGRGCTRHAQTATLMSRLP SEQ ID NO: 135 >*Streptomyces*_sp._PBH53
VYERPLYREDRDGVVLAFLHHHPLALVVTAHEGVPVATHAPVLFRHGPDGADAEAVAAGT
VPLAGSTLIGHMNVENPQWRRMRSGDRALIVFQGPHGYVSPTVYDVTPAAPTWNFTAVHV
TGTVEPTAEPADVLDIVSDTARRLEGRFGRGWDQESSLDYFRQIAPGVGAFTLRVESVQT
MFKLSQEKPTPMRRRVAEQFEASESGTHRALAGMMRAHGLTDADEERETAG SEQ ID NO: 136 >*Salinispora_arenicola*_CNS-991_DSM_45545
MLVPHMYEAPSAAQVDAVITGHPMAVLVTNGPDVPHATHLPVIRTVDTEQTGPGSVLLGH
MNRTNPHWSALTSGTPGKLIFTGPNTYVCPVLYQTEPAAPTWDFVVVHVSGRVMPLDAGE
PTLAVVQRTAATLEGAFGAGWDHTGSIDYFRSIVGGVGAFEFVVEQVESMFKLSQEKDHT
VRQRLIDDFTSAPRNGSAQVGQLMSDLNLGVAP SEQ ID NO: 137 >*Streptomyces*_sp._MNU77
MFVPRIYQVDGEHWPSEIIDRHPLALLTTNGDDVPHATHVPVIRPPHDEQLVGSELLVHM
NRANPHWAALSDHDAAKLVFQGPDGYVTPSVYHVEPAVPTWDFVTVHLTGTLRISEDVDE
VLSIVTATARTLERRFGAGFDVDRAADHHARIASGVGAIRFRVTKAEAMFKFSQEKDAEI
RDRVMQWFEDSDIGEYADLGRLMRQFLDRPDITAPAAG SEQ ID NO: 138 >*Micromonospora_halophytica*_DSM_43171
MFVPRSFAVEDAGPVVELMRSNPLACFVLGGESPSVSHLPVVFADDDERDDLAGITLLTH
MNRQNPLWGSLSDGARVLVVFQGPHGYVSPTVYGVSPAAPTWNFTVVHAHGVVRLLGAGE
PALRVVKRTVQVLEGRFGAGWDMTGSLGYFERIVHAVGALEIHVDAVQSMFKLSQDQPVE
LQSKVAAAFAGSGRGTHRELAEQMYTHLRLKADVDGF SEQ ID NO: 139 >*Streptacidiphilus_carbonis*_NBRC_100919
MFVPPPYRPPDGSWTAELIRSNPLAILASNGSTADGPFATHLPVIPDPGT
PDLLSAELTGAVLLGHMNRANPHWAALAEGGTSLLTFTGPHAYVSPTVYG
VTPAAPTWNFTSVHARGTIERIESSEETLEVVKATVRAFEERFGAEWDMS
ESISYFRQILPGVGGFRFTVTGTDGMFKLSQEQAPEIRCRVQRSFTGREC
SRHRETAALMGSLP SEQ ID NO: 140 >*Streptomyces*_sp._MnatMP-M27
MFVPQHYRTDDRRWPVRIVQDNPLALLMSTRDGRAPFASHVPVIVLPRQR
EELERTGRWQGAVLHGHMNRANPHWKSLADGQPAGLVFQGPAGYVSPAVY
NTSPAVPTWNFTAVHVQGRLKLVADEEATLGVVSATARQLEERFGARWTV
EPSVDHFRQILPGVGAFELRVEECDSMFKLSQEKEHEVRHAVMDWCARSP
RGRSNDLAAVMRDYYPPTTAWPS SEQ ID NO: 141 >*Pseudonocardia*_sp._EC080625-04
MFVPEQYREQDSNWMLDIVRSNPLALMASDGTPEGCGPAATHLPCIPDPS
APHDWSDGPRGAVLLGHMNRANPQWRHLHDGQIVLLVFTGPHAYVSPAVY
DTTPAAPTWDFTAVHVHGVVTKLEPHKAERTTLDVVTDTVTALEGRFGAG
WDMTDSIEYFHRLLPGVGAFRVRVGSAEGMFKLSQEQPSDIRDRVRCHFA
AAQHGRSSEIAHLMTTLDGH SEQ ID NO: 142 >*Pseudonocardia*_sp._HH130629-09
MFVPEQYREQDSNWMLDIVRSNPLALMASDGTPEGCGPAATHLPCIPDPS
APHDWSDGPRGAVLLGHMNRANPQWRHLHDGQIVLLVFTGPHAYVSPAVY
DTTPAAPTWDFTAVHVHGVVTKLEPHKAERTTLDVVTDTVTALEGRFGAG
WDMTDSIEYFHRLLPGVGAFRVRVGSAEGMFKLSQEQPSDIRDRVRCHFA
AAQHGRSSEIAHLMTTLDGH SEQ ID NO: 143 >*Streptomyces_parvulus*_2297
MFVPSFYREPSNSWMVDLIRGNPLALAVANGQPDEGPFATHLPVIFDPDH
PLDRDDDLTGATLLGHMNRANPHWGSLETGGVLLLTFTGPHSYVSPTVYE
VTPAAPTWNFTAVHVRGVVEKLDSTDETLAVVQSTVRAFEGEFGNGWDMT
DSLGYFRKIAPGVGAFRFTVTGAEGMFKLSQEQPGEVRDRVRESFGQSGC
VHKRGTAGLMSRLP SEQ ID NO: 144 >Streptomyces_sp._OK885
MFVPDPYREPNTTWMVDLIRRNPLALLTTNGPAECGPFATHLPVIQDPGM -continued

SEQUENCE LISTING

TAEWSADLSGSLLLGHMNAQNPHWSALRDGDSVLLAFTGPHAYVSPTVYQ
KIPAAPTWNFTSVHVHGVIEKIESEEETLTVVRSTVRAFEEEFGTDWNME
GSVDYFRKILPGVGAFRITVSRADGMFKLSQEQEPQIRDRVRQSFAQRKC
SLHRETADLMGRLP

SEQ ID NO: 145 >*Streptomyces*_sp._CFMR 7
MYVPSIYQAEDRAWLRHVVERYPLATVITNGPQAPYATHVPVIPAPDTTS
WNDGPEGATLLGHMNRANSHWGSLTDGTHAQLVFTGPNGYVSPTVYETSP
AAPTWNFVSVHLRGRLRPISDFEETLEVVRLTVEAYEKNFGDGWEMDSSL
EYFRNIGPAVGGFRFDVESADGMFKLSQEKHPETRRRIADRFGGRRSGRA
TELAFFMRQFTSADHHAS SEQ ID NO: 146 >*Streptomyces*_sp._DvalAA-19
MYVPSIYQAEDRAWLRHVVERYPLATVITNGPQAPYATHVPVIPAPDTTS
WNDGPEGATLLGHMNRANSHWGSLTDGTHAQLVFTGPNGYVSPTIYETSP
AAPTWNFVSVHLRGRLRPISDFEETLEVVRLTVEAYEKNFGDGWEMDSSL
EYFRNIGPAVGGFRFDVESADGMFKLSQEKHPETRRRIADRFGGRRSGRA
TELAFFMRQFTSADRHAS SEQ ID NO: 147 >*Rhodococcus_fascians*_A3b
MYVPRIYKASDRTWLRRVVAQYPFAALISNGPKAPYATHLPVICAPCAPS
ESEDLEGSTLFGHMNRANPHWDSLVDGADAQLIFTGPHGYVTPSVYQRDS
VAPTWNYVSVHLRGKLQPVADFEETLKVVQLTVSTYEQKFGSGWEMDSSL
DHYRRIGPAVGAFSFEVESADGMFKLSQEQNLETRRRVADHFSANHAGRG
KELASFMREYSHGDYNNF SEQ ID NO: 148 >*Rhodococcus_fascians*_A73a
MYVPRIYKASDRTWLRRVVAQYPFAALISNGPKAPYATHLPVICAPCAPS
ESEDLEGSTLFGHMNRANPHWDSLVDGADAQLIFTGPHGYVTPSVYQRDS
VAPTWNYVSVHLRGKLQPVADFEETLKVVQLTVSTYEQKFGSGWEMDSSL
DHYRRIGPAVGAFSFEVESADGMFKLSQEQNLETRRRVADHFSANHAGRG
KELASFMREYSHGDYNNF SEQ ID NO: 149 >*Rhodococcus_fascians*_A76
MYVPRIYKASDRTWLRRVVAQYPFAALISNGPKAPYATHLPVICAPCAPS
ESEDLEGSTLFGHMNRANPHWDSLVDGADAQLIFTGPHGYVTPSVYQRDS
VAPTWNYVSVHLRGKLQPVADFEETLKVVQLTVSTYEQKFGSGWEMDSSL
DHYRRIGPAVGAFSFEVESADGMFKLSQEQNLETRRRVADHFSANHAGRG
KELASFMREYSHGDYNNF SEQ ID NO: 150 >*Rhodococcus_fascians*_A78
MYVPRIYKASDRTWLRRVVAQYPFAALISNGPKAPYATHLPVICAPCAPS
ESEDLEGSTLFGHMNRANPHWDSLVDGADAQLIFTGPHGYVTPSVYQRDS
VAPTWNYVSVHLRGKLQPVADFEETLKVVQLTVSTYEQKFGSGWEMDSSL
DHYRRIGPAVGAFSFEVESADGMFKLSQEQNLETRRRVADHFSANHAGRG
KELASFMREYSHGDYNNF SEQ ID NO: 151 >*Rhodococcus_fascians*_D188
MYVPRIYKASDRTWLRRVVAQYPFAALISNGPKAPYATHLPVICAPCAPS
ESEDLEGSTLFGHMNRANPHWDSLVDGADAQLIFTGPHGYVTPSVYQRDS
VAPTWNYVSVHLRGKLQPVADFEETLKVVQLTVSTYEQKFGSGWEMDSSL
DHYRRIGPAVGAFSFEVESADGMFKLSQEQNLETRRRVADHFSANHAGRG
KELASFMREYSHGDYNNF SEQ ID NO: 152 >*Rhodococcus_fascians*_02-816c
MYVPRIYKASDRTWLRRVVAQYPFAALISNGPKAPYATHLPVICAPCAPS
ESEDLEGSTLFGHMNRANPHWDSLVDGADAQLIFTGPHGYVTPSVYQRDS
VAPTWNYVSVHLRGKLQPVADFEETLKVVQLTVSTYEQKFGSGWEMDSSL
DHYRRIGPAVGAFSFEVESADGMFKLSQEQNLETRRRVADHFSANHAGRG
KELASFMREYSHGDYNNF SEQ ID NO: 153 >*Rhodococcus_fascians*_05-339-1
MYVPRIYKASDRTWLRRVVAQYPFAALISNGPKAPYATHLPVICAPCAPS
ESEDLEGSTLFGHMNRANPHWDSLVDGADAQLIFTGPHGYVTPSVYQRDS
VAPTWNYVSVHLRGKLQPVADFEETLKVVQLTVSTYEQKFGSGWEMDSSL
DHYRRIGPAVGAFSFEVESADGMFKLSQEQNLETRRRVADHFSANHAGRG
KELASFMREYSHGDYNNF SEQ ID NO: 154 >*Rhodococcus_fascians*_LMG_3605
MYVPRIYKASDRTWLRRVVAQYPFAALISNGPKAPYATHLPVICAPCAPS
ESEDLEGSTLFGHMNRANPHWDSLVDGADAQLIFTGPHGYVTPSVYQRDS
VAPTWNYVSVHLRGKLQPVADFEETLKVVQLTVSTYEQKFGSGWEMDSSL
DHYRRIGPAVGAFSFEVESADGMFKLSQEQNLETRRRVADHFSANHAGRG
KELASFMREYSHGDYNNF SEQ ID NO: 155 >*Rhodococcus_fascians*_LMG_3616
MYVPRIYKASDRTWLRRVVAQYPFAALISNGPKAPYATHLPVICAPCAPS -continued

SEQUENCE LISTING

ESEDLEGSTLFGHMNRANPHWDSLVDGADAQLIFTGPHGYVTPSVYQRDS
VAPTWNYVSVHLRGKLQPVADFEETLKVVQLTVSTYEQKFGSGWEMDSSL
DHYRRIGPAVGAFSFEVESADGMFKLSQEQNLETRRRVADHFSANHAGRG
KELASFMREYSHGDYNNF

SEQ ID NO: 156 >Rhodococcus_fascians_LMG_3623
MYVPRIYKASDRTWLRRVVAQYPFAALISNGPKAPYATHLPVICAPCAPS
ESEDLEGSTLFGHMNRANPHWDSLVDGADAQLIFTGPHGYVTPSVYQRDS
VAPTWNYVSVHLRGKLQPVADFEETLKVVQLTVSTYEQKFGSGWEMDSSL
DHYRRIGPAVGAFSFEVESADGMFKLSQEQNLETRRRVADHFSANHAGRG
KELASFMREYSHGDYNNF SEQ ID NO: 157 >*Rhodococcus_fascians*_A22b
MYVPRIYKASDRTWLRRVVAQYPFAALISNGPKAPYATHLPVICAPCAPS
ESEDLEGSTLFGHMNRANPHWDSLVDGADAQLIFTGPHGYVTPSVYQRDS
VAPTWNYVSVHLRGKLQPVADFEETLKVVQLTVSTYEQKFGSGWEMDSSL
DHYRRIGPAVGAFSFEVESADGMFKLSQEQNLETRRRVADHFSANHAGRG
KELASFMREYSHGDYNNF SEQ ID NO: 158 >*Streptomyces*_sp._CNT360
MYVPQHFAVDETEPVVELIRANPLAVFVTTQGGVPVASHIPVVFASEDEA
EQADDLVGVTLFGHLNVQNPQYGVLADGDRVLVVFQGSHGYISPTVYDTV
PAAPTWNFSAVHVTGTVRLLGPGEPALKVVRRIVTALERRFGAGWDMTES
LPYFERIVPGVGAFEIAVEAVDSIFKLSQDQPAELRDKAECAFRNSDAGV
HRELAAQMRRHNGAACSHQERTARDGD SEQ ID NO: 159 >*Salinispora_arenicola*_CNS848
MLVPHMYEAPSAAQVDAVITGHPMAVLVTNGPDVPHATHLPVIRTVDTEQ
TGPGSVLLGHMNRTNPHWSALTSGTPGKLIFTGPNTYVCPVLYQTEPAAP
TWDFVVVHVSGRVMPLDAGEPTLAVVQRTAATLEGAFGAGWDHTGSIDYF
RSIVGGVGAFEFVVEQVESMFKLSQEKDHTVRQRLIDDFTSAPRNGSAQV
GQLMSDLNLGVAP SEQ ID NO: 160 >*Salinispora_arenicola*_CNY231
MLVPHMYEAPSAAQVDAVITGHPMAVLVTNGPDVPHATHLPVIRTVDTEQ
TGPGSVLLGHMNRTNPHWSALTSGTPGKLIFTGPNTYVCPVLYQTEPAAP
TWDFVVVHVSGRVMPLDAGEPTLAVVQRTAATLEGAFGAGWDHTGSIDYF
RSIVGGVGAFEFVVEQVESMFKLSQEKDHTVRQRLIDDFTSAPRNGSAQV
GQLMSDLNLGVAP SEQ ID NO: 161 >*Salinispora_arenicola*_CNY280
MLVPHMYEAPSAAQVDAVITGHPMAVLVTNGPDVPHATHLPVIRTVDTEQ
TGPGSVLLGHMNRTNPHWSALTSGTPGKLIFTGPNTYVCPVLYQTEPAAP
TWDFVVVHVSGRVMPLDAGEPTLAVVQRTAATLEGAFGAGWDHTGSIDYF
RSIVGGVGAFEFVVEQVESMFKLSQEKDHTVRQRLIDDFTSAPRNGSAQV
GQLMSDLNLGVAP SEQ ID NO: 162 >*Salinispora_arenicola*_CNT005
MLVPHMYEAPSAAQVDAVITGHPMAVLVTNGPDVPHATHLPVIRTVDTEQ
TGPGSVLLGHMNRTNPHWSALTSGTPGKLIFTGPNTYVCPVLYQTEPAAP
TWDFVVVHVSGRVMPLDAGEPTLAVVQRTAATLEGAFGAGWDHTGSIDYF
RSIVGGVGAFEFVVEQVESMFKLSQEKDHTVRQRLIDDFTSAPRNGSAQV
GQLMSDLNLGVAP SEQ ID NO: 163 >*Salinispora_arenicola*_CNY230
MLVPHMYEAPSAAQVDAVITGHPMAVLVTNGPDVPHATHLPVIRTVDTEQ
TGPGSVLLGHMNRTNPHWSALTSGTPGKLIFTGPNTYVCPVLYQTEPAAP
TWDFVVVHVSGRVMPLDAGEPTLAVVQRTAATLEGAFGAGWDHTGSIDYF
RSIVGGVGAFEFVVEQVESMFKLSQEKDHTVRQRLIDDFTSAPRNGSTQV
GQLMSDLNLGVAP SEQ ID NO: 164 >*Salinispora_arenicola*_CNY486
MLVPHMYEAPSAAQVDAVITGHPMAVLVTNGPDVPHATHLPVIRTVDTEQ
TGPGSVLLGHMNRTNPHWSALTSGTPGKLIFTGPNTYVCPVLYQTEPAAP
TWDFVVVHVSGRVMPLDAGEPTLAVVQRTAATLEGAFGAGWDHTGSIDYF
RSIVGGVGAFEFVVEQVESMFKLSQEKDHTVRQRLIDDFTSAPRNGSTQV
GQLMSDLNLGVAP SEQ ID NO: 165 >*Salinispora_pacifica*_CNY331
MLVPHMYEAPSAAQVDAVITGHPMAVLVTNGPDVPHATHLPVIRTVDTEQ
TGPGSVLLGHMNRTNPHWSALTSGTPGKLIFTGPNTYVCPVLYQTEPAAP
TWDFVVVHVSGRVMPLDAGEPTLAVVQRTAATLEGAFGAGWDHTGSIDYF
RSIVGGVGAFEFVVEQVESMFKLSQEKDHTVRQRLIDDFTSAPRNGSTQV
GQLMSDLNLGVAP SEQ ID NO: 166 >*Streptomyces_aureofaciens*_NRRL_2209
VFTPKLYQVDGDDWPLRIIERHPLAVLVSNGDPVPNATHVPVIAPPDAAP -continued

SEQUENCE LISTING

EDALSGMRLWAHLTRANPHWQQLAAAGGGPAKLVFHGPNGYVTPSLYSAD
MVAPTWNYVAVHLEGTVELAGDDETLAIVHTTAQTLEDRFGDGMALAPSL
EYHRQIVGAVGGLFFTVTKVDVMFKLSQEKDPEVQQRVLDRFAASGSGLH
REVADTMRALRLGGSAG

PzbAB
SEQ ID NO: 167 >*Streptomyces*_sp._CFMR_7
VRNAHATHPDDDPVGTTTERPYDLLGIGFGPSNLALAVCAREQKLPLSCL
FVERQDTVAWHPGMLIDGARMQISFLKDLVSLRNPSSPYSFLQYTKAKGR
LERFVNLNESRPTRIEYDDYLKWVAQDFADQVRFGSQVDRVTPVQGPDGG
DLSLFRVETQDVATGRHSVHYARNVVHAGGGRPPARTAGVAEVSSVVHSS
EFLTRFPDQFKDHDGAYRFVVVGGGQSAGEISEYLLDHYDRAEVHVVVSG
YTLLPTDNSPFVNEQFYSGNADAFYRMRPEQRAAVSGRLRAANYGVVRED
LLERLFNTDYLDQVKGRKRLHIHPFSRLSEVRENGDALAVTLRQHLDEGP
EEPLRCDGVVLATGYDRSLDPAVFGDVLPHLTAGEGEGVGGVALSRHYRA
RTSPELRAGLYLQGFGEAQFGLGDTLLSLLPFRSQEIVEDIADRVPVAGV
GGCPVMSPYGSGVVSTSPHGPARSAVYPPKWYLEHDREKLYGLMERFRFA
TLISARSGDQPFATHLPLILDRSRGANGVLFGHLDRGNEHADLIDGRHML
AVFHGPNAYMPPGVFESDPLPTWNSMSVHVRGRVRVVRDRDALVHGLIGI
AERSQPDNRLAADDPRIDRIIGSIVGFEFEVEELVGRFKLSQDRDETDRR
HAAVALARATERGERDFIEYVVGLSLITEDDPRDLAGRPLSPLAIGGVHE SEQ ID NO: 168 >*Micromonospora_tulbaghiae*_DSM_45142
MRNDPAPDARSSEPGSEQNPYDLIGVGFGPSNLALAIAAEELDGERTCLF
FERSPSLQWHPGMLLEGSRMQISFLKDLVSLRNPASPYTFLQYAKAKDRL
ERFVNLSEFRPTRLEYQDYLRWVAEFFAGQVRYHTEVTRVSPVRRPGEDV
HRLFRVEARDIRTGETTVHHAANVVHAAGGRPRLPPGGVCASPAVIHSSD
FLPHFPERFADRSRPYEFAVAGDGQSAGEVALYLMRTYPESRVHLFLSGQ
ALRATDNSPFVNEQFFESSANAFSARPRDERTALRAELRNTNYGVVEAGT
LDDLYRTVYDDEVRGRHRLIVHPATRVVAVREGDEGPLVAILDRRSGAEG
EIRCDGVVLATGYVRALDESIFSELTPFLRTESDKLLLSGYRVRTTAEVA
GGFYVQGYGEQHFGLGDTLLSLLPFRSRQIFTDICRRTPPPRQAVAVSDA
SAYPPPHYLEHDPEKLYAVMERFNFATVISARAAEDPVVTHVPLTLDRSR
GAHGVLFGHLDRANPHAQLIDGKQVTVVFHGPNTYLSPYALETDALPTWN
SMNVHVGGRGRLLADRAALVTGLSGICEKSDPGVDSYRLDPDDPRIDRLV
DYVVGFEIEIQALVGRFKLSQELDDRNRRLAASALMATARRDESEVIGKV
FGMSPVNGRQNGSSALWSAHSR SEQ ID NO: 169 >*Amycolatopsis_alba*_DSM_44262
MRNDAPPNPLTAELGAEGNPYDLIGVGFGPSNLALAIAAEELDSERNCLF
FERSSRLRWHPGMLIDGSRMQISFLKDLVSLRNLASPYTFLQYTKAKGRL
EQFVNLNDFRPTRLEYQDYLEWVAESFSGQVRYNSEVTRVTPVRRTGEDA
HRLFRVEARDVVTGQTTVRYAANVVHAAGGRPRLPDGGVCDSPAVVHSSD
FLPRFPGHFADRSRPYEFGVAGDGQSAGEIAAYLLSRYPASRVHLLLSGS
ALRAADSNPFVNEQFFEGRANHFHARTKPDRTGLLAELRNTNYAVVEPGF
LDDLYRLVYDDEVRGTRRLIVHPGTKVTAVGADGASLRVAVTDRRGGDEE
MRCDGVVLATGYVRALDESMFADLLPFLREESGDLVLSPDYRVGTTAELE
GGFYVQGYGESSFGLGDTLLSLLPFRAKQIFTDICKQTPPPVRTRRPVEV
SKASAYPPPHYVETDPKKIYAVMERFSFATLISARGAEDPVVTHLPLTLD
RARGAHGVLFGHLDRANPHVQLIDGHQLTVLFHGPNAYLSPQVFETSVLP
TWNSMNVHVRGRGRLLPDRAALLAGLSGICVKSDPGDDSYRLDLDDPRID
RMIEHIVGFEIEIHELVGRFKLSQELDDQNRMLAASALSATARRGELELI
EEVVGLNVVQG SEQ ID NO: 170 >*Mycobacterium*_sp._IS-1556
MTSMPPGEGHDSDLDFIGIGFGPSNLALAVAADEIVPDRKGLFFERSGTF
QWHPGMLLDGTKMQISFLKDLATLRNPASRYTFLQYAKARGRLEQFVNLH
EFHPSRLEYNDYLRWVAEFFTDRVCYNTIVTAVVPVGHSPSSNGHLTRFR
VHVRDMATGAESCFFTANVIFGGGGVPRLLGARADASAVLHSSAFLPNFT
NRFNESQKPYRFAVIGNGQSAAEIVDYLLNHYPGATIHLFISDCTLRATD
HSPFINEHFFSTSAADFYNHPPAQRVALRSALRSTNYGVVDADLLQKLYQ
ITYLDEVKGCRRLLLHRESRLSQIEEIDDQVVASFEDRFSGDSSEFHFDG
AVLATGYERVLDAEVFRHVLPHVLWDESGAISLTRSCRVNTVPAVTARLF
LQGYGEAWFGIGDTLLSLLPFRAQAIAQEIGNAPSGAPIRRKQRVHGEYP
PKRYLETDPDRLHDVINRYRFATLVSASGVDEPVVTQLPLTLDTSRGSLG
VLFGHMDFANPHTELLDGRRVLVLFHGPNGYISPHVYESAQLPTWNSITV
EVRGRARILRDKDAVVNGLRGIAAAADPTPGGFRLTREAASDQRLFPLLV
GFEIDIDDMRGRFKLSQERDDRDRWHAAHALANGVEQDDRDLISSIVGLP
LDVDEEPKPQQQAQIHQYGNAPADTAYRRVDG SEQ ID NO: 171 >*Streptomyces*_sp._Root55
MSSEAGAVFPCANGRPAAEVAPGPSRGSHPADPYDLIGVGFGPSNMALAI
AVEELDPGRSCLFLERNTGVRWHPGMLIEGARMQISYLKDLVSLRNLASP
YTFLSYLKAKGRLEKFINVGASRPTRLEYQDYLSWVAEDFGHVVRYESEV
VAVVPVAGPGSETLDLLRVRVRDAGSAEFHDLYARNVVHAGGGTPRRGAP
GQICDASSVIHSSTFLDAFPARFPDHDAALDLGVVGDGQSAAEITSHVLK
GYPNARVHLFVPGYALRATDNNPFANEQFYQRNAGEFYASGARRRTILRT -continued

SEQUENCE LISTING

ELRNTNYGAVEAGHLDELYDITYADEVRGAPRLVVHRASHVSRVVEDGER
LSVEVRDRTDGPDRTMVCDGLVLATGYTRELHPAVFGELTPLLSRDDSGE
LLVTADCRVRTDERVTAGFYVQGYAESAYGIGDTLLSLLPFRSQQIVDDI
RGRLPAGRPVAVEESAPYPPSHYVETDLDRIRSLMERFNFATVISVARDA
RVLVTHVPLVVERDRGGEHGMLIGHLDRSNPQVELLRDRPVTVVFHGPDA
YLSPDVLKTDRLPTWNSMSVHVRGHARLFSGRDELMRVFNGLCEQAEGES
GSYWLRPDDTRIEQLRGQVVGFEVDIHELTGRFKLSQELDEANRELAAAD
MARGTSAERQAFIERAFDLQPRPDVLGPPGGPGVGGCPVGGARAAGGTTA
VADNERETAR

SEQ ID NO: 172 >*Streptomyces*_sp._2AW
MLDLLGIGFGPSNVALAAAMAEGGKPPRALFLEAKERFGWHPGMLLDGAR
MQISFLKDLVTLRNPESPYSFLAYLKAKGRLEEFANLREFYPSRIEFQDY
LRWVAGHFEHQAVFGARVASVSPDFGIDGMARSFTVRAELADSGEYVTYQ
ARNVVYAPGGTPNRVAGVAPRDERVIHTAEFLERFPKSFPDHSADLSFAV
VGGGQSAAEIIEYILAKYPLSRVHAILPGYSFRPADDSPYSNEVFFSAEV
DDHFTAHDQAARLAEARSTNYGVVDLDLIEDLYRMGYEDQVRGNVPRLTF
CRSSRLLSADAGPSGIEVTVGGPEGSRSLNLDGLVLATGYHRELDPEMFR
DVIPHLQRNESGNFLVSRAYRADSVPELTAGIYFQGLTELSHGIGDTLLS
LLSFRSAEIAEDVRKRSEVPSADEVEYPPARHIEPYRAAILETLQRFPLA
TLISSDDESEVFATHLPLILDRERGEQGVLFGHLDVGNPQVPNLNGRRVL
AVFHGPNSYISPRTYTTDQLPTWNYVAVHVRGHVRVLENQDQVVSGLASI
SEKADRSDGAYRLDENDSRIEKLIGGIVGFELDIESLTGRFKLSQDRSDE
DRKRAMAVLREGAGDEHHDFVARIHQQ SEQ ID NO: 173 >*Streptomyces*_sp._SolWspMP-5a-2
MPKKGGAVTPRAQGLPSGEAGPAPRRGTDPADPLDLIGIGFGPSNLALAI
AAEELDPAADRLFLERNAGVHWHPGMLLEGARMQISYLKDLVSLRNLASP
YTFLSYLKAKGRLEKFINIGVTRPTRLEYQDYLTWVAGHFADVVRYRSEV
VSVTPVSGPGSTALDLLHVRVRDTATGTPYSLYARNVVHAGGGTPRRGTP
DRICDTPSVIHSSRFLPAFPRRFPDHDAALDLGVVGDGQSAAEIAAHMLT
HYPDATVHLFVPGYALRATDNNPFVNEQFYRHNADAFYADEPHRRALLRT
ELRNTNYGAVEAGYLDTLYDITYADEVRGAPRLLVHRGCDVTRITEDGPR
LDVLVRDRTGGPDRTVRCDGVVLATGYTRALDPAVFAGLDPLLRRDESGA
LLVSADCRVDAEAPLTAGFYVQGYAEGAYGIGDTLLSLLPFRSQRIIDDL
RARRPEDLPSGGPYPPDHYVEKDLERVRAVMERFNFATVISADRDARVLV
THVPLVVERDRGGEHGTLIGHLDRSNPQVELLRDRPVTVVFHGPNSYLSP
DVLTTDKLPTWNSMSVHVRGHARLFSGRDELMRVFNGLCEQAEPGPGSYR
LRPDDERIDQLLGHVVGFEVDIQEVTGRFKLSQDLDEDNRALAAADMQRD
LGEERRTFVADVFDLAPRPDGPEAGPRACGCPLGGPPAGTGAALAEEAGQ
TVR SEQ ID NO: 174 >*Streptomyces*_sp._ScaeMP-e83
VRNAHATHPDDDPVGTTTERPYDLLGIGFGPSNLALAVCAREQKLPLSCL
FVERQDTVAWHPGMLIDGARMQISFLKDLVSLRDPSSPYSFLRYTKAKGR
LERFVNLNESRPTRIEYDDYLKWVAQDFADQVRFGSQVDRVTPVQGPDGG
DLSLFRVETEDVATGRRSVHYARNVVHAGGGRPPTRTAGVAEVPSVVHSS
EFLTRFPGQFKDHDGAYRFVVVGGGQSAGEISEYLLDHYDRAEVHVVVPG
YTLLPTDNSPFVNEQFYSGNADAFYRMRPEQRAAVSGRLRAANYGVVRED
LLERLFNTDYLDQVKGRKRLHIHSFSRLSEVREDGEALAVTLQPRLDEGP
EESLRCDGVVLATGYDRSLDPAVFGDVLPHLTPGEGEGAAGVVLSRHYRA
RTSPELRAGLYLQGFGEAQFGLGDTLLSLLPFRSQEIVEDIADRVPAAGV
GGCPVMSPYGSGVVSTSPHGPVPSAVYPPKWYLEHDREKLYGLMERFRFA
TLISARSGDEPFATHLPLILDRSRGANGVLFGHLDRGNEHAELIDGRHML
AVFHGPNAYMPPGVFESDPLPTWNSMSVHVRGRVRAVRDQDALVRGLIGI
AERSQPDNRLAADDPRIDRIIGSIVGFEFEVEELVGRFKLSQDRDETDRR
HAAVALARATERGERDFIEYVVGLSLITEDDPRDLAGRPLSPSP SEQ ID NO: 175 >*Mycobacterium*_sp._GA-0227b
MTSMPPGEGHDSDLDFIGIGFGPSNLALAVAADEIVPDRKGLFFERSGTF
QWHPGMLLDGTKMQISFLKDLATLRNPASRYTFLQYAKARGRLEQFVNLH
EFHPSRLEYNDYLRWVAEFFTDRVCYNTIVTAVVPVGHSPSSNGHLTRFR
VHVRDMATGAESCFFTANVIFGGGGVPRLLGARADASAVLHSSAFLPNFT
NRFNESQKPYRFAVIGNGQSAAEIVDYLLNHYPGATIHLFISDCTLRATD
HSPFINEHFFSTSAADFYNHPPAQRVALRSALRSTNYGVVDADLLQKLYQ
ITYLDEVKGCRRLLLHRESRLSQIEEIDDQVVASFEDRFSGDSSEFHFDG
AVLATGYERVLDAEVFRHVLPHVLWDESGAISLTRSCRVNIVPAVTARLF
LQGYGEAWFGIGDTLLSLLPFRAQAIAQEIGNAPSGAPIRRKQRVHGEYP
PKRYLETDPDRLHDVINRYRFATLVSASGVDEPVVTQLPLTLDTSRGSLG
VLFGHMDFANPHTELLDGRRVLVLFHGPNGYISPHVYESAQLPTWNSITV
EVRGRARILRDKDAVVNGLRGIAAAADPTPGGFRLTREAASDQRLFPLLV
GFEIDIDDMRGRFKLSQERDDRDRWHAAHALANGVEQDDRDLISSIVGLP
LDVDEEPKPQQQAQIHQYGNAPADTAYRRVDG SEQ ID NO: 176 >Mycobacterium_sp._GA-1999
MTSMPPGEGHDSDLDFIGIGFGPSNLALAVAADEIVPDRKGLFFERSGTF
QWHPGMLLDGTKMQISFLKDLATLRNPASRYTFLQYAKARGRLEQFVNLH -continued

SEQUENCE LISTING

EFHPSRLEYNDYLRWVAEFFTDRVCYNTIVTAVVPVGHSPSSNGHLTRFR
VHVRDMATGAESCFFTANVIFGGGGVPRLLGARADASAVLHSSAFLPNFT
NRFNESQKPYRFAVIGNGQSAAEIVDYLLNHYPGATIHLFISDCTLRATD
HSPFINEHFFSTSAADFYNHPPAQRVALRSALRSTNYGVVDADLLQKLYQ
ITYLDEVKGCRRLLLHRESRLSQIEEIDDQVVASFEDRFSGDSSEFHFDG
AVLATGYERVLDAEVFRHVLPHVLWDESGAISLTRSCRVNIVPAVTARLF
LQGYGEAWFGIGDTLLSLLPFRAQAIAQEIGNAPSGAPIRRKQRVHGEYP
PKRYLETDPDRLHDVINRYRFATLVSASGVDEPVVTQLPLTLDTSRGSLG
VLFGHMDFANPHTELLDGRRVLVLFHGPNGYISPHVYESAQLPTWNSITV
EVRGRARILRDKDAVVNGLRGIAAAADPTPGGFRLTREAASDQRLFPLLV
GFEIDIDDMRGRFKLSQERDDRDRWHAAHALANGVEQDDRDLISSIVGLP
LDVDEEPKPQQQAQIHQYGNAPADTAYRRVDG

Plasmids:
SEQ ID NO: 177 SfaB (PzbA) expression

```
   1      tatggctgcc gcgcggcacc aggccgctgc tgtgatgatg atgatgatgg ctgctgccca
  61      tggtatatct ccttcttaaa gttaaacaaa attatttcta gaggggaatt gttatccgct
 121      cacaattccc ctatagtgag tcgtattaat ttcgcgggat cgagatctcg atcctctacg
 181      ccggacgcat cgtggccggc atcaccggcg ccacaggtgc ggttgctggc gcctatatcg
 241      ccgacatcac cgatggggaa gatcgggctc gccacttcgg gctcatgagc gcttgtttcg
 301      gcgtgggtat ggtggcaggc cccgtggccg ggggactgtt gggcgccatc tccttgcatg
 361      caccattcct tgcggcggcg gtgctcaacg gcctcaacct actactgggc tgcttcctaa
 421      tgcaggagtc gcataaggga gagcgtcgag atcccggaca ccatcgaatg gcgcaaaacc
 481      tttcgcggta tggcatgata gcgcccggaa gagagtcaat tcagggtggt gaatgtgaaa
 541      ccagtaacgt tatacgatgt cgcagagtat gccggtgtct cttatcagac cgtttcccgc
 601      gtggtgaacc aggccagcca cgtttctgcg aaaacgcggg aaaaagtgga agcggcgatg
 661      gcggagctga attacattcc caaccgcgtg gcacaacaac tggcgggcaa acagtcgttg
 721      ctgattggcg ttgccacctc cagtctggcc ctgcacgcgc cgtcgcaaat tgtcgcggcg
 781      attaaatctc gcgccgatca actgggtgcc agcgtggtgg tgtcgatggt agaacgaagc
 841      ggcgtcgaag cctgtaaagc ggcggtgcac aatcttctcg cgcaacgcgt cagtgggctg
 901      atcattaact atccgctgga tgaccaggat gccattgctg tggaagctgc ctgcactaat
 961      gttccggcgt tatttcttga tgtctctgac cagacaccca tcaacagtat tattttctcc
1021      catgaagacg gtacgcgact gggcgtggag catctggtcg cattgggtca ccagcaaatc
1081      gcgctgttag cgggcccatt aagttctgtc tcggcgcgtc tgcgtctggc tggctggcat
1141      aaatatctca ctcgcaatca aattcagccg atagcggaac gggaaggcga ctggagtgcc
1201      atgtccggtt ttcaacaaac catgcaaatg ctgaatgagg gcatcgttcc cactgcgatg
1261      ctggttgcca acgatcagat ggcgctgggc gcaatgcgcg ccattaccga gtccgggctg
1321      cgcgttggtg cggatatctc ggtagtggga tacgacgata ccgaagacag ctcatgttat
1381      atcccgccgt taaccaccat caaacaggat tttcgcctgc tggggcaaac cagcgtggac
1441      cgcttgctgc aactctctca gggccaggcg gtgaagggca atcagctgtt gcccgtctca
1501      ctggtgaaaa gaaaaaccac cctggcgccc aatacgcaaa ccgcctctcc ccgcgcgttg
1561      gccgattcat taatgcagct ggcacgacag gtttcccgac tggaaagcgg gcagtgagcg
1621      caacgcaatt aatgtaagtt agctcactca ttaggcaccg ggatctcgac cgatgccctt
1681      gagagccttc aacccagtca gctccttccg gtgggcgcgg ggcatgacta tcgtcgccgc
1741      acttatgact gtcttcttta tcatgcaact cgtaggacag gtgccggcag cgctctgggt
1801      cattttcggc gaggaccgct ttcgctggag cgcgacgatg atcggcctgt cgcttgcggt
```

-continued

SEQUENCE LISTING 1861 attcggaatc ttgcacgccc tcgctcaagc cttcgtcact ggtcccgcca ccaaacgttt
1921 cggcgagaag caggccatta tcgccggcat ggcggccgac gcgctgggct acgtcttgct
1981 ggcgttcgcg acgcgaggct ggatggcctt ccccattatg attcttctcg cttccggcgg
2041 catcgggatg cccgcgttgc aggccatgct gtccaggcag gtagatgacg accatcaggg
2101 acagcttcaa ggatcgctcg cggctcttac cagcctaact tcgatcactg gaccgctgat
2161 cgtcacggcg atttatgccg cctcggcgag cacatggaac gggttggcat ggattgtagg
2221 cgccgcccta taccttgtct gcctccccgc gttgcgtcgc ggtgcatgga gccgggccac
2281 ctcgacctga atggaagccg gcggcacctc gctaacggat tcaccactcc aagaattgga
2341 gccaatcaat tcttgcggag aactgtgaat gcgcaaacca acccttggca gaacatatcc
2401 atcgcgtccg ccatctccag cagccgcacg cggcgcatct cgggcagcgt tgggtcctgg
2461 ccacgggtgc gcatgatcgt gctcctgtcg ttgaggaccc ggctaggctg gcggggttgc
2521 cttactggtt agcagaatga atcaccgata cgcgagcgaa cgtgaagcga ctgctgctgc
2581 aaaacgtctg cgacctgagc aacaacatga atggtcttcg gtttccgtgt ttcgtaaagt
2641 ctggaaacgc ggaagtcagc gccctgcacc attatgttcc ggatctgcat cgcaggatgc
2701 tgctggctac cctgtggaac acctacatct gtattaacga agcgctggca ttgaccctga
2761 gtgatttttc tctggtcccg ccgcatccat accgccagtt gtttaccctc acaacgttcc
2821 agtaaccggg catgttcatc atcagtaacc cgtatcgtga gcatcctctc tcgtttcatc
2881 ggtatcatta cccccatgaa cagaaatccc ccttacacgg aggcatcagt gaccaaacag
2941 gaaaaaaccg cccttaacat ggcccgcttt atcagaagcc agacattaac gcttctggag
3001 aaactcaacg agctggacgc ggatgaacag gcagacatct gtgaatcgct tcacgaccac
3061 gctgatgagc tttaccgcag ctgcctcgcg cgtttcggtg atgacggtga aaacctctga
3121 cacatgcagc tcccggagac ggtcacagct tgtctgtaag cggatgccgg gagcagacaa
3181 gcccgtcagg gcgcgtcagc gggtgttggc gggtgtcggg gcgcagccat gacccagtca
3241 cgtagcgata gcggagtgta tactggctta actatgcggc atcagagcag attgtactga
3301 gagtgcacca tatatgcggt gtgaaatacc gcacagatgc gtaaggagaa aataccgcat
3361 caggcgctct tccgcttcct cgctcactga ctcgctgcgc tcggtcgttc ggctgcggcg
3421 agcggtatca gctcactcaa aggcggtaat acggttatcc acagaatcag gggataacgc
3481 aggaaagaac atgtgagcaa aaggccagca aaaggccagg aaccgtaaaa aggccgcgtt
3541 gctggcgttt ttccataggc tccgcccccc tgacgagcat cacaaaaatc gacgctcaag
3601 tcagaggtgg cgaaacccga caggactata aagataccag gcgtttcccc ctggaagctc
3661 cctcgtgcgc tctcctgttc cgaccctgcc gcttaccgga tacctgtccg cctttctccc
3721 ttcgggaagc gtggcgcttt ctcatagctc acgctgtagg tatctcagtt cggtgtaggt
3781 cgttcgctcc aagctgggct gtgtgcacga accccccgtt cagcccgacc gctgcgcctt
3841 atccggtaac tatcgtcttg agtccaaccc ggtaagacac gacttatcgc cactggcagc
3901 agccactggt aacaggatta gcagagcgag gtatgtaggc ggtgctacag agttcttgaa
3961 gtggtggcct aactacggct acactagaag gacagtattt ggtatctgcg ctctgctgaa
4021 gccagttacc ttcggaaaaa gagttggtag ctcttgatcc ggcaaacaaa ccaccgctgg
4081 tagcggtggt ttttttgttt gcaagcagca gattacgcgc agaaaaaaag gatctcaaga
4141 agatcctttg atcttttcta cggggtctga cgctcagtgg aacgaaaact cacgttaagg -continued

SEQUENCE LISTING 4201 gattttggtc atgagattat caaaaaggat cttcacctag atccttttaa attaaaaatg
4261 aagttttaaa tcaatctaaa gtatatatga gtaaacttgg tctgacagtt accaatgctt
4321 aatcagtgag gcacctatct cagcgatctg tctatttcgt tcatccatag ttgcctgact
4381 ccccgtcgtg tagataacta cgatacggga gggcttacca tctggcccca gtgctgcaat
4441 gataccgcga gacccacgct caccggctcc agatttatca gcaataaacc agccagccgg
4501 aagggccgag cgcagaagtg gtcctgcaac tttatccgcc tccatccagt ctattaattg
4561 ttgccgggaa gctagagtaa gtagttcgcc agttaatagt ttgcgcaacg ttgttgccat
4621 tgctgcaggc atcgtggtgt cacgctcgtc gtttggtatg gcttcattca gctccggttc
4681 ccaacgatca aggcgagtta catgatcccc catgttgtgc aaaaaagcgg ttagctcctt
4741 cggtcctccg atcgttgtca gaagtaagtt ggccgcagtg ttatcactca tggttatggc
4801 agcactgcat aattctctta ctgtcatgcc atccgtaaga tgcttttctg tgactggtga
4861 gtactcaacc aagtcattct gagaatagtg tatgcggcga ccgagttgct cttgcccggc
4921 gtcaacacgg gataataccg cgccacatag cagaacttta aaagtgctca tcattggaaa
4981 acgttcttcg gggcgaaaac tctcaaggat cttaccgctg ttgagatcca gttcgatgta
5041 acccactcgt gcacccaact gatcttcagc atcttttact ttcaccagcg tttctgggtg
5101 agcaaaaaca ggaaggcaaa atgccgcaaa aaagggaata agggcgacac ggaaatgttg
5161 aatactcata ctcttccttt ttcaatatta ttgaagcatt tatcagggtt attgtctcat
5221 gagcggatac atatttgaat gtatttagaa aaataaacaa ataggggttc cgcgcacatt
5281 tccccgaaaa gtgccacctg acgtctaaga aaccattatt atcatgacat taacctataa
5341 aaataggcgt atcacgaggc cctttcgtct tcaagaattc tcatgtttga cagcttatca
5401 tcgataagct ttaatgcggt agtttatcac agttaaattg ctaacgcagt caggcaccgt
5461 gtatgaaatc taacaatgcg ctcatcgtca tcctcggcac cgtcaccctg gatgctgtag
5521 gcataggctt ggttatgccg gtactgccgg gcctcttgcg ggatatccgg atatagttcc
5581 tcctttcagc aaaaaacccc tcaagacccg tttagaggcc ccaaggggtt atgctagtta
5641 ttgctcagcg gtggcagcag ccaactcagc ttcctttcgg gctttgttag cagccggatc
5701 ctcagcccct gttccccgct gctgccttgc ttccggtgga gcggtccggg tcgcaccggc
5761 cgccggtgat cgaccgggcg atctcgcccg cgcggaccgc caccatggac agcagggtgg
5821 aggcgatgcc gtgggtcgcc tcggtggcgc cctggacgta gatgccgcac cggaaatccc
5881 cggtggtgcc gagccggtag tcgcggccga tcagcaactc ccccgcctcg tcccggcgga
5941 gggcgccgga gacgccgccg agcagttcgg ccgggtcggt ggagtcgtac ccggtggcgt
6001 acacgaccag gtcggcgtcc aggtcggtgt gttcgcccgt gggcaggaac tccacgcgta
6061 cggcggcgga ttcctggcgc ggttcgacgg acaccaggcg ggaggcgttc atcacccgca
6121 gccgcggggc gccggacacc ttctgctcgt actggcggcg gtagaggccc tggaggacgt
6181 cctcgtcgac gacggcgtag ttggtgccgc cgtggtagcg catgatggcc tgcttgacct
6241 cgggcggggc gaagtagaag tcgtccacgg cggccgggtc gaagacgcgg ttggcgaacg
6301 ggctggagtc ggcgacgctg tagccgtagc gggcgaacac cgcgcacacc tcggcctgcg
6361 ggtagcggtc catgaggtgc gcggcgacct cggccgcgct ctggccggcg ccgaccacga
6421 cggcccggcg gggcgggcgt tcgtcgaacg cgggcagccg gtgcagcaac tgggagctgt -continued

SEQUENCE LISTING 6481 gccagacgcg ttcgccggtc tccgcgccct cgggcagccg ggggcgcagg ccggaggcga
6541 ggacgaggtt tctggtccgg gcgaccaccc ggtccccggc gagcacgtcg agcgcgacga
6601 cctcaccggc ttcggtcacc ggccgcacac cggtggcctc cacgccgtac tcgaccaggt
6661 ggttcagccg gtcggcggcc cactggaggt agtcgtggta ctcgatccgg gagggcagca
6721 gggtgtgctg gttgatgaag tcgaccagcc ggtccttctc ctggagatag gacaggaatc
6781 cgaaatcact ggtgggattg cgcatcgtgg cgatgtcctt gagaaaggac acctggagcg
6841 aggagccccc caggagcatc cccgatgcc agccgaattc cttctgcttc tccaggaaaa
6901 gggccttccc ggcggcttcg gattcatgga gcgccaccgc cagggcgaga ttcgcggcac
6961 cgaatccgat tccggtgacg tccagtactt ctgattccgg gctctgctgc gcagtggatg
7021 attgctctgc gagccgggtc a SEQ ID NO: 178 SfaB (PzbA) in vivo expression
1 gtaggagggc gtggatatgt cctgcgggta aactatagtc gttgagagga ggagtctgac
61 tcctgttgat agatccagta atgacctcag aactccatct ggatttgttc agaacgctcg
121 gttgccgccg ggcgtttttt attggtgaga ataggtcttg acggctggcg agaggtgcgg
181 ggaggatctg accgacgcgg tccacacgtg gcaccgcgat gctgttgtgg gcacaatcgt
241 gccggttggt aggatccggt taattaagca gtaccagatc tgactgagtg accaaaggag
301 gcggacatat gacccggctc gcagagcaat catccactgc gcagcagagc ccggaatcag
361 aagtactgga cgtcaccgga atcggattcg gtgccgcgaa tctcgccctg gcggtggcgc
421 tccatgaatc cgaagccgcc gggaaggccc ttttcctgga gaagcagaag gaattcggct
481 ggcatcgggg gatgctcctg gggggctcct cgctccaggt gtcctttctc aaggacatcg
541 ccacgatgcg caatcccacc agtgatttcg gattcctgtc ctatctccag gagaaggacc
601 ggctggtcga cttcatcaac cagcacaccc tgctgccctc ccggatcgag taccacgact
661 acctccagtg ggccgccgac cggctgaacc acctggtcga gtacggcgtg gaggccaccg
721 gtgtgcggcc ggtgaccgaa gccggtgagg tcgtcgcgct cgacgtgctc gccggggacc
781 gggtggtcgc ccggaccaga aacctcgtcc tcgcctccgg cctgcgcccc cggctgcccg
841 agggcgcgga gaccggcgaa cgcgtctggc acagctccca gttgctgcac cggctgcccg
901 cgttcgacga acgcccgccc cgccgggccg tcgtggtcgg cgccggccag agcgcggccg
961 aggtcgccgc gcacctcatg gaccgctacc cgcaggccga ggtgtgcgcg gtgttcgccc
1021 gctacggcta cagcgtcgcc gactccagcc cgttcgccaa ccgcgtcttc gacccggccg
1081 ccgtggacga cttctacttc gccccgcccg aggtcaagca ggccatcatg cgctaccacg
1141 gcggcaccaa ctacgccgtc gtcgacgagg acgtcctcca gggcctctac cgccgccagt
1201 acgagcagaa ggtgtccggc gccccgcggc tgcgggtgat gaacgcctcc cgcctggtgt
1261 ccgtcgaacc gcgccaggaa tccgccgccg tacgcgtgga gttcctgccc acgggcgaac
1321 acaccgacct ggacgccgac ctggtcgtgt acgccaccgg gtacgactcc accgacccgg
1381 ccgaactgct cggcggcgtc tccggcgccc tccgccggga cgaggcgggg gagttgctga
1441 tcggccgcga ctaccggctc ggcaccaccg gggatttccg gtgcggcatc tacgtccagg
1501 gcgccaccga ggcgacccac ggcatcgcct ccaccctgct gtccatggtg gcggtccgcg
1561 cgggcgagat cgcccggtcg atcaccggcg gccggtgcga cccggaccgc tccaccggaa
1621 gcaaggcagc agcggggaac aggggctgag gatccccggg taccttcgaa aaaaaaaggc -continued

| SEQUENCE LISTING | |
|---|---|
| 1681 | tccaaaagga gcctttaatt gttcctccag accttacttg accggcgctc actgcccgct |
| 1741 | ttccagtcgg gaaacctgtc gtgccagctg cattaatgaa tcggccaacg cgcgggggaga |
| 1801 | ggcggtttgc gtattgggcg ctcttccgct tcctcgctca ctgactcgct gcgctcggtc |
| 1861 | gttcggctgc ggcgagcggt atcagctcac tcaaaggcgg taatacggtt atccacagaa |
| 1921 | tcaggggata acgcaggaaa gaacatgtga gcaaaaggcc agcaaaaggc caggaaccgt |
| 1981 | aaaaaggccg cgttgctggc gtttttccat aggctccgcc cccctgacga gcatcacaaa |
| 2041 | aatcgacgct caagtcagag gtggcgaaac ccgacaggac tataaagata ccaggcgttt |
| 2101 | ccccctggaa gctccctcgt gcgctctcct gttccgaccc tgccgcttac cggatacctg |
| 2161 | tccgcctttc tcccttcggg aagcgtggcg ctttctcata gctcacgctg taggtatctc |
| 2221 | agttcggtgt aggtcgttcg ctccaagctg ggctgtgtgc acgaaccccc cgttcagccc |
| 2281 | gaccgctgcg ccttatccgg taactatcgt cttgagtcca acccggtaag acacgactta |
| 2341 | tcgccactgg cagcagccac tggtaacagg attagcagag cgaggtatgt aggcggtgct |
| 2401 | acagagttct tgaagtggtg gcctaactac ggctacacta gaagaacagt atttggtatc |
| 2461 | tgcgctctgc tgaagccagt taccttcgga aaaagagttg gtagctcttg atccggcaaa |
| 2521 | caaaccaccg ctggtagcgg tggttttttt gtttgcaagc agcagattac gcgcagaaaa |
| 2581 | aaaggatctc aagaagatcc tttgatcttt tctacggggt ctgacgctca gtggaacgaa |
| 2641 | aactcacgtt aagggatttt ggtcatgaga ttatcaaaaa ggatcttcac ctagatcctt |
| 2701 | ttggttcatg tgcagctcca ctgctttaga ctctacatct gtatgaagtc ttcagatcct |
| 2761 | ctacgccgga cgcatcgtgg ccggatctaa aaaaaagccc gctcattagg cgggctgaca |
| 2821 | gttaccaatg cttaatcagt gaggcaccta tctcagcgat ctgtctattt cgttcatcca |
| 2881 | tagttgcctg actccccgtc gtgtagataa ctacgatacg ggagggctta ccatctggcc |
| 2941 | ccagtgctgc aatgataccg cgagacccac gctcaccggc tccagattta tcagcaataa |
| 3001 | accagccagc cggaagggcc gagcgcagaa gtggtcctgc aactttatcc gcctccatcc |
| 3061 | agtctattaa ttgttgccgg gaagctagag taagtagttc gccagttaat agtttgcgca |
| 3121 | acgttgttgc cattgctaca ggcatcgtgg tgtcacgctc gtcgtttggt atggcttcat |
| 3181 | tcagctccgg ttcccaacga tcaaggcgag ttacatgatc ccccatgttg tgcaaaaaag |
| 3241 | cggttagctc cttcggtcct ccgatcgttg tcagaagtaa gttggccgca gtgttatcac |
| 3301 | tcatggttat ggcagcactg cataattctc ttactgtcat gccatccgta agatgctttt |
| 3361 | ctgtgactgg tgagtactca accaagtcat tctgagaata gtgtatgcgg cgaccgagtt |
| 3421 | gctcttgccc ggcgtcaata cgggataata ccgcgccaca tagcagaact ttaaaagtgc |
| 3481 | tcatcattgg aaaacgttct tcggggcgaa aactctcaag gatcttaccg ctgttgagat |
| 3541 | ccagttcgat gtaacccact cgtgcaccca actgatcttc agcatctttt actttcacca |
| 3601 | gcgtttctgg gtgagcaaaa acaggaaggc aaaatgccgc aaaaaaggga ataagggcga |
| 3661 | cacggaaatg ttgaatactc atactcttcc tttttcaata ttattgaagc atttatcagg |
| 3721 | gttattgtct catgagcgga tacatatttg aatgtattta gaaaaataaa caaatagggg |
| 3781 | ttccgcgcac atttccccga aaagtgccac ctggcgcgcc acaaaacagc agggaagcag |
| 3841 | cgcttttccg ctgcataacc ctgcttcggg gtcattatag cgattttttc ggtatatcca |
| 3901 | tcctttttcg cacgatatac aggattttgc caaagggttc gtgtagactt tccttggtgt |
| 3961 | atccaacggc gtcagccggg caggataggt gaagtaggcc cacccgcgag cgggtgttcc |

-continued

SEQUENCE LISTING 4021 ttcttcactg tcccttattc gcacctggcg gtgctcaacg ggaatcctgc tctgcgaggc 4081 tggccggcta ccgccggcgt aacagatgag ggcaagcgga tggctgatga aaccaagcca 4141 accaggaagg gcagcccacc tatcaaggtg tactgccttc cagacgaacg aagagcgatt 4201 gaggaaaagg cggcggcggc cggcatgagc ctgtcggcct acctgctggc cgtcggccag 4261 ggctacaaaa tcacgggcgt cgtggactat gagcacgtcg gcgcgcctct agtatgcagg 4321 agtggggagg cacgatggcc gctttggtcg acctcaacga gacgatgaag ccgtggaacg 4381 acaccacccc ggcggccctg ctggaccaca cccggcacta caccttcgac gtctgatcat 4441 cactgacgaa tcgaggtcga ggaaccgagc gtccgaggaa cagaggcgct tatcggttgg 4501 ccgcgagatt cctgtcgatc ctctcgtgca gcgcgattcc gagggaaacg gaaacgttga 4561 gagactcggt ctggctcatc atggggatgg aaaccgaggc ggaagacgcc tcctcgaaca 4621 ggtcggaagg cccacccttt tcgctgccga acagcaaggc cagccgatcc ggattgtccc 4681 cgagttcctt cacggaaatg tcgccatccg ccttgagcgt catcagctgc ataccgctgt 4741 cccgaatgaa ggcgatggcc tcctcgcgac cggagagaac gacgggaagg gagaagacgt 4801 aacctcggct ggccctttgg agacgccggt ccgcgatgct ggtgatgtca ctgtcgacca 4861 ggatgatccc cgacgctccg agcgcgagcg acgtgcgtac tatcgcgccg atgttcccga 4921 cgatcttcac cccgtcgaga acgacgacgt ccccacgccg gctcgcgata tcgccgaacc 4981 tggccgggcg agggacgcgg gcgatgccga atgtcttggc cttccgctcc cccttgaaca 5041 actggttgac gatcgaggag tcgatgaggc ggaccggtat gttctgccgc ccgcacagat 5101 ccagcaactc agatggaaaa ggactgctgt cgctgccgta gacctcgatg aactccaccc 5161 cggccgcgat gctgtgcatg aggggctcga cgtcctcgat caacgttgtc tttatgttgg 5221 atcgcgacgg cttggtgaca tcgatgatcc gctgcaccgc gggatcggac ggatttgcga 5281 tggtgtccaa ctcagtcatg gtcgtcctac cggctgctgt gttcagtgac gcgattcctg 5341 gggtgtgaca ccctacgcga cgatggcgga tggctgccct gaccggcaat caccaacgca 5401 aggggaagac tacgccttcc actagaccgg tcgacctgca ggcctgctgg cgccggacgg 5461 ggcttcagac gtttcgggtg ctgggttgtt gtctctggac agtgatccat gggaaactac 5521 tcagcaccac caatgttccc aaaagaaagc gcaggtcagc gcccatgagc caatatctag 5581 gcatgtcgcc cttcatcgct cccgaggtcc ctgagcacct tctcgacact gttcgcgtct 5641 tcctgtacgc gcgtcagtct aagggccggt ccgacggctc agacgtgtcg accgaagcac 5701 agctcgcggc cggtcgtgcg ttggtcgcgt ctcgcaacgc ccaggggggt gcgcgctggg 5761 tcgtggcagg tgagttcgtg gacgtcgggc gctccggctg ggacccgaac gtgacccgtg 5821 ccgacttcga gcgcatgatg ggcgaagtcc gcgccggcga aggtgacgtt gtcgttgtga 5881 atgagctttc ccggctcact cgcaagggcg cccatgacgc gctcgaaatc gacaacgaat 5941 tgaagaagca cggcgtgcgc ttcatgtcgg ttcttgagcc gttccttgac acgtctaccc 6001 ctatcggcgt cgccattttc gcgctgatcg ctgcccttgc gaaacaggac agtgacctga 6061 aggcggagcg cctgaagggt gcgaaagacg agattgccgc gctgggtggc gttcactcgt 6121 cttccgcccc gttcggaatg cgcgccgtgc gcaagaaggt cgataatctc gtgatctccg 6181 ttcttgagcc ggacgaagac aacccggatc acgtcgagct agttgagcgc atggcgaaaa 6241 tgtcgttcga gggcgtgtcc gacaacgcca ttgcaacgac cttcgagaag gaaaagatcc -continued

SEQUENCE LISTING

```
6301      cgtcgcccgg aatggctgag agacgcgcca cggaaaagcg tcttgcgtcc atcaaggcac
6361      gtcgcctgaa cggcgctgaa aagccgatca tgtggcgcgc tcaaacggtc cgatggattc
6421      tcaaccatcc cgcaatcggc ggtttcgcat tcgagcgtgt gaagcacggt aaggcgcaca
6481      tcaacgtcat acggcgcgac cccggcggca agccgctaac gccccacacg ggcattctca
6541      gcggctcgaa gtggcttgag cttcaagaga agcgttccgg gaagaatctc agcgaccgga
6601      agcctggggc cgaagtcgaa ccgacgcttc tgagcgggtg gcgtttcctg gggtgccgaa
6661      tctgcggcgg ctcaatgggt cagtcccagg gtggccgtaa gcgcaacggc gaccttgccg
6721      aaggcaatta catgtgcgcc aacccgaagg ggcacggcgg cttgtcggtc aagcgcagcg
6781      aactggacga gttcgttgct tcgagggtgt gggcacggct ccgcacagcc gacatggaag
6841      atgaacacga tcaggcatgg attgccgccg ctgcggagcg cttcgccctt cagcacgacc
6901      tagcgggggt ggccgatgag cggcgcgaac aacaggcgca cctagacaac gtgcggcgct
6961      ccatcaagga ccttcaggcg gaccgtaagg ccggtctgta cgtcgggcgt gaagagctgg
7021      aaacgtggcg ctcaacggtg ctgcaatacc ggtcctacga agcggagtgc acgacccgac
7081      tcgctgagct tgacgagaag atgaacggca gcacccgcgt tccgtctgag tggttcagcg
7141      gcgaagaccc gacggccgaa gggggcatct gggcaagctg ggacgtgtac gagcgtcggg
7201      agttcctgag cttcttcctt gactccgtca tggtcgaccg gggcgccac cctgagacga
7261      agaaatacat ccccctgaag gaccgtgtga cgctcaagtg ggcggagctg ctgaaggagg
7321      aagacgaagc gagcgaagcc actgagcggg agcttgcggc gctgtaggta caatcataat
7381      gaggctagac tacagacgcg aagaatctcg tgctttcagc ttcgat
```

SEQ ID NO: 179 SfaC (PzbB) expression

```
   1      tatgtacgaa cgtccgctgt accgggagga ttgcgacggc gtcgtcctgg cgtttctgcg
  61      acacaaccca ctggcaatgg tcgtcacctc gcacgacgac gtcccggtgg ccacccacgc
 121      gccggtgctg ttccggcacg gacccgacgg cgccgacgcc gaggccgtcg ccgcgggcac
 181      cgtcccgctc gccggctcca ccctgatcgg ccacatgaac gtcgagaacc cgcagtggcg
 241      ccggatgcgc tccggcgacc gggcgctcat cgtcttccag ggcccgcacg gctatgtctc
 301      gccgacggtc tacggggtca cgcccgcggc ccccacctgg gacttcatcg ccgtccacgt
 361      gaacggcaca gtggagccca ccgccgaccc cgccgccgtg ctggacatcg tctccgacac
 421      cgcccggcgg ctggagtccg gcttcgggcg cggctgggac caggagtcct ccctcgacta
 481      cttccgccag atcgcgcccg gcgtgggcgc cttcaccctg cgggtcgatt ccgtgcagac
 541      gatgttcaag ctcagccagg agaagcccgc cccgatgcgg cggcgcgtgg tcgagcagtt
 601      cgaagcaagc gagtccggca cccaccgcgc cctggccagc gtgatgcgcg accgcggact
 661      caccgaagcc gacgaggagc gggagacagc cggatgagga tccggctgct aacaaagccc
 721      gaaaggaagc tgagttggct gctgccaccg ctgagcaata actagcataa ccccttgggg
 781      cctctaaacg ggtcttgagg ggttttttgc tgaaaggagg aactatatcc ggatatcccg
 841      caagaggccc ggcagtaccg gcataaccaa gcctatgcct acagcatcca gggtgacggt
 901      gccgaggatg acgatgagcg cattgttaga tttcatacac ggtgcctgac tgcgttagca
 961      atttaactgt gataaactac cgcattaaag cttatcgatg ataagctgtc aaacatgaga
1021      attcttgaag acgaaagggc ctcgtgatac gcctattttt ataggttaat gtcatgataa
1081      taatggtttc ttagacgtca ggtggcactt ttcggggaaa tgtgcgcgga acccctattt
```

-continued

SEQUENCE LISTING 1141 gtttattttt ctaaatacat tcaaatatgt atccgctcat gagacaataa ccctgataaa
1201 tgcttcaata atattgaaaa aggaagagta tgagtattca acatttccgt gtcgccctta
1261 ttcccttttt tgcggcattt tgccttcctg tttttgctca cccagaaacg ctggtgaaag
1321 taaaagatgc tgaagatcag ttgggtgcac gagtgggtta catcgaactg gatctcaaca
1381 gcggtaagat ccttgagagt tttcgccccg aagaacgttt tccaatgatg agcactttta
1441 aagttctgct atgtggcgcg gtattatccc gtgttgacgc cgggcaagag caactcggtc
1501 gccgcataca ctattctcag aatgacttgg ttgagtactc accagtcaca gaaaagcatc
1561 ttacggatgg catgacagta agagaattat gcagtgctgc cataaccatg agtgataaca
1621 ctgcggccaa cttacttctg acaacgatcg gaggaccgaa ggagctaacc gcttttttgc
1681 acaacatggg ggatcatgta actcgccttg atcgttggga accggagctg aatgaagcca
1741 taccaaacga cgagcgtgac accacgatgc ctgcagcaat ggcaacaacg ttgcgcaaac
1801 tattaactgg cgaactactt actctagctt cccggcaaca attaatagac tggatggagg
1861 cggataaagt tgcaggacca cttctgcgct cggcccttcc ggctggctgg tttattgctg
1921 ataaatctgg agccggtgag cgtgggtctc gcggtatcat tgcagcactg gggccagatg
1981 gtaagccctc ccgtatcgta gttatctaca cgacggggag tcaggcaact atggatgaac
2041 gaaatagaca gatcgctgag ataggtgcct cactgattaa gcattggtaa ctgtcagacc
2101 aagtttactc atatatactt tagattgatt taaaacttca tttttaattt aaaaggatct
2161 aggtgaagat cctttttgat aatctcatga ccaaaatccc ttaacgtgag ttttcgttcc
2221 actgagcgtc agaccccgta gaaaagatca aaggatcttc ttgagatcct ttttttctgc
2281 gcgtaatctg ctgcttgcaa acaaaaaaac caccgctacc agcggtggtt tgtttgccgg
2341 atcaagagct accaactctt tttccgaagg taactggctt cagcagagcg cagataccaa
2401 atactgtcct tctagtgtag ccgtagttag gccaccactt caagaactct gtagcaccgc
2461 ctacatacct cgctctgcta atcctgttac cagtggctgc tgccagtggc gataagtcgt
2521 gtcttaccgg gttggactca agacgatagt taccggataa ggcgcagcgg tcgggctgaa
2581 cggggggttc gtgcacacag cccagcttgg agcgaacgac ctacaccgaa ctgagatacc
2641 tacagcgtga gctatgagaa agcgccacgc ttcccgaagg gagaaaggcg gacaggtatc
2701 cggtaagcgg cagggtcgga acaggagagc gcacgaggga gcttccaggg ggaaacgcct
2761 ggtatcttta tagtcctgtc gggtttcgcc acctctgact tgagcgtcga tttttgtgat
2821 gctcgtcagg ggggcggagc ctatggaaaa acgccagcaa cgcggccttt ttacggttcc
2881 tggccttttg ctggcctttt gctcacatgt tctttcctgc gttatcccct gattctgtgg
2941 ataaccgtat taccgccttt gagtgagctg ataccgctcg ccgcagccga acgaccgagc
3001 gcagcgagtc agtgagcgag gaagcggaag agcgcctgat gcggtatttt ctccttacgc
3061 atctgtgcgg tatttcacac cgcatatatg gtgcactctc agtacaatct gctctgatgc
3121 cgcatagtta agccagtata cactccgcta tcgctacgtg actgggtcat ggctgcgccc
3181 cgacacccgc caacacccgc tgacgcgccc tgacgggctt gtctgctccc ggcatccgct
3241 tacagacaag ctgtgaccgt ctccgggagc tgcatgtgtc agaggttttc accgtcatca
3301 ccgaaacgcg cgaggcagct gcggtaaagc tcatcagcgt ggtcgtgaag cgattcacag
3361 atgtctgcct gttcatccgc gtccagctcg ttgagtttct ccagaagcgt taatgtctgg
3421 cttctgataa agcgggccat gttaagggcg gtttttttcct gtttggtcac tgatgcctcc -continued

SEQUENCE LISTING 3481 gtgtaagggg gatttctgtt catgggggta atgataccga tgaaacgaga gaggatgctc 3541 acgatacggg ttactgatga tgaacatgcc cggttactgg aacgttgtga gggtaaacaa 3601 ctggcggtat ggatgcggcg ggaccagaga aaaatcactc agggtcaatg ccagcgcttc 3661 gttaatacag atgtaggtgt tccacagggt agccagcagc atcctgcgat gcagatccgg 3721 aacataatgg tgcagggcgc tgacttccgc gtttccagac tttacgaaac acggaaaccg 3781 aagaccattc atgttgttgc tcaggtcgca gacgttttgc agcagcagtc gcttcacgtt 3841 cgctcgcgta tcggtgattc attctgctaa ccagtaaggc aaccccgcca gcctagccgg 3901 gtcctcaacg acaggagcac gatcatgcgc acccgtggcc aggacccaac gctgcccgag 3961 atgcgccgcg tgcggctgct ggagatggcg gacgcgatgg atatgttctg ccaagggttg 4021 gtttgcgcat tcacagttct ccgcaagaat tgattggctc caattcttgg agtggtgaat 4081 ccgttagcga ggtgccgccg gcttccattc aggtcgaggt ggcccggctc catgcaccgc 4141 gacgcaacgc ggggaggcag acaaggtata gggcggcgcc tacaatccat gccaacccgt 4201 tccatgtgct cgccgaggcg gcataaatcg ccgtgacgat cagcggtcca gtgatcgaag 4261 ttaggctggt aagagccgcg agcgatcctt gaagctgtcc ctgatggtcg tcatctacct 4321 gcctggacag catggcctgc aacgcgggca tcccgatgcc gccggaagcg agaagaatca 4381 taatggggaa ggccatccag cctcgcgtcg cgaacgccag caagacgtag cccagcgcgt 4441 cggccgccat gccggcgata atggcctgct tctcgccgaa acgtttggtg gcgggaccag 4501 tgacgaaggc ttgagcgagg gcgtgcaaga ttccgaatac cgcaagcgac aggccgatca 4561 tcgtcgcgct ccagcgaaag cggtcctcgc cgaaaatgac ccagagcgct gccggcacct 4621 gtcctacgag ttgcatgata aagaagacag tcataagtgc ggcgacgata gtcatgcccc 4681 gcgcccaccg gaaggagctg actgggttga aggctctcaa gggcatcggt cgagatcccg 4741 gtgcctaatg agtgagctaa cttacattaa ttgcgttgcg ctcactgccc gctttccagt 4801 cgggaaacct gtcgtgccag ctgcattaat gaatcggcca acgcgcgggg agaggcggtt 4861 tgcgtattgg gcgccagggt ggtttttctt ttcaccagtg agacgggcaa cagctgattg 4921 cccttcaccg cctggccctg agagagttgc agcaagcggt ccacgctggt ttgccccagc 4981 aggcgaaaat cctgtttgat ggtggttaac ggcgggatat aacatgagct gtcttcggta 5041 tcgtcgtatc ccactaccga gatatccgca ccaacgcgca gcccggactc ggtaatggcg 5101 cgcattgcgc ccagcgccat ctgatcgttg gcaaccagca tcgcagtggg aacgatgccc 5161 tcattcagca tttgcatggt ttgttgaaaa ccggacatgg cactccagtc gccttcccgt 5221 tccgctatcg gctgaatttg attgcgagtg agatatttat gccagccagc cagacgcaga 5281 cgcgccgaga cagaacttaa tgggcccgct aacagcgcga tttgctggtg acccaatgcg 5341 accagatgct ccacgcccag tcgcgtaccg tcttcatggg agaaaataat actgttgatg 5401 ggtgtctggt cagagacatc aagaaataac gccggaacat tagtgcaggc agcttccaca 5461 gcaatggcat cctggtcatc cagcggatag ttaatgatca gcccactgac gcgttgcgcg 5521 agaagattgt gcaccgccgc tttacaggct tcgacgccgc ttcgttctac catcgacacc 5581 accacgctgg cacccagttg atcggcgcga gatttaatcg ccgcgacaat ttgcgacggc 5641 gcgtgcaggg ccagactgga ggtggcaacg ccaatcagca acgactgttt gcccgccagt 5701 tgttgtgcca cgcggttggg aatgtaattc agctccgcca tcgccgcttc cactttttcc -continued

SEQUENCE LISTING

```
5761   cgcgttttcg cagaaacgtg gctggcctgg ttcaccacgc gggaaacggt ctgataagag
5821   acaccggcat actctgcgac atcgtataac gttactggtt tcacattcac caccctgaat
5881   tgactctctt ccgggcgcta tcatgccata ccgcgaaagg ttttgcgcca ttcgatggtg
5941   tccgggatct cgacgctctc ccttatgcga ctcctgcatt aggaagcagc ccagtagtag
6001   gttgaggccg ttgagcaccg ccgccgcaag gaatggtgca tgcaaggaga tggcgcccaa
6061   cagtcccccg gccacggggc ctgccaccat acccacgccg aaacaagcgc tcatgagccc
6121   gaagtggcga gcccgatctt ccccatcggt gatgtcggcg atataggcgc cagcaaccgc
6181   acctgtggcg ccggtgatgc cggccacgat gcgtccggcg tagaggatcg agatctcgat
6241   cccgcgaaat taatacgact cactataggg gaattgtgag cggataacaa ttcccctcta
6301   gaaataattt tgtttaactt taagaaggag atataccatg ggcagcagcc atcatcatca
6361   tcatcacagc agcggcctgg tgccgcgcgg cagcca
```

SEQ ID NO: 180 SfaC (PzbB) complementation of flaveolus

```
   1   gtaggagggc gtggatatgt cctgcgggta aactatagtc gttgagagga ggagtctgac
  61   tcctgttgat agatccagta atgacctcag aactccatct ggatttgttc agaacgctcg
 121   gttgccgccg ggcgtttttt attggtgaga ataggtcttg acggctggcg agaggtgcgg
 181   ggaggatctg accgacgcgg tccacacgtg gcaccgcgat gctgttgtgg gcacaatcgt
 241   gccggttggt aggatccggt taattaagca gtaccagatc tgactgagtg accaaaggag
 301   gcggacatat gtacgaacgt ccgctgtacc gggaggattg cgacggcgtc gtcctggcgt
 361   ttctgcgaca caacccactg gcaatggtcg tcacctcgca cgacgacgtc ccggtggcca
 421   cccacgcgcc ggtgctgttc cggcacggac ccgacggcgc cgacgccgag gccgtcgccg
 481   cgggcaccgt cccgctcgcc ggctccaccc tgatcggcca catgaacgtc gagaacccgc
 541   agtggcgccg gatgcgctcc ggcgaccggg cgctcatcgt cttccagggc ccgcacggct
 601   atgtctcgcc gacggtctac ggggtcacgc ccgcggcccc cacctgggac ttcatcgccg
 661   tccacgtgaa cggcacagtg gagcccaccg ccgacccccgc cgccgtgctg gacatcgtct
 721   ccgacaccgc ccggcggctg gagtccggct tcgggcgcgg ctgggaccag gagtcctccc
 781   tcgactactt ccgccagatc gcgcccggcg tgggcgcctt caccctgcgg gtcgattccg
 841   tgcagacgat gttcaagctc agccaggaga agcccgcccc gatgcggcgg cgcgtggtcg
 901   agcagttcga agcaagcgag tccggcaccc accgcgccct ggccagcgtg atgcgcgacc
 961   gcggactcac cgaagccgac gaggagcggg agacagccgg atgaggatcc ccgggtacct
1021   tcgaaaaaaa aaggctccaa aaggagcctt taattgttcc tccagacctt acttgaccgg
1081   cgctcactgc ccgctttcca gtcgggaaac ctgtcgtgcc agctgcatta atgaatcggc
1141   caacgcgcgg ggagaggcgg tttgcgtatt gggcgctctt ccgcttcctc gctcactgac
1201   tcgctgcgct cggtcgttcg gctgcggcga gcggtatcag ctcactcaaa ggcggtaata
1261   cggttatcca cagaatcagg ggataacgca ggaaagaaca tgtgagcaaa aggccagcaa
1321   aaggccagga accgtaaaaa ggccgcgttg ctggcgtttt tccataggct ccgccccccct
1381   gacgagcatc acaaaaatcg acgctcaagt cagaggtggc gaaacccgac aggactataa
1441   agataccagg cgtttccccc tggaagctcc ctcgtgcgct ctcctgttcc gaccctgccg
1501   cttaccggat acctgtccgc ctttctccct tcgggaagcg tggcgctttc tcatagctca
1561   cgctgtaggt atctcagttc ggtgtaggtc gttcgctcca agctgggctg tgtgcacgaa
```

-continued

| SEQUENCE LISTING | |
|---|---|
| 1621 | cccccgttc agcccgaccg ctgcgcctta tccggtaact atcgtcttga gtccaacccg |
| 1681 | gtaagacacg acttatcgcc actggcagca gccactggta acaggattag cagagcgagg |
| 1741 | tatgtaggcg gtgctacaga gttcttgaag tggtggccta actacggcta cactagaaga |
| 1801 | acagtatttg gtatctgcgc tctgctgaag ccagttacct tcggaaaaag agttggtagc |
| 1861 | tcttgatccg gcaaacaaac caccgctggt agcggtggtt tttttgtttg caagcagcag |
| 1921 | attacgcgca gaaaaaaagg atctcaagaa gatcctttga tcttttctac ggggtctgac |
| 1981 | gctcagtgga acgaaaactc acgttaaggg attttggtca tgagattatc aaaaaggatc |
| 2041 | ttcacctaga tccttttggt tcatgtgcag ctccactgct ttagactcta catctgtatg |
| 2101 | aagtcttcag atcctctacg ccggacgcat cgtggccgga tctaaaaaaa agcccgctca |
| 2161 | ttaggcgggc tgacagttac caatgcttaa tcagtgaggc acctatctca gcgatctgtc |
| 2221 | tatttcgttc atccatagtt gcctgactcc ccgtcgtgta gataactacg atacgggagg |
| 2281 | gcttaccatc tggccccagt gctgcaatga taccgcgaga cccacgctca ccggctccag |
| 2341 | atttatcagc aataaaccag ccagccggaa gggccgagcg cagaagtggt cctgcaactt |
| 2401 | tatccgcctc catccagtct attaattgtt gccgggaagc tagagtaagt agttcgccag |
| 2461 | ttaatagttt gcgcaacgtt gttgccattg ctacaggcat cgtggtgtca cgctcgtcgt |
| 2521 | ttggtatggc ttcattcagc tccggttccc aacgatcaag gcgagttaca tgatccccca |
| 2581 | tgttgtgcaa aaaagcggtt agctccttcg gtcctccgat cgttgtcaga agtaagttgg |
| 2641 | ccgcagtgtt atcactcatg gttatggcag cactgcataa ttctcttact gtcatgccat |
| 2701 | ccgtaagatg cttttctgtg actggtgagt actcaaccaa gtcattctga gaatagtgta |
| 2761 | tgcggcgacc gagttgctct tgcccggcgt caatacggga taataccgcg ccacatagca |
| 2821 | gaactttaaa agtgctcatc attggaaaac gttcttcggg gcgaaaactc tcaaggatct |
| 2881 | taccgctgtt gagatccagt tcgatgtaac ccactcgtgc acccaactga tcttcagcat |
| 2941 | cttttacttt caccagcgtt tctgggtgag caaaaacagg aaggcaaagt gccgcaaaaa |
| 3001 | agggaataag ggcgacacgg aaatgttgaa tactcatact cttccttttt caatattatt |
| 3061 | gaagcattta tcagggttat tgtctcatga gcggatacat atttgaatgt atttagaaaa |
| 3121 | ataaacaaat aggggttccg cgcacatttc cccgaaaagt gccacctggc gcgccacaaa |
| 3181 | acagcaggga agcagcgctt ttccgctgca taaccctgct tcggggtcat tatagcgatt |
| 3241 | ttttcggtat atccatcctt tttcgcacga tatacaggat tttgccaaag ggttcgtgta |
| 3301 | gactttcctt ggtgtatcca acggcgtcag ccgggcagga taggtgaagt aggcccaccc |
| 3361 | gcgagcgggt gttccttctt cactgtccct tattcgcacc tggcggtgct caacgggaat |
| 3421 | cctgctctgc gaggctggcc ggctaccgcc ggcgtaacag atgagggcaa gcggatggct |
| 3481 | gatgaaacca agccaaccag gaagggcagc ccacctatca aggtgtactg ccttccagac |
| 3541 | gaacgaagag cgattgagga aaaggcggcg gcggccggca tgagcctgtc ggcctacctg |
| 3601 | ctggccgtcg gccagggcta caaaatcacg ggcgtcgtgg actatgagca cgtcggcgcg |
| 3661 | cctctagtat gcaggagtgg ggaggcacga tggccgcttt ggtcgacctc aacgagacga |
| 3721 | tgaagccgtg gaacgacacc accccggcgg ccctgctgga ccacacccgg cactacacct |
| 3781 | tcgacgtctg atcatcactg acgaatcgag gtcgaggaac cgagcgtccg aggaacagag |
| 3841 | gcgcttatcg gttggccgcg agattcctgt cgatcctctc gtgcagcgcg attccgaggg |
| 3901 | aaacggaaac gttgagagac tcggtctggc tcatcatggg gatggaaacc gaggcggaag |

-continued

SEQUENCE LISTING

```
3961      acgcctcctc gaacaggtcg gaaggcccac ccttttcgct gccgaacagc aaggccagcc
4021      gatccggatt gtccccgagt tccttcacgg aaatgtcgcc atccgccttg agcgtcatca
4081      gctgcatacc gctgtcccga atgaaggcga tggcctcctc gcgaccggag agaacgacgg
4141      gaagggagaa gacgtaacct cggctggccc tttggagacg ccggtccgcg atgctggtga
4201      tgtcactgtc gaccaggatg atccccgacg ctccgagcgc gagcgacgtg cgtactatcg
4261      cgccgatgtt cccgacgatc ttcaccccgt cgagaacgac gacgtcccca cgccggctcg
4321      cgatatcgcc gaacctggcc gggcgaggga cgcgggcgat gccgaatgtc ttggccttcc
4381      gctccccctt gaacaactgg ttgacgatcg aggagtcgat gaggcggacc ggtatgttct
4441      gccgcccgca cagatccagc aactcagatg gaaaaggact gctgtcgctg ccgtagacct
4501      cgatgaactc caccccggcc gcgatgctgt gcatgagggg ctcgacgtcc tcgatcaacg
4561      ttgtctttat gttggatcgc gacggcttgg tgacatcgat gatccgctgc accgcgggat
4621      cggacggatt tgcgatggtg tccaactcag tcatggtcgt cctaccggct gctgtgttca
4681      gtgacgcgat tcctggggtg tgacacccta cgcgacgatg gcggatggct gccctgaccg
4741      gcaatcacca acgcaagggg aagactacgc cttccactag accggtcgac ctgcaggcct
4801      gctggcgccg gacggggctt cagacgtttc gggtgctggg ttgttgtctc tggacagtga
4861      tccatgggaa actactcagc accaccaatg ttcccaaaag aaagcgcagg tcagcgccca
4921      tgagccaata tctaggcatg tcgcccttca tcgctcccga ggtccctgag caccttctcg
4981      acactgttcg cgtcttcctg tacgcgcgtc agtctaaggg ccggtccgac ggctcagacg
5041      tgtcgaccga agcacagctc gcggccggtc gtgcgttggt cgcgtctcgc aacgcccagg
5101      ggggtgcgcg ctgggtcgtg gcaggtgagt tcgtggacgt cgggcgctcc ggctgggacc
5161      cgaacgtgac ccgtgccgac ttcgagcgca tgatgggcga agtccgcgcc ggcgaaggtg
5221      acgttgtcgt tgtgaatgag ctttcccggc tcactcgcaa gggcgcccat gacgcgctcg
5281      aaatcgacaa cgaattgaag aagcacggcg tgcgcttcat gtcggttctt gagccgttcc
5341      ttgacacgtc taccccctatc ggcgtcgcca ttttcgcgct gatcgctgcc cttgcgaaac
5401      aggacagtga cctgaaggcg gagcgcctga agggtgcgaa agacgagatt gccgcgctgg
5461      gtggcgttca ctcgtcttcc gccccgttcg gaatgcgcgc cgtgcgcaag aaggtcgata
5521      atctcgtgat ctccgttctt gagccggacg aagacaaccc ggatcacgtc gagctagttg
5581      agcgcatggc gaaaatgtcg ttcgagggcg tgtccgacaa cgccattgca acgaccttcg
5641      agaaggaaaa gatcccgtcg cccggaatgg ctgagagacg cgccacggaa aagcgtcttg
5701      cgtccatcaa ggcacgtcgc ctgaacggcg ctgaaaagcc gatcatgtgg cgcgctcaaa
5761      cggtccgatg gattctcaac catcccgcaa tcggcggttt cgcattcgag cgtgtgaagc
5821      acggtaaggc gcacatcaac gtcatacggc gcgaccccgg cggcaagccg ctaacgcccc
5881      acacgggcat tctcagcggc tcgaagtggc ttgagcttca agagaagcgt tccgggaaga
5941      atctcagcga ccggaagcct ggggccgaag tcgaaccgac gcttctgagc gggtggcgtt
6001      tcctggggtg ccgaatctgc ggcggctcaa tgggtcagtc ccagggtggc cgtaagcgca
6061      acggcgacct tgccgaaggc aattacatgt gcgccaaccc gaaggggcac ggcggcttgt
6121      cggtcaagcg cagcgaactg gacgagttcg ttgcttcgag ggtgtgggca cggctccgca
6181      cagccgacat ggaagatgaa cacgatcagg catggattgc cgccgctgcg gagcgcttcg
```

-continued

SEQUENCE LISTING

```
6241      cccttcagca cgacctagcg ggggtggccg atgagcggcg cgaacaacag gcgcacctag
6301      acaacgtgcg gcgctccatc aaggaccttc aggcggaccg taaggccggt ctgtacgtcg
6361      ggcgtgaaga gctggaaacg tggcgctcaa cggtgctgca ataccggtcc tacgaagcgg
6421      agtgcacgac ccgactcgct gagcttgacg agaagatgaa cggcagcacc cgcgttccgt
6481      ctgagtggtt cagcggcgaa gacccgacgg ccgaaggggg catctgggca agctgggacg
6541      tgtacgagcg tcgggagttc ctgagcttct tccttgactc cgtcatggtc gaccgggggc
6601      gccaccctga gacgaagaaa tacatccccc tgaaggaccg tgtgacgctc aagtgggcgg
6661      agctgctgaa ggaggaagac gaagcgagcg aagccactga gcgggagctt gcggcgctgt
6721      aggtacaatc ataatgaggc tagactacag acgcgaagaa tctcgtgctt tcagcttcga
6781      t
```

SEQ ID NO: 181 SfaC (PzbB) in vivo expression

```
   1      atctacgtct gtcgagaagt ttctgatcga aaagttcgac agcgtctccg acctgatgca
  61      gctctcgcag ggcgaagaat ctcgtgcttt cagcttcgat gtaggagggc gtggatatgt
 121      cctgcgggta aactatagtc gttgagagga ggagtctgac tcctgttgat agatccagta
 181      atgacctcag aactccatct ggatttgttc agaacgctcg gttgccgccg ggcgtttttt
 241      attggtgaga ataggtcttg acggctggcg agaggtgcgg ggaggatctg accgacgcgg
 301      tccacacgtg gcaccgcgat gctgttgtgg gcacaatcgt gccggttggt aggatccggt
 361      taattaagca gtaccagatc tgactgagtg accaaaggag gcggacatat gtacgaacgt
 421      ccgctgtacc gggaggattg cgacggcgtc gtcctggcgt ttctgcgaca caacccactg
 481      gcaatggtcg tcacctcgca cgacgacgtc ccggtggcca cccacgcgcc ggtgctgttc
 541      cggcacggac ccgacggcgc cgacgccgag gccgtcgccg cgggcaccgt cccgctcgcc
 601      ggctccaccc tgatcggcca catgaacgtc gagaacccgc agtggcgccg gatgcgctcc
 661      ggcgaccggg cgctcatcgt cttccagggc ccgcacggct atgtctcgcc gacggtctac
 721      ggggtcacgc ccgcggcccc cacctgggac ttcatcgccg tccacgtgaa cggcacagtg
 781      gagcccaccg ccgaccccgc cgccgtgctg gacatcgtct ccgacaccgc ccggcggctg
 841      gagtccggct tcgggcgcgg ctgggaccag gagtcctccc tcgactactt ccgccagatc
 901      gcgcccggcg tgggcgcctt caccctgcgg gtcgattccg tgcagacgat gttcaagctc
 961      agccaggaga agcccgcccc gatgcggcgg cgcgtggtcg agcagttcga agcaagcgag
1021      tccggcaccc accgcgccct ggccagcgtg atgcgcgacc gcggactcac cgaagccgac
1081      gaggagcggg agacagccgg atgaggatcc ccgggtacct tcgaaaaaaa aaggctccaa
1141      aaggagcctt taattgttcc tccagacctt acttgaccgg cgctcactgc ccgctttcca
1201      gtcgggaaac ctgtcgtgcc agctgcatta atgaatcggc caacgcgcgg ggagaggcgg
1261      tttgcgtatt gggcgctctt ccgcttcctc gctcactgac tcgctgcgct cggtcgttcg
1321      gctgcggcga gcggtatcag ctcactcaaa ggcggtaata cggttatcca cagaatcagg
1381      ggataacgca ggaaagaaca tgtgagcaaa aggccagcaa aaggccagga accgtaaaaa
1441      ggccgcgttg ctggcgtttt tccataggct ccgcccccct gacgagcatc acaaaaatcg
1501      acgctcaagt cagaggtggc gaaacccgac aggactataa agataccagg cgtttccccc
1561      tggaagctcc ctcgtgcgct ctcctgttcc gaccctgccg cttaccggat acctgtccgc
1621      ctttctccct tcgggaagcg tggcgctttc tcatagctca cgctgtaggt atctcagttc
```

-continued

| SEQUENCE LISTING | |
|---|---|
| 1681 | ggtgtaggtc gttcgctcca agctgggctg tgtgcacgaa ccccccgttc agcccgaccg |
| 1741 | ctgcgcctta tccggtaact atcgtcttga gtccaacccg gtaagacacg acttatcgcc |
| 1801 | actggcagca gccactggta acaggattag cagagcgagg tatgtaggcg gtgctacaga |
| 1861 | gttcttgaag tggtggccta actacggcta cactagaaga acagtatttg gtatctgcgc |
| 1921 | tctgctgaag ccagttacct tcggaaaaag agttggtagc tcttgatccg gcaaacaaac |
| 1981 | caccgctggt agcggtggtt tttttgtttg caagcagcag attacgcgca gaaaaaaagg |
| 2041 | atctcaagaa gatcctttga tcttttctac ggggtctgac gctcagtgga acgaaaactc |
| 2101 | acgttaaggg attttggtca tgagattatc aaaaaggatc ttcacctaga tccttttggt |
| 2161 | tcatgtgcag ctccatcagc aaaaggggat gataagttta tcaccaccga ctatttgcaa |
| 2221 | cagtgccgtt gatcgtgcta tgatcgactg atgtcatcag cggtggagtg caatgtcgtg |
| 2281 | caatacgaat ggcgaaaagc cgagctcatc ggtcagcttc tcaaccttgg ggttaccccc |
| 2341 | ggcggtgtgc tgctggtcca cagctccttc cgtagcgtcc ggcccctcga agatgggcca |
| 2401 | cttggactga tcgaggccct gcgtgctgcg ctgggtccgg gagggacgct cgtcatgccc |
| 2461 | tcgtggtcag gtctggacga cgagccgttc gatcctgcca cgtcgcccgt tacaccggac |
| 2521 | cttggagttg tctctgacac attctggcgc ctgccaaatg taaagcgcag cgcccatcca |
| 2581 | tttgcctttg cggcagcggg gccacaggca gagcagatca tctctgatcc attgcccctg |
| 2641 | ccacctcact cgcctgcaag cccggtcgcc cgtgtccatg aactcgatgg gcaggtactt |
| 2701 | ctcctcggcg tgggacacga tgccaacacg acgctgcatc ttgccgagtt gatggcaaag |
| 2761 | gttccctatg ggtgccgag acactgcacc attcttcagg atggcaagtt ggtacgcgtc |
| 2821 | gattatctcg agaatgacca ctgctgtgag cgctttgcct tggcggacag gtggctcaag |
| 2881 | gagaagagcc ttcagaagga aggtccagtc ggtcatgcct ttgctcggtt gatccgctcc |
| 2941 | cgcgacattg tggcgacagc cctgggtcaa ctgggccgag atccgttgat cttcctgcat |
| 3001 | ccgccagagg cgggatgcga agaatgcgat gccgctcgcc agtcgattgg ctgagctcat |
| 3061 | gagcggagaa cgagatgacg ttggaggggc aaggtcgcgc tgattgctgg ggcaacacgt |
| 3121 | ggagcggatc ggggattgtc tttcttcagc tcgctgatga tatgctgacg ctcaatgccg |
| 3181 | tttggcctcc gactaacgaa aatcccgcat ttggacggct gatccgattg gcacggcgga |
| 3241 | cggcgaatgg cggagcagac gctcgtccgg gggcaatgag atatgaaaaa gcctgaactc |
| 3301 | accgcgacgt atcgggccct ggccagctag ctagagtcga cctgcaggtc cccggggatc |
| 3361 | ggtcttgcct tgctcgtcgg tgatgtactt caccagctcc gcgaagtcgc tcttcttgat |
| 3421 | ggagcgcatg gggacgtgct tggcaatcac gcgcaccccc cggccgtttt agcggctaaa |
| 3481 | aaagtcatgg ctctgccctc gggcggacca cgcccatcat gaccttgcca agctcgtcct |
| 3541 | gcttctcttc gatcttcgcc agcagggcga ggatcgtggc atcaccgaac cgcgccgtgc |
| 3601 | gcgggtcgtc ggtgagccag agtttcagca ggccgcccag gcggcccagg tcgccattga |
| 3661 | tgcgggccag ctcgcggacg tgctcatagt ccacgacgcc cgtgattttg tagccctggc |
| 3721 | cgacggccag caggtaggcc gacaggctca tgccggccgc cgccgccttt tcctcaatcg |
| 3781 | ctcttcgttc gtctggaagg cagtacacct tgataggtgg gctgcccttc ctggttggct |
| 3841 | tggtttcatc agccatccgc ttgccctcat ctgttacgcc ggcggtagcc ggccagcctc |
| 3901 | gcagagcagg attcccgttg agcaccgcca ggtgcgaata agggacagtg aagaaggaac |
| 3961 | acccgctcgc gggtgggcct acttcaccta tcctgcccgg ctgacgccgt tggatacacc |

-continued

SEQUENCE LISTING 4021 aaggaaagtc tacacgaacc ctttggcaaa atcctgtata tcgtgcgaaa aaggatggat
4081 ataccgaaaa aatcgctata atgaccccga agcagggtta tgcagcggaa aagatccgtc
4141 gacctgcagg catgcaagct ctagcgattc cagacgtccc gaaggcgtgg cgcggcttcc
4201 ccgtgccgga gcaatcgccc tgggtgggtt acacgacgcc cctctatggc ccgtactgac
4261 ggacacaccg aagccccggc ggcaaccctc agcggatgcc ccggggcttc acgttttccc
4321 aggtcagaag cggttttcgg gagtagtgcc ccaactgggg taacctttga gttctctcag
4381 ttgggggcgt agggtcgccg acatgacaca aggggttgtg accggggtgg acacgtacgc
4441 gggtgcttac gaccgtcagt cgcgcgagcg cgaaaattcg agcgcagcaa gcccagcgac
4501 acagcgtagc gccaacgaag acaaggcggc cgaccttcag cgcgaagtcg agcgcgacgg
4561 gggccggttc aggttcgtcg ggcatttcag cgaagcgccg ggcacgtcgg cgttcgggac
4621 ggcggagcgc ccggagttcg aacgcatcct gaacgaatgc cgcgccgggc ggctcaacat
4681 gatcattgtc tatgacgtgt cgcgcttctc gcgcctgaag gtcatggacg cgattccgat
4741 tgtctcggaa ttgctcgccc tgggcgtgac gattgtttcc actcaggaag gcgtcttccg
4801 gcagggaaac gtcatggacc tgattcacct gattatgcgg ctcgacgcgt cgcacaaaga
4861 atcttcgctg aagtcggcga agattctcga cacgaagaac cttcagcgcg aattgggcgg
4921 gtacgtcggc gggaaggcgc cttacggctt cgagcttgtt tcggagacga aggagatcac
4981 gcgcaacggc cgaatggtca atgtcgtcat caacaagctt gcgcactcga ccactcccct
5041 taccggaccc ttcgagttcg agcccgacgt aatccggtgg tggtggcgtg agatcaagac
5101 gcacaaacac cttcccttca agccgggcag tcaagccgcc attcacccgg gcagcatcac
5161 ggggctttgt aagcgcatgg acgctgacgc cgtgccgacc cggggcgaga cgattgggaa
5221 gaagaccgct tcaagcgcct gggacccggc aaccgttatg cgaatccttc gggacccgcg
5281 tattgcgggc ttcgccgctg aggtgatcta caagaagaag ccggacggca cgccgaccac
5341 gaagattgag ggttaccgca ttcagcgcga cccgatcacg ctccggccgg tcgagcttga
5401 ttgcggaccg atcatcgagc ccgctgagtg gtatgagctt caggcgtggt tggacggcag
5461 ggggcgcggc aaggggcttt cccgggggca agccattctg tccgccatgg acaagctgta
5521 ctgcgagtgt ggcgccgtca tgacttcgaa gcgcggggaa gaatcgatca aggactctta
5581 ccgctgccgt cgccggaagg tggtcgaccc gtccgcacct gggcagcacg aaggcacgtg
5641 caacgtcagc atggcggcac tcgacaagtt cgttgcggaa cgcatcttca acaagatcag
5701 gcacgccgaa ggcgacgaag agacgttggc gcttctgtgg gaagccgccc gacgcttcgg
5761 caagctcact gaggcgcctg agaagagcgg cgaacgggcg aaccttgttg cggagcgcgc
5821 cgacgccctg aacgcccttg aagagctgta cgaagaccgc gcggcaggcg cgtacgacgg
5881 acccgttggc aggaagcact tccggaagca acaggcagcg ctgacgctcc ggcagcaagg
5941 ggcggaagag cggcttgccg aacttgaagc cgccgaagcc ccgaagcttc cccttgacca
6001 atggttcccc gaagacgccg acgctgaccc gaccggccct aagtcgtggt gggggcgcgc
6061 gtcagtagac gacaagcgcg tgttcgtcgg gctcttcgta gacaagatcg ttgtcacgaa
6121 gtcgactacg ggcagggggc agggaacgcc catcgagaag cgcgcttcga tcacgtgggc
6181 gaagccgccg accgacgacg acgaagacga cgcccaggac ggcacggaag acgtagcggc
6241 gtagcgagac acccgggaag cctg

What is claimed is:

1. A transgenic microorganism transformed with an artificial DNA construct consisting of, as operably associated components in a 5' to 3' direction of transcription, (a) a promoter functional in the transgenic microorganism;

(b) a first polynucleotide and a second polynucleotide, wherein the first polynucleotide consists of a nucleotide sequence encoding a first polypeptide consisting of:

the amino acid sequence of any one of SEQ ID NO: 167-172, 174, 175, and 176, wherein the first polypeptide has L-Ornithine N° hydroxylase activity, and wherein the second polynucleotide consists of a nucleotide sequence encoding a second polypeptide consisting of:

an amino acid sequence with at least 85% sequence identity to the amino acid sequence of any one of SEQ ID NO: 82-166, wherein the second polypeptide has at least one of L-Ornithine $N^5$ cyclase activity or L-Ornithine $N^5$ dehydratase activity; and (c) a transcriptional termination sequence;

wherein, the transgenic microorganism:

is capable of expressing the first and second polypeptides from the first and second polynucleotides of the artificial DNA construct, respectively;

overexpresses the first and second polypeptides compared to a microorganism not comprising the artificial DNA construct; and accumulates increased levels of piperazic acid (Piz) produced from L-Ornithine compared to a microorganism not comprising the artificial DNA construct.

2. The transgenic microorganism of claim 1, wherein the first polynucleotide is an artificial polynucleotide.

3. The transgenic microorganism of claim 1, wherein a genome of the transgenic microorganism comprises at least one native copy of a polynucleotide encoding a polypeptide having L-Ornithine $N^5$ hydroxylase activity.

4. The transgenic microorganism of claim 1, wherein a genome of the transgenic microorganism comprises at least one native copy of a polynucleotide encoding a polypeptide having L-Omithine $N^5$ cyclase activity or L-Ornithine $N^5$ dehydratase activity.

5. The transgenic microorganism of claim 1, wherein a genome of the transgenic microorganism does not comprise a native copy of a polynucleotide encoding a polypeptide having L-Ornithine $N^5$ hydroxylase activity.

6. The transgenic microorganism of claim 1, wherein a genome of the transgenic microorganism does not comprise a native copy of a polynucleotide encoding a polypeptide having L-Ornithine $N^5$ cyclase activity or L-Ornithine $N^5$ dehydratase activity.

7. The transgenic microorganism of claim 1, wherein the second polynucleotides is cloned from a sanglifehrin biosynthetic locus of *Streptomyces flaveolus.*

8. The transgenic microorganism of claim 1, wherein the second polypeptide has L-Ornithine $N^5$ cyclase activity and L-Ornithine $N^5$ dehydratase activity.

9. The transgenic microorganism of claim 1, wherein the transgenic microorganism is a bacterium.

10. The transgenic microorganism of claim 9, wherein the bacterium is a proteobacterium.

11. The transgenic microorganism of claim 1, wherein the transgenic microorganism is fungi.

12. The transgenic microorganism of claim 11, wherein the fungi is yeast.

13. The transgenic microorganism of claim 1, wherein the transgenic microorganism is an Actinobacterium.

14. The transgenic microorganism of claim 13, wherein the Actinobacterium is an actinomycete.

15. The transgenic microorganism of claim 13, wherein the Actinobacterium is selected from the group consisting of *Streptomyces, Corynebacterium, Kutznena, Lentzea, Actinomadura, Actinoalloteichus*, and *Micromonospora.*

16. The transgenic microorganism of claim 15, wherein the transgenic microorganism is a *Streptomyces* microorganism.

17. The transgenic microorganism of claim 16, wherein the *Streptomyces* microorganism is *Streptomyces lividans.*

18. The transgenic microorganism of claim 15, wherein the *Corynebacterium* is *Corynebacterium glutamicum.*

19. The transgenic microorganism of claim 1, wherein the transgenic microorganism overproduces L-Ornithine compared to a microorganism not comprising the artificial DNA construct.

20. The transgenic microorganism of claim 1, wherein the Piz produced from L-Ornithine accumulates within the transgenic microorganism.

21. The transgenic microorganism of claim 1, wherein the transgenic microorganism produces a Piz-containing product selected from the group consisting of dehydropiperazic acid, chloropiperazic acid, and hydroxypiperazic acid.

22. The transgenic microorganism of claim 1, wherein the Piz is L-piperazic acid.

23. The transgenic microorganism of claim 1, wherein the transgenic microorganism produces a Piz-containing product, which is a sanglifehrin precursor.

24. The transgenic microorganism of claim 1, wherein the transgenic microorganism does not produce sanglifehrin from the Piz.

25. The transgenic microorganism of claim 1, wherein the transgenic microorganism produces a Piz-containing product comprising a compound of formula (I):

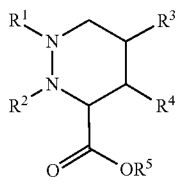

(I)

wherein:

$R^5$ is a hydrogen, an alkyl, a piperazic acid protecting group, an acetyl protecting group, or a carboxyl protecting group;

each $R^1$ and $R^2$ are independently selected from hydrogen or an amino protecting group, wherein $R^1$ and $R^2$ may be taken together to form a fused bicyclic or tricyclic amino protecting group; and each $R^3$ and $R^4$ independently selected from a hydrogen, a chloro, a fluoro, a bromo, an iodo, or hydroxyl.

26. The transgenic microorganism of claim 25, wherein $R^1$ and $R^2$ of the compound of formula (I) are not simultaneously hydrogen.

* * * * *